(12) United States Patent
Dahnke et al.

(10) Patent No.: US 7,601,850 B2
(45) Date of Patent: Oct. 13, 2009

(54) PHENYL-THIOPHENE TYPE VITAMIN D RECEPTOR MODULATORS

(75) Inventors: Karl Robert Dahnke, Carmel, IN (US); Robert Peter Gajewski, Indianapolis, IN (US); Charles David Jones, Indianapolis, IN (US); Jared Harris Linebarger, Indianapolis, IN (US); Jianliang Lu, Fishers, IN (US); Tianwei Ma, Carmel, IN (US); Sunil Nagpal, Carmel, IN (US); Todd Parker Simard, Fishers, IN (US); Ying Kwong Yee, Carmel, IN (US); Emilio Enrique Bunel, Thousand Oaks, CA (US); Ryan Edward Stites, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 145 days.

(21) Appl. No.: 10/515,403

(22) PCT Filed: May 22, 2003

(86) PCT No.: PCT/US03/14539

§ 371 (c)(1),
(2), (4) Date: Jan. 25, 2006

(87) PCT Pub. No.: WO03/101978

PCT Pub. Date: Dec. 11, 2003

(65) Prior Publication Data

US 2006/0287536 A1    Dec. 21, 2006

Related U.S. Application Data

(60) Provisional application No. 60/384,151, filed on May 29, 2002.

(51) Int. Cl.
*C07D 333/06* (2006.01)
*C07D 333/26* (2006.01)
(52) U.S. Cl. ..................................... 549/80
(58) Field of Classification Search ............... 549/80
See application file for complete search history.

(56) References Cited

U.S. PATENT DOCUMENTS

| | | | | |
|---|---|---|---|---|
| 2,831,859 | A | * 4/1958 | Werner et al. | 544/146 |
| 5,300,499 | A | * 4/1994 | Chow | 514/231.5 |
| 6,288,277 | B1 | 9/2001 | Anderskewitz et al. | |
| 6,706,725 | B1 | 3/2004 | Bernardon | |
| 2006/0094778 | A1 | 5/2006 | Nagpal et al. | |
| 2006/0135484 | A1 | 6/2006 | Nagpal et al. | |
| 2006/0293385 | A1 | 12/2006 | Gajewski et al. | |
| 2007/0105951 | A1 | 5/2007 | Gajewski et al. | |
| 2007/0106095 | A1 | 5/2007 | Lu et al. | |
| 2007/0149810 | A1 | 6/2007 | Lu et al. | |
| 2007/0225377 | A1 | 9/2007 | Flatt | |

FOREIGN PATENT DOCUMENTS

| | | |
|---|---|---|
| WO | WO 00/10958 | 3/2000 |
| WO | WO 01/38320 | 5/2001 |
| WO | WO 2004/048309 | 6/2004 |
| WO | WO 2005/051893 | 6/2005 |
| WO | WO 2006/069153 | 6/2006 |
| WO | WO 2006/069154 | 6/2006 |

OTHER PUBLICATIONS

Skin cancer [online], [retrieved on Mar. 12, 2008]. Retrieved from the Internet, URL; http://www.healthline.com/adamcontent/skin-cancer?utm_medium=ask&utm_source=sma . . . .*
Cecil Textbook of Medicine, 20th edition (1996), vol. 2, pp. 1992-1996.*
Cecil Textbook of Medicine, 20th edition (1996), vol. 2, pp. 2050-2057.*
FDA mulls drug to slow late-stage Alzheimer's [online], [retrieved on Sep. 23, 2003]. Retrieved from the Internet, URL; http://www.cnn.com/2003/HEALTH/conditions/09/24/alzheimer's.drug.ap/index.html>.*
*Novel nonsecosteroidal vitamin D mimics exert VDR-modulating activities with less calcium mobilization than 1,25-dihydroxyvitamin $D_3$*, Boehm, et al., Chemistry & Biology, vol. 6, No. 5, pp. 265-275 (1999).
*Condensation of Some Alkenylthiophenes with Phenol and Hexachlorocyclpentadiene*, Torikov, et al., Bashkir Republic Board, All-Union Chemical Society named for D.I. Mendeleev, Reports of Petrochemical Section No. 6, 1971.
Chem. Abst. No. 77:164354, Torikov, et al., *Condensation of Some Alkenylthiophenes with Phenol and Hexachlorocyclpentadiene*, 1971.
Nagpal, S. et al. "Vitamin D Analogs: Mechanism of Action of Therapeutic Applications", *Curr. Med. Chem.* 2001, 1661-1679, vol. 8.
Bouillon R., et al. Structure-Function Relationships in the Vitamin D Endocrine System, Endocrine Rev. 1995, 200-257, vol. 16.
Swann et al. "Rational Design of Vitamin D3 Analogues Which Selectively Restore Activity to a Vitamin D Receptor Mutant Associated with Rickets" *Org. Lett.* 2002, p. 1863-3866 vol. 4.
Swann et al. "Structure-Based Design of Selective Agonists for a Rickets-Associated Mutant of the Vitamin D Receptor" *J. Am. Chem. Soc.* 2002 13795-13805, vol. 124.
Basak, et al., "Comparative effects of calcipotriol and betamethasone 17-valerate solution in the treatment of seborrhoeic dermatitis of the scalp," *European Academy of Dermatology and Venereology JEADV*, vol. 15, pp. 77-92 (2001).

(Continued)

*Primary Examiner*—Rebecca L Anderson
*Assistant Examiner*—Shawquia Young
(74) *Attorney, Agent, or Firm*—James B. Myers

(57) ABSTRACT

The present invention relates to novel, non-secosteroidal, phenyl-thiophene compounds with vitamin D receptor (VDR) modulating activity that are less hypercalcemic than 1α,25 dihydroxy vitamin D3. These compounds are useful for treating bone disease and psoriasis.

19 Claims, No Drawings

OTHER PUBLICATIONS

Böhm, et al., "Disseminated superficial actinic porokeratosis: Treatment with topical tacalcitol," *Journal of the American Academy of Dermatology*, vol. 40, pp. 479-480 (1999).

Cunningham, et al., "Topical calcipotriene for morphea/linear scleroderma," *Journal of the American Academy of Dermatology*, vol. 39, pp. 211-215 (1998).

Harrison, "Disseminated superficial actinic porokeratosis responding to calcipotriol," *Clinical Exp. Dermatol.*, vol. 19, No. 1, p. 95 (1994).

Lin, et al., "The pleiotropic actions of vitamin D," *BioEssays*, vol. 26, pp. 21-28 (2003).

Nakayama, et al., "Four cases of sebopsoriasis or seborrheic dermatitis of the face and scalp successfully treated with 1a-24(R)-dihydroxycholecalciferol (tacalcitol) cream," *European Journal of Dermatology*, vol. 10, No. 7, pp. 528-532, (2000).

Sapadin, et al., "Treatment of Scleroderma," *Arch Dermatology*, vol. 138, pp. 99-105 (2002).

Sato, et al., "Epidermal Growth Factor and $1\alpha,25$-Dihydroxyvitamin $D_3$ Suppress Kipogenesis in Hamster Sebaceous Gland Cells In Vitro," *The Society of Investigative Dermatology*, vol. 117, pp. 965-970 (2001).

Zinser, et al., "Vitamin $D_3$ receptor ablation sensitizes skin to chemically induced tumorigenesis," *Carcinogenesis*, vol. 23, No. 12, pp. 2103-2109 (2002).

*Comedolytic effect of topically applied active vitamin $D_3$ analogue on pseudocomedones in the rhino mouse*, Hayashi et al., British Journal of Dermatology 2006, 155, pp. 895-901.

*Transcriptional Profiling of Keratinocytes Reveals a Vitamin D-Regulated Epidermal Differentiation Network*, Lu, et al., J Invest Dermatol 124:778-785 (2005).

*Vitamin D and the skin: an ancient friend, revisited*, Reichrath, J. Experimental Dermatology, 16, 618-625 (2007).

*Vitamin D Receptor Modulators for Inflammation and Cancer*, Yee, et al., Mini-Reviews in Medicinal Chemistry, 2005, 5, 761-778.

*Sunlight, Vitamin D, and the Innate Immune Defenses of the Human Skin*, Zasloff, M., The Society for Investigative Dermatology, Inc., pp. xvi, (2005).

*The Organic Chemistry of Drug Design and Drug Action, $2^{nd}$ Ed.*, pp. 29-34, Elsevier Academic Press (2004).

* cited by examiner

PHENYL-THIOPHENE TYPE VITAMIN D RECEPTOR MODULATORS

REFERENCE TO RELATED APPLICATION

This application is submitted as a United States national phase entry, pursuant to 35 U.S.C. §371, of PCT/US2003/14539, filed on 22 May 2003, which claims the benefit of U.S. provisional patent application Ser. No. 60/384,151, filed 29 May 2002, each of which is incorporated by reference herein.

CROSS REFERENCE TO RELATED APPLICATIONS

This patent application claims the benefit of priority under Title 35 United States Code, section 119(e), of Provisional Patent Application No. 60/384,151 filed May 29, 2002; the disclosure of which is incorporated herein by reference.

BACKGROUND OF THE INVENTION

Vitamin $D_3$ Receptor (VDR) is a ligand dependent transcription factor that belongs to the superfamily of nuclear hormone receptors. The VDR protein is 427 amino acids, with a molecular weight of ~50 kDa. The VDR ligand, $1\alpha,25$-dihydroxyvitamin D3 (the hormonally active form of Vitamin D) has its action mediated by its interaction with the nuclear receptor known as Vitamin D receptor ("VDR"). The VDR ligand, $1\alpha,25$-dihydroxyvitamin D3 ($1\alpha,25(OH)_2D_3$) acts upon a wide variety of tissues and cells both related to and unrelated to calcium and phosphate homeostasis.

The activity of $1\alpha,25$-dihydroxyvitamin D3 ($1\alpha,25(OH)_2D_3$) in various systems suggests wide clinical applications. However, use of conventional VDR ligands is hampered by their associated toxicity, namely hypercalcemia (elevated serum calcium). Currently, $1\alpha,25(OH)_2D_3$, marketed as Rocaltrol® pharmaceutical agent (product of Hoffmann-La Roche), is administered to kidney failure patients undergoing chronic kidney dialysis to treat hypocalcemia and the resultant metabolic bone disease. Other therapeutic agents, such as Calcipotriol® (synthetic analog of $1\alpha,25(OH)_2D_3$) show increased separation of binding affinity on VDR from hypercalcemic activity.

Recently, chemical modifications of $1\alpha,25(OH)_2D_3$ have yielded analogs with attenuated calcium mobilization effects (R. Bouillon et. al., Endocrine Rev. 1995, 16, 200-257). One such analog, Dovonex® pharmaceutical agent (product of Bristol-Meyers Squibb Co.), is currently used in Europe and the United States as a topical treatment for mild to moderate psoriasis (K. Kragballe et. al., Br. J. Dermatol. 1988, 119, 223-230).

Other vitamin $D_3$ mimics have been described in the publication, *Vitamin D Analogs: Mechanism of Action of Therapeutic Applications*, by Nagpal, S.; Lu, J.; Boehm, M. F., Curr. Med. Chem. 2001, 8, 1661-1679.

Although some degree of separation between the beneficial action and calcium raising (calcemic) effects has been achieved with these VDR ligands, to date the separation has been insufficient to allow for oral administration to treat conditions such as osteoporosis, cancers, leukemias, and severe psoriasis.

One example of a major class of disorder that could benefit from VDR mediated biological efficacy in the absence of hypercalcemia is osteoporosis. Osteoporosis is a systemic disorder characterized by decreased bone mass and microarchitectural deterioration of bone tissue leading to bone fragility and increased susceptibility to fractures of the hip, spine, and wrist (World Health Organization WHO 1994). Osteoporosis affects an estimated 75 million people in the United States, Europe, and Japan.

Within the past few years, several antiresorptive therapies have been introduced. These include bisphosphonates, hormone replacement therapy (HRT), a selective estrogen receptor modulator (SERM), and calcitonins. These treatments reduce bone resorption, bone formation, and increase bone density. However, none of these treatments increase true bone volume nor can they restore lost bone architecture.

Synthetic vitamin D receptor (VDR) ligands with reduced calcemic potential have been synthesized. For example, a class of bis-phenyl compounds stated to mimic $1\alpha, 25$-dihydroxyvitamin $D_3$ is described in U.S. Pat. No. 6,218,430 and the article; "Novel nonsecosteroidal vitamin D mimics exert VDR-modulating activities with less calcium mobilization than $1\alpha, 25$-Dihydroxyvitamin $D_3$", by Marcus F. Boehm, et. al., *Chemistry & Biology* 1999, Vol 6, No. 5, pgs. 265-275.

There remains a need for improved treatments using alternative or improved pharmaceutical agents that mimic $1\alpha, 25$-dihydroxyvitamin $D_3$ to stimulate bone formation, restore bone quality, and treat other diseases without the attendant disadvantage of hypercalcemia.

SUMMARY OF THE INVENTION

Novel compounds having a nucleus of formula "(A)" have been found effective as Vitamin D Receptor (VDR) modulators:

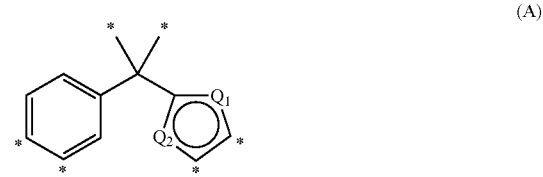

(A)

where one of the pair of ring atoms $(Q_1,Q_2)$ is sulfur and the other is carbon and each asterisk mark ("*") is a point of substitution. Compounds of the present invention with VDR modulating activities are represented by formula (I) formula I:

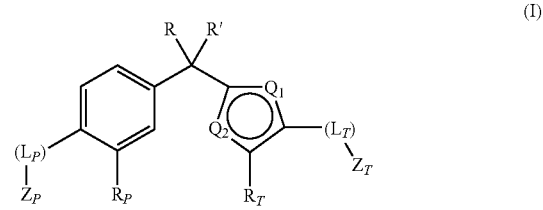

(I)

wherein the variables R, R', $Q_1$, $Q_2$, $R_P$, $R_T$, $L_T$, $L_P$, $Z_T$, and $Z_P$ are as hereinafter defined. The inventors have discovered that compounds described herein display the desirable cell differentiation and antiproliferative effects of $1,25(OH)_2D_3$ with reduced calcium mobilization (calcemic) effects.

In another aspect, the present invention is directed towards pharmaceutical compositions containing pharmaceutically effective amounts of compounds of formulae I or a pharmaceutically acceptable salt or prodrug thereof, either singly or in combination, together with pharmaceutically acceptable carriers and/or auxiliary agents.

Another aspect of the invention are novel chemical intermediates suitable for preparing the compounds of Formula I.

Another aspect of the invention is to use the compounds of the invention to treat or prevent disease states responsive to Vitamin D receptor ligands.

Another aspect of the invention is the prevention and treatment of abscess, acne, adhesion, actinic keratosis, alopecia, Alzheimer's disease, autoimmune induced diabetes, bone fracture healing, breast cancer, Crohn's disease, colon cancer, Type I diabetes, host-graft rejection, hypercalcemia, Type II diabetes, leukemia, multiple sclerosis, insufficient sebum secretion, osteomalacia, osteoporosis, insufficient dermal firmness, insufficient dermal hydration, myelodysplastic syndrome, psoriatic arthritis, prostate cancer, psoriasis, renal osteodystrophy, rheumatoid arthritis, scleroderma, seborrheic dermatitis, skin cancer, systemic lupus erythematosis, ulcerative colitis and wrinkles; by administering to a mammal in need thereof a pharmaceutically effective amount of a compound of Formula I.

Another aspect of the invention is the use of the compounds of Formula I for treating or preventing disease states mediated by the Vitamin D receptor.

DETAILED DESCRIPTION OF THE INVENTION

I. Definitions:

In accordance with the present invention and as used herein, the following terms are defined to have the following meanings, unless explicitly stated otherwise:

The structural formula:

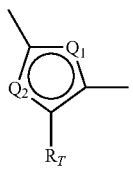

is a substructure of Formula I and represents alternative thiophene substructures, namely;

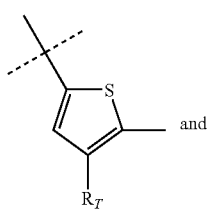

and

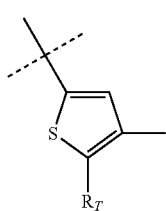

(A1)

(A2)

dependent on whether Q1 is sulfur when Q2 is carbon (A1) or Q1 is carbon when Q2 is sulfur (A2).

The term "alkenyl" refers to aliphatic groups wherein the point of attachment is a carbon-carbon double bond, for example vinyl, 1-propenyl, and 1-cyclohexenyl. Alkenyl groups may be straight-chain, branched-chain, cyclic, or combinations thereof, and may be optionally substituted. Suitable alkenyl groups have from 2 to about 20 carbon atoms.

The term "alkoxy" refers to —OR wherein R is an aliphatic or aromatic group which may be optionally substituted. Methoxy, ethoxy, propoxy, butoxy, and phenoxy are examples of alkoxy groups.

The term "alkyl" refers to saturated aliphatic groups including straight-chain, branched-chain, cyclic and any combinations thereof. Alkyl groups may further be divided into "primary", "secondary", and "tertiary" alkyl groups. In primary alkyl groups, the carbon atom of attachment is substituted with zero (methyl) or one organic radical. In secondary alkyl groups, the carbon atom of attachment is substituted with two organic radicals. In tertiary alkyl groups, the carbon atom of attachment is substituted with three organic radicals.

The term "cycloalkyl" includes organic radicals such as cyclopropanyl, cyclobutanyl, and cyclopentyl.

The term, "cycloalkenyl" includes organic radicals such as cyclopropenyl, cyclobutenyl, cyclopentenyl, and cyclohexenyl.

The term, "terminal hydroxyalkyl" is a group selected from 3-methyl-3-hydroxypentyl; 3-ethyl-3-hydroxypentyl; 3-ethyl-3-hydroxy-4-methylpentyl; 3-ethyl-3-hydroxy-4,4-dimethylpentyl; 3-methyl-3-hydroxy-4,4-dimethylpentyl; 1-hydroxycycloalkenyl; and 1-hydroxycycloalkyl.

The term, "$C_1$-$C_5$ fluoroalkyl" is an alkyl group containing fluorine and includes organic radicals such as —$CF_3$, —$CHF_2$, —$CH_2F$, —$CF_2CF_3$, —$CHFCF_3$, —$CH_2CF_3$, —$CH_2CHF_2$, and —$CH_2CH_2F$, with —$CF_3$ being preferred.

The term, "Active Ingredient" refers to a compound of the invention represented by any of (i) formulae I, II, III, IV, (ii) the product of any example set out herein, or (iii) a compound identified in any row of Tables 1, 2, 3, or 4; or a salt or prodrug derivative of the preceding compound.

The abbreviation, "Me" means methyl.

The abbreviation, "Et" means ethyl.

The abbreviation, "iPr" means 1-methylethyl.

The abbreviation, "tBu" means 1,1-dimethylethyl.

The symbol "—(CH2)2— is equivalent to —$CH_2$—$CH_2$—.

The symbol, "*" in a structural formula identifies a chiral center (except in formula "A" where is symbolizes substitution).

The univalent symbol "—O" in any structural formula is a hydroxyl group (—OH).

The term, "3-methyl-3-hydroxypentyl" refers to the radical having the structural formula:

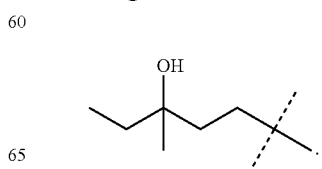

The term, "3-methyl-3-hydroxypentenyl" refers to the radical having the structural formula:

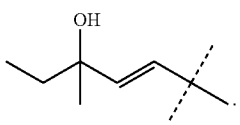

The term, "3-methyl-3-hydroxypentynyl" refers to the radical having the structural formula:

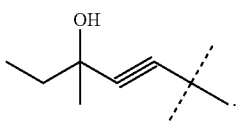

The term, "3-ethyl-3-hydroxypentyl" refers to the radical having the structural formula:

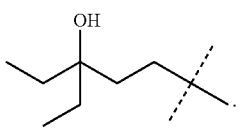

The term, "3-ethyl-3-hydroxypentenyl" refers to the radical having the structural formula:

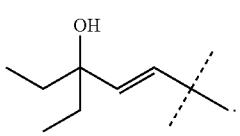

The term, "3-ethyl-3-hydroxypentynyl" refers to the radical having the structural formula:

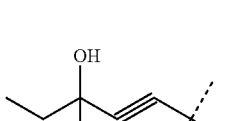

The term, "3-ethyl-3-hydroxy-4-methylpentyl" refers to the radical having the structural formula:

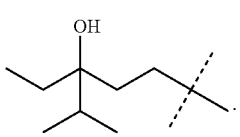

The term, "3-ethyl-3-hydroxy-4,4-dimethylpentyl" refers to the radical having the structural formula:

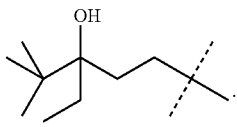

The term, "3-methyl-3-hydroxy-4,4-dimethylpentyl" refers to the radical having the structural formula:

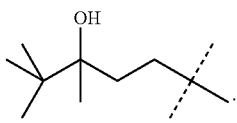

The term, "1-hydroxycycloalkenyl" refers to a radical selected from 1-hydroxycyclopentenyl, 1-hydroxycyclohexenyl, 1-hydroxycycloheptenyl, or 1-hydroxycyclooctenyl.

The term "hydroxycycloalkyl" refers to a radical having the general structural formula:

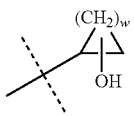

where w is an integer from 1 to 6 and the hydroxyl radical is substituted on any ring carbon atom.

The term "1-hydroxycycloalkyl" refers to a radical having the general structural formula:

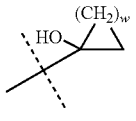

Examples of 1-hydroxycycloalkyl radicals are 1-hydroxycyclopropyl, 1-hydroxycyclobutyl, 1-hydroxycyclopentyl, 1-hydroxycyclohexyl, 1-hydroxycycloheptyl, and 1-hydroxycyclooctyl.

The abbreviation, "Me" means methyl.
The abbreviation, "Et" means ethyl.
The abbreviation, "ipr" means 1-methylethyl.
The abbreviation, "tBu" means 1,1-dimethylethyl.
The abbreviation, "3Me3OH-Pentyl" means 3-methyl-3-hydroxypentyl.
The abbreviation, "3Me3OH-Pentenyl" means 3-methyl-3-hydroxypentynyl
The abbreviation, "3Me3OH-Pentynyl" means 3-methyl-3-hydroxypentynyl
The abbreviation, "3Et3OH-Pentyl" means 3-ethyl-3-hydroxypentyl.
The abbreviation, "3Et3OH-Pentenyl" means 3-ethyl-3-hydroxypentenyl
The abbreviation, "3Et3OH-Pentynyl" means 3-ethyl-3-hydroxypentynyl
The abbreviation, "3Et3OH4Me-Pentyl" means 3-ethyl-3-hydroxy-4-methylpentyl.
The abbreviation, "3Et3OH44DiMe-Pentyl" means 3-ethyl-3-hydroxy-4,4-dimethylpentyl.

The abbreviation, "3Me3OH44DiMe-Pentyl" means 3-methyl-3-hydroxy-4,4-dimethylpentyl.

The term "$C_1$-$C_5$ alkyl" is an alkyl substituent selected from the group consisting of: methyl; ethyl; propyl; 1-methylethyl; 1-methylpropyl; 2-methylpropyl; 1,1-dimethylethyl; 1,1-dimethylpropyl; 1,2-dimethylpropyl; and 2,2-dimethylpropyl. The preferred groups are 2-methylpropyl and 1,1-dimethylethyl, with the 1,1-dimethylethyl group being most preferred.

The symbol "—($C_1$-$C_5$ alkyl)$_2$" when included as part of a substituent group means two independently selected $C_1$-$C_5$ alkyl groups, for example, the generic formula:

would be descriptive of species including;

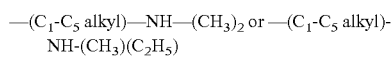

The term "amide" refers to derivatives of acids wherein one or more hydroxyl groups is replaced with a amino groups. The amino groups are optionally substituted with one or two organic radicals which may be aliphatic or aromatic. Amides may be cyclic. The term "carboxamide" refers to an amide of a carboxylic acid. The term "aminocarbonyl" refers to carboxamide radicals wherein the point of attachment is the carbonyl carbon. The term "acylamido" refers to carboxamide radicals wherein the point of attachment is the nitrogen atom.

The term, "amine", includes primary, secondary and tertiary amines having respectively one, two, or three organic groups that are attached to the nitrogen atom.

The symbol, "—C(O)—N-pyrrolidine" refers to the radical represented by the formula:

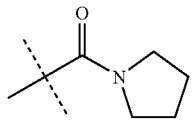

The symbol, "—C(O)—N-pyrrolidin-2-one" refers to the radical represented by the formula:

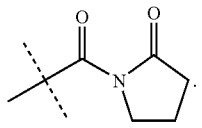

The symbol, "—C(O)—C(O)—N-pyrrolidine" refers to the radical represented by the formula:

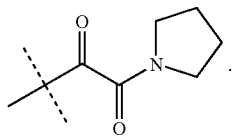

The symbol, "—C(O)—C(O)—N-pyrrolidin-2-one" refers to the radical represented by the formula:

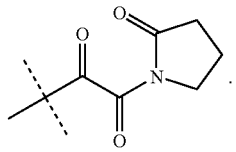

The symbol, "—CH$_2$—C(O)—N-pyrrolidin-2-one is the organic radical represented by the structural formula:

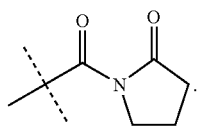

The dotted line symbol crossing a solid line representing a bond

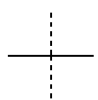

means that the bond so marked is the bond attached to the nucleus of formula "(A)" of the parent molecule or to a divalent linking group that is attached to the nucleus of the parent molecule. For example, the group;

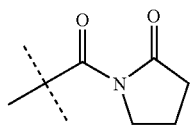

is attached to a parent aryl-thiophene nucleus to provide a compound of the invention as shown;

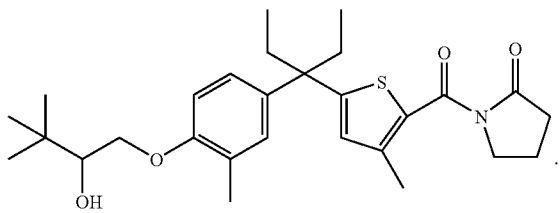

The term, "(Acidic Group)" means an organic group that acts as a proton donor capable of hydrogen bonding. Illustrative of an (Acidic Group) is a group selected from the following:

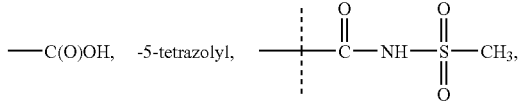

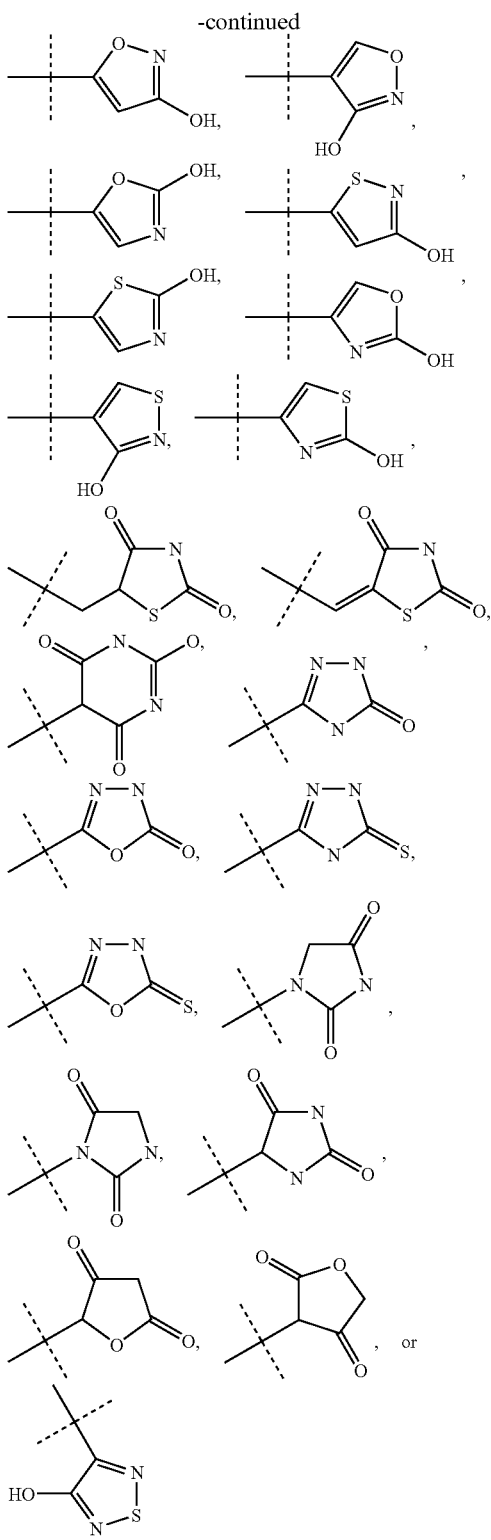

or corresponding salts of the above acids (e.g., Na, K, Ca, or Mg).

The term, "mammal" includes humans.

The term, "combined group" refers to the pendent binary groups of linkers, -(L)-, and Z substituents represented in formula I by either of:

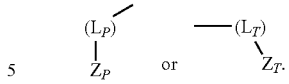

The term "ester" refers to compounds wherein a hydroxy group of an acid is replaced with an alkoxide group. For example, a carboxylic ester is one in which the hydroxy group of a carboxylic acid is replaced with an alkoxide. Esters may derive from any acid comprising one or more hydroxy groups: for example, carbonic acid, carbamic acids, phosphonic acids, sulfonic acids, and boronic acids. The terms "alkoxycarbonyl" and "carboalkoxy" refer to carboxylic ester radicals wherein the point of attachment is the carbonyl carbon.

The term "halo" refer to fluorine, chlorine, bromine, and iodine.

The term "substituted" indicate that the group in question is substituted with from one or a plurality of independently selected conventional organic substituents such as acyl, acyloxy, alkenyl, alkoxy, alkyl, amino, aminocarbonyl, aryl, carboxy, halo, hydroxy, oxa, oxo, perhaloalkyl, perhaloaryl, phosphino, phosphinyl, phosphonyl, sulfinyl, sulfonyl, thia, thio, and combinations and protected derivatives thereof.

The term "pharmaceutically acceptable salt" includes salts of the compounds of the present invention derived from the combination of the compound and an organic or inorganic acid or base. In practice, acidic members of the compounds of formulae I and II would be combined with a base or bases, basic members of the compounds of formulae I and II would be combined with an acid or acids, and members of the compounds of formulae I and II with both acid and base functionalities would be combined with one or more acids, bases or any combination thereof. Both the neutral and salt forms fall within the scope of the present invention. Examples of cationic salts are sodium, aluminum, zinc, potassium, calcium, magnesium and ammonium.

The word "abscess" is a complication often associated with surgery, trama, or diseases that predispose the host to abscess formation from encapsulated bacteria lymphocytes, macrophages, and etc.

The word "adhesion" refers to the abnormal union of surfaces normally separate by the formulation of new fibrous tissue resulting from an inflammatory process.

The term, "combined groups" refers to the groups in Formula I represented by either of the groups

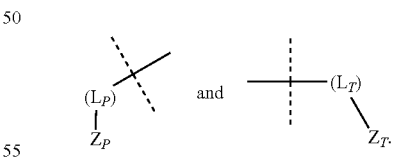

The term, "urethane" refers to the radical:

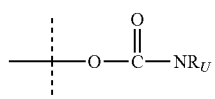

wherein each $R_U$ is independently hydrogen or $C_1$-$C_8$ alkyl, for example, methyl, ethyl, n-propyl, and isopropyl.

The term, "thiourethane" refers to the radical:

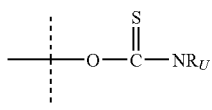

wherein $R_U$ is hydrogen or $C_1$-$C_8$ alkyl, for example, methyl, ethyl, n-propyl, and isopropyl.

Some of the structural formulae used herein omit depiction of hydrogen atoms. For example, the formula:

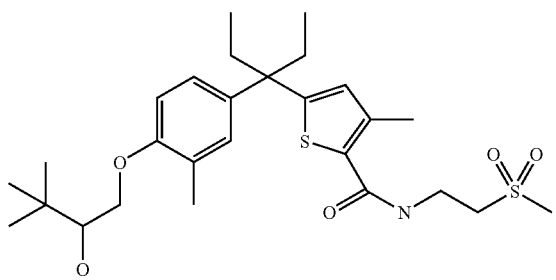

is understood to be the equivalent of the formula:

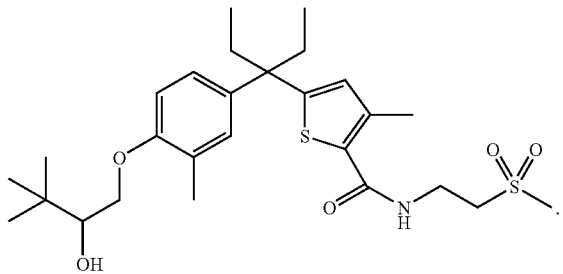

The term, "urethane-type radical" refers to either urethane or thiourethane radicals.

Definitions IA: Rule of Polarity and Lipophilicity for Substituents Pendant on the Compounds of the Invention:

The substituents $L_P$, $L_T$, $Z_P$, and $Z_T$ pendant on the compounds of the invention are constrained both by (i) the identity of each substituent, and (ii) the polar or lipophilic nature of each substituent. The occurance of "polar" and "lipophilic" is to be done in accord with the following Rule:

RULE: The combined groups in formula I, II, III, IV and V represented by

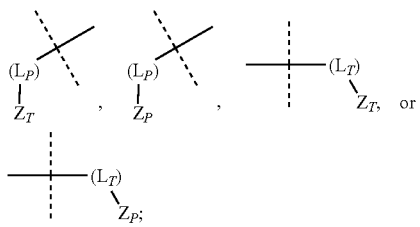

may all be lipophilic, or one may be lipophilic and the other one polar; but both combined groups may not be polar. If any part of a combined group is polar, then the "combined group" itself is deemed polar. For example, in the group

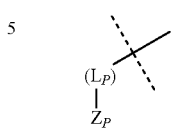

if the divalent linking group -($L_P$)- is the polar group, —C(O)—NH— and $Z_P$ is the lipophilic group, —$CH_2$—$CH_2$-(t-butyl); then the combined group is defined as "polar."

Definitions IB: Definition of "Polar" and "Lipophilic"

The term "lipophilic group" refers to any linking group

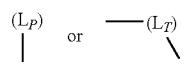

or any of the Z substituents

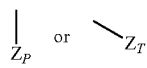

that is hydrophobic, preferring or attracted to a hydrocarbon loving, non-aqueous environment. Lipophilic linking groups in the practice of the invention are a bond, —$(CH_2)_m$—≡≡—, —$(CH_2)_m$—≡≡—, —$(CH_2)_m$—O—, —$(CH_2)_m$—S—, or —$(CH_2)_m$—C(R40)(R40)—, where m is 0, 1, or 2, and each R40 is independently hydrogen, —$CH_3$, —F, —$CH_2F$, —$CHF_2$, and —$CF_3$. All other exemplified linking groups are polar.

Generally all linking groups containing only hydrocarbon subunit groups or hydrocarbon subunit groups in combination with ether or thioether groups are lipophilic. Moreover, fluorinated derivatives of such groups are considered lipophilic.

Lipophilic $Z_T$ or $Z_P$ groups in the practice of the invention are partially exemplified by —O—$CH_2$—C(O)—$C_1$-$C_5$alkyl,
—O—$CH_2$—CH(OH)—$C_1$-$C_5$alkyl,
—O—$CH_2$—C($CH_3$)(OH)—$C_1$-$C_5$alkyl,
—O—$CH_2$—CH(O$CH_3$)—$C_1$-$C_5$alkyl,
—O—CH($CH_3$)—C(O)—$C_1$-$C_5$alkyl
—O—CH($CH_3$)—CH(OH)—$C_1$-$C_5$alkyl,
—O—$CH_2$—C(O)—C($CH_3$)$_2$—$C_1$-$C_5$alkyl
—O—$CH_2$—CH(OH)—C($CH_3$)$_2$—$C_1$-$C_5$alkyl,
—O—$CH_2$—C(O)—$C_1$-$C_5$alkyl,
—O—$CH_2$—CH(OH)—$C_1$-$C_5$alkyl,
—O—$CH_2$—CH(O$CH_3$)—$C_1$-$C_5$alkyl,
—$CH_2$—$CH_2$—C(O)—$C_1$-$C_5$alkyl,
—$CH_2$—$CH_2$—CH(OH)—$C_1$-$C_5$alkyl,
—$CH_2$—$CH_2$—CH(O$CH_3$)—$C_1$-$C_5$alkyl, —CH$_2$—C(O)—C$_1$-C$_5$alkyl,
—CH$_2$—CH(OH)—C$_1$-C$_5$alkyl,
—CH$_2$—C(CH$_3$)(OH)—C$_1$-C$_5$alkyl,
—CH(CH$_3$)—C(O)—C$_1$-C$_5$alkyl,
—CH(CH$_3$)—CH(OH)—C$_1$-C$_5$alkyl,
—CH(CH$_3$)—C(CH$_3$)(OH)—C$_1$-C$_5$alkyl,

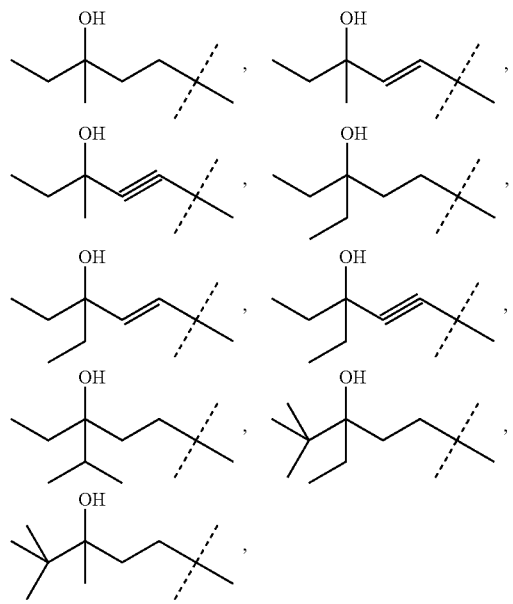

1-hydroxycyclopentenyl,
1-hydroxycyclohexenyl,
1-hydroxycycloheptenyl,
1-hydroxycyclooctenyl,
1-hydroxycyclopropyl,
1-hydroxycyclobutyl,
1-hydroxycyclopentyl,
1-hydroxycyclohexyl,
1-hydroxycycloheptyl,
and
1-hydroxycyclooctyl.

Conversely, the term "polar group" refers to any linking group

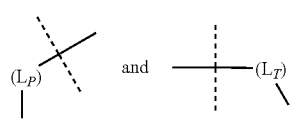

that is not a lipophilic group. The term "polar group" also refers to any Z substituent

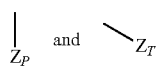

that is not a lipophilic group. The term, "polar" as used herein generally refers to chemical substituents that are hydrophilic, preferring or attracted to an aqueous environment. An example of a polar linking group is a linking group selected from the following:

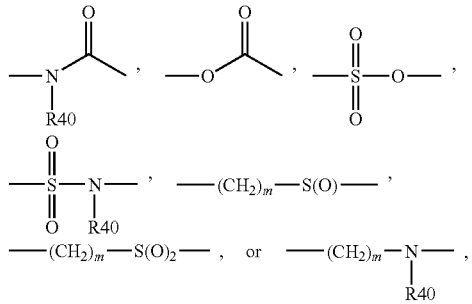

where m is 0, 1, or 2 and R40 is as previously defined.

Exemplary polar $Z_T$ or $Z_P$ groups in the practice of the invention are depicted by the following formulae:

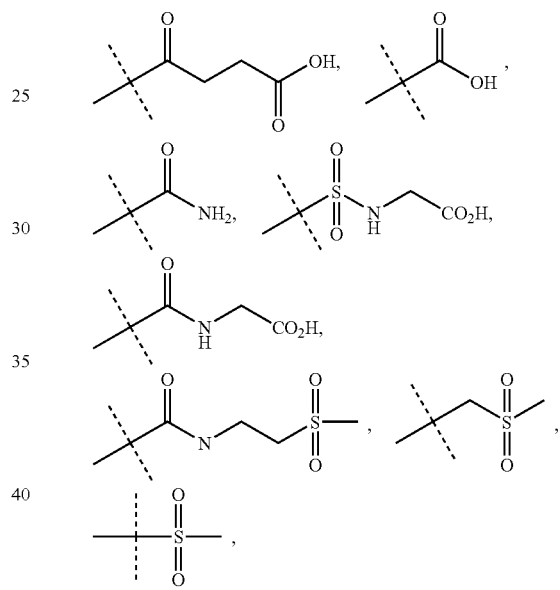

II. Compounds of the Invention:

The compounds of the invention are Vitamin D Receptor Modulators represented by formula I or a pharmaceutically acceptable salt or prodrug derivative thereof:

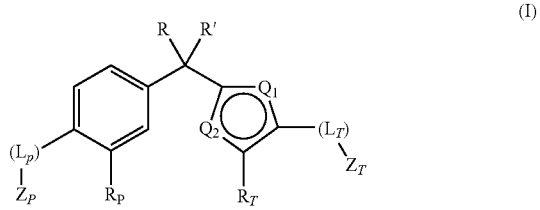

(I)

wherein;

R and R' are independently C$_1$-C$_5$ alkyl, C$_1$-C$_5$ fluoroalkyl, or together R and R' form a substituted or unsubstituted, saturated or unsaturated carbocyclic ring having from 3 to 8 carbon atoms;

Ring atoms $Q_1$ and $Q_2$ are independently selected from carbon or sulfur, with the proviso that one atom is sulfur and the other atom is carbon;

$R_P$ and RT are independently selected from the group consisting of hydrogen, halo, $C_1$-$C_5$ alkyl, $C_1$-$C_5$ fluoroalkyl, —O—$C_1$-$C_5$ alkyl, —S—$C_1$-$C_5$ alkyl, —O—$C_1$-$C_5$ fluoroalkyl, —CN, —NO$_2$, acetyl, —S—$C_1$-$C_5$ fluoroalkyl, $C_2$-$C_5$ alkenyl, $C_3$-$C_5$ cycloalkyl, and $C_3$-$C_5$ cycloalkenyl;

($L_P$) and ($L_T$) are divalent linking groups independently selected from the group consisting of

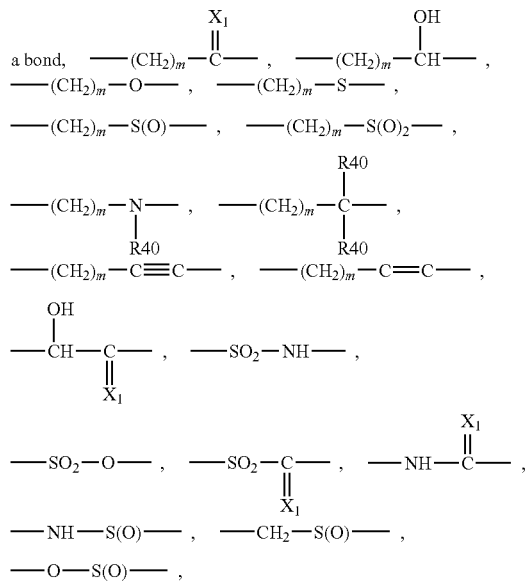

where m is 0, 1 or 2, $X_1$ is oxygen or sulfur, and each R40 is independently hydrogen or $C_1$-$C_5$ alkyl or $C_1$-$C_5$ fluoroalkyl;

$Z_P$ and $Z_T$ are independently selected from
-hydrogen,
-phenyl,
-benzyl,
-fluorophenyl,
—($C_1$-$C_5$ alkyl),
—($C_2$-$C_5$ alkenyl),
—($C_3$-$C_5$ cycloalkyl),
—($C_3$-$C_5$ cycloalkenyl),
—($C_1$-$C_5$ hydroxyalkyl),
—($C_1$-$C_5$ fluoroalkyl),
—($C_1$-$C_5$ alkyl)-phenyl,
—($C_1$-$C_5$ alkyl)-O—($C_1$-$C_5$)alkyl,
—($C_1$-$C_5$ alkyl)-NH$_2$,
—($C_1$-$C_5$ alkyl)-NH—($C_1$-$C_5$ alkyl),
—($C_1$-$C_5$ alkyl)-N—($C_1$-$C_5$ alkyl)$_2$,
—($C_1$-$C_5$ alkyl)-C(O)—NH$_2$,
—($C_1$-$C_5$ alkyl)-C(O)—NH—($C_1$-$C_5$ alkyl),
—($C_1$-$C_5$ alkyl)-C(O)—N—($C_1$-$C_5$ alkyl)$_2$,
—($C_1$-$C_5$ alkyl)-C(O)—($C_1$-$C_5$ alkyl),
—($C_1$-$C_5$ alkyl)-NH—SO$_2$—($C_1$-$C_5$ alkyl),
—($C_1$-$C_5$ alkyl)-N-pyrrolidin-2-one,
—($C_1$-$C_5$ alkyl)-N-pyrrolidine,
—($C_1$-$C_5$ alkyl)-(1-methylpyrrolidin-2-one-3-yl),
—($C_1$-$C_5$ alkyl)-C(O)—(O—$C_1$-$C_5$ alkyl),
—($C_1$-$C_5$ alkyl)-C(O)—OH,
—($C_1$-$C_5$ alkyl)-5-tetrazolyl,
—($C_1$-$C_5$ alkyl)-P(O)—(O—$C_1$-$C_5$ alkyl)$_2$,
—($C_1$-$C_5$ alkyl)-SO$_2$—($C_1$-$C_5$ alkyl),
—($C_1$-$C_5$ alkyl)-SO$_2$—NH$_2$,
—($C_1$-$C_5$ alkyl)-SO$_2$—NH—($C_1$-$C_5$ alkyl),
—($C_1$-$C_5$ alkyl)-SO$_2$—N—($C_1$-$C_5$ alkyl)$_2$,
—($C_1$-$C_5$ alkyl)-SO$_2$—($C_1$-$C_5$ alkyl),
—($C_1$-$C_5$ alkyl)-S(O)—($C_1$-$C_5$ alkyl),
—($C_1$-$C_5$ alkyl)-S(O)—NH$_2$,
—($C_1$-$C_5$ alkyl)-S(O)—NH—($C_1$-$C_5$ alkyl),
—($C_1$-$C_5$ alkyl)-S(O)—N—($C_1$-$C_5$ alkyl)$_2$,
—($C_1$-$C_5$ alkyl)-S(O)—($C_1$-$C_5$ alkyl),
—($C_1$-$C_5$ alkyl)-N(C(O)($C_1$-$C_5$ alkyl)CH$_2$C(O)OH,
—($C_1$-$C_5$ alkyl)-N(C(O)($C_1$-$C_5$ alkyl)CH$_2$C(O)—($C_1$-$C_5$ alkyl),
—CH(OH)—($C_1$-$C_5$ alkyl)
—CH(OH)—($C_2$-$C_5$ alkenyl),
—CH(OH)—($C_3$-$C_5$ cycloalkyl),
—CH(OH)—($C_3$-$C_5$ cycloalkenyl),
—CH(OH)—($C_1$-$C_5$ hydroxyalkyl),
—CH(OH)—($C_1$-$C_5$ fluoroalkyl),
—CH(OH)-phenyl
—CH(OH)-5-tetrazolyl,
—CH(OH)—(1-methylpyrrolidin-2-one-3-yl),
—C(O)—($C_1$-$C_5$ alkyl),
—C(O)—($C_1$-$C_5$ alkyl)-C(O)OH,
—C(O)—($C_1$-$C_5$ alkyl)-C(O)(O—$C_1$-$C_5$ alkyl),
—C(O)—($C_2$-$C_5$ alkenyl),
—C(O)—($C_3$-$C_5$ cycloalkyl),
—C(O)—($C_3$-$C_5$ cycloalkenyl),
—C(O)—($C_1$-$C_5$ hydroxyalkyl),
—C(O)—($C_1$-$C_5$ fluoroalkyl),
—C(O)—($C_1$-$C_5$ alkyl)-phenyl
—C(O)—O—($C_1$-$C_5$ alkyl),
—C(O)—O—($C_2$-$C_5$ alkenyl),
—C(O)—O—($C_3$-$C_5$ cycloalkyl),
—C(O)—O—($C_3$-$C_5$ cycloalkenyl),
—C(O)—O—($C_1$-$C_5$ hydroxyalkyl),
—C(O)—O—($C_1$-$C_5$ fluoroalkyl),
—C(O)—O—($C_1$-$C_5$ alkyl)-phenyl,
—C(O)—NH$_2$,
—C(O)—NH(OH),
—C(O)—NH—($C_1$-$C_5$ alkyl),
—C(O)—N—($C_1$-$C_5$ alkyl)$_2$,
—C(O)—NH—($C_2$-$C_5$ alkenyl),
—C(O)—NH—($C_3$-$C_5$ cycloalkyl),
—C(O)—NH—($C_3$-$C_5$ cycloalkenyl),
—C(O)—NH—($C_1$-$C_5$ fluoroalkyl),
—C(O)—NH—($C_1$-$C_5$ alkyl)-phenyl,
—C(O)—NH—SO$_2$—($C_1$-$C_5$ alkyl),
—C(O)—NH—SO$_2$—($C_2$-$C_5$ alkenyl),
—C(O)—NH—SO$_2$—($C_3$-$C_5$ cycloalkyl),
—C(O)—NH—SO$_2$—($C_3$-$C_5$ cycloalkenyl),
—C(O)—NH—S(O)—($C_1$-$C_5$ alkyl),
—C(O)—NH—S(O)—($C_2$-$C_5$ alkenyl),
—C(O)—NH—S(O)—($C_3$-$C_5$ cycloalkyl),
—C(O)—NH—S(O)—($C_3$-$C_5$ cycloalkenyl),
—C(O)—NH—($C_1$-$C_5$ fluoroalkyl),
—C(O)—NH—($C_1$-$C_5$ alkyl)-phenyl
—C(O)—NH—($C_1$-$C_5$ alkyl)-SO$_2$—($C_1$-$C_5$ alkyl),
—C(O)—NH—($C_1$-$C_5$ alkyl)-S(O)—($C_1$-$C_5$ alkyl),
—C(O)—NH—CH$_2$—C(O)OH
—C(O)—NH—CH$_2$—C(O)-(O—$C_1$-$C_5$ alkyl),
—C(O)—N—($C_1$-$C_5$ alkyl)(C(O)OH),
—C(O)—N—($C_1$-$C_5$ alkyl)(C(O)—(O—$C_1$-$C_5$ alkyl)),
—C(O)—NH—CH((CH$_2$)(CO$_2$H))(CO$_2$H),
—C(O)—NH—CH((CH$_2$)(C(O)—($C_1$-$C_5$ alkyl)))(C(O)—(O—$C_1$-$C_5$ alkyl)),
—C(O)—NH—CH((CH$_2$OH)(CO$_2$H)), —C(O)—NH—CH((CH$_2$OH)(C(O)(O—C$_1$-C$_5$ alkyl)),
—C(O)—NH—C((C$_1$-C$_5$ alkyl)(C$_1$-C$_5$ alkyl))(CO$_2$H),
—C(O)—NH—C((C$_1$-C$_5$ alkyl)(C$_1$-C$_5$ alkyl))(C(O)—(O—C$_1$-C$_5$ alkyl)),
—C(O)—NH-5-tetrazolyl,
—C(O)—N-pyrrolidin-2-one,
—C(O)—N-pyrrolidine,
—C(O)-(1-methylpyrrolidin-2-one-3-yl),
—C(O)—(C$_1$-C$_5$ alkyl)-N-pyrrolidin-2-one,
—C(O)—(C$_1$-C$_5$ alkyl)-N-pyrrolidine,
—C(O)—(C$_1$-C$_5$ alkyl)-(1-methylpyrrolidin-2-one-3-yl),
—C(O)—N-pyrrolidin-2-(CO$_2$H),
—C(O)—N-pyrrolidin-2-(C(O)—(O—C$_1$-C$_5$ alkyl)),
—C(O)—N—(C(O)—(C$_1$-C$_5$ alkyl))CH$_2$)(CO$_2$H),
—C(O)—N—(C(O)—(C$_1$-C$_5$ alkyl))CH$_2$)(C(O)—(O—C$_1$-C$_5$ alkyl)),
—C(O)—N—(C$_1$-C$_5$ alkyl))CH$_2$(CO$_2$H),
—C(O)—C(O)—OH,
—C(O)—C(O)—(C$_1$-C$_5$ alkyl),
—C(O)—C(O)—(C$_2$-C$_5$ alkenyl),
—C(O)—C(O)—(C$_3$-C$_5$ cycloalkyl),
—C(O)—C(O)—(C$_3$-C$_5$ cycloalkenyl),
—C(O)—C(O)—(C$_1$-C$_5$ hydroxyalkyl),
—C(O)—C(O)—(C$_1$-C$_5$ fluoroalkyl),
—C(O)—C(O)—(C$_1$-C$_5$ alkyl)-phenyl,
—C(O)—C(O)—NH$_2$,
—C(O)—C(O)—NH—(C$_1$-C$_5$ alkyl),
—C(O)—C(O)—N—(C$_1$-C$_5$ alkyl)$_2$,
—C(O)—C(O)-5-tetrazolyl,
—C(O)—C(O)—N-pyrrolidin-2-one,
—C(O)—C(O)—N-pyrrolidine,
—C(O)—C(O)-(1-methylpyrrolidin-2-one-3-yl),
—O—(C$_1$-C$_5$ alkyl),
—O—(C$_2$-C$_5$ alkenyl),
—O—(C$_3$-C$_5$ cycloalkyl),
—O—(C$_3$-C$_5$ cycloalkenyl),
—O—(C$_1$-C$_5$ hydroxyalkyl),
—O—(C$_1$-C$_5$ fluoroalkyl),
—O—(C$_1$-C$_5$ alkyl)-phenyl,
—O—(C$_1$-C$_5$ alkyl)-(O)—(C$_1$-C$_5$ alkyl),
—O—(C$_1$-C$_5$ alkyl) NH$_2$,
—O—(C$_1$-C$_5$ alkyl)-NH—(C$_1$-C$_5$ alkyl)$_2$,
—O—(C$_1$-C$_5$ alkyl)-C(O)—NH$_2$,
—O—(C$_1$-C$_5$ alkyl)-C(O)—NH—(C$_1$-C$_5$ alkyl),
—O—(C$_1$-C$_5$ alkyl)-C(O)—N—(C$_1$-C$_5$ alkyl)$_2$,
—O—(C$_1$-C$_5$ alkyl)-C(O)—OH,
—O—(C$_1$-C$_5$ alkyl)-C(O)—NH-5-tetrazolyl,
—O—(C$_1$-C$_5$ alkyl)-C(O)—(C$_1$-C$_5$ alkyl),
—O—(C$_1$-C$_5$ alkyl)-C(O)—(O—C$_1$-C$_5$ alkyl),
—O—(C$_1$-C$_5$ alkyl)-NH$_2$,
—O—(C$_1$-C$_5$ alkyl)-NH-(C$_1$-C$_5$ alkyl),
—O—(C$_1$-C$_5$ alkyl)-N—(C$_1$-C$_5$ alkyl)$_2$,
—O—(C$_1$-C$_5$ alkyl)-NH—SO$_2$—(C$_1$-C$_5$ alkyl),
—O—(C$_1$-C$_5$ alkyl)-N-pyrrolidin-2-one,
—O—(C$_1$-C$_5$ alkyl)-N-pyrrolidine,
—O—(C$_1$-C$_5$ alkyl)-(1-methylpyrrolidin-2-one-3-yl),
—O—(C$_1$-C$_5$ alkyl)-SO$_2$—(C$_1$-C$_5$ alkyl,)
—O—(C$_1$-C$_5$ alkyl)-SO$_2$—NH$_2$,
—O—(C$_1$-C$_5$ alkyl)-SO$_2$—NH—(C$_1$-C$_5$ alkyl),
—O—(C$_1$-C$_5$ alkyl)-SO$_2$—N—(C$_1$-C$_5$ alkyl)$_2$,
—O—(C$_1$-C$_5$ alkyl)-SO$_2$—(C$_1$-C$_5$ alkyl),
—O—(C$_1$-C$_5$ alkyl)-S(O)—(C$_1$-C$_5$ alkyl,)
—O—(C$_1$-C$_5$ alkyl)-S(O)—NH$_2$,
—O—(C$_1$-C$_5$ alkyl)-S(O)—NH—(C$_1$-C$_5$ alkyl),
—O—(C$_1$-C$_5$ alkyl)-S(O)—N—(C$_1$-C$_5$ alkyl)$_2$,
—O—(C$_1$-C$_5$ alkyl)-S(O)—(C$_1$-C$_5$ alkyl),
—O—(C$_1$-C$_5$ alkyl)-P(O)—(O—C$_1$-C$_5$ alkyl)$_2$,
—O—(C$_1$-C$_5$ alkyl)-5-tetrazolyl,
—O—CH$_2$—CO$_2$H,
—O—CH$_2$-5-tetrazolyl,
—O—(C$_1$-C$_5$ alkyl),
—O—C(O)—NH$_2$,
—O—C(O)—N—(CH$_3$)$_2$,
—O—C(S)—N—(CH$_3$)$_2$,
—C(O)—O—(C$_1$-C$_5$ alkyl)—O—(5-tetrazolyl),
—O—SO$_2$—(C$_1$-C$_5$ alkyl,)
—O—SO$_2$—NH$_2$,
—O—SO$_2$—NH—(C$_1$-C$_5$ alkyl),
—O—SO$_2$—N—(C$_1$-C$_5$ alkyl)$_2$,
—O—S(O)—(C$_1$-C$_5$ alkyl,)
—O—S(O)—NH$_2$,
—O—S(O)—NH—(C$_1$-C$_5$ alkyl),
—O—S(O)—N—(C$_1$-C$_5$ alkyl)$_2$,
—S—(C$_1$-C$_5$ alkyl),
—S—(C$_2$-C$_5$ alkenyl),
—S—(C$_3$-C$_5$ cycloalkyl),
—S—(C$_3$-C$_5$ cycloalkenyl),
—S—(C$_1$-C$_5$ fluoroalkyl),
—S—(C$_1$-C$_5$ hydroxyalkyl),
—S—(C$_1$-C$_5$ alkyl)-phenyl,
—S—(C$_1$-C$_5$ alkyl)-O—(C$_1$-C$_5$ alkyl),
—S—(C$_1$-C$_5$ alkyl)-C(O)—OH,
—S—(C$_1$-C$_5$ alkyl)-C(O)—(C$_1$-C$_5$ alkyl),
—S—(C$_1$-C$_5$ alkyl)-C(O)—O—(C$_1$-C$_5$ alkyl),
—S—(C$_1$-C$_5$ alkyl)-C(O)—NH$_2$,
—S—(C$_1$-C$_5$ alkyl)-C(O)—NH—(C$_1$-C$_5$ alkyl),
—S—(C$_1$-C$_5$ alkyl)-C(O)—N—(C$_1$-C$_5$ alkyl)$_2$,
—S—(C$_1$-C$_5$ alkyl) NH$_2$,
—S—(C$_1$-C$_5$ alkyl)-NH-(C$_1$-C$_5$ alkyl),
—S—(C$_1$-C$_5$ alkyl)-N—(C$_1$-C$_5$ alkyl)$_2$,
—S—(C$_1$-C$_5$ alkyl)-NH—SO$_2$—(C$_1$-C$_5$ alkyl),
—S—(C$_1$-C$_5$ alkyl)-N-pyrrolidin-2-one,
—S—(C$_1$-C$_5$ alkyl)-N-pyrrolidine,
—S—(C$_1$-C$_5$ alkyl)-(1-methylpyrrolidin-2-one-3-yl),
—S—(C$_1$-C$_5$ alkyl)-SO$_2$—(C$_1$-C$_5$ alkyl),
—S—(C$_1$-C$_5$ alkyl)-SO$_2$—NH$_2$,
—S—(C$_1$-C$_5$ alkyl)-SO$_2$—NH—(C$_1$-C$_5$ alkyl),
—S—(C$_1$-C$_5$ alkyl)-SO$_2$—N—(C$_1$-C$_5$ alkyl)$_2$,
—S—(C$_1$-C$_5$ alkyl)-SO$_2$—(C$_1$-C$_5$ alkyl),
—S—(C$_1$-C$_5$ alkyl)-P(O)—(O—C$_1$-C$_5$ alkyl)$_2$,
—S—(C$_1$-C$_5$ alkyl)-5-tetrazolyl,
—S—(C$_1$-C$_5$ alkyl)-S(O)—(C$_1$-C$_5$ alkyl),
—S—(C$_1$-C$_5$ alkyl)-S(O)—NH$_2$,
—S—(C$_1$-C$_5$ alkyl)-S(O)—NH—(C$_1$-C$_5$ alkyl),
—S—(C$_1$-C$_5$ alkyl)-S(O)—N—(C$_1$-C$_5$ alkyl)$_2$,
—S—(C$_1$-C$_5$ alkyl)-S(O)—(C$_1$-C$_5$ alkyl),
—SO$_2$—(C$_1$-C$_5$ alkyl),
—SO$_2$—(C$_2$-C$_5$ alkenyl),
—SO$_2$—(C$_3$-C$_5$ cycloalkyl),
—SO$_2$—(C$_3$-C$_5$ cycloalkenyl),
—SO$_2$—(C$_1$-C$_5$ hydroxyalkyl),
—SO$_2$—(C$_1$-C$_5$ fluoroalkyl),
—SO$_2$—(C$_1$-C$_5$)-phenyl,
—SO$_2$—NH$_2$,
—SO$_2$—NH—(C$_1$-C$_5$ alkyl),
—SO$_2$—NH—CH$_2$—C(O)OH,
—SO$_2$—NH—CH$_2$—C(O)(O—C$_1$-C$_5$ alkyl),
—SO$_2$—NH—(C$_1$-C$_5$ alkyl)-C(O)OH,
—SO$_2$—NH—(C$_1$-C$_5$ alkyl)-C(O)(O—C$_1$-C$_5$ alkyl),
—SO$_2$—NHC(O)—(C$_3$-C$_6$ cycloalkyl),
—SO$_2$—NH—C(O)—(C$_1$-C$_5$ alkyl),
—SO$_2$—N—(C$_1$-C$_5$ alkyl)$_2$,
—SO$_2$—(C$_1$-C$_5$ alkyl)-O—(C$_1$-C$_5$ alkyl),
—SO$_2$—(C$_1$-C$_5$ alkyl)-C(O)—(C$_1$-C$_5$ alkyl), —SO$_2$—(C$_1$-C$_5$ alkyl)-NH$_2$,
—SO$_2$—(C$_1$-C$_5$ alkyl)-NH-(C$_1$-C$_5$ alkyl),
—SO$_2$—(C$_1$-C$_5$ alkyl)-N—(C$_1$-C$_5$ alkyl)$_2$,
—SO$_2$—(C$_1$-C$_5$ alkyl)-C(O)—NH$_2$,
—SO$_2$—(C$_1$-C$_5$ alkyl)-C(O)—NH—(C$_1$-C$_5$ alkyl),
—SO$_2$—(C$_1$-C$_5$ alkyl)-C(O)—N—(C$_1$-C$_5$ alkyl)$_2$,
—SO$_2$—(C$_1$-C$_5$ alkyl)-NH—SO$_2$—(C$_1$-C$_5$ alkyl),
—SO$_2$—(C$_1$-C$_5$ alkyl)-N-pyrrolidin-2-one,
—SO$_2$—(C$_1$-C$_5$ alkyl)-N-pyrrolidine,
—SO$_2$—(C$_1$-C$_5$ alkyl)-(1-methylpyrrolidin-2-one-3-yl),
—SO$_2$—(C$_1$-C$_5$ alkyl)-C(O)—O—(C$_1$-C$_5$ alkyl),
—SO$_2$—(C$_1$-C$_5$ alkyl)-C(O)—OH,
—SO$_2$—(C$_1$-C$_5$ alkyl)-5-tetrazolyl,
—SO$_2$—(C$_1$-C$_5$ alkyl)-SO$_2$—(C$_1$-C$_5$ alkyl),
—SO$_2$—(C$_1$-C$_5$ alkyl)-SO$_2$—NH$_2$,
—SO$_2$—(C$_1$-C$_5$ alkyl)-SO$_2$—NH—(C$_1$-C$_5$ alkyl),
—SO$_2$—(C$_1$-C$_5$ alkyl)-SO$_2$—N—(C$_1$-C$_5$ alkyl)$_2$,
—SO$_2$—(C$_1$-C$_5$ alkyl)-SO$_2$—(C$_1$-C$_5$ alkyl),
—SO$_2$—(C$_1$-C$_5$ alkyl)-P(O)—(O—C$_1$-C$_5$ alkyl)$_2$,
—SO$_2$—(C$_1$-C$_5$ alkyl),
—SO$_2$—(C$_2$-C$_5$ alkenyl),
—SO$_2$—(C$_3$-C$_5$ cycloalkyl),
—SO$_2$—(C$_3$-C$_5$ cycloalkenyl),
—SO$_2$—(C$_1$-C$_5$ hydroxyalkyl),
—SO$_2$—(C$_1$-C$_5$ fluoroalkyl),
—SO$_2$—(C$_1$-C$_5$)-phenyl,
—SO$_2$—N=CHN(C$_1$-C$_5$ alkyl) 2,
—S(O)—NH$_2$,
—S(O)—NH—(C$_1$-C$_5$ alkyl),
—S(O)—NH—CH$_2$—C(O)OH
—S(O)—NH—(C$_1$-C$_5$ alkyl)-C(O)OH,
—S(O)—NH—CH$_2$—C(O)(O—C$_1$-C$_5$ alkyl),
—S(O)—NH—(C$_1$-C$_5$ alkyl)-C(O)(O—C$_1$-C$_5$ alkyl),
—S(O)HC(O)—(C$_3$-C$_6$ cycloalkyl),
—S(O)—NH—C(O)—(C$_1$-C$_5$ alkyl),
—S(O)—N—(C$_1$-C$_5$ alkyl)$_2$,
—S(O)—(C$_1$-C$_5$ alkyl)-O—(C$_1$-C$_5$ alkyl),
—S(O)—(C$_1$-C$_5$ alkyl)-C(O)—(C$_1$-C$_5$ alkyl),
—S(O)—(C$_1$-C$_5$ alkyl)-C(O)-(O—C$_1$-C$_5$ alkyl),
—S(O)—(C$_1$-C$_5$ alkyl)-NH-(C$_1$-C$_5$ alkyl),
—S(O)—(C$_1$-C$_5$ alkyl)-N—(C$_1$-C$_5$ alkyl)$_2$,
—S(O)—(C$_1$-C$_5$ alkyl)-C(O)—NH$_2$,
—S(O)—(C$_1$-C$_5$ alkyl)-C(O)—NH—(C$_1$-C$_5$ alkyl),
—S(O)—(C$_1$-C$_5$ alkyl)-C(O)—N—(C$_1$-C$_5$ alkyl)$_2$,
—S(O)—(C$_1$-C$_5$alkyl)-NH—SO$_2$—(C$_1$-C$_5$alkyl),
—S(O)—(C$_1$-C$_5$ alkyl)-NH—S(O)—(C$_1$-C$_5$ alkyl),
—S(O)—(C$_1$-C$_5$ alkyl)-N-pyrrolidin-2-one,
—S(O)—(C$_1$-C$_5$ alkyl)-N-pyrrolidine,
—S(O)—(C$_1$-C$_5$ alkyl)-(1-methylpyrrolidin-2-one-3-yl),
—S(O)—(C$_1$-C$_5$ alkyl)-C(O)—(O—C$_1$-C$_5$ alkyl),
—S(O)—(C$_1$-C$_5$ alkyl)-C(O)—OH,
—S(O)—(C$_1$-C$_5$ alkyl)-5-tetrazolyl,
—S(O)—(C$_1$-C$_5$ alkyl)-SO$_2$—(C$_1$-C$_5$ alkyl),
—S(O)—(C$_1$-C$_5$ alkyl)-S(O)—(C$_1$-C$_5$ alkyl),
—S(O)—(C$_1$-C$_5$ alkyl)-SO$_2$—NH$_2$,
—S(O)—(C$_1$-C$_5$ alkyl)-S(O)—NH$_2$,
—S(O)—(C$_1$-C$_5$ alkyl)-SO$_2$—NH—(C$_1$-C$_5$ alkyl),
—S(O)—(C$_1$-C$_5$ alkyl)-S(O)—NH—(C$_1$-C$_5$ alkyl),
—S(O)—(C$_1$-C$_5$ alkyl)-SO$_2$—N—(C$_1$-C$_5$ alkyl)$_2$,
—S(O)—(C$_1$-C$_5$ alkyl)-S(O)—N—(C$_1$-C$_5$ alkyl)$_2$,
—S(O)—(C$_1$-C$_5$ alkyl)-SO$_2$—(C$_1$-C$_5$ alkyl),
—S(O)—(C$_1$-C$_5$ alkyl)-S(O)—(C$_1$-C$_5$ alkyl),
—S(O)—(C$_1$-C$_5$ alkyl)-P(O)—(O—C$_1$-C$_5$ alkyl)$_2$,
—S(O)—N=CHN(C$_1$-C$_5$ alkyl) 2,
—NHC(S)NH$_2$,
—NHC(S)NH—(C$_1$-C$_5$ alkyl),
—NHC(S)N—(C$_1$-C$_5$ alkyl)$_2$,
—NHC(S)NH—(C$_2$-C$_5$ alkenyl),
—NHC(S)NH—(C$_3$-C$_5$ cycloalkyl),
—NHC(S)NH—(C$_3$-C$_5$ cycloalkenyl),
—NHC(S)NH—(C$_1$-C$_5$ fluoroalkyl),
—NHC(S)NH-C$_1$-C$_5$ hydroxyalkyl,
—NHC(S)NH—(C$_1$-C$_5$ fluoroalkyl)
—NHC(S)NH-phenyl,
—NHC(S)NH—(C$_1$-C$_5$ alkyl)-C(O)—OH,
—NHC(S)NH—(C$_1$-C$_5$ alkyl)-O—(C$_1$-C$_5$ alkyl),
—NHC(S)NH—(C$_1$-C$_5$ alkyl)-C(O)—(C$_1$-C$_5$ alkyl),
—NHC(S)NH—(C$_1$-C$_5$ alkyl)-C(O)—(O—C$_1$-C$_5$ alkyl),
—NHC(S)NH—(C$_1$-C$_5$ alkyl)-NH$_2$,
—NHC(S)NH—(C$_1$-C$_5$ alkyl)-NH—(C$_1$-C$_5$ alkyl),
—NHC(S)NH—(C$_1$-C$_5$ alkyl)-N—(C$_1$-C$_5$ alkyl)$_2$,
—NHC(S)NH—(C$_1$-C$_5$ alkyl)-C(O)—NH$_2$,
—NHC(S)NH—(C$_1$-C$_5$ alkyl)-C(O)—NH—(C$_1$-C$_5$ alkyl),
—NHC(S)NH—(C$_1$-C$_5$ alkyl)-C(O)—N—(C$_1$-C$_5$ alkyl)$_2$,
—NHC(S)NH—(C$_1$-C$_5$ alkyl)-NH—SO$_2$—(C$_1$-C$_5$ alkyl),
—NHC(S)NH—(C$_1$-C$_5$ alkyl)-NH—S(O)—(C$_1$-C$_5$ alkyl),
—NHC(S)NH—(C$_1$-C$_5$ alkyl)-N-pyrrolidin-2-one,
—NHC(S)NH—(C$_1$-C$_5$ alkyl)-N-pyrrolidine,
—NHC(S)NH—(C$_1$-C$_5$ alkyl)-(1-methylpyrrolidin-2-one-3-yl),
—NHC(S)NH—(C$_1$-C$_5$ alkyl)-5-tetrazolyl,
—NHC(S)NH—(C$_1$-C$_5$ alkyl)-SO$_2$—(C$_1$-C$_5$ alkyl),
—NHC(S)NH—(C$_1$-C$_5$ alkyl)-SO$_2$—NH$_2$,
—NHC(S)NH—(C$_1$-C$_5$ alkyl)-SO$_2$—NH—(C$_1$-C$_5$ alkyl),
—NHC(S)NH—(C$_1$-C$_5$ alkyl)-SO$_2$—N—(C$_1$-C$_5$ alkyl)$_2$,
—NHC(S)NH—(C$_1$-C$_5$ alkyl)-S(O)—(C$_1$-C$_5$ alkyl),
—NHC(S)NH—(C$_1$-C$_5$ alkyl)-S(O)—NH$_2$,
—NHC(S)NH—(C$_1$-C$_5$ alkyl)-S(O)—NH—(C$_1$-C$_5$ alkyl),
—NHC(S)NH—(C$_1$-C$_5$ alkyl)-S(O)—N—(C$_1$-C$_5$ alkyl)$_2$,
—NHC(S)NH—(C$_1$-C$_5$ alkyl)-P(O)—(O—C$_1$-C$_5$ alkyl)$_2$,
—NHC(O)NH$_2$,
—NHC(O)NH—(C$_1$-C$_5$ alkyl),
—NHC(O)N—(C$_1$-C$_5$ alkyl)$_2$,
—NHC(O)NH—(C$_2$-C$_5$ alkenyl),
—NHC(O)NH—(C$_3$-C$_5$ cycloalkyl),
—NHC(O)NH—(C$_3$-C$_5$ cycloalkenyl),
—NHC(O)NH—(C$_1$-C$_5$ hydroxyalkyl),
—NHC(O)NH—(C$_1$-C$_5$ fluoroalkyl),
—NHC(O)NH-phenyl,
—NHC(O)NH—(C$_1$-C$_5$ alkyl)-NH$_2$,
—NHC(O)NH—(C$_1$-C$_5$ alkyl)-NH—(C$_1$-C$_5$ alkyl),
—NHC(O)NH—(C$_1$-C$_5$ alkyl)-N—(C$_1$-C$_5$ alkyl)$_2$,
—NHC(O)NH—(C$_1$-C$_5$ alkyl)-O—(C$_1$-C$_5$ alkyl),
—NHC(O)NH—(C$_1$-C$_5$ alkyl)-NH$_2$,
—NHC(O)NH—(C$_1$-C$_5$ alkyl)-NH—(C$_1$-C$_5$ alkyl),
—NHC(O)NH—(C$_1$-C$_5$ alkyl)-N—(C$_1$-C$_5$ alkyl)$_2$,
—NHC(O)NH—(C$_1$-C$_5$ alkyl)-C(O)—NH$_2$,
—NHC(O)NH—(C$_1$-C$_5$ alkyl)-C(O)—NH—(C$_1$-C$_5$ alkyl),
—NHC(O)NH—(C$_1$-C$_5$ alkyl)-C(O)—N—(C$_1$-C$_5$ alkyl)$_2$,
—NHC(O)NH—(C$_1$-C$_5$ alkyl)-C(O)—(C$_1$-C$_5$ alkyl),
—NHC(O)NH—(C$_1$-C$_5$ alkyl)-NH—SO$_2$—(C$_1$-C$_5$ alkyl),
—NHC(O)NH—(C$_1$-C$_5$ alkyl)-N-pyrrolidin-2-one,
—NHC(O)NH—(C$_1$-C$_5$ alkyl)-N-pyrrolidine,
—NHC(O)NH—(C$_1$-C$_5$ alkyl)-(1-methylpyrrolidin-2-one-3-yl),
—NHC(O)NH—(C$_1$-C$_5$ alkyl)-C(O)—OH,
—NHC(O)NH—(C$_1$-C$_5$ alkyl)-C(O)—O—(C$_1$-C$_5$ alkyl),
—NHC(O)NH—(C$_1$-C$_5$ alkyl)-5-tetrazolyl, —NHC(O)NH—(C$_1$-C$_5$ alkyl)-SO$_2$—(C$_1$-C$_5$ alkyl),
—NHC(O)NH—(C$_1$-C$_5$ alkyl)-SO$_2$—NH$_2$,
—NHC(O)NH—(C$_1$-C$_5$ alkyl)-SO$_2$—NH—(C$_1$-C$_5$ alkyl),
—NHC(O)NH—(C$_1$-C$_5$ alkyl)-SO$_2$—N—(C$_1$-C$_5$ alkyl)$_2$,
—NHC(O)NH—(C$_1$-C$_5$ alkyl)-P(O)—O—(C$_1$-C$_5$ alkyl)$_2$,
—NH$_2$,
—NH—(C$_1$-C$_5$ alkyl),
—NH—CH$_2$—C(O)OH,
—N—(C$_1$-C$_5$ alkyl)$_2$,
—NH—C(O)—NH$_2$,
—NH—C(O)—NH—(C$_1$-C$_5$ alkyl),
—NH—C(O)—N—(C$_1$-C$_5$ alkyl)$_2$,
—NH—C(O)—(C$_1$-C$_5$ alkyl),
—NH—SO$_2$—(C$_1$-C$_5$ alkyl),
—NH—S(O)—(C$_1$-C$_5$ alkyl),
—N(CH$_3$)(OCH$_3$),
—N(OH)(CH$_3$),
—N-pyrrolidin-2-one,
—N-pyrrolidine,
-(1-methylpyrrolidin-2-one-3-yl),

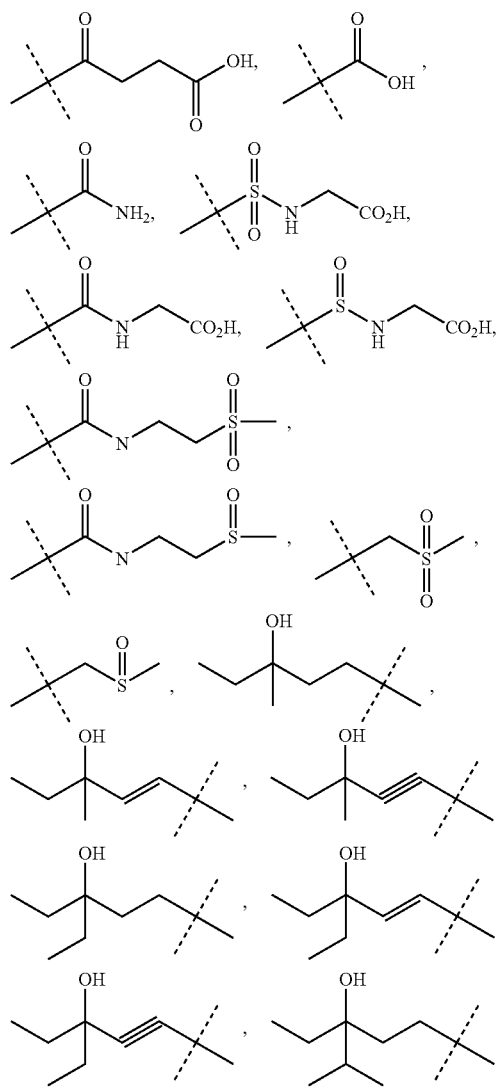

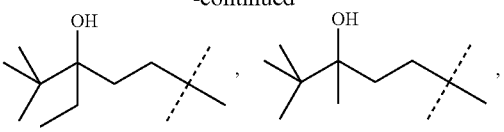

1-hydroxycyclopentenyl,
1-hydroxycyclohexenyl,
1-hydroxycycloheptenyl,
1-hydroxycyclooctenyl,
1-hydroxycyclopropyl,
1-hydroxycyclobutyl,
1-hydroxycyclopentyl,
1-hydroxycyclohexyl,
1-hydroxycycloheptyl,
1-hydroxycyclooctyl,
-5-tetrazolyl,
-carboxyl,
—OH,
—I,
—Br
—Cl
—F,
—CHO,
—NO$_2$,
—CN,
sulfonamide,
sulfinamide,
urethane-type radical, and
(Acidic Group);

provided that the combined groups of formula I represented by

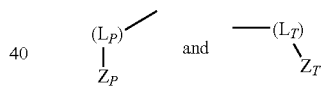

may both be lipophilic, or either one may be lipophilic and the other one polar; but both combined groups may not be polar.

Preferred compounds of the invention are represented by formula (II) or a pharmaceutically acceptable salt or prodrug derivative thereof:

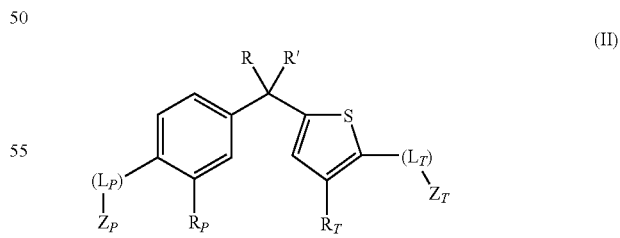

(II)

wherein;

R and R' are independently methyl, ethyl, propyl, 1-methylethyl, 1-methylpropyl, 2-methylpropyl, or 1,1-dimethylethyl;

R$_P$ and RT are independently selected from the group consisting of hydrogen, fluoro, —CF$_3$, —CH$_2$F, —CHF$_2$, —CH$_2$Cl, methoxy, ethoxy, vinyl, methyl, ethyl, propyl, cyclopropyl, 1-methylethyl, butyl, 1-methylpropyl, 2-methylpropyl, or 1,1-dimethylethyl;

$L_T$ and $L_P$ are independently selected from one the following divalent linking group;

a bond, —O—, —S(O)—, —S—, —SO$_2$—, —CH$_2$—, —NH—, or —C(=O)—;

$Z_P$ is selected from

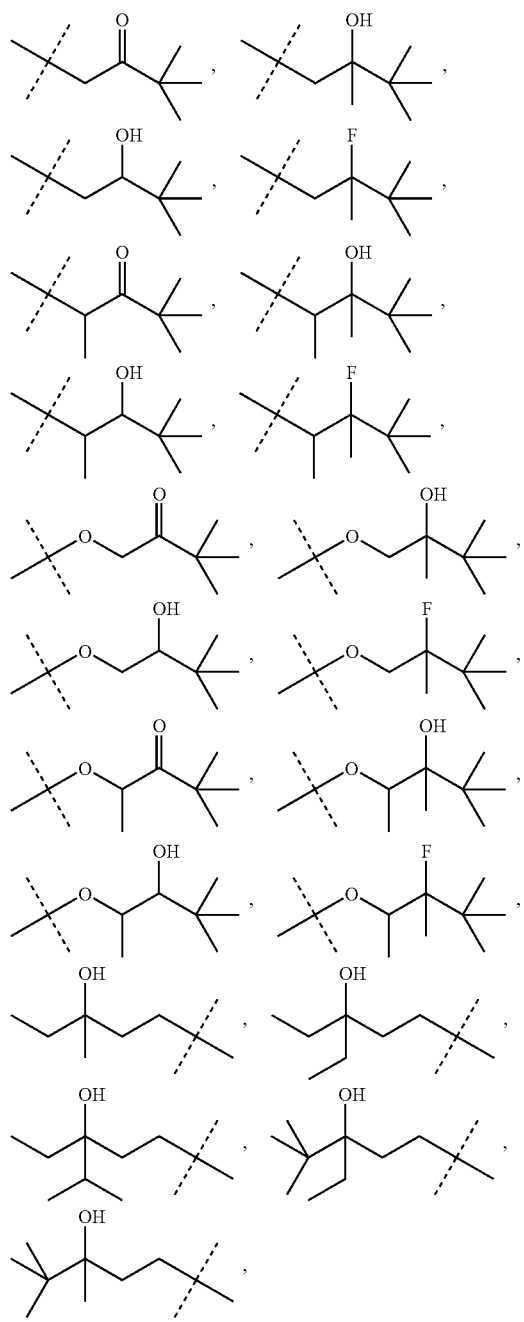

1-hydroxycyclopentenyl,
1-hydroxycyclohexenyl,
1-hydroxycycloheptenyl,
1-hydroxycyclooctenyl,
1-hydroxycyclopropyl,
1-hydroxycyclobutyl,
1-hydroxycyclopentyl,
1-hydroxycyclohexyl,
1-hydroxycycloheptyl,
and
1-hydroxycyclooctyl.

$Z_T$ is a group represented by one of the structural formulae:

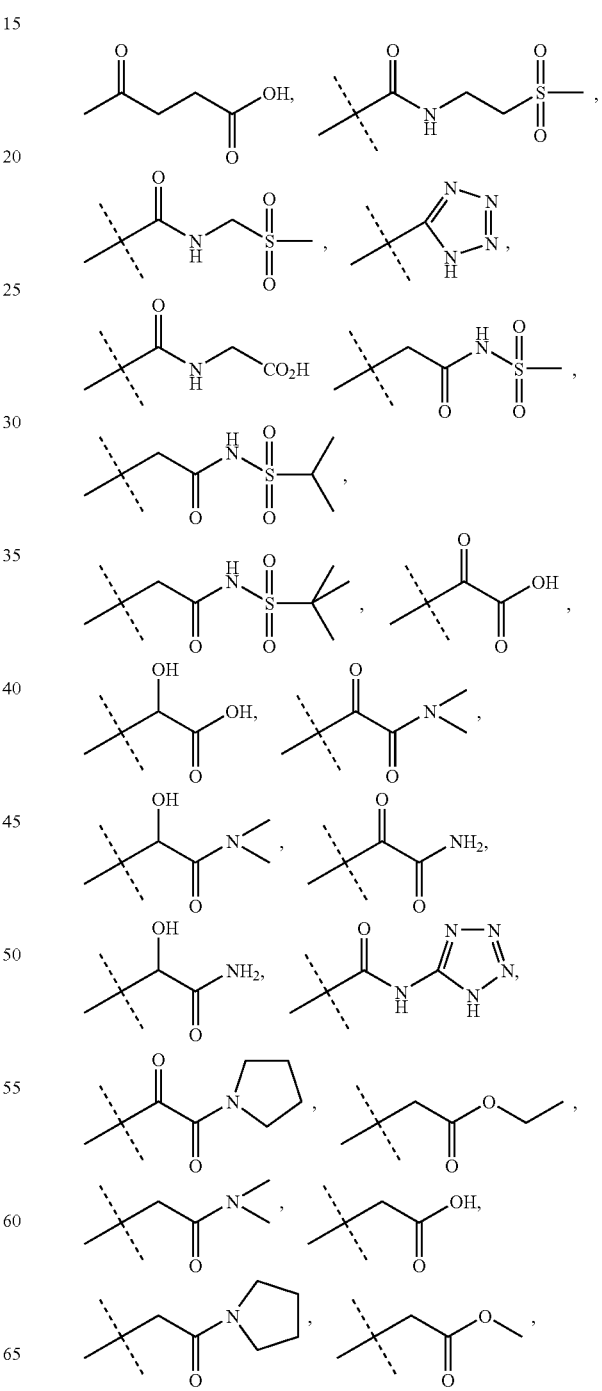

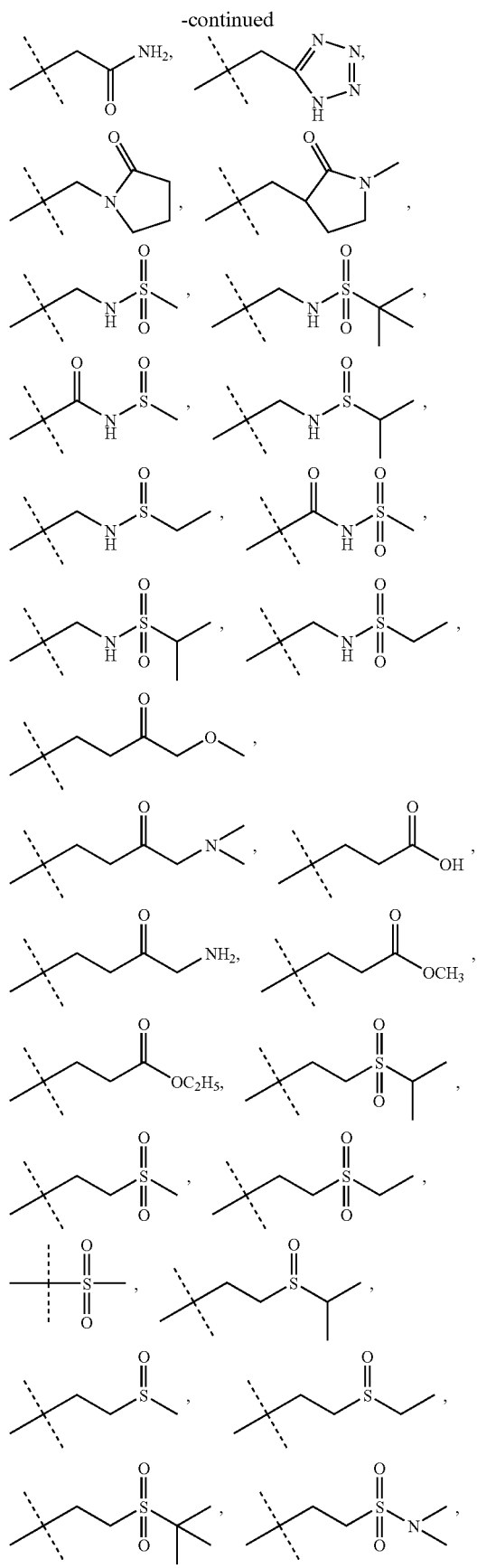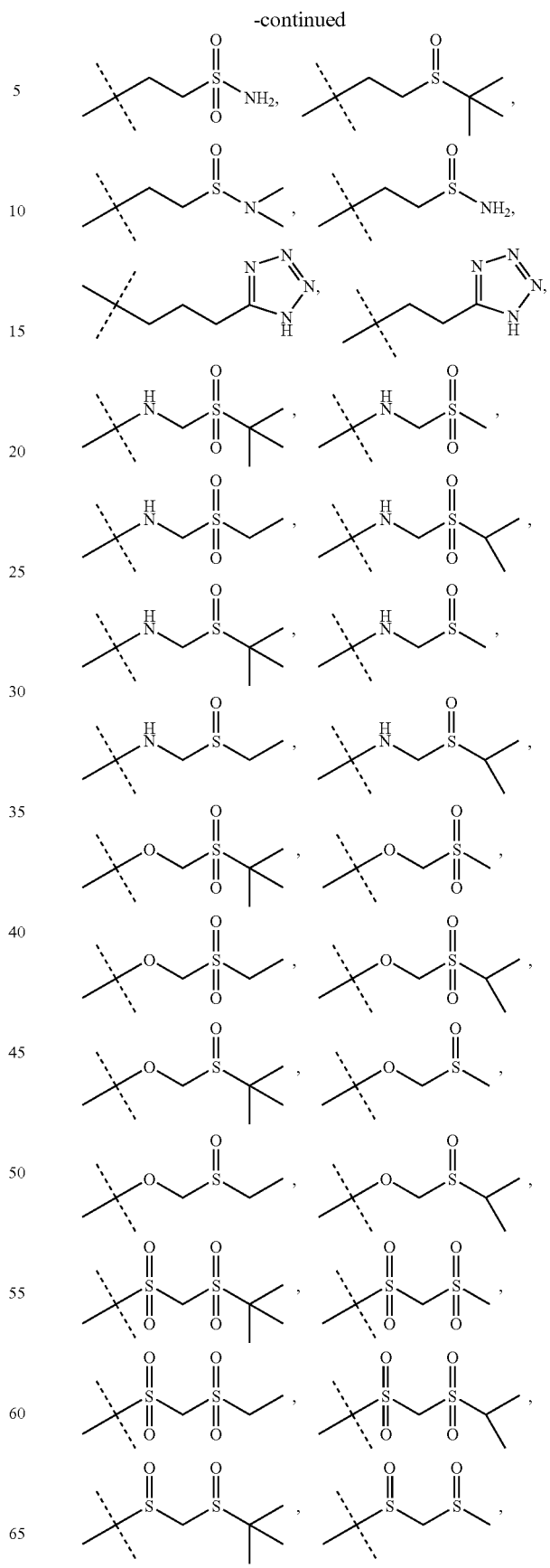

-continued
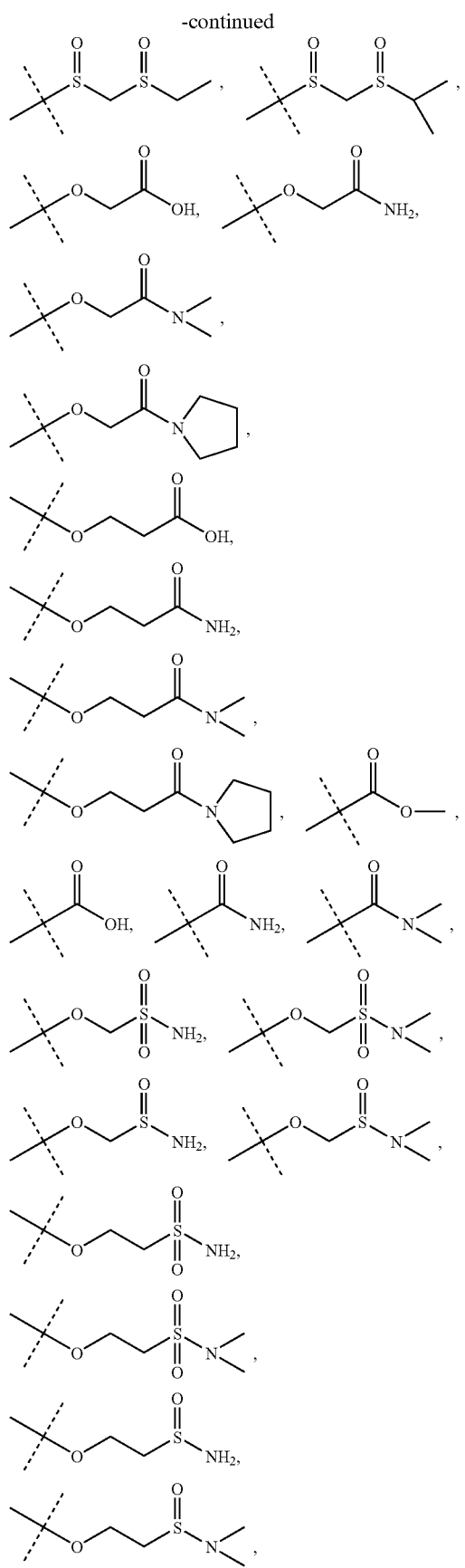
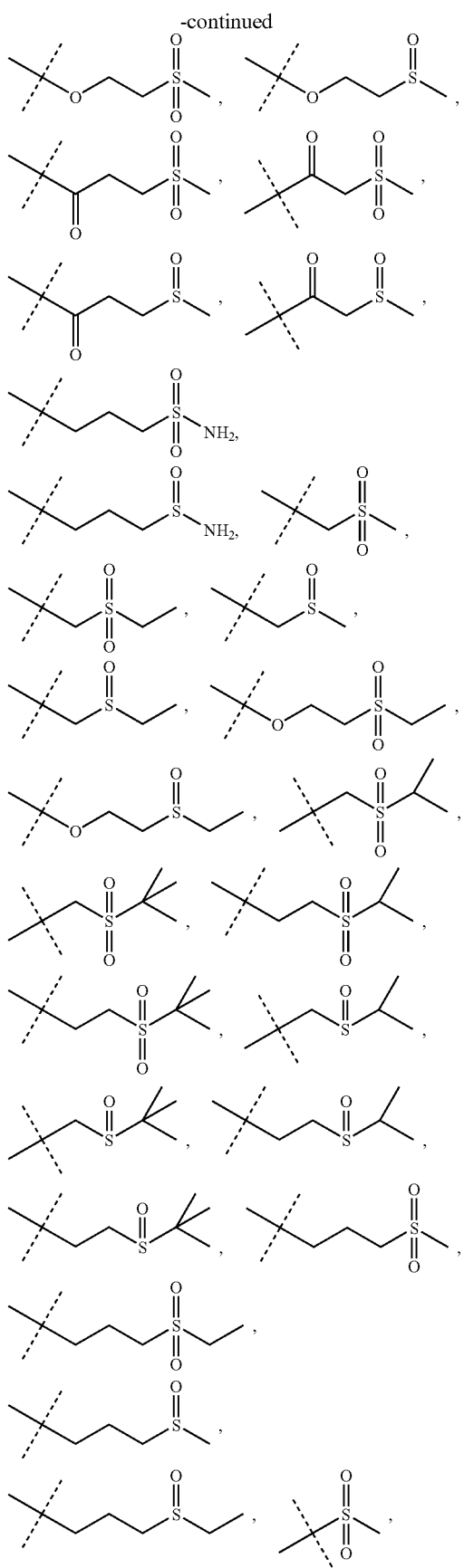

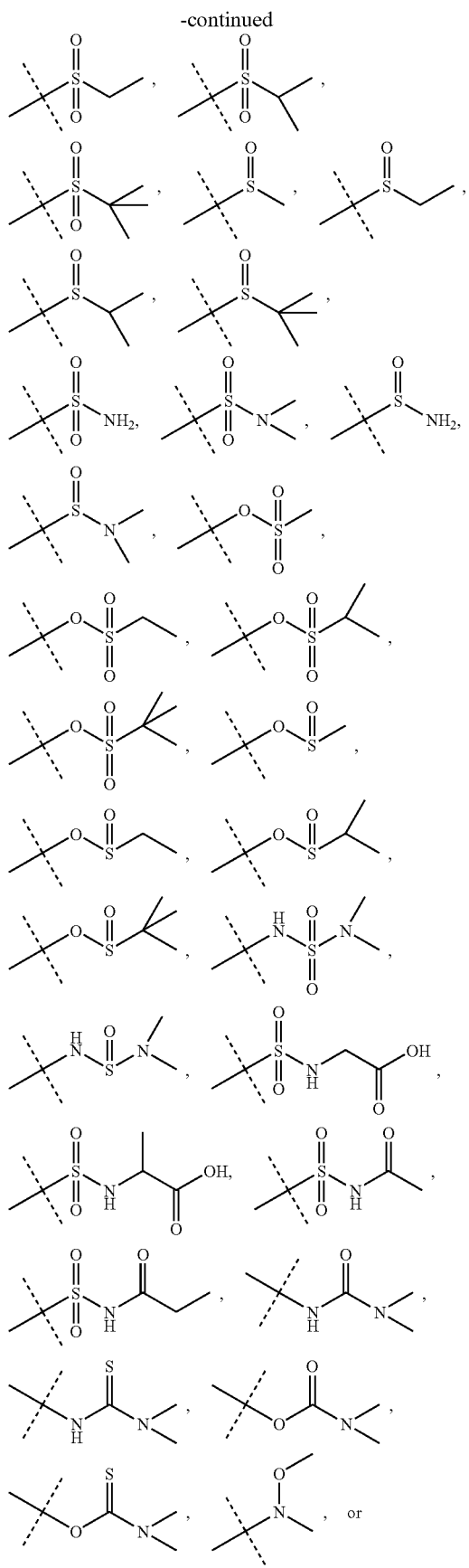

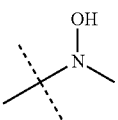

provided that the combined groups of formula I represented by

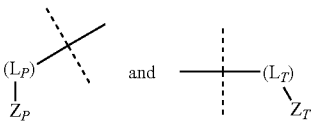

may both be lipophilic, or either one may be lipophilic and the other one polar; but both groups may not be polar.

Preferred compounds of the invention are also those represented by the formula III or a pharmaceutically acceptable salt or prodrug derivative thereof:

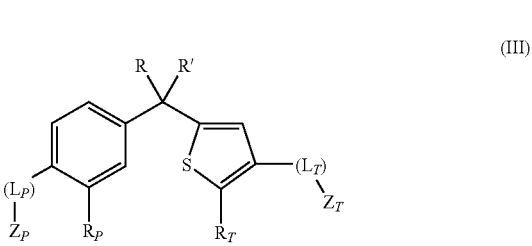

(III)

wherein the substituents R, R', $R_P$, $R_T$, $L_P$, $L_T$, $Z_P$, and $Z_T$ are the same as defined for formula II, supra., provided that the combined groups of formula I represented by

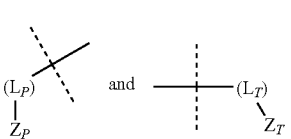

may both be lipophilic, or either one may be lipophilic and the other one polar; but both groups may not be polar.

Preferred compounds of the invention are also those represented by the formula IV or a pharmaceutically acceptable salt or prodrug derivative thereof:

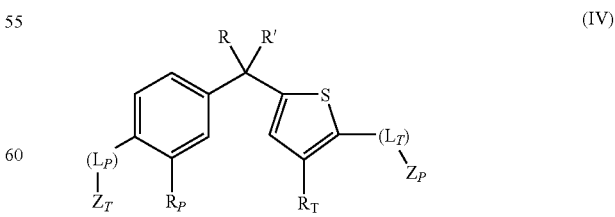

(IV)

wherein the substituents R, R', $R_P$, $R_T$, $L_P$, $L_T$, $Z_P$, and $Z_T$ are the same as defined for formula II, supra., provided that the combined groups of formula I represented by

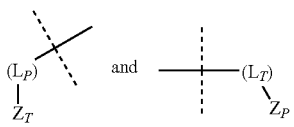

may both be lipophilic, or either one may be lipophilic and the other one polar; but both groups may not be polar.

Preferred compounds of the invention are also those represented by the formula V or a pharmaceutically acceptable salt or prodrug derivative thereof:

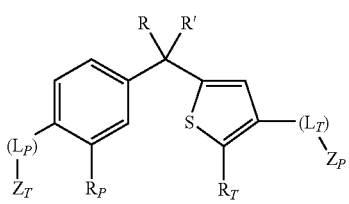

(V)

wherein the substituents R, R', $R_P$, $R_T$, $L_P$, $L_T$, $Z_P$, and $Z_T$ are the same as defined for formula II, supra., provided that the combined groups of formula I represented by

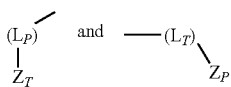

may both be lipophilic, or either one may be lipophilic and the other one polar; but both groups may not be polar.

Preferred Substituents of Compounds Represented by Formulae I, II, III, IV, and V:

Particularly preferred compounds of Formulae I thru V are those wherein the divalent linking group, -($L_T$)- is a bond, —O—, or —CH$_2$—.

Particularly preferred compounds of Formulae I thru V are those wherein both R and R' are ethyl.

Particularly preferred compounds of Formulae I thru V are those wherein both $R_P$ and RT are methyl.

Particularly preferred salt forms of Formulae I thru V are the potassium or sodium salts.

A particularly preferred $C_1$-$C_5$ alkyl group where $Z_P$ and/or $Z_T$ contain such group is 1,1-dimethylethyl.

Preferred compounds in useful in practicing the therapeutic methods of the invention as shown in the structural formulae X1 to X188, as follows:

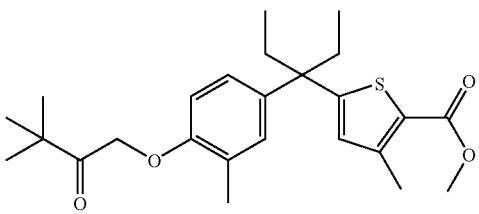

X1)

-continued

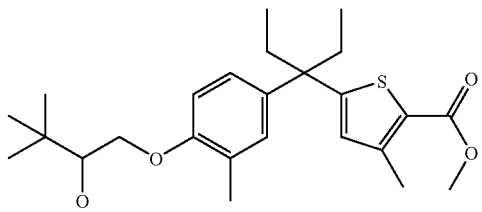

X2)

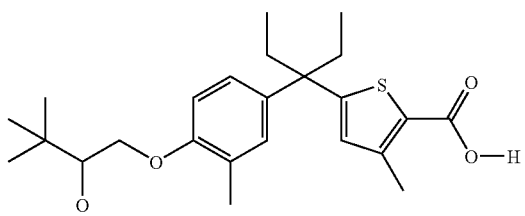

X3)

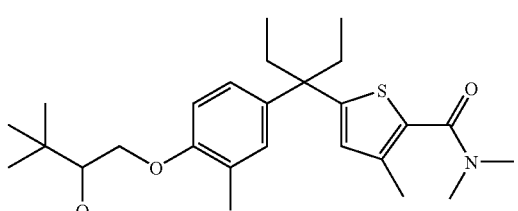

X4)

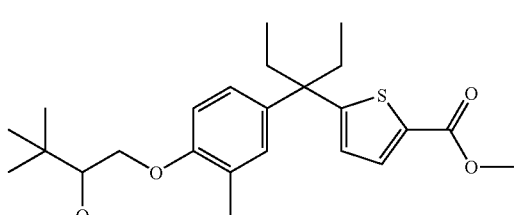

X5)

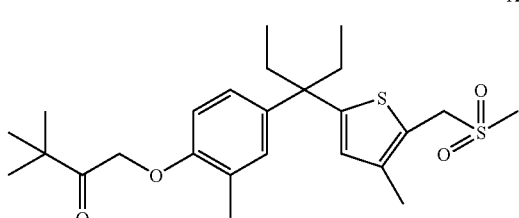

X9)

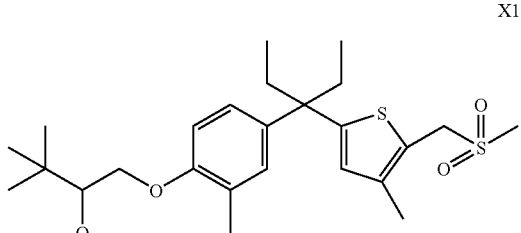

X10)

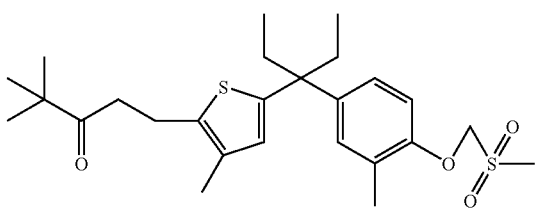

X13)

X14)
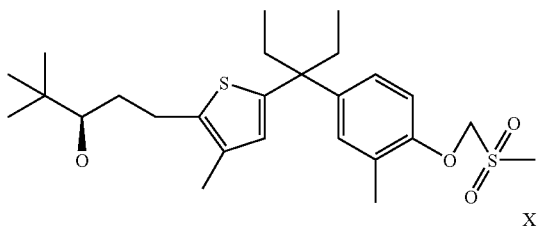
X17)
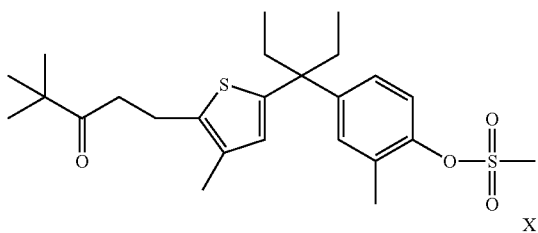
X19)
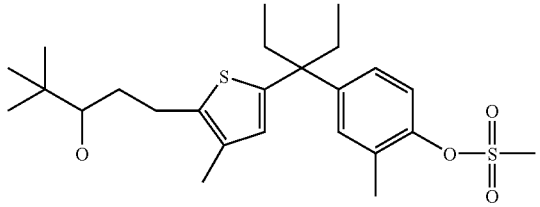
X20)
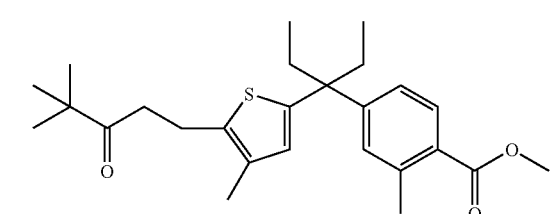
X21)
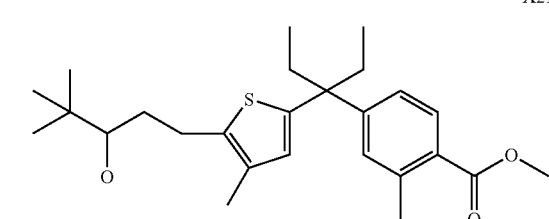
X22)
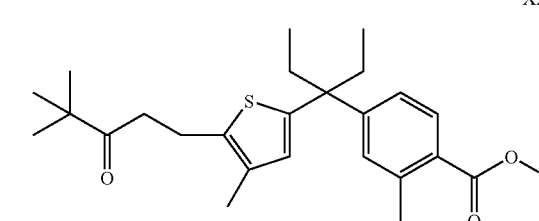
X24)
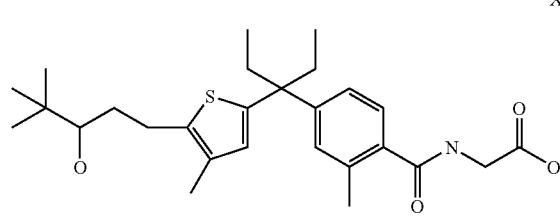
X26)
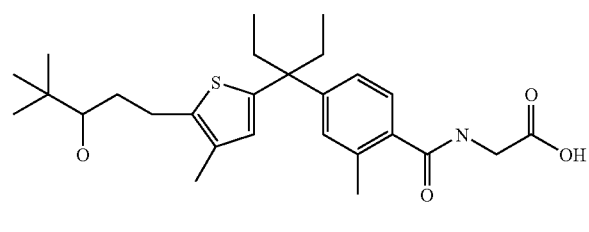
X28)
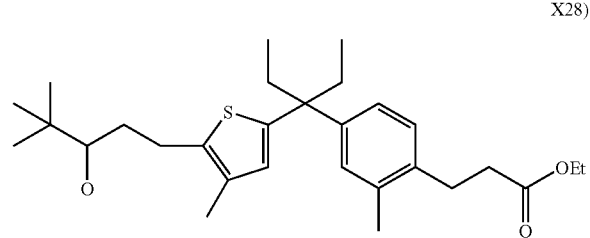
X29)
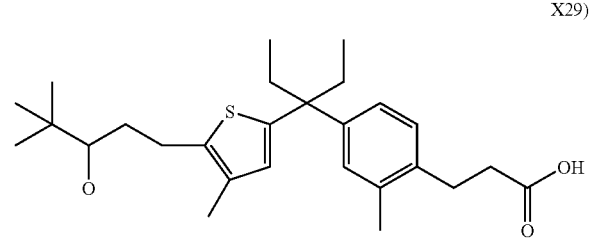
X31)
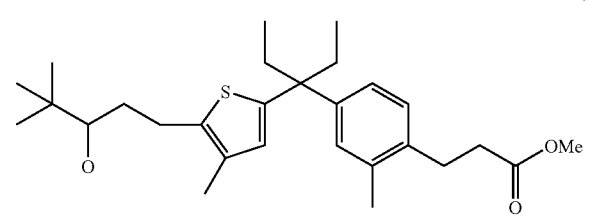
X32)
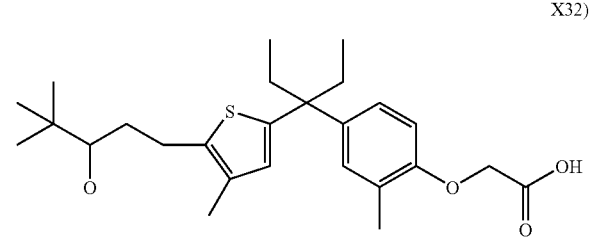
X34)
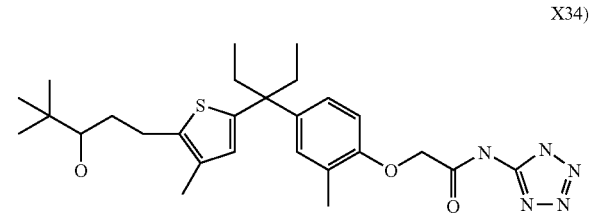

X38)
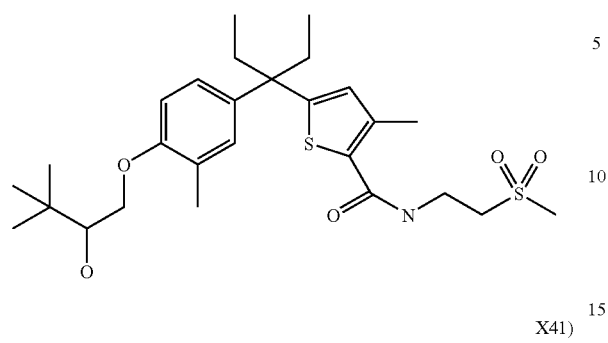
X41)
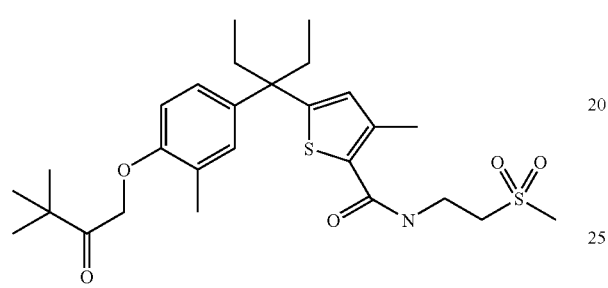
X42)
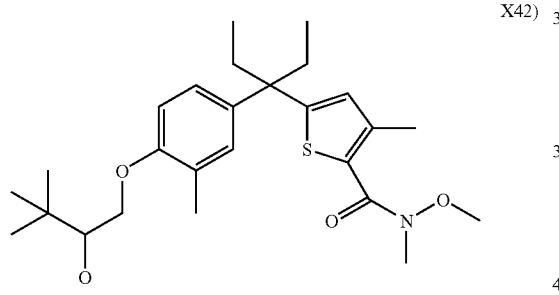
X45)
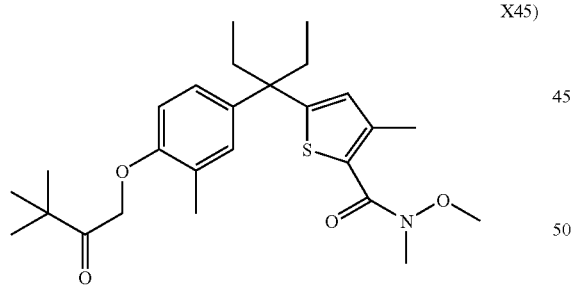
X46)
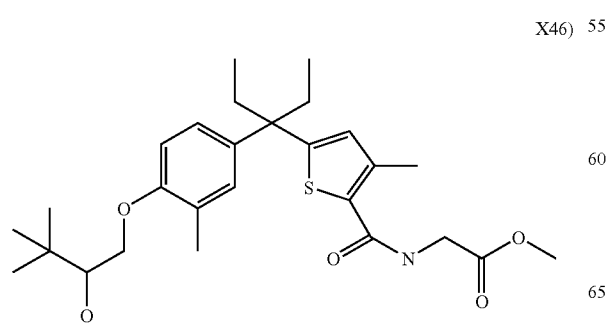
X47)
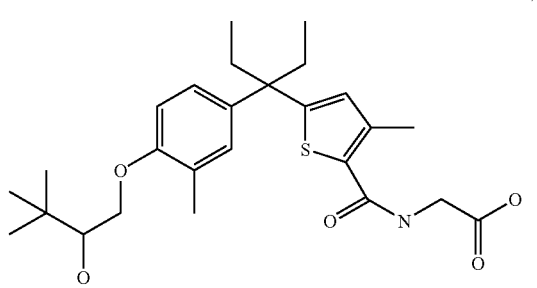
X50)
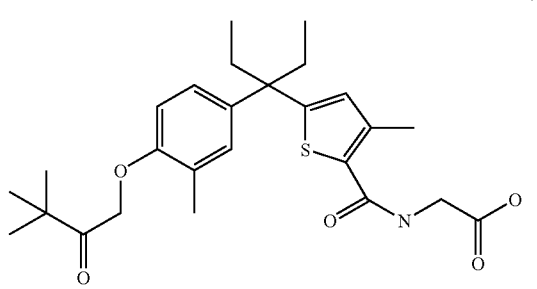
X51)
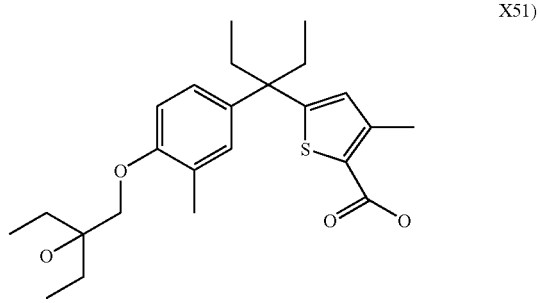
X52)
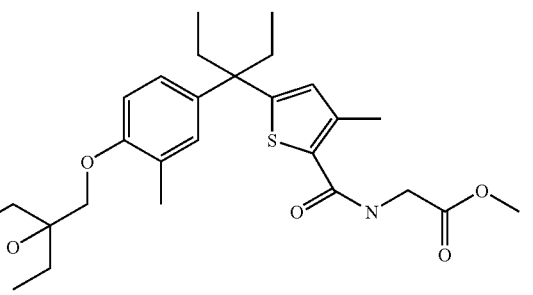
X53)
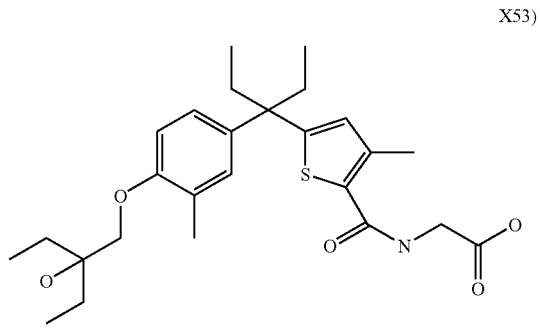

X54) 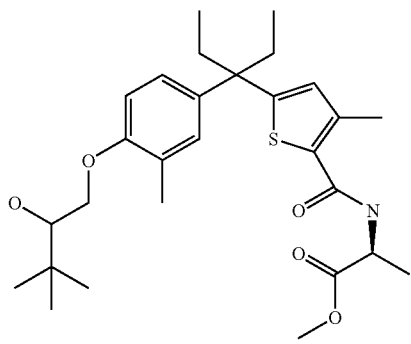
X56) 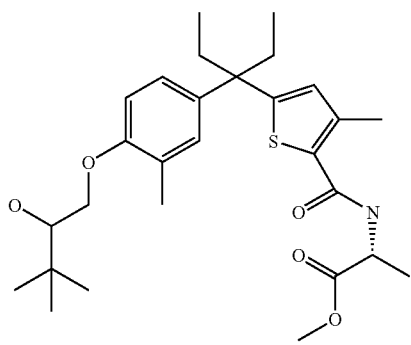
X58) 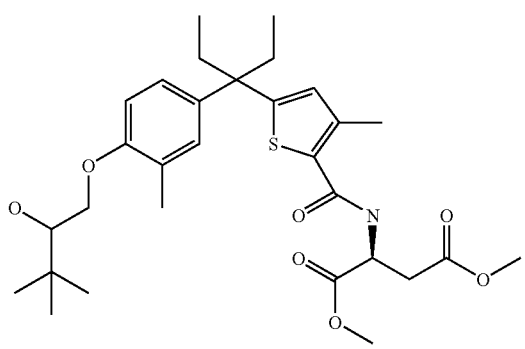
X60) 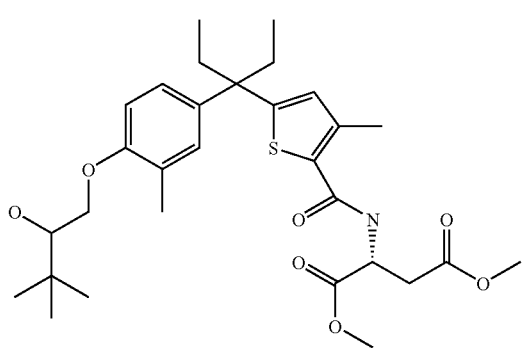
X62) 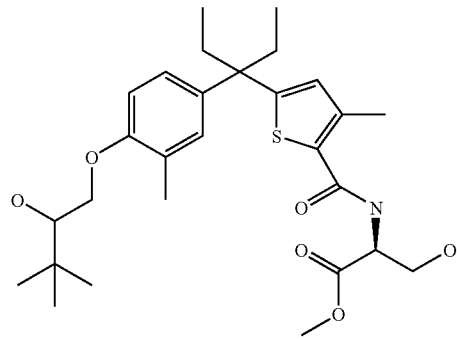
X64) 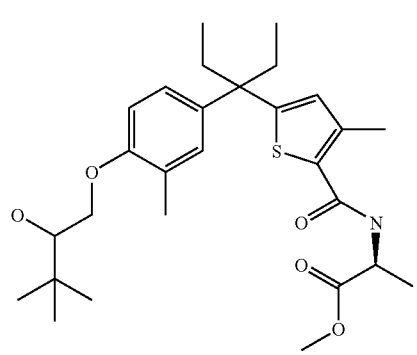
X65) 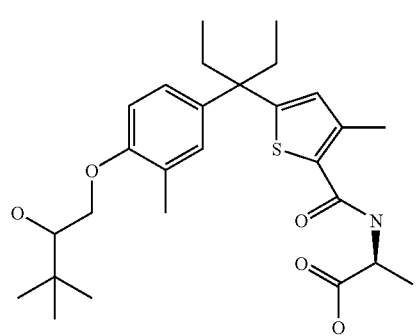
X66) 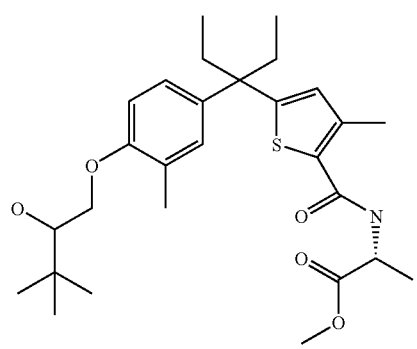

X69)
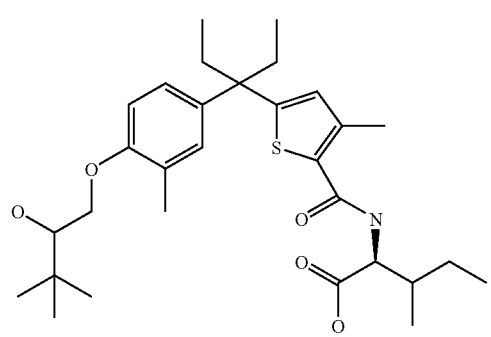
X78)
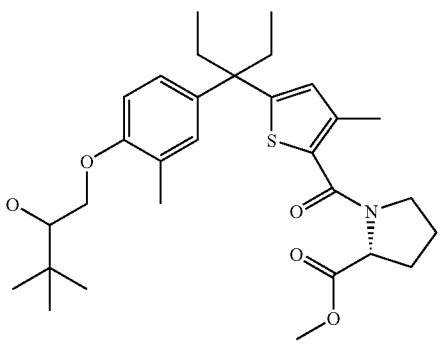
X70)
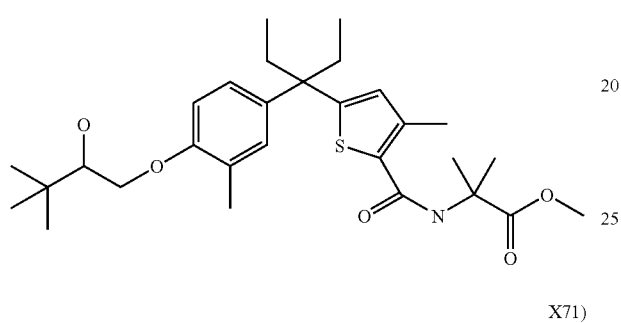
X81)
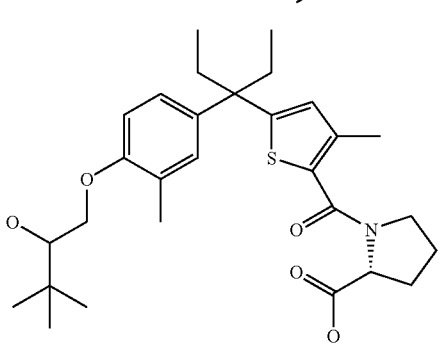
X71)
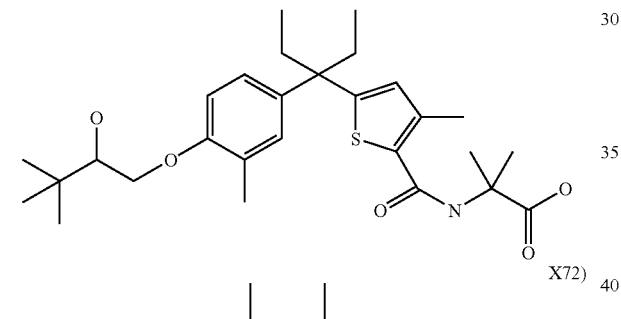
X83)
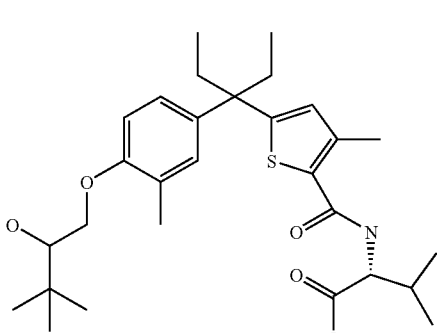
X72)
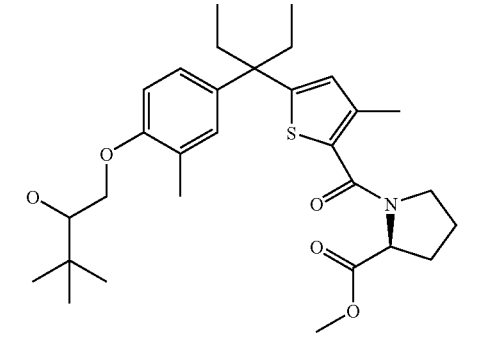
X86)
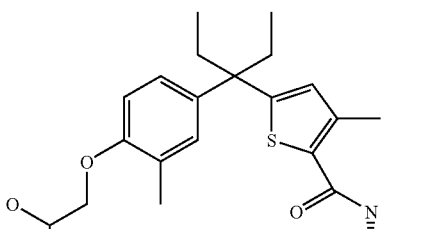
X75)
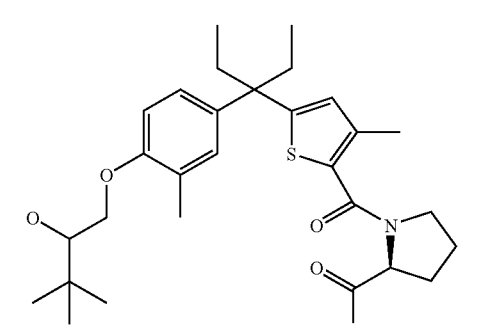
X88)
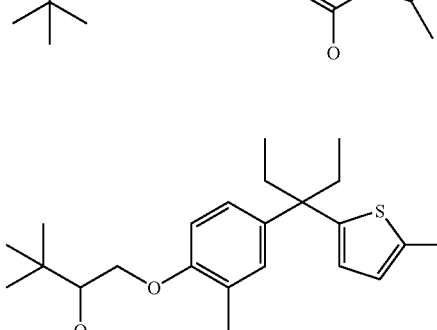

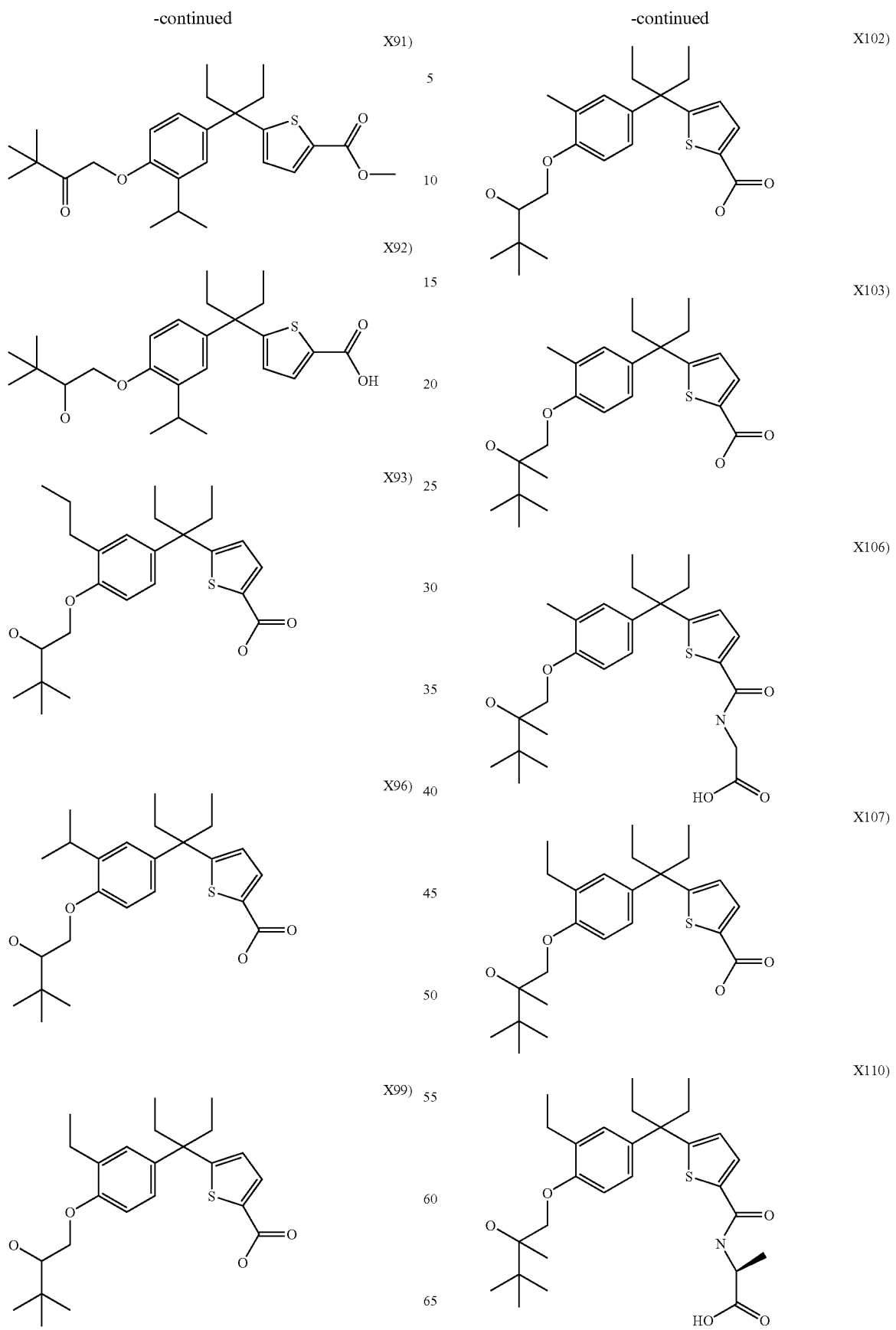

X111)
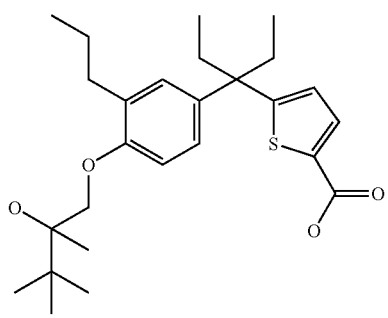
X114)
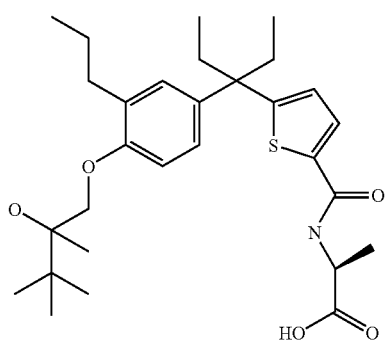
X118)
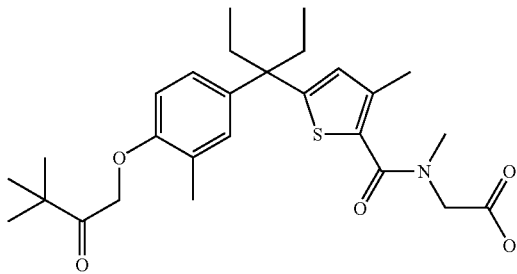
X119)
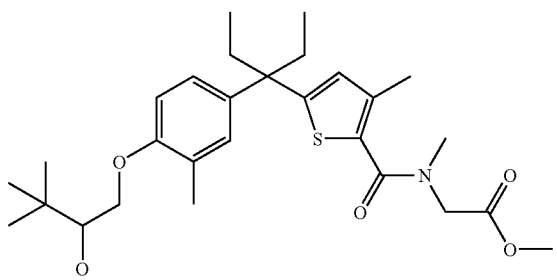
X122)
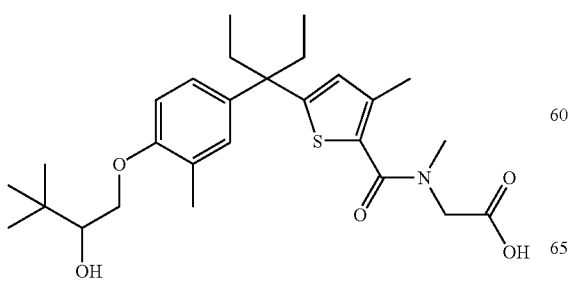
X124)
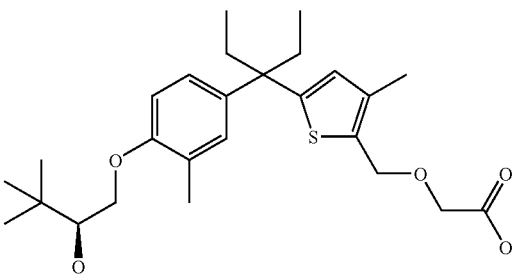
X125)
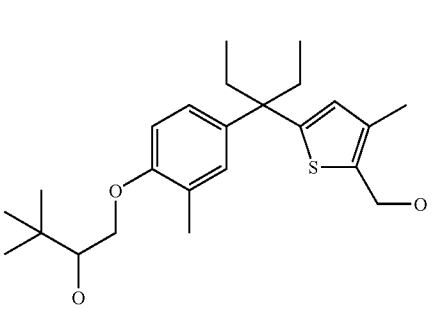
X128)
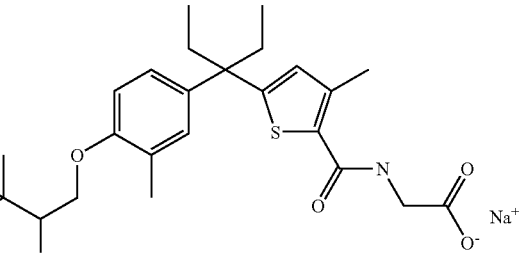
X130)
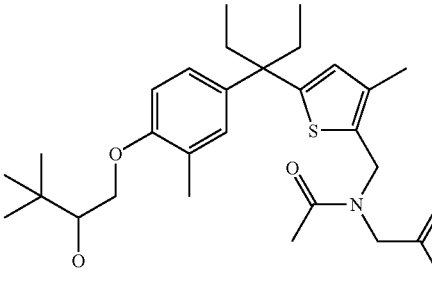
X131)
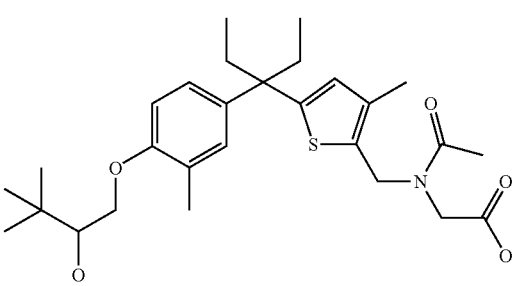

-continued

X134)
X137)
X139)
X140)
X141)
X144)
X145

-continued

X146)
X147)
X148)
X149)
X150)
X152)
X153)

X154)
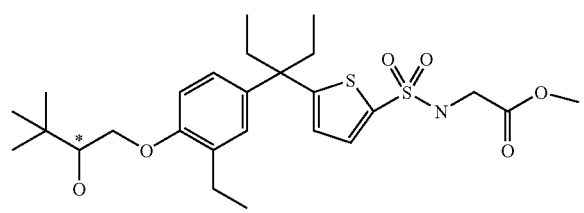
X155)
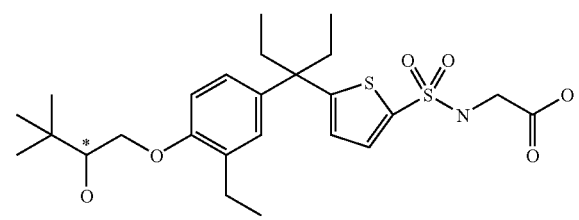
X156)
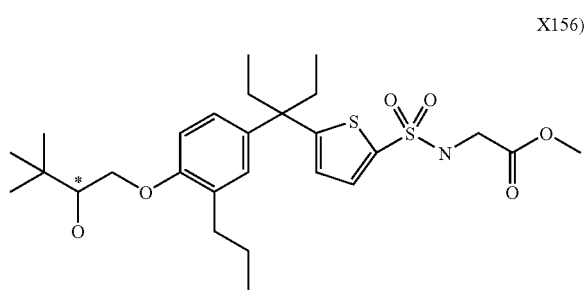
X157)
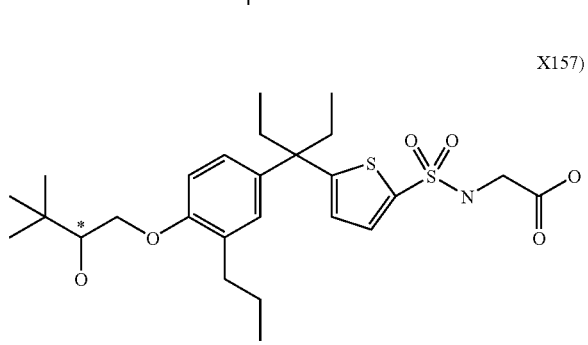
X158)
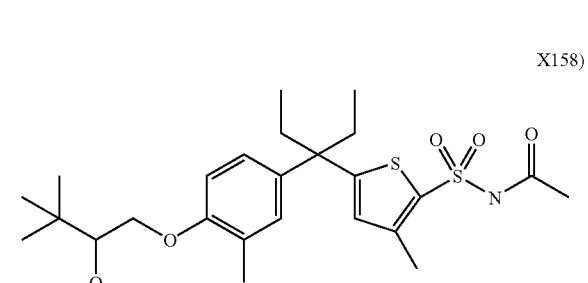
X159)
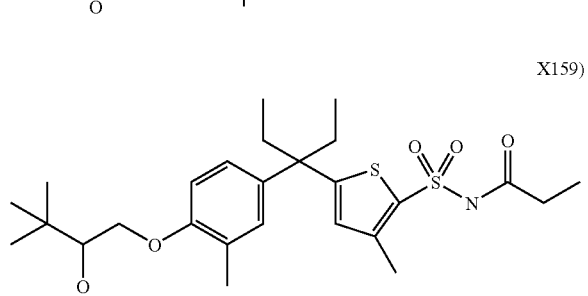
X160)
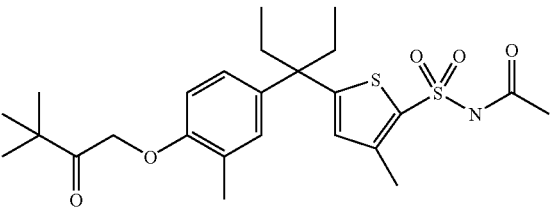
X161)
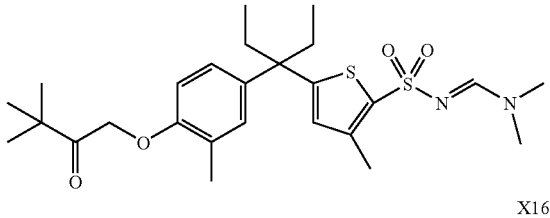
X162)
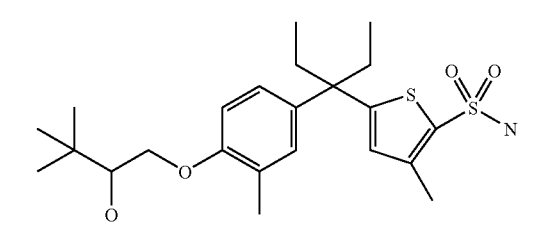
X163)
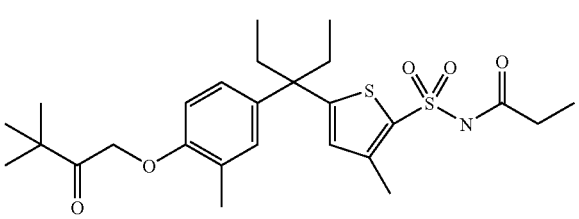
X164)
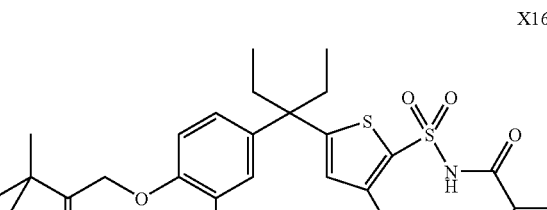
X165)
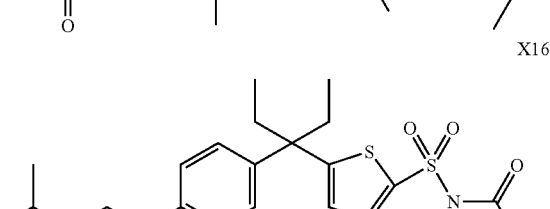
X166)
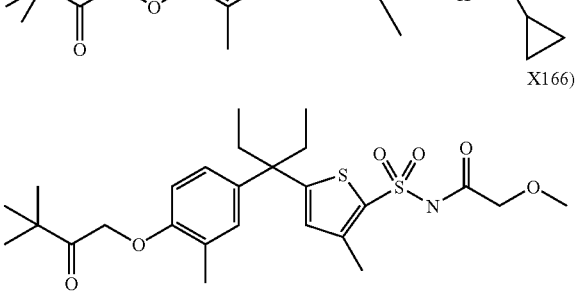

-continued
X169)
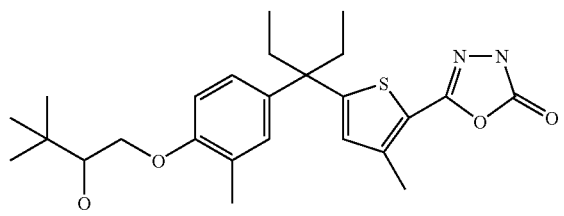
X171)
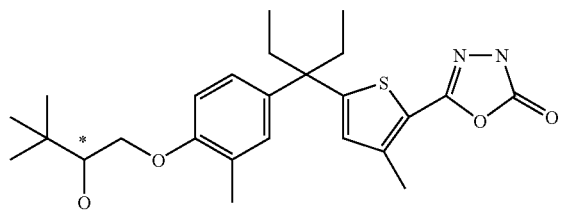
X172)
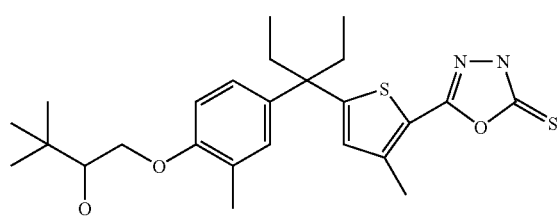
X174)
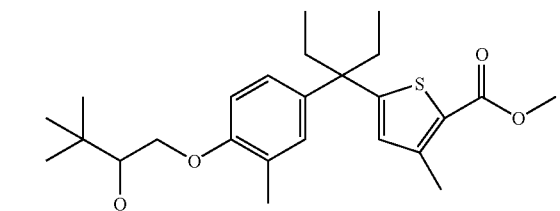
X175)
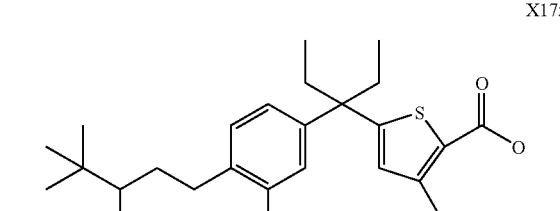
X176)
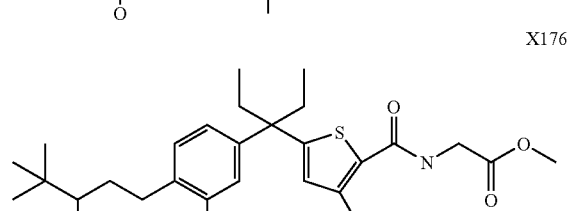
X177)
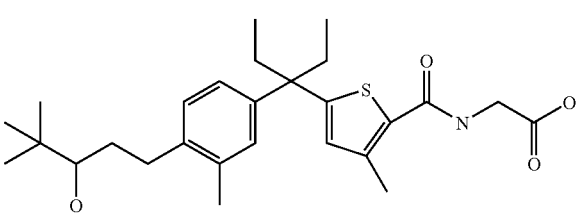
-continued
X178)
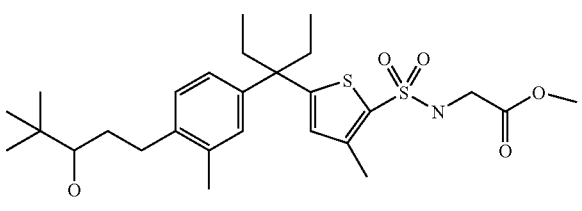
X179)
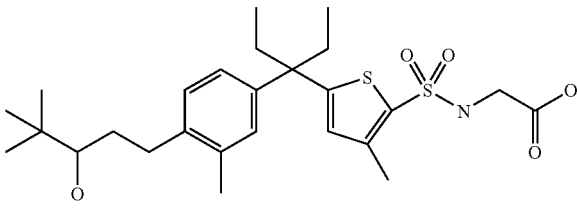
X183)
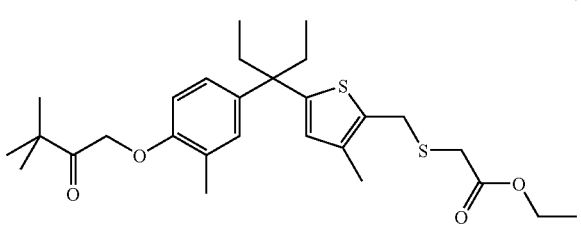
X184)
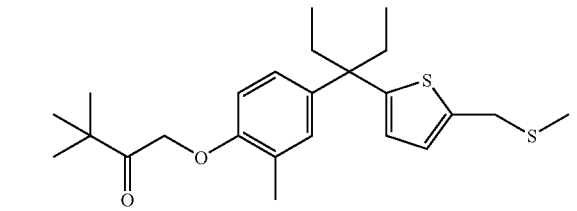
X185)
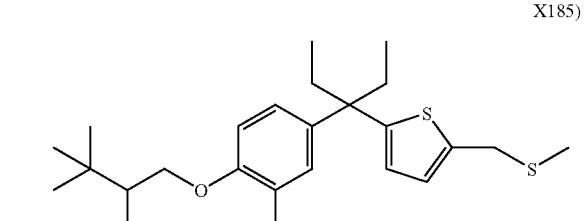
X187)
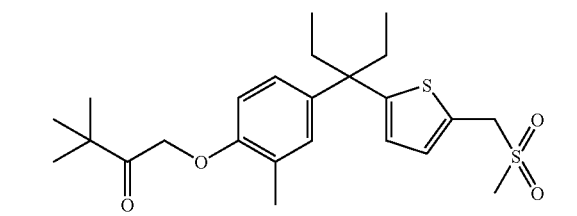

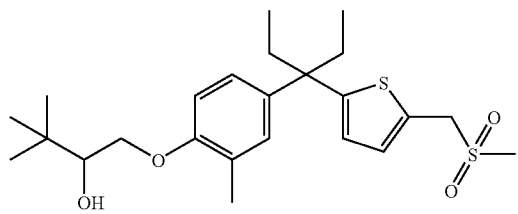

Other specific compounds that are preferred embodiments of this invention and are preferred for for practicing the method of treatment of the invention are set out in the following four Tables. All numbers in the Tables cells reciting chemical species are subscripts, for example, in row, Code 11, Column, $W_T$, the symbol, "CO2H" is to be understood as the conventional chemical nomenclature, —$CO_2H$—. Each row of Tables 1, 2, 3, and 4 is a single compound having an identifying "Code" (e.g., "206", "318A") defining the specific substituents in the structural formula displayed above the Tables, as follows:

TABLE 1

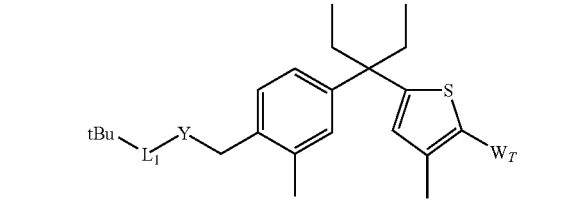

| Code | $L_1$ | Y | $W_T$ |
|---|---|---|---|
| 1 | C(O) | CH2 | —CO2Me |
| 2 | CHOH | CH2 | —CO2Me |
| 3 | C(Me)OH | CH2 | —CO2Me |
| 4 | C(O) | CH(Me) | —CO2Me |
| 5 | CHOH | CH(Me) | —CO2Me |
| 6 | C(Me)OH | CH(Me) | —CO2Me |
| 7 | C(O) | CH2 | —CO2H |
| 8 | CHOH | CH2 | —CO2H |
| 9 | C(Me)OH | CH2 | —CO2H |
| 10 | C(O) | CH(Me) | —CO2H |
| 11 | CHOH | CH(Me) | —CO2H |
| 12 | C(Me)OH | CH(Me) | —CO2H |
| 13 | C(O) | CH2 | —C(O)NH2 |
| 14 | CHOH | CH2 | —C(O)NH2 |
| 15 | C(Me)OH | CH2 | —C(O)NH2 |
| 16 | C(O) | CH(Me) | —C(O)NH2 |
| 17 | CHOH | CH(Me) | —C(O)NH2 |
| 18 | C(Me)OH | CH(Me) | —C(O)NH2 |
| 19 | C(O) | CH2 | —C(O)NMe2 |
| 20 | CHOH | CH2 | —C(O)NMe2 |
| 21 | C(Me)OH | CH2 | —C(O)NMe2 |
| 22 | C(O) | CH(Me) | —C(O)NMe2 |
| 23 | CHOH | CH(Me) | —C(O)NMe2 |
| 24 | C(Me)OH | CH(Me) | —C(O)NMe2 |
| 25 | C(O) | CH2 | 5-tetrazolyl |
| 26 | CHOH | CH2 | 5-tetrazolyl |
| 27 | C(Me)OH | CH2 | 5-tetrazolyl |
| 28 | C(O) | CH(Me) | 5-tetrazolyl |
| 29 | CHOH | CH(Me) | 5-tetrazolyl |
| 30 | C(Me)OH | CH(Me) | 5-tetrazolyl |
| 31 | C(O) | CH2 | —C(O)—NH-5-tetrazolyl |
| 32 | CHOH | CH2 | —C(O)—NH-5-tetrazolyl |
| 33 | C(Me)OH | CH2 | —C(O)—NH-5-tetrazolyl |
| 34 | C(O) | CH(Me) | —C(O)—NH-5-tetrazolyl |
| 35 | CHOH | CH(Me) | —C(O)—NH-5-tetrazolyl |
| 36 | C(Me)OH | CH(Me) | —C(O)—NH-5-tetrazolyl |
| 37 | C(O) | CH2 | —C(O)NHCH2SO2Me |
| 38 | CHOH | CH2 | —C(O)NHCH2SO2Me |
| 39 | C(Me)OH | CH2 | —C(O)NHCH2SO2Me |
| 40 | C(O) | CH(Me) | —C(O)NHCH2SO2Me |
| 41 | CHOH | CH(Me) | —C(O)NHCH2SO2Me |
| 42 | C(Me)OH | CH(Me) | —C(O)NHCH2SO2Me |
| 43 | C(O) | CH2 | —C(O)NHCH2CH2SO2Me |
| 44 | CHOH | CH2 | —C(O)NHCH2CH2SO2Me |
| 45 | C(Me)OH | CH2 | —C(O)NHCH2CH2SO2Me |
| 46 | C(O) | CH(Me) | —C(O)NHCH2CH2SO2Me |
| 47 | CHOH | CH(Me) | —C(O)NHCH2CH2SO2Me |
| 48 | C(Me)OH | CH(Me) | —C(O)NHCH2CH2SO2Me |
| 49 | C(O) | CH2 | —C(O)NHSO2Me |
| 50 | CHOH | CH2 | —C(O)NHSO2Me |
| 51 | C(Me)OH | CH2 | —C(O)NHSO2Me |
| 52 | C(O) | CH(Me) | —C(O)NHSO2Me |
| 53 | CHOH | CH(Me) | —C(O)NHSO2Me |
| 54 | C(Me)OH | CH(Me) | —C(O)NHSO2Me |
| 55 | C(O) | CH2 | —CH2—C(O)NHSO2Et |
| 56 | CHOH | CH2 | —CH2—C(O)NHSO2Et |
| 57 | C(Me)OH | CH2 | —CH2—C(O)NHSO2Et |
| 58 | C(O) | CH(Me) | —CH2—C(O)NHSO2Et |
| 59 | CHOH | CH(Me) | —CH2—C(O)NHSO2Et |
| 60 | C(Me)OH | CH(Me) | —CH2—C(O)NHSO2Et |
| 61 | C(O) | CH2 | —CH2—C(O)NHSO2iPr |
| 62 | CHOH | CH2 | —CH2—C(O)NHSO2iPr |
| 63 | C(Me)OH | CH2 | —CH2—C(O)NHSO2iPr |
| 64 | C(O) | CH(Me) | —CH2—C(O)NHSO2iPr |
| 65 | CHOH | CH(Me) | —CH2—C(O)NHSO2iPr |
| 66 | C(Me)OH | CH(Me) | —CH2—C(O)NHSO2iPr |
| 67 | C(O) | CH2 | —CH2—C(O)NHSO2tBu |
| 68 | CHOH | CH2 | —CH2—C(O)NHSO2tBu |
| 69 | C(Me)OH | CH2 | —CH2—C(O)NHSO2tBu |
| 70 | C(O) | CH(Me) | —CH2—C(O)NHSO2tBu |
| 71 | CHOH | CH(Me) | —CH2—C(O)NHSO2tBu |
| 72 | C(Me)OH | CH(Me) | —CH2—C(O)NHSO2tBu |
| 73 | C(O) | CH2 | —CH2NHSO2Me |
| 74 | CHOH | CH2 | —CH2NHSO2Me |
| 75 | C(Me)OH | CH2 | —CH2NHSO2Me |
| 76 | C(O) | CH(Me) | —CH2NHSO2Me |
| 77 | CHOH | CH(Me) | —CH2NHSO2Me |
| 78 | C(Me)OH | CH(Me) | —CH2NHSO2Me |
| 79 | C(O) | CH2 | —CH2NHSO2Et |
| 80 | CHOH | CH2 | —CH2NHSO2Et |
| 81 | C(Me)OH | CH2 | —CH2NHSO2Et |
| 82 | C(O) | CH(Me) | —CH2NHSO2Et |
| 83 | CHOH | CH(Me) | —CH2NHSO2Et |
| 84 | C(Me)OH | CH(Me) | —CH2NHSO2Et |
| 85 | C(O) | CH2 | —CH2NHSO2iPr |
| 86 | CHOH | CH2 | —CH2NHSO2iPr |
| 87 | C(Me)OH | CH2 | —CH2NHSO2iPr |
| 88 | C(O) | CH(Me) | —CH2NHSO2iPr |
| 89 | CHOH | CH(Me) | —CH2NHSO2iPr |
| 90 | C(Me)OH | CH(Me) | —CH2NHSO2iPr |
| 91 | C(O) | CH2 | —CH2NHSO2tBu |
| 92 | CHOH | CH2 | —CH2NHSO2tBu |
| 93 | C(Me)OH | CH2 | —CH2NHSO2tBu |
| 94 | C(O) | CH(Me) | —CH2NHSO2tBu |
| 95 | CHOH | CH(Me) | —CH2NHSO2tBu |
| 96 | C(Me)OH | CH(Me) | —CH2NHSO2tBu |
| 97 | C(O) | CH2 | —CH2—N-pyrrolidin-2-one |
| 98 | CHOH | CH2 | —CH2—N-pyrrolidin-2-one |
| 99 | C(Me)OH | CH2 | —CH2—N-pyrrolidin-2-one |
| 100 | C(O) | CH(Me) | —CH2—N-pyrrolidin-2-one |
| 101 | CHOH | CH(Me) | —CH2—N-pyrrolidin-2-one |
| 102 | C(Me)OH | CH(Me) | —CH2—N-pyrrolidin-2-one |
| 103 | C(O) | CH2 | —CH2-(1-methylpyrrolidin-2-one-3-yl) |

TABLE 1-continued

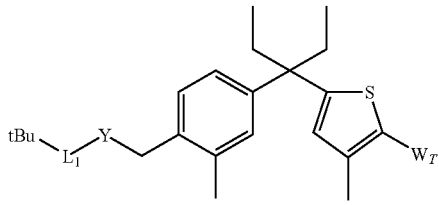

| Code | L₁ | Y | W_T |
|---|---|---|---|
| 104 | CHOH | CH2 | —CH2-(1-methylpyrrolidin-2-one-3-yl) |
| 105 | C(Me)OH | CH2 | —CH2-(1-methylpyrrolidin-2-one-3-yl) |
| 106 | C(O) | CH(Me) | —CH2-(1-methylpyrrolidin-2-one-3-yl) |
| 107 | CHOH | CH(Me) | —CH2-(1-methylpyrrolidin-2-one-3-yl) |
| 108 | C(Me)OH | CH(Me) | —CH2-(1-methylpyrrolidin-2-one-3-yl) |
| 109 | C(O) | CH2 | —CH2CO2Me |
| 110 | CHOH | CH2 | —CH2CO2Me |
| 111 | C(Me)OH | CH2 | —CH2CO2Me |
| 112 | C(O) | CH(Me) | —CH2CO2Me |
| 113 | CHOH | CH(Me) | —CH2CO2Me |
| 114 | C(Me)OH | CH(Me) | —CH2CO2Me |
| 115 | C(O) | CH2 | —CH2CO2H |
| 116 | CHOH | CH2 | —CH2CO2H |
| 117 | C(Me)OH | CH2 | —CH2CO2H |
| 118 | C(O) | CH(Me) | —CH2CO2H |
| 119 | CHOH | CH(Me) | —CH2CO2H |
| 120 | C(Me)OH | CH(Me) | —CH2CO2H |
| 121 | C(O) | CH2 | —CH2C(O)NH2 |
| 122 | CHOH | CH2 | —CH2C(O)NH2 |
| 123 | C(Me)OH | CH2 | —CH2C(O)NH2 |
| 124 | C(O) | CH(Me) | —CH2C(O)NH2 |
| 125 | CHOH | CH(Me) | —CH2C(O)NH2 |
| 126 | C(Me)OH | CH(Me) | —CH2C(O)NH2 |
| 127 | C(O) | CH2 | —CH2C(O)NMe2 |
| 128 | CHOH | CH2 | —CH2C(O)NMe2 |
| 129 | C(Me)OH | CH2 | —CH2C(O)NMe2 |
| 130 | C(O) | CH(Me) | —CH2C(O)NMe2 |
| 131 | CHOH | CH(Me) | —CH2C(O)NMe2 |
| 132 | C(Me)OH | CH(Me) | —CH2C(O)NMe2 |
| 133 | C(O) | CH2 | —CH2C(O)—N-pyrrolidine |
| 134 | CHOH | CH2 | —CH2C(O)—N-pyrrolidine |
| 135 | C(Me)OH | CH2 | —CH2C(O)—N-pyrrolidine |
| 136 | C(O) | CH(Me) | —CH2C(O)—N-pyrrolidine |
| 137 | CHOH | CH(Me) | —CH2C(O)—N-pyrrolidine |
| 138 | C(Me)OH | CH(Me) | —CH2C(O)—N-pyrrolidine |
| 139 | C(O) | CH2 | —CH2-5-tetrazolyl |
| 140 | CHOH | CH2 | —CH2-5-tetrazolyl |
| 141 | C(Me)OH | CH2 | —CH2-5-tetrazolyl |
| 142 | C(O) | CH(Me) | —CH2-5-tetrazolyl |
| 143 | CHOH | CH(Me) | —CH2-5-tetrazolyl |
| 144 | C(Me)OH | CH(Me) | —CH2-5-tetrazolyl |
| 145 | C(O) | CH2 | —C(O)C(O)OH |
| 146 | CHOH | CH2 | —C(O)C(O)OH |
| 147 | C(Me)OH | CH2 | —C(O)C(O)OH |
| 148 | C(O) | CH(Me) | —C(O)C(O)OH |
| 149 | CHOH | CH(Me) | —C(O)C(O)OH |
| 150 | C(Me)OH | CH(Me) | —C(O)C(O)OH |
| 151 | C(O) | CH2 | —CH(OH)C(O)OH |
| 152 | CHOH | CH2 | —CH(OH)C(O)OH |
| 153 | C(Me)OH | CH2 | —CH(OH)C(O)OH |
| 154 | C(O) | CH(Me) | —CH(OH)C(O)OH |
| 155 | CHOH | CH(Me) | —CH(OH)C(O)OH |
| 156 | C(Me)OH | CH(Me) | —CH(OH)C(O)OH |
| 157 | C(O) | CH2 | —C(O)C(O)NH2 |
| 158 | CHOH | CH2 | —C(O)C(O)NH2 |
| 159 | C(Me)OH | CH2 | —C(O)C(O)NH2 |
| 160 | C(O) | CH(Me) | —C(O)C(O)NH2 |
| 161 | CHOH | CH(Me) | —C(O)C(O)NH2 |
| 162 | C(Me)OH | CH(Me) | —C(O)C(O)NH2 |
| 163 | C(O) | CH2 | —CH(OH)C(O)NH2 |
| 164 | CHOH | CH2 | —CH(OH)C(O)NH2 |
| 165 | C(Me)OH | CH2 | —CH(OH)C(O)NH2 |
| 166 | C(O) | CH(Me) | —CH(OH)C(O)NH2 |
| 167 | CHOH | CH(Me) | —CH(OH)C(O)NH2 |
| 168 | C(Me)OH | CH(Me) | —CH(OH)C(O)NH2 |
| 169 | C(O) | CH2 | —C(O)C(O)NMe2 |

TABLE 1-continued

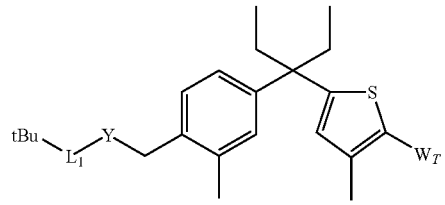

| Code | L₁ | Y | W_T |
|---|---|---|---|
| 170 | CHOH | CH2 | —C(O)C(O)NMe2 |
| 171 | C(Me)OH | CH2 | —C(O)C(O)NMe2 |
| 172 | C(O) | CH(Me) | —C(O)C(O)NMe2 |
| 173 | CHOH | CH(Me) | —C(O)C(O)NMe2 |
| 174 | C(Me)OH | CH(Me) | —C(O)C(O)NMe2 |
| 175 | C(O) | CH2 | —CH(OH)C(O)NMe2 |
| 176 | CHOH | CH2 | —CH(OH)C(O)NMe2 |
| 177 | C(Me)OH | CH2 | —CH(OH)C(O)NMe2 |
| 178 | C(O) | CH(Me) | —CH(OH)C(O)NMe2 |
| 179 | CHOH | CH(Me) | —CH(OH)C(O)NMe2 |
| 180 | C(Me)OH | CH(Me) | —CH(OH)C(O)NMe2 |
| 181 | C(O) | CH2 | —CH2CH2CO2H |
| 182 | CHOH | CH2 | —CH2CH2CO2H |
| 183 | C(Me)OH | CH2 | —CH2CH2CO2H |
| 184 | C(O) | CH(Me) | —CH2CH2CO2H |
| 185 | CHOH | CH(Me) | —CH2CH2CO2H |
| 186 | C(Me)OH | CH(Me) | —CH2CH2CO2H |
| 187 | C(O) | CH2 | —CH2CH2C(O)NH2 |
| 188 | CHOH | CH2 | —CH2CH2C(O)NH2 |
| 189 | C(Me)OH | CH2 | —CH2CH2C(O)NH2 |
| 190 | C(O) | CH(Me) | —CH2CH2C(O)NH2 |
| 191 | CHOH | CH(Me) | —CH2CH2C(O)NH2 |
| 192 | C(Me)OH | CH(Me) | —CH2CH2C(O)NH2 |
| 193 | C(O) | CH2 | —CH2CH2C(O)NMe2 |
| 194 | CHOH | CH2 | —CH2CH2C(O)NMe2 |
| 195 | C(Me)OH | CH2 | —CH2CH2C(O)NMe2 |
| 196 | C(O) | CH(Me) | —CH2CH2C(O)NMe2 |
| 197 | CHOH | CH(Me) | —CH2CH2C(O)NMe2 |
| 198 | C(Me)OH | CH(Me) | —CH2CH2C(O)NMe2 |
| 199 | C(O) | CH2 | —CH2CH2-5-tetrazolyl |
| 200 | CHOH | CH2 | —CH2CH2-5-tetrazolyl |
| 201 | C(Me)OH | CH2 | —CH2CH2-5-tetrazolyl |
| 202 | C(O) | CH(Me) | —CH2CH2-5-tetrazolyl |
| 203 | CHOH | CH(Me) | —CH2CH2-5-tetrazolyl |
| 204 | C(Me)OH | CH(Me) | —CH2CH2-5-tetrazolyl |
| 205 | C(O) | CH2 | —CH2S(O)2Me |
| 206 | CHOH | CH2 | —CH2S(O)2Me |
| 207 | C(Me)OH | CH2 | —CH2S(O)2Me |
| 208 | C(O) | CH(Me) | —CH2S(O)2Me |
| 209 | CHOH | CH(Me) | —CH2S(O)2Me |
| 210 | C(Me)OH | CH(Me) | —CH2S(O)2Me |
| 211 | C(O) | CH2 | —CH2CH2S(O)2Me |
| 212 | CHOH | CH2 | —CH2CH2S(O)2Me |
| 213 | C(Me)OH | CH2 | —CH2CH2S(O)2Me |
| 214 | C(O) | CH(Me) | —CH2CH2S(O)2Me |
| 215 | CHOH | CH(Me) | —CH2CH2S(O)2Me |
| 216 | C(Me)OH | CH(Me) | —CH2CH2S(O)2Me |
| 217 | C(O) | CH2 | —CH2CH2CH2S(O)2Me |
| 218 | CHOH | CH2 | —CH2CH2CH2S(O)2Me |
| 219 | C(Me)OH | CH2 | —CH2CH2CH2S(O)2Me |
| 220 | C(O) | CH(Me) | —CH2CH2CH2S(O)2Me |
| 221 | CHOH | CH(Me) | —CH2CH2CH2S(O)2Me |
| 222 | C(Me)OH | CH(Me) | —CH2CH2CH2S(O)2Me |
| 223 | C(O) | CH2 | —CH2S(O)2Et |
| 224 | CHOH | CH2 | —CH2S(O)2Et |
| 225 | C(Me)OH | CH2 | —CH2S(O)2Et |
| 226 | C(O) | CH(Me) | —CH2S(O)2Et |
| 227 | CHOH | CH(Me) | —CH2S(O)2Et |
| 228 | C(Me)OH | CH(Me) | —CH2S(O)2Et |
| 229 | C(O) | CH2 | —CH2CH2S(O)2Et |
| 230 | CHOH | CH2 | —CH2CH2S(O)2Et |
| 231 | C(Me)OH | CH2 | —CH2CH2S(O)2Et |
| 232 | C(O) | CH(Me) | —CH2CH2S(O)2Et |
| 233 | CHOH | CH(Me) | —CH2CH2S(O)2Et |
| 234 | C(Me)OH | CH(Me) | —CH2CH2S(O)2Et |
| 235 | C(O) | CH2 | —CH2CH2CH2S(O)2Et |

TABLE 1-continued

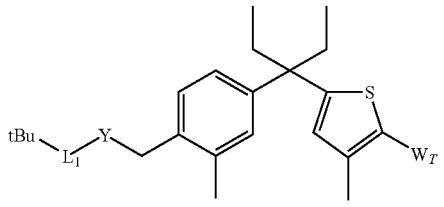

| Code | L₁ | Y | W$_T$ |
|---|---|---|---|
| 236 | CHOH | CH2 | —CH2CH2CH2S(O)2Et |
| 237 | C(Me)OH | CH2 | —CH2CH2CH2S(O)2Et |
| 238 | C(O) | CH(Me) | —CH2CH2CH2S(O)2Et |
| 239 | CHOH | CH(Me) | —CH2CH2CH2S(O)2Et |
| 240 | C(Me)OH | CH(Me) | —CH2CH2CH2S(O)2Et |
| 241 | C(O) | CH2 | —CH2S(O)2iPr |
| 242 | CHOH | CH2 | —CH2S(O)2iPr |
| 243 | C(Me)OH | CH2 | —CH2S(O)2iPr |
| 244 | C(O) | CH(Me) | —CH2S(O)2iPr |
| 245 | CHOH | CH(Me) | —CH2S(O)2iPr |
| 246 | C(Me)OH | CH(Me) | —CH2S(O)2iPr |
| 247 | C(O) | CH2 | —CH2CH2S(O)2iPr |
| 248 | CHOH | CH2 | —CH2CH2S(O)2iPr |
| 249 | C(Me)OH | CH2 | —CH2CH2S(O)2iPr |
| 250 | C(O) | CH(Me) | —CH2CH2S(O)2iPr |
| 251 | CHOH | CH(Me) | —CH2CH2S(O)2iPr |
| 252 | C(Me)OH | CH(Me) | —CH2CH2S(O)2iPr |
| 253 | C(O) | CH2 | —CH2S(O)2tBu |
| 254 | CHOH | CH2 | —CH2S(O)2tBu |
| 255 | C(Me)OH | CH2 | —CH2S(O)2tBu |
| 256 | C(O) | CH(Me) | —CH2S(O)2tBu |
| 257 | CHOH | CH(Me) | —CH2S(O)2tBu |
| 258 | C(Me)OH | CH(Me) | —CH2S(O)2tBu |
| 259 | C(O) | CH2 | —CH2CH2S(O)2tBu |
| 260 | CHOH | CH2 | —CH2CH2S(O)2tBu |
| 261 | C(Me)OH | CH2 | —CH2CH2S(O)2tBu |
| 262 | C(O) | CH(Me) | —CH2CH2S(O)2tBu |
| 263 | CHOH | CH(Me) | —CH2CH2S(O)2tBu |
| 264 | C(Me)OH | CH(Me) | —CH2CH2S(O)2tBu |
| 265 | C(O) | CH2 | —CH2CH2S(O)2NH2 |
| 266 | CHOH | CH2 | —CH2CH2S(O)2NH2 |
| 267 | C(Me)OH | CH2 | —CH2CH2S(O)2NH2 |
| 268 | C(O) | CH(Me) | —CH2CH2S(O)2NH2 |
| 269 | CHOH | CH(Me) | —CH2CH2S(O)2NH2 |
| 270 | C(Me)OH | CH(Me) | —CH2CH2S(O)2NH2 |
| 271 | C(O) | CH2 | —CH2CH2S(O)2NMe2 |
| 272 | CHOH | CH2 | —CH2CH2S(O)2NMe2 |
| 273 | C(Me)OH | CH2 | —CH2CH2S(O)2NMe2 |
| 274 | C(O) | CH(Me) | —CH2CH2S(O)2NMe2 |
| 275 | CHOH | CH(Me) | —CH2CH2S(O)2NMe2 |
| 276 | C(Me)OH | CH(Me) | —CH2CH2S(O)2NMe2 |
| 277 | C(O) | CH2 | —C(O)CH2S(O)2Me |
| 278 | CHOH | CH2 | —C(O)CH2S(O)2Me |
| 279 | C(Me)OH | CH2 | —C(O)CH2S(O)2Me |
| 280 | C(O) | CH(Me) | —C(O)CH2S(O)2Me |
| 281 | CHOH | CH(Me) | —C(O)CH2S(O)2Me |
| 282 | C(Me)OH | CH(Me) | —C(O)CH2S(O)2Me |
| 283 | C(O) | CH2 | —C(O)CH2CH2S(O)2Me |
| 284 | CHOH | CH2 | —C(O)CH2CH2S(O)2Me |
| 285 | C(Me)OH | CH2 | —C(O)CH2CH2S(O)2Me |
| 286 | C(O) | CH(Me) | —C(O)CH2CH2S(O)2Me |
| 287 | CHOH | CH(Me) | —C(O)CH2CH2S(O)2Me |
| 288 | C(Me)OH | CH(Me) | —C(O)CH2CH2S(O)2Me |
| 289 | C(O) | CH2 | —CH2CH2CH2S(O)2NH2 |
| 290 | CHOH | CH2 | —CH2CH2CH2S(O)2NH2 |
| 291 | C(Me)OH | CH2 | —CH2CH2CH2S(O)2NH2 |
| 292 | C(O) | CH(Me) | —CH2CH2CH2S(O)2NH2 |
| 293 | CHOH | CH(Me) | —CH2CH2CH2S(O)2NH2 |
| 294 | C(Me)OH | CH(Me) | —CH2CH2CH2S(O)2NH2 |
| 295 | C(O) | CH2 | —S(O)2Me |
| 296 | CHOH | CH2 | —S(O)2Me |
| 297 | C(Me)OH | CH2 | —S(O)2Me |
| 298 | C(O) | CH(Me) | —S(O)2Me |
| 299 | CHOH | CH(Me) | —S(O)2Me |
| 300 | C(Me)OH | CH(Me) | —S(O)2Me |
| 301 | C(O) | CH2 | —S(O)2Et |

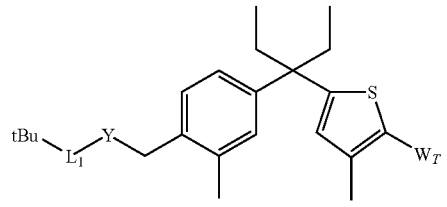

| Code | L₁ | Y | W$_T$ |
|---|---|---|---|
| 302 | CHOH | CH2 | —S(O)2Et |
| 303 | C(Me)OH | CH2 | —S(O)2Et |
| 304 | C(O) | CH(Me) | —S(O)2Et |
| 305 | CHOH | CH(Me) | —S(O)2Et |
| 306 | C(Me)OH | CH(Me) | —S(O)2Et |
| 307 | C(O) | CH2 | —S(O)2iPr |
| 308 | CHOH | CH2 | —S(O)2iPr |
| 309 | C(Me)OH | CH2 | —S(O)2iPr |
| 310 | C(O) | CH(Me) | —S(O)2iPr |
| 311 | CHOH | CH(Me) | —S(O)2iPr |
| 312 | C(Me)OH | CH(Me) | —S(O)2iPr |
| 313 | C(O) | CH2 | —S(O)2tBu |
| 314 | CHOH | CH2 | —S(O)2tBu |
| 315 | C(Me)OH | CH2 | —S(O)2tBu |
| 316 | C(O) | CH(Me) | —S(O)2tBu |
| 317 | CHOH | CH(Me) | —S(O)2tBu |
| 318 | C(Me)OH | CH(Me) | —S(O)2tBu |
| 319 | C(O) | CH2 | —S(O)2NH2 |
| 320 | CHOH | CH2 | —S(O)2NH2 |
| 321 | C(Me)OH | CH2 | —S(O)2NH2 |
| 322 | C(O) | CH(Me) | —S(O)2NH2 |
| 323 | CHOH | CH(Me) | —S(O)2NH2 |
| 324 | C(Me)OH | CH(Me) | —S(O)2NH2 |
| 325 | C(O) | CH2 | —S(O)2NMe2 |
| 326 | CHOH | CH2 | —S(O)2NMe2 |
| 327 | C(Me)OH | CH2 | —S(O)2NMe2 |
| 328 | C(O) | CH(Me) | —S(O)2NMe2 |
| 329 | CHOH | CH(Me) | —S(O)2NMe2 |
| 330 | C(Me)OH | CH(Me) | —S(O)2NMe2 |
| 331 | C(O) | CH2 | —S(O)2CH2S(O)2Me |
| 332 | CHOH | CH2 | —S(O)2CH2S(O)2Me |
| 333 | C(Me)OH | CH2 | —S(O)2CH2S(O)2Me |
| 334 | C(O) | CH(Me) | —S(O)2CH2S(O)2Me |
| 335 | CHOH | CH(Me) | —S(O)2CH2S(O)2Me |
| 336 | C(Me)OH | CH(Me) | —S(O)2CH2S(O)2Me |
| 337 | C(O) | CH2 | —S(O)2CH2S(O)2Et |
| 338 | CHOH | CH2 | —S(O)2CH2S(O)2Et |
| 339 | C(Me)OH | CH2 | —S(O)2CH2S(O)2Et |
| 340 | C(O) | CH(Me) | —S(O)2CH2S(O)2Et |
| 341 | CHOH | CH(Me) | —S(O)2CH2S(O)2Et |
| 342 | C(Me)OH | CH(Me) | —S(O)2CH2S(O)2Et |
| 343 | C(O) | CH2 | —S(O)2CH2S(O)2iPr |
| 344 | CHOH | CH2 | —S(O)2CH2S(O)2iPr |
| 345 | C(Me)OH | CH2 | —S(O)2CH2S(O)2iPr |
| 346 | C(O) | CH(Me) | —S(O)2CH2S(O)2iPr |
| 347 | CHOH | CH(Me) | —S(O)2CH2S(O)2iPr |
| 348 | C(Me)OH | CH(Me) | —S(O)2CH2S(O)2iPr |
| 349 | C(O) | CH2 | —S(O)2CH2S(O)2tBu |
| 350 | CHOH | CH2 | —S(O)2CH2S(O)2tBu |
| 351 | C(Me)OH | CH2 | —S(O)2CH2S(O)2tBu |
| 352 | C(O) | CH(Me) | —S(O)2CH2S(O)2tBu |
| 353 | CHOH | CH(Me) | —S(O)2CH2S(O)2tBu |
| 354 | C(Me)OH | CH(Me) | —S(O)2CH2S(O)2tBu |
| 355 | C(O) | CH2 | —C(O)NHCH2CO2H |
| 356 | CHOH | CH2 | —C(O)NHCH2CO2H |
| 357 | C(Me)OH | CH2 | —C(O)NHCH2CO2H |
| 358 | C(O) | CH(Me) | —C(O)NHCH2CO2H |
| 359 | CHOH | CH(Me) | —C(O)NHCH2CO2H |
| 360 | C(Me)OH | CH(Me) | —C(O)NHCH2CO2H |
| 361 | C(O) | CH2 | —SO2NHCH2CO2H |
| 362 | CHOH | CH2 | —SO2NHCH2CO2H |
| 363 | C(Me)OH | CH2 | —SO2NHCH2CO2H |
| 364 | C(O) | CH(Me) | —SO2NHCH2CO2H |
| 365 | CHOH | CH(Me) | —SO2NHCH2CO2H |
| 366 | C(Me)OH | CH(Me) | —SO2NHCH2CO2H |
| 367 | C(O) | CH2 | —CH2—S-Me |

TABLE 1-continued

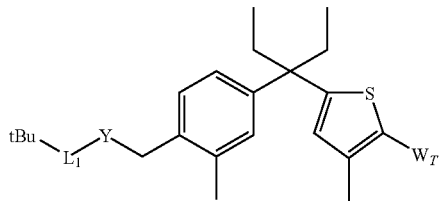

| Code | L₁ | Y | W$_T$ |
|---|---|---|---|
| 368 | CHOH | CH2 | —CH2—S-Me |
| 369 | C(Me)OH | CH2 | —CH2—S-Me |
| 370 | C(O) | CH(Me) | —CH2—S-Me |
| 371 | CHOH | CH(Me) | —CH2—S-Me |
| 372 | C(Me)OH | CH(Me) | —CH2—S-Me |

TABLE 2

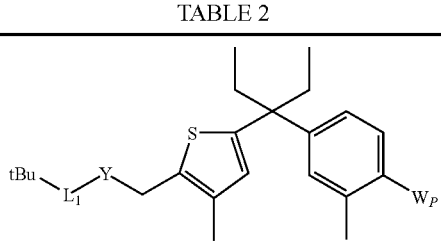

| Code | L₁ | Y | W$_P$ |
|---|---|---|---|
| 1A | C(O) | CH2 | —CO2Me |
| 2A | CHOH | CH2 | —CO2Me |
| 3A | C(Me)OH | CH2 | —CO2Me |
| 4A | C(O) | CH(Me) | —CO2Me |
| 5A | CHOH | CH(Me) | —CO2Me |
| 6A | C(Me)OH | CH(Me) | —CO2Me |
| 7A | C(O) | CH2 | —CO2H |
| 8A | CHOH | CH2 | —CO2H |
| 9A | C(Me)OH | CH2 | —CO2H |
| 10A | C(O) | CH(Me) | —CO2H |
| 11A | CHOH | CH(Me) | —CO2H |
| 12A | C(Me)OH | CH(Me) | —CO2H |
| 13A | C(O) | CH2 | —C(O)NH2 |
| 14A | CHOH | CH2 | —C(O)NH2 |
| 15A | C(Me)OH | CH2 | —C(O)NH2 |
| 16A | C(O) | CH(Me) | —C(O)NH2 |
| 17A | CHOH | CH(Me) | —C(O)NH2 |
| 18A | C(Me)OH | CH(Me) | —C(O)NH2 |
| 19A | C(O) | CH2 | —C(O)NMe2 |
| 20A | CHOH | CH2 | —C(O)NMe2 |
| 21A | C(Me)OH | CH2 | —C(O)NMe2 |
| 22A | C(O) | CH(Me) | —C(O)NMe2 |
| 23A | CHOH | CH(Me) | —C(O)NMe2 |
| 24A | C(Me)OH | CH(Me) | —C(O)NMe2 |
| 25A | C(O) | CH2 | 5-tetrazolyl |
| 26A | CHOH | CH2 | 5-tetrazolyl |
| 27A | C(Me)OH | CH2 | 5-tetrazolyl |
| 28A | C(O) | CH(Me) | 5-tetrazolyl |
| 29A | CHOH | CH(Me) | 5-tetrazolyl |
| 30A | C(Me)OH | CH(Me) | 5-tetrazolyl |
| 31A | C(O) | CH2 | —C(O)—NH-5-tetrazolyl |
| 32A | CHOH | CH2 | —C(O)—NH-5-tetrazolyl |
| 33A | C(Me)OH | CH2 | —C(O)—NH-5-tetrazolyl |
| 34A | C(O) | CH(Me) | —C(O)—NH-5-tetrazolyl |
| 35A | CHOH | CH(Me) | —C(O)—NH-5-tetrazolyl |
| 36A | C(Me)OH | CH(Me) | —C(O)—NH-5-tetrazolyl |
| 37A | C(O) | CH2 | —C(O)NHCH2SO2Me |
| 38A | CHOH | CH2 | —C(O)NHCH2SO2Me |
| 39A | C(Me)OH | CH2 | —C(O)NHCH2SO2Me |
| 40A | C(O) | CH(Me) | —C(O)NHCH2SO2Me |
| 41A | CHOH | CH(Me) | —C(O)NHCH2SO2Me |
| 42A | C(Me)OH | CH(Me) | —C(O)NHCH2SO2Me |
| 43A | C(O) | CH2 | —C(O)NHCH2CH2SO2Me |

TABLE 2-continued

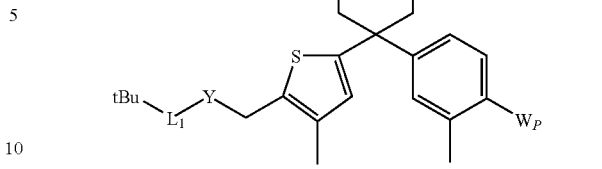

| Code | L₁ | Y | W$_P$ |
|---|---|---|---|
| 44A | CHOH | CH2 | —C(O)NHCH2CH2SO2Me |
| 45A | C(Me)OH | CH2 | —C(O)NHCH2CH2SO2Me |
| 46A | C(O) | CH(Me) | —C(O)NHCH2CH2SO2Me |
| 47A | CHOH | CH(Me) | —C(O)NHCH2CH2SO2Me |
| 48A | C(Me)OH | CH(Me) | —C(O)NHCH2CH2SO2Me |
| 49A | C(O) | CH2 | —C(O)NHSO2Me |
| 50A | CHOH | CH2 | —C(O)NHSO2Me |
| 51A | C(Me)OH | CH2 | —C(O)NHSO2Me |
| 52A | C(O) | CH(Me) | —C(O)NHSO2Me |
| 53A | CHOH | CH(Me) | —C(O)NHSO2Me |
| 54A | C(Me)OH | CH(Me) | —C(O)NHSO2Me |
| 55A | C(O) | CH2 | —CH2—C(O)NHSO2Et |
| 56A | CHOH | CH2 | —CH2—C(O)NHSO2Et |
| 57A | C(Me)OH | CH2 | —CH2—C(O)NHSO2Et |
| 58A | C(O) | CH(Me) | —CH2—C(O)NHSO2Et |
| 59A | CHOH | CH(Me) | —CH2—C(O)NHSO2Et |
| 60A | C(Me)OH | CH(Me) | —CH2—C(O)NHSO2Et |
| 61A | C(O) | CH2 | —CH2—C(O)NHSO2iPr |
| 62A | CHOH | CH2 | —CH2—C(O)NHSO2iPr |
| 63A | C(Me)OH | CH2 | —CH2—C(O)NHSO2iPr |
| 64A | C(O) | CH(Me) | —CH2—C(O)NHSO2iPr |
| 65A | CHOH | CH(Me) | —CH2—C(O)NHSO2iPr |
| 66A | C(Me)OH | CH(Me) | —CH2—C(O)NHSO2iPr |
| 67A | C(O) | CH2 | —CH2—C(O)NHSO2tBu |
| 68A | CHOH | CH2 | —CH2—C(O)NHSO2tBu |
| 69A | C(Me)OH | CH2 | —CH2—C(O)NHSO2tBu |
| 70A | C(O) | CH(Me) | —CH2—C(O)NHSO2tBu |
| 71A | CHOH | CH(Me) | —CH2—C(O)NHSO2tBu |
| 72A | C(Me)OH | CH(Me) | —CH2—C(O)NHSO2tBu |
| 73A | C(O) | CH2 | —CH2NHSO2Me |
| 74A | CHOH | CH2 | —CH2NHSO2Me |
| 75A | C(Me)OH | CH2 | —CH2NHSO2Me |
| 76A | C(O) | CH(Me) | —CH2NHSO2Me |
| 77A | CHOH | CH(Me) | —CH2NHSO2Me |
| 78A | C(Me)OH | CH(Me) | —CH2NHSO2Me |
| 79A | C(O) | CH2 | —CH2NHSO2Et |
| 80A | CHOH | CH2 | —CH2NHSO2Et |
| 81A | C(Me)OH | CH2 | —CH2NHSO2Et |
| 82A | C(O) | CH(Me) | —CH2NHSO2Et |
| 83A | CHOH | CH(Me) | —CH2NHSO2Et |
| 84A | C(Me)OH | CH(Me) | —CH2NHSO2Et |
| 85A | C(O) | CH2 | —CH2NHSO2iPr |
| 86A | CHOH | CH2 | —CH2NHSO2iPr |
| 87A | C(Me)OH | CH2 | —CH2NHSO2iPr |
| 88A | C(O) | CH(Me) | —CH2NHSO2iPr |
| 89A | CHOH | CH(Me) | —CH2NHSO2iPr |
| 90A | C(Me)OH | CH(Me) | —CH2NHSO2iPr |
| 91A | C(O) | CH2 | —CH2NHSO2tBu |
| 92A | CHOH | CH2 | —CH2NHSO2tBu |
| 93A | C(Me)OH | CH2 | —CH2NHSO2tBu |
| 94A | C(O) | CH(Me) | —CH2NHSO2tBu |
| 95A | CHOH | CH(Me) | —CH2NHSO2tBu |
| 96A | C(Me)OH | CH(Me) | —CH2NHSO2tBu |
| 97A | C(O) | CH2 | —CH2—N-pyrrolidin-2-one |
| 98A | CHOH | CH2 | —CH2—N-pyrrolidin-2-one |
| 99A | C(Me)OH | CH2 | —CH2—N-pyrrolidin-2-one |
| 100A | C(O) | CH(Me) | —CH2—N-pyrrolidin-2-one |
| 101A | CHOH | CH(Me) | —CH2—N-pyrrolidin-2-one |
| 102A | C(Me)OH | CH(Me) | —CH2—N-pyrrolidin-2-one |
| 103A | C(O) | CH2 | —CH2-(1-methylpyrrolidin-2-one-3-yl) |
| 104A | CHOH | CH2 | —CH2-(1-methylpyrrolidin-2-one-3-yl) |
| 105A | C(Me)OH | CH2 | —CH2-(1-methylpyrrolidin-2-one-3-yl) |
| 106A | C(O) | CH(Me) | —CH2-(1-methylpyrrolidin-2-one-3-yl) |
| 107A | CHOH | CH(Me) | —CH2-(1-methylpyrrolidin-2-one-3-yl) |
| 108A | C(Me)OH | CH(Me) | —CH2-(1-methylpyrrolidin-2-one-3-yl) |
| 109A | C(O) | CH2 | —CH2CO2Me |

TABLE 2-continued

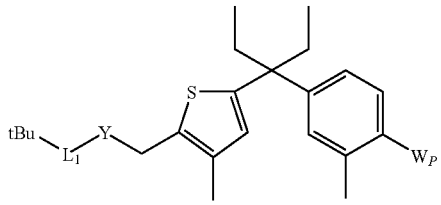

| Code | L₁ | Y | W_P |
|------|------|------|------|
| 110A | CHOH | CH2 | —CH2CO2Me |
| 111A | C(Me)OH | CH2 | —CH2CO2Me |
| 112A | C(O) | CH(Me) | —CH2CO2Me |
| 113A | CHOH | CH(Me) | —CH2CO2Me |
| 114A | C(Me)OH | CH(Me) | —CH2CO2Me |
| 115A | C(O) | CH2 | —CH2CO2H |
| 116A | CHOH | CH2 | —CH2CO2H |
| 117A | C(Me)OH | CH2 | —CH2CO2H |
| 118A | C(O) | CH(Me) | —CH2CO2H |
| 119A | CHOH | CH(Me) | —CH2CO2H |
| 120A | C(Me)OH | CH(Me) | —CH2CO2H |
| 121A | C(O) | CH2 | —CH2C(O)NH2 |
| 122A | CHOH | CH2 | —CH2C(O)NH2 |
| 123A | C(Me)OH | CH2 | —CH2C(O)NH2 |
| 124A | C(O) | CH(Me) | —CH2C(O)NH2 |
| 125A | CHOH | CH(Me) | —CH2C(O)NH2 |
| 126A | C(Me)OH | CH(Me) | —CH2C(O)NH2 |
| 127A | C(O) | CH2 | —CH2C(O)NMe2 |
| 128A | CHOH | CH2 | —CH2C(O)NMe2 |
| 129A | C(Me)OH | CH2 | —CH2C(O)NMe2 |
| 130A | C(O) | CH(Me) | —CH2C(O)NMe2 |
| 131A | CHOH | CH(Me) | —CH2C(O)NMe2 |
| 132A | C(Me)OH | CH(Me) | —CH2C(O)NMe2 |
| 133A | C(O) | CH2 | —CH2C(O)—N-pyrrolidine |
| 134A | CHOH | CH2 | —CH2C(O)—N-pyrrolidine |
| 135A | C(Me)OH | CH2 | —CH2C(O)—N-pyrrolidine |
| 136A | C(O) | CH(Me) | —CH2C(O)—N-pyrrolidine |
| 137A | CHOH | CH(Me) | —CH2C(O)—N-pyrrolidine |
| 138A | C(Me)OH | CH(Me) | —CH2C(O)—N-pyrrolidine |
| 139A | C(O) | CH2 | —CH2-5-tetrazolyl |
| 140A | CHOH | CH2 | —CH2-5-tetrazolyl |
| 141A | C(Me)OH | CH2 | —CH2-5-tetrazolyl |
| 142A | C(O) | CH(Me) | —CH2-5-tetrazolyl |
| 143A | CHOH | CH(Me) | —CH2-5-tetrazolyl |
| 144A | C(Me)OH | CH(Me) | —CH2-5-tetrazolyl |
| 145A | C(O) | CH2 | —C(O)C(O)OH |
| 146A | CHOH | CH2 | —C(O)C(O)OH |
| 147A | C(Me)OH | CH2 | —C(O)C(O)OH |
| 148A | C(O) | CH(Me) | —C(O)C(O)OH |
| 149A | CHOH | CH(Me) | —C(O)C(O)OH |
| 150A | C(Me)OH | CH(Me) | —C(O)C(O)OH |
| 151A | C(O) | CH2 | —CH(OH)C(O)OH |
| 152A | CHOH | CH2 | —CH(OH)C(O)OH |
| 153A | C(Me)OH | CH2 | —CH(OH)C(O)OH |
| 154A | C(O) | CH(Me) | —CH(OH)C(O)OH |
| 155A | CHOH | CH(Me) | —CH(OH)C(O)OH |
| 156A | C(Me)OH | CH(Me) | —CH(OH)C(O)OH |
| 157A | C(O) | CH2 | —C(O)C(O)NH2 |
| 158A | CHOH | CH2 | —C(O)C(O)NH2 |
| 159A | C(Me)OH | CH2 | —C(O)C(O)NH2 |
| 160A | C(O) | CH(Me) | —C(O)C(O)NH2 |
| 161A | CHOH | CH(Me) | —C(O)C(O)NH2 |
| 162A | C(Me)OH | CH(Me) | —C(O)C(O)NH2 |
| 163A | C(O) | CH2 | —CH(OH)C(O)NH2 |
| 164A | CHOH | CH2 | —CH(OH)C(O)NH2 |
| 165A | C(Me)OH | CH2 | —CH(OH)C(O)NH2 |
| 166A | C(O) | CH(Me) | —CH(OH)C(O)NH2 |
| 167A | CHOH | CH(Me) | —CH(OH)C(O)NH2 |
| 168A | C(Me)OH | CH(Me) | —CH(OH)C(O)NH2 |
| 169A | C(O) | CH2 | —C(O)C(O)NMe2 |
| 170A | CHOH | CH2 | —C(O)C(O)NMe2 |
| 171A | C(Me)OH | CH2 | —C(O)C(O)NMe2 |
| 172A | C(O) | CH(Me) | —C(O)C(O)NMe2 |
| 173A | CHOH | CH(Me) | —C(O)C(O)NMe2 |
| 174A | C(Me)OH | CH(Me) | —C(O)C(O)NMe2 |
| 175A | C(O) | CH2 | —CH(OH)C(O)NMe2 |
| 176A | CHOH | CH2 | —CH(OH)C(O)NMe2 |
| 177A | C(Me)OH | CH2 | —CH(OH)C(O)NMe2 |
| 178A | C(O) | CH(Me) | —CH(OH)C(O)NMe2 |
| 179A | CHOH | CH(Me) | —CH(OH)C(O)NMe2 |
| 180A | C(Me)OH | CH(Me) | —CH(OH)C(O)NMe2 |
| 181A | C(O) | CH2 | —CH2CH2CO2H |
| 182A | CHOH | CH2 | —CH2CH2CO2H |
| 183A | C(Me)OH | CH2 | —CH2CH2CO2H |
| 184A | C(O) | CH(Me) | —CH2CH2CO2H |
| 185A | CHOH | CH(Me) | —CH2CH2CO2H |
| 186A | C(Me)OH | CH(Me) | —CH2CH2CO2H |
| 187A | C(O) | CH2 | —CH2CH2C(O)NH2 |
| 188A | CHOH | CH2 | —CH2CH2C(O)NH2 |
| 189A | C(Me)OH | CH2 | —CH2CH2C(O)NH2 |
| 190A | C(O) | CH(Me) | —CH2CH2C(O)NH2 |
| 191A | CHOH | CH(Me) | —CH2CH2C(O)NH2 |
| 192A | C(Me)OH | CH(Me) | —CH2CH2C(O)NH2 |
| 193A | C(O) | CH2 | —CH2CH2C(O)NMe2 |
| 194A | CHOH | CH2 | —CH2CH2C(O)NMe2 |
| 195A | C(Me)OH | CH2 | —CH2CH2C(O)NMe2 |
| 196A | C(O) | CH(Me) | —CH2CH2C(O)NMe2 |
| 197A | CHOH | CH(Me) | —CH2CH2C(O)NMe2 |
| 198A | C(Me)OH | CH(Me) | —CH2CH2C(O)NMe2 |
| 199A | C(O) | CH2 | —CH2CH2-5-tetrazolyl |
| 200A | CHOH | CH2 | —CH2CH2-5-tetrazolyl |
| 201A | C(Me)OH | CH2 | —CH2CH2-5-tetrazolyl |
| 202A | C(O) | CH(Me) | —CH2CH2-5-tetrazolyl |
| 203A | CHOH | CH(Me) | —CH2CH2-5-tetrazolyl |
| 204A | C(Me)OH | CH(Me) | —CH2CH2-5-tetrazolyl |
| 205A | C(O) | CH2 | —OCH2S(O)2Me |
| 206A | CHOH | CH2 | —OCH2S(O)2Me |
| 207A | C(Me)OH | CH2 | —OCH2S(O)2Me |
| 208A | C(O) | CH(Me) | —OCH2S(O)2Me |
| 209A | CHOH | CH(Me) | —OCH2S(O)2Me |
| 210A | C(Me)OH | CH(Me) | —OCH2S(O)2Me |
| 211A | C(O) | CH2 | —OCH2CH2S(O)2Me |
| 212A | CHOH | CH2 | —OCH2CH2S(O)2Me |
| 213A | C(Me)OH | CH2 | —OCH2CH2S(O)2Me |
| 214A | C(O) | CH(Me) | —OCH2CH2S(O)2Me |
| 215A | CHOH | CH(Me) | —OCH2CH2S(O)2Me |
| 216A | C(Me)OH | CH(Me) | —OCH2CH2S(O)2Me |
| 217A | C(O) | CH2 | —CH2S(O)2Me |
| 218A | CHOH | CH2 | —CH2S(O)2Me |
| 219A | C(Me)OH | CH2 | —CH2S(O)2Me |
| 220A | C(O) | CH(Me) | —CH2S(O)2Me |
| 221A | CHOH | CH(Me) | —CH2S(O)2Me |
| 222A | C(Me)OH | CH(Me) | —CH2S(O)2Me |
| 223A | C(O) | CH2 | —CH2CH2S(O)2Me |
| 224A | CHOH | CH2 | —CH2CH2S(O)2Me |
| 225A | C(Me)OH | CH2 | —CH2CH2S(O)2Me |
| 226A | C(O) | CH(Me) | —CH2CH2S(O)2Me |
| 227A | CHOH | CH(Me) | —CH2CH2S(O)2Me |
| 228A | C(Me)OH | CH(Me) | —CH2CH2S(O)2Me |
| 229A | C(O) | CH2 | —CH2CH2CH2S(O)2Me |
| 230A | CHOH | CH2 | —CH2CH2CH2S(O)2Me |
| 231A | C(Me)OH | CH2 | —CH2CH2CH2S(O)2Me |
| 232A | C(O) | CH(Me) | —CH2CH2CH2S(O)2Me |
| 233A | CHOH | CH(Me) | —CH2CH2CH2S(O)2Me |
| 234A | C(Me)OH | CH(Me) | —CH2CH2CH2S(O)2Me |
| 235A | C(O) | CH2 | —OCH2S(O)2Et |
| 236A | CHOH | CH2 | —OCH2S(O)2Et |
| 237A | C(Me)OH | CH2 | —OCH2S(O)2Et |
| 238A | C(O) | CH(Me) | —OCH2S(O)2Et |
| 239A | CHOH | CH(Me) | —OCH2S(O)2Et |
| 240A | C(Me)OH | CH(Me) | —OCH2S(O)2Et |
| 241A | C(O) | CH2 | —OCH2CH2S(O)2Et |

TABLE 2-continued

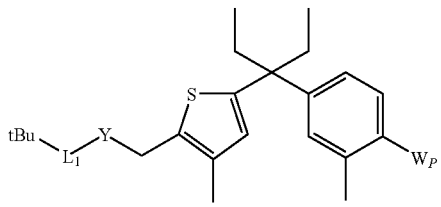

| Code | L₁ | Y | W_P |
|---|---|---|---|
| 242A | CHOH | CH2 | —OCH2CH2S(O)2Et |
| 243A | C(Me)OH | CH2 | —OCH2CH2S(O)2Et |
| 244A | C(O) | CH(Me) | —OCH2CH2S(O)2Et |
| 245A | CHOH | CH(Me) | —OCH2CH2S(O)2Et |
| 246A | C(Me)OH | CH(Me) | —OCH2CH2S(O)2Et |
| 247A | C(O) | CH2 | —CH2S(O)2Et |
| 248A | CHOH | CH2 | —CH2S(O)2Et |
| 249A | C(Me)OH | CH2 | —CH2S(O)2Et |
| 250A | C(O) | CH(Me) | —CH2S(O)2Et |
| 251A | CHOH | CH(Me) | —CH2S(O)2Et |
| 252A | C(Me)OH | CH(Me) | —CH2S(O)2Et |
| 253A | C(O) | CH2 | —CH2CH2S(O)2Et |
| 254A | CHOH | CH2 | —CH2CH2S(O)2Et |
| 255A | C(Me)OH | CH2 | —CH2CH2S(O)2Et |
| 256A | C(O) | CH(Me) | —CH2CH2S(O)2Et |
| 257A | CHOH | CH(Me) | —CH2CH2S(O)2Et |
| 258A | C(Me)OH | CH(Me) | —CH2CH2S(O)2Et |
| 259A | C(O) | CH2 | —CH2CH2CH2S(O)2Et |
| 260A | CHOH | CH2 | —CH2CH2CH2S(O)2Et |
| 261A | C(Me)OH | CH2 | —CH2CH2CH2S(O)2Et |
| 262A | C(O) | CH(Me) | —CH2CH2CH2S(O)2Et |
| 263A | CHOH | CH(Me) | —CH2CH2CH2S(O)2Et |
| 264A | C(Me)OH | CH(Me) | —CH2CH2CH2S(O)2Et |
| 265A | C(O) | CH2 | —OCH2S(O)2iPr |
| 266A | CHOH | CH2 | —OCH2S(O)2iPr |
| 267A | C(Me)OH | CH2 | —OCH2S(O)2iPr |
| 268A | C(O) | CH(Me) | —OCH2S(O)2iPr |
| 269A | CHOH | CH(Me) | —OCH2S(O)2iPr |
| 270A | C(Me)OH | CH(Me) | —OCH2S(O)2iPr |
| 271A | C(O) | CH2 | —CH2S(O)2iPr |
| 272A | CHOH | CH2 | —CH2S(O)2iPr |
| 273A | C(Me)OH | CH2 | —CH2S(O)2iPr |
| 274A | C(O) | CH(Me) | —CH2S(O)2iPr |
| 275A | CHOH | CH(Me) | —CH2S(O)2iPr |
| 276A | C(Me)OH | CH(Me) | —CH2S(O)2iPr |
| 277A | C(O) | CH2 | —CH2CH2S(O)2iPr |
| 278A | CHOH | CH2 | —CH2CH2S(O)2iPr |
| 279A | C(Me)OH | CH2 | —CH2CH2S(O)2iPr |
| 280A | C(O) | CH(Me) | —CH2CH2S(O)2iPr |
| 281A | CHOH | CH(Me) | —CH2CH2S(O)2iPr |
| 282A | C(Me)OH | CH(Me) | —CH2CH2S(O)2iPr |
| 283A | C(O) | CH2 | —OCH2S(O)2tBu |
| 284A | CHOH | CH2 | —OCH2S(O)2tBu |
| 285A | C(Me)OH | CH2 | —OCH2S(O)2tBu |
| 286A | C(O) | CH(Me) | —OCH2S(O)2tBu |
| 287A | CHOH | CH(Me) | —OCH2S(O)2tBu |
| 288A | C(Me)OH | CH(Me) | —OCH2S(O)2tBu |
| 289A | C(O) | CH2 | —CH2S(O)2tBu |
| 290A | CHOH | CH2 | —CH2S(O)2tBu |
| 291A | C(Me)OH | CH2 | —CH2S(O)2tBu |
| 292A | C(O) | CH(Me) | —CH2S(O)2tBu |
| 293A | CHOH | CH(Me) | —CH2S(O)2tBu |
| 294A | C(Me)OH | CH(Me) | —CH2S(O)2tBu |
| 295A | C(O) | CH2 | —CH2CH2S(O)2tBu |
| 296A | CHOH | CH2 | —CH2CH2S(O)2tBu |
| 297A | C(Me)OH | CH2 | —CH2CH2S(O)2tBu |
| 298A | C(O) | CH(Me) | —CH2CH2S(O)2tBu |
| 299A | CHOH | CH(Me) | —CH2CH2S(O)2tBu |
| 300A | C(Me)OH | CH(Me) | —CH2CH2S(O)2tBu |
| 301A | C(O) | CH2 | —OCH2S(O)2NH2 |
| 302A | CHOH | CH2 | —OCH2S(O)2NH2 |
| 303A | C(Me)OH | CH2 | —OCH2S(O)2NH2 |
| 304A | C(O) | CH(Me) | —OCH2S(O)2NH2 |
| 305A | CHOH | CH(Me) | —OCH2S(O)2NH2 |
| 306A | C(Me)OH | CH(Me) | —OCH2S(O)2NH2 |
| 307A | C(O) | CH2 | —OCH2S(O)2NMe2 |
| 308A | CHOH | CH2 | —OCH2S(O)2NMe2 |
| 309A | C(Me)OH | CH2 | —OCH2S(O)2NMe2 |
| 310A | C(O) | CH(Me) | —OCH2S(O)2NMe2 |
| 311A | CHOH | CH(Me) | —OCH2S(O)2NMe2 |
| 312A | C(Me)OH | CH(Me) | —OCH2S(O)2NMe2 |
| 313A | C(O) | CH2 | —CH2CH2S(O)2NH2 |
| 314A | CHOH | CH2 | —CH2CH2S(O)2NH2 |
| 315A | C(Me)OH | CH2 | —CH2CH2S(O)2NH2 |
| 316A | C(O) | CH(Me) | —CH2CH2S(O)2NH2 |
| 317A | CHOH | CH(Me) | —CH2CH2S(O)2NH2 |
| 318A | C(Me)OH | CH(Me) | —CH2CH2S(O)2NH2 |
| 319A | C(O) | CH2 | —CH2CH2S(O)2NMe2 |
| 320A | CHOH | CH2 | —CH2CH2S(O)2NMe2 |
| 321A | C(Me)OH | CH2 | —CH2CH2S(O)2NMe2 |
| 322A | C(O) | CH(Me) | —CH2CH2S(O)2NMe2 |
| 323A | CHOH | CH(Me) | —CH2CH2S(O)2NMe2 |
| 324A | C(Me)OH | CH(Me) | —CH2CH2S(O)2NMe2 |
| 325A | C(O) | CH2 | —C(O)CH2S(O)2Me |
| 326A | CHOH | CH2 | —C(O)CH2S(O)2Me |
| 327A | C(Me)OH | CH2 | —C(O)CH2S(O)2Me |
| 328A | C(O) | CH(Me) | —C(O)CH2S(O)2Me |
| 329A | CHOH | CH(Me) | —C(O)CH2S(O)2Me |
| 330A | C(Me)OH | CH(Me) | —C(O)CH2S(O)2Me |
| 331A | C(O) | CH2 | —C(O)CH2CH2S(O)2Me |
| 332A | CHOH | CH2 | —C(O)CH2CH2S(O)2Me |
| 333A | C(Me)OH | CH2 | —C(O)CH2CH2S(O)2Me |
| 334A | C(O) | CH(Me) | —C(O)CH2CH2S(O)2Me |
| 335A | CHOH | CH(Me) | —C(O)CH2CH2S(O)2Me |
| 336A | C(Me)OH | CH(Me) | —C(O)CH2CH2S(O)2Me |
| 337A | C(O) | CH2 | —OCH2CH2S(O)2NH2 |
| 338A | CHOH | CH2 | —OCH2CH2S(O)2NH2 |
| 339A | C(Me)OH | CH2 | —OCH2CH2S(O)2NH2 |
| 340A | C(O) | CH(Me) | —OCH2CH2S(O)2NH2 |
| 341A | CHOH | CH(Me) | —OCH2CH2S(O)2NH2 |
| 342A | C(Me)OH | CH(Me) | —OCH2CH2S(O)2NH2 |
| 343A | C(O) | CH2 | —OCH2CH2S(O)2NMe2 |
| 344A | CHOH | CH2 | —OCH2CH2S(O)2NMe2 |
| 345A | C(Me)OH | CH2 | —OCH2CH2S(O)2NMe2 |
| 346A | C(O) | CH(Me) | —OCH2CH2S(O)2NMe2 |
| 347A | CHOH | CH(Me) | —OCH2CH2S(O)2NMe2 |
| 348A | C(Me)OH | CH(Me) | —OCH2CH2S(O)2NMe2 |
| 349A | C(O) | CH2 | —CH2CH2CH2S(O)2NH2 |
| 350A | CHOH | CH2 | —CH2CH2CH2S(O)2NH2 |
| 351A | C(Me)OH | CH2 | —CH2CH2CH2S(O)2NH2 |
| 352A | C(O) | CH(Me) | —CH2CH2CH2S(O)2NH2 |
| 353A | CHOH | CH(Me) | —CH2CH2CH2S(O)2NH2 |
| 354A | C(Me)OH | CH(Me) | —CH2CH2CH2S(O)2NH2 |
| 355A | C(O) | CH2 | —S(O)2Me |
| 356A | CHOH | CH2 | —S(O)2Me |
| 357A | C(Me)OH | CH2 | —S(O)2Me |
| 358A | C(O) | CH(Me) | —S(O)2Me |
| 359A | CHOH | CH(Me) | —S(O)2Me |
| 360A | C(Me)OH | CH(Me) | —S(O)2Me |
| 361A | C(O) | CH2 | —S(O)2Et |
| 362A | CHOH | CH2 | —S(O)2Et |
| 363A | C(Me)OH | CH2 | —S(O)2Et |
| 364A | C(O) | CH(Me) | —S(O)2Et |
| 365A | CHOH | CH(Me) | —S(O)2Et |
| 366A | C(Me)OH | CH(Me) | —S(O)2Et |
| 367A | C(O) | CH2 | —S(O)2iPr |
| 368A | CHOH | CH2 | —S(O)2iPr |
| 369A | C(Me)OH | CH2 | —S(O)2iPr |
| 370A | C(O) | CH(Me) | —S(O)2iPr |
| 371A | CHOH | CH(Me) | —S(O)2iPr |
| 372A | C(Me)OH | CH(Me) | —S(O)2iPr |
| 373A | C(O) | CH2 | —S(O)2tBu |

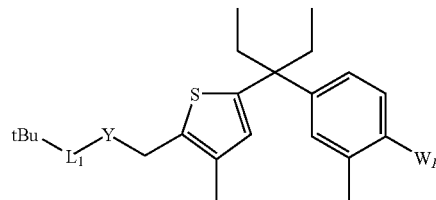

TABLE 2-continued


| Code | L₁ | Y | W$_P$ |
|---|---|---|---|
| 374A | CHOH | CH2 | —S(O)2tBu |
| 375A | C(Me)OH | CH2 | —S(O)2tBu |
| 376A | C(O) | CH(Me) | —S(O)2tBu |
| 377A | CHOH | CH(Me) | —S(O)2tBu |
| 378A | C(Me)OH | CH(Me) | —S(O)2tBu |
| 379A | C(O) | CH2 | —OCH2CO2H |
| 380A | CHOH | CH2 | —OCH2CO2H |
| 381A | C(Me)OH | CH2 | —OCH2CO2H |
| 382A | C(O) | CH(Me) | —OCH2CO2H |
| 383A | CHOH | CH(Me) | —OCH2CO2H |
| 384A | C(Me)OH | CH(Me) | —OCH2CO2H |
| 385A | C(O) | CH2 | —OCH2-5-tetrazolyl |
| 386A | CHOH | CH2 | —OCH2-5-tetrazolyl |
| 387A | C(Me)OH | CH2 | —OCH2-5-tetrazolyl |
| 388A | C(O) | CH(Me) | —OCH2-5-tetrazolyl |
| 389A | CHOH | CH(Me) | —OCH2-5-tetrazolyl |
| 390A | C(Me)OH | CH(Me) | —OCH2-5-tetrazolyl |
| 391A | C(O) | CH2 | —S(O)2NH2 |
| 392A | CHOH | CH2 | —S(O)2NH2 |
| 393A | C(Me)OH | CH2 | —S(O)2NH2 |
| 394A | C(O) | CH(Me) | —S(O)2NH2 |
| 395A | CHOH | CH(Me) | —S(O)2NH2 |
| 396A | C(Me)OH | CH(Me) | —S(O)2NH2 |
| 397A | C(O) | CH2 | —S(O)2NMe2 |
| 398A | CHOH | CH2 | —S(O)2NMe2 |
| 399A | C(Me)OH | CH2 | —S(O)2NMe2 |
| 400A | C(O) | CH(Me) | —S(O)2NMe2 |
| 401A | CHOH | CH(Me) | —S(O)2NMe2 |
| 402A | C(Me)OH | CH(Me) | —S(O)2NMe2 |
| 403A | C(O) | CH2 | —S(O)2CH2S(O)2Me |
| 404A | CHOH | CH2 | —S(O)2CH2S(O)2Me |
| 405A | C(Me)OH | CH2 | —S(O)2CH2S(O)2Me |
| 406A | C(O) | CH(Me) | —S(O)2CH2S(O)2Me |
| 407A | CHOH | CH(Me) | —S(O)2CH2S(O)2Me |
| 408A | C(Me)OH | CH(Me) | —S(O)2CH2S(O)2Me |
| 409A | C(O) | CH2 | —S(O)2CH2S(O)2Et |
| 410A | CHOH | CH2 | —S(O)2CH2S(O)2Et |
| 411A | C(Me)OH | CH2 | —S(O)2CH2S(O)2Et |
| 412A | C(O) | CH(Me) | —S(O)2CH2S(O)2Et |
| 413A | CHOH | CH(Me) | —S(O)2CH2S(O)2Et |
| 414A | C(Me)OH | CH(Me) | —S(O)2CH2S(O)2Et |
| 415A | C(O) | CH2 | —S(O)2CH2S(O)2iPr |
| 416A | CHOH | CH2 | —S(O)2CH2S(O)2iPr |
| 417A | C(Me)OH | CH2 | —S(O)2CH2S(O)2iPr |
| 418A | C(O) | CH(Me) | —S(O)2CH2S(O)2iPr |
| 419A | CHOH | CH(Me) | —S(O)2CH2S(O)2iPr |
| 420A | C(Me)OH | CH(Me) | —S(O)2CH2S(O)2iPr |
| 421A | C(O) | CH2 | —S(O)2CH2S(O)2tBu |
| 422A | CHOH | CH2 | —S(O)2CH2S(O)2tBu |
| 423A | C(Me)OH | CH2 | —S(O)2CH2S(O)2tBu |
| 424A | C(O) | CH(Me) | —S(O)2CH2S(O)2tBu |
| 425A | CHOH | CH(Me) | —S(O)2CH2S(O)2tBu |
| 426A | C(Me)OH | CH(Me) | —S(O)2CH2S(O)2tBu |
| 427A | C(O) | CH2 | —NHS(O)2Me |
| 428A | CHOH | CH2 | —NHS(O)2Me |
| 429A | C(Me)OH | CH2 | —NHS(O)2Me |
| 430A | C(O) | CH(Me) | —NHS(O)2Me |
| 431A | CHOH | CH(Me) | —NHS(O)2Me |
| 432A | C(Me)OH | CH(Me) | —NHS(O)2Me |
| 433A | C(O) | CH2 | —NHS(O)2Et |
| 434A | CHOH | CH2 | —NHS(O)2Et |
| 435A | C(Me)OH | CH2 | —NHS(O)2Et |
| 436A | C(O) | CH(Me) | —NHS(O)2Et |
| 437A | CHOH | CH(Me) | —NHS(O)2Et |
| 438A | C(Me)OH | CH(Me) | —NHS(O)2Et |
| 439A | C(O) | CH2 | —NHS(O)2iPr |

TABLE 2-continued

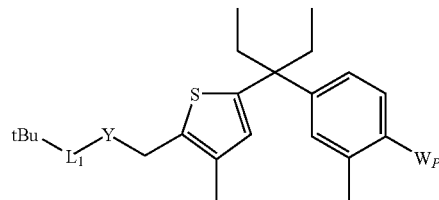

| Code | L₁ | Y | W$_P$ |
|---|---|---|---|
| 440A | CHOH | CH2 | —NHS(O)2iPr |
| 441A | C(Me)OH | CH2 | —NHS(O)2iPr |
| 442A | C(O) | CH(Me) | —NHS(O)2iPr |
| 443A | CHOH | CH(Me) | —NHS(O)2iPr |
| 444A | C(Me)OH | CH(Me) | —NHS(O)2iPr |
| 445A | C(O) | CH2 | —NHS(O)2tBu |
| 446A | CHOH | CH2 | —NHS(O)2tBu |
| 447A | C(Me)OH | CH2 | —NHS(O)2tBu |
| 448A | C(O) | CH(Me) | —NHS(O)2tBu |
| 449A | CHOH | CH(Me) | —NHS(O)2tBu |
| 450A | C(Me)OH | CH(Me) | —NHS(O)2tBu |
| 451A | C(O) | CH2 | —OS(O)2Me |
| 452A | CHOH | CH2 | —OS(O)2Me |
| 453A | C(Me)OH | CH2 | —OS(O)2Me |
| 454A | C(O) | CH(Me) | —OS(O)2Me |
| 455A | CHOH | CH(Me) | —OS(O)2Me |
| 456A | C(Me)OH | CH(Me) | —OS(O)2Me |
| 457A | C(O) | CH2 | —OS(O)2Et |
| 458A | CHOH | CH2 | —OS(O)2Et |
| 459A | C(Me)OH | CH2 | —OS(O)2Et |
| 460A | C(O) | CH(Me) | —OS(O)2Et |
| 461A | CHOH | CH(Me) | —OS(O)2Et |
| 462A | C(Me)OH | CH(Me) | —OS(O)2Et |
| 463A | C(O) | CH2 | —OS(O)2iPr |
| 464A | CHOH | CH2 | —OS(O)2iPr |
| 465A | C(Me)OH | CH2 | —OS(O)2iPr |
| 466A | C(O) | CH(Me) | —OS(O)2iPr |
| 467A | CHOH | CH(Me) | —OS(O)2iPr |
| 468A | C(Me)OH | CH(Me) | —OS(O)2iPr |
| 469A | C(O) | CH2 | —OS(O)2tBu |
| 470A | CHOH | CH2 | —OS(O)2tBu |
| 471A | C(Me)OH | CH2 | —OS(O)2tBu |
| 472A | C(O) | CH(Me) | —OS(O)2tBu |
| 473A | CHOH | CH(Me) | —OS(O)2tBu |
| 474A | C(Me)OH | CH(Me) | —OS(O)2tBu |
| 475A | C(O) | CH2 | —NHC(O)NMe2 |
| 476A | CHOH | CH2 | —NHC(O)NMe2 |
| 477A | C(Me)OH | CH2 | —NHC(O)NMe2 |
| 478A | C(O) | CH(Me) | —NHC(O)NMe2 |
| 479A | CHOH | CH(Me) | —NHC(O)NMe2 |
| 480A | C(Me)OH | CH(Me) | —NHC(O)NMe2 |
| 481A | C(O) | CH2 | —NHC(S)NMe2 |
| 482A | CHOH | CH2 | —NHC(S)NMe2 |
| 483A | C(Me)OH | CH2 | —NHC(S)NMe2 |
| 484A | C(O) | CH(Me) | —NHC(S)NMe2 |
| 485A | CHOH | CH(Me) | —NHC(S)NMe2 |
| 486A | C(Me)OH | CH(Me) | —NHC(S)NMe2 |
| 487A | C(O) | CH2 | —OC(O)NMe2 |
| 488A | CHOH | CH2 | —OC(O)NMe2 |
| 489A | C(Me)OH | CH2 | —OC(O)NMe2 |
| 490A | C(O) | CH(Me) | —OC(O)NMe2 |
| 491A | CHOH | CH(Me) | —OC(O)NMe2 |
| 492A | C(Me)OH | CH(Me) | —OC(O)NMe2 |
| 493A | C(O) | CH2 | —OC(S)NMe2 |
| 494A | CHOH | CH2 | —OC(S)NMe2 |
| 495A | C(Me)OH | CH2 | —OC(S)NMe2 |
| 496A | C(O) | CH(Me) | —OC(S)NMe2 |
| 497A | CHOH | CH(Me) | —OC(S)NMe2 |
| 498A | C(Me)OH | CH(Me) | —OC(S)NMe2 |
| 499A | C(O) | CH2 | —NHS(O)2NMe2 |
| 500A | CHOH | CH2 | —NHS(O)2NMe2 |
| 501A | C(Me)OH | CH2 | —NHS(O)2NMe2 |
| 502A | C(O) | CH(Me) | —NHS(O)2NMe2 |
| 503A | CHOH | CH(Me) | —NHS(O)2NMe2 |
| 504A | C(Me)OH | CH(Me) | —NHS(O)2NMe2 |
| 505A | C(O) | CH2 | —C(O)NHCH2CO2H |

TABLE 2-continued

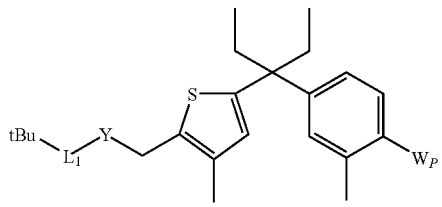

| Code | L₁ | Y | W_P |
|---|---|---|---|
| 506A | CHOH | CH2 | —C(O)NHCH2CO2H |
| 507A | C(Me)OH | CH2 | —C(O)NHCH2CO2H |
| 508A | C(O) | CH(Me) | —C(O)NHCH2CO2H |
| 509A | CHOH | CH(Me) | —C(O)NHCH2CO2H |
| 510A | C(Me)OH | CH(Me) | —C(O)NHCH2CO2H |
| 511A | C(O) | CH2 | —SO2NHCH2CO2H |
| 512A | CHOH | CH2 | —SO2NHCH2CO2H |
| 513A | C(Me)OH | CH2 | —SO2NHCH2CO2H |
| 514A | C(O) | CH(Me) | —SO2NHCH2CO2H |
| 515A | CHOH | CH(Me) | —SO2NHCH2CO2H |
| 516A | C(Me)OH | CH(Me) | —SO2NHCH2CO2H |
| 517A | C(O) | CH2 | —CH2—S—Me |
| 518A | CHOH | CH2 | —CH2—S—Me |
| 519A | C(Me)OH | CH2 | —CH2—S—Me |
| 520A | C(O) | CH(Me) | —CH2—S—Me |
| 521A | CHOH | CH(Me) | —CH2—S—Me |
| 522A | C(Me)OH | CH(Me) | —CH2—S—Me |

TABLE 3

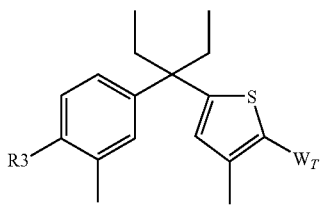

| Code | R3 | W_T |
|---|---|---|
| 1B | 3Me3OH-Pentyl | —CO2Me |
| 2B | 3Me3OH-Pentenyl | —CO2Me |
| 3B | 3Me3OH-Pentynyl | —CO2Me |
| 4B | 3Et3OH-Pentyl | —CO2Me |
| 5B | 3Et3OH-Pentenyl | —CO2Me |
| 6B | 3Et3OH-Pentynyl | —CO2Me |
| 7B | 3Me3OH-Pentyl | —CO2H |
| 8B | 3Me3OH-Pentenyl | —CO2H |
| 9B | 3Me3OH-Pentynyl | —CO2H |
| 10B | 3Et3OH-Pentyl | —CO2H |
| 11B | 3Et3OH-Pentenyl | —CO2H |
| 12B | 3Et3OH-Pentynyl | —CO2H |
| 13B | 3Me3OH-Pentyl | —C(O)NH2 |
| 14B | 3Me3OH-Pentenyl | —C(O)NH2 |
| 15B | 3Me3OH-Pentynyl | —C(O)NH2 |
| 16B | 3Et3OH-Pentyl | —C(O)NH2 |
| 17B | 3Et3OH-Pentenyl | —C(O)NH2 |
| 18B | 3Et3OH-Pentynyl | —C(O)NH2 |
| 19B | 3Me3OH-Pentyl | —C(O)NMe2 |
| 20B | 3Me3OH-Pentenyl | —C(O)NMe2 |
| 21B | 3Me3OH-Pentynyl | —C(O)NMe2 |
| 22B | 3Et3OH-Pentyl | —C(O)NMe2 |
| 23B | 3Et3OH-Pentenyl | —C(O)NMe2 |
| 24B | 3Et3OH-Pentynyl | —C(O)NMe2 |
| 25B | 3Me3OH-Pentyl | 5-tetrazolyl |
| 26B | 3Me3OH-Pentenyl | 5-tetrazolyl |
| 27B | 3Me3OH-Pentynyl | 5-tetrazolyl |
| 28B | 3Et3OH-Pentyl | 5-tetrazolyl |
| 29B | 3Et3OH-Pentenyl | 5-tetrazolyl |
| 30B | 3Et3OH-Pentynyl | 5-tetrazolyl |
| 31B | 3Me3OH-Pentyl | —C(O)—NH-5-tetrazolyl |

TABLE 3-continued

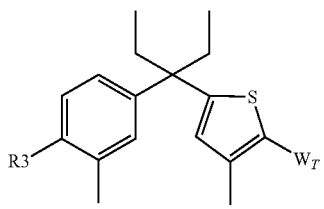

| Code | R3 | W_T |
|---|---|---|
| 32B | 3Me3OH-Pentenyl | —C(O)—NH-5-tetrazolyl |
| 33B | 3Me3OH-Pentynyl | —C(O)—NH-5-tetrazolyl |
| 34B | 3Et3OH-Pentyl | —C(O)—NH-5-tetrazolyl |
| 35B | 3Et3OH-Pentenyl | —C(O)—NH-5-tetrazolyl |
| 36B | 3Et3OH-Pentynyl | —C(O)—NH-5-tetrazolyl |
| 37B | 3Me3OH-Pentyl | —C(O)NHCH2SO2Me |
| 38B | 3Me3OH-Pentenyl | —C(O)NHCH2SO2Me |
| 39B | 3Me3OH-Pentynyl | —C(O)NHCH2SO2Me |
| 40B | 3Et3OH-Pentyl | —C(O)NHCH2SO2Me |
| 41B | 3Et3OH-Pentenyl | —C(O)NHCH2SO2Me |
| 42B | 3Et3OH-Pentynyl | —C(O)NHCH2SO2Me |
| 43B | 3Me3OH-Pentyl | —C(O)NHCH2CH2SO2Me |
| 44B | 3Me3OH-Pentenyl | —C(O)NHCH2CH2SO2Me |
| 45B | 3Me3OH-Pentynyl | —C(O)NHCH2CH2SO2Me |
| 46B | 3Et3OH-Pentyl | —C(O)NHCH2CH2SO2Me |
| 47B | 3Et3OH-Pentenyl | —C(O)NHCH2CH2SO2Me |
| 48B | 3Et3OH-Pentynyl | —C(O)NHCH2CH2SO2Me |
| 49B | 3Me3OH-Pentyl | —C(O)NHSO2Me |
| 50B | 3Me3OH-Pentenyl | —C(O)NHSO2Me |
| 51B | 3Me3OH-Pentynyl | —C(O)NHSO2Me |
| 52B | 3Et3OH-Pentyl | —C(O)NHSO2Me |
| 53B | 3Et3OH-Pentenyl | —C(O)NHSO2Me |
| 54B | 3Et3OH-Pentynyl | —C(O)NHSO2Me |
| 55B | 3Me3OH-Pentyl | —CH2—C(O)NHSO2Et |
| 56B | 3Me3OH-Pentenyl | —CH2—C(O)NHSO2Et |
| 57B | 3Me3OH-Pentynyl | —CH2—C(O)NHSO2Et |
| 58B | 3Et3OH-Pentyl | —CH2—C(O)NHSO2Et |
| 59B | 3Et3OH-Pentenyl | —CH2—C(O)NHSO2Et |
| 60B | 3Et3OH-Pentynyl | —CH2—C(O)NHSO2Et |
| 61B | 3Me3OH-Pentyl | —CH2—C(O)NHSO2iPr |
| 62B | 3Me3OH-Pentenyl | —CH2—C(O)NHSO2iPr |
| 63B | 3Me3OH-Pentynyl | —CH2—C(O)NHSO2iPr |
| 64B | 3Et3OH-Pentyl | —CH2—C(O)NHSO2iPr |
| 65B | 3Et3OH-Pentenyl | —CH2—C(O)NHSO2iPr |
| 66B | 3Et3OH-Pentynyl | —CH2—C(O)NHSO2iPr |
| 67B | 3Me3OH-Pentyl | —CH2—C(O)NHSO2tBu |
| 68B | 3Me3OH-Pentenyl | —CH2—C(O)NHSO2tBu |
| 69B | 3Me3OH-Pentynyl | —CH2—C(O)NHSO2tBu |
| 70B | 3Et3OH-Pentyl | —CH2—C(O)NHSO2tBu |
| 71B | 3Et3OH-Pentenyl | —CH2—C(O)NHSO2tBu |
| 72B | 3Et3OH-Pentynyl | —CH2—C(O)NHSO2IBu |
| 73B | 3Me3OH-Pentyl | —CH2NHSO2Me |
| 74B | 3Me3OH-Pentenyl | —CH2NHSO2Me |
| 75B | 3Me3OH-Pentynyl | —CH2NHSO2Me |
| 76B | 3Et3OH-Pentyl | —CH2NHSO2Me |
| 77B | 3Et3OH-Pentenyl | —CH2NHSO2Me |
| 78B | 3Et3OH-Pentynyl | —CH2NHSO2Me |
| 79B | 3Me3OH-Pentyl | —CH2NHSO2Et |
| 80B | 3Me3OH-Pentenyl | —CH2NHSO2Et |
| 81B | 3Me3OH-Pentynyl | —CH2NHSO2Et |
| 82B | 3Et3OH-Pentyl | —CH2NHSO2Et |
| 83B | 3Et3OH-Pentenyl | —CH2NHSO2Et |
| 84B | 3Et3OH-Pentynyl | —CH2NHSO2Et |
| 85B | 3Me3OH-Pentyl | —CH2NHSO2iPr |
| 86B | 3Me3OH-Pentenyl | —CH2NHSO2iPr |
| 87B | 3Me3OH-Pentynyl | —CH2NHSO2iPr |
| 88B | 3Et3OH-Pentyl | —CH2NHSO2iPr |
| 89B | 3Et3OH-Pentenyl | —CH2NHSO2iPr |
| 90B | 3Et3OH-Pentynyl | —CH2NHSO2iPr |
| 91B | 3Me3OH-Pentyl | —CH2NHSO2tBu |
| 92B | 3Me3OH-Pentenyl | —CH2NHSO2tBu |
| 93B | 3Me3OH-Pentynyl | —CH2NHSO2tBu |
| 94B | 3Et3OH-Pentyl | —CH2NHSO2tBu |
| 95B | 3Et3OH-Pentenyl | —CH2NHSO2tBu |
| 96B | 3Et3OH-Pentynyl | —CH2NHSO2tBu |
| 97B | 3Me3OH-Pentyl | —CH2—N-pyrrolidin-2-one |

TABLE 3-continued

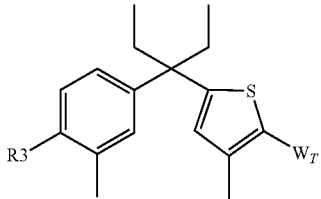

| Code | R3 | $W_T$ |
|---|---|---|
| 98B | 3Me3OH-Pentenyl | —CH2—N-pyrrolidin-2-one |
| 99B | 3Me3OH-Pentynyl | —CH2—N-pyrrolidin-2-one |
| 100B | 3Et3OH-Pentyl | —CH2—N-pyrrolidin-2-one |
| 101B | 3Et3OH-Pentenyl | —CH2—N-pyrrolidin-2-one |
| 102B | 3Et3OH-Pentynyl | —CH2—N-pyrrolidin-2-one |
| 103B | 3Me3OH-Pentyl | —CH2-(1-methylpyrrolidin-2-one-3-yl) |
| 104B | 3Me3OH-Pentenyl | —CH2-(1-methylpyrrolidin-2-one-3-yl) |
| 105B | 3Me3OH-Pentynyl | —CH2-(1-methylpyrrolidin-2-one-3-yl) |
| 106B | 3Et3OH-Pentyl | —CH2-(1-methylpyrrolidin-2-one-3-yl) |
| 107B | 3Et3OH-Pentenyl | —CH2-(1-methylpyrrolidin-2-one-3-yl) |
| 108B | 3Et3OH-Pentynyl | —CH2-(1-methylpyrrolidin-2-one-3-yl) |
| 109B | 3Me3OH-Pentyl | —CH2CO2Me |
| 110B | 3Me3OH-Pentenyl | —CH2CO2Me |
| 111B | 3Me3OH-Pentynyl | —CH2CO2Me |
| 112B | 3Et3OH-Pentyl | —CH2CO2Me |
| 113B | 3Et3OH-Pentenyl | —CH2CO2Me |
| 114B | 3Et3OH-Pentynyl | —CH2CO2Me |
| 115B | 3Me3OH-Pentyl | —CH2CO2H |
| 116B | 3Me3OH-Pentenyl | —CH2CO2H |
| 117B | 3Me3OH-Pentynyl | —CH2CO2H |
| 118B | 3Et3OH-Pentyl | —CH2CO2H |
| 119B | 3Et3OH-Pentenyl | —CH2CO2H |
| 120B | 3Et3OH-Pentynyl | —CH2CO2H |
| 121B | 3Me3OH-Pentyl | —CH2C(O)NH2 |
| 122B | 3Me3OH-Pentenyl | —CH2C(O)NH2 |
| 123B | 3Me3OH-Pentynyl | —CH2C(O)NH2 |
| 124B | 3Et3OH-Pentyl | —CH2C(O)NH2 |
| 125B | 3Et3OH-Pentenyl | —CH2C(O)NH2 |
| 126B | 3Et3OH-Pentynyl | —CH2C(O)NH2 |
| 127B | 3Me3OH-Pentyl | —CH2C(O)NMe2 |
| 128B | 3Me3OH-Pentenyl | —CH2C(O)NMe2 |
| 129B | 3Me3OH-Pentynyl | —CH2C(O)NMe2 |
| 130B | 3Et3OH-Pentyl | —CH2C(O)NMe2 |
| 131B | 3Et3OH-Pentenyl | —CH2C(O)NMe2 |
| 132B | 3Et3OH-Pentynyl | —CH2C(O)NMe2 |
| 133B | 3Me3OH-Pentyl | —CH2C(O)—N-pyrrolidine |
| 134B | 3Me3OH-Pentenyl | —CH2C(O)—N-pyrrolidine |
| 135B | 3Me3OH-Pentynyl | —CH2C(O)—N-pyrrolidine |
| 136B | 3Et3OH-Pentyl | —CH2C(O)—N-pyrrolidine |
| 137B | 3Et3OH-Pentenyl | —CH2C(O)—N-pyrrolidine |
| 138B | 3Et3OH-Pentynyl | —CH2C(O)—N-pyrrolidine |
| 139B | 3Me3OH-Pentyl | —CH2-5-tetrazolyl |
| 140B | 3Me3OH-Pentenyl | —CH2-5-tetrazolyl |
| 141B | 3Me3OH-Pentynyl | —CH2-5-tetrazolyl |
| 142B | 3Et3OH-Pentyl | —CH2-5-tetrazolyl |
| 143B | 3Et3OH-Pentenyl | —CH2-5-tetrazolyl |
| 144B | 3Et3OH-Pentynyl | —CH2-5-tetrazolyl |
| 145B | 3Me3OH-Pentyl | —C(O)C(O)OH |
| 146B | 3Me3OH-Pentenyl | —C(O)C(O)OH |
| 147B | 3Me3OH-Pentynyl | —C(O)C(O)OH |
| 148B | 3Et3OH-Pentyl | —C(O)C(O)OH |
| 149B | 3Et3OH-Pentenyl | —C(O)C(O)OH |
| 150B | 3Et3OH-Pentynyl | —C(O)C(O)OH |
| 151B | 3Me3OH-Pentyl | —CH(OH)C(O)OH |
| 152B | 3Me3OH-Pentenyl | —CH(OH)C(O)OH |
| 153B | 3Me3OH-Pentynyl | —CH(OH)C(O)OH |
| 154B | 3Et3OH-Pentyl | —CH(OH)C(O)OH |
| 155B | 3Et3OH-Pentenyl | —CH(OH)C(O)OH |
| 156B | 3Et3OH-Pentynyl | —CH(OH)C(O)OH |
| 157B | 3Me3OH-Pentyl | —C(O)C(O)NH2 |
| 158B | 3Me3OH-Pentenyl | —C(O)C(O)NH2 |
| 159B | 3Me3OH-Pentynyl | —C(O)C(O)NH2 |
| 160B | 3Et3OH-Pentyl | —C(O)C(O)NH2 |
| 161B | 3Et3OH-Pentenyl | —C(O)C(O)NH2 |
| 162B | 3Et3OH-Pentynyl | —C(O)C(O)NH2 |
| 163B | 3Me3OH-Pentyl | —CH(OH)C(O)NH2 |

TABLE 3-continued

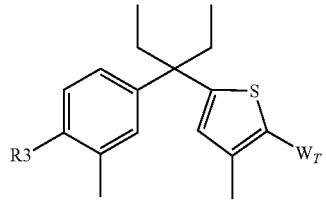

| Code | R3 | $W_T$ |
|---|---|---|
| 164B | 3Me3OH-Pentenyl | —CH(OH)C(O)NH2 |
| 165B | 3Me3OH-Pentynyl | —CH(OH)C(O)NH2 |
| 166B | 3Et3OH-Pentyl | —CH(OH)C(O)NH2 |
| 167B | 3Et3OH-Pentenyl | —CH(OH)C(O)NH2 |
| 168B | 3Et3OH-Pentynyl | —CH(OH)C(O)NH2 |
| 169B | 3Me3OH-Pentyl | —C(O)C(O)NMe2 |
| 170B | 3Me3OH-Pentenyl | —C(O)C(O)NMe2 |
| 171B | 3Me3OH-Pentynyl | —C(O)C(O)NMe2 |
| 172B | 3Et3OH-Pentyl | —C(O)C(O)NMe2 |
| 173B | 3Et3OH-Pentenyl | —C(O)C(O)NMe2 |
| 174B | 3Et3OH-Pentynyl | —C(O)C(O)NMe2 |
| 175B | 3Me3OH-Pentyl | —CH(OH)C(O)NMe2 |
| 176B | 3Me3OH-Pentenyl | —CH(OH)C(O)NMe2 |
| 177B | 3Me3OH-Pentynyl | —CH(OH)C(O)NMe2 |
| 178B | 3Et3OH-Pentyl | —CH(OH)C(O)NMe2 |
| 179B | 3Et3OH-Pentenyl | —CH(OH)C(O)NMe2 |
| 180B | 3Et3OH-Pentynyl | —CH(OH)C(O)NMe2 |
| 181B | 3Me3OH-Pentyl | —CH2CH2CO2H |
| 182B | 3Me3OH-Pentenyl | —CH2CH2CO2H |
| 183B | 3Me3OH-Pentynyl | —CH2CH2CO2H |
| 184B | 3Et3OH-Pentyl | —CH2CH2CO2H |
| 185B | 3Et3OH-Pentenyl | —CH2CH2CO2H |
| 186B | 3Et3OH-Pentynyl | —CH2CH2CO2H |
| 187B | 3Me3OH-Pentyl | —CH2CH2C(O)NH2 |
| 188B | 3Me3OH-Pentenyl | —CH2CH2C(O)NH2 |
| 189B | 3Me3OH-Pentynyl | —CH2CH2C(O)NH2 |
| 190B | 3Et3OH-Pentyl | —CH2CH2C(O)NH2 |
| 191B | 3Et3OH-Pentenyl | —CH2CH2C(O)NH2 |
| 192B | 3Et3OH-Pentynyl | —CH2CH2C(O)NH2 |
| 193B | 3Me3OH-Pentyl | —CH2CH2C(O)NMe2 |
| 194B | 3Me3OH-Pentenyl | —CH2CH2C(O)NMe2 |
| 195B | 3Me3OH-Pentynyl | —CH2CH2C(O)NMe2 |
| 196B | 3Et3OH-Pentyl | —CH2CH2C(O)NMe2 |
| 197B | 3Et3OH-Pentenyl | —CH2CH2C(O)NMe2 |
| 198B | 3Et3OH-Pentynyl | —CH2CH2C(O)NMe2 |
| 199B | 3Me3OH-Pentyl | —CH2CH2-5-tetrazolyl |
| 200B | 3Me3OH-Pentenyl | —CH2CH2-5-tetrazolyl |
| 201B | 3Me3OH-Pentynyl | —CH2CH2-5-tetrazolyl |
| 202B | 3Et3OH-Pentyl | —CH2CH2-5-tetrazolyl |
| 203B | 3Et3OH-Pentenyl | —CH2CH2-5-tetrazolyl |
| 204B | 3Et3OH-Pentynyl | —CH2CH2-5-tetrazolyl |
| 205B | 3Me3OH-Pentyl | —CH2S(O)2Me |
| 206B | 3Me3OH-Pentenyl | —CH2S(O)2Me |
| 207B | 3Me3OH-Pentynyl | —CH2S(O)2Me |
| 208B | 3Et3OH-Pentyl | —CH2S(O)2Me |
| 209B | 3Et3OH-Pentenyl | —CH2S(O)2Me |
| 210B | 3Et3OH-Pentynyl | —CH2S(O)2Me |
| 211B | 3Me3OH-Pentyl | —CH2CH2S(O)2Me |
| 212B | 3Me3OH-Pentenyl | —CH2CH2S(O)2Me |
| 213B | 3Me3OH-Pentynyl | —CH2CH2S(O)2Me |
| 214B | 3Et3OH-Pentyl | —CH2CH2S(O)2Me |
| 215B | 3Et3OH-Pentenyl | —CH2CH2S(O)2Me |
| 216B | 3Et3OH-Pentynyl | —CH2CH2S(O)2Me |
| 217B | 3Me3OH-Pentyl | —CH2CH2CH2S(O)2Me |
| 218B | 3Me3OH-Pentenyl | —CH2CH2CH2S(O)2Me |
| 219B | 3Me3OH-Pentynyl | —CH2CH2CH2S(O)2Me |
| 220B | 3Et3OH-Pentyl | —CH2CH2CH2S(O)2Me |
| 221B | 3Et3OH-Pentenyl | —CH2CH2CH2S(O)2Me |
| 222B | 3Et3OH-Pentynyl | —CH2CH2CH2S(O)2Me |
| 223B | 3Me3OH-Pentyl | —CH2S(O)2Et |
| 224B | 3Me3OH-Pentenyl | —CH2S(O)2Et |
| 225B | 3Me3OH-Pentynyl | —CH2S(O)2Et |
| 226B | 3Et3OH-Pentyl | —CH2S(O)2Et |
| 227B | 3Et3OH-Pentenyl | —CH2S(O)2Et |
| 228B | 3Et3OH-Pentynyl | —CH2S(O)2Et |
| 229B | 3Me3OH-Pentyl | —CH2CH2S(O)2Et |

TABLE 3-continued

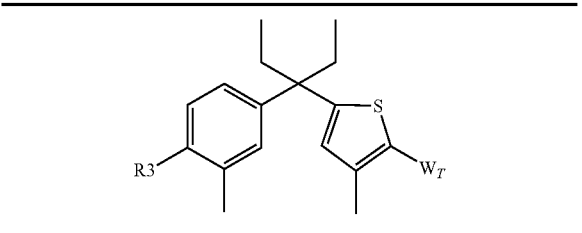

| Code | R3 | W$_T$ |
|---|---|---|
| 230B | 3Me3OH-Pentenyl | —CH2CH2S(O)2Et |
| 231B | 3Me3OH-Pentynyl | —CH2CH2S(O)2Et |
| 232B | 3Et3OH-Pentyl | —CH2CH2S(O)2Et |
| 233B | 3Et3OH-Pentenyl | —CH2CH2S(O)2Et |
| 234B | 3Et3OH-Pentynyl | —CH2CH2S(O)2Et |
| 235B | 3Me3OH-Pentyl | —CH2CH2CH2S(O)2Et |
| 236B | 3Me3OH-Pentenyl | —CH2CH2CH2S(O)2Et |
| 237B | 3Me3OH-Pentynyl | —CH2CH2CH2S(O)2Et |
| 238B | 3Et3OH-Pentyl | —CH2CH2CH2S(O)2Et |
| 239B | 3Et3OH-Pentenyl | —CH2CH2CH2S(O)2Et |
| 240B | 3Et3OH-Pentynyl | —CH2CH2CH2S(O)2Et |
| 241B | 3Me3OH-Pentyl | —CH2S(O)2iPr |
| 242B | 3Me3OH-Pentenyl | —CH2S(O)2iPr |
| 243B | 3Me3OH-Pentynyl | —CH2S(O)2iPr |
| 244B | 3Et3OH-Pentyl | —CH2S(O)2iPr |
| 245B | 3Et3OH-Pentenyl | —CH2S(O)2iPr |
| 246B | 3Et3OH-Pentynyl | —CH2S(O)2iPr |
| 247B | 3Me3OH-Pentyl | —CH2CH2S(O)2iPr |
| 248B | 3Me3OH-Pentenyl | —CH2CH2S(O)2iPr |
| 249B | 3Me3OH-Pentynyl | —CH2CH2S(O)2iPr |
| 250B | 3Et3OH-Pentyl | —CH2CH2S(O)2iPr |
| 251B | 3Et3OH-Pentenyl | —CH2CH2S(O)2iPr |
| 252B | 3Et3OH-Pentynyl | —CH2CH2S(O)2iPr |
| 253B | 3Me3OH-Pentyl | —CH2S(O)2tBu |
| 254B | 3Me3OH-Pentenyl | —CH2S(O)2tBu |
| 255B | 3Me3OH-Pentynyl | —CH2S(O)2tBu |
| 256B | 3Et3OH-Pentyl | —CH2S(O)2tBu |
| 257B | 3Et3OH-Pentenyl | —CH2S(O)2tBu |
| 258B | 3Et3OH-Pentynyl | —CH2S(O)2tBu |
| 259B | 3Me3OH-Pentyl | —CH2CH2S(O)2tBu |
| 260B | 3Me3OH-Pentenyl | —CH2CH2S(O)2tBu |
| 261B | 3Me3OH-Pentynyl | —CH2CH2S(O)2tBu |
| 262B | 3Et3OH-Pentyl | —CH2CH2S(O)2tBu |
| 263B | 3Et3OH-Pentenyl | —CH2CH2S(O)2tBu |
| 264B | 3Et3OH-Pentynyl | —CH2CH2S(O)2tBu |
| 265B | 3Me3OH-Pentyl | —CH2CH2S(O)2NH2 |
| 266B | 3Me3OH-Pentenyl | —CH2CH2S(O)2NH2 |
| 267B | 3Me3OH-Pentynyl | —CH2CH2S(O)2NH2 |
| 268B | 3Et3OH-Pentyl | —CH2CH2S(O)2NH2 |
| 269B | 3Et3OH-Pentenyl | —CH2CH2S(O)2NH2 |
| 270B | 3Et3OH-Pentynyl | —CH2CH2S(O)2NH2 |
| 271B | 3Me3OH-Pentyl | —CH2CH2S(O)2NMe2 |
| 272B | 3Me3OH-Pentenyl | —CH2CH2S(O)2NMe2 |
| 273B | 3Me3OH-Pentynyl | —CH2CH2S(O)2NMe2 |
| 274B | 3Et3OH-Pentyl | —CH2CH2S(O)2NMe2 |
| 275B | 3Et3OH-Pentenyl | —CH2CH2S(O)2NMe2 |
| 276B | 3Et3OH-Pentynyl | —CH2CH2S(O)2NMe2 |
| 277B | 3Me3OH-Pentyl | —C(O)CH2S(O)2Me |
| 278B | 3Me3OH-Pentenyl | —C(O)CH2S(O)2Me |
| 279B | 3Me3OH-Pentynyl | —C(O)CH2S(O)2Me |
| 280B | 3Et3OH-Pentyl | —C(O)CH2S(O)2Me |
| 281B | 3Et3OH-Pentenyl | —C(O)CH2S(O)2Me |
| 282B | 3Et3OH-Pentynyl | —C(O)CH2S(O)2Me |
| 283B | 3Me3OH-Pentyl | —C(O)CH2CH2S(O)2Me |
| 284B | 3Me3OH-Pentenyl | —C(O)CH2CH2S(O)2Me |
| 285B | 3Me3OH-Pentynyl | —C(O)CH2CH2S(O)2Me |
| 286B | 3Et3OH-Pentyl | —C(O)CH2CH2S(O)2Me |
| 287B | 3Et3OH-Pentenyl | —C(O)CH2CH2S(O)2Me |
| 288B | 3Et3OH-Pentynyl | —C(O)CH2CH2S(O)2Me |
| 289B | 3Me3OH-Pentyl | —CH2CH2CH2S(O)2NH2 |
| 290B | 3Me3OH-Pentenyl | —CH2CH2CH2S(O)2NH2 |
| 291B | 3Me3OH-Pentynyl | —CH2CH2CH2S(O)2NH2 |
| 292B | 3Et3OH-Pentyl | —CH2CH2CH2S(O)2NH2 |
| 293B | 3Et3OH-Pentenyl | —CH2CH2CH2S(O)2NH2 |
| 294B | 3Et3OH-Pentynyl | —CH2CH2CH2S(O)2NH2 |
| 295B | 3Me3OH-Pentyl | —S(O)2Me |

TABLE 3-continued

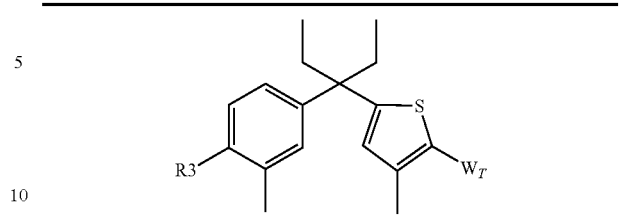

| Code | R3 | W$_T$ |
|---|---|---|
| 296B | 3Me3OH-Pentenyl | —S(O)2Me |
| 297B | 3Me3OH-Pentynyl | —S(O)2Me |
| 298B | 3Et3OH-Pentyl | —S(O)2Me |
| 299B | 3Et3OH-Pentenyl | —S(O)2Me |
| 300B | 3Et3OH-Pentynyl | —S(O)2Me |
| 301B | 3Me3OH-Pentyl | —S(O)2Et |
| 302B | 3Me3OH-Pentenyl | —S(O)2Et |
| 303B | 3Me3OH-Pentynyl | —S(O)2Et |
| 304B | 3Et3OH-Pentyl | —S(O)2Et |
| 305B | 3Et3OH-Pentenyl | —S(O)2Et |
| 306B | 3Et3OH-Pentynyl | —S(O)2Et |
| 307B | 3Me3OH-Pentyl | —S(O)2iPr |
| 308B | 3Me3OH-Pentenyl | —S(O)2iPr |
| 309B | 3Me3OH-Pentynyl | —S(O)2iPr |
| 310B | 3Et3OH-Pentyl | —S(O)2iPr |
| 311B | 3Et3OH-Pentenyl | —S(O)2iPr |
| 312B | 3Et3OH-Pentynyl | —S(O)2iPr |
| 313B | 3Me3OH-Pentyl | —S(O)2tBu |
| 314B | 3Me3OH-Pentenyl | —S(O)2tBu |
| 315B | 3Me3OH-Pentynyl | —S(O)2tBu |
| 316B | 3Et3OH-Pentyl | —S(O)2tBu |
| 317B | 3Et3OH-Pentenyl | —S(O)2tBu |
| 318B | 3Et3OH-Pentynyl | —S(O)2tBu |
| 319B | 3Me3OH-Pentyl | —S(O)2NH2 |
| 320B | 3Me3OH-Pentenyl | —S(O)2NH2 |
| 321B | 3Me3OH-Pentynyl | —S(O)2NH2 |
| 322B | 3Et3OH-Pentyl | —S(O)2NH2 |
| 323B | 3Et3OH-Pentenyl | —S(O)2NH2 |
| 324B | 3Et3OH-Pentynyl | —S(O)2NH2 |
| 325B | 3Me3OH-Pentyl | —S(O)2NMe2 |
| 326B | 3Me3OH-Pentenyl | —S(O)2NMe2 |
| 327B | 3Me3OH-Pentynyl | —S(O)2NMe2 |
| 328B | 3Et3OH-Pentyl | —S(O)2NMe2 |
| 329B | 3Et3OH-Pentenyl | —S(O)2NMe2 |
| 330B | 3Et3OH-Pentynyl | —S(O)2NMe2 |
| 331B | 3Me3OH-Pentyl | —S(O)2CH2S(O)2Me |
| 332B | 3Me3OH-Pentenyl | —S(O)2CH2S(O)2Me |
| 333B | 3Me3OH-Pentynyl | —S(O)2CH2S(O)2Me |
| 334B | 3Et3OH-Pentyl | —S(O)2CH2S(O)2Me |
| 335B | 3Et3OH-Pentenyl | —S(O)2CH2S(O)2Me |
| 336B | 3Et3OH-Pentynyl | —S(O)2CH2S(O)2Me |
| 337B | 3Me3OH-Pentyl | —S(O)2CH2S(O)2Et |
| 338B | 3Me3OH-Pentenyl | —S(O)2CH2S(O)2Et |
| 339B | 3Me3OH-Pentynyl | —S(O)2CH2S(O)2Et |
| 340B | 3Et3OH-Pentyl | —S(O)2CH2S(O)2Et |
| 341B | 3Et3OH-Pentenyl | —S(O)2CH2S(O)2Et |
| 342B | 3Et3OH-Pentynyl | —S(O)2CH2S(O)2Et |
| 343B | 3Me3OH-Pentyl | —S(O)2CH2S(O)2iPr |
| 344B | 3Me3OH-Pentenyl | —S(O)2CH2S(O)2iPr |
| 345B | 3Me3OH-Pentynyl | —S(O)2CH2S(O)2iPr |
| 346B | 3Et3OH-Pentyl | —S(O)2CH2S(O)2iPr |
| 347B | 3Et3OH-Pentenyl | —S(O)2CH2S(O)2iPr |
| 348B | 3Et3OH-Pentynyl | —S(O)2CH2S(O)2iPr |
| 349B | 3Me3OH-Pentyl | —S(O)2CH2S(O)2tBu |
| 350B | 3Me3OH-Pentenyl | —S(O)2CH2S(O)2tBu |
| 351B | 3Me3OH-Pentynyl | —S(O)2CH2S(O)2tBu |
| 352B | 3Et3OH-Pentyl | —S(O)2CH2S(O)2tBu |
| 353B | 3Et3OH-Pentenyl | —S(O)2CH2S(O)2tBu |
| 354B | 3Et3OH-Pentynyl | —S(O)2CH2S(O)2tBu |
| 355B | 3Me3OH-Pentyl | —C(O)NHCH2CO2H |
| 356B | 3Me3OH-Pentenyl | —C(O)NHCH2CO2H |
| 357B | 3Me3OH-Pentynyl | —C(O)NHCH2CO2H |
| 358B | 3Et3OH-Pentyl | —C(O)NHCH2CO2H |
| 359B | 3Et3OH-Pentenyl | —C(O)NHCH2CO2H |
| 360B | 3Et3OH-Pentynyl | —C(O)NHCH2CO2H |
| 361B | 3Me3OH-Pentyl | —SO2NHCH2CO2H |

TABLE 3-continued

| Code | R3 | $W_T$ |
|---|---|---|
| 362B | 3Me3OH-Pentenyl | —SO2NHCH2CO2H |
| 363B | 3Me3OH-Pentynyl | —SO2NHCH2CO2H |
| 364B | 3Et3OH-Pentyl | —SO2NHCH2CO2H |
| 365B | 3Et3OH-Pentenyl | —SO2NHCH2CO2H |
| 366B | 3Et3OH-Pentynyl | —SO2NHCH2CO2H |
| 367B | 3Me3OH-Pentyl | —CH2—S-Me |

TABLE 3-continued

| Code | R3 | $W_T$ |
|---|---|---|
| 368B | 3Me3OH-Pentenyl | —CH2—S-Me |
| 369B | 3Me3OH-Pentynyl | —CH2—S-Me |
| 370B | 3Et3OH-Pentyl | —CH2—S-Me |
| 371B | 3Et3OH-Pentenyl | —CH2—S-Me |
| 372B | 3Et3OH-Pentynyl | —CH2—S-Me |

TABLE 4

| Code | R4 | $L_1$ | $W_T$ |
|---|---|---|---|
| 1C | 1-hydroxycyclopentyl | —(CH2)2— | —CO2Me |
| 2C | 1-hydroxycyclopentyl | —C≡C— | —CO2Me |
| 3C | 1-hydroxycyclopentyl | —C=C— | —CO2Me |
| 4C | 1-hydroxycyclohexyl | —(CH2)2— | —CO2Me |
| 5C | 1-hydroxycyclohexyl | —C≡C— | —CO2Me |
| 6C | 1-hydroxycyclohexyl | —C=C— | —CO2Me |
| 7C | 1-hydroxycyclopentyl | —(CH2)2— | —CO2H |
| 8C | 1-hydroxycyclopentyl | —C≡C— | —CO2H |
| 9C | 1-hydroxycyclopentyl | —C=C— | —CO2H |
| 10C | 1-hydroxycyclohexyl | —(CH2)2— | —CO2H |
| 11C | 1-hydroxycyclohexyl | —C≡C— | —CO2H |
| 12C | 1-hydroxycyclohexyl | —C=C— | —CO2H |
| 13C | 1-hydroxycyclopentyl | —(CH2)2— | —C(O)NH2 |
| 14C | 1-hydroxycyclopentyl | —C≡C— | —C(O)NH2 |
| 15C | 1-hydroxycyclopentyl | —C=C— | —C(O)NH2 |
| 16C | 1-hydroxycyclohexyl | —(CH2)2— | —C(O)NH2 |
| 17C | 1-hydroxycyclohexyl | —C≡C— | —C(O)NH2 |
| 18C | 1-hydroxycyclohexyl | —C=C— | —C(O)NH2 |
| 19C | 1-hydroxycyclopentyl | —(CH2)2— | —C(O)NMe2 |
| 20C | 1-hydroxycyclopentyl | —C≡C— | —C(O)NMe2 |
| 21C | 1-hydroxycyclopentyl | —C=C— | —C(O)NMe2 |
| 22C | 1-hydroxycyclohexyl | —(CH2)2— | —C(O)NMe2 |
| 23C | 1-hydroxycyclohexyl | —C≡C— | —C(O)NMe2 |
| 24C | 1-hydroxycyclohexyl | —C=C— | —C(O)NMe2 |
| 25C | 1-hydroxycyclopentyl | —(CH2)2— | 5-tetrazolyl |
| 26C | 1-hydroxycyclopentyl | —C≡C— | 5-tetrazolyl |
| 27C | 1-hydroxycyclopentyl | —C=C— | 5-tetrazolyl |
| 28C | 1-hydroxycyclohexyl | —(CH2)2— | 5-tetrazolyl |
| 29C | 1-hydroxycyclohexyl | —C≡C— | 5-tetrazolyl |
| 30C | 1-hydroxycyclohexyl | —C=C— | 5-tetrazolyl |
| 31C | 1-hydroxycyclopentyl | —(CH2)2— | —C(O)—NH-5-tetrazolyl |
| 32C | 1-hydroxycyclopentyl | —C≡C— | —C(O)—NH-5-tetrazolyl |
| 33C | 1-hydroxycyclopentyl | —C=C— | —C(O)—NH-5-tetrazolyl |
| 34C | 1-hydroxycyclohexyl | —(CH2)2— | —C(O)—NH-5-tetrazolyl |
| 35C | 1-hydroxycyclohexyl | —C≡C— | —C(O)—NH-5-tetrazolyl |
| 36C | 1-hydroxycyclohexyl | —C=C— | —C(O)—NH-5-tetrazolyl |
| 37C | 1-hydroxycyclopentyl | —(CH2)2— | —C(O)NHCH2SO2Me |
| 38C | 1-hydroxycyclopentyl | —C≡C— | —C(O)NHCH2SO2Me |
| 39C | 1-hydroxycyclopentyl | —C=C— | —C(O)NHCH2SO2Me |
| 40C | 1-hydroxycyclohexyl | —(CH2)2— | —C(O)NHCH2SO2Me |
| 41C | 1-hydroxycyclohexyl | —C≡C— | —C(O)NHCH2SO2Me |
| 42C | 1-hydroxycyclohexyl | —C=C— | —C(O)NHCH2SO2Me |

TABLE 4-continued

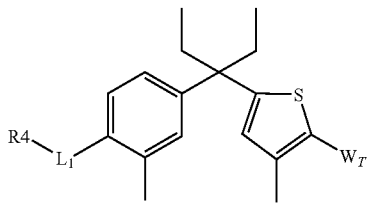

| Code | R4 | L₁ | W_T |
|---|---|---|---|
| 43C | 1-hydroxycyclopentyl | —(CH2)2— | —C(O)NHCH2CH2SO2Me |
| 44C | 1-hydroxycyclopentyl | —C≡C— | —C(O)NHCH2CH2SO2Me |
| 45C | 1-hydroxycyclopentyl | —C=C— | —C(O)NHCH2CH2SO2Me |
| 46C | 1-hydroxycyclohexyl | —(CH2)2— | —C(O)NHCH2CH2SO2Me |
| 47C | 1-hydroxycyclohexyl | —C≡C— | —C(O)NHCH2CH2SO2Me |
| 48C | 1-hydroxycyclohexyl | —C=C— | —C(O)NHCH2CH2SO2Me |
| 49C | 1-hydroxycyclopentyl | —(CH2)2— | —C(O)NHSO2Me |
| 50C | 1-hydroxycyclopentyl | —C≡C— | —C(O)NHSO2Me |
| 51C | 1-hydroxycyclopentyl | —C=C— | —C(O)NHSO2Me |
| 52C | 1-hydroxycyclohexyl | —(CH2)2— | —C(O)NHSO2Me |
| 53C | 1-hydroxycyclohexyl | —C≡C— | —C(O)NHSO2Me |
| 54C | 1-hydroxycyclohexyl | —C=C— | —C(O)NHSO2Me |
| 55C | 1-hydroxycyclopentyl | —(CH2)2— | —CH2—C(O)NHSO2Et |
| 56C | 1-hydroxycyclopentyl | —C≡C— | —CH2—C(O)NHSO2Et |
| 57C | 1-hydroxycyclopentyl | —C=C— | —CH2—C(O)NHSO2Et |
| 58C | 1-hydroxycyclohexyl | —(CH2)2— | —CH2—C(O)NHSO2Et |
| 59C | 1-hydroxycyclohexyl | —C≡C— | —CH2—C(O)NHSO2Et |
| 60C | 1-hydroxycyclohexyl | —C=C— | —CH2—C(O)NHSO2Et |
| 61C | 1-hydroxycyclopentyl | —(CH2)2— | —CH2—C(O)NHSO2iPr |
| 62C | 1-hydroxycyclopentyl | —C≡C— | —CH2—C(O)NHSO2iPr |
| 63C | 1-hydroxycyclopentyl | —C=C— | —CH2—C(O)NHSO2iPr |
| 64C | 1-hydroxycyclohexyl | —(CH2)2— | —CH2—C(O)NHSO2iPr |
| 65C | 1-hydroxycyclohexyl | —C≡C— | —CH2—C(O)NHSO2iPr |
| 66C | 1-hydroxycyclohexyl | —C=C— | —CH2—C(O)NHSO2iPr |
| 67C | 1-hydroxycyclopentyl | —(CH2)2— | —CH2—C(O)NHSO2tBu |
| 68C | 1-hydroxycyclopentyl | —C≡C— | —CH2—C(O)NHSO2tBu |
| 69C | 1-hydroxycyclopentyl | —C=C— | —CH2—C(O)NHSO2tBu |
| 70C | 1-hydroxycyclohexyl | —(CH2)2— | —CH2—C(O)NHSO2tBu |
| 71C | 1-hydroxycyclohexyl | —C≡C— | —CH2—C(O)NHSO2tBu |
| 72C | 1-hydroxycyclohexyl | —C=C— | —CH2—C(O)NHSO2tBu |
| 73C | 1-hydroxycyclopentyl | —(CH2)2— | —CH2NHSO2Me |
| 74C | 1-hydroxycyclopentyl | —C≡C— | —CH2NHSO2Me |
| 75C | 1-hydroxycyclopentyl | —C=C— | —CH2NHSO2Me |
| 76C | 1-hydroxycyclohexyl | —(CH2)2— | —CH2NHSO2Me |
| 77C | 1-hydroxycyclohexyl | —C≡C— | —CH2NHSO2Me |
| 78C | 1-hydroxycyclohexyl | —C=C— | —CH2NHSO2Me |
| 79C | 1-hydroxycyclopentyl | —(CH2)2— | —CH2NHSO2Et |
| 80C | 1-hydroxycyclopentyl | —C≡C— | —CH2NHSO2Et |
| 81C | 1-hydroxycyclopentyl | —C=C— | —CH2NHSO2Et |
| 82C | 1-hydroxycyclohexyl | —(CH2)2— | —CH2NHSO2Et |
| 83C | 1-hydroxycyclohexyl | —C≡C— | —CH2NHSO2Et |
| 84C | 1-hydroxycyclohexyl | —C=C— | —CH2NHSO2Et |
| 85C | 1-hydroxycyclopentyl | —(CH2)2— | —CH2NHSO2iPr |
| 86C | 1-hydroxycyclopentyl | —C≡C— | —CH2NHSO2iPr |
| 87C | 1-hydroxycyclopentyl | —C=C— | —CH2NHSO2iPr |
| 88C | 1-hydroxycyclohexyl | —(CH2)2— | —CH2NHSO2iPr |
| 89C | 1-hydroxycyclohexyl | —C≡C— | —CH2NHSO2iPr |
| 90C | 1-hydroxycyclohexyl | —C=C— | —CH2NHSO2iPr |
| 91C | 1-hydroxycyclopentyl | —(CH2)2— | —CH2NHSO2tBu |
| 92C | 1-hydroxycyclopentyl | —C≡C— | —CH2NHSO2tBu |
| 93C | 1-hydroxycyclopentyl | —C=C— | —CH2NHSO2tBu |
| 94C | 1-hydroxycyclohexyl | —(CH2)2— | —CH2NHSO2tBu |
| 95C | 1-hydroxycyclohexyl | —C≡C— | —CH2NHSO2tBu |
| 96C | 1-hydroxycyclohexyl | —C=C— | —CH2NHSO2tBu |
| 97C | 1-hydroxycyclopentyl | —(CH2)2— | —CH2—N-pyrrolidin-2-one |
| 98C | 1-hydroxycyclopentyl | —C≡C— | —CH2—N-pyrrolidin-2-one |
| 99C | 1-hydroxycyclopentyl | —C=C— | —CH2—N-pyrrolidin-2-one |
| 100C | 1-hydroxycyclohexyl | —(CH2)2— | —CH2—N-pyrrolidin-2-one |
| 101C | 1-hydroxycyclohexyl | —C≡C— | —CH2—N-pyrrolidin-2-one |
| 102C | 1-hydroxycyclohexyl | —C=C— | —CH2—N-pyrrolidin-2-one |
| 103C | 1-hydroxycyclopentyl | —(CH2)2— | —CH2-(1-methylpyrrolidin-2-one-3-yl) |
| 104C | 1-hydroxycyclopentyl | —C≡C— | —CH2-(1-methylpyrrolidin-2-one-3-yl) |
| 105C | 1-hydroxycyclopentyl | —C=C— | —CH2-(1-methylpyrrolidin-2-one-3-yl) |
| 106C | 1-hydroxycyclohexyl | —(CH2)2— | —CH2-(1-methylpyrrolidin-2-one-3-yl) |
| 107C | 1-hydroxycyclohexyl | —C≡C— | —CH2-(1-methylpyrrolidin-2-one-3-yl) |
| 108C | 1-hydroxycyclohexyl | —C=C— | —CH2-(1-methylpyrrolidin-2-one-3-yl) |

TABLE 4-continued

| Code | R4 | L₁ | W_T |
|---|---|---|---|
| 109C | 1-hydroxycyclopentyl | —(CH2)2— | —CH2CO2Me |
| 110C | 1-hydroxycyclopentyl | —C≡C— | —CH2CO2Me |
| 111C | 1-hydroxycyclopentyl | —C=C— | —CH2CO2Me |
| 112C | 1-hydroxycyclohexyl | —(CH2)2— | —CH2CO2Me |
| 113C | 1-hydroxycyclohexyl | —C≡C— | —CH2CO2Me |
| 114C | 1-hydroxycyclohexyl | —C=C— | —CH2CO2Me |
| 115C | 1-hydroxycyclopentyl | —(CH2)2— | —CH2CO2H |
| 116C | 1-hydroxycyclopentyl | —C≡C— | —CH2CO2H |
| 117C | 1-hydroxycyclopentyl | —C=C— | —CH2CO2H |
| 118C | 1-hydroxycyclohexyl | —(CH2)2— | —CH2CO2H |
| 119C | 1-hydroxycyclohexyl | —C≡C— | —CH2CO2H |
| 120C | 1-hydroxycyclohexyl | —C=C— | —CH2CO2H |
| 121C | 1-hydroxycyclopentyl | —(CH2)2— | —CH2C(O)NH2 |
| 122C | 1-hydroxycyclopentyl | —C≡C— | —CH2C(O)NH2 |
| 123C | 1-hydroxycyclopentyl | —C=C— | —CH2C(O)NH2 |
| 124C | 1-hydroxycyclohexyl | —(CH2)2— | —CH2C(O)NH2 |
| 125C | 1-hydroxycyclohexyl | —C≡C— | —CH2C(O)NH2 |
| 126C | 1-hydroxycyclohexyl | —C=C— | —CH2C(O)NH2 |
| 127C | 1-hydroxycyclopentyl | —(CH2)2— | —CH2C(O)NMe2 |
| 128C | 1-hydroxycyclopentyl | —C≡C— | —CH2C(O)NMe2 |
| 129C | 1-hydroxycyclopentyl | —C=C— | —CH2C(O)NMe2 |
| 130C | 1-hydroxycyclohexyl | —(CH2)2— | —CH2C(O)NMe2 |
| 131C | 1-hydroxycyclohexyl | —C≡C— | —CH2C(O)NMe2 |
| 132C | 1-hydroxycyclohexyl | —C=C— | —CH2C(O)NMe2 |
| 133C | 1-hydroxycyclopentyl | —(CH2)2— | —CH2C(O)—N-pyrrolidine |
| 134C | 1-hydroxycyclopentyl | —C≡C— | —CH2C(O)—N-pyrrolidine |
| 135C | 1-hydroxycyclopentyl | —C=C— | —CH2C(O)—N-pyrrolidine |
| 136C | 1-hydroxycyclohexyl | —(CH2)2— | —CH2C(O)—N-pyrrolidine |
| 137C | 1-hydroxycyclohexyl | —C≡C— | —CH2C(O)—N-pyrrolidine |
| 138C | 1-hydroxycyclohexyl | —C=C— | —CH2C(O)—N-pyrrolidine |
| 139C | 1-hydroxycyclopentyl | —(CH2)2— | —CH2-5-tetrazolyl |
| 140C | 1-hydroxycyclopentyl | —C≡C— | —CH2-5-tetrazolyl |
| 141C | 1-hydroxycyclopentyl | —C=C— | —CH2-5-tetrazolyl |
| 142C | 1-hydroxycyclohexyl | —(CH2)2— | —CH2-5-tetrazolyl |
| 143C | 1-hydroxycyclohexyl | —C≡C— | —CH2-5-tetrazolyl |
| 144C | 1-hydroxycyclohexyl | —C=C— | —CH2-5-tetrazolyl |
| 145C | 1-hydroxycyclopentyl | —(CH2)2— | —C(O)C(O)OH |
| 146C | 1-hydroxycyclopentyl | —C≡C— | —C(O)C(O)OH |
| 147C | 1-hydroxycyclopentyl | —C=C— | —C(O)C(O)OH |
| 148C | 1-hydroxycyclohexyl | —(CH2)2— | —C(O)C(O)OH |
| 149C | 1-hydroxycyclohexyl | —C≡C— | —C(O)C(O)OH |
| 150C | 1-hydroxycyclohexyl | —C=C— | —C(O)C(O)OH |
| 151C | 1-hydroxycyclopentyl | —(CH2)2— | —CH(OH)C(O)OH |
| 152C | 1-hydroxycyclopentyl | —C≡C— | —CH(OH)C(O)OH |
| 153C | 1-hydroxycyclopentyl | —C=C— | —CH(OH)C(O)OH |
| 154C | 1-hydroxycyclohexyl | —(CH2)2— | —CH(OH)C(O)OH |
| 155C | 1-hydroxycyclohexyl | —C≡C— | —CH(OH)C(O)OH |
| 156C | 1-hydroxycyclohexyl | —C=C— | —CH(OH)C(O)OH |
| 157C | 1-hydroxycyclopentyl | —(CH2)2— | —C(O)C(O)NH2 |
| 158C | 1-hydroxycyclopentyl | —C≡C— | —C(O)C(O)NH2 |
| 159C | 1-hydroxycyclopentyl | —C=C— | —C(O)C(O)NH2 |
| 160C | 1-hydroxycyclohexyl | —(CH2)2— | —C(O)C(O)NH2 |
| 161C | 1-hydroxycyclohexyl | —C≡C— | —C(O)C(O)NH2 |
| 162C | 1-hydroxycyclohexyl | —C=C— | —C(O)C(O)NH2 |
| 163C | 1-hydroxycyclopentyl | —(CH2)2— | —CH(OH)C(O)NH2 |
| 164C | 1-hydroxycyclopentyl | —C≡C— | —CH(OH)C(O)NH2 |
| 165C | 1-hydroxycyclopentyl | —C=C— | —CH(OH)C(O)NH2 |
| 166C | 1-hydroxycyclohexyl | —(CH2)2— | —CH(OH)C(O)NH2 |
| 167C | 1-hydroxycyclohexyl | —C≡C— | —CH(OH)C(O)NH2 |
| 168C | 1-hydroxycyclohexyl | —C=C— | —CH(OH)C(O)NH2 |
| 169C | 1-hydroxycyclopentyl | —(CH2)2— | —C(O)C(O)NMe2 |
| 170C | 1-hydroxycyclopentyl | —C≡C— | —C(O)C(O)NMe2 |
| 171C | 1-hydroxycyclopentyl | —C=C— | —C(O)C(O)NMe2 |
| 172C | 1-hydroxycyclohexyl | —(CH2)2— | —C(O)C(O)NMe2 |
| 173C | 1-hydroxycyclohexyl | —C≡C— | —C(O)C(O)NMe2 |
| 174C | 1-hydroxycyclohexyl | —C=C— | —C(O)C(O)NMe2 |

TABLE 4-continued

| Code | R4 | $L_1$ | $W_T$ |
|---|---|---|---|
| 175C | 1-hydroxycyclopentyl | —(CH2)2— | —CH(OH)C(O)NMe2 |
| 176C | 1-hydroxycyclopentyl | —C≡C— | —CH(OH)C(O)NMe2 |
| 177C | 1-hydroxycyclopentyl | —C=C— | —CH(OH)C(O)NMe2 |
| 178C | 1-hydroxycyclohexyl | —(CH2)2— | —CH(OH)C(O)NMe2 |
| 179C | 1-hydroxycyclohexyl | —C≡C— | —CH(OH)C(O)NMe2 |
| 180C | 1-hydroxycyclohexyl | —C=C— | —CH(OH)C(O)NMe2 |
| 181C | 1-hydroxycyclopentyl | —(CH2)2— | —CH2CH2CO2H |
| 182C | 1-hydroxycyclopentyl | —C≡C— | —CH2CH2CO2H |
| 183C | 1-hydroxycyclopentyl | —C=C— | —CH2CH2CO2H |
| 184C | 1-hydroxycyclohexyl | —(CH2)2— | —CH2CH2CO2H |
| 185C | 1-hydroxycyclohexyl | —C≡C— | —CH2CH2CO2H |
| 186C | 1-hydroxycyclohexyl | —C=C— | —CH2CH2CO2H |
| 187C | 1-hydroxycyclopentyl | —(CH2)2— | —CH2CH2C(O)NH2 |
| 188C | 1-hydroxycyclopentyl | —C≡C— | —CH2CH2C(O)NH2 |
| 189C | 1-hydroxycyclopentyl | —C=C— | —CH2CH2C(O)NH2 |
| 190C | 1-hydroxycyclohexyl | —(CH2)2— | —CH2CH2C(O)NH2 |
| 191C | 1-hydroxycyclohexyl | —C≡C— | —CH2CH2C(O)NH2 |
| 192C | 1-hydroxycyclohexyl | —C=C— | —CH2CH2C(O)NH2 |
| 193C | 1-hydroxycyclopentyl | —(CH2)2— | —CH2CH2C(O)NMe2 |
| 194C | 1-hydroxycyclopentyl | —C≡C— | —CH2CH2C(O)NMe2 |
| 195C | 1-hydroxycyclopentyl | —C=C— | —CH2CH2C(O)NMe2 |
| 196C | 1-hydroxycyclohexyl | —(CH2)2— | —CH2CH2C(O)NMe2 |
| 197C | 1-hydroxycyclohexyl | —C≡C— | —CH2CH2C(O)NMe2 |
| 198C | 1-hydroxycyclohexyl | —C=C— | —CH2CH2C(O)NMe2 |
| 199C | 1-hydroxycyclopentyl | —(CH2)2— | —CH2CH2-5-tetrazolyl |
| 200C | 1-hydroxycyclopentyl | —C≡C— | —CH2CH2-5-tetrazolyl |
| 201C | 1-hydroxycyclopentyl | —C=C— | —CH2CH2-5-tetrazolyl |
| 202C | 1-hydroxycyclohexyl | —(CH2)2— | —CH2CH2-5-tetrazolyl |
| 203C | 1-hydroxycyclohexyl | —C≡C— | —CH2CH2-5-tetra.zolyl |
| 204C | 1-hydroxycyclohexyl | —C=C— | —CH2CH2-5-tetrazolyl |
| 205C | 1-hydroxycyclopentyl | —(CH2)2— | —CH2S(O)2Me |
| 206C | 1-hydroxycyclopentyl | —C≡C— | —CH2S(O)2Me |
| 207C | 1-hydroxycyclopentyl | —C=C— | —CH2S(O)2Me |
| 208C | 1-hydroxycyclohexyl | —(CH2)2— | —CH2S(O)2Me |
| 209C | 1-hydroxycyclohexyl | —C≡C— | —CH2S(O)2Me |
| 210C | 1-hydroxycyclohexyl | —C=C— | —CH2S(O)2Me |
| 211C | 1-hydroxycyclopentyl | —(CH2)2— | —CH2CH2S(O)2Me |
| 212C | 1-hydroxycyclopentyl | —C≡C— | —CH2CH2S(O)2Me |
| 213C | 1-hydroxycyclopentyl | —C=C— | —CH2CH2S(O)2Me |
| 214C | 1-hydroxycyclohexyl | —(CH2)2— | —CH2CH2S(O)2Me |
| 215C | 1-hydroxycyclohexyl | —C≡C— | —CH2CH2S(O)2Me |
| 216C | 1-hydroxycyclohexyl | —C=C— | —CH2CH2S(O)2Me |
| 217C | 1-hydroxycyclopentyl | —(CH2)2— | —CH2CH2CH2S(O)2Me |
| 218C | 1-hydroxycyclopentyl | —C≡C— | —CH2CH2CH2S(O)2Me |
| 219C | 1-hydroxycyclopentyl | —C=C— | —CH2CH2CH2S(O)2Me |
| 220C | 1-hydroxycyclohexyl | —(CH2)2— | —CH2CH2CH2S(O)2Me |
| 221C | 1-hydroxycyclohexyl | —C≡C— | —CH2CH2CH2S(O)2Me |
| 222C | 1-hydroxycyclohexyl | —C=C— | —CH2CH2CH2S(O)2Me |
| 223C | 1-hydroxycyclopentyl | —(CH2)2— | —CH2S(O)2Et |
| 224C | 1-hydroxycyclopentyl | —C≡C— | —CH2S(O)2Et |
| 225C | 1-hydroxycyclopentyl | —C=C— | —CH2S(O)2Et |
| 226C | 1-hydroxycyclohexyl | —(CH2)2— | —CH2S(O)2Et |
| 227C | 1-hydroxycyclohexyl | —C≡C— | —CH2S(O)2Et |
| 228C | 1-hydroxycyclohexyl | —C=C— | —CH2S(O)2Et |
| 229C | 1-hydroxycyclopentyl | —(CH2)2— | —CH2CH2S(O)2Et |
| 230C | 1-hydroxycyclopentyl | —C≡C— | —CH2CH2S(O)2Et |
| 231C | 1-hydroxycyclopentyl | —C=C— | —CH2CH2S(O)2Et |
| 232C | 1-hydroxycyclohexyl | —(CH2)2— | —CH2CH2S(O)2Et |
| 233C | 1-hydroxycyclohexyl | —C≡C— | —CH2CH2S(O)2Et |
| 234C | 1-hydroxycyclohexyl | —C=C— | —CH2CH2S(O)2Et |
| 235C | 1-hydroxycyclopentyl | —(CH2)2— | —CH2CH2CH2S(O)2Et |
| 236C | 1-hydroxycyclopentyl | —C≡C— | —CH2CH2CH2S(O)2Et |
| 237C | 1-hydroxycyclopentyl | —C=C— | —CH2CH2CH2S(O)2Et |
| 238C | 1-hydroxycyclohexyl | —(CH2)2— | —CH2CH2CH2S(O)2Et |
| 239C | 1-hydroxycyclohexyl | —C≡C— | —CH2CH2CH2S(O)2Et |
| 240C | 1-hydroxycyclohexyl | —C=C— | —CH2CH2CH2S(O)2Et |

TABLE 4-continued

| Code | R4 | L₁ | W_T |
|---|---|---|---|
| 241C | 1-hydroxycyclopentyl | —(CH2)2— | —CH2S(O)2iPr |
| 242C | 1-hydroxycyclopentyl | —C≡C— | —CH2S(O)2iPr |
| 243C | 1-hydroxycyclopentyl | —C=C— | —CH2S(O)2iPr |
| 244C | 1-hydroxycyclohexyl | —(CH2)2— | —CH2S(O)2iPr |
| 245C | 1-hydroxycyclohexyl | —C≡C— | —CH2S(O)2iPr |
| 246C | 1-hydroxycyclohexyl | —C=C— | —CH2S(O)2iPr |
| 247C | 1-hydroxycyclopentyl | —(CH2)2— | —CH2CH2S(O)2iPr |
| 248C | 1-hydroxycyclopentyl | —C≡C— | —CH2CH2S(O)2iPr |
| 249C | 1-hydroxycyclopentyl | —C=C— | —CH2CH2S(O)2iPr |
| 250C | 1-hydroxycyclohexyl | —(CH2)2— | —CH2CH2S(O)2iPr |
| 251C | 1-hydroxycyclohexyl | —C≡C— | —CH2CH2S(O)2iPr |
| 252C | 1-hydroxycyclohexyl | —C=C— | —CH2CH2S(O)2iPr |
| 253C | 1-hydroxycyclopentyl | —(CH2)2— | —CH2S(O)2tBu |
| 254C | 1-hydroxycyclopentyl | —C≡C— | —CH2S(O)2tBu |
| 255C | 1-hydroxycyclopentyl | —C=C— | —CH2S(O)2tBu |
| 256C | 1-hydroxycyclohexyl | —(CH2)2— | —CH2S(O)2tBu |
| 257C | 1-hydroxycyclohexyl | —C≡C— | —CH2S(O)2tBu |
| 258C | 1-hydroxycyclohexyl | —C=C— | —CH2S(O)2tBu |
| 259C | 1-hydroxycyclopentyl | —(CH2)2— | —CH2CH2S(O)2tBu |
| 260C | 1-hydroxycyclopentyl | —C≡C— | —CH2CH2S(O)2tBu |
| 261C | 1-hydroxycyclopentyl | —C=C— | —CH2CH2S(O)2tBu |
| 262C | 1-hydroxycyclohexyl | —(CH2)2— | —CH2CH2S(O)2tBu |
| 263C | 1-hydroxycyclohexyl | —C≡C— | —CH2CH2S(O)2tBu |
| 264C | 1-hydroxycyclohexyl | —C=C— | —CH2CH2S(O)2tBu |
| 265C | 1-hydroxycyclopentyl | —(CH2)2— | —CH2CH2S(O)2NH2 |
| 266C | 1-hydroxycyclopentyl | —C≡C— | —CH2CH2S(O)2NH2 |
| 267C | 1-hydroxycyclopentyl | —C=C— | —CH2CH2S(O)2NH2 |
| 268C | 1-hydroxycyclohexyl | —(CH2)2— | —CH2CH2S(O)2NH2 |
| 269C | 1-hydroxycyclohexyl | —C≡C— | —CH2CH2S(O)2NH2 |
| 270C | 1-hydroxycyclohexyl | —C=C— | —CH2CH2S(O)2NH2 |
| 271C | 1-hydroxycyclopentyl | —(CH2)2— | —CH2CH2S(O)2NMe2 |
| 272C | 1-hydroxycyclopentyl | —C≡C— | —CH2CH2S(O)2NMe2 |
| 273C | 1-hydroxycyclopentyl | —C=C— | —CH2CH2S(O)2NMe2 |
| 274C | 1-hydroxycyclohexyl | —(CH2)2— | —CH2CH2S(O)2NMe2 |
| 275C | 1-hydroxycyclohexyl | —C≡C— | —CH2CH2S(O)2NMe2 |
| 276C | 1-hydroxycyclohexyl | —C=C— | —CH2CH2S(O)2NMe2 |
| 277C | 1-hydroxycyclopentyl | —(CH2)2— | —C(O)CH2S(O)2Me |
| 278C | 1-hydroxycyclopentyl | —C≡C— | —C(O)CH2S(O)2Me |
| 279C | 1-hydroxycyclopentyl | —C=C— | —C(O)CH2S(O)2Me |
| 280C | 1-hydroxycyclohexyl | —(CH2)2— | —C(O)CH2S(O)2Me |
| 281C | 1-hydroxycyclohexyl | —C≡C— | —C(O)CH2S(O)2Me |
| 282C | 1-hydroxycyclohexyl | —C=C— | —C(O)CH2S(O)2Me |
| 283C | 1-hydroxycyclopentyl | —(CH2)2— | —C(O)CH2CH2S(O)2Me |
| 284C | 1-hydroxycyclopentyl | —C≡C— | —C(O)CH2CH2S(O)2Me |
| 285C | 1-hydroxycyclopentyl | —C=C— | —C(O)CH2CH2S(O)2Me |
| 286C | 1-hydroxycyclohexyl | —(CH2)2— | —C(O)CH2CH2S(O)2Me |
| 287C | 1-hydroxycyclohexyl | —C≡C— | —C(O)CH2CH2S(O)2Me |
| 288C | 1-hydroxycyclohexyl | —C=C— | —C(O)CH2CH2S(O)2Me |
| 289C | 1-hydroxycyclopentyl | —(CH2)2— | —CH2CH2CH2S(O)2NH2 |
| 290C | 1-hydroxycyclopentyl | —C≡C— | —CH2CH2CH2S(O)2NH2 |
| 291C | 1-hydroxycyclopentyl | —C=C— | —CH2CH2CH2S(O)2NH2 |
| 292C | 1-hydroxycyclohexyl | —(CH2)2— | —CH2CH2CH2S(O)2NH2 |
| 293C | 1-hydroxycyclohexyl | —C≡C— | —CH2CH2CH2S(O)2NH2 |
| 294C | 1-hydroxycyclohexyl | —C=C— | —CH2CH2CH2S(O)2NH2 |
| 295C | 1-hydroxycyclopentyl | —(CH2)2— | —S(O)2Me |
| 296C | 1-hydroxycyclopentyl | —C≡C— | —S(O)2Me |
| 297C | 1-hydroxycyclopentyl | —C=C— | —S(O)2Me |
| 298C | 1-hydroxycyclohexyl | —(CH2)2— | —S(O)2Me |
| 299C | 1-hydroxycyclohexyl | —C≡C— | —S(O)2Me |
| 300C | 1-hydroxycyclohexyl | —C=C— | —S(O)2Me |
| 301C | 1-hydroxycyclopentyl | —(CH2)2— | —S(O)2Et |
| 302C | 1-hydroxycyclopentyl | —C≡C— | —S(O)2Et |
| 303C | 1-hydroxycyclopentyl | —C=C— | —S(O)2Et |
| 304C | 1-hydroxycyclohexyl | —(CH2)2— | —S(O)2Et |
| 305C | 1-hydroxycyclohexyl | —C≡C— | —S(O)2Et |
| 306C | 1-hydroxycyclohexyl | —C=C— | —S(O)2Et |

TABLE 4-continued

| Code | R4 | L₁ | W_T |
|---|---|---|---|
| 307C | 1-hydroxycyclopentyl | —(CH2)2— | —S(O)2iPr |
| 308C | 1-hydroxycyclopentyl | —C≡C— | —S(O)2iPr |
| 309C | 1-hydroxycyclopentyl | —C=C— | —S(O)2iPr |
| 310C | 1-hydroxycyclohexyl | —(CH2)2— | —S(O)2iPr |
| 311C | 1-hydroxycyclohexyl | —C≡C— | —S(O)2iPr |
| 312C | 1-hydroxycyclohexyl | —C=C— | —S(O)2iPr |
| 313C | 1-hydroxycyclopentyl | —(CH2)2— | —S(O)2tBu |
| 314C | 1-hydroxycyclopentyl | —C≡C— | —S(O)2tBu |
| 315C | 1-hydroxycyclopentyl | —C=C— | —S(O)2tBu |
| 316C | 1-hydroxycyclohexyl | —(CH2)2— | —S(O)2tBu |
| 317C | 1-hydroxycyclohexyl | —C≡C— | —S(O)2tBu |
| 318C | 1-hydroxycyclohexyl | —C=C— | —S(O)2tBu |
| 319C | 1-hydroxycyclopentyl | —(CH2)2— | —S(O)2NH2 |
| 320C | 1-hydroxycyclopentyl | —C≡C— | —S(O)2NH2 |
| 321C | 1-hydroxycyclopentyl | —C=C— | —S(O)2NH2 |
| 322C | 1-hydroxycyclohexyl | —(CH2)2— | —S(O)2NH2 |
| 323C | 1-hydroxycyclohexyl | —C≡C— | —S(O)2NH2 |
| 324C | 1-hydroxycyclohexyl | —C=C— | —S(O)2NH2 |
| 325C | 1-hydroxycyclopentyl | —(CH2)2— | —S(O)2NMe2 |
| 326C | 1-hydroxycyclopentyl | —C≡C— | —S(O)2NMe2 |
| 327C | 1-hydroxycyclopentyl | —C=C— | —S(O)2NMe2 |
| 328C | 1-hydroxycyclohexyl | —(CH2)2— | —S(O)2NMe2 |
| 329C | 1-hydroxycyclohexyl | —C≡C— | —S(O)2NMe2 |
| 330C | 1-hydroxycyclohexyl | —C=C— | —S(O)2NMe2 |
| 331C | 1-hydroxycyclopentyl | —(CH2)2— | —S(O)2CH2S(O)2Me |
| 332C | 1-hydroxycyclopentyl | —C≡C— | —S(O)2CH2S(O)2Me |
| 333C | 1-hydroxycyclopentyl | —C=C— | —S(O)2CH2S(O)2Me |
| 334C | 1-hydroxycyclohexyl | —(CH2)2— | —S(O)2CH2S(O)2Me |
| 335C | 1-hydroxycyclohexyl | —C≡C— | —S(O)2CH2S(O)2Me |
| 336C | 1-hydroxycyclohexyl | —C=C— | —S(O)2CH2S(O)2Me |
| 337C | 1-hydroxycyclopentyl | —(CH2)2— | —S(O)2CH2S(O)2Et |
| 338C | 1-hydroxycyclopentyl | —C≡C— | —S(O)2CH2S(O)2Et |
| 339C | 1-hydroxycyclopentyl | —C=C— | —S(O)2CH2S(O)2Et |
| 340C | 1-hydroxycyclohexyl | —(CH2)2— | —S(O)2CH2S(O)2Et |
| 341C | 1-hydroxycyclohexyl | —C≡C— | —S(O)2CH2S(O)2Et |
| 342C | 1-hydroxycyclohexyl | —C=C— | —S(O)2CH2S(O)2Et |
| 343C | 1-hydroxycyclopentyl | —(CH2)2— | —S(O)2CH2S(O)2iPr |
| 344C | 1-hydroxycyclopentyl | —C≡C— | —S(O)2CH2S(O)2iPr |
| 345C | 1-hydroxycyclopentyl | —C=C— | —S(O)2CH2S(O)2iPr |
| 346C | 1-hydroxycyclohexyl | —(CH2)2— | —S(O)2CH2S(O)2iPr |
| 347C | 1-hydroxycyclohexyl | —C≡C— | —S(O)2CH2S(O)2iPr |
| 348C | 1-hydroxycyclohexyl | —C=C— | —S(O)2CH2S(O)2iPr |
| 349C | 1-hydroxycyclopentyl | —(CH2)2— | —S(O)2CH2S(O)2tBu |
| 350C | 1-hydroxycyclopentyl | —C≡C— | —S(O)2CH2S(O)2tBu |
| 351C | 1-hydroxycyclopentyl | —C=C— | —S(O)2CH2S(O)2tBu |
| 352C | 1-hydroxycyclohexyl | —(CH2)2— | —S(O)2CH2S(O)2tBu |
| 353C | 1-hydroxycyclohexyl | —C≡C— | —S(O)2CH2S(O)2tBu |
| 354C | 1-hydroxycyclohexyl | —C=C— | —S(O)2CH2S(O)2tBu |
| 355C | 1-hydroxycyclopentyl | —(CH2)2— | —C(O)NHCH2CO2H |
| 356C | 1-hydroxycyclopentyl | —C≡C— | —C(O)NHCH2CO2H |
| 357C | 1-hydroxycyclopentyl | —C=C— | —C(O)NHCH2CO2H |
| 358C | 1-hydroxycyclohexyl | —(CH2)2— | —C(O)NHCH2CO2H |
| 359C | 1-hydroxycyclohexyl | —C≡C— | —C(O)NHCH2CO2H |
| 360C | 1-hydroxycyclohexyl | —C=C— | —C(O)NHCH2CO2H |
| 361C | 1-hydroxycyclopentyl | —(CH2)2— | —SO2NHCH2CO2H |
| 362C | 1-hydroxycyclopentyl | —C≡C— | —SO2NHCH2CO2H |
| 363C | 1-hydroxycyclopentyl | —C=C— | —SO2NHCH2CO2H |
| 364C | 1-hydroxycyclohexyl | —(CH2)2— | —SO2NHCH2CO2H |
| 365C | 1-hydroxycyclohexyl | —C≡C— | —SO2NHCH2CO2H |
| 366C | 1-hydroxycyclohexyl | —C=C— | —SO2NHCH2CO2H |
| 367C | 1-hydroxycyclopentyl | —(CH2)2— | —CH2—S-Me |
| 368C | 1-hydroxycyclopentyl | —C≡C— | —CH2—S-Me |
| 369C | 1-hydroxycyclopentyl | —C=C— | —CH2—S-Me |

TABLE 4-continued

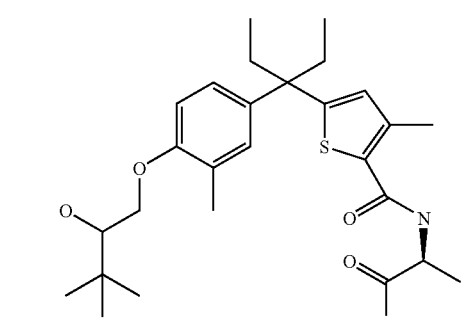

| Code | R4 | L₁ | W_T |
|---|---|---|---|
| 370C | 1-hydroxycyclohexyl | —(CH2)2— | —CH2—S-Me |
| 371C | 1-hydroxycyclohexyl | —C≡C— | —CH2—S-Me |
| 372C | 1-hydroxycyclohexyl | —C≡C— | —CH2—S-Me |

Particularly preferred chemical species of the invention are represented by structural formulae P101 to P106 and P200 to P206 a pharmaceutically acceptable salt solvate or prodrug derivative thereof:

For treatment of psoriasis, preferred compounds are those defined by structural formulae P100 to P106 as follows:

P100

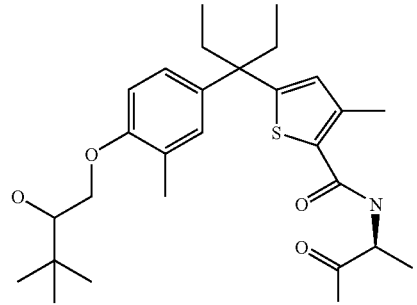

P101

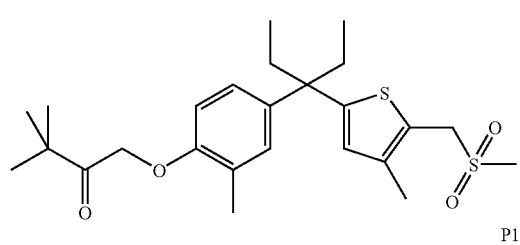

P102

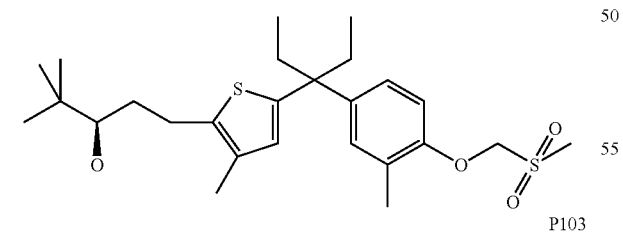

P103

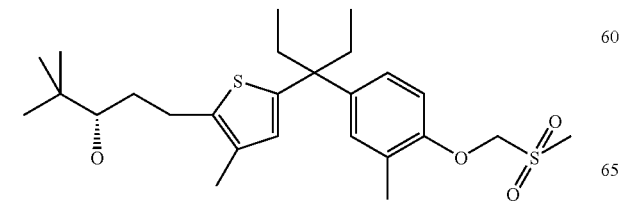

P104

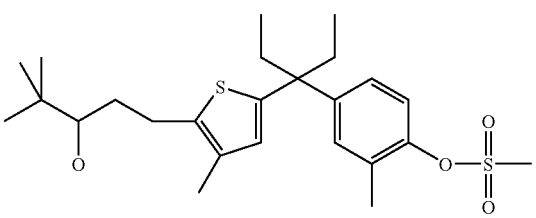

P105

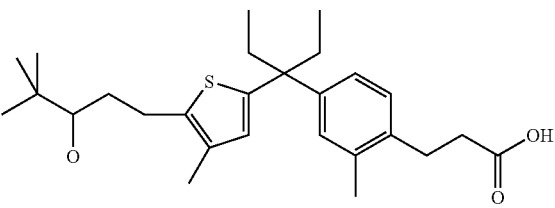

P106

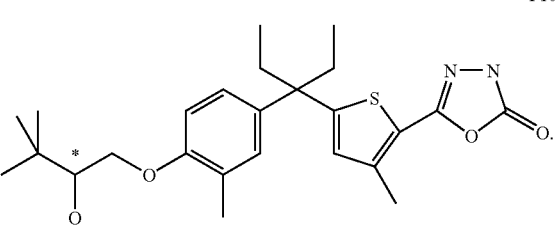

For treatment of osteoporosis, preferred compounds are those defined by structural formulae P101 and P200 to P206, as follows:

P101

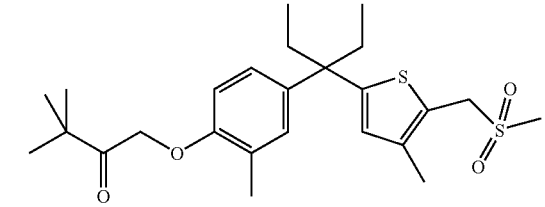

P200 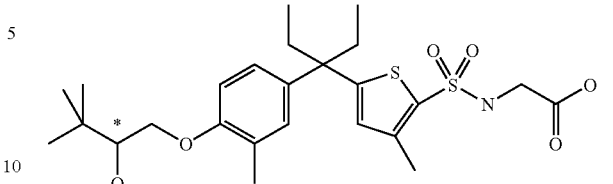

P201 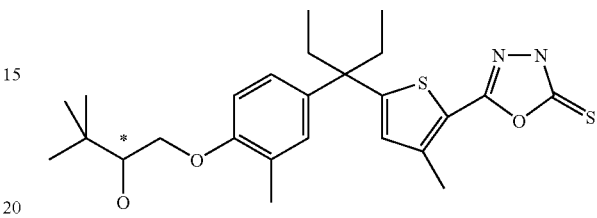

-continued

P205

P206

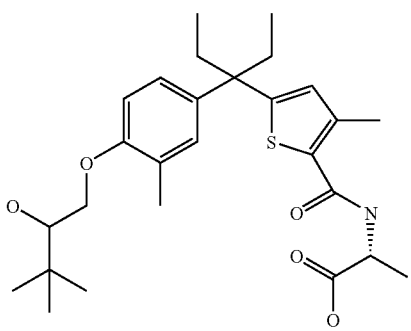

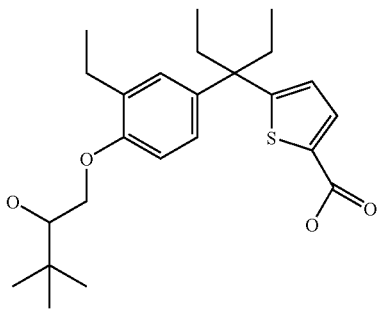

P202

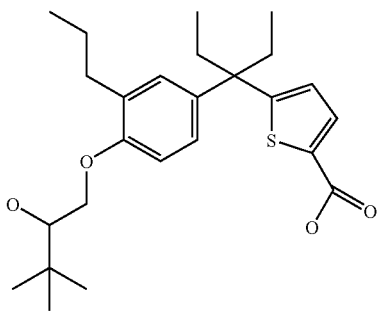

P203

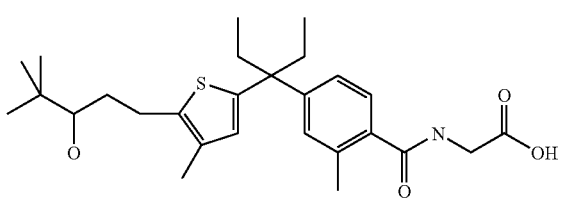

P204

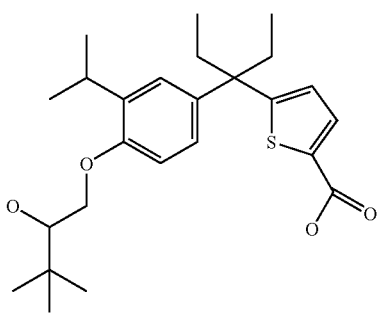

The salts of the Active Ingredients are an additional aspect of the invention. The skilled artisan will also appreciate that the family of compounds include acidic and basic members and that the present invention includes pharmaceutically acceptable salts thereof.

In those instances where the compounds of the invention possess acidic or basic functional groups various salts may be formed which are more water soluble and physiologically suitable than the parent compound. Representative pharmaceutically acceptable salts, include but are not limited to, the alkali and alkaline earth salts such as lithium, sodium, potassium, ammonium, calcium, magnesium, aluminum, zinc, and the like. Sodium and potassium salts are particularly preferred. Salts are conveniently prepared from the free acid by treating the acid in solution with a base or by exposing the acid to an ion exchange resin. For example, a carboxylic acid substituent on the compound of Formula I may be selected as —$CO_2H$ and salts may be formed by reaction with appropriate bases (e.g., NaOH, KOH) to yield the corresponding sodium and potassium salt.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1-19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, bromide, camsylate, carbonate, chloride, choline, clavulanate, citrate, chloride, chloroprocaine, choline, diethanolamine, dihydrochloride, diphosphate, edetate, edisylate, estolate, esylate, ethylenediamine, fluoride, fumarate, gluceptate, gluconate, glutamate, glycolylarsanilate, hexylresorcinate, hydrabamine, bromide, chloride, hydrobromide, hydrochloride, hydroxynaphthoate, iodide, isothionate, lactate, lactobionate, laurate, malate, maleate, malseate, mandelate, meglumine, mesylate, mesviate, methylbromide, methylnitrate, methylsulfate, mucate, napsylate, nitrate, oleate, oxalate, palmitate, pamoate, pantothenate, phosphate, polygalacturonate, procane, salicylate, stearate, subacetate, succinate, sulfate, tannate, tartrate, teoclate, tosylate, trifluoroacetate, trifluoromethane sulfonate, and valerate.

Certain compounds of the invention may possess one or more chiral centers and may thus exist in optically active forms. Likewise, when the compounds contain an alkenyl or alkenylene group there exists the possibility of cis- and trans-isomeric forms of the compounds. The R- and S-isomers and mixtures thereof, including racemic mixtures as well as mixtures of cis- and trans-isomers, and all tautomers are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a chiral column may be used such as those sold by Daicel Chemical Industries identified by the trademarks:

CHIRALPAK AD, CHIRALPAK AS, CHIRALPAK OD, CHIRALPAK OJ, CHIRALPAK OA, CHIRALPAK OB, CHIRALPAK OC, CHIRALPAK OF, CHIRALPAK OG, CHIRALPAK OK, and CHIRALPAK CA-1.

By another conventional method, a racemic mixture may be reacted with a single enantiomer of some other compound. This changes the racemic form into a mixture of diastereomers. These diastereomers, because they have different melting points, different boiling points, and different solubilities can be separated by conventional means, such as crystallization.

The present invention is also embodied in mixtures of Active Ingredients.

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters. Particularly preferred esters as prodrugs are methyl, ethyl, propyl, isopropyl, n-butyl, isobutyl, tert-butyl, morpholinoethyl, and N,N-diethylglycolamido.

Prodrugs may be prepared by methods as follows

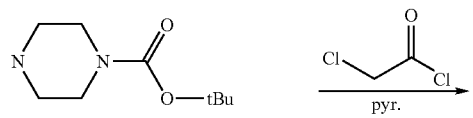

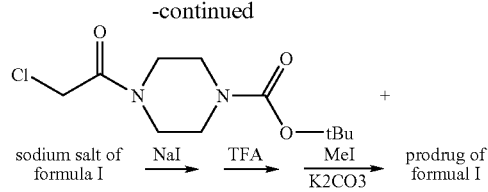

Prodrug of formula I is prepared by the following: treatment of

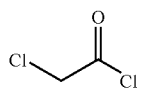

with

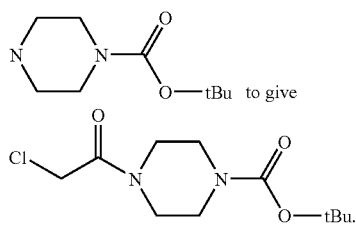

to give

Reaction of the sodium salt of I with

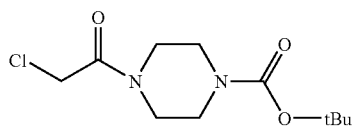

and NaI; treatment with TFA; and methylation with MeI and K2CO3. for example, to provide a combined group

in Formula I typlified by;

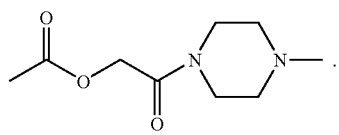

Pharmaceutical Formulations Containing the Novel Compounds of the Invention:

Pharmaceutical formulations of the invention are prepared by combining a therapeutically effective amount of Active Ingredient together with a pharmaceutically acceptable carrier or diluent. The present pharmaceutical formulations are prepared by known procedures using well-known and readily available ingredients.

In making the compositions of the present invention, the Active Ingredient will usually be admixed with a carrier, or diluted by a carrier, or enclosed within a carrier which may be in the form of a capsule, sachet, paper or other container. When the carrier serves as a diluent, it may be a solid, semisolid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the compound. The Active Ingredient is preferably formulated prior to administration.

The Active Ingredient may also be delivered by suitable formulations contained in a transderm patch. Alternatively, the Active Ingredient may be delived to a patient by sublingual administration.

For the pharmaceutical formulations any suitable carrier known in the art can be used. In such a formulation, the carrier may be a solid, liquid, or mixture of a solid and a liquid. Solid form formulations include powders, tablets and capsules. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with finely divided Active ingredient. In tablets the Active Ingredient is mixed with a carrier having the necessary binding properties in suitable proportions and compacted in the shape and size desired. The powders and tablets preferably contain from about 1 to about 99 weight percent of Active Ingredient. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The Active Ingredient may be dissolved or suspended in a pharmaceutically acceptable carrier, such as sterile water, sterile organic solvent or a mixture of both. The Active Ingredient may often be dissolved in a suitable organic solvent, for instance aqueous propylene glycol. Other compositions can be made by dispersing the finely divided Active Ingredient in aqueous starch or sodium carboxymethyl cellulose solution or in a suitable oil.

Ointment Formulation for Treatment of Psoriasis:

Treatment of psoriasis is preferably done with topical application by a formulation in the form of a cream, oil, emulsion, paste or ointment containing a therapeutically effective amount of Active Ingredient. The formulation for topical treatment contains from 0.5 to 0.00005 weight percent, preferably from 0.05 to 0.0005 weight percent, and most preferably from 0.025 to 0.001 of Active Ingredient.

For example, two semisolid topical preparations useful as vehicles for VDR modulators in treatment and prevention of psoriasis are as follows:

Polyethylene Glycol Ointment USP (R. 2495)
Prepare Polyethylene Glycol Ointment as follows:

| Polyethylene Glycol 3350 | 400 g. |
| Polyethylene Glycol 400 | 600 g. |
| To make | 1000 g. |

Heat the two ingredients on a water bath to 65C. Allow to cool, and stir until congealed. If a firmer preparation is desired, replace up to 100 g of the polyethylene glycol 400 with an equal amount of polyethylene glycol 3350.

Hydrophilic Ointment USP (p. 1216)
Prepare Hydrophilic Ointment as follows:

| Methylparaben | 0.25 g. |
| Propylparaben | 0.15 g. |
| Sodium Lauryl Sulfate | 10 g. |
| Propylene Glycol | 120 g. |
| Stearyl Alcohol | 250 g. |
| White Petrolatum | 250 g. |
| Purified Water | 370 g. |
| To make about | 1000 g. |

The Stearyl Alcohol and White Petrolatum are melted on a steam bath, and warmed to about 75C. The other ingredients, previously dissolved in the water are added, warmed to 75C, and the mixture stirred until it congeals.

For each of the above formulations Active Ingredient is added during the heating step in an amount that is from 0.5 to 0.00005 weight percent, preferably from 0.05 to 0.0005 weight percent, and most preferably from 0.025 to 0.001 weight percent of the total ointment weight. (Source: —United States Pharmacopoeia 24, United States Pharmacopeial Convention, 1999)

Combination Therapy for Osteoporosis:

Conventional therapy for osteoporosis includes; (i) estrogens, (ii) androgens, (iii) calcium supplements, (iv) vitamin D metabolites, (v) thiazide diuretics, (vi) calcitonin, (vii) bisphosphonates, (viii) SERMS, and (ix) fluorides (see, Harrison's Principles of Internal Medicine, 13$^{th}$ edition, 1994, published by McGraw Hill Publ., ISBN 0-07-032370-4, pgs. 2172-77; the disclosure of which is incorporated herein by reference.). Any one or combination of these conventional therapies may be used in combination with the method of treatment using Active Ingredient as taught herein. For example, in a method of treating osteoporosis, the vitamin D receptor modulator compounds of the invention may be administered separately or simultaneously with a conventional therapy. Alternatively, the Active Ingredient may be combined with conventional therapeutic agents in a formulation for treatment of osteoporosis such as set out below:

A formulation for treating osteoporosis comprising:
   Ingredient (A1):
      Active Ingredient,
   Ingredient (B1):
      one or more co-agents that are conventional for treatment osteoporosis selected from the group consisting of:
         a. estrogens,
         b. androgens,
         c. calcium supplements,
         d. vitamin D metabolites, e. thiazide diuretics,
f. calcitonin,
g. bisphosphonates,
h. SERMS, and
i. fluorides.
Ingredient (C1):
optionally, a carrier or diluent.

Typically useful formulations are those wherein the weight ratio of (A1) to (B11) is from 10:1 to 1:1000 and preferably from 1:1 to 1:100.

Combination Therapy for Psoriasis:

Conventional therapy for psoriasis includes topical glucocorticoids, salicylic acid, crude coal tar, ultraviolet light, and methotrexate (see, Harrison's Principles of Internal Medicine, 13$^{th}$ edition, 1994, published by McGraw Hill Publ., ISBN 0-07-032370-4, pgs. 2172-77). Any one or combination of these conventional therapies may be used in combination with the method of treatment using Active Ingredient as taught herein. For example, in a method of treating osteoporosis, the vitamin D receptor modulator compounds of the invention may be topically administered separately or simultaneously with a conventional therapy. Alternatively, the Active Ingredient may be combined with conventional therapeutic agents in a topically applied formulation for treatment of osteoporosis such as set out below:

A formulation for treating osteoporosis comprising:
Ingredient (A2):
Active Ingredient;
Ingredient (B2):
one or more co-agents that are conventional for treatment psoriasis selected from the group consisting of:
a. topical glucocorticoids,
b. salicylic acid, or
c. crude coal tar.
Ingredient (C2):
optionally, a carrier or diluent.

Typically useful formulations are those wherein the weight ratio of (A2) to (B2) is from 1:10 to 1:1000000 and preferably from 1:100 to 1:10000.

Methods of Using the Compounds of the Invention:

Generic disease states benefited by treatment with t Active Ingredient include, but are not limited to:
disease states characterized by abnormal calcium regulation
disease states characterized by abnormal cell proliferation
disease states characterized by abnormal immune response
disease states characterized by abnormal dermatological conditions
disease states characterized by neurodegenerative condition
disease states characterized by inflammation
disease states characterized by vitamin D sensitivity
disease states characterized by hyperproliferative disorders Specific disease states benefited by treatment with Active Ingredient include, but are not limited to:
Abscess
Acne
Adhesion
Actinic keratosis
Alopecia
Alzheimer's disease
Bone maintenance in zero gravity
Bone fracture healing
Breast cancer
Skin cancer
Crohn's disease
Colon cancer
Type I diabetes
Host-graft rejection
Hypercalcemia
Type II diabetes
Leukemia
Multiple sclerosis
Myelodysplastic syndrome
Insufficient sebum secretion
Osteomalacia
Osteoporosis
Insufficient dermal firmness
Insufficient dermal hydration
Psoriatic arthritis
Prostate cancer
Psoriasis
Renal osteodystrophy
Rheumatoid arthritis
Scleroderma
Systemic lupus erythematosus
Ulcerative colitis
Wrinkles Particularly preferred is the treatment of psoriasis and osteoporosis by administration to a mammal (including a human) of a therapeutically effective amount of Active Ingredient. By "therapeutically effective amount" it is meant that quantity of a compound of the invention prevents, removes or significantly reduces the deleterious effects of a disease state in mammals, including humans.

The specific dose of Active Ingredient administered according to this invention to obtain therapeutic or prophylactic effects will, of course, be determined by the particular circumstances surrounding the case, including, for example, the compound administered, the route of administration and the condition being treated. Typical daily doses will contain a pharmaceutically effective amount typically in the range of from about 0.0001 mg/kg/day to about 50 mg/kg/day of body weight of an active compound of this invention. Preferably the dose of compounds of the invention will be from 0.0001 to 5 mg/kg/day of body weight.

Preferably the Active Ingredient or pharmaceutical formulations containing Active Ingredient are in unit dosage form for administration to a mammal. The unit dosage form can be a capsule or tablet itself, or the appropriate number of any of these. The quantity of Active Ingredient in a unit dose of composition may be varied or adjusted from about 0.0001 to about 1000 milligrams or more according to the particular treatment involved. It may be appreciated that it is necessary to make routine variations to the dosage depending on the age and condition of the patient. The compounds of the invention may be administered by a variety of routes including oral, aerosol, rectal, transdermal, sublingual, subcutaneous, intravenous, intramuscular, and intranasal. The dosage will also depend on the route of administration.

EXAMPLES

General Experimental Conditions:

The starting material/intermediate is the compound from the immediate preceding experimental unless otherwise indicated.

All reactions are performed under nitrogen/argon atmosphere, in a stirred reaction vessel, and at room temperature unless indicated otherwise.

Unless otherwise indicated, the organic layer is MgSO4/Na2SO4 dried is defined as stirring the solution with a dessicant for 5-15 m and filtering off the dessicant to give an anhydrous filtrate.

For analogous multi-step reaction procedures, the yield is given either for the ultimate step or overall multi-steps as indicated.

Solutions are "concentrated" at a range of 25-75° C. with reduced pressure. in-vacuo—25-75° C.; 0.05 to 1 mm Unless otherwise indicated, "the residue is chromatographed" is defined as silica gel chromatography of residue with moderate nitrogen pressure (flash chromatography) or a medium pressure chromatography systems using a silica gel to crude product ratio of ~10-100.

Thin layer chromatography is performed with silica gel plates with UV and/or appropriate staining solution.

NMR spectra are obtained with either 300 or 400 mHz spectrometer.

NMR—denotes NMR spectrum is consistent with assigned structure.

HRMS—high resolution mass spectrum
ES-MS—electrospray mass spectrum

Abbreviations:
Aq—aqueous
d—day
eq—equivalent
h—hour
m—minute
satd—saturated
disp—dispersion
quant—quantitative
rt for retention time (both small caps to minimize confusion with RT)
RT—room temperature
Chemical Definitions:
BBr3—boron tribromide
BF3-OEt2—boron trifluoride etherate
BnBr—benzyl bromide
CH2Cl2-dichloromethane
CH3CN-acetonitrile
CO-carbon monoxide
Dess-Martin reagent—1,1,1-tris(acetyloxy)-1,1-dihydro-1,2-benziodoxol-3-(1H)-one
DIBAlH—Diisobutyl Aluminum Hydride
DMAP—4-(dimethylamino)pyridine
DMF—N,N-dimethylformamide
DMSO—dimethylsulfoxide
DPPB—1,4-bis(diphenylphosphino)butane
DPPF—dichloro[1,1'-bis(diphenylphosphino)ferrocene
EDCl—3-Ethyl-1-[3-(dimethylamino)propyl]carbodiimide hydrochloride
Et3N—triethylamine
EtMgBr—ethyl magnesium bromide
EtOAc—ethyl acetate
EtOH—ethanol
H2NCH2CO2Me—methyl glycinate
Hept—heptane
Hex—hexanes
HN(OMe)Me—N-methyl-O-methyl hydroxylamine
HNMe2—dimethyl amine
HATU—O-(7-azabenzotriazol-1-yl)-N,N,N',N'-tetramethyluronium hexafluorophosphate
HOAT—7-aza-1-hydroxybenzotriazole
HOBT—1-hydroxybenzotriazole
K2CO3—potassium carbonate
KOH—potassium hydroxide
LAH—lithium aluminum hydride
LiHMDS—lithium hexamethyldisilazide
mCPBA—meta-chloroperbenzoic acid
MeI—methyl iodide
MeOH—methanol
NaBH4—sodium borohydride
MgSO4—magnesium sulfate
NaH—sodium hydride
NaHCO3-sodium bicarbonate
NaI—sodium iodide
Na2SO4—sodium sulfate
NH4Cl—ammonium chloride
NMO—4-methylmorpholine N-oxide
NMP—N-methylpyrrolidin-2-one
Na—S—R3—sodium alkylmercaptide
PBr3—phosphorus tribromide
Pd(DPPF)—palladium dichloro[1,1'-bis(diphenylphosphino)ferrocene
Pd(OAc)2—palladium (II) acetate
Pd(TPP)4—palladium tetrakistriphenylphosphine
Pd—C—palladium on carbon
(PhO)2P(O)N3—diphenyl phosphorus azide
pTSA—para-toluenesulfonic acid
Pyr—pyridine
Red-Al —sodium bis(2-methoxyethoxy)aluminum hydride
R2MgBr—alkyl magnesium bromide
R3MgBr—alkyl magnesium bromide
R5MgBr—alkyl magnesium bromide
R2S(O)2NH2—alkylsulfonamide
TBAF—tetrabutylammonium fluoride
TBSCl—tert-butyldimethylsilyl chloride
tBuC(O)CH2Br-1-bromopinacolone
Tf2O—triflic anhydride
TFA—trifluoroacetic acid
THF—tetrahydrofuran
TPAP—tetrapropylammonium perruthenate
Zn(OTf)2—zinc trifluoromethane sulfonate.

Example 1

Preparation of 3'-[4-(2-Oxo-3,3-dimethylbutoxy-3-methylphenyl)-3-methylphenyl]-3'-[5-methoxycarbonyl-4-methylthiophen-2-yl]pentane

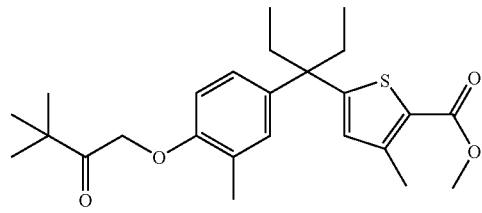

A. 2-(t-Butyldimethylsilyloxy)-5-bromotoluene

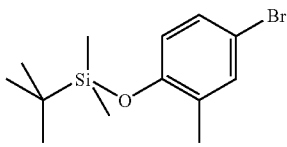

To a 0° C. mixture of 2-hydroxy-5-bromotoluene(48.63 g, 260 mmol), DMF (260 ml), imidazole (18.58 g, 273 mmol) is added t-butyldimethylsilyl chloride (41.15 g, 273 mol) in portions. After stirring for 30 m, the reaction is warmed to RT and stirred for 16 h. The reaction mixture is poured into ice/water (1.25 l) and extracted with Et$_2$O. The organic layer is washed with water (2×100 ml), 1N NaOH (2×5 ml), water, brine, MgSO$_4$ dried, concentrated, chromatographed (hex), and azeotroped with toluene to give the title compound as an oil (75.7 g, 97%)

$^1$NMR (400 MHz, DMSO-d$_6$) δ ppm: 0.21 (s, 6H), 0.99 (s, 9H), 2.15 (s, 3H), 6.77 (d, J=8.3 Hz, 1H), 7.25 (dd, J=6.8, 8.3 Hz, 1H), 7.37 (s, 1H).

EI-MS: 300,302

B. 3'-[4-(t-Butyldimethylsilyloxy)-3-methylphenyl]pentan-3-ol

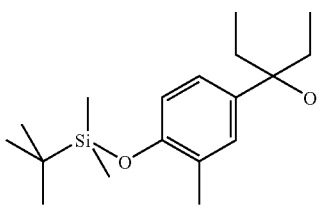

Magnesium turnings (6 g, 248 mmol) is vigorously stirred under nitrogen for 18 h. To the magnesium turnings is added THF (600 ml) and I$_2$ (100 mg, 0.39 nunol). This is followed by dropwise addition of 2-(t-butyldimethylsilyloxy)-5-bromotoluene (60 g, 200 mmol) in THF (500 ml) and at the same time the reaction is gradually heated by setting the oil bath to 70° C. After half of the addition of the 2-(t-butyldimethylsilyloxy)-5-bromotoluene/THF is complete, the mixture is heated to 90° C. for 2.5 h. The mixture is allowed to cool to RT and then cooled to 0° C. To this mixture is added 3-pentanone (21.2 ml, 200 mmol), warmed to RT, and then heated to 50° C. for 3 h. After cooling, the reaction is diluted with Et$_2$O and water, and quenched with 1N HCl to pH 7. The mixture is partitioned and the organic layer is washed with water, Na$_2$SO$_4$ dried, concentrated, chromatographed (1.25 kg silica gel, 40% CH$_2$Cl$_2$/Hex to 70% CH$_2$Cl$_2$/Hex; rf. 0.3) to give the title compound as an oil (44.3 g, 72%).

$^1$NMR (400 MHz, DMSO-d$_6$) δ ppm: 0.20 (s, 6H), 0.64 (t, J=7.8 Hz, 6H), 1.00 (s, 9H), 1.67 (m, 4H), 2.15 9s, 3H), 4.38 (s, 1H), 6.70 (d, J=8.8 Hz, 1H), 7.04 (dd, J=8.3, 2.0 Hz, 1H), 7.14 (d, J=2.0 Hz, 1H).

EI-MS: 308.37

C. 3'-[4-(Hydroxy)-3-methylphenyl]-3'-[4-methylthiophen-2-yl]pentane

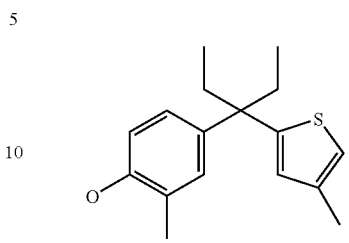

To a −78° C. mixture of 3'-[4-(t-butyldimethylsilyloxy)-3-methylphienyl]pentan-3-ol (44 g, 142 mmol) and 3-methylthiophene (83 ml, 854 mmol) is added BF$_3$-Et$_2$O (180 ml, 1.42 mol). After stirring for 45 m, the reaction is placed in a 0° C. bath, allowed to warm to RT and stirred for 6 h. The reaction is poured into Et$_2$O/water and washed with 5N HCl. The organic layer is washed with water, Na$_2$SO$_4$ dried, concentrated, and chromatographed (1.5 kg SiO$_2$, 70% CHCl$_3$/hex) to give the title compound (37 g, 95%).

$^1$NMR (400 MHz, DMSO-d$_6$) δ ppm: 0.63 (t, J=7.3 Hz, 3H), 2.01 (m, 4H), 2.08 (s, 3H), 2.16 (s, 3H), 6.67 (m, 2H), 6.88 (m, 2H), 6.93 (d, J=1.9 Hz, 1H), 9.10 (s, 1H).

High Res. EI-MS: 274.1389; calc. for C$_{17}$H$_{22}$OS: 274.1391

D. 3'-[4-(Benzyloxy)-3-methylphenyl]-3'-[4-methylthiophen-2-yl]pentane

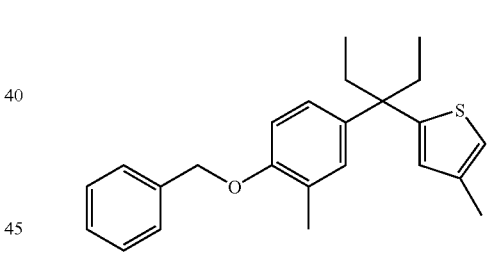

To a 0° C. mixture of 3'-[4-(hydroxy)-3-methylphenyl]-3'-[4-methylthiophen-2-yl]pentane (7.1 g, 25.9 mmol) and DMF (60 ml) is added 60% NaH disp (1.1 g, 28.5 mmol) and stirred for 15 m. The reaction is added benzyl bromide (3.4 ml, 28.5 mmol), warmed to RT and stirred overnight. The reaction is concentrated in-vacuo and partitioned between Et$_2$O/1N HCl. The organic layer is washed with water, dried with Na$_2$SO$_4$, concentrated, and chromatographed (20% CHCl$_3$/hex to 30% CHCl$_3$/hex) to give the title compound (8.7 g, 92%).

$^1$NMR (400 MHz, DMSO-d$_6$) δ ppm: 0.61 (t, J=7.3 Hz, 6H), 1.95-2.07 (m, 4H), 2.13 (s, 6H), 5.05 (s, 2H), 6.65 (d, J=1.5 Hz, 1H), 6.86 (m, 2H), 7.01 (m, 2H), 7.31 (d, J=7.3 Hz, 1H), 7.38 (m, 2H), 7.44 (d, J=6.8 Hz, 2H).

High Res. EI-MS: 364.1878; calc. for C$_{24}$H$_{28}$OS: 364.1861

E. 3'-[4-(Benzyloxy)-3-methylphenyl]-3'-[5-methoxycarbonyl-4-methylthiophen-2-yl]pentane

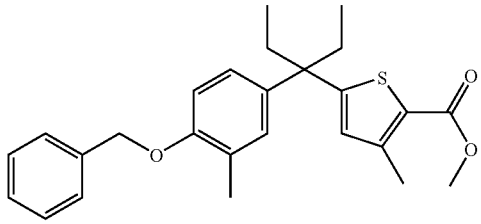

concentrated, and chromatographed (10% EtOAc/hex) to give the title To a −78° C. mixture of 3'-[4-(benzyloxy)-3-methylphenyl]-3'-[4-methylthiophen-2-yl]pentane (7.7 g, 21 mmol) and THF (50 ml) is added 1.6 M n-BuLi/hex (1.6 ml, 25.3 mmol) and warmed to 0° C. for 2 m. The reaction is cooled to −78° C., added methyl chloroformate (1.7 ml, 25 mmol) and warmed to RT over 2 h. The reaction is added Et$_2$O, quenched with 1N HCl, and partitioned. The organic layer is washed with brine, Na$_2$SO$_4$ dried, compound (4.8 g, 54%).

$^1$NMR (400 MHz, DMSO-d$_6$) δ ppm: 0.62 (t, J=7.3 Hz, 6H), 2.02-2.07 (m, 4H), 2.14 (s, 3H), 2.40 (s, 3H), 3.69 (s, 3H), 5.06 (s, 2H), 6.82 (s, 1H), 6.92 (d, J=8.8 Hz, 1H), 7.03 (m, 2H), 7.31 (d, J=7.3 Hz, 1H), 7.38 (t, J=7.3 Hz, 2H), 7.44 (t, J=7.3 Hz, 2H).

High Res. ES-MS: 423.2011; calc. for C$_{26}$H$_{30}$O$_3$S+H: 423.1994

F. 3'-[4-(Hydroxy)-3-methylphenyl]-3'-[5-methoxycarbonyl-4-methylthiophen-2-yl]entane

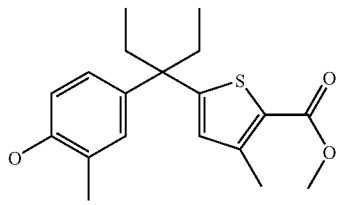

A mixture of 3'-[4-(benzyloxy)-3-methylphenyl]-3'-[5-methoxycarbonyl-4-methylthiophen-2-yl]pentane (290 mg, 0.686 mmol), 10% Pd/C (1.6 g, 1.5 mmol), EtOH (3 ml), and EtOAc (3 ml) is hydrogenated overnight at atmospheric pressure. The reaction is filtered through diatomaceous earth with EtOH/EtOAc wash, concentrated, and chromatographed (CH$_2$C$_2$ to 10% EtOAc/CH$_2$Cl$_2$) to give the title compound (220 mg, quant).

$^1$NMR (400 MHz, DMSO-d$_6$) δ ppm: 0.61 (t, J=7.3 Hz, 6H), 1.98-2.07 (m, 4H), 2.05 (s, 3H), 2.39 (s, 3H), 3.69 (s, 3 h), 6.66 (d, J=8.3 Hz, 1H), 6.79 (s, 1H), 6.86 (dd, J=8.3, 2.4 Hz, 1H), 6.91 (d, J=2.0 Hz, 1H), 9.15 (s, 1H).

High Res. ES-MS: 333.1528; calc. for C$_{19}$H$_{24}$O$_3$S+H: 333.1524

G. 3'-[4-(2-Oxo-3,3-dimethylbutoxy)-3-methylphenyl]-3'-[5-methoxycarbonyl-4-methylthiophen-2-yl]pentane

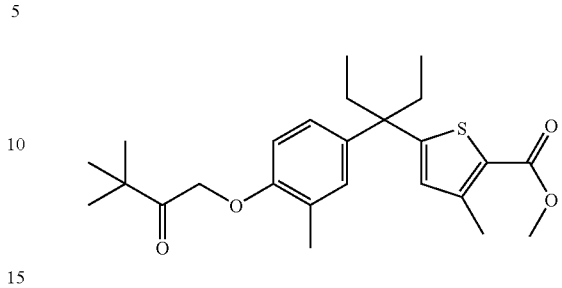

To a mixture of 3'-[4-(hydroxy)-3-methylphenyl]-3'-[5-methoxycarbonyl-4-methylthiophen-2-yl]pentane (210 mg, 0.63 mmol) and DMF (2 ml) is added 60% NaH disp (25 mg, 0.63 mmol) and warmed to RT. The reaction is cooled to 0° C., added 3,3-dimethyl-1-bromo-2-butanone (85 ul, 0.63 mmol), warmed to RT, and stirred overnight. The mixture is concentrated and partitioned between Et$_2$O/1N HCl. The organic layer is washed with water, dried with Na$_2$SO$_4$, and chromatographed (10% EtOAc/hex to 20% EtOAc/hex) to give the title compound (230 mg, 85%).

$^1$NMR (400 MHz, DMSO-d$_6$) δ ppm: 0.61 (t, J=7.3 Hz, 6H), 1.15 (s, 9H), 2.01-2.08 (m, 4H), 2.14 (s, 3H), 2.40 (s, 3H), 3.69 (s, 3H), 5.08 (s, 2H), 6.60 (d, J=8.3 Hz, 1H), 6.82 (s, 1H), 6.97 (d, J=8.8 Hz, 1H), 7.00 (s, 1H).

High Res. ES-MS: 453.2072; calc. for C$_{25}$H$_{34}$O$_4$S+Na: 453.2076

Example 2

Preparation of 3'-[4-(2-hydroxy-3,3-dimethylbutoxy)-3-methylphenyl]-3'-[5-methoxycarbonyl-4-methylthiophen-2-yl]pentane

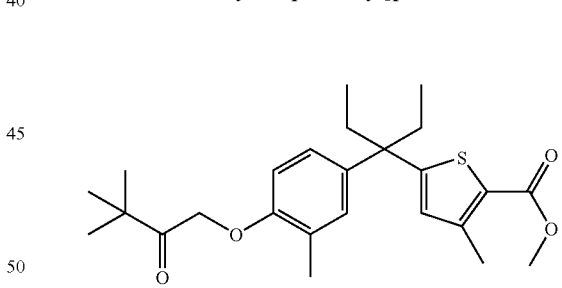

To a 0° C. mixture of 3'-[4-(2-oxo-3,3-dimethylbutoxy)-3-methylphenyl]-3'-[5-methoxycarbonyl-4-methylthiophen-2-yl]pentane (215 mg, 0.5 mmol) and MeOH (2 ml) is added NaBH$_4$ (28 mg, 0.75 mmol) and warmed to RT. The reaction is concentrated and partitioned between Et$_2$O/1N HCl. The organic layer is washed with water, dried with Na$_2$SO$_4$, and concentrated to give the title compound (220 mg, quant).

$^1$NMR (400 MHz, DMSO-d$_6$) δ ppm: 0.62 (t, J=7.3 Hz, 6H), 0.90 (s, 9H), 1.99-2.08 (m, 4H), 2.11 (s, 3H), 2.40 (s, 3H), 3.44 (m, 1H), 3.69 (s, 3H), 3.75 (dd, J=7.3, 10.2 Hz, 1H), 4.03 (dd, J=3.4, 10.2 Hz, 1H), 4.79 (d, J=5.4 Hz, 1H), 6.81 (s, 1H), 6.83 (d, J=8.8 Hz, 1H), 6.98 (s, 1H), 7.01 (d, J=8.8 Hz, 1H).

High Res. ES-MS: 450.2674; calc. for C$_{25}$H$_{36}$O$_4$S+NH$_4$: 450.2678

Example 3

Preparation of 3'-[4-(2-hydroxy-3,3-dimethylbutoxy)-3-methylphenyl]-3'-[5-carboxyl-4-methylthiophen-2-yl]pentane

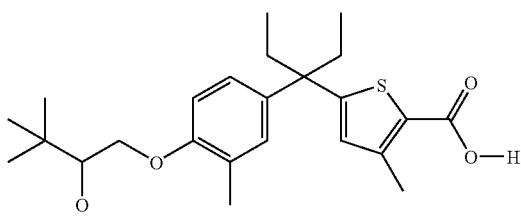

To a mixture of 3'-[4-(2-hydroxy-3,3-dimethylbutoxy)-3-methylphenyl]-3'-[5-methoxycarbonyl-4-methylthiophen-2-yl]pentane (200 mg, 0.46 mmol), EtOH (1.5 ml), and water (0.5 ml) is added KOH (200 mg, 3.56 mmol). The reaction is heated to 70° C. for 4 h. The mixture is concentrated, partitioned between 1:1 $Et_2O$:EtOAc and 1N HCl. The organic layer is washed with 1N HCl, $Na_2SO_4$ dried, and concentrated to give the title compound (200 mg, quant).

$^1$NMR (400 MHz, DMSO-$d_6$) δ ppm: 0.62 (t, J=7.3 Hz, 6H), 0.90 (s, 9H), 1.97-2.09 (m, 4H), 2.11 (s, 3H), 2.37 (s, 3 h), 3.44 (m, 1H), 3.74 (dd, J=7.3, 10.2 Hz, 1H), 4.01 (dd, J=3.4, 10.2 Hz, 1H), 4.78 (d, J=5.4 Hz, 1H), 6.76 (s, 1H), 6.82 (d, J=8.3 Hz, 1H), 6.98 (s, 1H), 7.01 (d, J=8.8 Hz, 1H), 12.58 (br s, 1H).

High Res. ES-MS: 436.2518; calc. for $C_{25}H_{36}O_4S+NH_4$: 436.2521

Example 4

Preparation of 3'-[4-(2-hydroxy-3,3-dimethylbutoxy)-3-methylphenyl]-3'-[5-(dimethylaminocarbonyl)-4-methylthiophen-2-yl]pentane

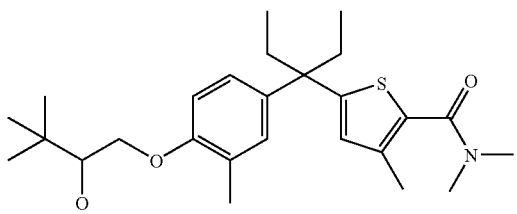

To a 0° C. mixture of 3'-[4-(2-hydroxy-3,3-dimethylbutoxy)-3-methylphenyl]-3'-[5-carboxyl-4-methylthiophen-2-yl]pentane (175 mg, 0.42 mmol) and $Et_3N$ (61 ul, 0.44 mmol) is added $(PhO)_2P(O)N_3$ (92 ul, 0.43 mmol). The reaction is warmed to RT and stirred for 30 m. After cooling to 0° C., the reaction is added DMAP (56 mg, 0.46 mmol) and 2M HNMe2/THF (0.46 ml, 0.92 mmol). The mixture is warmed to RT and stirred for 2 h. The reaction is concentrated and partitioned between $Et_2O$/1N HCl. The organic layer is washed with 1N HCl, $Na_2SO_4$ dried, and chromatographed ($CH_2Cl_2$ to 15% EtOAc/$CH_2C_{12}$) to give the title compound (110 mg, 59%).

$^1$NMR (400 MHz, DMSO-$d_6$) δ ppm: 0.62 (t, J=7.3 Hz, 6H), 1.96-2.06 (m, 4H), 2.09 (s, 3H), 2.11 (s, 3H), 2.90 (s, 6H), 3.44 (m, 1H), 3.73 (dd, J=7.3, 10.2 Hz, 1H), 4.01 (dd, J=3.4, 10.2 Hz, 1H), 4.79 (br s, 1H), 6.65 (s, 1H), 6.82 (d, J=8.8 Hz, 1H), 7.02 (m, 2H).

High Res. ES-MS: 446.2738; calc. for $C_{26}H_{39}NO_3S+H$: 446.2729

Example 5

Preparation of 3'-[4-(2-oxo-3,3-dimethylbutoxy)-3-methylphenyl]-3'-[5-methoxycarbonyl-thiophen-2-yl] pentane

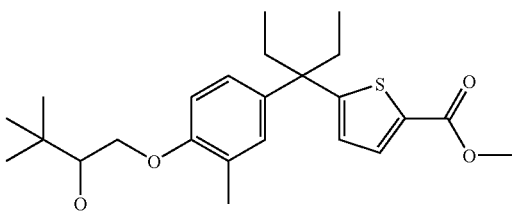

A. 2-(3-Hydroxy-3-pentyl)thiophene

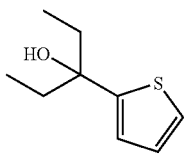

To a stirred 0° C. mixture of ethyl thiophene-2-carboxylate (3.12 g, 20.0 mmol) in diethyl ether (100 ml) is added 1M ethylmagnesium bromide (60 ml, 60 mmol). The reaction is allowed to warm to RT and stirred for 3 d. The reaction is partitioned between $Et_2O$ and 1N $NaHCO_3$. The organic layer was $Na_2SO_4$ dried and concentrated to give the title compound (3.4 g, 99%).

H-NMR (ppm, $CDC_3$): 7.98 (1H, d, 4.2 Hz), 6.95 (1H, m), 6.85 (1H, d, 3.0 Hz), 1.86 (4H, q, 7.5 Hz), 0.86 (6H, t, 7.5 Hz).

B. 5-(3-Hydroxy-3-pentyl)thiophene-2-carboxylic acid

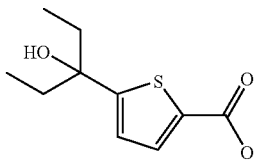

To a −78° C. mixture of 2-(3-hydroxy-3-pentyl)thiophene (0.34 g, 2.0 mmol) in THF (2 ml) is added of 1.6 M n-butyllithium in Hex (2.75 ml, 4.4 mmol). The mixture is allowed to warm to RT and powderized dry ice ($CO_2$) is added. After one h, the mixture is partitioned between diethyl ether and 1N $NaHCO_3$. The aqueous layer is washed with ether, acidified with conc. HCl and extracted with ether. The organic layer is $Na_2SO_4$ dried, filtered, and concentrated to give the title compound (0.236 g, 53%).

H-NMR (ppm, CDC$_3$): 7.75 (1H, d, 3.0 Hz), 6.87 (1H, d, 3.0 Hz), 1.86 (4H, q, 5.7 Hz), 0.86 (6H, t, 5.7 Hz).

C. Methyl, 5-(E/Z-2-penten-3-yl)thiophene-2-carboxylate

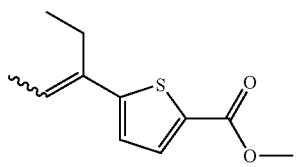

To a mixture of 5-(3-hydroxy-3-pentyl)thiophene-2-carboxylic acid 0.236 g (1.05 mmol) and methanol (15 ml) is bubbled HCl gas for a few minutes. The mixture is heated at reflux for 2 h and then concentrated under vacuum. The residue is partitioned between Et$_2$O and 1N NaHCO$_3$. The organic layer is Na$_2$SO$_4$ dried and concentrated to give the title compound (0.106 g, 62%).

D. 3'-[4-(Hydroxy)-3-metliylphenyl]-3'-[5-methoxycarbonyl-4-methylthiophen-2-yl]pentane

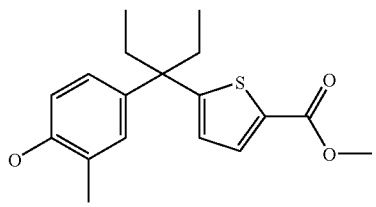

To a mixture of methyl 5-(E/Z-2-penten-3-yl)thiophene-2-carboxylate (0.106 g, 0.65 mmol) and o-cresol (0.282 g, 2.61 mmol) in a few drops of methylene chloride is added of BF3 etherate (37 mg, 0.26 mmol). The mixture is stirred overnight and partitioned between Et$_2$O and 1N NaHCO$_3$. The organic layer is Na$_2$SO$_4$ dried, concentrated, and excess o-cresol is distilled off (73° C./0.10 mm). The residue is chromatographed (7.5% to 10% EtOAc/hex) to give the title compound (0.104 g, 50%).

H-NMR (ppm, CDC$_3$): 7.62 (1H, d, 3.0 Hz), 6.96 (1H, s), 6.94 (1H, d, 6.0 Hz), 6.78 (1H, d, 3.0 Hz), 6.65 (1H, d, 6.0 Hz), 4.60 (1H, s), 3.82 (3H, s), 2.19 (3H, s), 2.10 (4H, q, 5.7 Hz), 0.69 (6H, t, 5.7 Hz).
LC/MS: 319.2 (M+1).

E. 3'-[4-(2-Oxo-3,3-dimethylbutoxy)-3-methylphenyl]-3'-[5-methoxycarbonyl-thiophen-2-yl]pentane

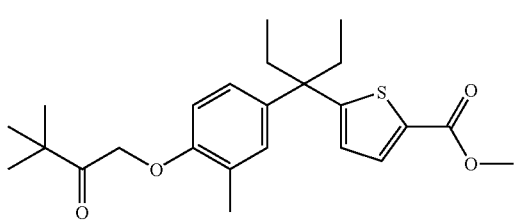

To a stirred 0° C. mixture of 60% disp NaH (15.7 mg, 0.39 mmol, hex washed) is added 3'-[4-(hydroxy)-3-methylphenyl]-3'-[5-metboxycarbonyl-4-methylthiophen-2-yl]pentane (100 mg, 0.31 mmol) in DMF (2.0 ml). The resulting mixture is added 1-chloropinacolone (46 mg, 0.34 mmol) with a crystal of KI. The reaction is allowed to warm to RT and stirred overnight. The mixture is partitioned between Et$_2$O and 1N NaHCO$_3$. The organic layer is Na$_2$SO$_4$ dried, filtered, concentrated, and chromatographed (on 4 g of silica gel with 5% EtOAc/hex) to give the title compound (0.114 g, 87%).

H-NMR (ppm, CDC$_3$): 7.62 (1H, d, 3.0 Hz), 6.99 (1H, s), 6.97 (1H, d, 6.0 Hz), 6.77 (1H, d, 3.0 Hz), 6.50 (1H, d, 6.0 Hz), 4.83 (2H, s), 3.82 (3H, s), 2.24 (3H, s), 2.10 (4H, q, 5.7 Hz), 1.24 (9H, s), 0.68 (6H, t, 5.7 Hz).
LC/MS: 417.3 (M+1).

F. 3'-[4-(2-Hydroxy-3,3-dimethylbutoxy)-3-methylphenyl]-3'-[5-methoxycarbonyl-thiophen-2-yl]pentane

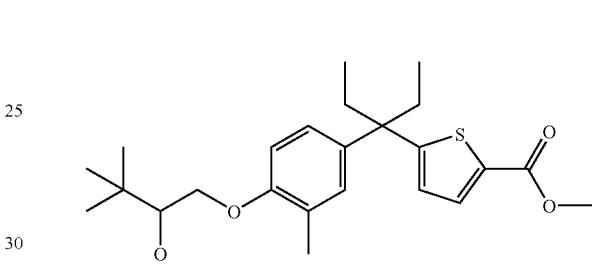

To a mixture of 3'-[4-(2-oxo-3,3-dimethylbutoxy)-3-methylphenyl]-3'-[5-methoxycarbonyl-thiophen-2-yl]pentane (28 mg, 0.067 mmol) and 95% EtOH (1 ml) is added NaBH$_4$ (3.8 mg, 0.1 mmol). After stirring overnight, the reaction is added acetone (several drops) and partitioned between CH$_2$Cl$_2$ and 1N NaHCO$_3$. The organic layer is washed with water, Na$_2$SO$_4$ dried, and concentrated to give the title compound (23 mg, 82%).

H-NMR (ppm, CDC13): 7.62 (1H, d, 2.7 Hz), 7.02 (1H, d, 6.0 Hz), 6.98 (1H, s), 6.78 (1H, d, 2.6 Hz), 6.71 (1H, d, 6.0 Hz), 4.06 (1H, d, 8.2 Hz), 3.86 (1H, d, 8.4 Hz), 3.82 (3H, s), 3.70 (1H, d, 8.2 Hz), 2.18 (3H, s), 2.10 (4H, q, 6.0 Hz), 1.00 (9H, s), 0.69 (6H, t, 5.8 Hz).
LC/MS: 418.2 (M+).

Example 6A and Example 6B

Preparation of enantiomers of 3'-[4-(2-hydroxy-3,3-dimethylbutoxy)-3-methylphenyl]-3'-[5-methoxycarbonyl-4-methylthiophen-2-yl]pentane

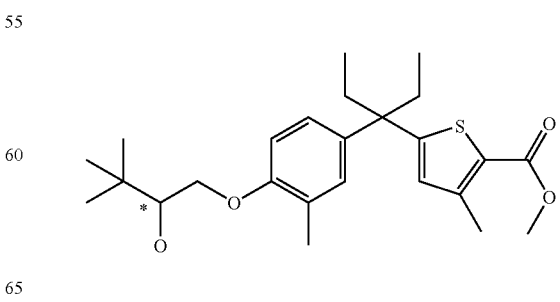

A mixture of racemic 3'-[4-(2-hydroxy-3,3-dimethylbutoxy)-3-methylphenyl]-3'-[5-methoxycarbonyl-4-methylthiophen-2-yl]pentane (1.4 g, 3.25 mmol) is chromatographed with a ChiralPak AD column to give enantiomer 1, Example 6A (666 mg, 48%) and enantiomer 2, Example 6B (686 mg, 49%).

Enantiomer 1, Example 6A

HPLC: ChiralPak AD (4.6×250 mm); 15% IPA/85% heptane; 1 ml/m (flow rate);

rt=5.8m $^1$NMR (300 MHz, DMSO-d$_6$) equivalent to Example 2.

High Res. ES-MS: 455.2231; calc. for $C_{25}H_{36}O_4S$+Na: 455.2232

Enantiomer 2, Example 6B

HPLC: ChiralPak AD (4.6×250 mm); 15% IPA/85% beptane; 1 ml/m (flow rate); rt=9.8m $^1$NMR (300 MHz, DMSO-d$_6$) equivalent to Example 2.

High Res. ES-MS: 433.2427; calc. for $C_{25}H_{36}O_4S$+H: 433.2413

Example 7

Preparation of enantiomer 1 of 3'-[4-(2-hydroxy-3,3-dimethylbutoxy)-3-methylphenyl]-3'-[5-carboxy-4-methylthiophen-2-yl]pentane

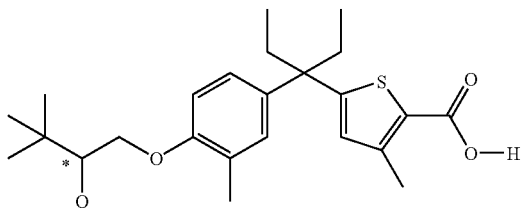

Using a procedure analogous to Example 3, enantiomer 1 of 3'-[4-(2-hydroxy-3,3-dimethylbutoxy)-3-methylphenyl]-3'-[5-methoxycarbonyl-4-methylthiophen-2-yl]pentane (Example 6A) gives the title compound as a white foamy solid (440 mg, quant.).

$^1$NMR (300 MHz, DMSO-d$_6$) equivalent to Example 3.

High Res. ES-MS: 441.2073; calc. for $C_{24}H_{34}O_4S$+Na: 441.2076

Example 8

Preparation of enantiomer 2 of 3'-[4-(2-hydroxy-3,3-dimethylbutoxy)-3-methylphenyl]-3'-[5-carboxy-4-methylthiophen-2-yl]pentane

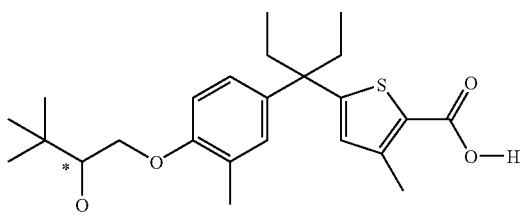

Using a procedure analogous to Example 3, enantiomer 2 (Example 6B) of 3'-[4-(2-hydroxy-3,3-dimethylbutoxy)-3-methylphenyl]-3'-[5-methoxycarbonyl-4-methylthiophen-2-yl]pentane gives the title compound as a white foamy solid (440 mg, quant.).

$^1$NMR (300 MHz, DMSO-d$_6$) equivalent to Example 3.

High Res. ES-MS: 441.2074; calc. for $C_{24}H_{34}O_4S$+Na: 441.2076

Example 9

Preparation of 3'-[4-(2-oxo-3,3-dimethylbutoxy)-3-methylphenyl]-3'-[5-methylsulfonylmethyl-4-methylthiophen-2-yl]pentane

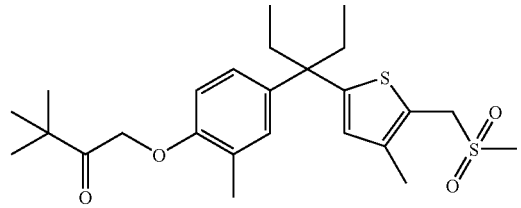

A. 3'-[4-(Benzyloxy)-3-methylphenyl]-3'-[4-methyl-5-(hydroxymethyl)thiophen-2-yl]pentane

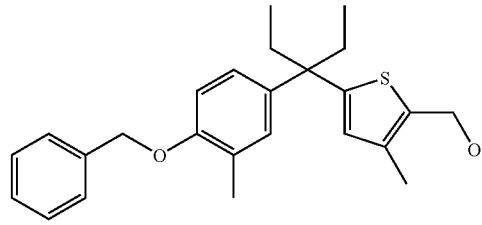

To a 0° C. mixture of 3'-[4-(benzyloxy)-3-methylphenyl]-3'-[5-methoxycarbonyl-4-methylthiophen-2-yl]pentane (1.55 g, 3.66 mmol) and THF (15 ml) is added LAH (417 mg, 11 mmol) and warmed to RT. The reaction is heated to 45° C. overnight and then cooled to 0° C. The mixture is quenched with sat'd Na$_2$SO$_4$, diluted with Et$_2$O, dried with Na$_2$SO$_4$ and filtered. After concentration, the residue is chromatographed (CHC$_3$) to give the title compound (1.1 g, 76%).

$^1$NMR (400 MHz, DMSO-d$_6$) δ ppm: 0.64 (t, J=7.3 Hz, 6H), 1.96-2.05 (m, 4H), 2.06 (s, 3H), 2.15 (s, 3H), 4.43 (s, 2H), 5.06 (m, 3H), 6.55 (s, 1H), 6.89 (d, J=9.3 Hz, 1H), 7.26 (br s, 2H), 7.31 (m, 1H), 7.37 (m, 2H), 7.44 (d, J=7.8 Hz, 2H).

High Res. ES-MS: 377.1950; calc. for $C_{25}H_{30}O_2S$+H−H$_2$O: 377.1939

B. 3'-[4-(Benzyloxy)-3-methylphenyl]-3'-[4-methyl-5-(methylmercaptylmethyl)thiophen-2-yl]pentane

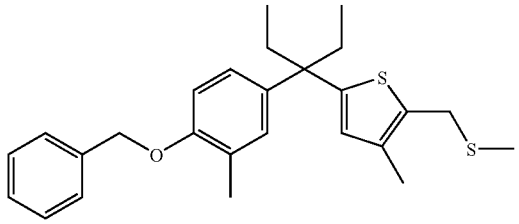

To a 0° C. mixture of 3'-[4-(benzyloxy)-3-methylphenyl]-3'-[4-methyl-5-(hydroxymethyl)thiophen-2-yl]pentane (450 mg, 1.1 mmol) and Et$_2$O (3 ml) is added PBr$_3$ (113 ul, 1.2 mmol) and stirred for 1 h. The reaction is diluted with Et$_2$O, washed with water (1×5 ml), brine (1×5 ml), Na$_2$SO$_4$ dried, and concentrated. The resulting solid is dissolved in DMF, cooled to 0° C., added NaSMe (330 mg, 4.8 mmol), and allowed to warmed RT. After stirring for 2 h, the reaction is concentrated and chromatographed (5% EtOAc/hex) to give the title compound (280 mg, 60%).

$^1$NMR (400 MHz, DMSO-d$_6$) δ ppm: 0.63 (t, J=7.3 Hz, 6H), 1.94-2.05 (m, 4H), 1.97 (s, 3H), 2.07 (s, 3H), 2.15 (s, 3H), 3.75 (s, 2H), 5.06 (s, 2H), 6.56 (s, 1H), 6.90 (d, J=9.3 Hz, 1H), 7.01 (m, 2H), 7.31 (m, 1H), 7.38 (m, 2H), 7.44 (d, J=6.8 Hz, 2H).

High Res. ES-MS: 425.1964; calc. for C$_{26}$H$_{32}$OS$_2$+H: 425.1973

C. 3'-[4-(Benzyloxy)-3-methylphenyl]-3'-[4-methyl-5-(methylsulfonylmethyl)thiophen-2-yl]pentane

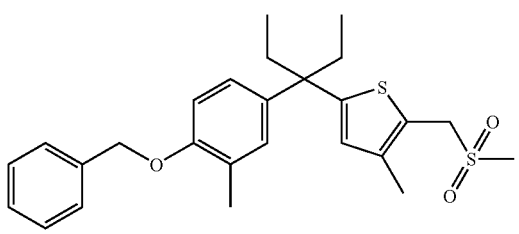

To a 0° C. mixture of 3'-[4-(benzyloxy)-3-methylphenyl]-3'-[4-methyl-5-(methylmercaptylmethyl)thiophen-2-yl]pentane (260 mg, 0.611 mmol) and CHC$_3$ (3 ml) is added 50% m-CPBA (465 mg, 1.35 mmol) and stirred for 1.5 h. The reaction is diluted with CHCl$_3$, washed with satd Na$_2$CO$_3$, Na$_2$SO$_4$ dried, concentrated, and chromatographed (CHCl$_3$ to 5% EtOAc/CHCl$_3$) to give the title compound as a white foamy solid (250 mg, 90%).

$^1$NMR (400 MHz, DMSO-d$_6$) δ ppm: 0.64 (t, J=7.3 Hz, 6H), 1.99-2.07 (m, 4H), 2.14 (s, 3H), 2.15 (s, 3H), 2.90 (s, 3H), 4.53 (s, 2H), 5.06 (s, 2H), 6.67 (s, 1H), 6.91 (d, J=9.3 Hz, 1H), 7.03 (m, 2H), 7.31 (m, 1H), 7.38 (m, 2H), 7.44 (d, J=7.3 Hz, 2H).

High Res. ES-MS: 474.2126; calc. for C$_{26}$H$_{32}$O$_3$S$_2$+NH$_4$: 474.2137

D. 3'-[4-(Hydroxy)-3-methylphenyl]-3'-[4-methyl-5-(methylsulfonylmethyl)thiophen-2-yl]pentane

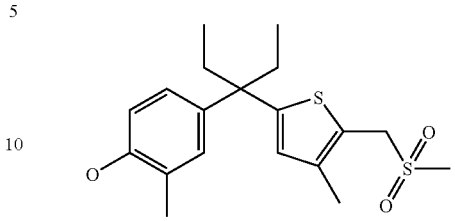

Using a procedure analogous to Example 1F, 3'-[4-(benzyloxy)-3-methylphenyl]-3'-[4-methyl-5-(methylsulfonylmethyl)thiophen-2-yl]pentane gives the title compound as a white foamy solid (160 mg, 81%).

$^1$NMR (400 MHz, DMSO-d$_6$) δ ppm: 0.63 (t, J=7.3 Hz, 6H), 1.94-2.03 (m, 4H), 2.06 (s, 3H), 2.14 (s, 3H), 2.89 (s, 3H), 4.52 (s, 2H), 6.65 (m, 2H), 6.85 (dd, J=2.4, 8.3 Hz, 1H), 6.92 (d, J=2.0 Hz, 1H), 9.09 (s, 1H).

High Res. ES-MS: 384.1648; calc. for C$_{19}$H$_{26}$O$_3$S$_2$+NH$_4$: 384.1667

E. 3'-[4-(2-Oxo-3,3-dimethylbutoxy)-3-methylphenyl]-3'-[5-methylsulfonylmethyl-4-methylthiophen-2-yl]pentane

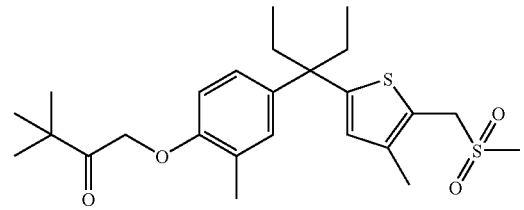

Using a procedure analogous to Example 1G, 3'-[4-(hydroxy)-3-methylphenyl]-3'-[4-methyl-5-(methylsulfonylmethyl)thiophen-2-yl]pentane gives the title compound (160 mg, 84%).

$^1$NMR (400 MHz, DMSO-d$_6$) δ ppm: 0.63 (t, J=7.3 Hz, 6H), 1.16 (s, 9H), 2.00-2.08 (m, 4H), 2.14 (s, 3H), 2.15 (s, 3H), 2.90 (s, 3H), 4.53 (s, 2H), 5.07 (s, 2H), 6.60 (d, J 8.3 Hz, 1H), 6.67 (s, 1H), 6.97 (d, J=8.3 Hz, 1H), 7.01 (s, 1H).

High Res. ES-MS: 482.2397; calc. for C$_{25}$H$_{26}$O$_4$S$_2$+NH$_4$: 482.2399

Example 10

Preparation of 3'-[4-(2-hydroxy-3,3-dimethylbutoxy)-3-methylphenyl]-3'-[5-methylsulfonylmethyl-4-methylthiophen-2-yl]pentane

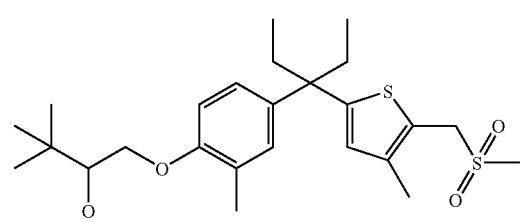

Using a procedure analogous to Example 2, 3'-[4-(2-oxo-3,3-dimethylbutoxy)-3-methylphenyl]-3'-[5-methylsulfonylmethyl-4-metliylthiophen-2-yl]pentane gives the title compound as a white foamy solid (440 mg, quant.).

¹NMR (400 MHz, DMSO-$d_6$) δ ppm: 0.62 (t, J=7.3 Hz, 6H), 0.92 (s, 9H), 1.97-2.08 (m, 4H), 2.12 (s, 3H), 2.14 (s, 3H), 2.89 (s, 3H), 3.45 (m, 1H), 3.76 (dd, J=7.3, 9.8 Hz, 1H), 4.02 (dd, J=2.9, 9.8 Hz, 1H), 4.52 (s, 2H), 4.78 (d, J=5.4 Hz, 1H), 6.66 (s, 1H), 6.82 (d, J=8.3 Hz, 1H), 7.01 (m, 2H).

High Res. ES-MS: 484.2553; calc. for $C_{25}H_{38}O_4S_2$+$NH_4$: 484.2555

Example 11A and 11B

Preparation of enantiomers of 3'-[4-(2-hydroxy-3,3-dimethylbutoxy)-3-methylphenyl]-3'-[5-methylsulfonylmethyl-4-methylthiophen-2-yl]pentane

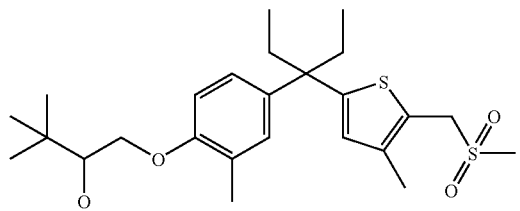

A racemic mixture of 3'-[4-(2-hydroxy-3,3-dimethylbutoxy)-3-methylphenyl]-3'-[5-methylsulfonylmethyl-4-methylthiophen-2-yl]pentane is chromatographed with a Chiralcel AD column to give enantiomer 1, Example 11A (205 mg, ~50%) and enantiomer 2, Example 11B (150 mg, 38%).

Enantiomer 1, Example 11A
HPLC: Chiralcel AD (4.6×250 mm); 40% IPA/60% hept; 1 ml/m (flow rate); rt=9.86 m; 260 nm.
¹NMR equivalent to Example 10.
High Res. ES-MS: 489.2127; calc. for $C_{25}H_{38}O_4S_2$+Na: 489.2109.

Enantiomer 2, Example 11B
HPLC: Chiralcel AD (4.6×250 mm); 40% IPA/60% hept; 1 ml/m (flow rate); rt=12.64 m; 260 nm.
¹NMR equivalent to Example 10.
High Res. ES-MS: 489.2132; calc. for $C_{25}H_{38}O_4S_2$+Na: 489.2109.

Example 12

Alternative preparation of 3'-[4-(2-oxo-3,3-dimethylbutoxy-3-methylphenyl)-3-methylphenyl]-3'-[5-methoxycarbonyl-4-methylthiophen-2-yl]pentane (Example 1)

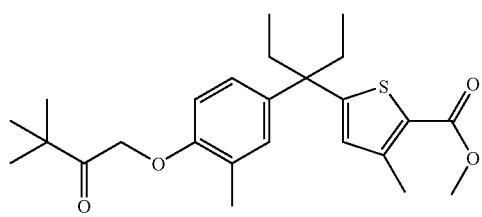

A. 4-Hydroxy-3-methylbenzoic acid methyl ester

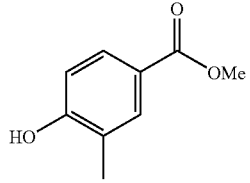

To a mixture of 3-methyl-4-hydroxybenzoic acid (342 g, 2.24 mol) in MeOH (3.5 l) is bubbled HCl (g) for 5 m. The mixture is stirred for 12 h at RT. The reaction is concentrated to give the title compound (372 g, quant).

H-NMR (ppm, CDCl₃): 7.82 (1H, s), 7.78 (1H, dd,), 6.80 (1H, d), 3.86 (3H, s), 2.22 (3H, s).

B. 3'-[4-hydroxy-3-methylphenyl]pentan-3-ol]

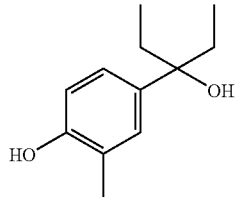

To a 0° C. mixture of 4-hydroxy-3-methylbenzoic acid methyl ester (373 g, 2.24 mol) in TBF (6 l) is added 3.0 M EtMgBr/Et₂O (2.3 l, 6.93 mol) over 3 h. The mixture is warmed to 40° C. for 2 h and cooled to 0° C. Saturated NaHCO₃ is added slowly until gas evolution ceases and the reaction is partitioned between EtOAc/water. The organic layer is washed with brine, water, MgSO₄ dried and concentrated. The residue is dissolved in CH₂Cl₂, dried with Na₂SO₄ and concentrated to give the title compound (440 g, quant).

H-NMR (ppm, CDCl₃): 7.06 (1H, s), 7.02 (1H, dd), 6.78 (1H, d), 4.60 (1H, s), 2.24 (3H, s), 1.80 (4H, m), 0.77 (6H, t).

C. 3'-[4-(Hydroxy)-3-methylphenyl]-3'-[4-methylthiophen-2-yl]pentane

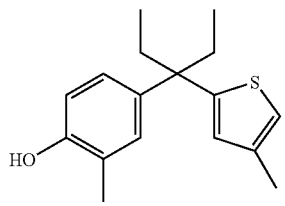

To a −78° C. mixture of 3'-[4-hydroxy-3-methylphenyl]pentan-3-ol] (415 g, 2.13 mol), 3-methylthiophene (627 g, 6.39 mol) and CH₂Cl₂ (6 l) is added BF₃-Et₂O (1.81 kg, 12.8 mol), maintaining the temperature below −75° C. The reaction is warmed to RT for 3 h and cooled to 0° C. Saturated NaHCO₃ is added until the gas evolution ceases and the mixture is partitioned with water. The organic layer is dried with Na₂SO₄, concentrated and chromatographed (EtOAc/hex) to give the title compound (425 g, 73%).

¹NMR (400 MHz, DMSO-d₆) δ ppm: 0.63 (t, J=7.3 Hz, 3H), 2.01 (m, 4H), 2.08 (s, 3H), 2.16 (s, 3H), 6.67 (m, 2H), 6.88 (m, 2H), 6.93 (d, J=1.9 Hz, 1H), 9.10 (s, 1H).

High Res. EI-MS: 274.1389; calc. for $C_{17}H_{22}OS$: 274.1391

D. 3'-[4-(t-Butyldimethylsilyloxy)-3-methylphenyl]-3'-[4-methylthiophen-2-yl]pentane

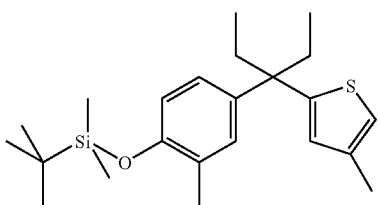

To a mixture of 3'-[4-(iydroxy)-3-methylphenyl]-3'-[4-methylthiophen-2-yl]pentane (5.00 g, 187.2 mmol) and t-butyldimethylsilyl chloride (2.75 g, 18.2 mmol) in $CH_2Cl_2$ (100 ml) is added imidazole (1.24 g, 18.2 mmol). The reaction is stirred for 24 h at RT. The mixture is diluted with Hex (100 ml), filtered and concentrated. The concentrate is suspended in Hex (100 ml), filtered and concentrated to give the title compound as an oil (6.91 g, 98%).

H-NMR (ppm, $CDCl_3$): 7.05 (1H, d, 2.0 Hz), 6.97 (1H, d, 9.0 Hz), 6.72 (1H, d, 1.1 Hz), 6.68 (1H, d, 8.3 Hz), 6.62 (1H, d, 1.3 Hz), 2.23 (3H, s), 2.20 (3H, s), 2.10 (4H, m), 1.03 (9H, s), 0.72 (6H, t, 7.3 Hz), 0.23 (6H, s).

E. 3'-[4-(t-Butyldimethylsilyloxy)-3-methylphenyl]-3'-[5-methoxycarbonyl-4-methylthiophen-2-yl]pentane

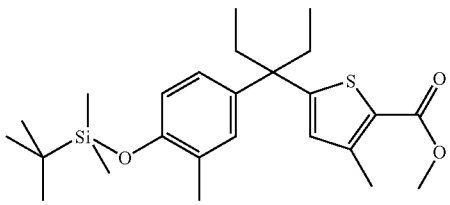

To a −78° C. mixture of 3'-[4-(t-butyldimethylsilyloxy)-3-methylphenyl]-3'-[4-methylthiophen-2-yl]pentane. (6.75 g, 17.4 mmol) and THF (100 ml) is added 2.5 M n-BuLi/hex (7.64 ml, 19.1 mmol). The mixture is stirred for 25 m and warmed to 0° C. over 15 m. The reaction is cooled to −78° C., added methyl chloroformate (1.48 ml, 19.1 mmol) and warmed to RT overnight. To the reaction is added water (25 ml). The mixture is concentrated and partitioned with $CH_2Cl_2$/water. The organic layer is concentrated to yield the title compound (7.8 g, quant.).

H-NMR (ppm, $CDCl_3$): 6.99 (1H, d, 2.0 Hz), 6.94 (1H, dd, 2.3, 8.5 Hz), 6.67 (1H, d, 8.5 Hz), 6.62 (1H, s), 3.77 (3H, s), 2.49 (3H, s), 2.17 (3H, s), 2.09 (4H, m), 1.01 (9H, s), 0.70 (6H, t, 7.3 Hz), 0.22 (6H, s).

F. 3'-[4-Hydroxy-3-methylphenyl]-3'-[5-methoxycarbonyl-4-methylthiophen-2-yl]pentane

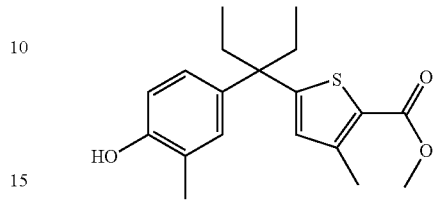

To a 0° C. mixture of 3'-[4-(t-butyldimethylsilyloxy)-3-methylphenyl]-3'-[5-methoxycarbonyl-4-methylthiophen-2-yl]pentane (130 g, 292 mmol) and THF (1 L) is added 1.0 M TBAF/THF (292 ml, 292 mmol) over 20 m. The reaction is warmed to RT and stirred for 1 d. The mixture is concentrated and partitioned with $CH_2Cl_2$/water. The organic layer is concentrated and chromatographed (EtOAc/hex) to give the title compound (40.2 g, 41%).

H-NMR (ppm, $CDCl_3$): 6.97 (1H, s), 6.95 (1H, d, 7.5 Hz), 6.69 (1H, d, 8.2 Hz), 6.61 (1H, s), 4.95 (1H, br s), 3.80 (3H, s), 2.47 (3H, s), 2.21 (3H, s), 2.08 (4H, m), 0.91 (3H, s), 0.70 (6H, t, 7.3 Hz).

G. 3'-[4-(2-Oxo-3,3-dimethylbutoxy)-3-methylphenyl]-3'-[5-methoxycarbonyl-4-methylthiophen-2-yl]pentane

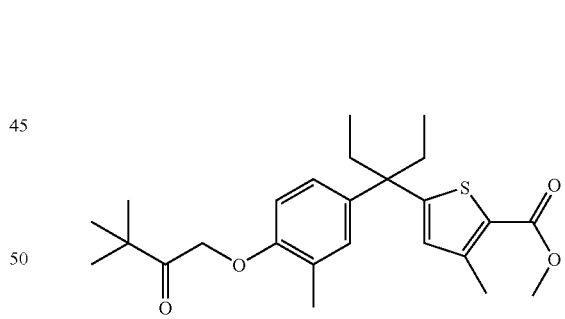

To a mixture of 3'-[4-hydroxy-3-methylphenyl]-3'-[5-methoxycarbonyl-4-methylthiophen-2-yl]pentane (14.5 g, 43.6 mmol), acetone (200 ml) and $K_2CO_3$ (12.1 g, 87.2 mmol) is added 3,3-dimethyl-1-chloro-2-butanone (5.73 ml, 43.6 mmol). The mixture is stirred overnight, refluxed for 9 h and cooled to RT overnight. The reaction is filtered and concentrated to give the title compound (18.8 g, quant.).

H-NMR (ppm, $CDC_3$): 6.99 (2H, m), 6.60 (1H, s), 6.51 (1H, d, 8.5 Hz), 4.84 (2H, s), 3.79 (3H, s), 2.47 (3H, s), 2.25 (3H, s), 2.08 (4H, m), 1.25 (9H, s), 0.70 (6H, t, 7 Hz).

Example 13

Preparation of 3'-[5-(3-oxo-4,4-dimethylpentyl)-4-methylthiophen-2-yl]-3'-[4-(methylsulfonylmethyloxy)-3-methylphenyl]pentane

H. 3'-[5-(3-Oxo-4,4-dimethylpentyl)-4-methylthiophen-2-yl]-3'-[4-benzyloxy-3-methylphenyl]pentane

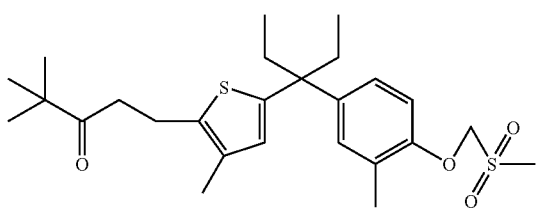

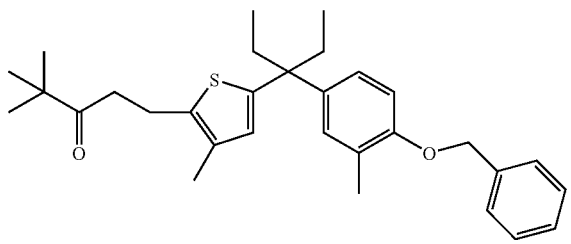

To a 0° C. mixture of 3'-[4-(benzyloxy)-3-methylphenyl]-3'-[4-methyl-5-(hydroxymethyl)thiophen-2-yl]pentane (900 mg, 2.3 mmol) and Et$_2$O (7 ml) is added PBr$_3$ (240 ul, 2.5 mmol) and stirred for 1.5 h. The reaction is diluted with Et$_2$O, washed with water (10 ml), brine (10 ml), Na$_2$SO$_4$ dried, and concentrated. The resulting residue is dissolved in THF (4 ml) and cooled to −78° C. to afford the bromide/THF solution. In a separate flask is charged with 1M LiHMDS (4.6 ml, 4.6 mmol), cooled to −78 C, and added pinacolone (570 ul, 4.6 mmol). The reaction is stirred for 1.5 h, warmed to −50 C and transferred (via syringe) to the −78° C. solution of bromide/THF. The reaction is warmed to RT with a cold water bath. After stirring for 15 m, the reaction is diluted with Et2O and washed with 1N HCl. The organic layer is Na2SO4 dried and chromatographed (30% CHCl3/hex to 80% CHCl3/hex) to give the title compound (900 mg, 82%).

$^1$NMR (400 MHz, DMSO-d$_6$) δ ppm: 0.62 (t, J=7.3 Hz, 6H), 1.00 (s, 9H), 1.93-2.04 (m, 4H), 2.15 (s, 3H), 2.71 (m, 2H), 2.80 (m, 2H), 5.08 (s, 2H), 6.55 (s, 1H), 6.90 (d, J=8.3 Hz, 1H), 7.01 (m, 2H), 7.34 (d, J=7.3 Hz, 1H), 7.41 (m, 2H), 7.46 (d, J=7.8 Hz, 2H).

High Res. ES-MS: 477.2830; calc. for C$_{31}$H$_{40}$O$_2$S+H: 477.2827.

I. 3'-[5-(3-Oxo-4,4-dimethylpentyl)-4-methylthiophen-2-yl]-3'-[4-hydroxy-3-methylphenyl]pentane

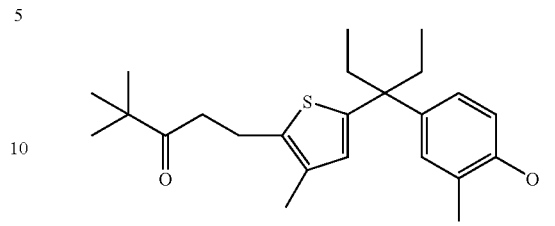

Using a procedure analogous to Example 1F, 3'-[5-(3-oxo-4,4-dimethylpentyl)-4-methylthiophen-2-yl]-3'-[4-benzyloxy-3-methylphenyl]pentane gives the title compound (600 mg, 97%).

$^1$NMR (400 MHz, DMSO-d$_6$) δ ppm: 0.59 (t, J=7.3 Hz, 6H), 0.99 (s, 9H), 1.91-1.98 (m, 4H), 2.03 (s, 3H), 2.04 (s, 3H), 2.71 (m, 2H), 2.75 (m, 2H), 6.49 (s, 1H), 6.62 (d, J=8.3 Hz, 1H), 6.82 (d, J=8.3 Hz, 1H), 6.86 (s, 1H), 9.04 (s, 1H).

High Res. ES-MS: 409.2167; calc. for C$_{24}$H$_{34}$O$_2$S+Na: 409.2177.

J. 3'-[5-(3-Oxo-4,4-dimethylpentyl)-4-methylthiophen-2-yl]-3'-[4-(methylmercaptylmethyloxy)-3-methylphenyl]pentane

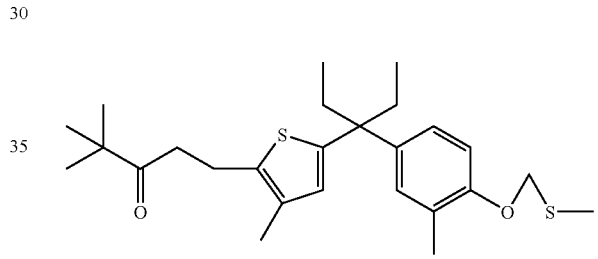

Using a procedure analogous to Example 1D, 3'-[5-(3-oxo-4,4-dimethylpentyl)-4-methylthiophen-2-yl]-3'-[4-hydroxy-3-methylphenyl]pentane and methylmercaptylmethyl chloride give the title compound (440 mg, 73%).

$^1$NMR (400 MHz, DMSO-d$_6$) δ ppm: 0.61 (t, J=7.3 Hz, 6H), 0.98 (s, 9H), 1.93-2.01 (m, 4H), 2.04 (s, 3H), 2.11 (s, 3H), 2.17 (s, 3H), 2.71 (m, 2H), 2.76 (m, 2H), 5.23 (s, 2H), 6.86 (d, J=8.3 Hz, 1H), 6.98 (m, 2H).

High Res. ES-MS: 469.2230; calc. for C$_{26}$H$_{38}$O$_2$S$_2$+Na: 469.2211.

K. 3'-[5-(3-Oxo-4,4-dimethylpentyl)-4-methylthiophen-2-yl]-3'-[4-(methylsulfonylmethyloxy)-3-methylphenyl]pentane

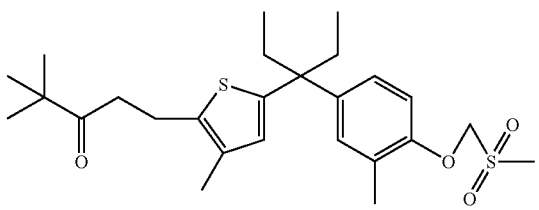

Using a procedure analogous to Example 9C, 3'-[5-(3-Oxo-4,4-dimethylpentyl)-4-methylthiopben-2-yl]-3'-[4-(methylmercaptylmethyloxy)-3-methylphenyl]pentane gives the title compound (140 mg, 33%).

[1]NMR (400 MHz, DMSO-$d_6$) δ ppm: 0.61 (t, J=7.3 Hz, 6H), 0.99 (s, 9H), 1.95-2.02 (m, 4H), 2.04 (s, 3H), 2.17 (s, 3H), 2.71 (m, 2H), 2.76 (m, 2H), 3.04 (s, 3H), 5.24 (s, 2H), 6.53 (s, 1H), 7.01 (m, 3H).

High Res. ES-MS: 501.2129; calc. for $C_{26}H_{38}O_4S_2$+Na: 501.2109.

Example 14

Preparation of 3'-[5-(3-hydroxy-4,4-dimethylpentyl)-4-methylthiophen-2-yl]-3'-[4-(methylsulfonylmethyloxy)-3-methylphenyl]pentane

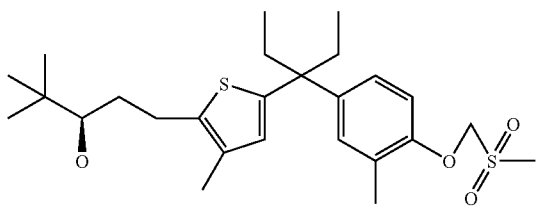

Using a procedure analogous to Example 2, 3'-[5-(3-oxo-4,4-dimethylpentyl)-4-methylthiophen-2-yl]-3'-[4-(methylsulfonylmethyloxy)-3-methylphenyl]pentane gives the title compound (100 mg, quant.).

[1]NMR (400 MHz, DMSO-$d_6$) δ ppm: 0.62 (t, J=7.3 Hz, 6H), 0.77 (s, 9H), 1.11-1.38 (m, 1H), 1.56-1.63 (m, 1H), 1.94-2.01 (m, 4H), 2.04 (s, 3H), 2.18 (s, 3H), 2.52-2.60 (m, 1H), 2.77-2.83 (m, 1H), 2.94-2.97 (m, 1H), 3.04 (s, 3H), 4.38 (d, J=5.9, 1H), 5.25 (s, 2H), 6.53 (s, 1H), 7.01 (m, 3H).

High Res. ES-MS: 503.2268; calc. for $C_{26}H_{40}O_4S_2$+Na: 503.2266.

Example 15A and 15B

Preparation of enantiomers of 3'-[5-(3-hydroxy-4,4-dimethylpentyl)-4-methylthiophen-2-yl]-3'-[4-(methylsulfonylmethyloxy)-3-methylphenyl]pentane

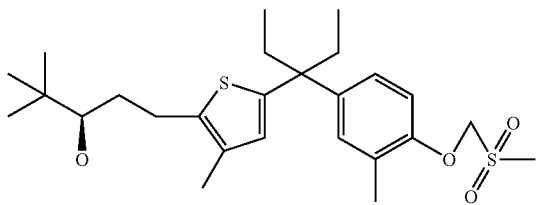

A mixture of racemic 3'-[5-(3-hydroxy-4,4-dimethylpentyl)-4-methylthiophen-2-yl]-3'-[4-(methylsulfonylmethyloxy)-3-methylphenyl]pentane is chromatographed with a Chiralcel OD column to give enantiomer 1 Example 3A (54 mg, 43%) and enantiomer 2, Example 3B (55 mg, 44%).

Enantiomer 1, Example 3A]

HPLC: Chiralcel OD (4.6×250 mm); 40% IPA/60% heptane; 1 ml/m (flow rate); rt=8.9 m; 225 nm.

[1]NMR equivalent to Example Yee-2.

High Res. ES-MS: 503.2269; calc. for $C_{26}H_{40}O_4S_2$+Na: 503.2266.

Enantiomer 2, Example 3B

HPLC: Chiralcel OD (4.6×250 mm);); 40% IPA/60% heptane; I ml/m (flow rate); rt=11.3 m; 225 nm.

[1]NMR equivalent to Example 2.

High Res. ES-MS: 503.2280; calc. for $C_{26}H_{40}O_4S_2$+Na: 503.2266.

Example 16

Preparation of 3'-[5-(3-hydroxy-4,4-dimethylpentyl)-4-methylthiophen-2-yl]-3'-[4-(methylsulfinylmethyloxy)-3-methylphenyl]pentane

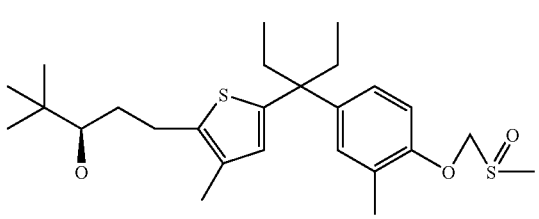

To a 0° C. mixture of 3'-[5-(3-hydroxy-4,4-dimethylpentyl)-4-methylthiophen-2-yl]-3'-[4-(methylmercaptylmethyloxy)-3-methylphenyl]pentane (725 mg, 1.67 mmol) and $CHCl_3$ (7 ml) is added 50% m-CPBA (1.3 g, 3.77 mmol). The stirred reaction is allowed to warm to RT over 1 h. The resulting suspension is added more $CHCl_3$ (7 ml) and stirred for 1 h. The mixture is diluted with $CHCl_3$ and washed with satd Na2CO3. The organic layer is concentrated and chromatographed ($CHCl_3$ to 50% EtOAc/$CHCl_3$, TLC Rf: 0.05) to give the title compound (175 mg, 23%).

[1]NMR (300 MHz, DMSO-$d_6$) δ ppm: 0.62 (t, J=7.3 Hz, 6H), 0.77 (s, 9H), 1.95-2.01 (m, 4H), 2.04 (s, 3H), 2.15 (s, 3H), 2.58 (m, 1H), 2.61 (s, 3H), 2.79 (m, 1H), 3.04 (m, 1H), 4.38 (m, 1H), 5.02 (d, J=10.2 Hz, 1H), 5.20 (d, J=10.7 Hz, 1H), 6.53 (s, 1H), 7.02 (m, 3H).

High Res. ES-MS: 465.2483; calc. for $C_{26}H_{40}O_3S_2$+H: 465.2497.

Example 17

Preparation of 3'-[5-(3-oxo-4,4-dimethylpentyl)-4-methylthiophen-2-yl]-3'-[4-(methylsulfonyloxy)-3-methylphenyl]pentane

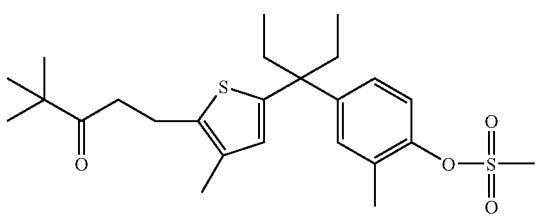

Using a procedure analogous to Example 1D, 3'-[5-(3-oxo-4,4-dimethylpentyl)-4-methylthiophen-2-yl]-3'-[4-(hydroxy)-3-methylphenyl]pentane gives the title compound (425 mg, 65%).

TLC: CHCl$_3$; Rf=0.4.

$^1$NMR (400 MHz, DMSO-d$_6$) δ ppm: 0.62 (t, J=7.3 Hz, 6H), 0.98 (s, 9H), 1.93-2.15 (m, 4H), 2.05 (s, 3H), 2.24 (s, 3H), 2.72 (m, 2H), 2.77 (m, 2H), 3.40 (s, 3H), 6.57 (s, 1H), 7.11 (d, J=2.5 Hz, 1H), 7.19 (m, 2H).

High Res. ES-MS: 487.1940; calc. for C$_{25}$H$_{36}$O$_4$S$_2$+Na: 487.1940.

Example 18

Preparation of 3'-[5-(3-hydroxy-4,4-dimethylpentyl)-4-methylthiophen-2-yl]-3'-[4-(methylsulfonyloxy)-3-methylphenyl]pentane

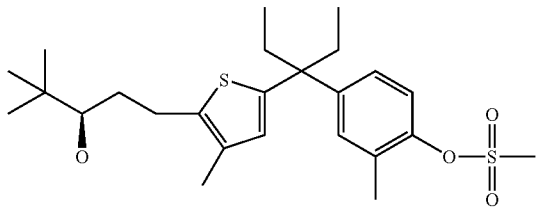

Using a procedure analogous to Example 2, 3'-[5-(3-oxo-4,4-dimethylpentyl)-4-methylthiophen-2-yl]-3'-[4-(methylsulfonyloxy)-3-methylphenyl]pentane gives the title compound (300 mg, 96%).

TLC: 5% EtOAc/CHCl$_3$; Rf 0.35.

$^1$NMR (300 MHz, DMSO-d$_6$) δ ppm: 0.62 (t, J=7.3 Hz, 6H), 0.77 (s, 9H), 1.35 (m, 1H), 1.62 (m, 1H), 1.95-2.12 (m, 4H), 2.04 (s, 3H), 2.25 (s, 3H), 2.60 (m, 1H), 2.81 (m, 1H), 2.98 (m, 1H), 3.42 (s, 3H), 4.37 (d, J=6.2 Hz, 1H), 6.59 (s, 1H), 7.13 (dd, J=2.2, 8.8 Hz, 1H), 7.22 (m, 2H).

High Res. ES-MS: 484.2539; calc. for C$_{25}$H$_{38}$O$_4$S$_2$+NH$_4$: 484.2555.

Example 19A and 19B

Preparation of enantiomers of 3'-[5-(3-hydroxy-4,4-dimethylpentyl)-4-methylthiophen-2-yl]-3'-[4-(methylsulfonyloxy)-3-methylphenyl]pentane

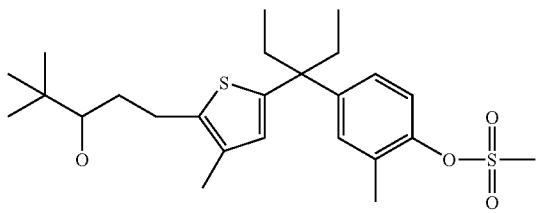

A mixture of racemic 3'-[5-(3-hydroxy-4,4-dimethylpentyl)-4-methylthiophen-2-yl]-3'-[4-(methylsulfonyloxy)-3-methylphenyl]pentane is chromatographed with a Chiralcel AD column to give enantiomer 1, Example 19A (108 mg, 43%) and enantiomer 2, Example 19B (109 mg, 44%).

Enantiomer 1, Example 19A

HPLC: Chiralcel AD (4.6×250 mm); 10% IPA/heptane; 1 ml/m (flow rate); rt=6.85 m; 250 nm.

$^1$NMR equivalent to Example 18.

High Res. ES-MS: 489.2106; calc. for C$_{25}$H$_{38}$O$_4$S$_2$+Na: 489.2109.

Enantiomer 2, Example 19B.

HPLC: Chiralcel AD (4.6×250 mm); 10% IPA/heptane; 1 ml/m (flow rate); rt=8.00 m; 250 nm.

$^1$NMR equivalent to Example 18.

High Res. ES-MS: 489.2112; calc. for C$_{25}$H$_{38}$O$_4$S$_2$+Na: 489.2109.

Example 20

Preparation of 3'-[5-(3-oxo-4,4-dimethylpentyl)-4-methylthiophen-2-yl]-3'-[4-methoxycarbonyl-3-methylphenyl]pentane

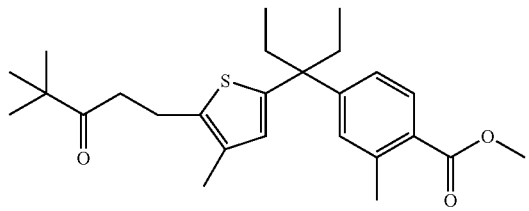

A. 3'-[5-(3-Oxo-4,4-dimethylpentyl)-4-methylthiophen-2-yl]-3'-[4-(trifluoromethylsulfonyloxy)-3-methylphenyl]pentane.

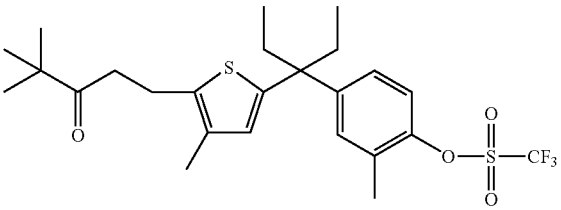

To a 0° C. mixture of 3'-[5-(3-oxo-4,4-dimethylpentyl)-4-methylthiophen-2-yl]-3'-[4-hydroxy-3-methylphenyl]pentane (2.7 g, 7.0 mmol) and pyridine (8 ml) is added Tf2O (1.3 ml, 7.7 mmol). The reaction is warmed to RT and stirred overnight. The reaction is diluted with Et2O, washed with 1N HCl and brine, Na2SO4 dried, and concentrated. The residue is chromatographed (30/hex) to give the title compound (2.9 g, 80%).

$^1$NMR (400 MHz, DMSO-d$_6$) δ ppm: 0.61 (t, J=7.3 Hz, 6H), 0.97 (s, 9H), 1.95-2.11 (m, 4H), 2.04 (s, 3H), 2.28 (s, 3H), 2.70 (m, 2H), 2.77 (m, 2H), 6.59 (s, 1H), 7.19 (dd, J=2.4, 8.8 Hz, 1H), 7.24 (d, J=8.8 Hz, 1H), 7.30 (d, J=2.0 Hz, 1H).

High Res. ES-MS: 519.1838; calc. for C$_{25}$H$_{33}$F$_3$O$_4$S$_2$+H: 519.1851.

B. 3'-[5-(3-Oxo-4,4-dimethylpentyl)-4-methylthiophen-2-yl]-3'-[4-methoxycarbonyl-3-methylphenyl]pentane A mixture of 3'-[5-(3-oxo-4,4-dimethylpentyl)-4-methylthiophen-2-yl]-3'-[4-(trifluoromethylsulfonyloxy)-3-methylphenyl]pentane (2.65 g, 5.1 mmol), DPPF (554 mg, 1.0 mmol), Pd(OAc)$_2$ (120 mg, 0.51 mmol), DMF (10 ml), MeOH (2.1 ml) and Et₃N (2.1 ml, 15.3 mmol) is heated in an autoclave at 110 C under CO pressure (1000 psi). After 48 h, the reaction is cooled to RT and diluted with Et2O. The mixture is washed with 5N HCl, water, and Na2SO4 dried and concentrated. The residue is chromatographed (10% EtOAc/hex) to give the title compound (1.86 g, 85%).

¹NMR (400 MHz, DMSO-$d_6$) δ ppm: 0.61 (t, J=7.3 Hz, 6H), 0.98 (s, 9H), 1.96-2.12 (m, 4H), 2.04 (s, 3H), 2.47 (s, 3H), 2.71 (m, 2H), 2.78 (m, 2H), 3.79 (s, 3H), 6.56 (s, 1H), 7.15 (m, 2H), 7.71 (d, J=7.8 Hz, 1H).

High Res. ES-MS: 446.2741; calc. for $C_{26}H_{36}O_3S+NH_4$: 446.2729.

Example 21

Preparation of 3'-[5-(3-hydroxy-4,4-dimethylpentyl)-4-methylthiophen-2-yl]-3'-[4-methoxycarbonyl-3-methylphenyl]pentane

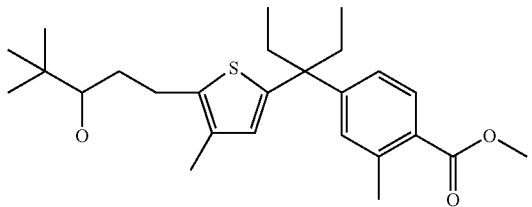

Using a procedure analogous to Example 2, 3'-[5-(3-Oxo-4,4-dimethylpentyl)-4-methylthiophen-2-yl]-3'-[4-methoxycarbonyl-3-methylphenyl]pentane gives the title compound (785 mg, 98%).

¹NMR (400 MHz, DMSO-$d_6$) δ ppm: 0.63 (t, J=7.3 Hz, 6H), 0.77 (s, 9H), 1.35 (m, 1H), 1.54 (m, 1H), 1.98-2.13 (m, 4H), 2.04 (s, 3H), 2.48 (s, 3H), 2.56 (m, 1H), 2.79 (m, 1H), 2.95 (m, 1H), 3.79 (s, 3H), 4.37 (br s, d, 1H), 6.57 (s, 1H), 7.17 (m, 2H), 7.72 (d, J=7.8 Hz, 1H).

High Res. ES-MS: 431.2630; calc. for $C_{26}H_{38}O_3S+H$: 431.2620.

Example 22

Preparation of 3'-[5-(3-oxo-4,4-dimethylpentyl)-4-methylthiophen-2-yl]-3'-[4-carboxyl-3-methylphenyl]pentane

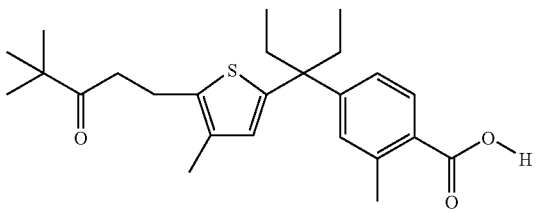

Using a procedure analogous to Example 3, 3'-[5-(3-oxo-4,4-dimethylpentyl)-4-methylthiophen-2-yl]-3'-[4-methoxycarbonyl-3-methylphenyl]pentane gives the title compound (800 mg, 92%).

¹NMR (400 MHz, DMSO-$d_6$) δ ppm: 0.62 (t, J=7.3 Hz, 6H), 0.98 (s, 9H), 1.96-2.11 (m, 4H), 2.04 (s, 3H), 2.47 (s, 3H), 2.71 (m, 2H), 2.77 (m, 2H), 6.56 (s, 1H), 7.11 (m, 2H), 7.71 (d, J=8.3 Hz, 1H), 12.64 (s, 1H).

High Res. ES-MS: 415.2297; calc. for $C_{25}H_{34}O_3S+H$: 415.2307.

Example 23

Preparation of 3'-[5-(3-hydroxy-4,4-dimethylpentyl)-4-methylthiophen-2-yl]-3'-[4-carboxyl-3-methylphenyl]pentane

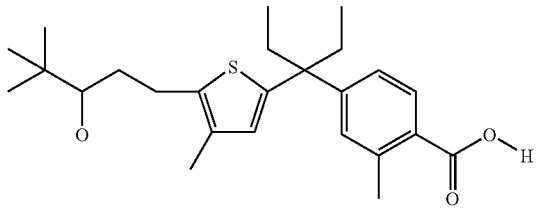

Using a procedure analogous to Example 3, 3'-[5-(3-hydroxy-4,4-dimethylpentyl)-4-methylthiophen-2-yl]-3'-[4-methoxycarbonyl-3-methylphenyl]pentane gives the title compound (700 mg, 99%).

¹NMR (400 MHz, DMSO-$d_6$) δ ppm: 0.62 (t, J=7.3 Hz, 6H), 0.77 (s, 9H), 1.36 (m, 1H), 1.58 (m, 1H), 1.96-2.11 (m, 4H), 2.04 (s, 3H), 2.48 (s, 3H), 2.55 (m, 1H), 2.60 (m, 1H), 4.37 (d, J=6.2 Hz, 1H), 6.58 (s, 1H), 7.17 (m, 2H), 7.73 (d, J=8.1 Hz, 1H), 12.65 (br s, 1H).

High Res. ES-MS: 439.2322; calc. for $C_{25}H_{36}O_3S+Na$: 439.2283.

Example 24

Preparation of 3'-[5-(3-hydroxy-4,4-dimethylpentyl)-4-methylthiophen-2-yl]-3'-[4-(methoxycarbonylmethylaminocarbonyl)-3-methylphenyl]pentane

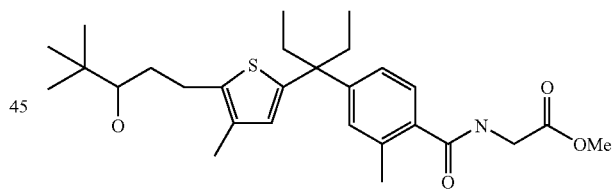

To a mixture of DMAP (256 mg, 2.1 mmol), methyl glycinate hydrochloride (123 mg, 1.01 mmol), EDCI (193 mg, 1.01 mmol) and $CH_2C_2$ (4 ml) is added 3'-[5-(3-hydroxy-4,4-dimethylpentyl)-4-methylthiophen-2-yl]-3'-[4-carboxyl-3-methylphenyl]pentane (350 mg, 0.84 mmol). The reaction is added $CH_2Cl_2$ (2 ml) and DMF (1 ml). The mixture is stirred for 16 h and concentrated. The residue is diluted with Et₂O, 1N HCl (3×), brine and $Na_2SO_4$ dried. The organic solution is concentrated and chromatograpbed (20% EtOAc/CHCl₃ to 50% EtOAc/CHCl₃) to give the title compound (320 mg, 78%).

¹NMR (400 MHz, DMSO-$d_6$) δ ppm: 0.64 (t, J=7.3 Hz, 6H), 0.77 (s, 9H), 1.35 (m, 1H), 1.57 (m, 1H), 1.98-2.12 (m, 4H), 2.32 (s, 3H), 2.53-2.61 (m, 1H), 2.77-2.84 (m, 1H), 2.95 (m, 1H), 3.65 (s, 3H), 3.94 (d, J=5.9 Hz, 2H), 4.39 (br s, 1H), 6.56 (s, 1H), 7.11 (m, 2H), 7.26 (d, J=8.3 Hz, 1H), 8.62 (t, J=5.9 Hz, 1H).

ES-MS: 488.2 (M+H).

Example 25A and 25B

Preparation of enantiomers of 3'-[5-(3-hydroxy-4,4-dimethylpentyl)-4-methylthiophen-2-yl]-3'-[4-(methoxycarbonylmethylaminocarbonyl)-3-methylphenyl]pentane

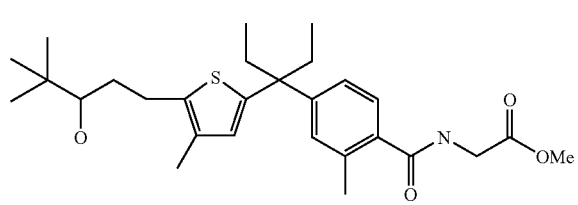

A racemic mixture of 3'-[5-(3-hydroxy-4,4-dimethylpentyl)-4-methylthiophen-2-yl]-3'-[4-(metboxycarbonylmethylaminocarbonyl)-3-methylphenyl]pentane is chromatographed with a Chiralcel AD column to give enantiomer 1, Example 25A (110 mg, 37%) and enantiomer 2, Example 25B (102 mg, 34%).

Enantiomer 1, Example 25A
HPLC: Chiralcel AD (4.6×250 mm); 10% IPA/heptane; 1 ml/m (flow rate); rt=16.90 m; 240 nm.
[1]NMR equivalent to Example 24.
High Res. ES-MS: 488.2812; calc. for $C_{28}H_{41}NO_4S+H$: 488.2835.

Enantiomer 2, Example 25B.
HPLC: Chiralcel AD (4.6×250 mm); 10% IPA/heptane; 1 ml/m (flow rate); rt=20.00 m; 240 nm.
[1]NMR equivalent to Example 24.
High Res. ES-MS: 488.2831; calc. for $C_{28}H_{41}NO_4S+H$: 488.2835.

Example 26

Preparation of isomer 1 of 3'-[5-(3-hydroxy-4,4-dimethylpentyl)-4-methylthiophen-2-yl]-3'-[4-(carboxylmethylaminocarbonyl)-3-methylphenyl]pentane

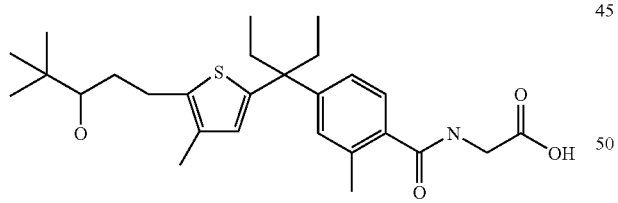

Using a procedure analogous to Example 3 but reacted at 50° C., isomer I of 3'-[5-(3-hydroxy-4,4-dimethylpentyl)-4-methylthiophen-2-yl]-3'-[4-(methoxycarbonylmethylaminocarbonyl)-3-methylphenyl]pentane (Example 13A) gives the title compound (95 mg, 98%).

[1]NMR (400 MHz, DMSO-$d_6$) δ ppm: 0.64 (t, J=7.3 Hz, 6H), 0.77 (s, 9H), 1.34 (m, 1H), 1.58 (m, 1H), 1.97-2.12 (m, 4H), 2.04 (s, 3H), 2.32 (s, 3H), 2.57 (m, 1H), 2.80 (m, 1H), 2.95 (m, 1H), 3.84 (d, J=6.3 Hz, 1H), 4.38 (br s, 1H), 6.56 (s, 1H), 7.10 (m, 2H), 7.26 (d, J=8.8 Hz, 1H), 8.48 (t, J=6.3 Hz, 1H), 12.47 (br s, 1H).
High Res. ES-MS: 474.2689; calc. for $C_{27}H_{39}NO_4S+H$: 474.2678.

Example 27

Preparation of isomer 2 of 3'-[5-(3-hydroxy-4,4-dimethylpentyl)-4-methylthiophen-2-yl]-3'-[4-(carboxylmethylaminocarbonyl)-3-methylphenyl]pentane

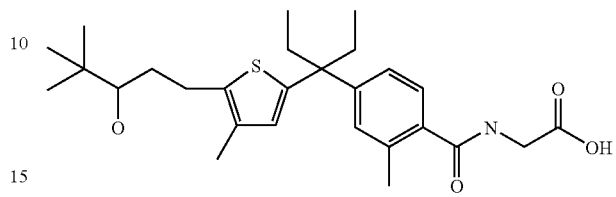

Using a procedure analogous to Example 3 except using LiOH at 60° C., isomer 2 of 3'-[5-(3-hydroxy-4,4-dimethylpentyl)-4-methylthiophen-2-yl]-3'-[4-(methoxycarbonylmethylaminocarbonyl)-3-methylphenyl]pentane gives the title compound (79 mg, 94%).

[1]NMR equivalent to Example 26.
High Res. ES-MS: 474.2672; calc. for $C_{27}H_{39}NO_4S+H$: 474.2678.

Example 28

Preparation of 3'-[5-(3-hydroxy-4,4-dimethylpentyl)-4-ethylthiophen-2-yl]-3'-[4-(ethoxycarbonylethyl)-3-methylphenyl]pentane

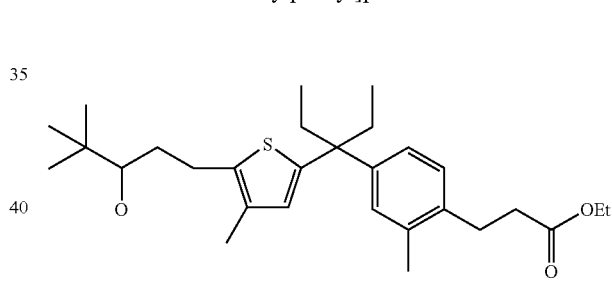

3'-[5-(3-Hydroxy-4,4-dimethylpentyl)-4-methylthiophen-2-yl]-3'-[4-(trifluoromethylsulfonyloxy)-3-methylphenyl]pentane

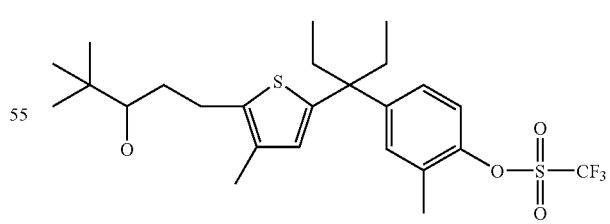

Using a procedure analogous to Example 8A, isomer 1 of 3'-[5-(3-hydroxy-4,4-dimethylpentyl)-4-methylthiophen-2-yl]-3'-[4-hydroxy-3-methylphenyl]pentane gives the title compound (1.1 g, 64%).

[1]NMR (400 MHz, DMSO-$d_6$) δ ppm: 0.63 (t, J=7.3 Hz, 6H), 0.77 (s, 9H), 1.35 (m, 1H), 1.59 (m, 1H), 1.97-2.12 (m, 4H), 2.04 (s, 3H), 2.29 (s, 3H), 2.58 (m, 1H), 2.80 (m, 1H), 2.94 (m, 1H), 4.38 (br s, 1H), 6.59 (s, 1H), 7.21 (dd, J=2.4, 8.8 Hz, 1H), 7.26 (m, 2H), 7.33 (d, J=2.0 Hz, 1H).

High Res. EI-MS: 520.1927; calc. for $C_{25}H_{35}F_3O_4S_2$: 520.1929.

A. 3'-[5-(3-Hydroxy-4,4-dimethylpentyl)-4-methylthiophen-2-yl]-3'-[4-(ethoxycarbonylethyl)-3-methylphenyl]pentane To a 0° C. mixture of 3'-[5-(3-hydroxy-4,4-dimethylpentyl)-4-methylthiophen-2-yl]-3'-[4-(trifluoromethylsulfonyloxy)-3-methylphenyl]pentane (1.08 g, 2.07 mmol), Pd(Dppf)2Cl2 (170 mg, 0.207 mmol), LiCl (350 mg, 8.3 mmol) and THF (1 ml) is added 0.5M of 2-(ethoxycarbonyl)ethylzinc bromide/THF (12.4 ml, 6.21 mmol). The reaction is heated to 60° C. for 1 h and concentrated (to ~8 ml of volume) with a stream of nitrogen. The reaction is heated under nitrogen for another 15 h. After cooling, the reaction is diluted with Et$_2$O, quenched with 2.5N HCl, washed with water, Na2SO4 dried, and concentrated. The residue is chromatographed (70% CHC$_3$/hex to 100% CHCl$_3$) to give the title compound (550 mg, 56%).

$^1$NMR (400 MHz, DMSO-d$_6$) δ ppm: 0.61 (t, J=7.3 Hz, 6H), 0.77 (s, 9H), 1.14 (t, J=6.8 Hz, 3H), 1.33 (m, 1H), 1.58 (m, 1H), 1.93-2.19 (m, 4H), 2.04 (s, 3H), 2.22 (s, 3H), 2.51-2.59 (m, 3H), 2.75-2.83 (m, 3H), 2.95 (m, 1H), 4.02 (q, J=7.3 Hz, 2H), 4.38 (br s, 1H), 6.53 (s, 1H), 6.98 (m, 3H).

High Res. ES-MS: 495.2926; calc. for $C_{29}H_{44}O_3S$+Na: 495.2909.

Example 29

Preparation of 3'-[5-[5-(3-hydroxy-4,4-dimethylpentyl)-4-methylthiopben-2-yl]-3'-[4-(2-carboxylethyl)-3-methylphenyl]pentane

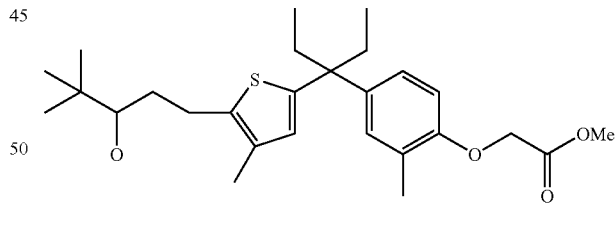

Using a procedure analogous to Example 3 but reacted at RT for 45 m, 3'-[5-10, (3-hydroxy-4,4-dimethylpentyl)-4-methylthiophen-2-yl]-3'-[4-(2-ethoxycarbonylethyl)-3-methylphenyl]pentane gives the title compound (450 mg, 95%).

$^1$NMR (400 MHz, DMSO-d$_6$) δ ppm: 0.62 (t, J=7.3 Hz, 6H), 0.77 (s, 9H), 1.34 (m, 1H), 1.59 (m, 1H), 1.97-2.19 (m, 4H), 2.04 (s, 3H), 2.21 (s, 3H), 2.45 (t, J=7.3 Hz, 2H), 2.54 (m, 1H), 2.74 (t, J=8.3 Hz, 2H), 2.79 (m, 1H), 2.96 (m, 1H), 4.38 (br s, 1H), 6.53 (s, 1H), 6.99 (m, 3H), 12.09 (br s, 1H).

ES-MS: 445.3 (M+H).

Example 30A and 30B

Preparation of enantiomers of 3'-[5-(3-hydroxy-4,4-dimethylpentyl)-4-methylthiophen-2-yl]-3'-[4-(2-carboxylethyl)-3-methylphenyl]pentane

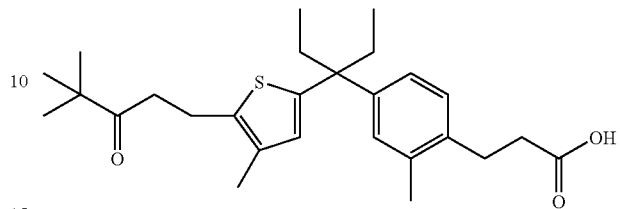

A racemic mixture of 3'-[5-(3-hydroxy-4,4-dimethylpentyl)-4-methylthiophen-2-yl]-3'-[4-(2-carboxylethyl)-3-methylphenyl]pentane is chromatographed with a Chiralcel AD column to give enantiomer 1, Example 30A (108 mg, 43%) and enantiomer 2, Example 30B (109 mg, 44%).

Enantiomer 1, Example 30A

HPLC: Chiralcel AD (4.6×250 mm); 0.1% TFA in 5% EtOH/hept; 1 ml/m (flow rate); rt=8.20 m; 210 nm.

$^1$NMR (300 MHz, DMSO-d$_6$) δ ppm: 0.62 (t, J=7.3 Hz, 6H), 0.77 (s, 9H), 1.35 (m, 1H), 1.61 (m, 1H), 1.97-2.10 (m, 4H), 2.04 (s, 3H), 2.22 (s, 3H), 2.47 (m, 2H), 2.56 (m, 1H), 2.77 (m, 3H), 2.95 (m, 1H), 4.37 (d, J=6.2 Hz, 1H), 6.54 (s, 1H), 7.02 (m, 3H), 12.12 (br s, 1H).

High Res. ES-MS: 462.3054; calc. for $C_{27}H_4ONO_3S$+NH$_4$: 462.3042.

Enantiomer 2, Example 30B.

HPLC: Chiralcel AD (4.6×250 mm); 0.1% TFA in 5% EtOH/hept; 1 ml/m (flow rate); rt=10.09 m; 210 nmn.

$^1$NMR equivalent to Example 29.

High Res. ES-MS: 462.3057; calc. for $C_{27}H_4ONO_3S$+NH$_4$: 462.3042.

Example 31

Preparation of 3'-[5-(3-hydroxy-4,4-dimethylpentyl)-4-methylthiophen-2-yl]-3'-[4-(methoxycarbonylmethoxy)-3-methylphenyl]pentane

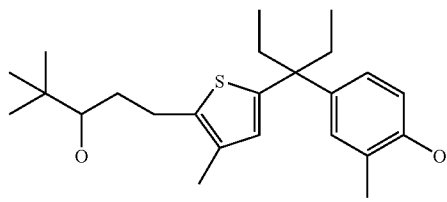

A. 3'-[5-(3-hydroxy-4,4-dimethylpentyl)-4-methylthiophen-2-yl]-3'-[4-hydroxy-3-methylphenyl]pentane Using a procedure analogous to Example 2, 3'-[5-(3-oxo-4,4-dimethylpentyl)-4-methylthiophen-2-yl]-3'-[4-hydroxy-3-methylphenyl]pentane gives the title compound (4.6 g, 98%).

$^1$NMR (300 MHz, DMSO-d$_6$) δ ppm: 0.61 (t, J=7.3 Hz, 6H), 0.78 (s, 9H), 1.35 (m, 1H), 1.57 (m, 1H), 1.87-2.11 (m, 4H), 2.04 (s, 3H), 2.06 (s, 3H), 2.58 (m, 1H), 2.96 (dd, J=6.2, 9.1 Hz, 1H), 4.36 (d, J=6.2 Hz, 1H), 6.51 (s, 1H), 6.65 (d, J=8.1 Hz, 1H), 6.85 (dd, J=2.2, 8.4 Hz, 1H), 6.90 (s, 1H), 9.03 (s, 1H).

High Res. ES-MS: 389.2502; calc. for C$_{24}$H$_{36}$O$_2$S+H: 389.2514.

B. 3'-[5-(3-Hydroxy-4,4-dimethylpentyl)-4-methylthiophen-2-yl]-3'-[4-(methoxycarbonylmethoxy)-3-methylphenyl]pentane

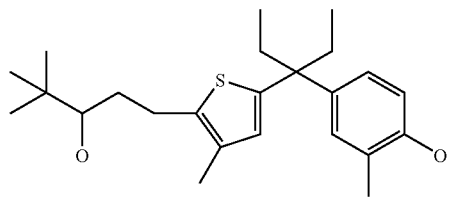

Using a procedure analogous to Example 1D, 3'-[5-(3-hydroxy-4,4-dimethylpentyl)-4-methylthiophen-2-yl]-3'-[4-hydroxy-3-methylphenyl]pentane is reacted with NaH and methyl chloroacetate to give the title compound (1.85 g, 92%).

$^1$NMR (400 MHz, DMSO-d$_6$) δ ppm: 0.62 (t, J=7.3 Hz, 6H), 0.78 (s, 9H), 1.35 (m, 1H), 1.58 (m, 1H), 1.92-2.02 (m, 4H), 2.04 (s, 3H), 2.14 (s, 3H), 2.55 (m, 1H), 2.78 (m, 1H), 2.95 (m, 1H), 3.69 (s, 3H), 4.38 (br s, 1H), 4.78 (s, 2H), 6.53 (s, 1H), 6.69 (d, J=8.3 Hz, 1H), 6.98 (m, 2H).

High Res. ES-MS: 461.2738; calc. for C$_{27}$H$_{40}$O$_4$S+H: 461.2726.

Example 32

Preparation of 3'-[5-(3-hydroxy-4,4-dimethylpentyl)-4-methylthiophen-2-yl]-3'-[4-(carboxylmethoxy)-3-methylphenyl]pentane

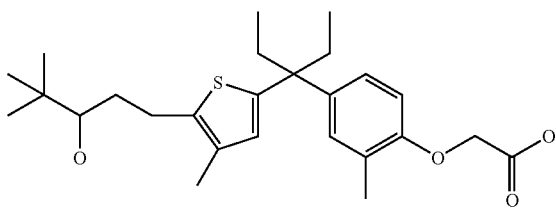

Using a procedure analogous to Example 3, 3'-[5-(3-hydroxy-4,4-dimethylpentyl)-4-methylthiophen-2-yl]-3'-[4-(methoxycarbonylmethoxy)-3-methylphenyl]pentane gives the title compound (1.4 g, 80%).

$^1$NMR (300 MHz, DMSO-d$_6$) δ ppm: 0.62 (t, J=7.3 Hz, 6H), 0.78 (s, 9H), 1.59 (m, 1H), 1.61 (m, 1H), 1.90-2.07 (m, 4H), 2.04 (s, 3H), 2.14 (s, 3H), 2.58 (m, 1H), 2.78 (m, 1H), 2.96 (m, 1H), 4.37 (d, J=6.2 Hz, 1H), 4.64 (s, 2H), 6.53 (s, 1H), 6.68 (d, J=9.1 Hz, 1H), 7.00 (m, 2H), 12.92 (br s, 1H).

High Res. ES-MS: 469.2392; calc. for C$_{26}$H$_{38}$O$_4$S+Na: 469.2389.

Example 33A & 33B

Preparation of enantiomers of 3'-[5-(3-hydroxy-4,4-dimethylpentyl)-4-methylthiophen-2-yl]-3'-[4-(carboxylmethoxy)-3-methylphenyl]pentane

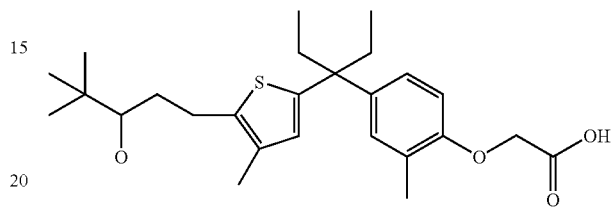

A racemic mixture of 3'-[5-(3-hydroxy-4,4-dimethylpentyl)-4-methylthiophen-2-yl]-3'-[4-(carboxylmethoxy)-3-methylphenyl]pentane is chromatographed with a Chiralcel OJ column to give enantiomer 1, Example 33A (600 mg, 46%) and enantiomer 2, Example 33B (600 mg, 46%).

Enantiomer 1, Example 33A

HPLC: Chiralcel OJ (4.6×250 mm); 0.1% TFA in (2% MeOH and 5% EtOH in hept); 0.6 ml/m (flow rate); rt=7.10 m; 240 nmn.

$^1$NMR equivalent to Example 32.

High Res. ES-MS: 469.2393; calc. for C$_{26}$H$_{38}$O$_4$S+Na: 469.2389.

Enantiomer 2, Example 33B.

HPLC: Chiralcel OJ (4.6×250 mm); 0.1% TFA in (2% MeOH and 5% EtOH in hept);

0.6 ml/m (flow rate); rt=10.50 m; 240 mm.

$^1$NMR equivalent to Example 32.

High Res. ES-MS: 469.2385; calc. for C$_{26}$H$_{38}$O$_4$S+Na: 469.2389.

Example 34

Preparation of isomer 1 of 3'-[5-(3-hydroxy-4,4-dimethylpentyl)-4-methylthiophen-2-yl]-3-[4-(tetrazol-5-yl-aminocarbonylmethoxy)-3-methylphenyl]pentane

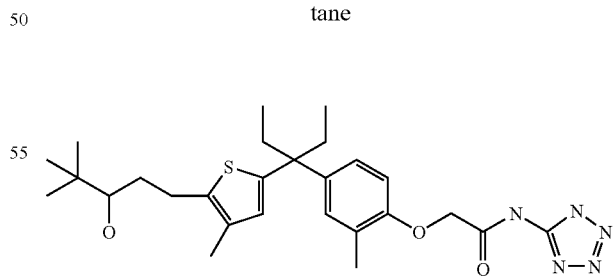

Using a procedure analogous to Example 24 and crystallization from Et2O/hex, enantiomer 1 of 3'-[5-(3-hydroxy-4,4-dimethylpentyl)-4-methylthiophen-2-yl]-3'-[4-(carboxylmethoxy)-3-methylphenyl]pentane (Example 33A) and 5-aminotetrazole give the title compound as a white solid (45 mg, 20%).

¹NMR (400 MHz, DMSO-d₆) δ ppm: 0.62 (t, J=7.3 Hz, 6H), 0.77 (s, 9H), 1.33 (m, 1H), 1.57 (m, 1H), 1.92-2.00 (m, 4H), 2.04 (s, 3H), 2.19 (s, 3H), 2.56 (m, 1H), 2.78 (m, 1H), 2.95 (m, 1H), 4.38 (d, J=6.3 Hz, 1H), 4.86 (s, 2H), 6.52 (s, 1H), 6.72 (d, J=8.8 Hz, 1H), 6.99 (m, 2H), 12.21 (br s, 1H), 15.97 (br s, 1H).

High Res. ES-MS: 536.2677; calc. for $C_{27}H_{39}O_3N_5S+Na$: 536.2671.

Example 35

Preparation of isomer 2 of 3'-[5-(3-hydroxy-4,4-dimethylpentyl)-4-methylthiophen-2-yl]-3'-[4-(tetrazol-5-yl-aminocarbonylmethoxy)-3-methylphenyl]pentane

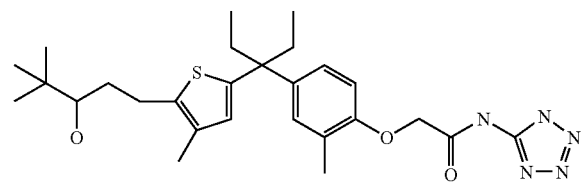

Using a procedure analogous to Example 24 with crystallization from Et₂O/hex, enantiomer 2 of 3'-[5-(3-hydroxy-4,4-dimethylpentyl)-4-methylthiophen-2-yl]-3'-[4-(carboxylmethoxy)-3-methylphenyl]pentane (Example 33B) and 5-aminotetrazole give the title compound as a white solid (70 mg, 32%).

¹NMR equivalent to Example 34.

High Res. ES-MS: 536.2690; calc. for $C_{27}H_{39}O_3N_5S+Na$: 536.2671.

Add Preparation of racemic 3'-[4-(2-hydroxy-3,3-dimethylbutoxy)-3-methylphenyl]-3'-[5-(tetrazol-5-yl-aminocarbonyl)-4-methylthiophen-2-yl]pentane.

Example 36

Preparation of isomer 1 of 3'-[4-(2-hydroxy-3,3-dimethylbutoxy)-3-methylphenyl]-3'-[5-(tetrazol-5-yl-aminocarbonyl)-4-methylthiophen-2-yl]pentane

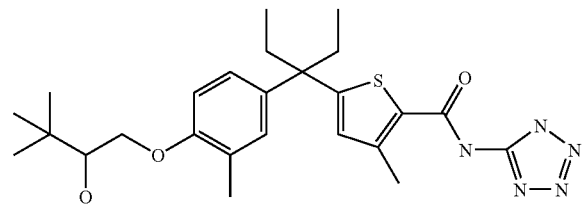

Using a procedure analogous to Example 24 and crystallization from CH2Cl₂, enantiomer 1 of 3'-[4-(2-hydroxy-3,3-dimethylbutoxy)-3-methylphenyl]-3'-[5-carboxyl-4-methylthiophen-2-yl]pentane (Example 7) and 5-aminotetrazole give the title compound as a white solid (335 mg, 77%).

¹NMR (300 MHZ, DMSO-4) δ ppm: 0.67 (t, J=7.3 Hz, 6H), 0.93 (s, 9H), 2.00-2.15 (m, 4H), 2.13 (s, 3H), 2.46 (s, 3H), 3.46 (m, 1H), 3.77 (dd, J=7.3, 9.9 Hz, 1H), 4.04 (dd, J=2.9, 10.2 Hz, 1H), 4.80 (d, J=5.5 Hz, 1H), 6.87 (m, 2H), 7.04 (m, 2H), 11.80 (s, 1H), 15.92 (br s, 1H).

High Res. ES-MS: 486.2556; calc. for $C_{25}H_{35}O_3N_5S+H$: 486.2539.

Example 37

Preparation of isomer 2 of 3'-[4-(2-hydroxy-3,3-dimethylbutoxy)-3-methylphenyl]-3'-[5-(tetrazol-5-yl-aminocarbonyl)-4-methylthiophen-2-yl]pentane

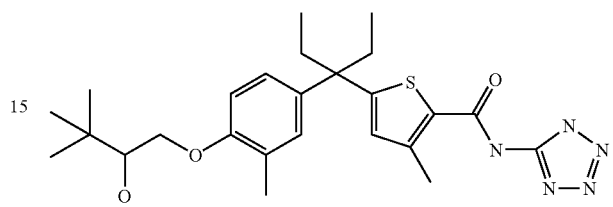

Using a procedure analogous to Example 24 and crystallization from CH2Cl2, enantiomer 2 of 3'-[4-(2-hydroxy-3,3-dimethylbutoxy)-3-methylphenyl]-3'-[5-carboxyl-4-methylthiophen-2-yl]pentane (Example 8) and 5-aminotetrazole give the title compound as a white solid (335 mg, 77%).

¹NMR (300 MHz, DMSO-d₆) δ ppm: 0.67 (t, J=7.3 Hz, 6H), 0.93 (s, 9H), 2.00-2.15 (m, 4H), 2.13 (s, 3H), 2.46 (s, 3H), 3.46 (m, 1H), 3.77 (dd, J=7.3, 9.9 Hz, 1H), 4.04 (dd, J=2.9, 10.2 Hz, 1H), 4.80 (d, J=5.1 Hz, 1H), 6.87 (m, 2H), 7.04 (m, 2H), 11.80 (s, 1H), 15.92 (br s, 1H).

High Res. ES-MS: 486.2545; calc. for $C_{25}H_{35}O_3N_5S+H$: 486.2539.

Example 38

Preparation of 5-[1-ethyl-1-[4-(2-hydroxy-3,3-dimethyl-butoxy)-3-methylphenyl]propyl]-3-methylthiophene-2-carboxylic acid (2-methylsulfonyl-ethyl) amide

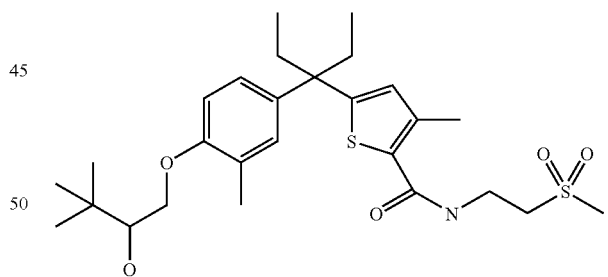

To a mixture of 5-{1-Ethyl-1-[4-(2-hydroxy-3,3-dimethyl-butyoxy)-3-methyl-phenyl]-propyl}-3-methyl-thiophene-2-carboxylic acid (0.6344 g, 1.52 mmol) and CH₂Cl₂ (10 mL) is added Et₃N (0.85 mL, 6.07 mmol), followed by hydrochloride salt of 2-aminoethylmethylsulfone (0.2416 g, 1.52 mmol), EDCl (0.320 g, 1.67 mmol), and HOBT (0.226 g, 1.67 mmol). The resulting solution is stirred at RT overnight, diluted with CH₂C₂ (30 mL), washed with 1.0 M HCl (3×20 mL), brine (20 mL), dried over MgSO₄, and concentrated. The resulting residue is purified by chromatography (50% EtOAc/Hex) to give the titled compound (0.4042 g, 0.77 mmol, 51%). ¹H NMR (CDC₃), δ 0.71 (t, J=7.3 Hz, 6H), 1.03

(s, 9H), 2.09 (q, J=7.3 Hz, 4H), 2.21 (s, 3H), 2.42 (d, J=3.0 Hz, 1H), 2.46 (s, 3H), 2.98 (s, 3H), 3.32 (t, J=6.4 Hz, 2H), 3.71 (dt, J=8.9, 2.9 Hz, 1H), 3.84-3.94 (m, 3H), 4.10 (dd, J=9.3, 2.5 Hz, 1H), 6.44 (t, J=5.8 Hz, 1H), 6.59 (s, 1H), 6.73 (d, J=8.4 Hz, 1H), 6.99 (d, J=1.7 Hz, 1H), 7.03 (dd, J=8.7, 2.5 Hz, 1H). LC/MS (m/z): calcd for $C_{27}H_{42}NO_5S_2$ (M+H)$^+$:524.8; found: 524.2.

Example 39 and Example 40

Preparation of enantiomers of 5-[1-ethyl-1-[4-(2-hydroxy-3,3-dimethyl-butoxy)-3-methylphenyl]propyl]-3-methylthiophene-2-carboxylic acid (2-methyl-sulfonyl-ethyl) amide Enantiomer 1

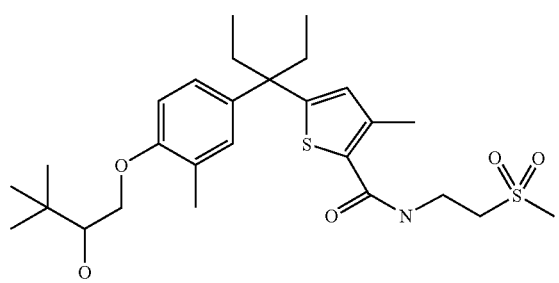

Enantiomer 2

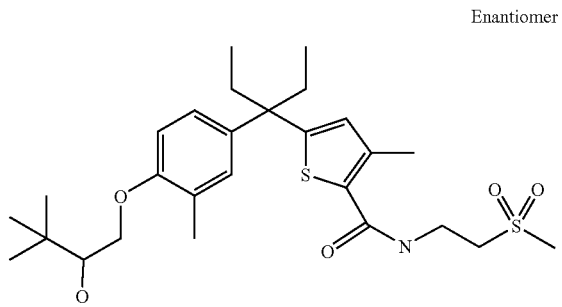

A racemic mixture of 5-[1-ethyl-1-[4-(2-hydroxy-3,3-dimethyl-butoxy)-3-methylphenyl]propyl]-3-methylthiophene-2-carboxylic acid (2-methylsulfonyl-ethyl) amide (247 mg) is chromatographed (CHIRALPAK AD column, 40% i-PrOH/Hept) to give enantiomer 1, Example 39 (100 mg, 40%) and enantiomer 2, Example 40 (80 mg, 32%).

Example 39, Enantiomer 1:

rt=6.0 m

NMR & LC/MS: Identical to the racemic material, Example 38.

Example 40, Enantiomer 2:

rt=10.2 m

NMR & LC/MS: Identical to the racemic material, Example 38.

Example 41

Preparation of 5-{1-[4-(3,3-Dimethyl-2-oxo-butyoxy)-3-methyl-phenyl]-1-ethyl-propyl}-3-methyl-thiophene-2-carbolic acid (2-methanesulfonyl-ethyl]-amide

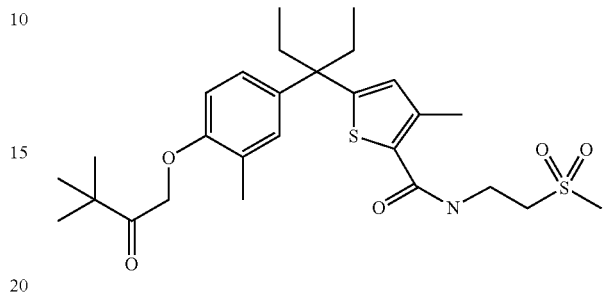

To a solution of 5-[1-ethyl-1-[4-(2-hydroxy-3,3-dimethyl-butoxy)-3-methylphenyl]propyl]-3-methylthiophene-2-carboxylic acid (2-methylsulfonyl-ethyl) amide, Example 38 (0.1096 g, 0.21 mmol) in $CH_2Cl_2$ (10 mL) is added NMO (37 mg, 0.31 mmol), and TPAP (3.7 mg, 0.01 mmol). The resulting solution is stirred at RT for 5 m, then it is filtered through a silica gel column, and washed with excess amount of EtOAc. Concentration of the solvent resulted in the title compound (62 mg, 0.12 mmol, 57%).

$^1$H NMR (CDCl$_3$), δ 0.70 (t, J=8.0 Hz, 6H), 1.27 (s, 9H), 1.99 (m, 4H), 2.18 (s, 3H), 2.38 (s, 3H), 2.90 (s, 3H), 3.24 (t, J=6.0 Hz, 2H), 3.82 (m, 2H), 6.36 (t, J=5.8 Hz, 1H), 6.42 (d, J=8.4 Hz, 1H), 6.50 (s, 1H), 6.85-6.95 (m, 2H).

LC/MS (m/z): 522.1 (M+H)$^+$.

Example 42

Preparation of 5-{1-Ethyl-1-[4-(2-hydroxy-3,3-dimetliyl-butyoxy)-3-methyl-phenyl]-propyl}-3methyl-thiophene-2-carboxylic acid methoxy-methyl-amide

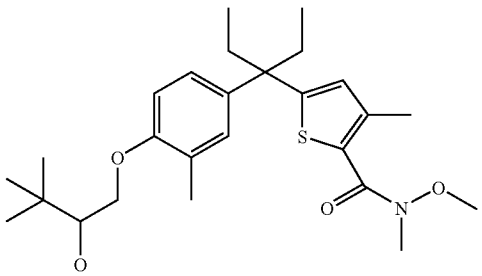

Using the procedure analogous to Example 38, from 5-{1-Ethyl-1-[4-(2-hydroxy-3,3-dimethyl-butyoxy)-3-methyl-phenyl]-propyl}-3-methyl-thiophene-2-carboxylic acid (0.34 g, 0.81 mmol) and N-methoxy-N-methylamine hydrochloride salt (0.087 g, 0.89 mmol) furnished the titled compound (0.2083 g, 0.45 mmol, 56%).

$^1$H NMR (CD$_3$OD), δ 0.65 (t, J=7.4 Hz, 6H), 0.95 (s, 9H), 2.07 (q, J=7.4 Hz, 4H), 2.14 (s, 3H), 2.35 (s, 3H), 3.25 (s, 3H), 3.57 (dd, J=7.8, 2.9 Hz, 1H), 3.58 (s, 3H), 3.82 (dd, J=9.7, 7.8 Hz, 1H), 4.07 (dd, J=9.7, 2.9 Hz, 1H), 6.62 (s, 1H), 6.73 (d,

J=8.9 Hz, 1H), 6.94 (d, J=2.4 Hz, 1H), 7.01 (dd, J=8.9, 2.4 Hz, 1H). LC/MS (m/z): calcd for $C_{26}H_{40}NO_4S$ (M+H)$^+$:462.2; found: 462.2.

Example 43 and Example 44

Preparation of enantiomers of 5-{1-Ethyl-1-[4-(2-hydroxy-3,3-dimethyl-butyoxy)-3-methyl-phenyl]-propyl}-3methyl-thiophene-2-carboxylic acid methoxy-methyl-amide Enantiomer 1

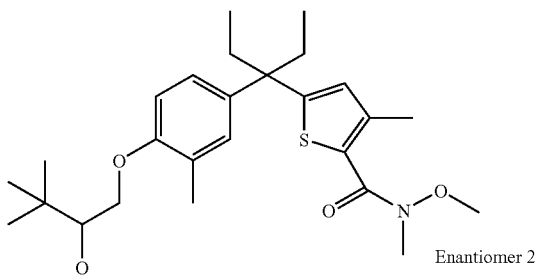

Enantiomer 2

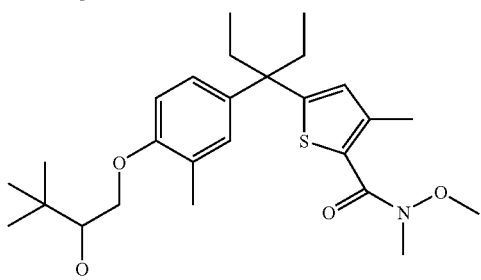

A racemic mixture of 5-{1-Ethyl-1-[4-(2-hydroxy-3,3-dimethyl-butyoxy)-3-methyl-phenyl]-propyl}-3methyl-thiophene-2-carboxylic acid methoxy-methyl-amide (92 mg) is chromatographed (CHIRALPAK AD column, 40% i-PrOH/Hept) to give enantiomer 1, Example 43 (42 mg, 46%) and enantiomer 2, Example 44 (34.5 mg, 38%).

Example 43, Enantiomer 1:

rt=4.4m

NMR & LC/MS: Identical to the racemic material, Example 42.

Example 44, Enantiomer 2:

rt=7.3m

NMR & LC/MS: Identical to the racemic material, Example 42.

Example 45

Preparation of 5-{1-[4-(3,3-dimethyl-2-oxo-butyoxy)-3-methyl-phenyl]-1-ethyl-propyl}-3methyl-thiophene-2-carboxylic acid methoxy-methyl-amide

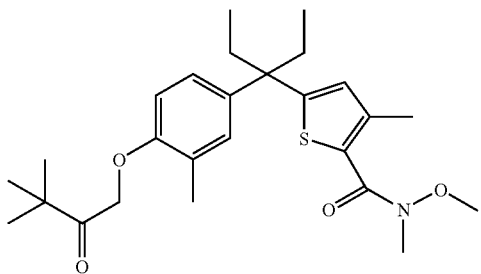

Using a procedure analogous to Example 41, from 5-{1-Ethyl-1-[4-(2-hydroxy-3,3-dimethyl-butyoxy)-3-methyl-phenyl]-propyl}-3-methyl-thiophene-2-carboxylic acid methoxy-methyl-amide (Example 42) (110 mg, 0.245 mmol) yielded the titled compound (107.9 mg, 98%). $^1$H NMR (CDC$_3$), δ 0.71 (t, J=6.4 Hz, 6H), 1.27 (s, 9H), 2.09 (q, J=6.4 Hz, 4H), 2.27 (s, 3H), 2.48 (s, 3H), 3.30 (s, 3H), 3.67 (s, 3H), 4.85 (s, 2H), 6.52 (d, J=8.6 Hz, 1H), 6.57 (s, 1H), 7.00 (d, J=8.6 Hz, 1H), 7.02 (s, 1H). LC/MS (m/z): calcd for $C_{26}H_{38}NO_4S$ (M+H)$^+$:460.2; found: 460.2.

Example 46

Preparation of 2-[5-{1-Ethyl-1-{4-(2-hydroxy-3,3-dimethyl-butyoxy)-3-methyl-phenyl-propyl}-3-methyl-thiophene-2-carbonyl)-amino]-acetic acid methyl ester

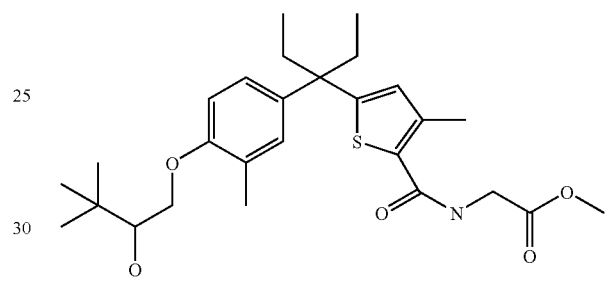

Using the procedure analogous to Example 38, from 5-{1-Ethyl-1-[4-(2-hydroxy-3,3-dimethyl-butyoxy)-3-methyl-phenyl]-propyl}-3-methyl-thiophene-2-carboxylic acid (0.4307 g, 1.03 mmol) and glycine methyl ester hydrochloride (0.129 g, 1.03 mmol) furnished the titled compound (0.2535 g, 50%). 3H NMR (CDCl$_3$), δ 0.71 (t, J=6.8 Hz, 6H), 1.03 (s, 9H), 2.09 (q, J=6.8 Hz, 4H), 2.21 (s, 3H), 2.44 (d, J 2.5 Hz, 1H), 2.48 (s, 3H), 3.72 (dt, J=8.3, 2.5 Hz, 1H), 3.78 (s, 3H), 3.87 (t, J=8.8 Hz, 1H), 4.11 (dd, J=9.2, 2.5 Hz, 1H), 4.17 (d, J=5.4 Hz, 2H), 6.20 (s, 1H), 6.61 (s, 1H), 6.73 (d, J=8.8 Hz, 1H), 6.99-7.01 (m, 1H), 7.04 (dd, J=8.8, 2.4 Hz, 1H).

LC/MS (m/z): 490.2 (M+H)$^+$.

Example 47

Preparation of 2-[5-{1-Ethyl-1-{4-(2-hydroxy-3,3-dimethyl-butyoxy)-3-methyl-phenyl-propyl}-3-methyl-thiophene-2-carbonyl)-amino]-acetic acid

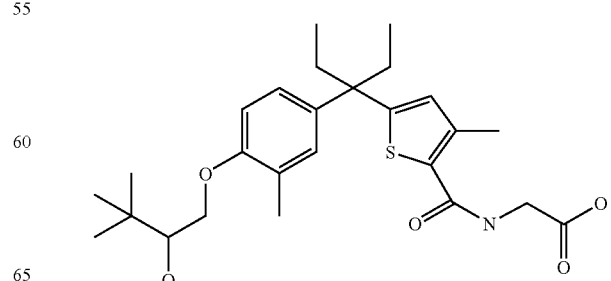

2-[5-{1-Ethyl-1-{4-(2-hydroxy-3,3-dimethyl-butyoxy)-3-methyl-phenyl-propyl}-3-methyl-thiophene-2-carbonyl)-amino]-acetic acid methyl ester (Example 46) (0.24 g, 0.49 mmol) is dissolved in THF (5 mL), treated with H₂O (1 mL) and LiOH (59 mg, 2.46 mmol) and the resulting mixture is stirred at RT overnight. The solution is diluted with H₂O (10 mL), the pH value is adjusted to ca. 3-4 using 1 M HCl, it is extracted with EtOAc (2×40 mL), dried with MgSO₄, filtered and concentrated to yield the titled compound (0.233 g, 0.49 mmol, 99%). $^1$H NMR (CD₃OD), δ 0.75 (t, J=7.4 Hz, 6H), 1.05 (s, 9H), 2.17 (q, J=7.4 Hz, 4H), 2.23 (s, 3H), 2.48 (s, 3H), 3.66 (dd, J=7.8 2.9 Hz, 1H), 3.91 (dd, J=9.6, 7.8 Hz, 1H), 4.01 (s, 2H), 4.16 (dd, J=9.6, 2.9 Hz, 1H), 6.74 (s, 1H), 6.84 (d, J=8.8 Hz, 1H), 7.03-7.06 (m, 1H), 7.11 (dd, J=8.2, 2.5 Hz, 1H). LC/MS (m/z): calcd for C₂₆H₃₈NO₅S (M+H)⁺:476.2; found: 476.2.

Example 48 and Example 49

Preparation of enantiomers of 2-[5-{1-Ethyl-1-{4-(2-hydroxy-3,3-dimethyl-butyoxy)-3-methyl-phenyl-propyl}-3-methyl-thiophene-2-carbonyl)-amino]-acetic acid Enantiomer 1

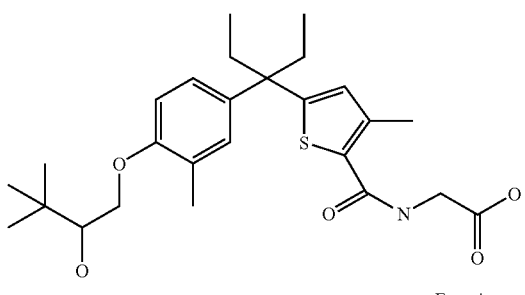

Enantiomer 2

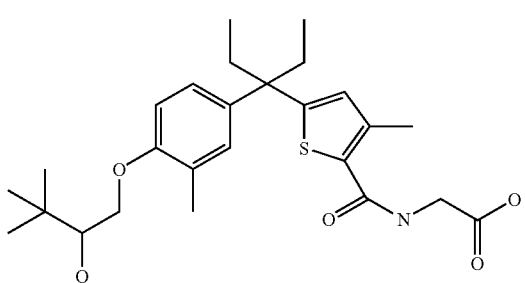

A racemic mixture of 2-[5-{1-Ethyl-1-{4-(2-hydroxy-3,3-dimethyl-butyoxy)-3-methyl-phenyl-propyl}-3-methyl-thiophene-2-carbonyl)-amino]-acetic acid, Example 47 (130 mg) is chromatographed (CHIRALPAK AD column, 20% i-PrOH/Hept, 0.2% TFA) to give enantiomer 1, Example 48 (47.9 mg, 37%) and enantiomer 2, Example 49 (39 mg, 30%).

Example 48. Enantiomer 1:

rt=6.5m

NMR & LC/MS: Identical to the racemic material, Example 47.

Example 49, Enantiomer 2:

rt=15.2m

NMR & LC/MS: Identical to the racemic material, Example 47.

Example 50

Preparation of 2-[5-{1-[4-(3,3-Dimethyl-2-oxo-butyoxy)-3-methyl-phenyl]-1-ethyl-propyl}-3-methyl-thiophene-2-carbonyl)-amino]-acetic acid

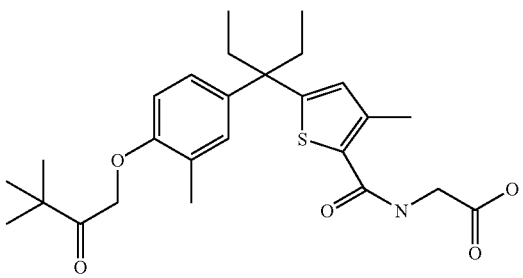

2-[5-{1-Ethyl-1-{4-(2-hydroxy-3,3-dimethyl-butyoxy)-3-methyl-phenyl-propyl}-3-methyl-thiophene-2-carbonyl)-amino]-acetic acid (Example 47) (99 mg, 0.21 mmol) is dissolved in CH₂Cl₂ (4 mL), treated with Dess-Martin reagent (97 mg, 0.23 mmol). The resulting mixture is stirred at RT 2 h. It is diluted with EtOAc (25 mL), washed with 10% Na₂SO₃ (2×20 mL) along with 0.1 M HCl (20 mL); dried with MgSO₄, filtered and concentrated. Purification of the resulting crude product by flash chromatography, eluted with 15% CH₃OH/EtOAc with 0.5% HOAc yielded the titled compound (56.2 mg, 0.11 mmol, 53/O). $^1$H NMR (CD₃OD), δ 0.75 (t, J=7.2 Hz, 6H), 1.29 (s, 9H), 2.19 (q, J=7.2 Hz, 4H), 2.25 (s, 3H), 2.47 (s, 3H), 4.02 (s, 2H), 5.05 (s, 2H), 6.66 (d, J=7.6 Hz, 1H), 6.74 (s, 1H), 7.00-7.11 (m, 2H), 7.96 (bs, 1H). LC/MS (m/z): calcd for C₂₆H₃₆NO₅S (M+H)⁺:474.2; found: 474.2.

Example 51

Preparation of (5-{1-ethyl-1-[4-(2-ethyl-2-hydroxy-butoxy)-3-methyl-phenyl]-propyl}-3-methyl-thiophene-2-carboxylic acid

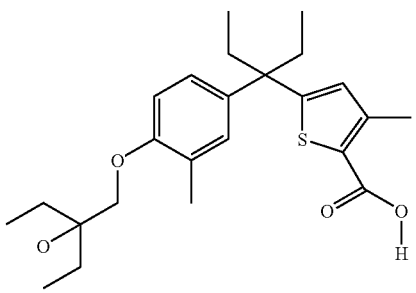

133

A. 2-{4-[1-Ethyl-1-(4-methyl-thiophen-2-yl)-propyl]-2-methyl-phenoxy}-acetic acid methyl ester

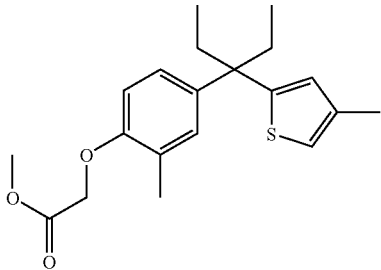

4-[1-Ethyl-1-(4-methyl-thiophen-2-yl)-propyl]-2-methyl-phenol (10.66 g, 38.9 mmol) is reacted with methyl bromoacetate (4.4 ml, 46.7 mmol) and $K_2CO_3$ (10.70 g, 77.81 mmol) in acetone (100 m) at refluxing temperature overnight. The reaction is cooled to RT, filtered and washed with $Et_2O$ and concentrated. The crude product is purified by chromatography to give the titled compound (12.15 g, 35.1 mmol, 90%). $^1$H NMR (CD$_3$Cl$_3$), δ 0.70 (t, J=7.2 Hz, 6H), 2.04-2.12 (m, 4H), 2.21 (s, 3H), 2.26 (s, 3H), 3.81 (s, 3H), 4.63 (s, 2H), 6.57-6.61 (m, 2H), 6.69-6.71 (m, 1H), 7.02-7.06 (m, 2H). LC/MS (m/z): calcd for $C_{20}H_{27}O_3S$ (M+H)$^+$:347.5; found: 347.1.

B. 3-{4-[1-Ethyl-1-(4-methyl-thiophen-2-yl)-propyl]-2-methyl-phenoxymethyl}-pentan-3-ol

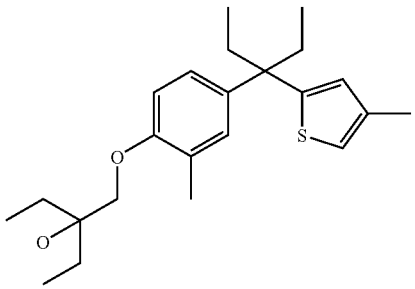

{4-[1-Ethyl-1-(4-methyl-thiophen-2-yl)-propyl]-2-methyl-phenoxy}acetic acid methyl ester (5.52 g, 15.95 mmol) is dissolved in THF (50 mL). The solution is cooled to 0° C., and treated with Ethyl magnesiumbromide (3.0 M, 13.3 mL) in a dropwise fashion. The reaction is stirred at 0° C. for 10 m, and refluxed for 3 h. It is cooled to 0° C., quenched with sat. NH4Cl (50 mL), then 1.0 M HCl (30 mL) is added. It is extracted with EtOAc (2×100 mL), dried and concentrated. The crude product is purified by chromatography to give the titled compound (5.22 g, 13.96 mmol, 87%). $^1$H NMR (CD$_3$Cl$_3$), δ 0.71 (t, J=7.4 Hz, 6H), 0.95 (t, J=7.1 Hz, 6H), 1.62-1.73 (m, 4H), 2.04-2.14 (m, 4H), 2.21 (s, 6H), 3.81 (s, 2H), 6.59-6.61 (m, 1H), 6.69-6.74 (m, 2H), 7.02-7.08 (m, 2H). LC/MS (m/z): calcd for $C_{23}H_{35}O_2S$ (M+H)$^+$:375.6; found: 375.3.

134

C. 5-{1-Ethyl-1-[4-(2-ethyl-2-hydroxy-butoxy)-3-methyl-phenyl]-propyl}-3-methyl-thiophene-2-carboxylic acid methyl ester

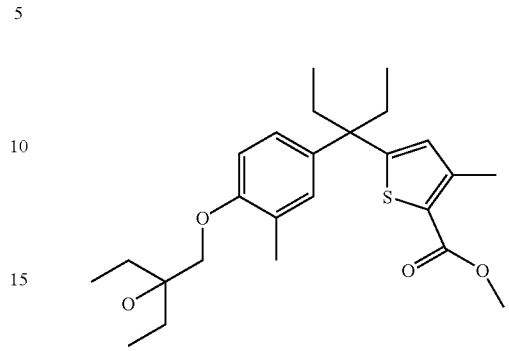

3-{4-[1-Ethyl-1-(4-methyl-thiophen-2-yl)-propyl]-2-methyl-phenoxymethyl}-pentan-3-ol, Example 51B (0.50 g, 1.34 mmol) is dissolved in THF (10 mL). The solution is cooled to 0° C., treated with nBuLi (1.6 M, 1.8 mL, 2.95 mmol). It is stirred at 0° C. for 20 min, and methyl chloroformate (113 µL, 1.47 mmol) is added. The reaction is stirred at 0° C. for 10 min and RT for 20 m before it is quenched with satd NH$_4$Cl (5 mL). It is diluted with H$_2$O (10 mL), treated with 0.1 M HCl (10 ml) and extracted with EtOAc (3×15 mL), dried and concentrated. The crude product is purified by chromatography to give the titled compound (0.24 g, 0.56 mmol, 41%). $^1$H NMR (CD$_3$C$_3$), δ 0.71 (t, J=7.1 Hz, 6H), 0.95 (t, J=7.9 Hz, 6H), 1.64-1.72 (m, 4H), 2.11 (q, J=7.1 Hz, 4H), 2.21 (s, 3H), 2.49 (s, 3H), 3.81 (s, 3H), 6.61 (s, 1H), 6.72 (d, J=8.4 Hz, 1H), 6.85-7.01 (m, 2H). LC/MS (m/z): calcd for $C_{25}H_{40}NO_4S$ (M+NH$_4$)$^+$: 450.3; found: 450.3.

D. 5-{1-Ethyl-1-[4-(2-ethyl-2-hydroxy-butoxy)-3-methyl-phenyl]-propyl}-3-methyl-thiophene-2-carboxylic acid

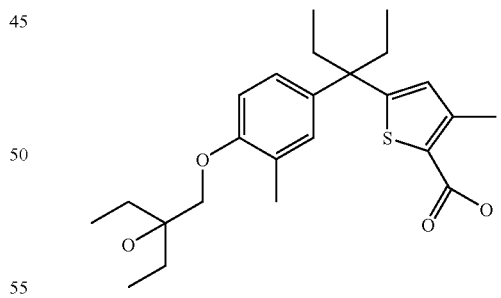

Using a procedure analogous to Example 47, 5-{1-Ethyl-1-[4-(2-ethyl-2-hydroxy-butoxy)-3-methyl-phenyl]-propyl}-3-methyl-thiophene-2-carboxylic acid methyl ester (0.23 g, 0.53 mmol) gives the title compound (0.20 g, 0.48 mmol, 91%). $^1$H NMR (CD$_3$Cl$_3$), δ 0.72 (t, J=7.6 Hz, 6H), 0.95 (t, J=7.1 Hz, 6H), 1.64-1.72 (m, 4H), 2.11 (q, J=7.6 Hz, 4H), 2.22 (s, 3H), 2.49 (s, 3H), 3.82 (s, 3H), 6.62 (s, 1H), 6.73 (d, J=8.3 Hz, 1H), 6.99-7.06 (m, 2H). LC/MS (m/z): calcd for $C_{24}H_{33}O_4S$ (M–H)$^+$: 417.6; found: 417.2.

Example 52

Preparation of 2-[(5-{1-Ethyl-1-[4-(2-ethyl-2-hydroxy-butoxy)-3-methyl-phenyl]-propyl}-3-methyl-thiophene-2-carbonyl)-amino]-acetic acid methyl ester

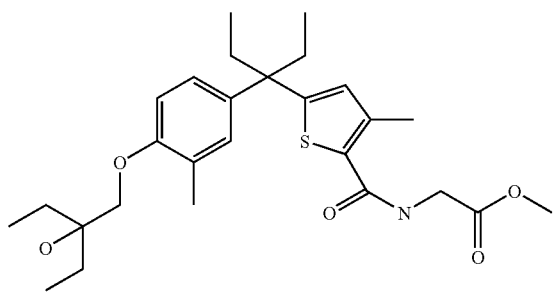

Using a procedure analogous to Example 38, 5-{1-Ethyl-1-[4-(2-ethyl-2-hydroxy-butoxy)-3-methyl-phenyl]-propyl}-3-methyl-thiophene-2-carboxylic acid (Example 51) (0.3 g, 0.72 mmol), glycine methyl ester hydrochloride, and DMF (2 mL) as reaction solvent to give the title compound (0.34 g, 0.69 mmol, 97%). $^1$H NMR (CDC$_3$), δ 0.71 (t, J=7.1 Hz, 6H), 0.95 (t, J=7.1 Hz, 6H), 1.63-1.72 (m, 4H), 2.04-2.14 (m, 4H), 2.21 (s, 3H), 2.48 (s, 3H), 3.78 (s, 3H), 3.81 (s, 3H), 4.15 (d, J=5.2 Hz, 2H), 6.20 (t, J=5.2 Hz, 1H), 6.63 (s, 1H), 6.72 (d, J=8.4 Hz, 1H), 6.98-7.01 (m, 1H), 7.01-7.06 (m, 1H). LC/MS (m/z): calcd. for $C_{27}H_{38}NO_5S$ (M−H)$^-$: 488.7; found: 488.5.

Example 53

Preparation of 2-[(5-{1-Ethyl-1-[4-(2-ethyl-2-hydroxy-butoxy)-3-methyl-phenyl]-propyl}-3-methyl-thiophene-2-carbonyl)-amino]-acetic acid

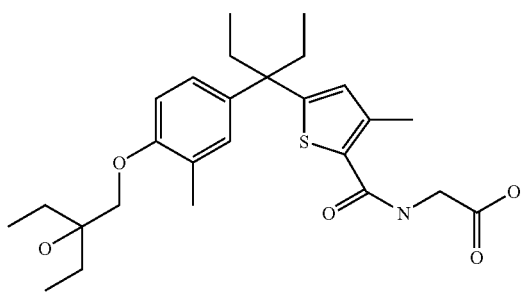

2-[(5-{1-Ethyl-1-[4-(2-ethyl-2-hydroxy-butoxy)-3-methyl-phenyl]-propyl}-3-methyl-thiophene-2-carbonyl)-amino]-acetic acid methyl ester (Example 52) (0.34 g, 0.69 mmol) is dissolved in MeOH (2 mL), treated with H$_2$O (0.5 mL) and NaOH (0.14 g, 3.47 mmol) and the resulting mixture is heated at a reflux for two hours cooled to at ambient temperature and stirred overnight. The solution is diluted with H$_2$O (10 mL), the pH value is adjusted to about 3-4 using 1 M HCl, it is extracted with EtOAc (40 mL). The EtOAc layer is washed with brine (20 mL), dried with MgSO$_4$, filtered and concentrated to yield the titled compound (0.244 g, 0.51 mmol, 74%). $^1$H NMR (CD$_3$OD), δ 0.72 (t, J=7.4 Hz, 6H), 0.94 (t, J=7.4 Hz, 6H), 1.64-1.74 (m, 4H), 2.03-2.20 (m, 4H), 2.18 (s, 3H), 2.44 (s, 3H), 3.79 (s, 2H), 3.97-3.99 (m, 2H), 6.71 (s, 1H), 6.79 (d, J=8.2 Hz, 1H), 6.99-7.02 (m, 1H), 7.06-7.10 (m, 1H), 7.88-7.94 (t, J=5.7 Hz, 1H). LC/MS (m/z): calcd. for $C_{26}H_{36}NO_5S$ (M−H)$^-$: 475.6; found: 474.3

Example 54

Preparation of epimer 2 of L-2-[(5-{1-Ethyl-1-[4-(2-hydroxy-3,3-dimethyl-butoxy)-3-methyl-phenyl]-propyl}-3-methyl-thiophene-2-carbonyl)amino]propionic acid methyl ester

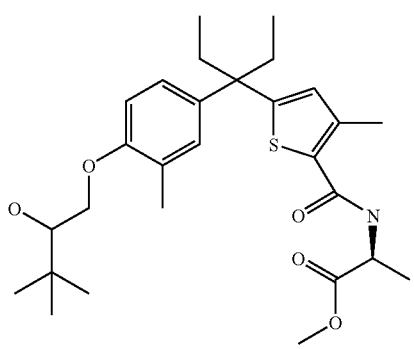

L-Epimer-2

Using a procedure analogous to Example 52, enantiomer 2 of 5-{1-Ethyl-1-[4-(2-hydroxy-3,3-dimethyl-butoxy)-3-methyl-phenyl]-propyl}-3-methyl-thiophene-2-carboxylic acid (Example 8) (0.50 g, 1.2 mmol) and L-alanine methyl ester hydrochloride salt (0.18 g, 1.3 mmol) to give the titled compound (0.44 g, 0.87 mmol, 73%). $^1$H NMR (CDC$_3$), 30.71 (t, J=7.2 Hz, 6H), 1.02 (s, 9H), 1.47 (d, J=7.2 Hz, 3H), 2.04-2.14 (m, 4H), 2.21 (s, 3H), 2.47 (s, 3H), 3.71 (dd, J=8.6, 2.5 Hz, 1H), 3.77 (s, 3H), 3.88 (t, J=8.6 Hz, 1H), 4.10 (dd, J=9.2, 2.5 Hz, 1H), 4.67-4.75 (m, 1H), 6.26 (d, J=7.1 Hz, 1H), 6.60 (s, 1H), 6.73 (d, J=7.6 Hz, 1H), 6.97-7.06 (m, 2H). LC/MS (m/z): calcd. for $C_{28}H_{42}NO_5S$ (M+H)$^+$: 504.7; found: 504.4.

Example 55

Preparation of epimer 2 of L-2-[(5-{1-Ethyl-1-[4-(2-hydroxy-3,3-dimethyl-butoxy)-3-methyl-phenyl]-propyl}-3-methyl-thiophene-2-carbonyl)-amino]-propionic acid

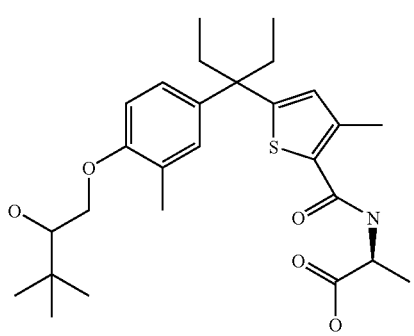

L-Epimer 2

Using a procedure analogous to Example 53, epimer 2 of L-2-[(5-{1-Ethyl-1-[4-(2-hydroxy-3,3-dimethyl-butoxy)-3- methyl-phenyl]-propyl}-3-methyl-thiophene-2-carbonyl)-amino]-propionic acid methyl ester (0.42 g, 1.0 mmol) gives the title compound (0.37 g, 0.76 mmol, 73%). $^1$H NMR (CDC$_3$), δ 0.71 (t, J=7.4 Hz, 6H), 1.02 (s, 9H), 1.51 (d, J=7.7 Hz, 3H), 2.04-2.14 (m, 4H), 2.20 (s, 3H), 2.47 (s, 3H), 3.72 (dd, J=8.7, 2.5 Hz, 1H), 3.87 (t, J-=8.7, 1H), 4.10 (dd, J=9.3, 2.8 Hz, 1H), 4.64-4.72 (m, 1H), 6.22 (d, J=7.4 Hz, 1H), 6.62 (s, 1H), 6.73 (d, J=8.4 Hz, 1H), 6.97-7.06 (m, 2H). LC/MS (m/z): calcd. for $C_{27}H_{40}NO_5S$ (M+H)$^+$: 490.7; found: 490.4.

Example 56

Preparation of epimer 2 of D-2-[(5-{1-Ethyl-1-[4-(2-hydroxy-3,3-dimethyl-butoxy)-3-methyl-phenyl]-propyl}-3-methyl-thiophene-2-carbonyl)-amino]-propionic acid methyl ester

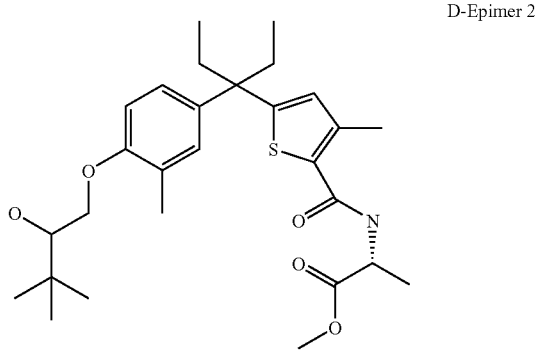

D-Epimer 2

Using a procedure analogous to Example 52, enantiomer 2 of 5-{1-Ethyl-1-[4-(2-hydroxy-3,3-dimethyl-butoxy)-3-methyl-phenyl]-propyl}-3-methyl-thiophene-2-carboxylic acid (Example 8) (0.40 g, 0.96 mmol) and D-alanine methyl ester hydrochloride salt (0.15 g, 1.05 mmol) to give the title compound (0.48 g, 0.95 mmol, 71%). $^1$H NMR (CDC$_3$), δ 0.71 (t, J=7.5 Hz, 6H), 1.02 (s, 9H), 1.47 (d, J=7.0 Hz, 3H), 2.04-2.15 (m, 4H), 2.21 (s, 3H), 2.47 (s, 3H), 3.71 (d, J=8.6 Hz, 1H), 3.77 (s, 3H), 3.87 (t, J=9.2, 1H) 4.10 (dd, J=9.1, 2.7 Hz, 1H), 4.66-4.76 (m, 1H), 6.26 (d, J=7.6, 1H), 6.60 (s, 1H), 6.73 (d, J=8.6 Hz, 1H), 6.98-7.07 (m, 2H). LC/MS (m/z): calcd. for $C_{28}H_{42}NO_5S$ (M+H)$^+$: 504.7; found: 504.4.

Example 57

Preparation of epimer 2 of D-2-[(5-{1-Ethyl-1-[4-(2-hydroxy-3,3-dimethyl-butoxy)-3-methyl-phenyl]-propyl}-3-methyl-thiophene-2-carbonyl)-amino]-propionic acid

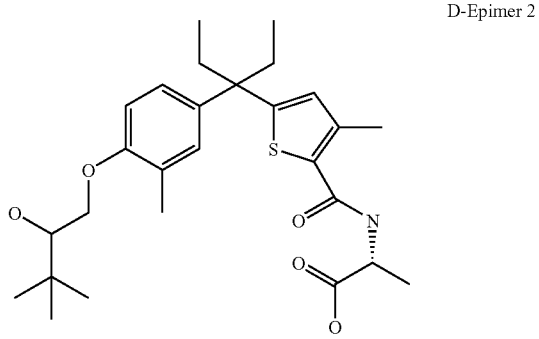

D-Epimer 2

Using a procedure analogous to Example 53, epimer 2 of D-2-[(5-{1-Ethyl-1-[4-(2-hydroxy-3,3-dimethyl-phenyl]-propyl}-3-methyl-thiophene-2-carbonyl)-amino]-propionic acid methyl ester (0.34 g, 0.68 mmol) gives the title compound (0.33 g, 0.66 mmol, 79%). $^1$H NMR (CDC$_3$), δ 0.71 (t, J=7.5 Hz, 6H), 1.02 (s, 9H), 1.52 (d, J=7.1 Hz, 3H), 2.04-2.14 (m, 4H), 2.21 (s, 3H), 2.47 (s, 3H), 3.71 (dd, J=8.8, 2.7 Hz, 1H), 3.88 (t, J=8.8, 1H), 4.10 (dd, J=9.2, 2.7 Hz, 1H), 4.64-4.73 (m, 1H), 6.21 (d, J=6.9 Hz, 1H), 6.62 (s, 1H), 6.73 (d, J=8.6 Hz, 1H), 6.98-7.06 (m, 2H). LC/MS (m/z): calcd. for $C_{27}H_{40}NO_5S$ (M+H)$^+$: 490.7; found: 490.2.

Example 58

Preparation of L-2-[(5-{1-ethyl-1-[4-(2-hydroxy-3,3-dimethyl-butoxy)-3-methyl-phenyl]-propyl}-3-methyl-thiophene-2-carbonyl)-amino]-succinic acid dimethyl ester

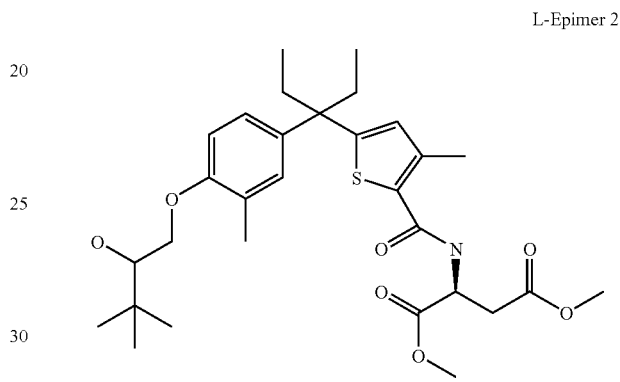

L-Epimer 2

Using a procedure analogous to Example 52, enantiomer 2 of 5-{1-Ethyl-1-[4-(2-hydroxy-3,3-dimethyl-butoxy)-3-methyl-phenyl]-propyl}-3-methyl-thiophene-2-carboxylic acid (Example 8) (0.4 g, 0.96 mmol) and L-aspartic acid dimethyl ester hydrochloride salt (0.21 g, 1.05 mmol) to give the title compound (0.42 g, 0.758 mmol, 78%). $^1$H NMR (CDCl$_3$), δ 0.71 (t, J=7.7 Hz, 6H), 1.02 (s, 9H), 2.04-2.14 (m, 4H), 2.20 (s, 3H), 2.47 (s, 3H), 2.93 (dd, J=17.2, 4.5 Hz, 1H), 3.10 (dd, J=17.2, 4.3 Hz, 1H), 3.69-3.73 (m, 4H), 3.78 (s, 3H), 3.87 (t, J=9.1, 1H), 4.10 (dd, J=9.1, 2.6, 1H), 4.96-5.01 (m, 1H), 6.58 (s, 1H), 6.72 (d, J=7.7, 1H), 6.78 (d, J=7.8, 1H), 7.00 (d, J=1.7, 1H), 7.04 (dd, J=2.7, 8.5, 1H). LC/MS (m/z): calcd. for $C_{30}H_{44}NO_7S$ (M+H)$^+$: 562.7; found: 562.4.

Example 59

Preparation of epimer 2 of L-2-[(5-{1-Ethyl-1-[4-(2-hydroxy-3,3-dimethyl-butoxy)-3-methyl-phenyl]-propyl}-3-methyl-thiophene-2-carbonyl)-amino]-succinic acid

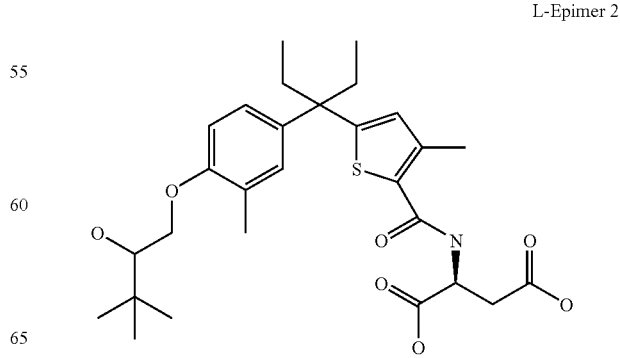

L-Epimer 2

Using a procedure analogous to Example 53, L-2-[(5-{1-Ethyl-1-[4-(2-hydroxy-3,3-dimethyl-butoxy)-3-methyl-phenyl]-propyl}-3-methyl-thiophene-2-carbonyl)-amino]-succinic acid dimethyl ester, gives to the title compound (0.29 g, 0.54 mmol, 78%). $^1$H NMR (CDC$_3$), δ 0.70 (t, J=7.4 Hz, 6H), 1.01 (s, 9H), 2.04-2.14 (m, 4H), 2.19 (s, 3H), 2.45 (s, 3H), 2.89-3.01 (m, 1H), 3.09-3.19 (m, 1H), 3.72 (d, J=8.0 Hz, 1H), 3.87 (t, J=8.8 Hz, 1H), 4.09 (d, J-=8.2 Hz, 1H), 4.98-5.05 (m, 1H), 6.60 (s, 1H), 6.71 (d, J=8.8 Hz, 1H), 6.78 (d, J=7.9 Hz, 1H), 6.98-7.05 (m, 2H), 7.30-7.60 (bs, 2H). LC/MS (m/z): calcd. for C$_{28}$H$_{40}$NO$_7$S (M+H)$^+$: 534.7; found: 534.4.

Example 60

Preparation of epimer 2 of D-2-[(5-{1'-Ethyl-1-[4-(2-hydroxy-3,3-dimethyl-butoxy)-3-methyl-phenyl]-propyl}-3-methyl-thiophene-2-carbonyl)-amino]-succinic acid dimethyl ester D-Epimer 2

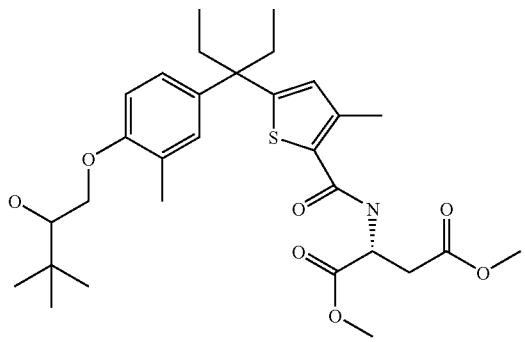

Using a procedure analogous to Example 52, enantiomer 2 of 5-{1-Ethyl-1-[4-(2-hydroxy-3,3-dimethyl-butoxy)-3-methyl-phenyl]-propyl}-3-methyl-thiophene-2-carboxylic acid (Example 8) (0.4 g, 0.96 mmol) and D-aspartic acid dimethyl ester hydrochloride salt (0.21 g, 1.05 mmol) to give the title compound (0.42 g, 0.75 mmol, 78%). $^1$H NMR (CDCl$_3$), δ 0.71 (t, J=7.4 Hz, 6H), 1.02 (s, 9H), 2.04-2.14 (m, 4H), 2.21 (s, 3H), 2.47 (s, 3H), 2.94 (dd, J=17.0, 4.6 Hz, 1H), 3.10 (dd, J=17.0, 4.6 Hz, 1H), 3.69-3.74 (m, 4H), 3.78 (s, 3H), 3.87 (t, J=9.1 Hz, 1H), 4.10 (dd, J=9.1, 3.0 Hz, 1H), 4.96-5.02 (m, 1H), 6.59 (s, 1H), 6.73 (d, J=8.4 Hz, 1H), 6.78 (d, J=7.2 Hz, 1H), 7.00 (d, J=2.3 Hz, 1H), 7.04 (dd, J=2.7, 8.4 Hz, 1H). LC/MS (m/z): calcd. for C$_{30}$H$_{44}$NO$_7$S (M+H)$^+$: 562.7; found: 562.4.

Example 61

Preparation of epimer 2 of D-2-[(5-{1-Ethyl-1-[4-(2-hydroxy-3,3-dimethyl-butoxy)-3-methyl-phenyl]-propyl}-3-methyl-thiophene-2-carbonyl)-amino]-succinic acid D-Epimer 2

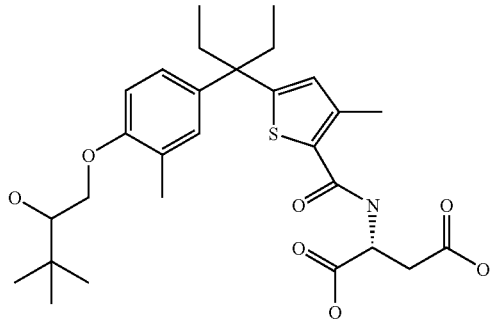

Using the procedure analogous to Example 53, epimer 2 of D-2-[(5-{1-Ethyl-1-[4-(2-hydroxy-3,3-dimethyl-butoxy)-3-methyl-phenyl]-propyl}-3-methyl-thiophene-2-carbonyl)-amino]-succinic acid dimethyl ester (0.40 g, 0.71 mmol) gives the titled compound (0.30 g, 0.56 mmol, 79%). $^1$H NMR (CDC$_3$), δ 0.70 (t, J=7.4 Hz, 6H), 1.01 (s, 9H), 2.04-2.14 (m, 4H), 2.19 (s, 3H), 2.45 (s, 3H), 2.89-3.01 (m, 1H), 3.09-3.19 (m, 1H), 3.72 (d, J=8.0 Hz, 1H), 3.87 (t, J=8.8 Hz, 1H), 4.09 (d, J=8.2 Hz, 1H), 4.98-5.05 (m, 1H), 6.60 (s, 1H), 6.71 (d, J=8.8 Hz, 1H), 6.78 (d, J=7.9 Hz, 1H), 6.98-7.05 (m, 2H), 7.30-7.60 (bs, 2H). LC/MS (m/z): calcd. for C$_{28}$H$_{40}$N$_7$S (M+H)$^+$: 534.7; found: 534.4.

Example 62

Preparation of epimer 2 of L-2-[(5-{1-Ethyl-1-[4-(2-hydroxy-3,3-dimethyl-butoxy)-3-methyl-phenyl]-propyl}-3-methyl-thiophene-2-carbonyl)-amino]-3-hydroxy-propionic acid methyl ester L-Epimer 2

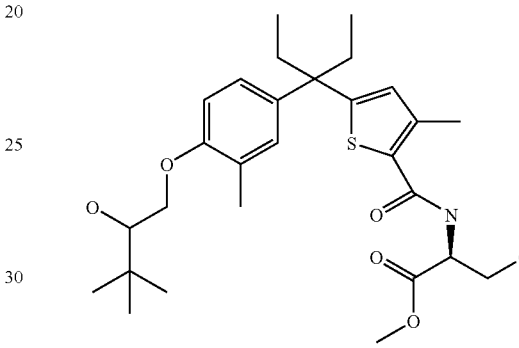

Using a procedure analogous to Example 52, enantiomer 2 of 5-{1-Ethyl-1-[4-(2-hydroxy-3,3-dimethyl-butoxy)-3-methyl-phenyl]-propyl}-3-methyl-thiophene-2-carboxylic acid (Example 8) (0.4 g, 0.96 mmol) and L-serine methyl ester hydrochloride salt (0.16 g, 1.05 mmol) to give the title compound (0.41 g, 0.79 mmol, 82%). $^1$H NMR (CDC$_3$), δ 0.71 (t, J=7.7 Hz, 6H), 1.02 (s, 9H), 2.04-2.14 (m, 4H), 2.21 (s, 3H), 2.49 (s, 3H), 3.71 (dd, J=8.6, 2.6 Hz, 2H), 3.81 (s, 3H), 3.87 (t, J=8.7 Hz, 1H), 4.01 (d, J=3.5 Hz, 2H), 4.09 (dd, J=5.0, 2.7 Hz, 1H), 4.77-4.81 (m, 1H), 6.61 (s, 1H), 6.65 (d, J=6.6 Hz, 1H), 6.73 (d, J=8.9 Hz, 1H), 6.99 (d, J=1.8 Hz, 1H), 7.04 (dd, J=8.9, 2.6 Hz, 1H). LC/MS (m/z): calcd. for C$_{28}$H$_{42}$NO$_6$S (M+H)$^+$: 520.7; found: 520.2.

Example 63

Preparation of epimer 2 of L-2-[(5-{1-ethyl-1-[4-(2-hydroxy-3,3-dimethyl-butoxy)-3-methyl-phenyl]-propyl}-3-methyl-thiophene-2-carbonyl)-amino]-3-hydroxy-propionic acid L-Epimer 2

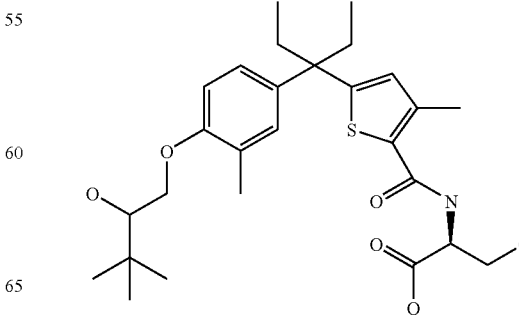

Using a procedure analogous to Example 53, epimer 2 of L-2-[(5-{1-Ethyl-1-[4-(2-hydroxy-3,3-dimethyl-butoxy)-3-methyl-phenyl]-propyl}-3-methyl-thiophene-2-carbonyl)-amino]-3-hydroxy-propionic acid methyl ester (0.40 g, 0.77 mmol) gives the titled compound (0.33 g, 0.66 mmol, 85%). $^1$H NMR (CDC$_3$) δ 0.69 (t, J=7.2 Hz, 6H), 1.01 (s, 9H), 2.00-2.14 (m, 4H), 2.18 (s, 3H), 2.44 (s, 3H), 3.50 (dd, J=13.9, 6.8 Hz, 1H), 3.71 (d, J=8.0 Hz, 1H), 3.88 (t, J=8.6 Hz, 1H), 4.02 (d, J=9.2 Hz, 1H), 4.06-4.12 (m, 1H), 4.62-4.71 (m, 1H), 5.53 (bs, 2H), 6.60 (s, 1H), 6.70 (d, J=8.7 Hz, 1H), 6.79 (d, J=6.6 Hz, 1H), 6.95-7.05 (m, 2H). LC/MS (m/z): calcd. for $C_{27}H_{40}NO_6S$ (M+H)$^+$: 506.7; found: 506.2.

Example 64

Preparation of epimer 1 of L-2-[(5-{1-Ethyl-1-[4-(2-hydroxy-3,3-dimethyl-butoxy)-3-methyl-phenyl]-propyl}-3-methyl-thiophene-2-carbonyl)-amino]-propionic acid methyl ester L-Epimer 1

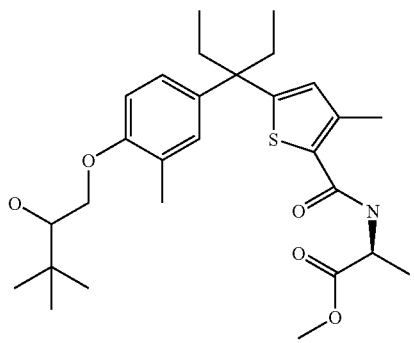

Using a procedure analogous to Example 52, enantiomer 1 of 5-{1-Ethyl-1-[4-(2-hydroxy-3,3-dimethyl-butoxy)-3-methyl-phenyl]-propyl}-3-methyl-thiophene-2-carboxylic acid (Example 1) (0.50 g, 1.19 mmol) and L-alanine methyl ester hydrochloride salt (0.18 g, 1.31 mmol) to give the title compound (0.3 g, 0.60 mmol, 50%). $^1$H NMR and LC/MS: identical to (D-epimer-2), Example 56.

Example 65

Preparation of epimer 1 of L-2-[(5-{1-Ethyl-1-[4-(2-hydroxy-3,3-dimethyl-butoxy)-3-methyl-phenyl]-propyl}-3-methyl-thiophene-2-carbonyl)-amino]-propionic acid L-Epimer 1

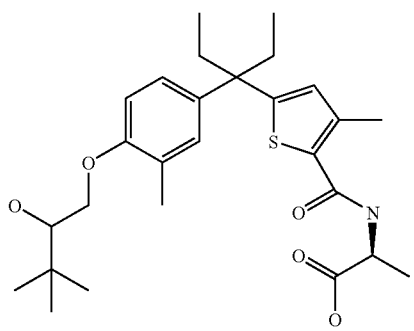

Using a procedure analogous to 53, epimer 1 of L-2-[(5-{1-Ethyl-1-[4-(2-hydroxy-3,3-dimethyl-butoxy)-3-methyl-phenyl]-propyl}-3-methyl-thiophene-2-carbonyl)-amino]-propionic acid methyl ester (0.3 g, 0.60 mmol) gives the title compound (0.27 g, 0.55 mmol, 93%). $^1$H NMR and LC/MS: identical to (D-epimer-2), Example 57.

Example 66

Preparation of epimer 1 of D-2-[(5-{1-Ethyl-1-[4-(2-hydroxy-3,3-dimethyl-butoxy)-3-methyl-phenyl]-propyl}-3-methyl-thiophene-2-carbonyl)-amino]-propionic acid methyl ester D-Epimer 1

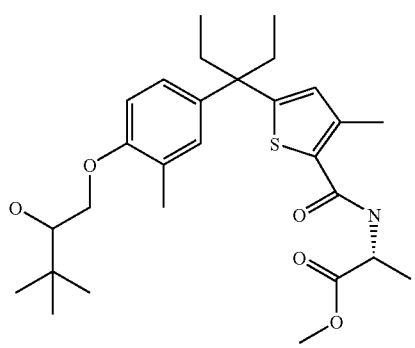

Using a procedure analogous to Example 52, enantiomer 1 of 5-{1-Ethyl-1-[4-(2-hydroxy-3,3-dimethyl-butoxy)-3-methyl-phenyl]-propyl}-3-methyl-thiophene-2-carboxylic acid (Example 7) (0.5 g, 1.19 mmol) and D-alanine methyl ester hydrochloride salt (0.18 g, 1.31 mmol) to give the title compound (0.4 g, 0.79 mmol, 66%). $^1$H NMR and LC/MS: identical to 2133006 (L-Epimer-2), Example 54.

Example 67

Preparation of epimer 1 of D-2-[(5-{1-Ethyl-1-[4-(2-hydroxy-3,3-dimethyl-butoxy)-3-methyl-phenyl]-propyl}-3-methyl-thiophene-2-carbonyl)-amino]-propionic acid D-Epimer 1

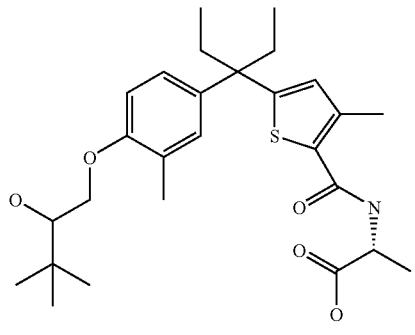

Using a procedure analogous to Example 53, epimer 1 of D-2-[(5-{1-Ethyl-1-[4-(2-hydroxy-3,3-dimethyl-butoxy)-3-methyl-phenyl]-propyl}-3-methyl-thiophene-2-carbonyl)-amino]-propionic acid methyl ester (0.4 g, 0.79 mmol) gives the title compound (0.33 g, 0.67 mmol, 85%). $^1$H NMR and LC/MS: identical to (L-epimer-2), Example 55.

Example 68

Preparation of epimer 1 of L-2-[(5-{1-Ethyl-1-[4-(2-hydroxy-3,3-dimethyl-butoxy)-3-methyl-phenyl]-propyl}-3-methyl-thiophene-2-carbonyl)-amino]-3-methyl-pentanoic acid methyl ester L-Epimer 1

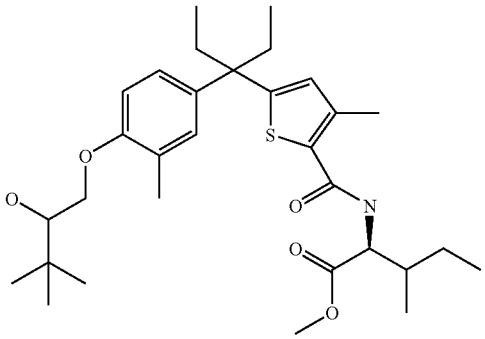

Using a procedure analogous to Example 52, enantiomer 1 of 5-{1-Ethyl-1-[4-(2-hydroxy-3,3-dimethyl-butoxy)-3-methyl-phenyl]-propyl}-3-methyl-thiophene-2-carboxylic acid (Example 7) (0.20 g, 048 mmol) and L-isoleucine methyl ester hydrochloride salt (0.095 g, 0.53 mmol) to give the title compound (0.20 g, 0.37 mmol, 76%). $^1$H NMR (CDC$_3$), δ 0.71 (t, J=7.4 Hz, 6H), 0.91-0.98 (m, 6H), 1.02 (s, 9H), 1.16-1.29 (m, 1H), 1.43-1.55 (m, 1H), 1.90-2.00 (m, 1H), 2.02-2.16 (m, 4H), 2.21 (s, 3H), 2.49 (s, 3H), 3.71 (dd, J=8.7, 2.6 Hz, 1H), 3.74 (s, 3H), 3.87 (t, J=8.7 Hz, 1H), 4.10 (dd, J=9.2, 2.6 Hz, 1H), 4.74 (dd, J=8.4, 4.9 Hz, 1H), 6.21 (d, J=8.4, 1H), 6.59 (s, 1H), 6.73 (d, J=8.8 Hz, 1H), 7.00 (d, J=2.3 Hz, 1H), 7.04 (dd, J=8.6, 2.3 Hz, 1H). LC/MS (m/z): calcd. for $C_{31}H_{48}NO_5S$ (M+H)$^+$: 546.8; found: 546.2.

Example 69

Preparation of epimer 1 of L-2-[(5-{1-Ethyl-1-[4-(2-hydroxy-3,3-dimethyl-butoxy)-3-methyl-phenyl]-propyl}-3-methyl-thiophene-2-carbonyl)-amino]-3-methyl-pentanoic acid L-Epimer 1

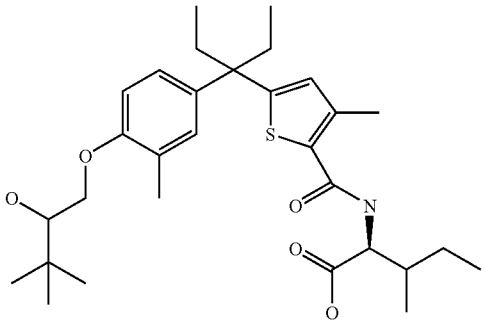

Using a procedure analogous to Example 53, epimer 1 of L-2-[(5-{1-Ethyl-1-[4-(2-hydroxy-3,3-dimethyl-butoxy)-3-methyl-phenyl]-propyl}-3-methyl-thiophene-2-carbonyl)-amino]-3-methyl-pentanoic acid methyl ester (0.2 g, 0.37 mmol) gives the title compound (0.16 g, 0.30 mmol, 84%). $^1$H NMR (CDC$_3$), δ 0.71 (t, J=7.5 Hz, 6H), 0.94-1.02 (m, 6H), 1.03 (s, 9H), 1.21-1.32 (m, 1H), 1.48-1.62 (m, 1H), 1.98-2.16 (m, 5H), 2.21 (s, 3H), 2.47 (s, 3H), 3.72 (dd, J=8.5, 2.6 Hz, 1H), 3.88 (t, J=8.5 Hz, 1H), 4.10 (dd, J=9.3, 2.7 Hz, 1H), 4.73 (dd, J=7.8, 4.8 Hz, 1H), 6.18 (d, J=8.7, 1H), 6.60 (s, 1H), 6.73 (d, J=8.4 Hz, 1H), 7.00 (d, J=2.2 Hz, 1H), 7.04 (dd, J=8.4, 2.2 Hz, 1H). LC/MS (m/z): calcd. for $C_{30}H_{46}NO_5S$ (M+H)$^+$: 531.8; found: 532.1.

Example 70

Preparation of enantiomer 1 of 2-[(5-{1-Ethyl-1-[4-(2-hydroxy-3,3-dimethyl-butoxy)-3-methyl-phenyl]-propyl}-3-methyl-thiophene-2-carbonyl)-amino]-2-methyl-propionic acid methyl ester Enantiomer 1

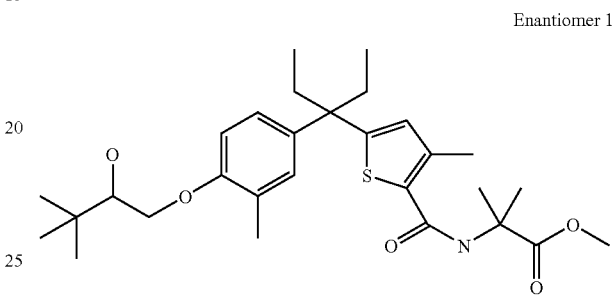

Using the procedure analogous to Example 52, enantiomer 1 of 5-{1-Ethyl-1-[4-(2-hydroxy-3,3-dimethyl-butoxy)-3-methyl-phenyl]-propyl}-3-methyl-thiophene-2-carboxylic acid (Example 7) (0.2 g, 0.48 mmol) and 2-amino-2-methyl-propionic acid methyl ester hydrochloride salt (0.018 g, 0.53 mmol) to give the title compound (0.20 g, 0.39 mmol, 71%). $^1$HNMR (CDC$_3$), δ 0.69 (t, J=7.0 Hz, 6H), 1.01 (s, 9H), 1.60 (s, 6H), 2.02-2.13 (m, 4H), 2.19 (s, 3H), 2.44 (s, 3H), 3.70 (dd, J=8.9, 2.6 Hz, 1H), 3.76 (s, 3H), 3.86 (t, J=8.7 Hz, 1H), 4.09 (dd, J=9.4, 2.6 Hz, 1H), 6.28 (s, 1H), 6.59 (s, 1H), 6.73 (d, J=8.4 Hz, 1H), 6.99 (d, J=2.2 Hz, 1H), 7.04 (dd, J=8.4, 2.2 Hz, 1H). LC/MS (m/z): calcd. for $C_{29}H_{44}NO_5S$ (M+H)$^+$: 518.7; found: 518.2.

Example 71

Preparation of enantiomer 1 of 2-[(5-{1-Ethyl-1-[4-(2-hydroxy-3,3-dimethyl-butoxy)-3-methyl-phenyl]-propyl}-3-methyl-thiophene-2-carbonyl)-amino]-2-methyl-propionic acid Enantiomer 1

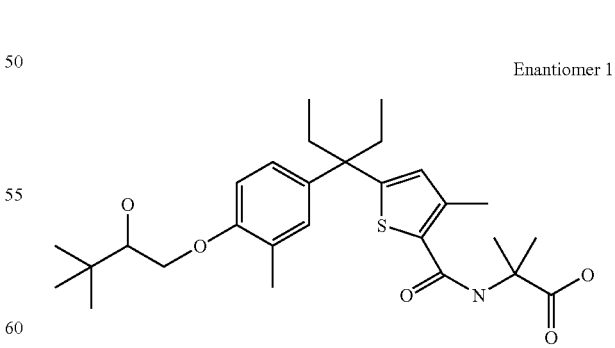

Using a procedure analogous to Example 53, enantiomer 1 of 2-[(5-{1-Ethyl-1-[4-(2-hydroxy-3,3-dimethyl-butoxy)-3-methyl-phenyl]-propyl}-3-methyl-thiophene-2-carbonyl)-amino]-2-methyl-propionic acid methyl ester (0.20 g, 0.39 mmol) gives the title compound (0.17 g, 0.34 mmol, 84%). $^1$H NMR (CDCl₃), δ 0.71 (t, J=7.5 Hz, 6H), 1.02 (s, 9H), 1.65 (s, 6H), 2.03-2.14 (m, 4H), 2.21 (s, 3H), 2.47 (s, 3H), 3.71 (dd, J=8.6, 2.5 Hz, 1H), 3.87 (t, J=8.6, 1H), 4.09 (dd, J=9.2, 2.5 Hz, 1H), 6.11 (s, 1H), 6.63 (s, 1H), 6.73 (d, J=8.3 Hz, 1H), 6.73 (d, J=8.4 Hz, 1H), 6.98 (d, J=2.2 Hz, 1H), 7.04 (dd, J=8.4, 2.2 Hz, 1H). LC/MS (m/z): calcd. for $C_{28}H_{42}NO_5S$ (M+H)⁺: 504.7; found: 504.2.

Example 72

Preparation of epimer 1 of L-1-(5-{1-Ethyl-1-[4-(2-hydroxy-3,3-dimethyl-butoxy)-3-methyl-phenyl]-propyl}-3-methyl-thiophene-2-carbonyl)pyrrolidine-2-carboxylic acid methyl ester L-Epimer 1

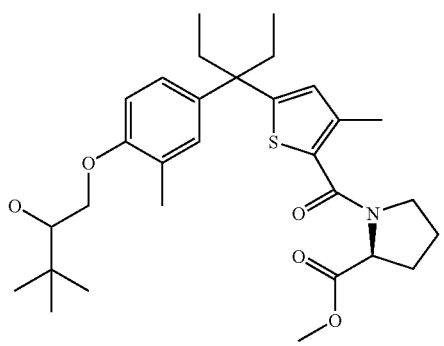

Using a procedure analogous to Example 52, enantiomer 1 of 5-{1-Ethyl-1-[4-(2-hydroxy-3,3-dimethyl-butoxy)-3-methyl-phenyl]-propyl}-3-methyl-thiophene-2-carboxylic acid (Example 7) (0.20 g, 0.4778 mmol) and L-proline methyl ester hydrochloride salt (0.09 g, 0.53 mmol) to give the title compound (0.14 g, 0.26 mmol, 56%). ¹H NMR (CDC₃), δ 0.69 (t, J=7.4 Hz, 3H), 0.70 (t, J=7.1 Hz, 3H), 1.00 (s, 9H), 1.85-2.14 (m, 7H), 2.19 (s, 3H), 2.21-2.36 (m, 4H), 3.60-3.78 (m, 6H), 3.86 (t, J=9.3, 1H), 4.09 (dd, J=9.3, 2.8 Hz, 1H), 4.53-4.65 (m, 1H), 6.53 (s, 1H), 6.71 (d, J=8.9 Hz, 1H), 6.96-7.06 (m, 2H). LC/MS (m/z): calcd. for $C_{30}H_{44}NO_5S$ (M+H)⁺: 530.8; found: 530.2.

Example 73

Preparation of epimer 1 of L-1-(5-{1-Ethyl-1-[4-(2-hydroxy-3,3-dimethyl-butoxy)-3-methyl-phenyl]-propyl}-3-methyl-thiophene-2-carbonyl)pyrrolidine-2-carboxylic acid L-Enantiomer 1

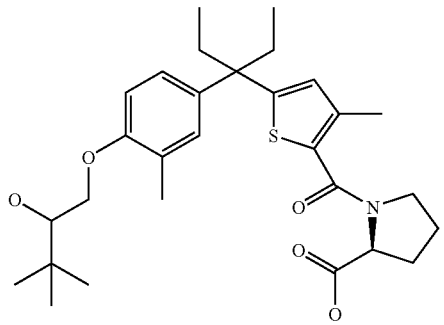

Using a procedure analogous to Example 53, epimer 1 of L-1-(5-{1-Ethyl-1-[4-(2-hydroxy-3,3-dimethyl-butoxy)-3-methyl-phenyl]-propyl}-3-methyl-thiophene-2-carbonyl)

pyrrolidine-2-carboxylic acid methyl ester (0.20 g, 0.39 mmol) gives the title compound (0.17 g, 0.34 mmol, 84%). ¹HNMR (CDCl₃), δ 0.71 (t, J=7.5 Hz, 6H), 1.02 (s, 9H), 1.91-2.15 (m, 8H), 2.20 (s, 3H), 2.36 (s, 3H), 2.42 (bs, 1H), 3.63-3.76 (m, 3H), 3.87 (t, J=9.2, 1H), 4.09 (dd, J=9.2, 2.6 Hz, 1H), 4.68-4.75 (m, 1H), 6.60 (s, 1H), 6.72 (d, J=8.3 Hz, 1H), 6.99 (d, J=2.2 Hz, 1H), 7.03 (dd, J=8.3, 2.2 Hz, 1H). LC/MS (m/z): calcd. for $C_{29}H_{42}NO_5S$ (M+H)⁺: 516.7; found: 516.2.

Example 74

Preparation of epimer 2 of L-1-(5-{1-Ethyl-1-[4-(2-hydroxy-3,3-dimethyl-butoxy)-3-methyl-phenyl]-propyl}-3-methyl-thiophene-2-carbonyl)-pyrrolidine-2-carboxylic acid methyl ester L-Epimer 2

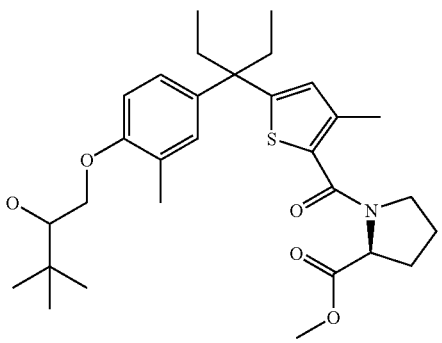

Using the procedure analogous to Example 52, enantiomer 2 of 5-{1-Ethyl-1-[4-(2-hydroxy-3,3-dimethyl-butoxy)-3-methyl-phenyl]-propyl}-3-methyl-thiophene-2-carboxylic acid (Example 8) (0.50 g, 1.19 mmol) and L-proline methyl ester hydrochloride salt (0.22 g, 1.3 mmol) to give the title compound (0.31 g, 0.59 mmol, 49%). ¹H NMR (CDC₃), δ 0.70 (t, J=7.1 Hz, 3H), 0.71 (t, J=7.5 Hz, 1H), 1.02 (s, 9H), 1.87-2.15 (m, 7H), 2.20 (s, 3H), 2.22-2.38 (m, 4H), 3.60-3.78 (m, 6H), 3.87 (t, J=9.3, 1H), 4.09 (dd, J=9.3, 2.7 Hz, 1H), 4.53-4.65 (m, 1H), 6.54 (s, 1H), 6.71 (d, J=8.9 Hz, 1H), 6.96-7.06 (m, 2H). LC/MS (m/z): calcd. for $C_{30}H_{44}NO_5S$ (M+H)⁺: 530.8; found: 530.2.

Example 75

Preparation of epimer 2 of L-1-(5-{1-Ethyl-1-[4-(2-hydroxy-3,3-dimethyl-butoxy)-3-methyl-phenyl]-propyl}-3-methyl-thiophene-2-carbonyl)-pyrrolidine-2-carboxylic acid L-Epimer 2

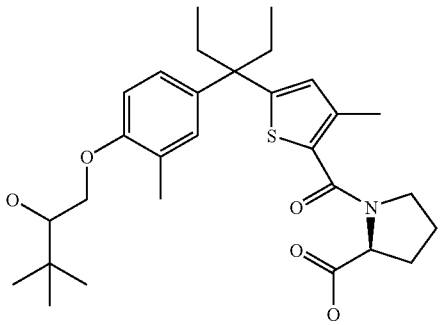

Using the procedure analogous to Example 53, epimer 2 of 2-[(5-{1-Ethyl-1-[4-(2-hydroxy-3,3-dimethyl-butoxy)-3-methyl-phenyl]-propyl}-3-methyl-thiophene-2-carbonyl)- amino]-2-methyl-propionic acid methyl ester, (0.31 g, 0.59 mmol) gives the title compound (0.29 g, 0.56 mmol, 97%). $^1$H NMR (CDCl$_3$), δ 0.71 (t, J=7.5 Hz, 6H), 1.02 (s, 9H), 1.92-2.15 (m, 8H), 2.20 (s, 3H), 2.36 (s, 3H), 2.41 (bs, 1H), 3.63-3.76 (m, 3H), 3.90 (t, J=8.9, 1H), 4.10 (dd, J=8.9, 2.5 Hz, 1H), 4.68-4.75 (m, 1H), 6.60 (s, 1H), 6.72 (d, J=8.5 Hz, 1H), 6.99 (d, J=2.3 Hz, 1H), 7.03 (dd, J=8.5, 2.3 Hz, 1H). LC/MS (m/z): calcd. for C$_{29}$H$_{42}$NO$_5$S (M+H)$^+$: 516.7; found: 516.3.

Example 76

Preparation of enantiomer 2 of 2-[(5-{1-Ethyl-1-[4-(2-hydroxy-3,3-dimethyl-butoxy)-3-methyl-phenyl]-propyl}-3-methyl-thiophene-2-carbonyl)-amino]-2-methyl-propionic acid methyl ester Enantiomer 2

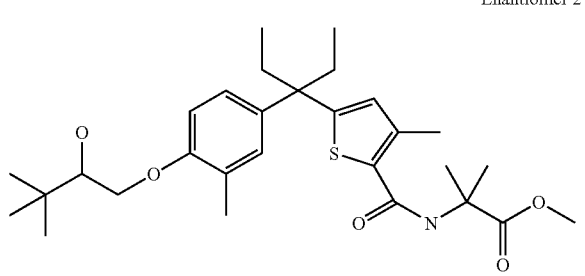

Using the procedure analogous to Example 52, enantiomer 2 of 5-{1-Ethyl-1-[4-(2-hydroxy-3,3-dimethyl-butoxy)-3-methyl-phenyl]-propyl}-3-methyl-thiophene-2-carboxylic acid (Example 8) (0.5 g, 1.19 mmol) and 2-amino-2-methyl-propionic acid methyl ester hydrochloride salt (0.2 g, 1.31 mmol) to give the title compound (0.44 g, 0.85 mmol, 71%). $^1$H NMR and LC/MS: identical to (enantiomer-1), Example 70.

Example 77

Preparation of enantiomer of 2-[(5-{1-Ethyl-1-[4-(2-hydroxy-3,3-dimethyl-butoxy)-3-methyl-phenyl]-propyl}-3-methyl-thiophene-2-carbonyl)-amino]-2-methyl-propionic acid Enantiomer 2

Using the procedure analogous to Example 53, enantiomer 2 of 2-[(5-{1-Ethyl-1-[4-(2-hydroxy-3,3-dimethyl-butoxy)-3-methyl-phenyl]-propyl}-3-methyl-thiophene-2-carbonyl)-amino]-2-methyl-propionic acid methyl ester (0.44 g, 0.85 mmol) gives the title compound (0.35 g, 0.69 mmol, 81%). $^1$H NMR and LC/MS: identical to (enantiomer-1), Example 71.

Example 78

Preparation of D-1-(5-{1-ethyl-1-[4-(2-hydroxy-3,3-dimethyl-butoxy)-3-methyl-phenyl]-propyl}-3-methyl-thiophene-2-carbonyl)-pyrrolidine-2-carboxylic acid methyl ester

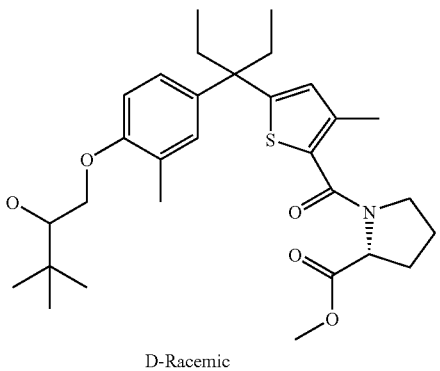

D-Racemic

Using a procedure analogous to Example 52, a racemic mixture of 5-{1-Ethyl-1-[4-(2-hydroxy-3,3-dimethyl-butoxy)-3-methyl-phenyl]-propyl}-3-methyl-thiophene-2-carboxylic acid (0.6 g, 1.39 mmol) and D-proline methyl ester hydrochloride salt (0.28 g, 1.53 mmol) give the title compound (0.54 g, 1.02 mmol, 73%). $^1$H NMR (CDC$_3$), δ 0.70 (t, J=7.1 Hz, 3H), 0.71 (t, J=7.5 Hz, 3H) 1.02 (s, 9H), 1.88-2.16 (m, 7H), 2.20 (s, 3H), 2.22-2.38 (m, 4H), 3.61-3.79 (m, 6H), 3.87 (t, J=8.8, 1H), 4.09 (dd, J=9.1, 2.6 Hz, 1H), 4.56-4.65 (m, 1H), 6.54 (s, 1H), 6.71 (d, J=8.4 Hz, 1H), 6.98-7.06 (m, 2H). LC/MS (m/z): calcd. for C$_{30}$H$_{44}$NO$_5$S (M+H)$^+$: 530.8; found: 530.2.

Example 79 and 80

Preparation of epimers of D-1-(5-{1-Ethyl-1-[4-(2-hydroxy-3,3-dimethyl-butoxy)-3-methyl-phenyl]-propyl}-3-methyl-thiophene-2-carbonyl)-pyrrolidine-2-carboxylic acid methyl ester D-Epimer 1

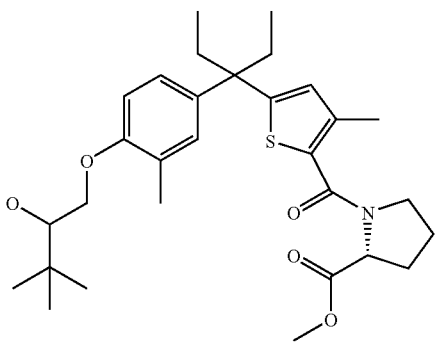

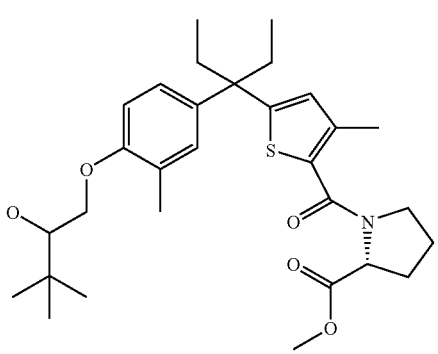

D-Epimer 2

A racemic mixture of D-1-(5-{1-ethyl-1-[4-(2-hydroxy-3,3-dimethyl-butoxy)-3-methyl-phenyl]-propyl}-3-methyl-thiophene-2-carbonyl)-pyrrolidine-2-carboxylic acid methyl ester (0.54 g) is chromatographed (CHIRALPAK AD column, 40% i-PrOH/Hept) to give epimer1, Example 79 (0.244 g, 45%) and epimer 2, Example 80 (0.283 g, 52%).

Example 79, Epimer1 rt=10.2 m

NMR & LC/MS: identical to 2158904 (L-epimer-2), Example 78.

Example 80, Epimer 2 rt=18.1 m

NMR & LC/MS: identical to (L-epimer-1), Example 78.

Example 81

Preparation of epimer 1 of D-1-(5-{1-ethyl-1-[4-(2-hydroxy-3,3-dimethyl-butoxy)-3-methyl-phenyl]-propyl}-3-methyl-thiophene-2-carbonyl)-pyrrolidine-2-carboxylic acid

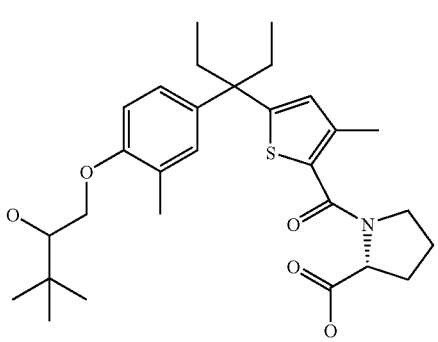

D-Epimer 1

Using the procedure analogous to Example 53, epimer 1 of D-2-[(5-{1-Ethyl-1-[4-(2-hydroxy-3,3-dimethyl-butoxy)-3-methyl-phenyl]-propyl}-3-methyl-thiophene-2-carbonyl)-amino]-2-methyl-propionic acid methyl ester (Example 79) (0.24 g, 0.46 mmol) gives the title compound (0.15 g, 0.29 mmol, 63%). $^1$H NMR and LC/MS: identical to (L-enantiomer-2), Example 75.

Example 82

Preparation of epimer 2 of D-1-(5-{1-Ethyl-1-[4-(2-hydroxy-3,3-dimethyl-butoxy)-3-methyl-phenyl]-propyl}-3-methyl-thiophene-2-carbonyl)-pyrrolidine-2-carboxylic acid

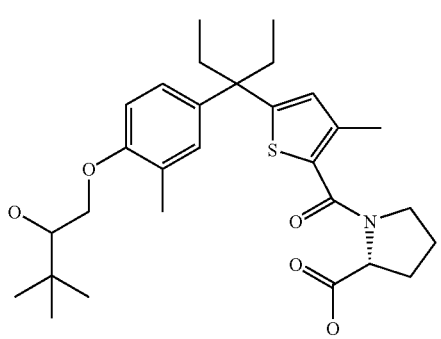

D-Enantiomer 2

Using a procedure analogous to Example 53, epimer-2 of D-1-(5-{1-Ethyl-1-[4-(2-hydroxy-3,3-dimethyl-butoxy)-3-methyl-phenyl]-propyl}-3-methyl-thiophene-2-carbonyl)-pyrrolidine-2-carboxylic acid methyl ester (Example 80) (0.28 g, 0.53 mmol) gives the title compound (0.22 g, 0.43 mmol, 79%). $^1$H NMR and LC/MS: identical to (L-epimer-1), Example 73.

Example 83

Preparation of D-2-[(5-{1-ethyl-1-[4-(2-hydroxy-3,3-dimethyl-butoxy)-3-methyl-phenyl]-propyl}-3-methyl-thiophene-2-carbonyl)-amino]-3-methyl-butyric acid methyl ester

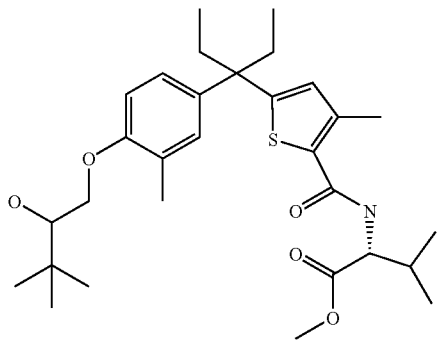

D-Racemic

Using a procedure analogous to Example 52, a racemic mixture of 5-{1-ethyl-1-[4-(2-hydroxy-3,3-dimethyl-butoxy)-3-methyl-phenyl]-propyl}-3-methyl-thiophene-2-carboxylic acid (Example 3) (0.60 g, 1.39 mmol) and D-valine methyl ester hydrochloride salt (0.29 g, 1.53 mmol) to give the title compound (0.54 g, 1.02 mmol, 73%). LC/MS (m/z): calcd. for $C_3OH_{46}NO_5S$ (M+H)$^+$: 532.8; found: 532.2.

Example 84 and 85

Preparation of epimers of D-2-[(5-{1-Ethyl-1-[4-(2-hydroxy-3,3-dimethyl-butoxy)-3-methyl-phenyl]-propyl}-3-methyl-thiophene-2-carbonyl)-amino]-3-methyl-butyric acid methyl ester D-Epimer 1

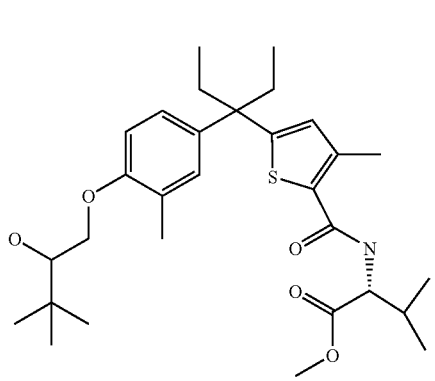

D-Epimer 2

A racemic mixture of D-2-[(5-{1-ethyl-1-[4-(2-hydroxy-3,3-dimethyl-butoxy)-3-methyl-phenyl]-propyl}-3-methyl-thiophene-2-carbonyl)-amino]-3-methyl-butyric acid methyl ester (Example 83) (0.54 g) is chromatographed (CHIRALPAK AD column, 40% i-PrOH/Hept) to give epimer 1, Example 84 (0.36 g, 48%) and epimer 2, Example 85 (0.33 g, 45%).

Example 84, Epimer 1
rt=6.8m
$^1$H NMR (CDC$_3$), δ 0.71 (t, J=7.2 Hz, 6H), 0.96 (d, J=6.6 Hz, 3H), 0.99 (d, J=7.1H, 3H), 1.02 (s, 9H), 2.04-2.15 (m, 4H), 2.18 (s, 3H), 2.20-2.21 (m, 2H), 2.47 (s, 3H), 3.71 (dd, J=8.8, 2.6 Hz, 1H), 3.76 (s, 3H), 3.88 (t, J=8.8 Hz, 1H), 4.11 (dd, J=9.2, 2.6 Hz, 1H), 4.69 (dd, J=8.4, 4.9 Hz, 1H), 6.19 (d, J=8.4 Hz, 1H), 6.60 (s, 1H), 6.73 (d, J=8.3 Hz, 1H), 6.90-7.06 (m, 2H). LC/MS (m/z): calcd. for C$_{30}$H$_{46}$NO$_5$S (M+H)$^+$: 532.8; found: 532.2.

Example 85, Epimer 2
rt=10.6 m
$^1$H NMR and LC/MS: identical to (D-enantiomer-1), example 33.

Example 86

Preparation of epimer 1 of D-2-[(5-{1-Ethyl-1-[4-(2-hydroxy-3,3-dimethyl-butoxy)-3-methyl-phenyl]-propyl}-3-methyl-thiophene-2-carbonyl)-amino]-3-methyl-butyric acid D-Epimer 1

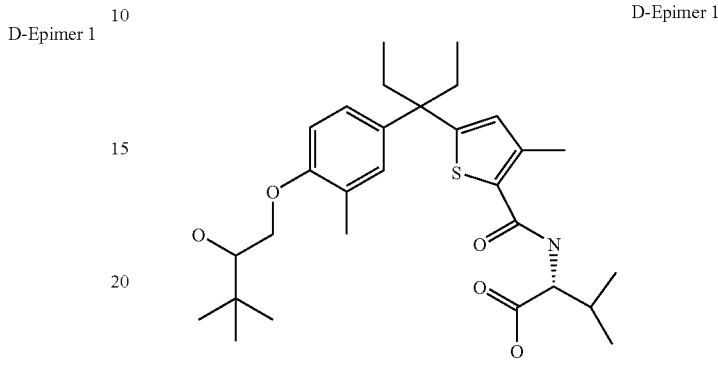

Using the procedure analogous to Example 53, epimer I of D-2-[(5-{1-ethyl-1-[4-(2-hydroxy-3,3-dimethyl-butoxy)-3-methyl-phenyl]-propyl}-3-methyl-thiophene-2-carbonyl)-amino]-2-methyl-propionic acid methyl ester (Example 84) (0.28 g, 0.53 mmol) gives the title compound (0.22 g, 0.43 mmol, 79%). $^1$H NMR (CDC$_3$), δ 0.71 (t, J=7.4 Hz, 6H), 1.00 (d, J=6.6 Hz, 3H), 1.03 (s, 9H), 1.04 (d, J=6.6 Hz, 3H), 2.04-2.14 (m, 4H), 2.21 (s, 3H), 2.25-2.35 (m, 1H), 2.47 (s, 3H), 3.72 (dd, J=8.4, 2.6 Hz, 1H), 3.88 (t, J=9.2 Hz, 1H), 4.10 (dd, J=9.2, 2.6 Hz, 1H), 4.69 (dd, J=8.0, 4.4 Hz, 1H), 6.19 (d, J=8.0 Hz), 6.60 (s, 1H), 6.73 (d, J=8.4 Hz, 1H), 7.00 (dd, J=2.2 Hz, 1H), 7.04 (dd, J=8.4, 2.6 Hz, 1H). LC/MS (m/z): calcd. for C$_{29}$H$_{44}$NO$_5$S (M+H)$^+$: 518.7; found: 518.2.

Example 87

Preparation of epimer 2 of D-2-[(5-{1-ethyl-1-[4-(2-hydroxy-3,3-dimethyl-butoxy)-3-methyl-phenyl]-propyl}-3-methyl-thiophene-2-carbonyl)-amino]-3-methyl-butyric acid D-Epimer 2

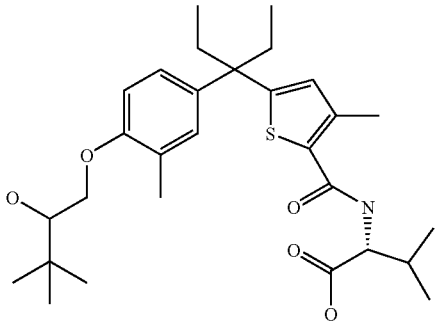

Using a procedure analogous to Example 53, epimer 2 of D-2-[(5-{1-Ethyl-1-[4-(2-hydroxy-3,3-dimethyl-butoxy)-3-methyl-phenyl]-propyl}-3-methyl-thiophene-2-carbonyl)-amino]-2-methyl-propionic acid methyl ester (Example 85)

(0.33 g, 0.62 mmol) gives the title compound (0.23 g, 0.44 mmol, 79%). ¹H NMR and LC/MS: equivalent to (D-epimer-1), Example 86.

Example 88

Preparation of 3'-[4-(2-hydroxy-3,3-dimethylbutoxy)-3-methylphenyl]-3'-[5-carboxy-thiophen-2-yl]pentane

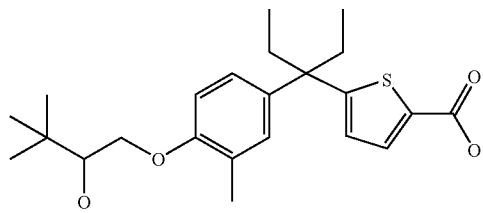

Using a procedure analogous to Example 3, 3'-[4-(2-Hydroxy-3,3-dimethylbutoxy)-3-methylphenyl]-3'-[5-methoxycarbonyl-thiophen-2-yl]pentane (0.23 g, 0.55 mmol) and 5N sodium hydroxide (220 ul, 1.1 mmol) give the title compound (0.18 g, 81%).

H-NMR (ppm, CDC₃): 7.68 (1H, d, 4.0 Hz), 7.03 (1H, d, 8.2 Hz), 6.98 (1H, s), 6.79 (1H, d, 4.0 Hz), 6.72 (1H, d, 8.2 Hz), 4.09 (1H, d, 9.3 Hz), 3.85 (1H, t, 9.3 Hz), 3.73 (1H, d, 9.3 Hz), 2.19 (3H, s), 2.13 (4H, q, 7.0 Hz), 1.02 (9H, s), 0.71 (6H, t, 7.0 Hz).

ES/MS: 403.2 (M+1) 422.2 (M+NH4).

Example 89 and 90

Preparation of enantiomers of 3'-[4-(2-hydroxy-3,3-dimethylbutoxy)-3-methylphenyl]-3'-[5-carboxy-thiophen-2-yl]pentane

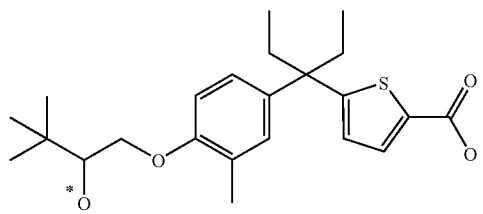

A mixture of racemic 3'-[4-(2-hydroxy-3,3-dimethylbutoxy)-3-methylphenyl]-3'-[5-carboxy-thiophen-2-yl]pentane (166 mg) is chromatographed with a ChiralPak AD column (10% IPA/hept to 15% IPA/hept) to give enantiomer 1 (63 mg), Example 89 and enantiomer 2 (67 mg), Example 90.

Enantiomer 1, Example 89

HPLC: ChiralPak AD (4.6×250 mm); 15% IPA/85% heptane; I ml/m (flow rate); rt=4.9 m; 225 nm.

Enantiomer 2, Example 90

HPLC: ChiralPak AD (4.6×250 mm); 15% IPA/85% heptane; 1 ml/m (flow rate); rt=6.9 m; 225 nm.

Example 91

Preparation of 3'-[4-(2-oxo-3,3-dimethylbutoxy)-3-(1-methylethyl)phenyl]-3'-[5-methoxycarbonyl-thiophen-2-yl]pentane

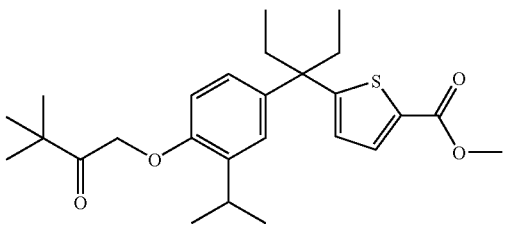

A. 3'-[4-(Hydroxy)-3-(1-methylethyl)phenyl]-3'-[5-methoxycarbonyl-4-methylthiophen-2-yl]pentane.

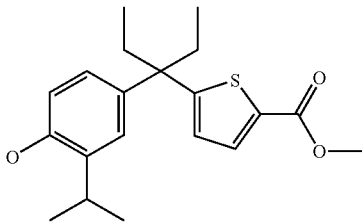

Methyl, 5-(E/Z-2-penten-3-yl)thiophene-2-carboxylate (Example 5C) (0.21 g, 1.0 mmol), o-isopropylphenol (1.09 g, 4.0 mmol), and BF3-etherate (58 mg, 0.2 mmol) are reacted and purified as described in Example 5D to give the title compound (0.28 g, 81%).

H-NMR (ppm, CDC₃): 7.62 (1H, d, 4.0 Hz), 7.05 (1H, s), 6.90 (1H, d, 8.8 Hz), 6.78 (1H, d, 4.0 Hz), 6.63 (1H, d, 8.8 Hz), 4.58 (1H, s), 3.83 (3H, s), 3.15 (1H, m), 2.11 (4H, q, 7.2 Hz), 1.21 (6H, d, 6.8 Hz), 0.71 (6H, t, 7.4 Hz).

ES/MS: 347.2 (M+1).

B. 3'-[4-(2-Oxo-3,3-dimethylbutoxy)-3-(1-methylethyl)phenyl]-3'-[5-methoxycarbonyl-thiophen-2-yl]pentane

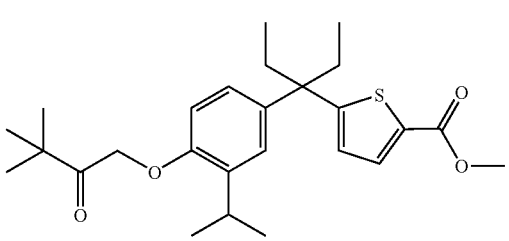

3'-[4-(Hydroxy)-3-(1-methylethyl)phenyl]-3'-[5-methoxycarbonyl-4-methylthiophen-2-yl]pentane (0.18 g, 0.52 mmol), sodium hydride 60% (23 mg, 0.56 mmol), and 1-chloropinacolone (71 mg, 0.52 mmol) with a catalytic amount of potassium iodide (7 mg, 0.04 mmol) are reacted and purified as described in Example SE to give the title compound (0.13 g, 56%).

H-NMR (ppm, CDC$_3$): 7.61 (1H, d, 4.0 Hz), 7.08 (1H, s), 6.93 (1H, d, 6.0 Hz), 6.77 (1H, d, 4.0 Hz), 6.52 (1H, d, 6.0 Hz), 4.84 (2H, s), 3.83 (3H, s), 3.38 (1H, m), 2.11 (4H, q, 7.2 Hz), 1.26 (9H, s), 1.19 (6H, d, 7.2 Hz), 0.71 (6H, t, 7.4 Hz). ES/MS: 445.2 (M+H) 462.2 (M+NH4).

Example 92

3'-[4-(2-Hydroxy-3,3-dimethylbutoxy)-3-(1-methylethyl)phenyl]-3'-[5-carboxy-thiophen-2-yl]pentane

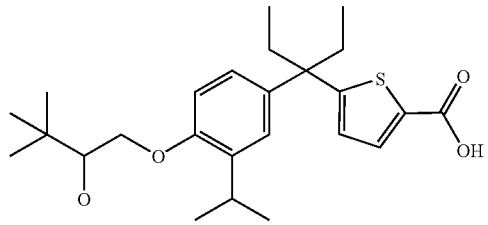

A. 3'-[4-(2-Hydroxy-3,3-dimethylbutoxy)-3-(1-methylethyl)phenyl]-3'-[5-methoxycarbonyl-thiophen-2-yl]pentane

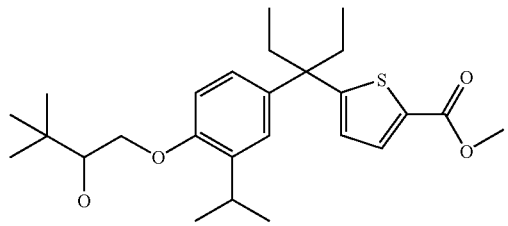

3'-[4-(2-Oxo-3,3-dimethylbutoxy)-3-(1-methylethyl)phenyl]-3'-[5-methoxycarbonyl-thiophen-2-yl]pentane 1 (16 mg 0.26 mmol) and sodium borohydride (9.8 mg, 0.26 mmol) are reacted in methanol and purified as described in Example SF to give the title compound (93 mg, 80%).

H-NMR (ppm, CDC$_3$): 7.63 (1H, d, 4.0 Hz), 7.08 (1H, s), 6.99 (1H, d, 9.0 Hz), 6.78 (1H, d, 4.0 Hz), 6.74 (1H, d, 9.0 Hz), 4.09 (1H, d, 8.2 Hz), 3.85 (1H, t, 8.2 Hz), 3.83 (3H, s), 3.72 (1H, d, 8.2 Hz), 3.25 (1H, m), 2.40 (1H, s), 2.12 (4H, q, 7.2 Hz), 1.17 (6H, d, 6.8 Hz), 1.02 (9H, s), 0.71 (6H, t, 7.2 Hz). ES/MS: 447.2 (M+1).

B. 3'-[4-(2-Hydroxy-3,3-dimethylbutoxy)-3-(1-methylethyl)phenyl]-3'-[5-carboxy-thiophen-2-yl]pentane

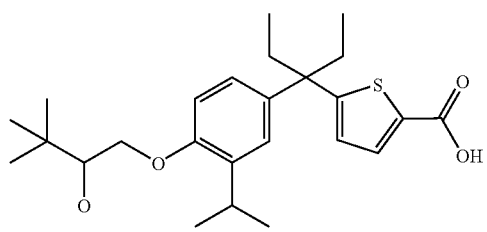

Using a procedure analogous to Example 3, 3'-[4-(2-Hydroxy-3,3-dimethylbutoxy)-3-(1-methylethyl)phenyl]-3'-[5-methoxycarbonyl-thiophen-2-yl]pentane (93 mg, 0.21 mmol) and 5N sodium hydroxide (1 ml, 5 mmol) are reacted and purified to give the title compound (66 mg, 73%).

H-NMR (ppm, CDC$_3$): 7.69 (1H, d, 4.0 Hz), 7.08 (1H, s), 6.99 (1H, d, 6.0 Hz), 6.80 (1H, d, 4.0 Hz), 6.74 (1H, d, 6.0 Hz), 4.08 (1H, d, 8.0 Hz), 3.84 (1H, t, 8.0 Hz), 3.73 (1H, d, 8.0 Hz), 3.25 (1H, m), 2.13 (4H, q, 6.8 Hz), 1.17 (6H, d, 6.0 Hz), 1.02 (9H, s), 0.72 (6H, t, 7.0 Hz).

ES/MS: 431.2 (M−1) 450.2 (M+NH4).

Example 93

Preparation of 3'-[4-(2-hydroxy-3,3-dimethylbutoxy)-3-n-propylphenyl]-3'-[5-carboxy-thiophen-2-yl]pentane

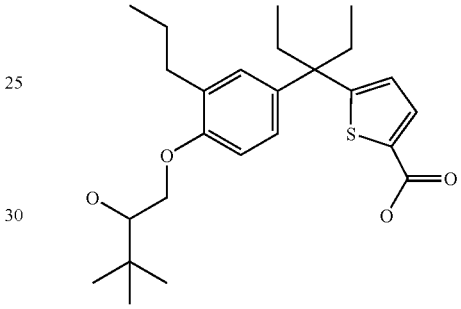

A. 3'-(4-hydroxy-3-n-propylphenyl)-3'-[5-methoxycarbonyl-thiophen-2-yl]pentane

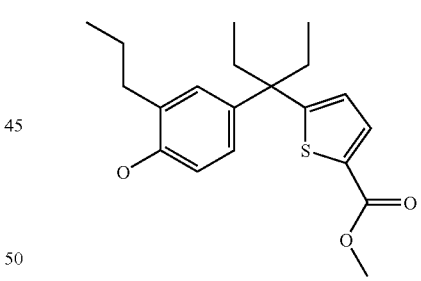

To a mixture of o-propylphenol (1.09 g, 8.0 mol) and methyl, 5-(z/e-2-penten-3-yl)thiophene-2-carboxylate (0.21 g, 1.0 mmol) in methylene chloride (1 ml) is added BF3-etherate (56 mg, 0.2 mmol) under nitrogen and stirred for 16 h. The mixture is partitioned between satd NaHCO$_3$ and diethylether. The organic layer is washed with water, Na$_2$SO$_4$ dried, and concentrated. The excess phenol is removed from the residue by vacuum distillation at 70° C./0.04 mm. The residue is chromatographed (4% EtOAc/hex) to give the title compound as an oil (0.27 g, 78%). NMR (CDC13): 7.62 (d, 1H, J=3.6 Hz); 6.96 (s, 1H); 6.94 (d, 1H, J=7.3 Hz); 6.77 (d, 1H, J=3.6 Hz); 6.66 (d, 1H, J=8.0 Hz); 4.61 (s, 1H); 3.83 (s, 3H); 2.55 (t, 2H, J=7.3 Hz); 2.11 (q, 4H, J=7.2 Hz); 1.60 (m, 2H); 0.93 (t, 3H, J=7.3 Hz); 0.71 (t, 6H, J=7.2 Hz). FAB/MS: 347 M+1.

B. 3'-[4-(2-Oxo-3,3-dimethylbutoxy)-3-n-propylphenyl]-3'-[5-methoxycarbonyl-thiophen-2-yl]pentane

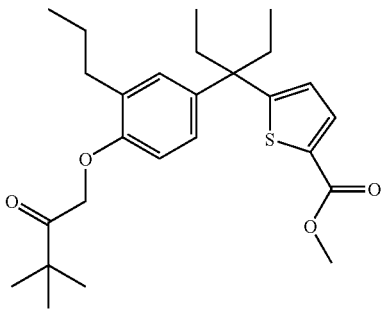

Using a procedure analogous to Example 91B, 3'-(4-hydroxy-3-n-propylphenyl)-3'-[5-methoxycarbonyl-thiophen-2-yl]pentane (0.27 g, 0.78 mmol) give the title compound as an oil (0.21 g, 60%).

NMR (CDCl3): 7.61 (d, 1H, J=4.4 Hz); 6.97 (s, 1H); 6.95 (d, 1H, J=7.3 Hz); 6.77 (d, 1H, J=4.4 Hz); 6.50 (d, 1H, J=7.3 Hz); 4.83 (s, 2H); 3.83, (s, 3H); 2.61 (t, 2H, J=7.3 Hz); 2.10 (q, 4H, J=7.3 Hz); 1.59 (m, 2H); 1.26 (s, 9H); 0.90 (t, 3H, 7.3 Hz); 0.70 (t, 6H, 7.3 Hz).

FAB-MS: 444.3 molecular ion.

C. 3'-[4-(2-hydroxy-3,3-dimethylbutoxy)-3-n-propylphenyl]-3'-[5-methoxycarbonyl-thiophen-2-yl]pentane

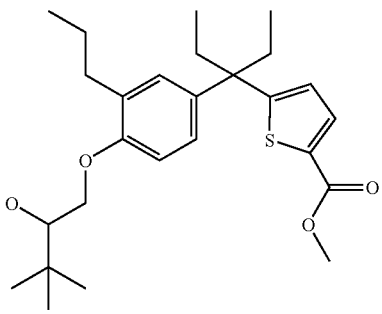

To a mixture of 3'-[4-(2-oxo-3,3-dimethylbutoxy)-3-n-propylphenyl]-3'-[5-methoxycarbonyl-thiophen-2-yl]pentane (0.199 g, 0.45 mmol) and MeOH (5 ml) is added NaBH4 (17 mg, 0.45 mmol) in portions. After stirring for 4.5 h at room temperature, the reaction is concentrated and partitioned between satd NaHCO3 and diethylether. The organic layer is washed with water, Na2SO4 dried, and concentrated to give the title compound as an oil (0.18 g, 90%).

NMR(CDCl3): 7.62 (d, 1H, J=3.6 Hz); 7.02 (1H, d, J=7.5 Hz); 6.98 (s, 1H); 6.78 (d, 1H, 3.6 Hz); 6.73 (d, 1H, 7.5 Hz); 4.08 (1H, d, J=9.0); 3.85 (t, 1H, J=9.0); 3.83 (s, 3H); 3.71 (d, 1H, J=9.0 Hz); 2.55 (t, 2H, 7.5 Hz); 2.40 (s, 1H); 2.12 (q, 4H, J=7.6 Hz); 1.55 (m, 2H); 1.02 (s, 9H); 0.90 (t, 3H, J=7.6 Hz); 0.71 (t, 6H, J=7.2 Hz).

LC/MS: 447.2 M+1.

D. 3'-[4-(2-Hydroxy-3,3-dimethylbutoxy)-3-n-propylphenyl]-3'-[5-carboxy-tbiophen-2-yl]pentane A mixture of 3'-[4-(2-hydroxy-3,3-dimethylbutoxy)-3-n-propylphenyl]-3'-[5-methoxycarbonyl-thiophen-2-yl]pentane (0.18 g, 0.4 mmol), methanol (3 ml) and 5N NaOH (161 uL, 0.8 mmol) is heated to 50° C. for 16 h. The reaction mixture is concentrated and the residue dissolved in water (4 mL). The solution is added conc. HCl, filtered with water wash, and air dried to give the title compound (0.16 g, 92%).

NMR(CDCl3): 7.69 (d, 1H, J=4.0 Hz); 7.02 (d, 1H, J=7.5 Hz); 6.98 (s, 1H); 6.79 (d, 1H, J=4.0 Hz); 6.75 (d, 1H, J=7.5 Hz); 5.29 (s, 1H); 4.08 (d, 1H, J=9.0); 3.85 (t, 1H, J=9.0 Hz); 3.70 (d, 1H, J=9.0 Hz); 2.55 (t, 2H, J=7.5 Hz); 2.13 (q, 4H, J=7.2 Hz); 1.55 (m, 1H); 1.02 (s, 9H); 0.90 (t, 3H, H=7.4 Hz); 0.72 (t, 6H, J=7.4 Hz).

LC/MS: 413.2 M-1.

Example 94 and 95

Preparation of enantiomers of 3'-[4-(2-hydroxy-3,3-dimethylbutoxy)-3-n-propylphenyl]-3'-[5-carboxy-thiophen-2-yl]pentane

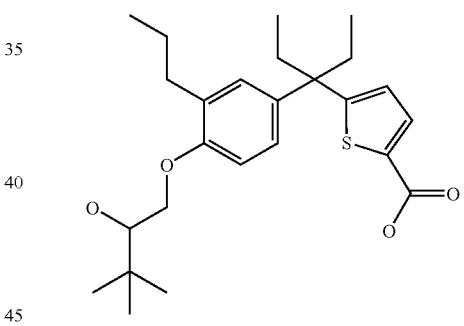

A mixture of racemic 3'-[4-(2-hydroxy-3,3-dimethylbutoxy)-3-n-propylphenyl]-3'-[5-carboxy-thiophen-2-yl]pentane (200 mg) is chromatographed on a ChiralPak AD column with IPA/heptane. Enantiomer 1 is further chromatographed on 4 g of Silica Gel from 0% EtOAc/Hex to 50% EtOAc/Hex over 38 min at 12 ml/min to give pure enantiomer 1 (66 mg), Example 94. Enantiomer 2 from ChiralPak is further chromatographed on 4 g of Silica Gel from 0% EtOAc/Hex to 50% EtOAc/Hex over 38 min at 12 ml/min. to give pure enantiomer 2 (66 mg), Example 95.

Enantiomer 1, Example 94

HPLC: ChiralPak AD (4.6×250 mm); 15% IPA/85% heptane; 1 ml/m (flow rate);

rt=6.22 m; 225 nmn.

Enantiomer 2, Example 95

HPLC: ChiralPak AD (4.6×250 mm); 15% IPA/85% heptane; 1 ml/m (flow rate); rt=9.0 m; 225 nm.

Example 96

Preparation of 3'-[4-(2-hydroxy-3,3-dimethylbutoxy)-3-i-propylphenyl]-3'-[5-carboxy-thiophen-2-yl]pentane

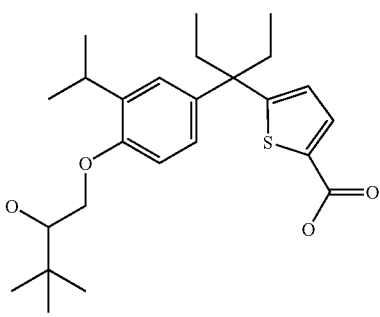

A. 3'-(4-hydroxy-3-i-propylphenyl)-3'-[5-methoxycarbonyl-thiophen-2-yl]pentane

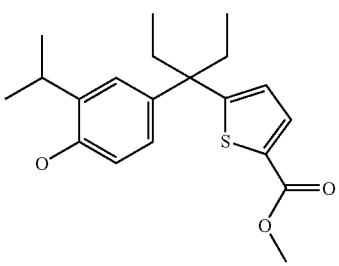

Using a procedure analogous to Example 93A, o-isopropylphenol (1.09 g, 8 mol) and methyl, 5-(E/Z-2-penten-3-yl) thiophene-2-carboxylate (0.21 g, 1.0 mol) give the title compound as an oil (0.28 g, 81%).

NMR (CDCl3): 7.62 (d, 1H, J=4.0 Hz); 7.05 (s, 1H); 6.90 (d, 1H, J=8.4 Hz); 6.78 (d, 1H, J=4.0 Hz); 6.63 (d, 1H, J=8.8 Hz); 4.58 (s, 1H); 3.83 (s, 3H); 3.15 (m, 1H); 2.11 (q, 4H, J=7.2 Hz); 1.21 (d, 6H, J=6.1 Hz); 0.71 (t, 6H, J=7.4 Hz).
LC/MS: 347.2 M+1.

B. 3'-[4-(2-Oxo-3,3-dimethylbutoxy)-3-i-propylphenyl]-3'-[5-methoxycarbonyl-thiophen-2-yl]pentane

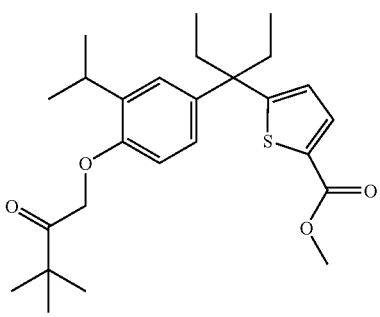

Using a procedure analogous to Example 91B, 3'-(4-hydroxy-3-i-propylphenyl)-3'-[5-methoxycarbonyl-thiophen-2-yl]pentane (0.28 g, 0.81 mmol) gives the title compound as an oil (0.13 g, 56%).

NMR (CDCl3): 7.61 (d, 1H, J=4.4 Hz); 7.09 (s, 1H); 6.94 (d, 1H, J=8.4 Hz); 6.77 (d, 1H, J=4.4 Hz); 6.53 (d, 1H, J=8.4 Hz); 4.84 (s, 2H); 3.83, (s, 3H); 3.38 (m, 2H); 2.11 (q, 4H, J=7.2 Hz); 1.26 (s, 9H); 1.19 (d, 6H, J=7.2 Hz); 0.70 (t, 6H, 7.2 Hz).
FAB-MS: 444.3 molecular ion.
LC/MS: 445.2 M+1 and 462.2 M+NH4.

C. 3'-[4-(2-Hydroxy-3,3-dimetliylbutoxy)-3-i-propylphenyl]-3'-[5-methoxycarbonyl-thiophen-2-yl]pentane

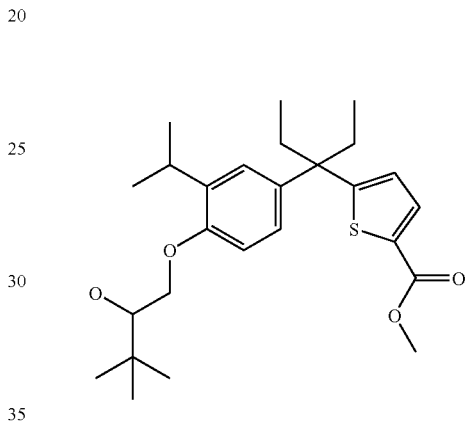

Using a procedure analogous to Example 2, 3'-[4-(2-Oxo-3,3-dimethylbutoxy)-3-i-propylphenyl]-3'-[5-methoxycarbonyl-thiophen-2-yl]pentane gives the title compound as an oil (0.09 g, 80%).

NMR(CDCl3): 7.62 (d, 1H, J=3.6 Hz); 7.08 (s, 1H); 6.99 (1H, d, J=8.8 Hz); 6.78 (d, 1H, 3.6 Hz); 6.73 (d, 1H, 8.8 Hz); 4.08 (1H, d, J=8.8); 3.85 (t, 1H, J=8.8); 3.83 (s, 3H); 3.71 (d, 1H, J=8.8 Hz); 3.28 (m, 1H); 2.12 (q, 4H, J=7.2 Hz); 1.17 (d, 6H, J=6.8 Hz); 1.02 (s, 9H); 0.71 (t, 6H, J=7.2 Hz).
LC/MS: 447.2 M+1.

D. 3'-[4-(2-Hydroxy-3,3-dimethylbutoxy)-3-i-propylphenyl]-3'-[5-carboxyl-thiophen-2-yl]pentane Using a procedure analogous to Example 3, 3'-[4-(2-hydroxy-3,3-dimethylbutoxy)-3-i-propylphenyl]-3'-[5-methoxycarbonyl-thiophen-2-yl]pentane (0.93 g, 0.21 mmol) and 5N NaOH aq (1 mL, 5 mmol) give the title compound as an oil (66 mg, 73%).

NMR(CDCl3): 7.69 (d, 1H, J=3.6 Hz); 7.08 (s, 1H); 6.98 (d, 1H, J=8.1 Hz); 6.79 (d, 1H, J=3.6 Hz); 6.74 (d, 1H, J=8.1 Hz); 4.08 (d, 1H, J=7.4); 3.85 (t, 1H, J=7.4 Hz); 3.72 (d, 1H, J=7.4 Hz); 3.25 (m, 1H); 2.13 (q, 4H, J=6.8 Hz); 1.17 (d, 6H, J=6.0 Hz); 1.02 (s, 9H); 0.72 (t, 6H, J=6.8 Hz).
LC/MS: 450.2 M+NH4.

Example 97 and Example 98

Preparation of enantiomers of 3'-[4-(2-hydroxy-3,3-dimethylbutoxy)-3-i-propylphenyl]3'-[5-carboxy-thiophen-2-yl]pentane

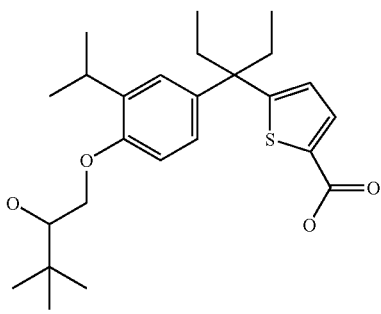

A mixture of racemic 3'-[4-(2-hydroxy-3,3-dimethylbutoxy)-3-i-propylphenyl]-3'-[5-carboxy-thiophen-2-yl]pentane (22 mg) is chromatographed on a ChiralPak AD column with IPA/heptane) to give enantiomer 1 (8 mg), Example 97 and enantiomer 2 (7 mg), Example 98.

Enantiomer 1, Example 97
HPLC: ChiralPak AD (4.6×250 mm); 15% IPA/85% heptane; 1 ml/m (flow rate); rt Enantiomer 2, Example 98
HPLC: ChiralPak AD (4.6×250 mm); 15% IPA/85% heptane; 1 ml/m (flow rate); rt=6.53 m; 225 nm.

Example 99

Preparation of 3'-[4-(2-hydroxy-3,3-dimethylbutoxy)-3-ethylphenyl]-3'-[5-carboxy-thiophen-2-yl]pentane

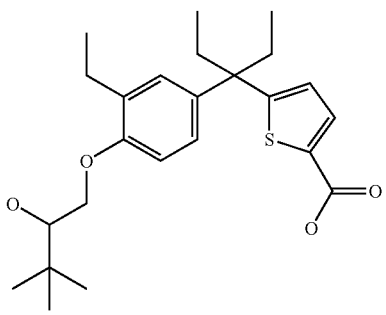

A. 3'-(4-hydroxy-3-ethylphenyl)-3'-[5-methoxycarbonyl-thiophen-2-yl]pentane

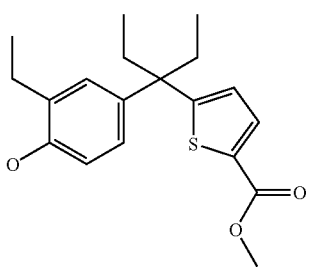

Using a procedure analogous to Example 93A, o-ethylphenol (0.98 g, 8.0 mol) and methyl, 5-(E/Z-2-penten-3-yl)thiophene-2-carboxylate (0.21 g, 1.0 mol) give the title compound as an oil (0.26 g, 78%).

NMR (CDC13): 7.62 (d, 1H, J=4.0 Hz); 6.98 (s, 1H); 6.94 (d, 1H, J=7.2 Hz); 6.78 (d, 1H, J=4.0 Hz); 6.66 (d, 1H, J=7.2 Hz); 4.60 (s, 1H); 3.83 (s, 3H); 2.59 (q, 2H, J=7.7 Hz); 2.11 (q, 4H, J=7.2 Hz); 1.19 (t, 3H, J=7.6 Hz); 0.71 (t, 6H, J=7.2 Hz). FAB/MS: 333 M+1.

B. 3'-[4-(2-Oxo-3,3-dimethylbutoxy)-3-ethylphenyl]-3'-[5-methoxycarbonyl-thiophen-2-yl]pentane

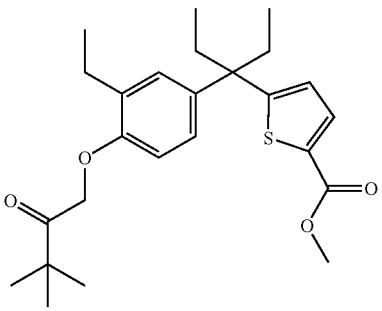

Using a procedure analogous to Example 91B, 3'-(4-hydroxy-3-ethylphenyl)-3'-[5-methoxycarbonyl-thiophen-2-yl]pentane (0.26 g, 0.78 mmol) gives the title compound as an oil (0.24 g, 71%).

NMR (CDC13): 7.61 (d, 1H, J=3.6 Hz); 7.02 (s, 1H); 6.96 (d, 1H, J=7.3 Hz); 6.77 (d, 1H, J=3.6 Hz); 6.52 (d, 1H, J=7.3 Hz); 4.83 (s, 2H); 3.83, (s, 3H); 2.66 (q, 2H, J=7.3 Hz); 2.12 (q, 4H, J=7.6 Hz); 1.21 (s, 9H); 1.18 (t, 3H, 7.3 Hz); 0.70 (t, 6H, 7.6 Hz).
LC/MS:431.2M+1.

C. 3'-[4-(2-Hydroxy-3,3-dimethylbutoxy)-3-ethylphenyl]-3'-[5-methoxycarbonyl-thiophen-2-yl]pentane

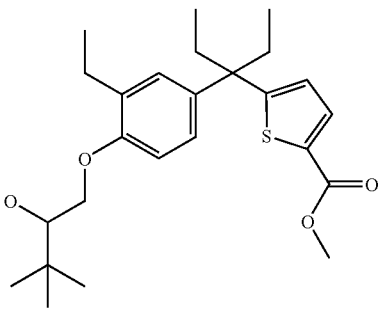

Using a procedure analogous to Example 2, 3'-[4-(2-Oxo-3,3-dimethylbutoxy)-3-ethylphenyl]-3'-[5-methoxycarbonyl-thiophen-2-yl]pentane (0.22 g, 0.5 mmol) gives the title compound as an oil (0.16 g, 75%).

NMR(CDC13): 7.62 (d, 1H, J=3.2 Hz); 7.01 (1H, d, J=7.4 Hz); 7.00 (s, 1H); 6.78 (d, 1H, 3.2 Hz); 6.73 (d, 1H, 7.4 Hz); 4.08 (1H, d, J=8.1); 3.85 (t, 1H, J=8.1); 3.83 (s, 3H); 3.70 (d, 1H, J=8.1 Hz); 2.60 (t, 2H, 7.6 Hz); 2.40 (s, 1H); 2.12 (q, 4H, J=7.2 Hz); 1.49 (t, 3H, J=7.2 Hz); 1.02 (s, 9H); 0.71 (t, 6H, J=7.2 Hz).

LC/MS showed a 433.2 M+1.

D. 3'-[4-(2-Hydroxy-3,3-dimethylbutoxy)-3-ethylphenyl]-3'-[5-carboxyl-thiophen-2-yl]pentane Using a procedure analogous to Example 3, 3'-[4-(2-hydroxy-3,3-dimethylbutoxy)-3-ethylphenyl]-3'-[5-methoxycarbonyl-tliiophen-2-yl]pentane, methanol, and 5N NaOH at 50° C. for 16 h to give the title compound (0.15 g, 94%).

NMR(DMS0-D6): 7.53 (d, 1H, J=3.6 Hz); 7.01 (d, 1H, J=8.8 Hz); 7.00 (s, 1H); 6.90 (d, 1H, J=3.6 Hz); 6.85 (d, 1H, J=8.8 Hz); 4.04 (d, 1H, J=9.4); 3.86 (t, 1H, J=9.4 Hz); 3.44 (d, 1H, J=9.4 Hz); 2.56 (m, 2H); 2.09 (m, 4H); 1.08 (t, 3H, J=8.0 Hz); 0.93 (s, 9H); 0.65 (t, 6H, J=7.4 Hz).

LC/MS: 417.2 M-1.

Example 100 and Example 101

Preparation of enantiomers of 3'-[4-(2-hydroxy-3,3-dimethylbutoxy)-3-ethylphenyl]-3'-[5-carboxy-thiophen-2-yl]pentane

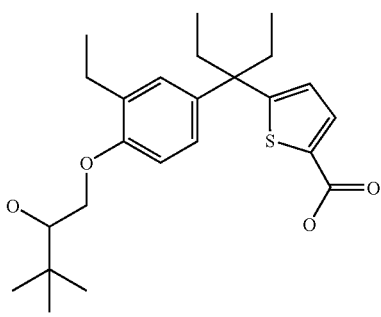

A mixture of racemic 3'-[4-(2-hydroxy-3,3-dimethylbutoxy)-3-ethylphenyl]-3'-[5-carboxy-thiophen-2-yl]pentane (140 mg) is chromatographed on a ChiralPak AD column with IPA/heptane to give enantiomer 1 (59 mg), Example 100 and enantiomer 2 (51 mg), Example 101.

Enantiomer 1, Example 100

HPLC: ChiralPak AD (4.6×250 mm); 15% IPA/85% heptane; 1 ml/m (flow rate);

rt=4.42 m; 225 nm.

Enantiomer 2, Example 101

HPLC: ChiralPak AD (4.6×250 mm); 15% IPA/85% heptane; 1 ml/m (flow rate);

rt=6.61 m; 225 nm.

Example 103

Preparation of 3'-[4-(2-hydroxy-2,3,3-trimethylbutoxy)-3-methylphenyl]-3'-[5-carboxy-thiophen-2-yl]pentane

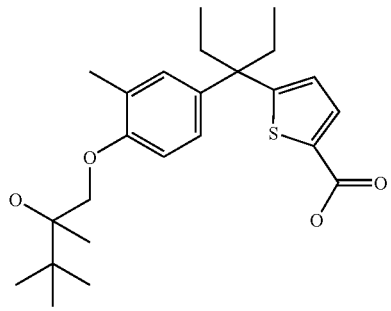

A. 3'-[4-Hydroxy-3-methylphenyl]pentan-3-ol.

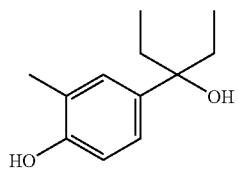

To a mixture of methyl, 4-hydroxy-3-methylbenzoate (21.8 g (0.13 mol) and 200 ml of THF is added 1 M ethylmagnesium bromide/THF (432 mL (0.43 mol) under nitrogen. The mixture is stirred for 60 h and quenched with satd NaHCO3. The mixture is triturated five times with ether and the combined organic layers is washed with satd NaHCO3 and brine. The organic layer is Na2SO4 dried, filtered, and concentrated to give 27 g (99%) of the title compound.

NMR (CDC13): 7.12 (s, 1H); 7.03 (d, 1H, 8.0 Hz); 6.72 (d, 1H, J=8.0 Hz); 4.69 (s, 1H); 2.26 (s, 3H); 1.80 (m, 4H); 0.79 (t, 6H, 7.4 Hz).

ES/MS: 193 (M-1).

B. 3'-[4-Hydroxy-3-methylphenyl]-3'-(thiophen-2-yl)pentane

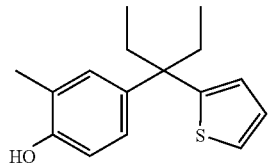

To a mixture of thiophene (6 mL) and 3'-[4-hydroxy-3-methylphenyl]pentan-3-ol (0.92 g, 5 mmol) is added boron trifluoride etherate (100 ul, 0.8 mmol). The mixture is stirred for 96 h and partitioned between diethyl ether and satd NaHCO₃. The organic layer is washed with satd NaHCO₃, brine, Na₂SO₄ dried, and concentrated. The residue is chromatographed (12 g of SiO₂, Hex to 8% EtOAc/Hex) to give the title compound (0.53 g, 41%).

[ES/MS 259.1 (M-1)].

C. 3'-[4-(2-Oxo-3,3-dimethylbutoxy)-3-methylphenyl]-3'-(thiophen-2-yl)pentane

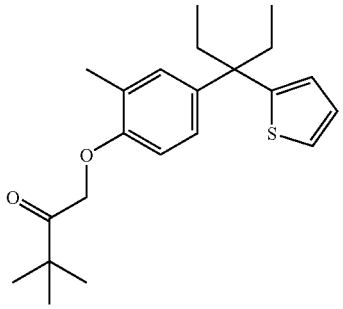

Using a procedure analogous to Example 91B, 3'-[4-hydroxy-3-methylphenyl]-3'-(thiophen-2-yl)pentane (0.53 g, 2.2 mmol) gives the title compound as an oil (0.47 g, 64%).

NMR (CDC13): 7.14 (d, 1H, J=6.3 Hz); 7.03 (s, 1H); 6.98 (d, 1H, J=9.0 Hz); 6.90 (m, 1H); 6.79 (d, 1H, J=6.3 Hz), 6.52 (d, 1H, J=9.0 Hz), 4.83 (s, 2H); 2.26 (s, 3H); 2.09 (m, 4H); 1.24 (s, 9H), 0.68 (t, 6H, 7.0 Hz).

ES/MS: 359.2 (M+1) 376.2 (M+NH4).

D. 3'-[4-(2-Hydroxy-2,3,3-trimethylbutoxy)-3-methylphenyl]-3'-(thiophen-2-yl)pentane

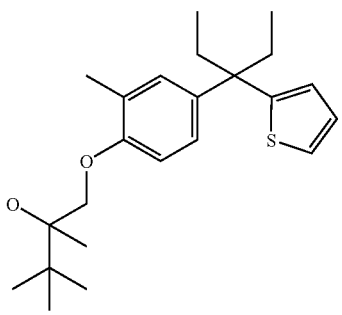

To a mixture of 3'-[4-(2-oxo-3,3-dimethylbutoxy)-3-methylphenyl]-3'-(thiophen-2-yl)pentane (0.47 g (1.3 mmol) and diethyl ether (15 mL) is added 3 M methylmagnesium iodide/THF (1.3 ml, 3.9 mmol). After stirring for 2 h, the mixture is quenched with satd NaHCO$_3$ and triturated five times with diethyl ether. The combined organic layers is washed with water, brine, Na$_2$SO$_4$ dried, and concentrated to give the title compound (0.6 g, 99%).

NMR (CDCl3): 7.13 (d, 1H, J=5.0 Hz); 7.02 (s, 1H); 7.03 (d, 1H, J=8.4 Hz); 6.90 (m, 1H); 6.80 (d, 1H, J=5.0 Hz), 6.70 (d, 1H, J=8.4 Hz), 4.00 (d, 1H, J=8.8 Hz); 3.83 (d, 1H, J=8.8 Hz); 2.27 (s, 1H); 2.21 (s, 3H); 2.11 (m, 4H); 1.32 (s, 3H); 1.05 (s, 9H), 0.70 (t, 6H, 7.2 Hz).

ES-MS: 375.2 (M+1) 357.2 (M−H2O).

E. 3'-[4-(2-hydroxy-2,3,3-trimethylbutoxy)-3-methylphenyl]-3'-[5-carboxy-thiophen-2-yl]pentane

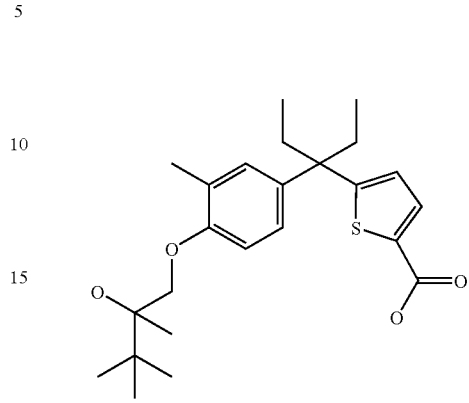

To a 0° C. mixture of 3'-[4-(2-Hydroxy-2,3,3-trimethylbutoxy)-3-methylphenyl]-3'-(thiophen-2-yl)pentane (0.6 g, 1.3 mmol) and cycloHex (20 ml) and ether (2 ml) is added 1.4 M sec-butyl lithium/cycloHex (2.85 ml, 3.2 mmol). The mixture is allowed to warm to RT and excess CO$_2$ gas is bubbled in. After two h, the mixture is partitioned between satd NaHCO$_3$ and diethyl ether. The aq phase is acidified with conc. perchloric acid and extracted into diethyl ether. The organic phase is washed with water, brine, Na$_2$SO$_4$ dried and concentrated. The residue is chromatographed (2% EtOAc/Hex to 50% EtOAc/Hex) to give of the title compound (0.3 g (44%).

NMR (CDC$_3$): 7.69 (d, 1H, J=3.6 Hz); 6.99 (s, 1H); 7.03 (d, 1H, J=8.4 Hz); 6.80 (d, 1H, J=3.6 Hz), 6.72 (d, 1H, J=8.4 Hz), 4.00 (d, 1H, J=8.8 Hz); 3.83 (d, 1H, J=8.8 Hz); 2.22 (s, 3H); 2.13 (q, 4H, J=7.2 Hz); 1.33 (s, 3H); 1.04 (s, 9H), 0.72 (t, 6H, 7.2 Hz).

ES-MS: 417.3 (M−1) 436.3 (M+NH4).

Example 104 and Example 105

Preparation of enantiomers of 3'-[4-(2-hydroxy-2,3,3-trimethylbutoxy)-3-methylphenyl]-3'-[5-carboxy-thiophen-2-yl]pentane A mixture of racemic 3'-[4-(2-hydroxy-2,3,3-trimethylbutoxy)-3-methylphenyl]-3'-[5-carboxy-thiophen-2-yl]pentane (~290 mg) is chromatographed on a ChiralPak AD column with IPA/heptane to give enantiomer 1 (125 mg, 43), Example 104 and enantiomer 2 (140 mg, 48%), Example 105.

Enantiomer 1, Example 104

HPLC: ChiralPak AD (4.6×250 mm); 20% IPA/80% heptane; 1 ml/m (flow rate);

rt=6.09 m; 225 nm.

Enantiomer 2, Example 105

HPLC: ChiralPak AD (4.6×250 mm); 20% IPA/80% heptane; 1 ml/m (flow rate);

rt=8.00 m; 225 nm.

Example 106

Preparation of enantiomer 1 of 3'-[4-(2-hydroxy-2,3, 3-trimethylbutoxy)-3-methylphenyl]-3'-[5-(carboxymethylamino)carbonyl-thiophen-2-yl]pentane

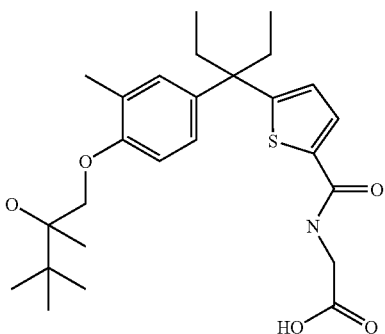

A. of 3'-[4-(2-hydroxy-2,3,3-trimethylbutoxy)-3-methylphenyl]-3'-[5-(methylcarbonyl-methylamino)carbonyl-thiophen-2-yl]pentane To a mixture of enantiomer 1 of 3'-[4-(2-hydroxy-2,3,3-trimethylbutoxy)-3-methylphenyl]-3'-[5-carboxy-thiophen-2-yl]pentane and DMSO (1 ml) is added EDCl (55 mg, 0.29 mmol), 0.5 M HOAT (523 uL, 0.26 mmol), methyl, aminoacetic acid hydrochloride (33 mg, 0.26 mmol), and triethylamine (136 uL, 1 mmol). The mixture is stirred for 72 h at RT, partitioned between diethyl ether and satd NaHCO3. The organic layer is washed with water, 2M HCl, water, satd NaHCO$_3$, then Na2SO$_4$ dried, and concentrated. The residue is chromatographed (Hex to 30% EtOAc/Hex) to give the title compound (60 mg, 51%).

NMR (CDC$_3$): 7.40 (d, 1H, J=3.6 Hz); 7.04 (d, 1H, J=8.8 Hz); 6.98 (s, 1H); 6.77 (d, 1H, J=3.6 Hz); 6.71 (d, 1H, J=8.8 Hz), 4.00 (d, 1H, J=8.8 Hz); 6.53 (m, 1H); 4.18 (d, 1H, J=4.8 Hz); 4.00 (d, 1H, J=8.8 Hz); 3.84 (d, 1H, J=8.8 Hz); 3.78 (s, 3H); 2.21 (s, 3H); 2.11 (q, 4H, J=7.2 Hz); 1.33 (s, 3H); 1.04 (s, 9H), 0.70 (t, 6H, 7.2 Hz).

ES-MS: 490.4 (M+1) 488.4 (M−1).

B. 3'-[4-(2-hydroxy-2,3,3-trimethylbutoxy)-3-methylphenyl]-3'-[5-(carboxymethyl-amino)carbonyl-thiophen-2-yl]pentane, enantiomer 1

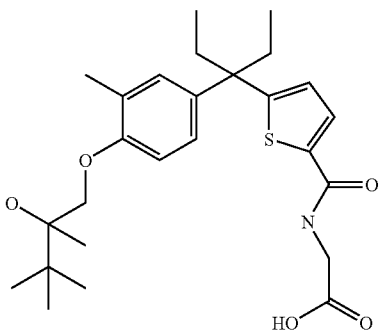

To a mixture of enantiomer 1 of 3'-[4-(2-hydroxy-2,3,3-trimethylbutoxy)-3-methylphenyl]-3'-[5-(methylcarbonyl-methylamino)carbonyl-thiophen-2-yl]pentane (60 mg, 0.12 mmol) and 50% methanol/water (0.5 ml) is added lithium hydroxide (6 mg, 0.24 mmol). The mixture is heated to 40° C. for one h and concentrated. The residue is added ice and acidified with conc. HCl (pH~1). The suspension is filtered, washed with water, and air dried to give the title compound as a solid (50 mg, 86%).

NMR (CDCl3): 7.45 (d, 1H, J=4.0 Hz); 7.04 (d, 1H, J=8.4 Hz); 6.97 (s, 1H); 6.79 (d, 1H, J=4.0 Hz), 6.70 (d, 1H, J=8.4 Hz), 4.00 (d, 1H, J3=8.8 Hz); 6.59 (m, 1H); 4.17 (s, 1H); 4.00 (d, 1H, J=8.8 Hz); 3.83 (d, 1H, J=8.8 Hz); 3.02 (m, 1H); 2.20 (s, 3H); 2.11 (q, 4H, J=7.2 Hz); 1.33 (s, 3H); 1.01 (s, 9H), 0.70 (t, 6H, 7.2 Hz).

ES/MS: 476.3 (M+1) 474.3 (M−1).

Example 107

Preparation of 3'-[4-(2-hydroxy-2,3,3-trimethylbutoxy)-3-ethylphenyl]-3'-[5-carboxy-thiophen-2-yl]pentane

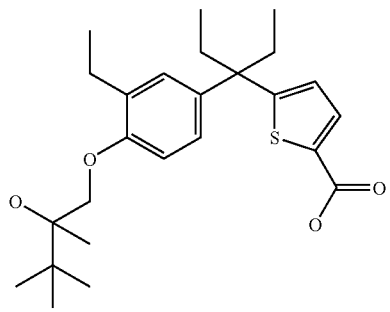

A. 3'-[4-Hydroxy-3-ethylphenyl]pentan-3-ol

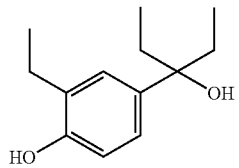

Using a procedure analogous to Example 103A, methyl, 4-hydroxy-3-ethylbenzoate (7.7 g, 43 mmol) gives the title compound as an oil (9.2 g, 99%).

NMR (CDC13): 7.13 (s, 1H); 7.04 (d, 1H, 8.0 Hz); 6.71 (d, 1H, J=8.0 Hz); 4.65 (s, 1H); 2.64 (q, 2H. J=7.2 Hz); 1.81 (m, 4H); 1.23 (m, 3H); 0.77 (t, 6H, 7.2 Hz).

ES/MS: 207.1 (M−1).

B. 3'-[4-(2-oxo-3,3-dimethylbutoxy)-3-ethylphenyl]pentan-3-ol

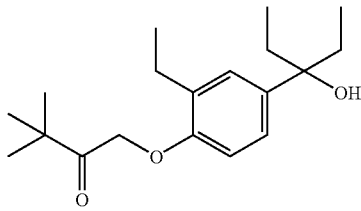

Using a procedure analogous to Example 91B, 3'-[4-hydroxy-3-ethylphenyl]pentan-3-ol (9.2 g, 43 mmol) gives the title compound (11.9 g, 91%).

NMR (CDCl3): 7.14 (s, 1H); 7.10 (d, 1H, J=8.0 Hz); 6.58 (d, 1H, 3 =8.0 Hz); 4.85 (s, 2H); 2.71 (q, 2H. J=7.6 Hz); 1.80 (m, 4H); 1.25 (s, 9H); 1.23 (t, 3H, J=7.6 Hz); 0.76 (t, 6H, 7.2 Hz).

ES/MS: 289.1 (M+H–H2O).

C. 3'-[4-(2-Oxo-3,3-dimethylbutoxy)-3-ethylphenyl]-3'-(thiophen-2-yl)pentane

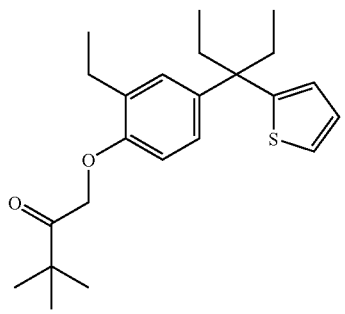

Using a procedure analogous to Example 103B, 3'-[4-(2-oxo-3,3-dimethylbutoxy)-3-ethylphenyl]pentan-3-ol (10.9 g, 36 mmol) gives the title compound (6.1 g, 46%).

NMR (CDC13): 7.14 (d, 1H, J=1.2 Hz); 7.06 (s, 1H); 6.96 (d, 1H, J=8.4 Hz); 6.90 (t, 1H, J=5.2 Hz); 6.80 (d, 1H, J=1.2 Hz); 6.52 (d, 1H, J=8.4 Hz); 4.83 (s, 2H); 2.67 (q, 2H, J=7.2 Hz); 2.10 (q, 4H, J=7.4); 1.25 (s, 9H); 1.20 (t, 3H, J=7.2 Hz); 0.70 (t, 6H, 7.4 Hz).

ES/MS: 373.2 (M+1) 390.2 (M+NH4).

D. 3'-[4-(2-Hydroxy-2,3,3-trimethylbutoxy)-3-ethylphenyl]-3'-(thiophen-2-yl)pentane

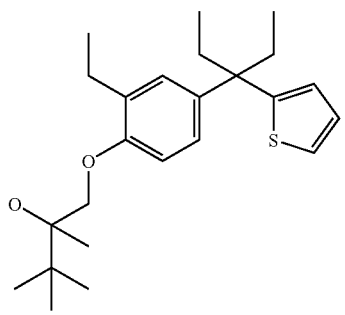

Using a procedure analogous to Example 103D, 3'-[4-(2-Oxo-3,3-dimethylbutoxy)-3-ethylphenyl]-3'-(thiophen-2-yl)pentane (3.7 g, 10 mmol) gives the title compound after silica gel chromatography (1.8 g, 46%).

NMR (CDC$_3$): 7.15 (d, 1H, J=6.3 Hz); 7.04 (s, 1H); 7.03 (d, 1H, underlying); 6.90 (t, 1H, J=5.2 Hz); 6.81 (m, 1H); 6.53 (d, 1H, J=8.4 Hz); 4.00 (d, 1H, J=8.4 Hz); 3.84 (d, 1H, J=8.4 Hz); 2.62 (q, 2H, J=7.6 Hz); 2.11 (q, 4H, J=7.6); 1.33 (s, 3H); 1.16 (t, 3H, J=7.6 Hz); 1.04 (s, 9H); 0.71 (t, 6H, 7.6 Hz).

ES/MS: 371.2 (M–H2O+1) 389.2 (M+1).

E. 3'-[4-(2-Hydroxy-2,3,3-trimethylbutoxy)-3-ethylphenyl]-3'-[5-carboxy-thiophen-2-yl]pentane

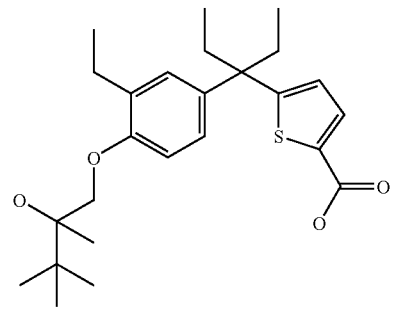

Using a procedure analogous to Example 103E, 3'-[4-(2-Hydroxy-2,3,3-trimethylbutoxy)-3-ethylphenyl]-3'-(thiophen-2-yl)pentane (1.45 g, 3.7 mmol) gives the title compound (0.75 g, 46%).

NMR (CDC13): 7.70 (d, 1H, J=3.6 Hz); 7.02 (s, 1H); 7.03 (d, 1H, underlying); 6.80 (d, 1H, J=3.6 Hz); 6.73 (d, 1H, J=8.4 Hz); 4.00 (d, 1H, J=8.8 Hz); 3.85 (d, 1H, J=8.8 Hz); 2.62 (q, 2H, J=7.6 Hz); 2.14 (q, 4H, J=7.2); 1.33 (s, 3H); 1.17 (t, 3H, J=7.6 Hz); 1.04 (s, 9H); 0.72 (t, 6H, 7.2 Hz).

ES/MS: 431.5 (M–1).

Example 108 and Example 109

Preparation of enantiomers of 3'-[4-(2-hydroxy-2,3,3-trimethylbutoxy)-3-ethylphenyl]-3'-[5-carboxy-thiophen-2-yl]pentane enantiomer 1 enantiomer 2

A mixture of racemic 3'-[4-(2-hydroxy-2,3,3-trimethylbutoxy)-3-ethylphenyl]-3'-[5-carboxy-thiophen-2-yl]pentane (0.93 g) is chromatographed (ChiralPak AD column;

5% ethyl alcohol/95% Hept to give enantiomer 1 (453 mg), Example 108 and enantiomer 2 (438 mg), Example 109.

Enantiomer 1, Example 108

HPLC: ChiralPak AD (4.6×250 mm); 5% IPA/95% heptane; 1 ml/m (flow rate); rt=10.2 m; 225 nm.

Enantiomer 2, Example 109

HPLC: ChiralPak AD (4.6×250 mm); 5% IPA/95% heptane; 1 ml/m (flow rate); rt=13.0 m; 225 nm.

Example 110

Preparation of enantiomer 1 of d-3'-[4-(2-hydroxy-2,3,3-trimethylbutoxy)-3-ethylphenyl]-3'-[5-(carboxy-1-ethylamino)carbonyl-thiophen-2-yl]pentane

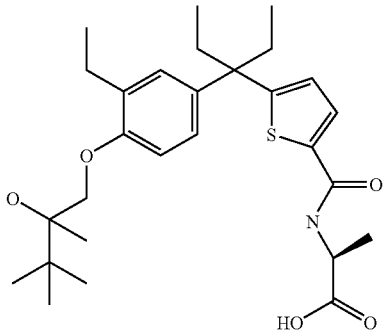

A. Enantiomer 1 of d-3'-[4-(2-hydroxy-2,3,3-trimethylbutoxy)-3-ethylphenyl]-3'-[5-(methoxycarbonyl-1-ethylamino)carbonyl-thiophen-2-yl]pentane

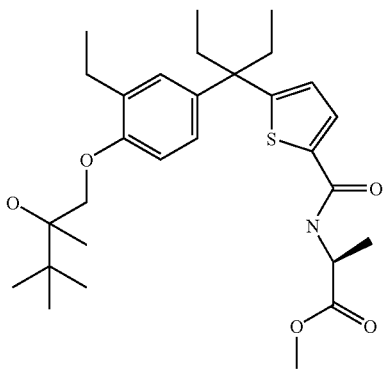

Using a procedure analogous to Example 106A, enantiomer 1 of 3'-[4-(2-hydroxy-2,3,3-trimethylbutoxy)-3-ethylphenyl]-3'-[5-carboxy-thiophen-2-yl]pentane (310 mg, 0.71 mmol) and d-alanine methylester HCl give the title compound (173 mg, 47%). NMR (CDC13): 7.39 (d, 1H, J=4.0 Hz); 7.01 (s, 1H); 7.02 (d, 1H, underlying); 6.78 (d, 1H, J=4.0 Hz); 6.64 (d, 1H, J=8.0 Hz); 6.38 (d, 1H, J=6.5 Hz); 4.74 (m, 1H); 4.00 (d, 1H, J=7.2 Hz); 3.85 (d, 1H, J=7.2 Hz); 3.77 (s, 3H); 2.62 (q, 2H, J=7.6 Hz); 2.22 (s, 1H); 2.11 (q, 4H, J=7.6); 1.48 (d, 3H, J=7.2 Hz); 1.33 (s, 3H); 1.17 (t, 3H, J=7.6 Hz); 1.04 (s, 9H); 0.71 (t, 6H, 7.2 Hz).

B. Enantiomer 1 of d-3'-[4-(2-hydroxy-2,3,3-trimethylbutoxy)-3-ethylphenyl]-3'-[5-(carboxy-1-ethylamino)carbonyl-thiophen-2-yl]pentane

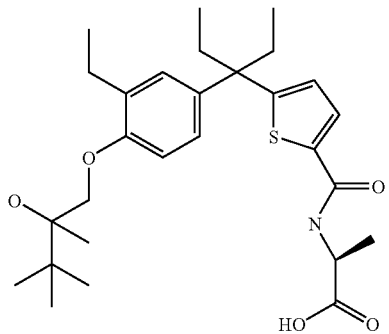

Using a procedure analogous to Example 106B, enantiomer 1 of 3'-[4-(2-hydroxy-2,3,3-trimethylbutoxy)-3-ethylphenyl]-3'-[5-(methoxycarbonyl-1-ethylamino)carbonyl-thiophen-2-yl]pentane (173 mg, 0.33 mmol) gives the title compound as a solid (147 mg, 87%).

NMR (CDC$_3$): 7.43 (d, 1H, J=3.6 Hz); 7.01 (s, 1H); 7.02 (d, 1H, underlying); 6.79 (d, 1H, J=3.6 Hz); 6.73 (d, 1H, J=8.0 Hz); 6.35 (d, 1H, J=8.0 Hz); 4.70 (m, 1H); 4.00 (d, 1H, J=8.8 Hz); 3.84 (d, 1H, J=8.8 Hz); 2.61 (q, 2H, J=7.6 Hz); 2.10 (q, 4H, J=7.2); 1.52 (d, 3H, J=7.6 Hz); 1.32 (s, 3H); 1.15 (t, 3H, J=7.6 Hz); 1.03 (s, 9H); 0.70 (t, 6H, 7.2 Hz).

ES/MS: 504.2 (M+1) 502.3 (M−1).

Example 111

Preparation of 3'-[4-(2-hydroxy-2,3,3-trimethylbutoxy)-3-n-propylphenyl]-3'-[5-carboxy-thiophen-2-yl]pentane

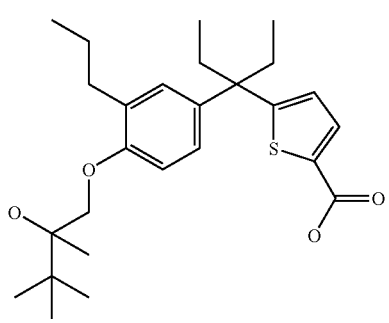

A. 3'-[4-Hydroxy-3-n-propylphenyl]pentan-3-ol.

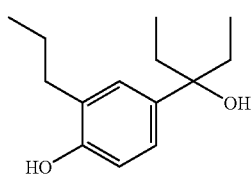

Using a procedure analogous to Example 103A, ethyl, 4-hydroxy-3-n-propylbenzoate (5.0, 24 mmol) gives the title compound as an oil (5.7 g, 99%).

NMR (CDC13): 7.09 (s, 1H); 7.04 (d, 1H, 8.4 Hz); 6.71 (d, 1H, J=8.4 Hz); 4.62 (s, 1H); 3.75 (m, 1H); 2.59 (t, 2H. J=7.4 Hz); 1.80 (m, 4H); 1.64 (m, 2H); 0.94 (t, 3H, J=7.4 Hz); 0.76 (t, 6H, 7.6 Hz).

ES/MS: 205.1 (M+H−H2O).

B. 3'-[4-(2-oxo-3,3-dimethylbutoxy)-3-n-propylphenyl]pentan-3-ol

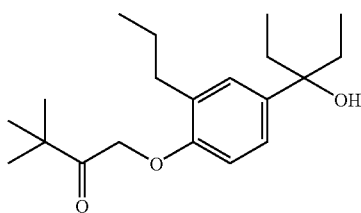

Using a procedure analogous to Example 91B, 3'-[4-hydroxy-3-n-propylphenyl]pentan-3-ol (5.7 g, 24 mmol) gives the title compound (7.1 g, 93%). NMR (CDC13): 7.11 (s, 1H); 7.09 (d, 1H, J=8.0 Hz); 6.57 (d, 1H, J=8.0 Hz); 4.84 (s, 2H); 2.66 (t, 2H. J=7.6 Hz); 1.80 (m, 4H); 1.65 (m, 2H); 1.26 (s, 9H); 0.95 (t, 3H, J=7.2 Hz); 0.76 (t, 6H, 7.4 Hz).

ES/MS: 303.1 (M−H2O+1).

C. 3'-[4-(2-Oxo-3,3-dimetliylbutoxy)-3-n-propylphenyl]-3'-(thiophen-2-yl)pentane

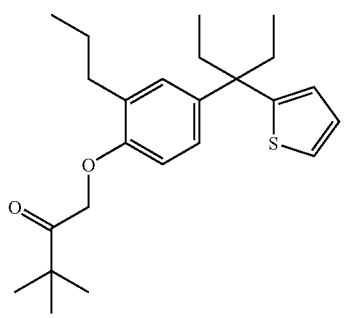

Using a procedure analogous to Example 103B, 3'-[4-(2-oxo-3,3-dimethylbutoxy)-3-n-propylphenyl]pentan-3-ol (7.1 g, 22 mmol) gives the title compound after silica gel chromatography (4.0 g, 47%).

NMR (CDC13): 7.12 (d, 1H, J=1.2 Hz); 7.03 (s, 1H); 6.97 (d, 1H, J=8.0 Hz); 6.90 (t, 1H, J=5.2 Hz); 6.80 (d, 1H, J=1.2 Hz); 6.51 (d, 1H, J=8.0 Hz); 4.82 (s, 2H); 2.62 (t, 2H, J=7.8 Hz); 2.09 (q, 4H, J=7.6); 1.59 (m, 2H); 1.25 (s, 9H); 0.90 (m, 3H); 0.71 (t, 6H, 7.6 Hz).

ES/MS: 387.2 (M+1) 404.2 (M+NH4).

D. 3'-[4-(2-Hydroxy-2,3,3-trimethylbutoxy)-3-n-propylphenyl]-3'-(thiophen-2-yl)pentane

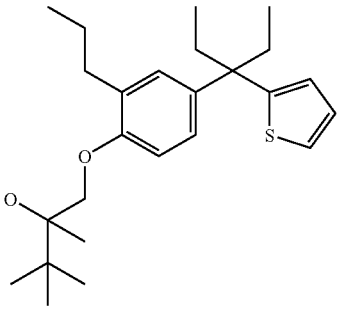

Using a procedure analogous to Example 103D, 3'-[4-(2-oxo-3,3-dimethylbutoxy)-3-n-propylphenyl]-3'-(thiophen-2-yl)pentane (1.3 g, 3.4 mmol) gives the title compound (1.2 g, 86%).

NMR (CDC13): 7.13 (d, 1H, J=6.0 Hz); 7.03 (s, 1H); 7.04 (d, 1H, underlying); 6.90 (t, 1H, J=5.2 Hz); 6.8 (d, 1H, J=6.0 Hz); 6.73 (d, 1H, J=8.4 Hz); 3.99 (d, 1H, J=8.4 Hz); 3.84 (d, 1H, J=8.4 Hz); 2.57 (q, 2H, J=7.6 Hz); 2.32 (s, 1H); 2.11 (q, 4H, J=7.6); 1.56 (m, 2H); 1.32 (s, 3H); 1.04 (s, 9H); 0.90 (t, 3H, J=7.4 Hz); 0.71 (t, 6H, 7.6 Hz).

ES/MS: 403.2 (M+1).

E. 3'-[4-(2-Hydroxy-2,3,3-trimethylbutoxy)-3-n-propylphenyl]-3'-[5-carboxy-thiophen-2-yl]pentane

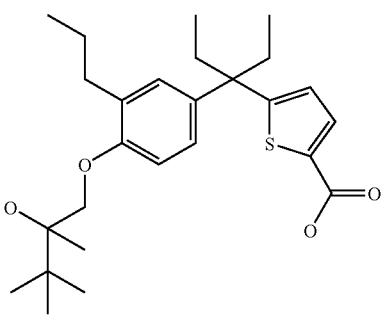

Using a procedure analogous to Example 103E, 3'-[4-(2-Hydroxy-2,3,3-trimethylbutoxy)-3-n-propylphenyl]-3'-(thiophen-2-yl)pentane (1.2 g, 2.9 mmol) gives the title compound (0.53 g, 41%).

NMR (CDC13): 7.70 (d, 1H, J=3.6 Hz); 7.03 (d, 1H, J=8.0 Hz); 6.98 (s, 1H); 6.80 (d, 1H, J=3.6 Hz); 6.74 (d, 1H, J=8.0 Hz); 4.00 (d, 1H, J=8.8 Hz); 3.84 (d, 1H, J 8.8 Hz); 2.57 (t, 2H, J=8.0 Hz); 2.13 (q, 4H, J=7.0); 1.57 (m, 2H); 1.33 (s, 3H); 1.05 (s, 9H); 0.92 (t, 3H, J=7.2 Hz); 0.72 (t, 6H, 7.0 Hz).

ES/MS: 445.5 (M−1).

Example 114

Preparation of enantiomer 1 of d-3'-[4-(2-hydroxy-2,3,3-trimethylbutoxy)-3-n-propylphenyl]-3'-[5-(carboxy-1-ethylamino)carbonyl-thiophen-2-yl]pentane A. Enantiomers of 3'-[4-(2-hydroxy-2,3,3-trimethylbutoxy)-3-n-propylphenyl]-3'-[5-carboxy-thiophen-2-yl]pentane.

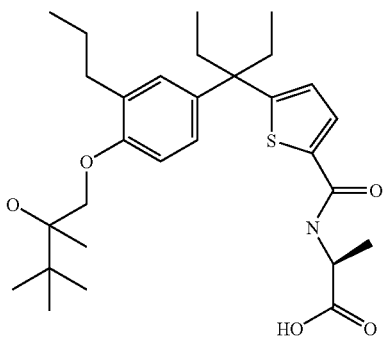

enantiomer 1

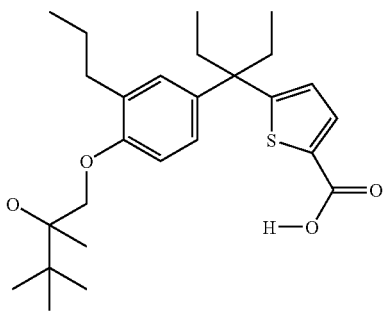

enantiomer 2

A racemic mixture of 3'-[4-(2-hydroxy-2,3,3-trimethylbutoxy)-3-n-propylphenyl]-3'-[5-carboxy-thiophen-2-yl]pentane (0.265 g) is chromatographed (ChiralPak AD column; 0.1% TFA in IPA/heptane to give enantiomer 1 (130 mg; TFA occluded, ~49%), Example 112 and enantiomer 2 (105 mg; TFA occluded, ~40%), Example 113.

Enantiomer 1, Example 112

HPLC: ChiralPak AD (4.6×250 mm); 20% IPA/80% heptane; 1 ml/m (flow rate); rt=5.3 m; 225 nm.

Enantiomer 2, Example 113

HPLC: ChiralPak AD (4.6×250 mm); 20% IPA/80% heptane; 1 ml/m (flow rate); rt=6.7 m; 225 nm.

B. Enantiomer 1 of d-3'-[4-(2-hydroxy-2,3,3-trimethylbutoxy)-3-n-propylphenyl]-3'-[5-(methoxycarbonyl-1-ethylamino)carbonyl-thiophen-2-yl]pentane

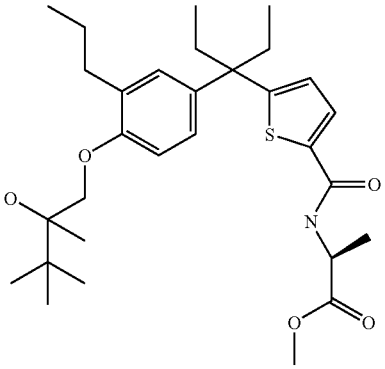

Using a procedure analogous to Example 106A, enantiomer 1 of 3'-[4-(2-hydroxy-2,3,3-trimethylbutoxy)-3-n-propylphenyl]-3'-[5-carboxy-thiophen-2-yl]pentane (130 mg, 0.3 mmol) and d-alanine methylester HCl give the title compound (49 mg, 32%). NMR (CDC13): 7.39 (d, 1H, J=3.6 Hz); 6.99 (s, 1H); 7.02 (d, 1H, J=8.4 Hz); 6.76 (d, 1H, J=3.6 Hz); 6.73 (d, 1H, J=8.4 Hz); 6.38 (d, 1H, J=7.0 Hz); 4.73 (m, 1H); 4.00 (d, 1H, J=7.6 Hz); 3.85 (d, 1H, J=7.6 Hz); 3.77 (s, 3H); 2.55 (t, 2H, J=8.0 Hz); 2.21 (s, 1H); 2.11 (q, 4H, J=7.2); 1.56 (m, 2H); 1.47 (d, 3H, J=6.8 Hz); 1.33 (s, 3H); 1.03 (s, 9H); 0.91 (t, 3H, J=7.6 Hz); 0.71 (t, 6H, 7.4 Hz).

ES/MS: 532.2 (M+1) 530.3 (M−1).

C. Enantiomer 1 of d-3'-[4-(2-hydroxy-2,3,3-trimethylbutoxy)-3-n-propylphenyl]-3'-[5-(carboxy-1-ethyl amino)carbonyl-thiophen-2-yl]pentane

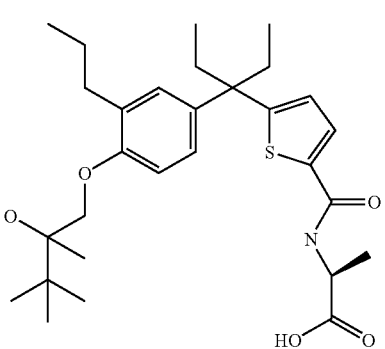

Using a procedure analogous to Example 106B, enantiomer 1 of 3'-[4-(2-hydroxy-2,3,3-trimethylbutoxy)-3-n-propylphenyl]-3'-[5-(methoxycarbonyl-1-ethylamino)carbonyl-thiophen-2-yl]pentane (48 mg, 0.1 mmol) gives the title compound as a solid (38 mg, 81%).

NMR (CDC13): 7.43 (d, 1H, J=4.0 Hz); 6.97 (s, 1H); 7.02 (d, 1H, J=8.4 Hz); 6.79 (d, 1H, J=4.0 Hz); 6.73 (d, 1H, J=8.4 Hz); 6.28 (d, 1H, J=7.0 Hz); 4.70 (m, 1H); 3.99 (d, 1H, J=8.8 Hz); 3.84 (d, 1H, J=8.8 Hz); 2.56 (t, 2H, J=7.8 Hz); 2.11 (q, 4H, J=8.0); 1.56 (m, 2H); 1.53 (d, 3H, J=7.6 Hz); 1.33 (s, 3H); 1.04 (s, 9H); 0.91 (t, 3H, J=7.8 Hz); 0.71 (t, 6H, 8.0 Hz).

ES/MS: 518.2 (M+1) 516.2 (M−1).

Example 115

Preparation of d-3'-[4-(2-hydroxy-2,3,3-trimethylbutoxy)-3-methoxyphenyl]-3'-[5-(carboxy-1-ethylamino)carbonyl-thiophen-2-yl]pentane

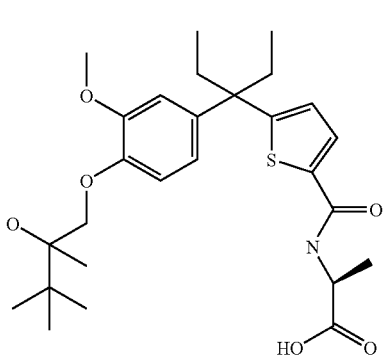

A. 3'-[4-Hydroxy-3-methoxyphenyl]pentan-3-ol

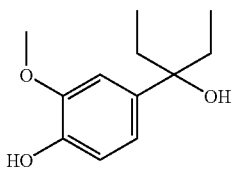

Using a procedure analogous to Example 103A, methyl, 4-hydroxy-3-methoxybenzoate (7.3, 40 mmol) gives the title compound as an oil (7.7 g, 91%). NMR (CDCl3): 6.96 (s, 1H); 6.86 (d, 1H, 8.4 Hz); 6.98 (d, 1H, J=8.4 Hz); 5.51 (s, 1H); 3.90 (s, 3H); 1.81 (m, 4H); 0.78 (t, 6H, 7.6 Hz).

ES/MS: 193.0 (M+H−H2O).

B. 3'-[4-(2-Oxo-3,3-dimethylbutoxy)-3-methoxyphenyl]pentan-3-ol

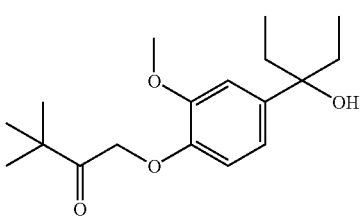

Using a procedure analogous to Example 91B, 3'-[4-hydroxy-3-methoxyphenyl]pentan-3-ol (7.7 g, 36 mmol) gives the title compound (10 g, 89%). NMR (CDC3): 6.97 (s, 1H); 6.78 (d, 1H, J=8.4 Hz); 6.66 (d, 1H, J=8.4 Hz); 4.93 (s, 2H); 3.88 (s, 3H); 1.80 (m, 4H); 1.23 (s, 9H); 0.76 (t, 6H, 7.2 Hz).

ES/MS: 291.1 (M+H−H2O).

C. 3'-[4-(2-Oxo-3,3-dimethylbutoxy)-3-methoxyphenyl]-3'-(thiophen-2-yl)pentane

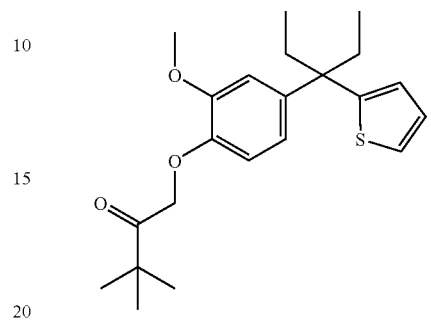

Using a procedure analogous to Example 103B, 3'-[4-(2-oxo-3,3-dimethylbutoxy)-3-metboxyphenyl]pentan-3-ol (4.9 g, 16 mmol) gives the title compound (1.5 g, 25%).

NMR (CDCl3): 7.13 (d, 1H, J=5.2 Hz); 6.89 (t, 1H, J=4.2 Hz); 6.80 (d, 1H, J=4.8 Hz); 6.76 (m, 2H); 6.60 (d, 1H, J=9.2 Hz); 4.91 (s, 2H); 3.78 (s, 3H); 2.10 (q, 4H, J 7.2); 1.28 (s, 9H); 0.70 (t, 6H, 7.2 Hz).

ES-MS: 375.2 (M+1) 393.2 (M+NH4).

D. 3'-[4-(2-Hydroxy-2,3,3-trimethylbutoxy)-3-methoxyphenyl]-3'-(thiophen-2-yl)pentane

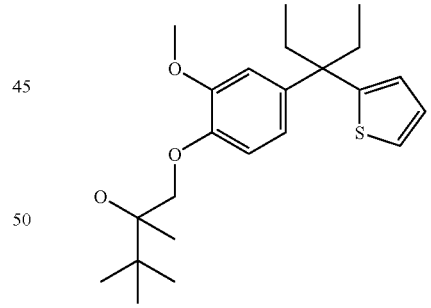

Using a procedure analogous to Example 103D, 3'-[4-(2-oxo-3,3-dimethylbutoxy)-3-metboxyphenyl]-3'-(tbiopben-2-yl)pentane (1.5 g, 4 mmol) gives the title compound (1.4 g, 89%).

NMR (CDC13): 7.13 (d, 1H, J=5.0 Hz); 6.90 (t, 1H, J=8.4 Hz) 8.81 (m, 3H); 6.76 (s, 1H); 3.98 (d, 1H, J=8.8 Hz); 3.90 (d, 1H, J=8.8 Hz); 3.75 (s, 3H); 2.76 (s, 1H); 2.11 (q, 4H, J=7.2); 1.85 (m, 1H); 1.31 (s, 3H); 1.02 (s, 9H); 0.70 (t, 6H, 7.2 Hz).

ES/MS: 373.2 (M+H−H2O).

E. 3'-[4-(2-Hydroxy-2,3,3-trimethylbutoxy)-3-methoxyphenyl]-3'-[5-carboxy-thiophen-2-yl]pentane

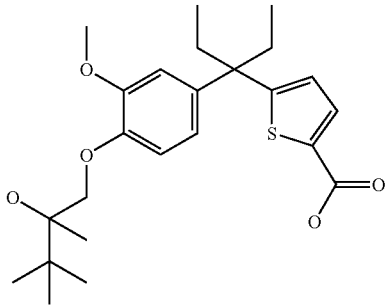

Using a procedure analogous to Example 103E, 3'-[4-(2-hydroxy-2,3,3-trimethylbutoxy)-3-methoxyphenyl]-3'-(thiophen-2-yl)pentane (1.4 g, 3.5 mmol) gives the title compound (1.2 g, 77%).

NMR (CDCl$_3$): 7.70 (d, 1H, J=3.6 Hz); 6.81 (m, 3H); 6.72 (d, 1H, J=3.6 Hz); 3.99 (d, 1H, J=9.2 Hz); 3.91 (d, 1H, J=9.2 Hz); 3.76 (s, 3H); 2.13 (q, 4H, J=7.2); 1.32 (s, 3H); 1.02 (s, 9H); 0.73 (t, 6H, 7.2 Hz).

ES/MS: 433.2 (M−1).

F. d-3'-[4-(2-hydroxy-2,3,3-trimethylbutoxy)-3-methoxyphenyl]-3'-[5-(methoxycarbonyl-1-ethylamino)carbonyl-thiophen-2-yl]pentane

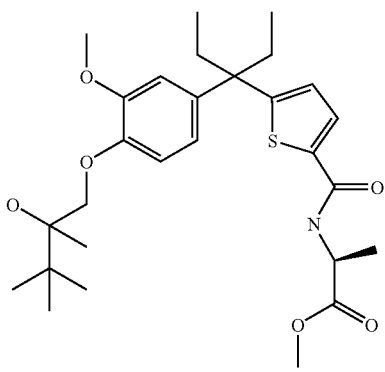

Using a procedure analogous to Example 106A, 3'-[4-(2-hydroxy-2,3,3-trimethylbutoxy)-3-methoxyphenyl]-3'-[5-carboxy-thiophen-2-yl]pentane (600 mg, 1.4 mmol) and d-alanine methylester HCl give the title compound (206 mg, 28%). NMR (CDC13): 7.39 (d, 1H, J=3.6 Hz); 6.81 (s, 2H); 6.77 (d, 1H, J=3.6 Hz); 6.72 (s, 1H); 6.40 (d, 1H, J=7.6 Hz); 4.75 (m, 1H); 3.99 (d, 1H, J=7.6 Hz); 3.90 (d, 1H, J=7.6 Hz); 3.77 (s, 3H); 3.75 (s, 3H); 2.72 (s, 1H); 2.11 (q, 4H, J=7.2); 1.48 (d, 3H, J=7.6 Hz); 1.31 (s, 3H); 1.02 (s, 9H); 0.71 (t, 6H, 7.2 Hz).

ES/MS: 520.2 (M+1) 518.2 (M−1).

G. d-3'-[4-(2-hydroxy-2,3,3-trimethylbutoxy)-3-methoxyphenyl]-3'-[5-(carboxy-1-ethylamino)carbonyl-thiophen-2-yl]pentane

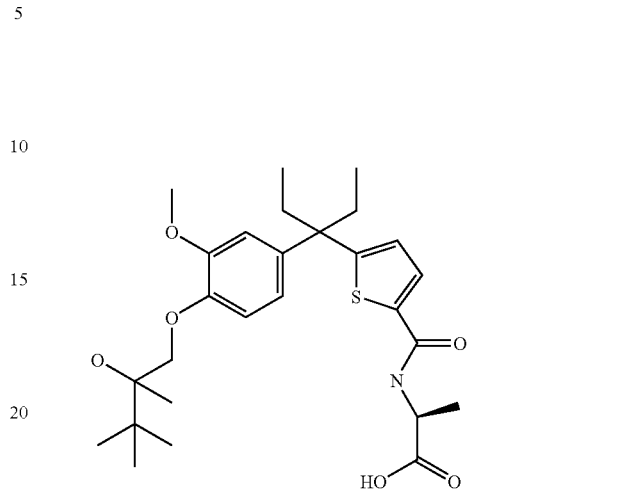

Using a procedure analogous to Example 106B, d-3'-[4-(2-hydroxy-2,3,3-trimethylbutoxy)-3-methoxyphenyl]-3'-[5-(methoxycarbonyl-1-etbylamino)carbonyl-thiophen-2-yl]pentane (140 mg, 0.3 mmol) gives the title compound as a solid (134 mg, 98%).

NMR (CDC$_3$): 7.44 (d, 1H, J=4.0 Hz); 6.80 (m, 3H); 6.71 (s, 1H); 6.38 (d, 1H, J=7.0 Hz); 4.70 (m, I H); 3.99 (d, 1H, J=9.2 Hz); 3.91 (d, IH, J=9.2 Hz); 2.11 (q, 4H, J=7.4); 1.54 (d, 3H, J=6.8 Hz); 1.32 (s, 3H); 1.02 (s, 9H); 0.72 (t, 6H, 7.4 Hz).

ES/MS: 504.2 (M−1).

Example 116 and 117

Preparation of enantiomers of d-3'-[4-(2-hydroxy-2,3,3-trimethylbutoxy)-3-methoxyphenyl]-3'-[5-(carboxy-1-ethylamino)carbonyl-thiophen-2-yl]pentane enantiomer 1
enantiomer 2

A racemic mixture of d-3'-[4-(2-hydroxy-2,3,3-trimethylbutoxy)-3-methoxyphenyl]-3'-[5-(carboxy-1-ethylamino)carbonyl-thiopben-2-yl]pentane (0.133 g) is chromatographed (ChiralPak AD column; 0.1% TFA in IPA/Hept) to give enantiomer 1 (72 mg, quant), Example 116 and enantiomer 2 (78 mg, quant), Example 117.

Enantiomer 1, Example 116

HPLC: ChiralPak AD (4.6×250 mm); 40% IPA/60% heptane; 1 ml/m (flow rate);

rt=5.1 m; 225 nm.

Enantiomer 2, Example 117

HPLC: ChiralPak AD (4.6×250 mm); 40% IPA/60% heptane; 1 ml/m (flow rate);

rt=6.2 m; 225 nm.

Example 118

Preparation of N-methyl-2-[(5-{1-[4-(3,3-Dimethyl-2-oxo-butoxy)-3-methyl-phenyl]-1-ethyl-propyl}-3-methyl-thiophene-2-carbonyl)-methylamino]-acetic acid

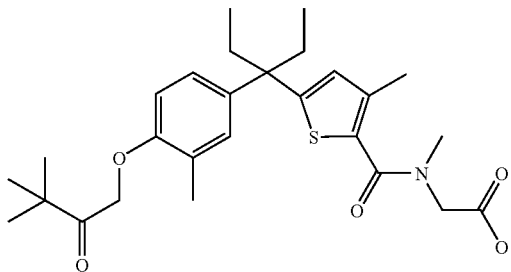

A. 5-[1-Ethyl-1-(4-hydroxy-3-methyl-phenyl)-propyl]-3-methyl-thiophene-2-carboxylic acid

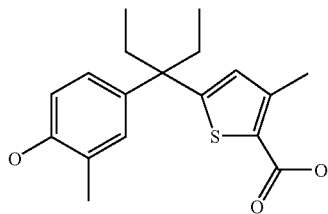

Using a procedure analogous to Example 47, 5-[1-Ethyl-1-(4-hydroxy-3-methyl-phenyl)-propyl]-3-methyl-thiophene-2-carboxylic acid methyl ester, (Example 1F) (6.68 g, 20.12 mmol) gives the title compound (6.30 g, 19.81 mmol, 90%). $^1$H NMR (CDCl$_3$), δ 0.71 (t, J=6.9 Hz, 6H), 2.11 (q, J=6.9 Hz, 4H), 2.23 (s, 3H), 2.48 (s, 3H), 6.61 (s, 1H), 6.69 (d, J=7.9 Hz, 1H), 6.94-7.00 (m, 2H). LC/MS (m/z): calcd for C$_{18}$H$_{22}$O$_3$S: 318.1; found: 318.1.

B. N-methyl-2-{5-[1-Ethyl-1-(4-hydroxy-3-methyl-phenyl)-propyl]-3-methyl-thiophene-2-carbonyl}-methylamino)-acetic acid methyl ester

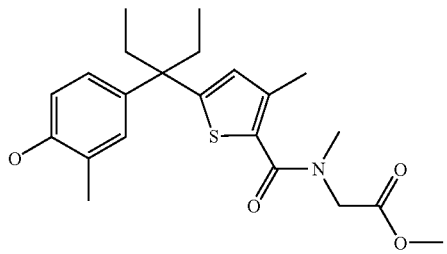

Using a procedure analogous to Example 38, from [1-ethyl-1-(4-hydroxy-3-methyl-phenyl)-propyl]-3-methyl-thiophene-2-carboxylic acid (1.90 g, 5.96 mmol) and sarcosine methyl ester hydrochloride (0.89 g, 6.55 mmol) gives the title compound (1.99 g, 4.94 mmol, 83%). $^1$H NMR (CDCl$_3$), d 0.70 (t, J=7.1 Hz, 6H), 2.01-2.09 (m, 4H), 2.21 (s, 3H), 2.24 (s, 3H), 3.10 (s, 3H), 3.74 (s, 3H), 4.20 (bs, 2H), 6.52 (s, 1H), 6.63 (d, J=8.4 Hz, 1H), 6.90-7.01 (m, 2H). LC/MS (m/z): calcd for C$_{22}$H$_{30}$NO$_4$S (M+H)$^+$: 404.2; found: 404.2.

C. N-methyl-2-[(5-{1-[4-(3,3-Dimethyl-2-oxo-butoxy)-3-methyl-phenyl]-1-ethyl-propyl}-3-methyl-thiophene-2-carbonyl)-methylamino]-acetic acid methyl ester

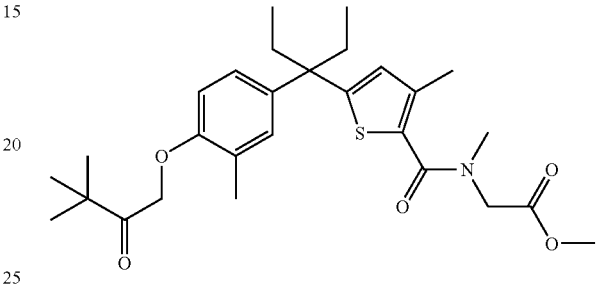

Using a procedure analogous to Example 1G, from 2-({5-[1-Ethyl-1-(4-hydroxy-3-methyl-phenyl)-propyl]-3-methyl-thiophene-2-carbonyl}-methylamino)-acetic acid methyl ester (1.99 g, 4.94 mmol) gives the title compound (1.14 g, 2.28 mmol, 46%). $^1$H NMR (CDC$_3$), d 0.70 (t, J=7.4 Hz, 6H), 1.27 (s, 9H), 2.00-2.14 (m, 4H), 2.24 (s, 3H), 2.26 (s, 3H), 3.01 (s, 3H), 3.75 (s, 3H), 4.16-4.24 (bs, 2H), 4.84 (s, 2H), 6.49-6.53 (m, 2H), 6.90-7.03 (m, 2H). LC/MS (m/z): calcd for C$_{28}$H$_{40}$NO$_5$S (M+H)$^+$: 502.7; found: 502.2.

D. N-methyl-2-[(5-{1-[4-(3,3-Dimethyl-2-oxo-butoxy)-3-methyl-phenyl]-1-ethyl-propyl}-3-methyl-thiophene-2-carbonyl)-methylamino]-acetic acid

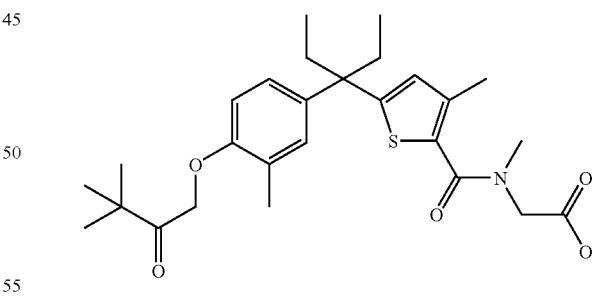

To a mixture of 2-[(5-{1-[4-(3,3-Dimethyl-2-oxo-butoxy)-3-methyl-phenyl]-1-ethyl-propyl}-3-methyl-thiophene-2-carbonyl)-methylamino]-acetic acid methyl ester (0.16 g, 0.32 mmol) and THF (2 mL) is added and H$_2$O (2 mL) and 1.0 M NaOH (0.35 mL, 0.35 mmol). The reaction is stirred at RT overnight, acidified with 0.1 M HCl to pH 3-4 and extracted with EtOAc (2×30 mL). The organic layer is MgSO$_4$ dried and concentrated to give the title compound (0.14 g, 90%). $^1$H NMR (CDCl$_3$), δ 0.71 (t, J=7.2 Hz, 6H), 1.27 (s, 9H), 2.02-2.10 (m, 4H), 2.24 (s, 3H), 2.26 (s, 3H), 3.12 (s, 3H), 4.21 (bs, 2H), 4.86 (s, 2H), 6.49-6.55 (m, 2H), 6.96-7.03 (m, 2H). LC/MS (m/z): calcd for $C_{27}H_{38}NO_5S$ (M+H)⁺: 488.7; found: 488.2.

Example 119

Preparation of N-methyl-2-[(5-{1-ethyl-1-[4-(2-hydroxy-3,3-dimethyl-butoxy)-3-methyl-phenyl]-propyl}-3-methyl-thiophene-2-carbonyl)-methylamino]-acetic acid methyl ester

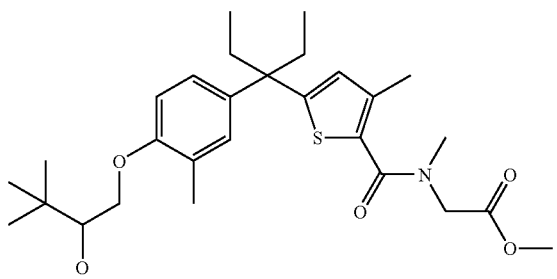

Using a procedure analogous to Example 2, N-methyl-2-[(5-{1-[4-(3,3-Dimethyl-2-oxo-butoxy)-3-methyl-phenyl]-1-ethyl-propyl}-3-methyl-thiophene-2-carbonyl)-methylamino]-acetic acid methyl ester (0.96 g, 1.92 mmol) gives the title compound (0.75 g, 1.49 mmol, 78%). 3H NMR (CDC₃), d 0.71 (t, J=7.0 Hz, 6H), 1.03 (s, 9H), 2.04-2.14 (m, 4H), 2.21 (s, 3H), 2.24 (s, 3H), 3.09 (s, 3H), 3.71 (dd, J=8.4, 2.6 Hz, 1H), 3.75 (s, 3H), 3.87 (t, J=8.9 Hz, 1H), 4.10 (dd, J=9.2, 2.6 Hz, 1H), 4.20 (bs, 2H), 6.52 (s, 1H), 6.72 (d, J=8.7 Hz, 1H), 7.00-7.07 (m, 2H). LC/MS (m/z): calcd for $C_{28}H_{42}NO_5S$ (M+H)⁺: 504.7; found: 504.2.

Example 120 and 121

Preparation of enantiomers of N-methyl-2-[(5-{1-ethyl-1-[4-(2-hydroxy-3,3-dimethyl-butoxy)-3-methyl-phenyl]-propyl}-3-methyl-thiophene-2-carbonyl)-methylamino]-acetic acid methyl ester Enantiomer 1

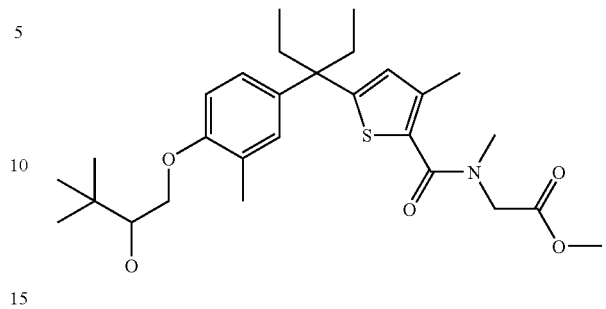

Enantiomer 2

A racemic mixture of N-methyl-2-[(5-{1-ethyl-1-[4-(2-hydroxy-3,3-dimethyl-butoxy)-3-methyl-phenyl]-propyl}-3-methyl-thiophene-2-carbonyl)-methylamino]-acetic acid methyl ester (740 mg) is chromatographed (CHIRALPAK AD column, 40% i-PrOH/Hept) to give enantiomer 1 of the title compound (Example 120) (205 mg, 28%) and enantiomer 2 of the title compound (Example 121) (179 mg, 24%).

Enantiomer 1, Example 120:

rt=7.1 m

NMR & LC/MS: Identical to the racemic material,1 Example 119.

Enantiomer 2, Example 121 rt=22.8m

NMR & LC/MS: Identical to the racemic material, Example 119.

Example 122

Preparation of enantiomer 1 of N-methyl-2-[(5-{1-ethyl-1-[4-(2-hydroxy-3,3-dimethyl-butoxy)-3-methyl-phenyl]-propyl}-3-methyl-thiophene-2-carbonyl)-methylamino]-acetic acid Enantiomer 1

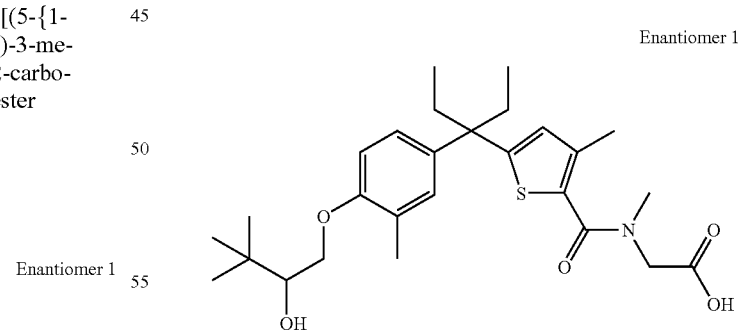

Using a procedure analogous to Example 47, enantiomer 1 of N-methyl-2-[(5-{1-ethyl-1-[4-(2-hydroxy-3,3-dimethyl-butoxy)-3-methyl-phenyl]-propyl}-3-methyl-thiophene-2-carbonyl)-methylamino]-acetic acid methyl ester (200 mg) yields the title compound (189 mg, 97%). ¹H NMR (CDC₃), d 0.71 (t, J=7.2 Hz, 6H), 1.02 (s, 9H), 2.01-2.13 (m, 4H), 2.20 (s, 3H), 2.24 (s, 3H), 3.12 (s, 3H), 3.72 (dd, J=8.8, 2.7 Hz, 1H), 3.88 (t, J=8.9 Hz, 1H), 4.12 (dd, J=9.1, 2.7 Hz, 1H), 4.21

(s, 2H), 6.53 (s, 1H), 6.72 (d, J=8.6 Hz, 1H), 7.00-7.06 (m, 2H). LC/MS (m/z): calcd for $C_{27}H_{40}NO_5S$ (M+H)$^+$: 490.7; found: 490.3.

Example 123

Preparation of enantiomer 2 of N-2-[(5-{1-ethyl-1-[4-(2-hydroxy-3,3-dimethyl-butoxy)-3-methyl-phenyl]-propyl}-3-methyl-thiophene-2-carbonyl)-methylamino]-acetic acid Enantiomer 2

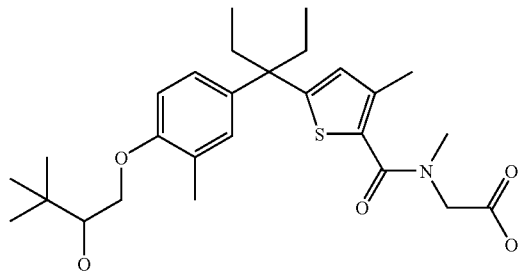

Using a procedure analogous to Example 47, enantiomer 2 of N-methyl-2-[(5-{1-ethyl-1-[4-(2-hydroxy-3,3-dimethyl-butoxy)-3-methyl-phenyl]-propyl}-3-methyl-thiophene-2-carbonyl)-methylamino]-acetic acid methyl ester (172 mg, 0.34 mmol) yields the title compound (168.8 mg, 98%). $^1$H NMR and LC/MS (m/z): identical to Example 122.

Example 124

Preparation of 2-(5-{1-ethyl-1-[4-(2-hydroxy-3,3-dimethyl-butoxy)-3-methyl-phenyl]-propyl}-3-methyl-thiophen-2-yl-methoxy)acetic acid

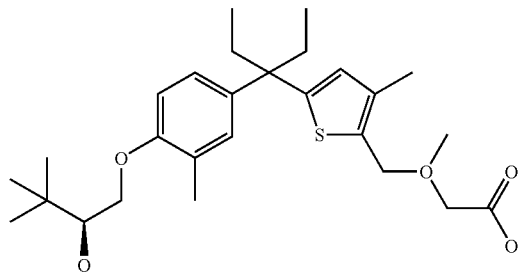

A. 5-(1-{4-[2-(tert-Butyl-dimethyl-silanyloxy)-3,3-dimethyl-butoxy]-3-methyl-phenyl}-1-ethyl-propyl)-3-methyl-thiophene-2-carboxylic acid methyl ester

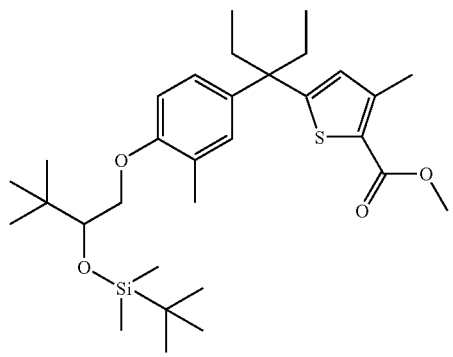

To a mixture of 5-{1-Ethyl-1-[4-(2-hydroxy-3,3-dimethyl-butoxy)-3-methyl-phenyl]-propyl}-3-methyl-thiophene-2-carboxylic acid methyl ester (Example 2) (1.15 g, 2.66 mmol), imidazole (0.27 g, 4.00 mmol), and DMF (15 mL) is added TBSCl (0.54 g, 2.80 mmol). The reaction is stirred for 24 h. The reaction is diluted with Et$_2$O (120 mL) and washed with 0.1 M HCl (3×40 ml). The organic layer is MgSO$_4$ dried and concentrated. The resulting residue is chromatographed to give the title compound (0.94 g, 64%). $^1$H NMR (CDCl$_3$), δ 0.01 (s, 3H), 0.06 (s, 3H), 0.65 (t, J=7.4 Hz, 6H), 0.85 (s, 9H), 0.91 (s, 9H), 2.00-2.14 (m, 4H), 2.14 (s, 3H), 2.43 (s, 3H), 3.67 (dd, J=5.8, 3.4 Hz, 1H), 3.74 (s, 3H), 3.85 (dd, J=9.8, 5.8 Hz, 1H), 3.98 (dd, J=9.8, 3.4 Hz, 1H), 6.56 (s, 1H), 6.68 (d, J=8.3 Hz, 1H), 6.96-7.03 (m, 2H). LC/MS (m/z): calcd for $C_{31}H_{51}O_4SSi$ (M+H)$^+$: 547.9; found: 547.2.

B. 5-(1-{4-[2-(tert-Butyl-dimethyl-silanyloxy)-3,3-dimethyl-butoxy]-3-methyl-phenyl}-1-ethyl-propyl)-3-methyl-thiophen-2-yl-methanol

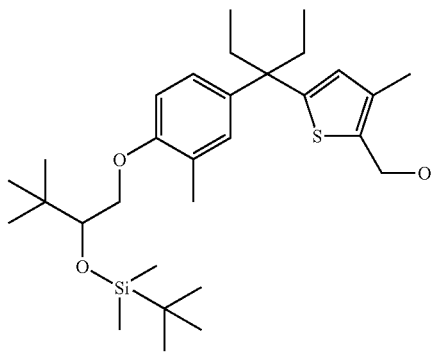

To a 0° C. solution of 5-(1-{4-[2-(tert-Butyl-dimethyl-silanyloxy)-3,3-dimethyl-butoxy]-3-methyl-phenyl}-1-ethyl-propyl)-3-methyl-thiophene-2-carboxylic acid methyl ester (0.94 g, 1.71 mmol) and THF (50 mL) is added LAH (71 mg, 1.89 mmol). The mixture is stirred for 10 m, warmed to RT and stirred for 2 h. The reaction is quenched with H$_2$O (70 ul), 15% NaOH (70 uL) and H$_2$O (210 uL) and diluted with EtOAc (50 mL). The mixture is filtered through diatomaceous earth and concentrated to give the title compound (0.89 g, 1.72 mmol, 100%). $^1$H NMR (CDC$_3$), B 0.07 (s, 3H), 0.12 (s, 3H), 0.72 (t, J=7.4 Hz, 6H), 0.91 (s, 9H), 0.98 (s, 9H), 2.01-2.14 (m, 4H), 2.19 (s, 3H), 2.21 (s, 3H), 3.68 (dd, J=5.3, 3.4 Hz, 1H), 3.86 (dd, J=9.0, 5.3 Hz, 1H), 3.98 (dd, J=9.0, 3.4 Hz, 1H), 4.67 (s, 22H), 6.54 (s, 1H), 6.67 (d, J=8.1 Hz, 1H), 7.00-7.06 (m, 2H). LC/MS (m/z): calcd for $C_{30}H_{50}O_3SSi$ M+: 518.9; found: 518.0.

C. 2-[5-(1-{4-[2-(tert-Butyl-dimethyl-silanyloxy)-3,3-dimethyl-butoxy]-3-methyl-phenyl}-1-ethyl-propyl)-3-methyl-thiophen-2-ylmethoxy]-acetic acid methyl ester

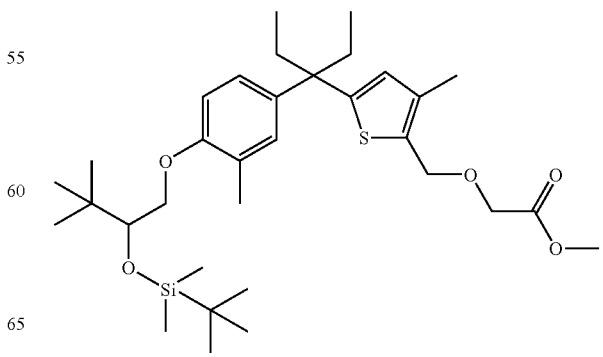

T a 0° C. solution of 5-(1-{4-[2-(tert-butyl-dimethyl-silanyloxy)-3,3-dimethyl-butoxy]-3-methyl-phenyl}-1-ethyl-propyl)-3-methyl-thiophen-2-yl-methanol (0.96 g, 1.85 mmol) in THF (10 mL) is added 60% NaH (81 mg, 2.0 mmol) and stirred for 20 m. The mixture is added methyl bromoacetate (0.21 mL, 2.22 mmol)warmed to RT, and stirred overnight. The reaction is quenched with satd NH₄Cl (10 mL), diluted with H₂O (10 mL), and extracted with EtOAc (2×20 mL). The combined organic layers is MgSO4 dried and concentrated. The resulting residue is chromatographed to give the title compound (0.33 g, 0.57 mmol, 31%). ¹H NMR (CDC₃), δ 0.06 (s, 3H), 0.12 (s, 3H), 0.70 (t, J=7.3 Hz, 6H), 0.91 (s, 9H), 0.97 (s, 9H), 2.01-2.10 (m, 4H), 2.19 (s, 3H), 2.20 (s, 3H), 3.67 (dd, J=5.8, 3.4 Hz, I H), 3.76 (s, 3H), 3.85 (dd, J=9.8, 5.8 Hz, 1H), 3.98 (dd, J=9.8, 3.4 Hz, 1H), 4.09 (s, 2H), 4.64 (s, 2H), 6.53 (s, 1H), 6.67 (d, J=8.3 Hz, I H), 7.00-7.06 (m, 2H). LC/MS (m/z): calcd for C 10 $_{33}$H$_{58}$NO$_5$SSi (M+NH4)+: 608.9; found: 608.3.

D. 2-(5-{1-Ethyl-1-[4-(2-hydroxy-3,3-dimethyl-butoxy)-3-methyl-phenyl]-propyl}-3-methyl-thiophen-2-yl-methoxy)-acetic acid

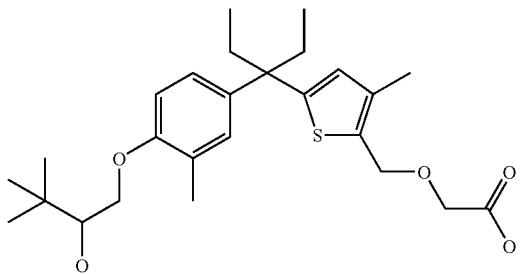

A solution of 2-[5-(1-{4-[2-(tert-butyl-dimethyl-silanyloxy)-3,3-dimethyl-butoxy]-3-methyl-phenyl}-1-ethyl-propyl)-3-methyl-thiophen-2-ylmethoxy]-acetic acid methyl ester (0.33 g, 0.57 mmol), 1.0 M TBAF/THF (0.62 m L, 0.62 mmol) and THF (4 mL) is refluxed for 3 h. The mixture filtered through silica gel, washed with EtOAc and concentrated. The resulting residue is hydrolyzed using a procedure analogous to Example 47 to give the title compound (0.13 g, 0.28 mmol) in an overall yield of 49%. ¹H NMR (CDC₃), δ 0.71 (t, J=7.4 Hz, 6H), 1.02 (s, 9H), 2.01-2.10 (m, 4H), 2.19 (s, 3H), 2.20 (s, 3H), 2.21 (bs, 2H), 3.72 (dd, J=8.8, 2.9 Hz, 1H), 3.87 (t, J=8.8 Hz, 1H), 4.08-4.12 (m, 2H), 4.16 (s, 1H), 4.66 (s, 1H), 5.24 (s, 1H), 6.54 (d, J=3.4 Hz, 1H), 6.62 (d, J=8.3 Hz, 1H), 7.01-7.08 (m, 2H). LC/MS (m/z): calcd for $C_{26}H_{37}O_5S$ (M−H)⁻: 461.7; found: 461.2.

Example 125

Preparation of 1-{4-[1-ethyl-1-(5-hydroxymethyl-4-methyl-thiophen-2-yl)-propyl]-2-methyl-phenoxy}-3,3-dimethyl-butan-2-ol

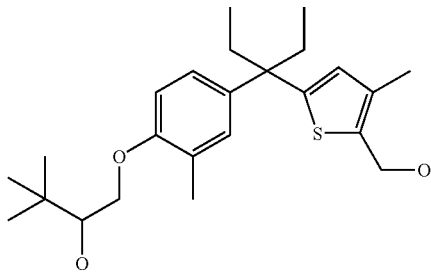

A solution of 1-{4-[1-ethyl-1-(5-hydroxymethyl-4-methyl-thiophen-2-yl)-propyl]-2-methyl-phenoxy}-3,3-dimethyl-butan-2-ol, Example B (71.5 mg, 0.14 mmol) in THF (3 mL) is treated with 1.0 M TBAF (0.15 mL, 0.15 mmol). The reaction is refluxed for 14 h, diluted with EtOAc (20 mL), washed with H₂O (10 mL), MgSO₄ dried, and concentrated. The resulting residue is chromatographed to give the title compound (41.1 mg, 0.10 mmol, 71%). %). ¹H NMR (CDCl₃), δ0.71 (t, J=6.8 Hz, 6H), 1.02 (s, 9H), 2.02-2.11 (m, 4H), 2.19 (s, 3H), 2.21 (s, 3H), 2.44 (d, J=2.9 Hz, 1H), 3.71 (dt, J=8.9, 2.4 Hz, 1H), 3.87 (t, J=8.9 Hz, 1H), 4.10 (dd, J=8.9, 2.4 Hz, 1H), 4.66 (d, J=5.4 Hz, 2H), 6.53 (s, 1H), 6.72 (d, J=8.3 Hz, 1H), 7.02-7.08 (m, 2H). LC/MS (n/z): calcd for $C_{24}H36NaO_3S$ (M+Na)+: 427.6; found: 427.2.

Example 126 and 127

Preparation of enantiomers of 1-{4-[1-ethyl-1-(5-hydroxymethyl-4-methyl-thiopben-2-yl)-propyl]-2-methyl-phenoxy}-3,3-dimethyl-butan-2-ol Enantiomer 1

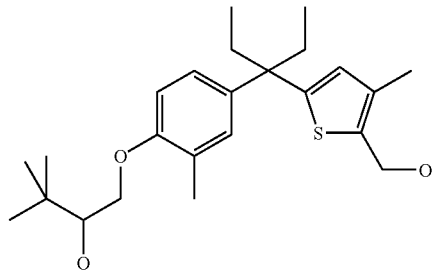

Enantiomer 2

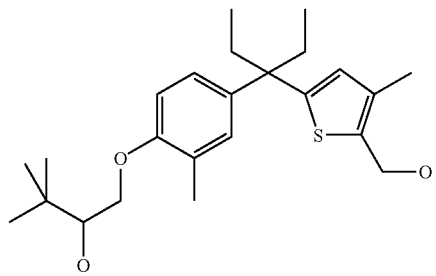

A racemic mixture of 1-{4-[1-ethyl-1-(5-hydroxymethyl-4-methyl-thiophen-2-yl)-propyl]-2-methyl-phenoxy}-3,3-dimethyl-butan-2-ol (37.5 mg) is chromatographed (CHIRALPAK AD column, 40% i-PrOH/Hept) to give enantiomer 1 of the title compound, Example 126 (3.6 mg, 10%) and enantiomer 2 of the title compound, Example 127 (2.8 mg, 7%).

Example 126, Enantiomer 1 rt=5.3m

NMR & LC/MS: Identical to the racemic material, Example 125.

Example 127, Enantiomer 2 rt=8.5 m

NMR & LC/MS: Identical to the racemic material, Example 125.

Example 128

Preparation of sodium salt of enantiomer 1 of 2-[(5-{1-ethyl-1-[4-(2-hydroxy-3,3-dimethyl-butoxy)-3-methyl-phenyl]-propyl}-3-methyl-thiophene-2-carbonyl)-amino]-acetic acid Enantiomer 1

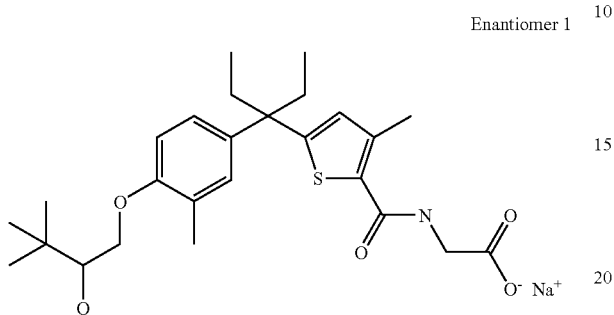

A solution of enantiomer 1 of 2-[(5-{1-ethyl-1-[4-(2-hydroxy-3,3-dimethyl-butoxy)-3-methyl-phenyl]-propyl}-3-methyl-thiophene-2-carbonyl)-amino]-acetic acid, Example 48 (597 mg, 1.26 mmol) in $CH_3OH$ (5 mL) is treated with 0.5 M $NaOCH_3$ (2.7 mL, 1.4 mmol) and stirred for 5 m. The mixture is concentrated to give the title compound (626 mg, 1.26 mmol, 100%). $^1H$ NMR ($CD_3OD$), δ 0.75 (t, J=7.1 Hz, 6H), 1.05 (s, 9H), 2.10-2.20 (m, 4H), 2.23 (s, 3H), 2.50 (s, 3H), 3.66 (dd, J=7.9, 3.0 Hz, 1H), 3.89 (s, 2H), 3.90-3.95 (m, 1H), 4.16 (dd, J=10.1, 3.0 Hz, 1H), 6.72 (s, 1H), 6.83 (d, J=8.8 Hz, 1H), 7.02-7.12 (m, 2H). LC/MS (m/z): calcd for $C_{26}H38NO_5S$ $(M+H)^+$: 476.2; found: 476.2

Example 129

Preparation of sodium salt of enantiomer 2 of [(5-{1-ethyl-1-[4-(2-hydroxy-3,3-dimethyl-butoxy)-3-methyl-phenyl]-propyl}-3-methyl-thiophene-2-carbonyl)-amino]-acetic acid Enantiomer 2

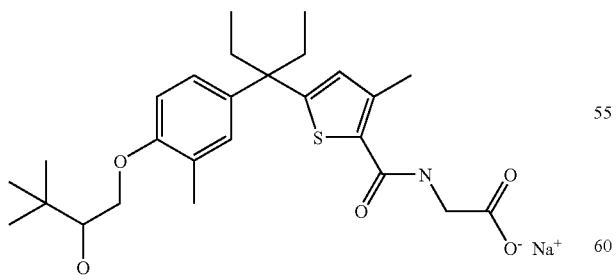

Using a procedure analogous to Example 128, enantiomer 2 of 2-[(5-{1-ethyl-1-[4-(2-hydroxy-3,3-dimethyl-butoxy)-3-methyl-phenyl]-propyl}-3-methyl-thiophene-2-carbonyl)-amino]-acetic acid (Example 49) (0.69 g, 1.15 mmol) gives the title compound (0.69 g, 1.15 mmol, 100%). $^1H$ NMR and LC/MS: identical to Example 128.

Example 130

Preparation of 2-[N-acetyl-(5-{1-ethyl-1-[4-(2-hydroxy-3,3-dimethyl-butoxy)-3-methyl-phenyl]-propyl}-3-methyl-thiophen-2-ylmethyl)-amino]-acetic acid

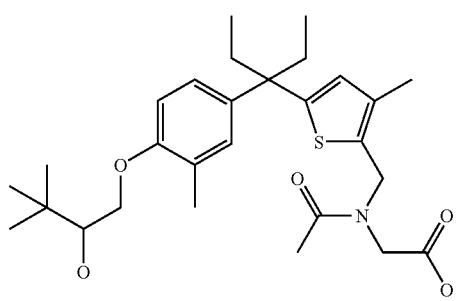

A. Preparation of 5-(1-{4-[2-(tert-Butyl-dimethyl-silanyloxy)-3,3-dimethyl-butoxy]-3-methyl-phenyl}-1-ethyl-propyl)-3-methyl-thiophene-2-carbaldehyde

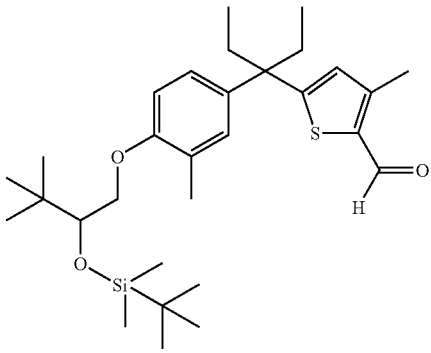

Using a procedure analogous to Example 41, 1-{4-[1-ethyl-1-(5-hydroxymethyl-4-methyl-thiophen-2-yl)-propyl]-2-methyl-phenoxy}-3,3-dimethyl-butan-2-ol (Example 124B) (0.88 g, 1.69 mmol) gives the title compound (0.77 g, 1.49 mmol, 88%). $^1H$ NMR ($CDC_3$), δ 0.07 (s, 3H), 0.12 (s, 3H), 0.72 (t, J=7.4 Hz, 6H), 0.91 (s, 9H), 0.98 (s, 9H), 2.12 (q, J=7.4 Hz, 4H), 2.21 (s, 3H), 2.50 (s, 3H), 3.68 (dd, J=5.4, 3.5 Hz, 1H), 3.86 (dd, J=9.9, 5.4 Hz, 1H), 3.98 (dd, J=9.9, 3.5 Hz, 1H), 6.64 (s, 1H), 6.68 (d, J=8.7 Hz, 1H), 6.95-7.03 (m, 2H), 9.92 (s, 1H). LC/MS (m/z): calcd for $C_{30}H_{49}O_3SSi$ $(M+H)^+$: 517.9; found: 517.2

B. 2-{[5-(1-{4-[2-(tert-Butyl-dimethyl-silanyloxy)-3,3-dimethyl-butoxy]-3-methyl-phienyl}-1-ethyl-propyl)-3-methyl-thiopben-2-ylmethyl-3-yl]-amino}-acetic acid methyl ester

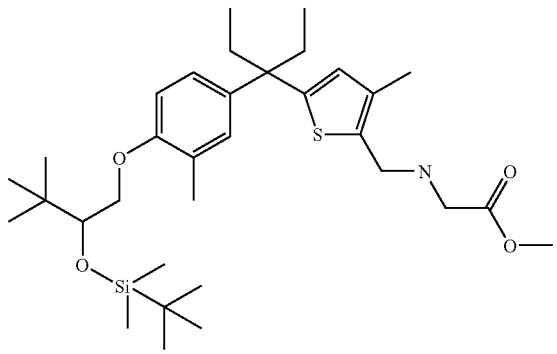

A mixture of 5-(1-{4-[2-(tert-butyl-dimethyl-silanyloxy)-3,3-dimethyl-butoxy]-3-methyl-phenyl}-1-ethyl-propyl)-3-methyl-thiophene-2-carbaldehyde (2.11 g, 4.09 mm) and glycine methyl ester hydrochloride (0.56 g, 4.50 mmol) with Et$_3$N (0.74 mL, 5.3 mmol) is treated with Ti(Oi-Pr)$_4$ (1.6 mL, 5.3 mmol) at RT for 1 h. It is diluted with CH$_3$OH (20 mL), treated with NaB(CN)H$_3$ (282 mg, 4.5 mmol). The reaction is stirred overnight. It is then quenched with H$_2$O (3 mL) and stirred at RT for 1 h, and filtered through silica gel washed with EtOAC (100 mL) and concentrated. Chromatographic purification gives the title compound (1.54 g, 2.61 mmol, 64%).

$^1$H NMR (CDCl$_3$), δ 0.06 (s, 3H), 0.12 (s, 3H), 0.70 (t, J=6.9 Hz, 6H), 0.91 (s, 9H), 0.97 (s, 9H), 2.02-2.10 (m, 4H), 2.13 (s, 3H), 2.20 (s, 3H), 3.45 (s, 2H), 3.67 (dd, J=5.4, 3.4 Hz, 1H), 3.73 (s, 3H), 3.82-3.87 (m, 3H), 3.98 (dd, J=9.6, 3.4 Hz, 1H), 6.49 (s, 1H), 6.67 (d, J=8.3 Hz, 1H), 7.00-7.05 (m, 2H). LC/MS (m/z): calcd for C$_{33}$H$_{55}$NO$_4$SSi (M)+: 589.9; found: 589.0.

C. 2-{[5-(1-{4-[2-(tert-Butyl-dimethyl-silanyloxy)-3,3-dimethyl-butoxy]-3-methyl-phenyl}-1-ethyl-propyl)-3-methyl-thiophen-2-ylmethyl]-amino}-acetic acid methyl ester

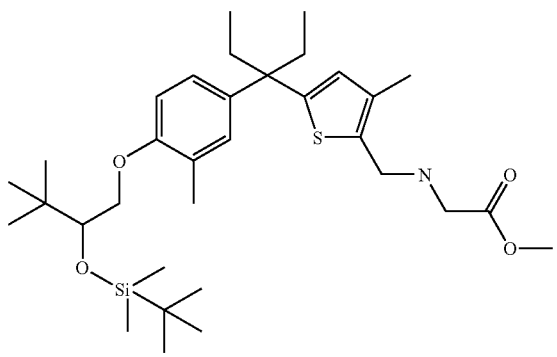

Using a procedure analogous to Example 41, 5-(1-{4-[2-(tert-Butyl-dimethyl-silanyloxy)-3,3-dimethyl-butoxy]-3-methyl-phenyl}-1-ethyl-propyl)-3-methyl-thiophene-2-carbaldehyde (additional example Lu-13-A) (2.11 g, 4.09 mm) and glycine methyl ester hydrochloride (0.56 g, 4.50 mmol) give the title compound (1.54 g, 2.61 mmol, 64%). %). $^1$H NMR (CDCl$_3$), δ 0.06 (s, 3H), 0.12 (s, 3H), 0.70 (t, J=6.9 Hz, 6H), 0.91 (s, 9H), 0.97 (s, 9H), 2.02-2.10 (m, 4H), 2.13 (s, 3H), 2.20 (s, 3H), 3.45 (s, 2H), 3.67 (dd, J=5.4, 3.4 Hz, 1H), 3.73 (s, 3H), 3.82-3.87 (m, 3H), 3.98 (dd, J=9.6, 3.4 Hz, 1H), 6.49 (s, 1H), 6.67 (d, J=8.3 Hz, 1H), 7.00-7.05 (m, 2H). LC/MS (m/z): calcd for C$_{33}$H$_{55}$NO$_4$SSi (M)+: 589.9; found: 589.0.

D. 2-{N-Acetyl-[5-(1-{4-[2-(tert-butyl-dimethyl-silanyloxy)-3,3-dimethyl-butoxy]-3-methyl-phenyl}-1-ethyl-propyl)-3-methyl-thiophen-2-ylmethyl]-amino}-acetic acid methyl ester

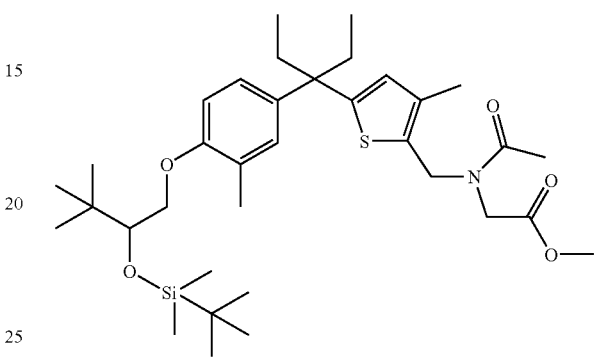

To a 0° C. solution of 2-{[5-(1-{4-[2-(tert-Butyl-dimethyl-silanyloxy)-3,3-dimethyl-butoxy]-3-methyl-phenyl}-1-ethyl-propyl)-3-methyl-thiophen-2-ylmethyl]-amino}-acetic acid metlhyl ester (1.54 g, 2.61 mmol) in CH$_2$C$_2$ (10 mL) is added acetyl chloride (0.20 mL, 2.88 mmol). The reaction is stirred at RT for 1 h, diluted with CH$_2$C$_2$ (100 mL), washed with 1.0 M HCl (2×30 mL), H$_2$O (25 mL); Na2SO4 dried, and concentrated. The resulting residue is chromatographed to give the title compound (1.32 g, 2.09 mmol, 80%). $^1$H NMR (CDCl$_3$), δ 0.06 (s, 3H), 0.12 (s, 3H), 0.69 (t, J=7.1 Hz, 6H), 0.91 (s, 9H), 0.97 (s, 9H), 2.00-2.05 (m, 4H), 2.06 (s, 3H), 2.07 (s, 1.11H), 2.10 (s, 1.89H), 2.21 (s, 1.89H), 2.24 (s, 1.11H), 3.66-3.71 (m, 4H), 3.83-3.89 (m, 1H), 3.95 (s, 0.74H), 3.96-4.01 (m, 1H), 4.04 (1.26H), 4.60 (1.26H), 4.68 (0.74H), 6.49 (s, 0.37H), 6.51 (s, 0.63H), 6.65-6.69 (m, 1H), 6.97-7.03 (m, 2H). LC/MS (m/z): calcd for C$_{35}$H$_{58}$NO$_5$SSi (M+H)$^+$: 632.4; found: 632.3.

E. 2-[N-Acetyl-(5-{1-ethyl-1-[4-(2-hydroxy-3,3-dimethyl-butoxy)-3-methyl-phenyl]-propyl}-3-methyl-thiophen-2-ylmethyl)-amino]-acetic acid

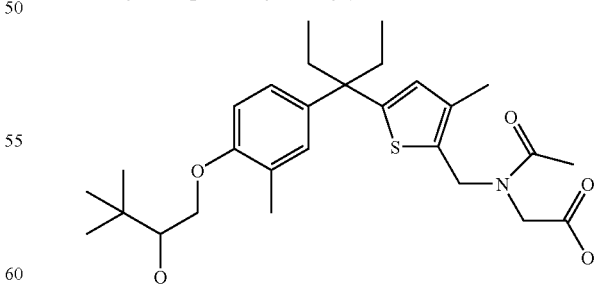

Using a procedure analogous to Example 124D, 2-{N-Acetyl-[5-(1-{4-[2-(tert-butyl-dimethyl-silanyloxy)-3,3-dimethyl-butoxy]-3-methyl-phenyl}-1-ethyl-propyl)-3-methyl-thiophen-2-ylmethyl]-amino}-acetic acid methyl ester (1.32 g, 2.09 mmol) gives the title compound (0.95 g, 1.83 mmol, 88%). ¹H NMR (CD30D), δ 0.72 (t, J=7.3 Hz, 3H), 0.73 (t, J=7.3 Hz, 3H), 1.05 (s, 9H), 2.03 (s, 3H), 2.05-2.14 (m, 4H), 2.16 (s, 1.5H), 2.18 (s, 1.5H), 2.22 (s, 1.5H), 2.24 (s, 1.5H), 3.66 (dd, J=7.6, 2.7 Hz, 1H), 3.91 (dd, J=10.1, 7.6 Hz, 1H), 3.98 (s, 1H), 4.03 (s, 1H), 4.16 (dd, J=10.1, 2.7 Hz, 1H), 4.67 (s, 1H), 4.71 (s, 1H), 6.59 (s, 0.5H), 6.63 (s, 0.5H), 6.80 (d, J=3.1 Hz, 0.5H), 6.82 (d, J=2.7 Hz, 0.5H), 7.01-7.10 (m, 2H). LC/MS (m/z): calcd for $C_{28}H_{40}NO_5SSi$ (M–H)⁻: 502.7; found: 502.2.

Example 131 and 132

Preparation of enantiomers of 2-[N-Acetyl-(5-{1-ethyl-1-[4-(2-hydroxy-3,3-dimethyl-butoxy)-3-methyl-phenyl]-propyl}-3-methyl-thiophen-2-ylmethyl)-amino]-acetic acid Enantiomer 1

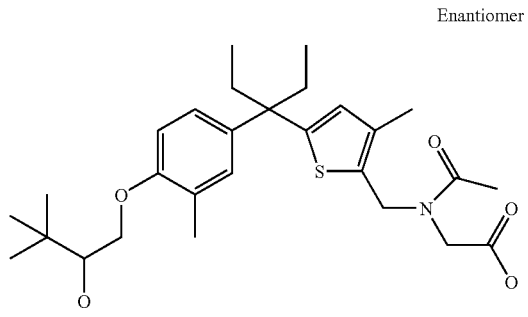

Enantiomer 2

A racemic mixture of 2-[N-acetyl-(5-{-ethyl-1-[4-(2-hydroxy-3,3-dimethyl-butoxy)-3-methyl-phenyl]-propyl}-3-methyl-thiophen-2-ylmethyl)-amino]-acetic acid (560 mg) is chromatographed (CHIRALPAK AD, 0.1% TFA in i-PrOH/MeOH/Hept (20/5/75),) to give fraction-1 (338 mg, rt=6.4 m), and fraction-2, (343 mg, rt=13.7 m). Fraction-1 is chromatographed to give the low Rf component (TLC: (EtOAc/ CH₃OH/HOAc, 85/15/0.5; Rf=0.5). The low Rf component is dissolved in CH₃OH (5 mL), treated with 0.5 M NaOCH₃ (1.2 ml, 0.59 mmol), and stirred at RT for 10 m. The reaction is concentrated and partitioned between 1.0 M HCl (2 ml)/H₂O (10 ml)/EtOAc (3×15 ml). The organic layer is MgSO4 dried and concentrated to give the enantiomer 1 of the title compound (Example 131) (153.7 mg, 27%).

Fraction-2 from the chiral resolution is manipulated as described for fraction-1 to give the enantiomer 2 of the title compound (Example 132) (149.9 mg, 27%).

Example 131, Enantiomer I CHIRALPAK AD, 0.1% TFA in i-PrOH/MeOH/Hept (20/5/75); rt=6.4 m.

NMR & LC/MS: identical to the racemic material, Example 130.

Example 132, Enantiomer 2 CHIRALPAK AD, 0.1% TFA in i-PrOH/MeOH/Hept (20/5/75); rt=13.7 m.

NMR & LC/MS: Identical to the racemic material, Example 130.

Example 133

Preparation of 2-[N-Acetyl-(5-{1-[4-(3,3-dimethyl-2-oxo-butoxy)-3-methyl-phenyl]-1-ethyl-propyl}-3-methyl-thiophen-2-yl-methyl)-amino]-acetic acid

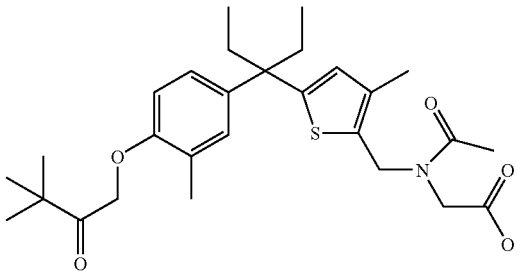

Using a procedure analogous to Example 50, from 2-[N-acetyl-(5-{1-[4-(3,3-dimethyl-2-oxo-butoxy)-3-methyl-phenyl]-1-ethyl-propyl}-3-methyl-thiophen-2-yl-methyl)-amino]acetic acid, Example 130 (0.35 g, 0.70 mmol) and Dess-Martin reagent (0.33 g, 0.77 mmol) give the title compound (0.11 g, 0.22 mmol, 31%). ¹H NMR (CD30D), δ 0.72 (t, J=7.6 Hz, 3H), 0.73 (t, J=7.0 Hz, 3H), 1.29 (s, 9H), 2.04-2.14 (m, 7H), 2.16 (s, 1.5H), 2.18 (s, 1.5H), 2.25 (s, 3H), 3.97 (s, 1H), 4.01 (s, 1H), 4.68 (s, 1H), 4.71 (s, 1H), 5.03 (s, 1H), 5.04 (s, 1H), 6.59 (s, 1H), 6.66-6.67 (m, 1H), 7.00-7.08 (m, 2H).

LC/MS (m/z): calcd for $C_{28}H_{38}NO_5SSi$ (M–H)⁻: 500.7; found: 500.3. δ

Example 134

Preparation of (5-{1-Ethyl-1-[4-(2-hydroxy-3,3-dimethyl-butoxy)-3-methyl-phenyl]-propyl}-3-methyl-thiophene-2-sulfonylamine)-acetic acid methyl ester

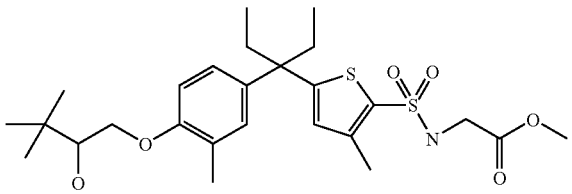

A. 1-{4-[1-Ethyl-1-(4-methyl-thiophen-2-yl)-propyl]-2-methyl-phenoxy}-3,3-dimethyl-butan-2-one

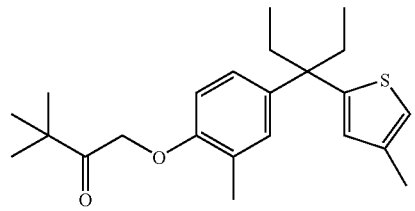

A mixture of 3'-[4-(hydroxy)-3-methylphenyl]-3'-[4-methylthiophen-2-yl]pentane (4.4 g, 16.4 mmol), 1-chloro-3,3-dimethyl-butan-2-one (2.37 ml, 18.1 mmol) and $K_2CO_3$ (3.39 g, 24.6 mmol) in acetone (40 ml) is refluxed overnight. After cooling, the reaction is filtered, concentrated and partitioned between EtOAc and 1N HCl. The organic phase is Na2SO4 dried and concentrated to give the title compound (6.2 g, quantitative).

$^1$H NMR (CDCl$_3$): δ 7.05 (d, 1H, J=1.2 Hz), 7.02 (dd, 1H, J=8.8, 2.4 Hz), 6.70 (s, 1H), 6.60 (d, 1H, J=1.2 Hz), 6.52 (d, 1H, J=8.8 Hz), 4.84 (s, 2H), 2.27 (s, 3H), 2.21 (s, 3H), 2.09 (q, 4H), 1.27 (s, 9H), 0.70 (t, 6H).

B. 1-{4-[1-Ethyl-1-(4-methyl-thiophen-2-yl)-propyl]-2-methyl-phenoxy}-3,3-dimethyl-butan-2-ol

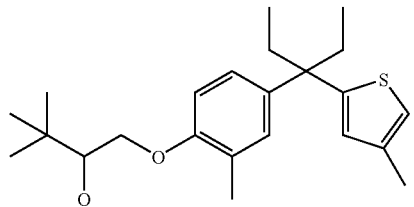

To a stirred solution of 1-{4-[1-Ethyl-1-(4-methyl-tliiophen-2-yl)-propyl]-2-methyl-phenyl}-3,3-dimethyl-butan-2-one (5.2 g, 14 mmol) in THF/MeOH (40 ml/10 ml) at 0° C. is added NaBH$_4$ (528 mg, 14 mmol), warmed to RT, and stirred for 1 h. The reaction is concentrated and the residue is partitioned between EtOAc and 0.2 N HCl. The organic layer is MgSO$_4$ dried and concentrated to give the title compound (5.4 g, quantitative).

$^1$H NMR (CDCl$_3$): δ 7.05 (s, 2H), 6.73 (s, 1H), 6.70 (s, 1H), 6.60 (s, 1H), 4.09 (dd, 1H, J=20 =8.1, 2.4 Hz), 3.87 (dd, 1H, J=8.1, 8.9 Hz), 3.70 (dd, 1H, J=8.9, 2.4 Hz), 2.20 (s, 6H), 2.07 (q, 4H), 1.01 (s, 9H), 0.70 (t, 6H);
ES-MS: 375 (M+1).

C. 1-{4-[1-Ethyl-1-(4-methyl-thiophen-2-yl)-propyl]-2-methyl-phenoxy}-2-(t-butyldimethylsilyloxy)-3,3-dimethyl-butane

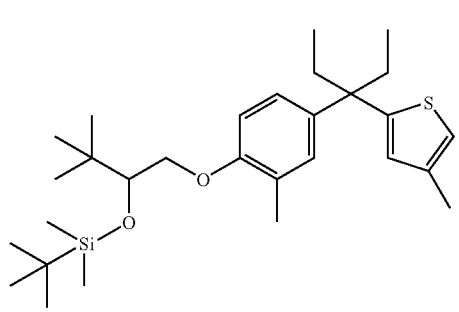

To a solution of 1-{4-[1-ethyl-1-(4-methyl-thiophen-2-yl)-propyl]-2-methyl-phenoxy}-3,3-dimethyl-butan-2-ol (7.5 g, 20 mmol) in dichloromethane (100 ml) at −78° C. is added 2,6-dimethylpyridine (5.8 ml, 50 mmol) followed by tert-butyldimethylsilyl trifluoromethanesulfonate (6.0 ml, 26 mmol). After stirring at RT for 2 h, the reaction diluted with dichoromethane and washed successively with 1N HCl followed by satd NaHCO$_3$. The organic layer is dried over MgSO$_4$ and concentrated to give the title product (9.5 g, 97%).

$^1$H NMR (CDCl$_3$): δ 7.02, 7.06 (m, 2H), 6.61, 6.71 (m, 3H), 3.98 (dd, 1H, J=3.5, 9.9 Hz), 3.84 (dd, 1H, J=5.8, 9.9 Hz), 3.66 (dd, 1H, J=3.5, 5.8 Hz), 2.20 (s, 3H), 2.19 (s, 3H), 2.08 (q, 4H), 0.96 (s, 9H), 0.90 (s, 9H), 0.70 (t, 6H), 0.10 (s, 3H), 0.05 (s, 3H).

D. 5-(1-{4-[2-(tert-Butyl-dimethyl-silanyloxy)-3,3-dimethyl-butoxy]-3-methyl-phenyl}-1-ethyl-propyl)-3-methyl-thiopliene-2-sulfonyl chloride

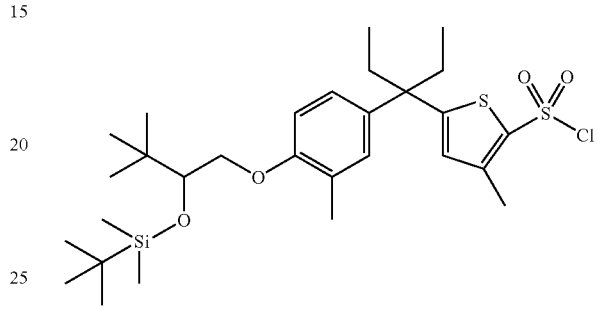

Add n-BuLi (6 ml, 9.6 mmol, 1.6 M/Hex) to a solution of 1-{4-[1-Ethyl-1-(4-methyl-thiopben-2-yl)-propyl]-2-methyl-phenoxy}-2-(t-butyldimethylsilyloxy)-3,3-dimethyl-butane (3.9 g, 8 mmol) in THF (20 ml) at 0° C. After 1 h, the mixture is transferred through cannula into a solution of SO$_2$C$_2$ (0.65 ml, 8 mmol) in pentane (30 ml) at −78° C. It is stirred at RT for 2 h and concentrated. The residue is dissolved in dichlorornethane (20 ml) and used for the next reaction without further purification.

E. [5-(1-{4-[2-(tert-Butyl-dimethyl-silanyloxy)-3,3-dimethyl-butoxy]-3-methyl-phenyl}-1-ethyl-propyl)-3-methyl-thiophene-2-sulfonylamine]-acetic acid methyl ester

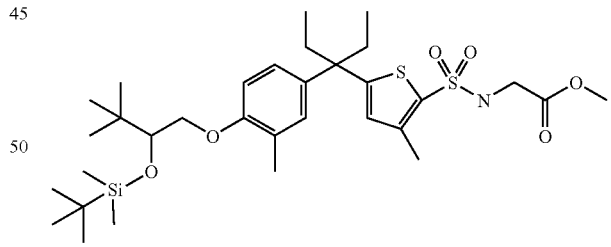

An aliquot of 5-(1-{4-[2-(tert-butyl-dimethyl-silanyloxy)-3,3-dimethyl-butoxy]-3-methyl-phenyl}-1-ethyl-propyl)-3-methyl-thiophene-2-sulfonyl chloride (step D) (4 ml, 1.5 mmol) is added to a suspension of glycine methyl ester hydrochloride (565 mg, 4.5 mmol) and Et$_3$N (0.94 ml, 6.75 mmol) in dichloromethane (10 ml) at 0° C. It is stirred at RT overnight, concentrated, and partitioned between EtOAc and 1N HCl. The organic layer is concentrated and chromatographed (Hex to 20% EtOAc/Hex) to give the title product (380 mg, 40%).

$^1$H NMR (CDCl$_3$): δ 7.01 (dd, 1H, J=2.0, 8.3 Hz), 6.97 (d, 1H, J=2.0 Hz), 6.68 (d, 1H, J=8.3 Hz), 6.59 (s, 1H), 5.10 (t,

1H), 3.98 (dd, 1H, J=3.5, 9.9 Hz), 3.84, 3.88 (m, 3H), 3.65, 3.69 (m, 4H), 2.41 (s, 3H), 2.20 (s, 3H), 2.09 (q, 4H), 0.97 (s, 9H), 0.90 (s, 9H), 0.70 (t, 6H), 0.11 (s, 3H), 0.05 (s, 3H);
ES-MS: 640 (M+1).

F. (5-{1-Ethyl-1-[4-(2-hydroxy-3,3-dimethyl-butoxy)-3-methyl-phenyl]-propyl}-3-methyl-thiophene-2-sulfonylamine)-acetic acid methyl ester

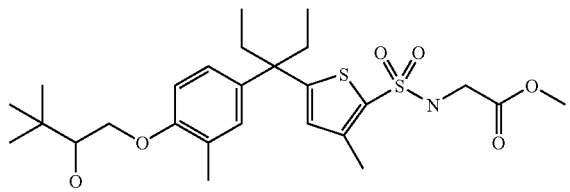

To a solution of [5-(1-{4-[2-(tert-butyl-dimethyl-silanyloxy)-3,3-dimethyl-butoxy]-3-methyl-phenyl}-1-ethyl-propyl)-3-methyl-thiophene-2-sulfonylamine]-acetic acid methyl ester (380 mg, 0.59 mmol) in acetonitrile (10 ml) at 0° C. is added hydrofluoride solution (3 ml, 48% in water). After stirring at RT for 2 h, the reaction is concentrated and partitioned between EtOAc and 1N HCl. The organic layer is washed successively with 1N HCl and brine. Tle organic layer is concentrated and chromatographed (Hex to 25% EtOAc/Hex) to give the title compound (250 mg, 82%).
$^1$H NMR (CDC$_3$): δ 7.02 (dd, 1H, J=2.5, 8.3 Hz), 6.97 (d, 1H, J=2.0 Hz), 6.73 (d, 1H, J=8.3 Hz), 6.58 (s, 1H), 5.12 (t, 1H), 4.10 (dd, 1H, J=2.5, 8.6 Hz), 3.87 (dd, 1H, J=8.6, 8.8 Hz), 3.84 (d, 2H, J=5.3 Hz), 3.71 (dd, 1H, J=2.5, 8.8 Hz), 3.66 (s, 3H), 2.40 (s, 3H), 2.20 (s, 3H), 2.07 (q, 4H), 1.02 (s, 9H), 0.69 (t, 6H);
HRMS: Calcd. for C26H43N2O6S2 (M+18), 543.2563, found, 543.2550.

Example 135 and Example 136

Preparation of enantiomers of (5-{1-ethyl-1-[4-(2-hydroxy-3,3-dimethyl-butoxy)-3-methyl-phenyl]-propyl}-3-methyl-thiophene-2-sulfonylamine)-acetic acid methyl ester

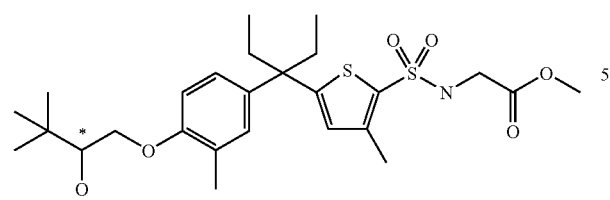

A racemic mixture of (5-{(1-ethyl-1-[4-(2-hydroxy-3,3-dimethyl-butoxy)-3-methyl-phenyl]-propyl}-3-methyl-thiophene-2-sulfonylanine)-acetic acid methyl ester (750 mg) is chromatographed on Chiralpak AD column to give enantiomer 1, Example 135 (400 mg, 53%) and enantiomer 2, Example 136 (320 mg, 43%).
HPLC: Chiralpak AD (4.6×150 mm); 35% heptane, 65% EtOH; flow rate: 0.6 ml/m;
UV: 260 nm
Enantiomer 1, Example 135: rt=4.5 m;
$^1$H NMR (CDCl$_3$): equivalent to Example 134

Enantiomer 2, equivalent to Example 136: rt=5.6 m.
$^1$H NMR (CDCl$_3$): equivalent to Example 134

Example 137

Preparation of (5-{1-Ethyl-1-[4-(2-hydroxy-3,3-dimethyl-butoxy)-3-methyl-phenyl]-propyl}-3-methyl-thiophene-2-sulfonylamine)-acetic acid To a solution of (5-{1-ethyl-1-[4-(2-hydroxy-3,3-dimethyl-butoxy)-3-methyl-phenyl]-propyl}-3-methyl-thiophene-2-sulfonylamine)-acetic acid methyl ester (210 mg, 0.4 mmol) in dioxane (10 ml) is added 2N LiOH/H20 solution (10 ml) and stirred at RT overnight. The reaction is concentrated and partitioned between EtOAc/1N HCl. The organic layer is concentrated to give the title compound (180 mg, 88%).
$^1$H NMR (CDCl$_3$): δ 7.01 (dd, 1H, J=2.5, 8.3 Hz), 6.97 (d, 1H, J=2.0 Hz), 6.73 (d, 1H, J=8.3 Hz), 6.60 (s, 1H), 5.16 (t, 1H), 4.12 (dd, 1H, J=2.9, 9.3 Hz), 3.88 (dd, 1H, J=8.8, 9.3 Hz), 3.86(d, 2H, J=5.5 Hz), 3.72 (dd, 1H, J=2.9, 8.8 Hz), 2.40 (s, 3H), 2.20 (s, 3H), 2.05 (q, 4H), 1.01 (s, 9H), 0.70 (t, 6H);
HRMS: Calcd. for C25H38NO6S2 (M+1), 512.2146, found, 512.2141.

Example 138

Preparation of enantiomers of (5-{1-ethyl-1-[4-(2-hydroxy-3,3-dimethyl-butoxy)-3-methyl-phenyl]-propyl}-3-methyl-thiophene-2-sulfonylamine)-acetic acid Using aprocedure analogous to Example 136, enantiomer 1 of (5-{1-Ethyl-1-[4-(2-hydroxy-3,3-dimethyl-butoxy)-3-methyl-phenyl]-propyl}-3-methyl-thiophene-2-sulfonylamine)-acetic acid methyl ester (390 mg, 0.74 mmol) (Example 135) gives the title compound (250 mg, 66%). $^1$H NMR (CDCl$_3$): equivalent to Example 134;
ES-MS: 512 (M+1).

Example 139

Preparation of (5-{1-[4-(3,3-Dimethyl-2-oxo-butoxy)-3-methyl-phenyl]-1-ethyl-propyl}-3-methyl-thiophene-2-sulfonylamine)-acetic acid

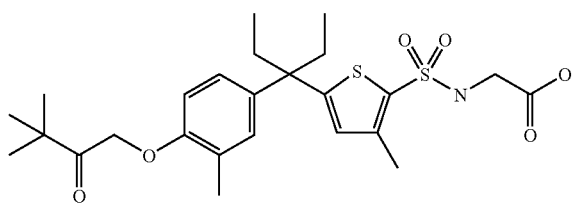

A. [5-(1-{4-[2-(tert-Butyl-dimethyl-silanyloxy)-3,3-dimethyl-butoxy]-3-methyl-phenyl}-1-ethyl-propyl)-3-methyl-thiophene-2-sulfonylamine]-acetic acid tert-butyl ester

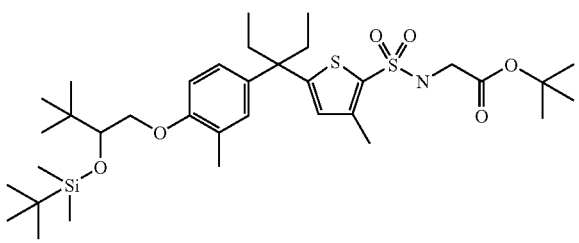

Using a procedure analogous to Example 134E, 5-(1-{4-[2-(tert-butyl-dimethyl-silanyloxy)-3,3-dimethyl-butoxy]-3-methyl-phenyl}-1-ethyl-propyl)-3-methyl-thiophene-2-sulfonyl chloride and 2-amino-acetic acid tert-butyl ester (787 mg, 6 mmol) give the title compound (670 mg, 20%).

$^1$H NMR (CDCl$_3$): δ 7.01 (dd, 1H, J=2.5, 8.8 Hz), 6.97 (d, 1H, J=2.0 Hz), 6.68 (d, 1H, J=8.8 Hz), 6.57 (s, 1H), 5.09 (t, 1H), 3.98 (dd, 1H, J=3.5, 9.8 Hz), 3.86 (d, 1H, J=5.9, 9.8 Hz), 3.71 (d, 2H, J=5.4 Hz), 3.67 (dd, 1H, J=3.5, 5.9 Hz), 2.40 (s, 3H), 2.20 (s, 3H), 2.08 (q, 4H), 1.40 (s, 9H), 0.97 (s, 9H), 0.90 (s, 9H), 0.70 (t, 6H), 0.11 (s, 3H), 0.05 (s, 3H).

B. (5-{1-Ethyl-1-[4-(2-hydroxy-3,3-dimethyl-butoxy)-3-methyl-phenyl]-propyl}-3-methyl-thiophene-2-sulfonylamine)-acetic acid tert-butyl ester

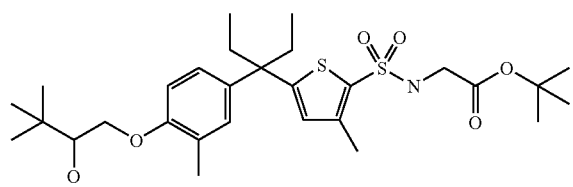

A mixture of [5-(1-{4-[2-(tert-butyl-dimetiyl-silanyloxy)-3,3-dimethyl-butoxy]-3-methyl-phenyl}-1-ethyl-propyl)-3-methyl-thiophene-2-sulfonylaminel-acetic acid tert-butyl ester (667 mg, 1 mmol) and tetra-n-butylammonium fluoride (6 ml, 1 M in THF) is stirred at RT for 3 d. It is diluted with EtOAc and washed with NH$_4$Cl. The organic layer is concentrated and chromatographed (Hex to 15% EtOAc/Hex) to give the title compound (360 mg, 63%).

ES-MS: 568 (M+1).

C. (5-{1-[4-(3,3-Dimethyl-2-oxo-butoxy)-3-methyl-phenyl]-1-ethyl-propyl}-3-methyl-thiophene-2-sulfonylamine)-acetic acid tert-butyl ester

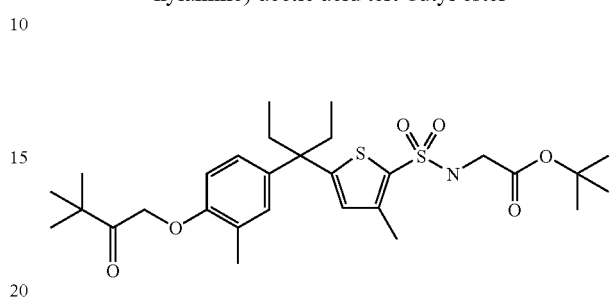

A mixture of (5-{1-ethyl-1-[4-(2-hydroxy-3,3-dimethyl-butoxy)-3-methyl-phenyl]-propyl}-3-methyl-thiophene-2-sulfonylamine)-acetic acid tert-butyl ester (360 mg, 0.63 mmol), pyridinium dichromate (179 mg, 0.48 mmol) and Ac$_2$O (66 μL, 0.7 mmol) in dichloromethane (10 ml) is refluxed for 3 h. The reaction is concentrated and chromatographed (Hex to 15% EtOAc/Hex) to give the title compound (330 mg, 92%); $^1$H NMR (CDC$_3$): δ 6.96, 7.23 (m, 2H), 6.56 (s, 1H), 6.51 (d, 1H, J=8.3 Hz), 6.57 (s, 1H), 5.08 (t, 1H), 4.85 (s, 2H), 3.71 (d, 2H, J=5.4 Hz), 2.40 (s, 3H), 2.26 (s, 3H), 2.07 (q, 4H), 1.40 (s, 9H), 1.26 (s, 9H), 0.90 (s, 9H), 0.70 (t, 6H);

HRMS: calcd. for C29H47N2O6S2 (M+18), 583.2876, found, 583.2876.

D. (5-{1-[4-(3,3-Dimethyl-2-oxo-butoxy)-3-methyl-phenyl]-1-ethyl-propyl}-3-methyl-thiophene-2-sulfonylamine)-acetic acid

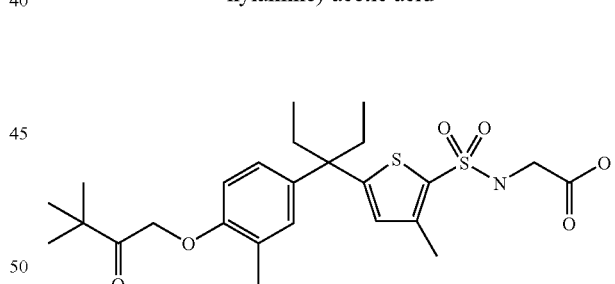

A solution of (5-{1-[4-(3,3-dimethyl-2-oxo-butoxy)-3-methyl-phenyl]-1-ethyl-propyl}-3-methyl-thiophene-2-sulfonylamine)-acetic acid tert-butyl ester (320 mg, 0.57 mmol) in 4N HCl/dioxane (10 ml) is stirred at RT overnight. The reaction is concentrated and chromatographed (Hex to 0.5% AcOH in 50% EtOAc/Hex) to give the title compound (250 mg, 87%).

$^1$H NMR (CDCl$_3$): δ 7.01 (d, 1H, J=2.5 Hz), 6.92 (dd, 1H, J=2.5, 8.8 Hz), 6.62 (s, 1H), 6.45 (d, 1H, J=8.8 Hz), 5.10 (t, 1H), 4.91 (s, 2H), 3.86(d, 2H, J=5.4 Hz), 2.41 (s, 3H), 2.25 (s, 3H), 2.04 (q, 4H), 1.25 (s, 9H), 0.71 (t, 6H);

HRMS: Calcd. for C25H39N2O6S2 (M+18), 527.2250, found, 527.2245.

Example 140

Preparation of 3-(5-{1-ethyl-1-[4-(2-hydroxy-3,3-dimethyl-butoxy)-3-methyl-phenyl]-propyl}-3-methyl-thiophene-2-sulfonylamine)-propionic acid ethyl ester

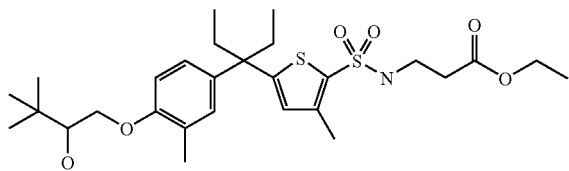

Using procedures analogous to Example 134E and Example 134F, an aliquot of 5-(1-{4-[2-(tert-butyl-dimethyl-silanyloxy)-3,3-dimethyl-butoxy]-3-methyl-phenyl}-1-ethyl-propyl)-3-methyl-tliiophene-2-sulfonyl chloride (Example 134D) and 3-amino-propionic acid ethyl ester hydrochloride give the title compound (19% overall yield).

$^1$H NMR (CDC$_3$): δ 7.02 (dd, 1H, J=2.5, 8.8 Hz), 6.98 (d, 1H, J=2.0 Hz), 6.73 (d, 1H, J=8.8 Hz), 6.58 (s, 1H), 5.26 (t, 1H), 4.14 (q, 2H), 4.10 (dd, 1H, J=2.9, 8.9 Hz), 3.87 (dd, 1H, J=8.8, 8.9 Hz), 3.71 (dd, 1H, J=2.9, 8.8 Hz), 3.25 (m, 2H), 2.50 (t, 2H), 2.39 (s, 3H), 2.20 (s, 3H), 2.06 (q, 4H), 1.02 (s, 9H), 0.70 (t, 6H);

HRMS: Calcd. for C28H44NO6S2 (M+1), 554.2610, found, 554.2590.

Example 141

Preparation of 3-(5-{1-ethyl-1-[4-(2-hydroxy-3,3-dimethyl-butoxy)-3-methyl-phenyl]-propyl}-3-methyl-thiophene-2-sulfonylamine)-propionic acid

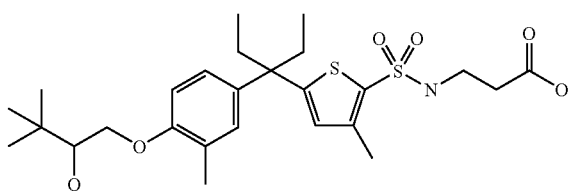

The title compound is obtained from 3-(5-{1-ethyl-1-[4-(2-hydroxy-3,3-dimethyl-butoxy)-3-methyl-phenyl]-propyl}-3-methyl-thiophene-2-sulfonylamine)-propionic acid ethyl ester using an analogous procedure as described for Example 137.

$^1$H NMR (CDC$_3$): δ 7.02 (d, 1H, J=8.3 Hz), 6.98 (s, 1H), 6.73 (d, 1H, J=8.3 Hz), 6.60 (s, 1H), 5.50 (t, 1H), 4.13 (d, 1H), 4.12 (dd, 1H, J=2.0, 8.9 Hz), 3.88 (dd, 1H, J=8.8, 8.9 Hz), 3.72 (dd, 1H, J=2.0, 8.8 Hz), 3.26 (m, 2H), 2.55 (t, 2H), 2.39 (s, 3H), 2.20 (s, 3H), 2.06 (q, 4H), 1.02 (s, 9H), 0.70 (t, 6H);

HRMS: Calcd. for C26H40NO6S2 (M+1), 526.2297, found, 526.2275.

Example 142 and Example 143

Preparation of enantiomners of 3-(5-{1-Ethyl-1-[4-(2-hydroxy-3,3-dimethyl-butoxy)-3-methyl-phenyl]-propyl}-3-methyl-thiophene-2-sulfonylamine)-propionic acid

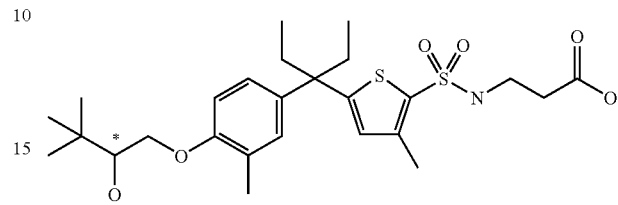

A racemic mixture of 3-(5-{1-ethyl-1-[4-(2-hydroxy-3,3-dimethyl-butoxy)-3-methyl-phenyl]-propyl}-3-methyl-thiophene-2-sulfonylamine)-propionic acid (200 mg) is chromatographed on a Chiralpak AD column to give enantiomer 1, example 142 (79 mg, 40%) and enantiomer 2, Example 143 (79 mg, 40%).

HPLC: Chiralpak AD (4.6×250 mm); 0.1% TFA in 15% EtOH/85% Hept; flow rate: 1.0 ml/m; UV: 260 nm Enantiomer 1: rt=12 m;

$^1$H NMR (CDCl$_3$): equivalent to Example 141;

ES-MS: 526 (M+1)

Enantiomer 2: rt=21 m;

$^1$H NMR (CDCl$_3$): equivalent to Example 141;

ES-MS: 526 (M+1).

Example 144

Preparation of 3-(5-{1-[4-(3,3-Dimethyl-2-oxo-butoxy)-3-methyl-phenyl]-1-ethyl-propyl}-3-methyl-thiophene-2-sulfonylamine)-propionic acid

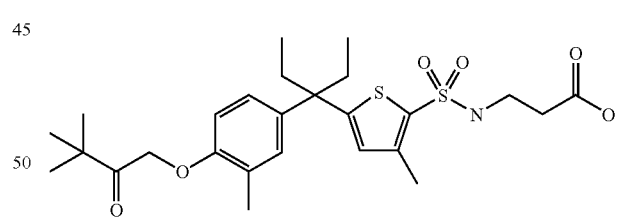

The title compound is obtained from 5-(1-{4-[2-(tert-butyl-dimethyl-silanyloxy)-3,3-dimethyl-butoxy]-3-methyl-phenyl}-1-ethyl-propyl)-3-methyl-thiophene-2-sulfonyl chloride and 2-amino-acetic acid tert-butyl ester and 3-amino-propionic acid t-butyl ester hydrochloride using an analogous procedures as described for Example 139A to Example 139D.

$^1$H NMR (CDCl$_3$): δ 6.99 (s, 1H), 6.97 (d, 1H, J=8.4 Hz), 6.59 (s, 1H), 6.50 (d, 1H, J=8.4 Hz), 5.61 (t, 1H), 4.87 (s, 2H), 3.26 (m, 2H), 2.55 (t, 2H), 2.39 (s, 3H), 2.25 (s, 3H), 2.06 (q, 4H), 1.26 (s, 9H), 0.69 (t, 6H);

ES-MS: 524 (M+1).

Example 145

Preparation of 3-[(5-{1-[4-(3,3-Dimethyl-2-oxo-butoxy)-3-methyl-phenyl]-1-ethyl-propyl}-3-methyl-thiophene-2-sulfonyl)-methyl-amine]-propionic acid

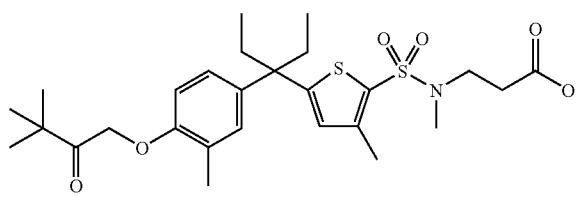

A. 3-[(5-{1-[4-(3,3-Dimethyl-2-oxo-butoxy)-3-methyl-phenyl]-1-ethyl-propyl}-3-methyl-thiophene-2-sulfonyl)-methyl-amine]-propionic acid tert-butyl ester

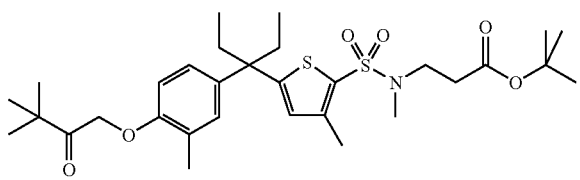

To a mixture of 3-(5-{1-[4-(3,3-dimethyl-2-oxo-butoxy)-3-methyl-phenyl]-1-ethyl-propyl}-3-methyl-thiophene-2-sulfonylamine)-propionic acid tert-butyl ester (Example 143C) (400 mg, 0.69 mmol) and THF (15 ml) is added PPh$_3$ (272 mg, 1.04 mmol), diethyl azodicarboxylate (163 μL, 1.04 mmol) and methanol (42 μL, 1.04 mmol). The reaction is stirred at RT overnight, concentrated and chromatographed (Hex to 20% EtOAc/Hex) to give the title compound (240 mg, 59%).

$^1$H NMR (CDCl$_3$): δ 6.99 (s, 1H), 6.97 (d, 1H, J=8.4 Hz), 6.57 (s, 1H), 6.52 (d, 1H, J=8.4 Hz), 4.85 (s, 2H), 3.37 (t, 2H), 2.81 (s, 3H), 2.51 (t, 2H), 2.41 (s, 3H), 2.26 (s, 3H), 2.06 (q, 4H), 1.44 (s, 9H), 1.26 (s, 9H), 0.69 (t, 6H).

B. 3-[(5-{1-[4-(3,3-Dimethyl-2-oxo-butoxy)-3-methyl-phenyl]-1-ethyl-propyl}-3-methyl-thiophene-2-sulfonyl)-methyl-amine]-propionic acid

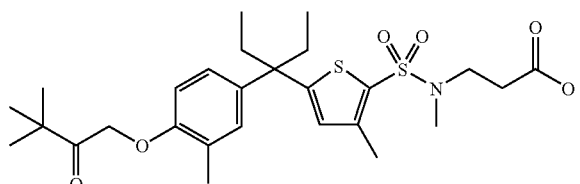

The title compound is prepared from 3-[(5-{1-[4-(3,3-dimethyl-2-oxo-butoxy)-3-methyl-phenyl]-1-ethyl-propyl}-3-methyl-thiophene-2-sulfonyl)-methyl-amine]-propionic acid tert-butyl ester using a procedure analogous to Example 139D.

$^1$H NMR (CDCl$_3$): δ 6.99 (s, 1H), 6.97 (d, 1H, J=8.4 Hz), 6.60 (s, 1H), 6.50 (d, 1H, J=8.4 Hz), 4.87 (s, 2H), 3.41 (t, 2H), 2.84 (s, 3H), 2.63 (t, 2H), 2.41 (s, 3H), 2.26 (s, 3H), 2.06 (q, 4H), 1.26 (s, 9H), 0.69 (t, 6H).

HRMS: calcd. for C27H40NO6S2, 538.2297, found, 538.2296.

Example 146

2-(R)-(5-{1-[4-(3,3-Dimethyl-2-oxo-butoxy)-3-methyl-phenyl]-1-ethyl-propyl}-3-methyl-thiophene-2-sulfonylamine)-propionic acid

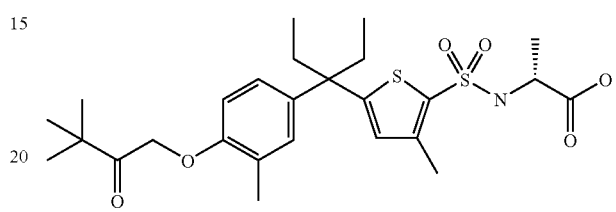

The title compound is prepared from 2-(R)-amino-propionic acid tert-butyl ester hydrochloride following an analogous procedure as described for Example 139.

$^1$H NMR (CDCl$_3$): δ 6.96 (d, 1H, J=2.5 Hz), 6.97 (dd, 1H, J=2.0, 8.8 Hz), 6.61 (s, 1H), 6.44 (d, 1H, J=8.5 Hz), 5.26 (d, 1H, J=8.3 Hz), 4.92 (s, 2H), 4.11 (m, 1H), 2.40 (s, 3H), 2.25 (s, 3H), 2.06 (q, 4H), 1.42 (d, 3H, J=7.4 Hz), 1.25 (s, 9H), 0.69 (t, 6H);

ES-MS: 524 (M+1).

Example 147

2-(R)-(5-{1-[4-(3,3-Dimethyl-2-tbioxo-butoxy)-3-methyl-phenyl]-1-ethyl-propyl}-3-methyl-thiophene-2-sulfonylamine)-propionic acid

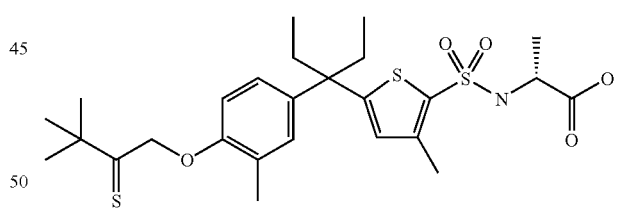

A mixture of 2-(R)-(5-{1-[4-(3,3-dimethyl-2-oxo-butoxy)-3-methyl-phenyl]-1-etbyl-propyl}-3-methyl-thiophene-2-sulfonylamine)-propionic acid (125 mg, 0.2 mmol) and Lawesson's reagent (236 mg, 0.5 mmol) in dichloroethane (7 ml) is refluxed for 3 d. The solvent is concentrated and chromatographed (0.1% AcOH in 50% EtOAc/Hex) to give the title compound (67 mg, 52%).

$^1$H NMR (CDC$_3$): δ 6.97 (s, 1H), 6.96 (d, 1H, J=8.4 Hz), 6.60 (s, 1H), 6.50 (d, 1H, J=8.4 Hz), 5.19 (d, 1H, J=8.8 Hz), 4.86 (s, 2H), 4.14 (m, 1H), 2.40 (s, 3H), 2.25 (s, 3H), 2.06 (m, 4H), 1.38 (d, 3H), 1.26 (s, 9H), 0.69 (t, 6H);

HRMS: calcd. for C26H38NO5S3, 540.1912, found, 540.1908.

Example 148

Preparation of 2-(5-{1-Ethyl-1-[4-(2-hydroxy-3,3-dimethyl-butoxy)-3-methyl-phenyl]-propyl}-3-methyl-thiophene-2-sulfonylamine)-2-methyl-propionic acid methyl ester

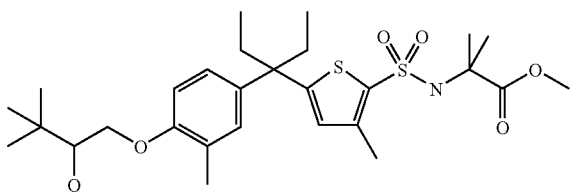

Using analogous procedures as described for Example 134D to Example 134F, 2-amino-2-methyl-propionic acid methyl ester hydrochloride gives the title compound (20% overall yield).

$^1$H NMR (CDCl$_3$): δ 7.03 (dd, 1H, J=2.4, 8.4 Hz), 6.96 (d, 1H, J=2.3 Hz), 6.72 (d, 1H, J=8.8 Hz), 6.53 (s, 1H), 5.42 (s, 1H), 4.10 (dd, 1H, J=2.6, 9.2 Hz), 3.87 (dd, 1H, J=8.8, 9.2 Hz), 3.69 (dd, 1H, J=2.6, 8.8 Hz), 3.67 (s, 3H), 2.38 (s, 3H), 2.19 (s, 3H), 2.06 (q, 4H), 1.48 (s, 6H), 1.02 (s, 9H), 0.69 (t, 6H);

HRMS: Calcd. for C28H44NO6S2 (M+1), 554.2610, found, 554.2610.

Example 149

Preparation of 2-(5-{1-ethyl-1-[4-(2-hydroxy-3,3-dimethyl-butoxy)-3-methyl-phenyl]-propyl}-3-methyl-thiophene-2-sulfonylamine)-benzoic acid

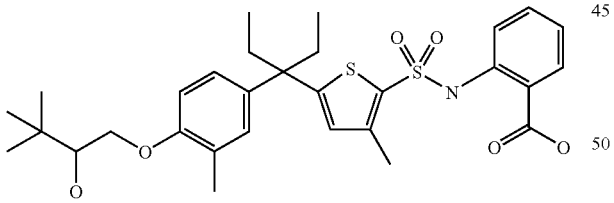

Using analogous procedures as described for Example 134D to Example 134F and Example 137, 2-amino-benzoic acid methyl ester gives the title compound (8% overall yield).

$^1$NMR (400 MHz, CDCl$_3$) δ 10.54 (s, 1H), 8.03 (d, 1H, J=7.9 Hz), 7.71 (d, 1H, J=8.4 Hz), 7.48 (t, 1H, =7.9 Hz), 7.09 (t, 1H, J=7.7 Hz), 6.93 (dd, 1H, J=8.6, 2.4 Hz), 6.86 (s, 1H), 6.70 (d, 1H, J=8.4 Hz), 6.48 (s, 1H), 4.14-4.07 (m, 1H), 3.89 (t, 1H, J=9.0 Hz), 3.72 (dd, 1H, J=8.6, 2.4 Hz), 2.30 (s, 3H), 2.16 (s, 3H), 2.04-1.93 (m, 4H), 1.02 (s, 9H), 0.60 (t, 6H, J=7.3 Hz).

High Res. EI-MS: 574.2305; calc. for C$_{30}$H$_{39}$NO$_6$S$_2$+H: 574.2297

Example 150

Preparation of epimer 1 of 2-(R)-(5-{1-ethyl-1-[4-(2-hydroxy-3,3-dimethyl-butoxy)-3-methyl-phenyl]-propyl}-3-methyl-thiophene-2-sulfonylamine)-propionic acid methyl ester

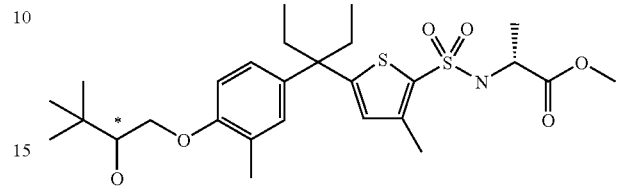

A. Enantiomer 1 of 1-{4-[1-ethyl-1-(4-methyl-thiophen-2-yl)-propyl]-2-methyl-phenoxy}-3,3-dimethyl-butan-2-ol

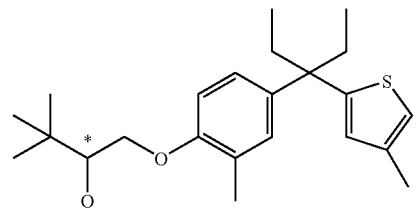

To a mixture of (R)-2-methyl-CBS-oxazaborolidine (0.1 ml, 0.1 mmol, 1M in toluene), borane-N,N-dimethyl aniline complex (0.18 ml, 1 mmol) in THF (5 ml) is added a solution of 1-{4-[1-ethyl-1-(4-methyl-thiophen-2-yl)-propyl]-2-methyl-phenoxy}-3,3-dimethyl-butan-2-one (372 mg, 1 mmol) in THF (5 ml) over a period of m. The reaction is stirred at RT for 2 h and MeOH (2 ml) is added followed by 1N hydrochloric acid. The mixture is extracted with EtOAc and the organic phase is concentrated and chromatographed (Hex to 25% EtOAc/Hex) to give the title compound (305 mg, 82%).

HPLC: Chiralpak AD (0.46×25 cm); 20% 2-propanol, 80% heptane; flow rate: 1.0 ml/m; UV: 225 nm;
Enantiomer 1: 91% ee; rt: 4.03 m.
$^1$H NMR (CDC$_3$) equivalent to Example 134B

B. Epimer 1 of 2-(R)-(5-{1-Ethyl-1-[4-(2-hydroxy-3,3-dimethyl-butoxy)-3-methyl-phenyl]-propyl}-3-methyl-tliiophene-2-sulfonylamine)-propionic acid methyl ester

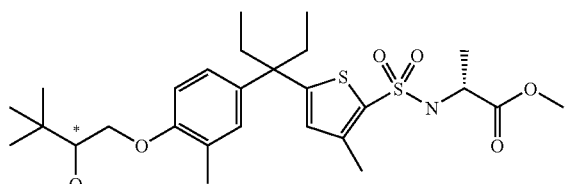

Using analogous procedures described in Example 134C to Example 134F, enantiomer 1 of 1-{4-[1-ethyl-1-(4-methylthiophen-2-yl)-propyl]-2-methyl-phenoxy}-3,3-dimethyl-butan-2-ol and 2-(R)-amino-propionic acid methyl ester hydrochloride give the title compound (27% overall yield).

$^1$NMR (400 MHz, CDCl$_3$) δ 7.01 (d, 1H, J=8.4 Hz), 6.96 (s, 1H), 6.72 (d, 1H, J=8.4 Hz), 6.56 (s, 1H), 5.26 (d, 1H, J=8.8 Hz), 4.10-4.03 (m, 2H), 3.86 (t, 1H, J=9.0 Hz), 3.71 (dd, 1H, J=8.8, 2.2 Hz), 3.59 (s, 3H), 2.38 (s, 3H), 2.19 (s, 3H), 2.11-2.03 (m, 4H), 1.38 (d, 3H, J=7.0 Hz), 1.01 (s, 9H), 0.68 (t, 6H, J=7.3 Hz).

High Res. EI-MS: 540.24556; calc. for C$_{27}$H$_{41}$NO$_6$S$_2$+H: 540.2454

Example 151

Preparation of epimer 1 of 2-(R)-(5-{1-Ethyl-1-[4-(2-hydroxy-3,3-dimethyl-butoxy)-3-methyl-phenyl]-propyl}-3-methyl-thiophene-2-sulfonylamine)-propionic acid

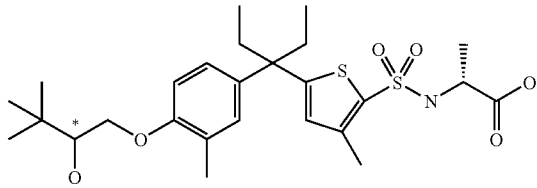

Using an analogous procedure to Example 137, epimer 1 of 2-(R)-(5-{1-ethyl-1-[4-(2-hydroxy-3,3-dimethyl-butoxy)-3-methyl-phenyl]-propyl}-3-methyl-thiophene-2-sulfonylamine)-propionic acid methyl ester (Example 150) gives the title compound (98%).

$^1$NMR (400 MHz, CDCl$_3$) δ 7.04-6.98 (m, 1H), 6.96 (s, 1H), 6.73 (d, 1H, J=8.8 Hz), 6.59 (s, 1H), 5.29 (d, 1H, J=8.8 Hz), 4.14-4.07 (m, 2H), 3.88 (t, 1H, J=9.0 Hz), 3.74-3.69 (m, 1H), 2.38 (s, 3H), 2.19 (s, 3H), 2.12-2.01 (m, 4H), 1.41 (d, 3H, J=7.0 Hz), 1.01 (s, 9H), 0.69 (t, 6H, J=7.3 Hz).

High Res. EI-MS: 526.2284; calc. for C$_{26}$H$_{39}$NO$_6$S$_2$+H: 526.2297

Example 152

Preparation of enantiomer 1 of (5-{1-Ethyl-1-[4-(2-hydroxy-3,3-dimethyl-butoxy)-3-methyl-phenyl]-propyl}-thiophene-2-sulfonylaamine)-acetic acid methyl ester

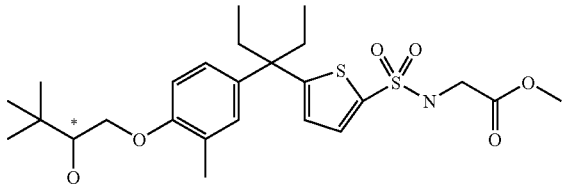

Using a procedure analogous to Example 150A, 1-[4-(1-ethyl-1-thiophen-2-yl-propyl)-2-methyl-phenoxy]-3,3-dimethyl-butan-2-one gives the title compound (18%). $^1$H NMR (CDCl$_3$) δ 7.43 (d, 1H, J=4.0 Hz), 7.02 (dd, 1H, J=2.0, 8.5 Hz), 6.98 (s, 1H), 6.74 (d, 1H, J=8.8 Hz), 6.73 (d, 1H, J=8.8 Hz), 5.11 (t, 1H), 4.10 (dd, 1H, J=2.6, 9.2 Hz), 3.88 (dd, 1H, J=8.8, 9.2 Hz), 3.85 (d, 2H, J=4.8 Hz), 3.71 (dd, 1H, J=2.6, 8.8 Hz), 3.66 (s, 3H), 2.19 (s, 3H), 2.07 (m, 4H), 1.01 (s, 9H), 0.70 (t, 6H);

HRMS: Calcd. for C25H41N2O6S2 (M+18), 529.2406, found, 529.2413.

Example 153

Preparation of enantiomer 1 of (5-{1-Ethyl-1-[4-(2-hydroxy-3,3-dimethyl-butoxy)-3-methyl-phenyl]-propyl}-thiophene-2-sulfonylamine)-acetic acid

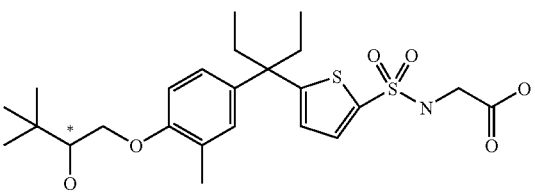

Using an analogous precedure to Example 137, enantiomer 1 of (5-{1-ethyl-1-[4-(2-hydroxy-3,3-dimethyl-butoxy)-3-methyl-phenyl]-propyl}-thiophene-2-sulfonylamine)-acetic acid methyl ester give the title compound (quant).

$^1$H NMR (CDC$_3$) δ 7.44 (d, 1H, J=4.0 Hz), 7.0 (d, 1H, J=8.4 Hz), 6.98 (s, 1H), 6.78 (d, 1H, J=4.0 Hz), 6.74 (d, 1H, J=8.4 Hz), 5.11 (t, 1H), 4.10 (dd, 1H, J=2.5, 9.2 Hz), 3.88 (dd, 1H, J=8.8, 9.2 Hz), 3.85 (d, 2H, J=4.4 Hz), 3.71 (dd, 1H, J=2.5, 8.8 Hz), 2.19 (s, 3H), 2.07 (m, 4H), 1.01 (s, 9H), 0.70 (t, 6H);

HRMS: Calcd. for C24H39N2O6S2 (+18), 515.2249, found, 515.2267.

Example 154

Preparation of enantiomer 1 of (5-{1-ethyl-1-[3-ethyl-4-(2-hydroxy-3,3-dimethyl-butoxy)-phenyl]-propyl}-thiophene-2-sulfonylamine)-acetic acid methyl ester

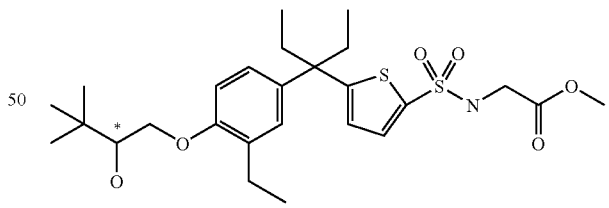

Using a procedure analogous to Example 150A, 1-[2-ethyl-4-(1-ethyl-1-thiophen-2-yl-propyl)-phenoxy]-3,3-dimethyl-butan-2-one gives the title compound (34%). $^1$H NMR (CDCl$_3$) δ 7.43 (d, 1H, J=3.5 Hz), 7.02 (d, 1H, J=8.3 Hz), 7.00 (s, 1H), 6.76 (d, 1H, J=3.5 Hz), 6.75 (d, 1H, J=8.3 Hz), 5.06 (t, 1H), 4.10 (dd, 1H, J=2.6, 9.3 Hz), 3.88 (dd, 1H, J=8.8, 9.3 Hz), 3.85 (d, 2H, J=5.8 Hz), 3.71 (dd, 1H, J=2.6, 8.8 Hz), 3.67 (s, 3H), 2.60 (q, 2H), 2.06 (q, 4H), 1.14 (t, 3H), 1.01 (s, 9H), 0.70 (t, 6H);

HRMS: Calcd. for C26H40NO6S2 (M+1), 526.2297, found; 526.2285.

Example 155

Preparation of enantiomer 1 of (5-{1-Ethyl-1-[3-ethyl-4-(2-hydroxy-3,3-dimethyl-butoxy)-phenyl]-propyl}-thiophene-2-sulfonylamine)-acetic acid

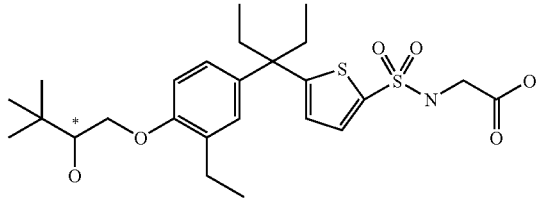

Using a procedure analogous to Example 137, enantiomer 1 of (5-{1-ethyl-1-[3-ethyl-4-(2-hydroxy-3,3-dimethyl-butoxy)-phenyl]-propyl}-thiophene-2-sulfonylamine)-acetic acid methyl ester gives the title compound (quant).
$^1$H NMR (CDCl$_3$) δ 7.44 (d, 1H, J=4.0 Hz), 6.98, 7.01 (m, 2H), 6.74, 6.79 (m, 2H), 5.11 (t, 1H), 4.13 (dd, 1H, J=3.0, 9.4 Hz), 3.90 (dd, 1H, J=8.9, 9.4 Hz), 3.86 (d, 2H, J=5.3 Hz), 3.73 (dd, 1H, J=3.0, 8.9 Hz), 2.60 (q, 2H), 2.09 (m, 4H), 1.16 (t, 3H), 1.03 (s, 9H), 0.72 (t, 6H);
HRMS: Calcd. for C25H41N2O6S2 (M+18), 529.2406, found, 529.2397.

Examnle 156

Preparation of enantiomer 1 of (5-{1-Ethyl-1-[4-(2-hydroxy-3,3-dimethyl-butoxy)-3-propyl-phenyl]-propyl}-thiophene-2-sulfonylamine)-acetic acid methyl ester

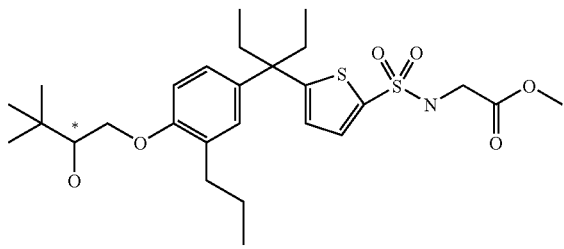

Using a procedure analogous to Example 150, 1-[4-(1-ethyl-1-thiophen-2-yl-propyl)-2-propyl-phenoxy]-3,3-dimethyl-butan-2-one gives the title compound (25%). $^1$H NMR (CDC$_3$) δ 7.43 (d, 1H, J=4.0 Hz), 7.02 (dd, 1H, J=1.8, 8.8 Hz), 7.00 (d, 1H, J=1.8 Hz), 6.77 (d, 1H, J=4.0 Hz), 6.75 (d, 1H, J=8.8 Hz), 5.05 (t, 1H), 4.10 (dd, 1H, J=2.4, 8.8 Hz), 3.88 (dd, 1H, J=8.8, 9.2 Hz), 3.85 (d, 2H, J=5.2 Hz), 3.71 (dd, 1H, J=2.4, 8.8 Hz), 3.67 (s, 3H), 2.55 (t, 2H), 2.06 (q, 4H), 1.56 (m, 2H), 1.02 (s, 9H), 0.89 (t, 3H), 0.70 (t, 6H);
HRMS: Calcd. for C27H45N2O6S2 (M+18), 557.2719, found, 557.2698.

Example 157

Preparation of (5-{1-Etbyl-1-[4-(2-hydroxy-3,3-dimethyl-butoxy)-3-propyl-phenyl]-propyl}-thiophene-2-sulfonylamine)-acetic acid

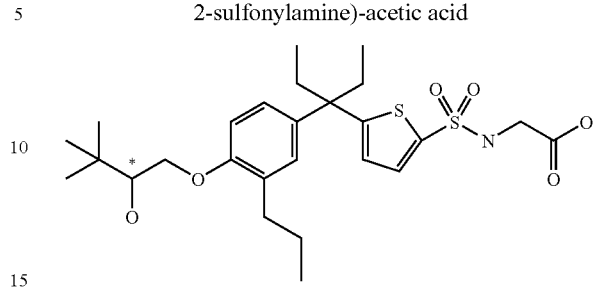

Using a procedure analogous to Example 137, (5-{1-ethyl-1-[4-(2-hydroxy-3,3-dimethyl-butoxy)-3-propyl-phenyl]-propyl}-thiophene-2-sulfonylamine)-acetic acid methyl ester gives the title compound (quant).
$^1$H NMR (CDCl$_3$) δ 7.43 (d, 1H, J=4.0 Hz), 6.99 (d, 1H, J=8.4 Hz), 6.98 (s, 1H), 6.78 (d, 1H, J=4.0 Hz), 6.75 (d, 1H, J=8.4 Hz), 5.09 (t, 1H), 4.10 (dd, 1H, J=2.4, 9.4 Hz), 3.88 (dd, 1H, J=8.8, 9.4 Hz), 3.86 (d, 2H, J=5.3 Hz), 3.72 (dd, 1H, J=2.4, 8.8 Hz), 2.55 (t, 2H), 2.07 (m, 4H), 1.56 (m, 2H), 1.01 (s, 9H), 0.89 (t, 3H), 0.71 (t, 6H);
HRMS: Calcd. for C26H43N2O6S2 (M+18), 543.2563, found, 543.2541.

Example 158

Preparation of 5-{1-Ethyl-1-[4-(2-hydroxy-3,3-dimethyl-butoxy)-3-methyl-phenyl]-propyl}-3-methyl-thiophene-2-sulfonic acid acetyl-amide

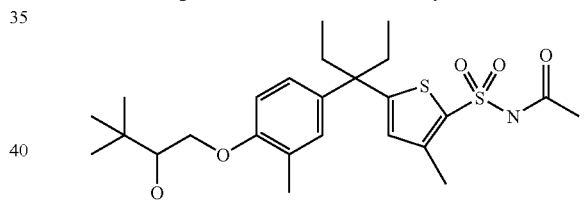

A. 5-(1-{4-[2-(tert-Butyl-dimethyl-silanyloxy)-3,3-dimethyl-butoxy]-3-methyl-phenyl}-1-ethyl-propyl)-3-methyl-thiophene-2-sulfonic acid amide

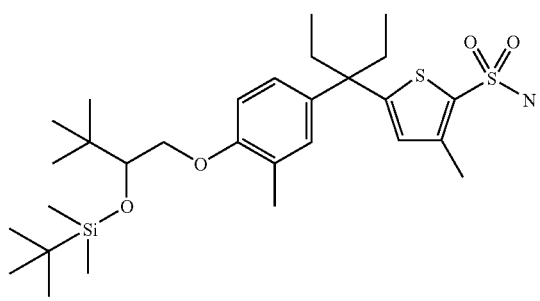

Using a procedure analogous to Example 134E, 5-(1-{4-[2-(tert-butyl-dimethyl-silanyloxy)-3,3-dimethyl-butoxy]-3-methyl-phenyl}-1-ethyl-propyl)-3-methyl-thiophene-2-sulfonyl chloride and NH$_4$OH give the title compound (39%).
$^1$H NMR (CDCl$_3$) δ 7.02 (dd, 1H, J=2.9, 8.6 Hz), 6.96 (d, 1H, J=2.2 Hz), 6.68 (d, 1H, J=8.6 Hz), 6.60 (s, 1H), 4.83 (s, 2H), 3.98 (dd, 1H, J=3.3, 9.9 Hz), 3.85 (dd, 1H, J=5.5, 9.9

Hz), 3.67 (dd, 1H, J=3.3, 5.5 Hz), 2.43 (s, 3H), 2.20 (s, 3H), 2.06 (q, 4H), 0.96 (s, 9H), 0.89 (s, 9H), 0.70 (t, 6H), 0.11 (s, 3H), 0.05 (s, 3H).

B. 5-(1-{4-[2-(tert-Butyl-dimethyl-silanyloxy)-3,3-dimethyl-butoxy]-3-methyl-phenyl}-1-ethyl-propyl)-3-methyl-thiophene-2-sulfonic acid acetyl-amide

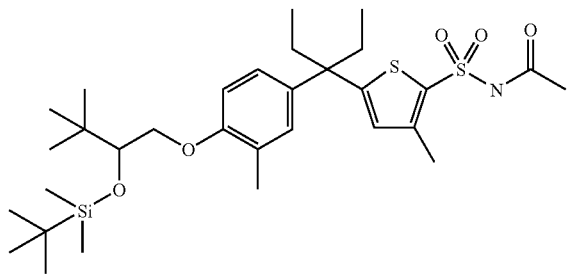

A mixture of 5-(1-{4-[2-(tert-Butyl-dimethyl-silanyloxy)-3,3-dimethyl-butoxy]-3-methyl-phenyl}-1-ethyl-propyl)-3-methyl-thiophene-2-sulfonic acid amide (227 mg, 0.4 mmol), EDCI (92 mg, 0.48 mmol), acetic acid (27 μL, 0.48 mmol) and DMAP (50 mg) in dichloromethane (10 ml) is stirred at RT overnight. The reaction is diluted with dichloromethane and washed with 1N HCl. The organic phase is concentrated and chromatographed (Hex to 20% EtOAc/Hex) to give the title compound (240 mg, 98%). $^1$H NMR (CDC$_3$) δ 7.99 (s, 1H), 7.02 (d 1H, J=8.8 Hz), 6.96 (s, 1H), 6.69 (d, 1H, J=8.8 Hz), 6.59 (s, 1H), 3.98 (dd, 1H, J=3.4, 9.8 Hz), 3.85 (dd, 1H, J=5.8, 9.8 Hz), 3.67 (dd, 1H, J=3.4, 5.8 Hz), 2.43 (s, 3H), 2.20 (s, 3H), 2.13 9s, 3H), 2.06 (q, 4H), 0.96 (s, 9H), 0.89 (s, 9H), 0.70 (t, 6H), 0.11 (s, 3H), 0.05 (s, 3H);

ES-MS: 610 (M+1).

C. 5-{1-Ethyl-1-[4-(2-hydroxy-3,3-dimethyl-butoxy)-3-methyl-phenyl]-propyl}-3-methyl-thiophene-2-sulfonic acid acetyl-amide

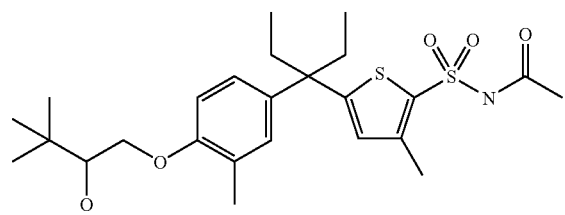

Using a procedure analogous to example-TWM-1F, 5-(1-{4-[2-(tert-butyl-dimethyl-silanyloxy)-3,3-dimethyl-butoxy]-3-methyl-phenyl}-1-ethyl-propyl)-3-methyl-thiophene-2-sulfonic acid acetyl-amide gives the title compound (240 mg, 62%).

$^1$H NMR (CDC$_3$) δ 7.97 (s, 1H), 7.02 (dd, 1H, J=2.4, 8.3 Hz), 6.99 (s, 1H), 6.74 (d, 1H, J=8.3 Hz), 6.58 (s, 1H), 4.10 (dd, 1H, J=2.4, 9.3 Hz), 3.88 (dd, 1H, J=8.8, 9.3 Hz), 3.72 (dd, 1H, J=2.4, 8.8 Hz), 2.46 (s, 3H), 2.21 (s, 3H), 2.13 (s, 3H), 2.07 (m, 4H), 1.02 (s, 9H), 0.70 (t, 6H).

HRMS: calcd. for C25H38NO5S2 (M+1), 496.2191, found, 496.2188.

Example 159

Preparation of 5-{1-Ethyl-1-[4-(2-hydroxy-3,3-dimethyl-butoxy)-3-methyl-phenyl]-propyl}-3-methyl-thiophene-2-sulfonic acid propionyl-amide

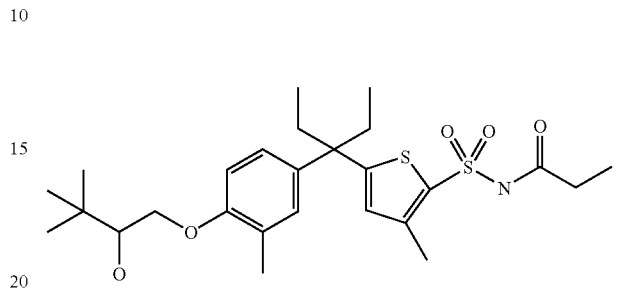

Using procedures analogous to Example 158B and Example 158C, 5-(1-{4-[2-(tert-butyl-dimethyl-silanyloxy)-3,3-dimethyl-butoxy]-3-methyl-phenyl}-1-ethyl-propyl)-3-methyl-thiophene-2-sulfonic acid amide and propionic acid give the title compound (66%).

$^1$H NMR (CDCl$_3$) δ 8.56 (s, 1H), 7.02 (dd, 1H, J=2.4, 8.3 Hz), 6.98 (d, 1H, J=2.4 Hz), 6.73 (d, 1H, J=8.3 Hz), 6.56 (s, 1H), 4.10 (dd, 1H, J=3.0, 9.3 Hz), 3.88 (dd, 1H, J=8.8, 9.3 Hz), 3.71 (dd, 1H, J=3.0, 8.8 Hz), 2.47 (s, 3H), 2.33 (q, 2H), 2.19 (s, 3H), 2.07 (m, 4H), 1.08 (t, 3H), 1.02 (s, 9H), 0.68 (t, 6H);

HRMS: calcd. for C26H40NO5S2 (M+1), 510.2348, found, 510.2359.

Example 160

Preparation of 5-{1-[4-(3,3-Dimethyl-2-oxo-butoxy)-3-methyl-phenyl]-1-ethyl-propyl}-3-methyl-thiophene-2-sulfonic acid acetyl-amide

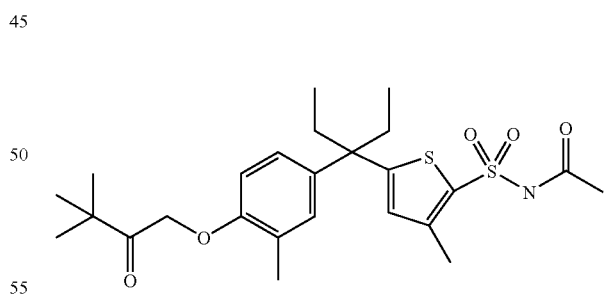

Using a procedure analogous to Example 138C, 5-{1-ethyl-1-[4-(2-hydroxy-3,3-dimethyl-butoxy)-3-methyl-phenyl]-propyl}-3-methyl-thiophene-2-sulfonic acid acetyl-amide gives the title compound (84%).

$^1$H NMR (CDC$_3$) δ 8.05 (s, 1H), 6.91, 6.99 (m, 2H), 6.57 (s, 1H), 6.51 (d, 1H, J=8.5 Hz), 4.86 (s, 2H), 2.46 (s, 3H), 2.26 (s, 3H), 2.13 (s, 3H), 2.07 (m, 4H), 1.26 (s, 9H), 0.69 (t, 6H).

HRMS: calcd. for C25H36NO5S2 (M+1), 494.2035, found, 494.2040.

Example 161

Preparation of 5-{1-[4-(3,3-Dimethyl-2-oxo-butoxy)-3-methyl-phenyl]-1-ethyl-propyl}-3-methyl-thiophene-2-sulfonic acid dimethylaminemethyleneamide

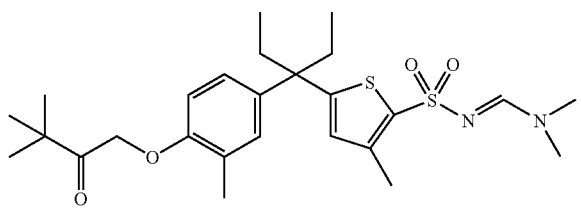

A. 5-{1-[4-(tert-Butyl-dimethyl-silanyloxy)-3-methyl-phenyl]-1-ethyl-propyl}-3-methyl-thiophene-2-sulfonic acid amide

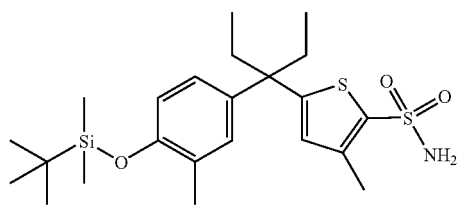

To a 0° C. solution of tert-butyl-{4-[1-ethyl-1-(4-methyl-thiophen-2-yl)-propyl]-2-methyl-phenoxy}-dimethyl-silane (28.37 g, 72.99 mmol) in THF (360 ml) is added dropwise n-butyllithium (47.90 ml, 76.64 mmol, 1.6M in Hex) and stirred at 0° C. for 30 m. The reaction mixture is cannulated into a −78° C. solution of sulfuryl chloride (11.73 ml, 145.98 mmol) in pentane (360 ml) and the reaction warms to RT for 2 h. The reaction mixture is concentrated and the residue is dissolved in acetone (100 ml) and added to a 0° C. mixture of acetone (1 L) and concentrated NH$_4$OH (150 ml) and stirs at 0° C. for 2 h. The reaction mixture is concentrated and the residue is partitioned between EtOAc (700 ml) and satd aqueous NHCl (200 ml). The organic layer is MgSO$_4$ dried, concentrated and chromatographed (330 g SiO$_2$, 50% EtOAc/Hex) to yield the title compound (5.34 g, 16%).

$^1$NMR (400 MHz, CDC$_3$) δ 6.97 (d, 1H, J=2.2 Hz), 6.91 (dd, 1H, J=8.6, 2.4 Hz), 6.66 (d, 1H, J=8.4 Hz), 6.58 (s, 1H), 4.90 (s, 2H), 2.42 (s, 3H), 2.17 (s, 3H), 2.09-2.04 (m, 4H), 1.00 (s, 9H), 0.69 (t, 6H, J=7.3 Hz), 0.21 (s, 6H).

B. 5-{1-[4-(tert-Butyl-dirmethyl-silanyloxy)-3-methyl-phenyl]-1-ethyl-propyl}-3-methyl-thiophene-2-sulfonic acid dimethylaminemethyleneamide

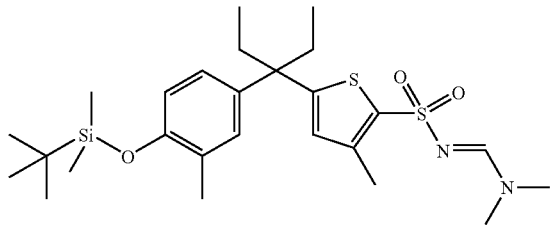

To a solution of 5-{1-[4-(tert-butyl-dimethyl-silanyloxy)-3-methyl-phenyl]-1-ethyl-propyl}-3-methyl-thiophene-2-sulfonic acid amide (5.34 g, 11.42 mmol) in THF (200 ml) is added dimethyl formamide dimethyl acetamide (1.52 ml, 11.42 mmol) and sitrred overnight. The reaction mixture is diluted with EtOAc (500 ml) and washed with 0.2N HCl (100 ml). The organic layer is MgSO$_4$ dried, concentrated and chromatographed (120 g SiO$_2$, 50% EtOAc/Hex) to yield the title compound (6.0 g, quant.).

$^1$NMR (400 MHz, CDCl$_3$) δ 8.10 (s, 1H), 6.98 (d, 1H, J=2.2 Hz), 6.92 (dd, 1H, J=8.4, 2.6 Hz), 6.65 (d, 1H, J=8.4 Hz), 6.52 (s, 1H), 3.12 (s, 3H), 3.05 (s, 3H), 2.41 (s, 3H), 2.16 (s, 3H), 2.09-1.99 (m, 4H), 1.00 (s, 9H), 0.68 (t, 6H, J=7.3 Hz), 0.20 (s, 6H).

C. 5-[1-Ethyl-1-(4-hydroxy-3-methyl-phenyl)-propyl]-3-methyl-thiophene-2-sulfonic acid dimethylaminemethyleneamide

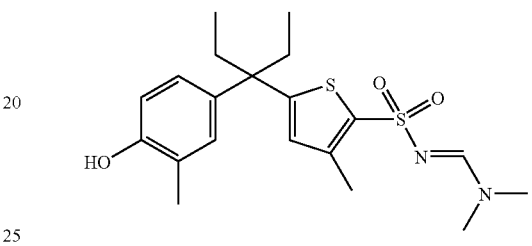

To a 0° C. solution of 5-{1-[4-(tert-butyl-dimethyl-silanyloxy)-3-methyl-phenyl]-1-ethyl-propyl}-3-methyl-thiophene-2-sulfonic acid dimethylaminemethyleneamide (6.1 g, 11.68 mmol) in THF (150 ml) is added dropwise tetrabutylammonium fluoride (15.62 ml, 15.62 mmol, 1.0 M in THF) and is warmed to RT for 1 h. The reaction is quenched with satd aqueous NH$_4$Cl (100 ml) and extracted with Et$_2$O (2×200 ml). The combined organic layers are dried MgSO$_4$ dried, concentrated and chromatographed (120 g SiO$_2$, 50% EtOAc/Hex) to yield the title compound (4.63 g, 97%).

$^1$NMR (400 MHz, CDCl$_3$) δ 8.09 (s, 1H), 6.97 (s, 1H), 6.95 (d, 1H, J=8.4 Hz), 6.68 (d, 1H, J=8.4 Hz), 6.52 (s, 1H), 4.84 (s, 1H), 3.12 (s, 3H), 3.04 (s, 3H), 2.40 (s, 3H), 2.21 (s, 3H), 2.08-2.01 (m, 4H), 0.68 (t, 6H, J=7.3 Hz).

D. 5-{1-[4-(3,3-Dimethyl-2-oxo-butoxy)-3-methyl-phenyl]-1-ethyl-propyl}-3-methyl-thiophene-2-sulfonic acid dimethylaminemethyleneamide

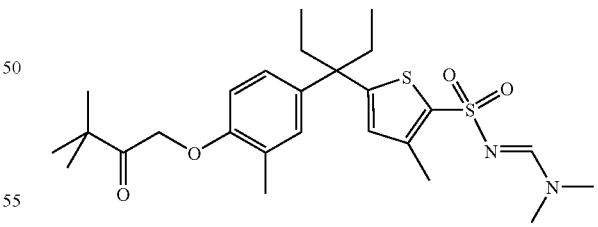

To a solution of 5-[1-ethyl-1-(4-hydroxy-3-methyl-phenyl)-propyl]-3-methyl-thiophene-2-sulfonic acid dimethylaminemethyleneamide (5.1 g, 12.48 mmol) in 2-butanone (50 ml) is added potassium carbonate (2.59 g, 18.72 mmol), and chloropinacolone (3.28 ml, 24.91 mmol). The reaction is refluxed overnight, filtered, and concentrated. The residue is partitioned between EtOAc (400 ml) and 0.2N HCl (100 ml). The organic layer is washed with brine (100 ml), MgSO$_4$ dried, concentrated, and chromatographed (120 g SiO$_2$, 50% EtOAc/Hex) to yield the title compound (6.11 g, 97%).

1NMR (400 MHz, CDC₃) δ 8.10 (s, 1H), 7.01 (s, 1H), 6.98 (d, 1H, J=9.2 Hz), 6.52 (s, 1H), 6.50 (d, 1H, J=8.4 Hz), 4.85 (s, 2H), 3.13 (s, 3H), 3.05 (s, 3H), 2.41 (s, 3H), 2.26 (s, 3H), 2.09-2.01 (m, 4H), 1.26 (s, 9H), 0.68 (t, 6H, J=7.3 Hz).

HRMS: calcd. for C26H39N2O4S2 (M+1), 507.2351, found, 507.2349.

Example 162

Preparation of 5-{1-[4-(3,3-Dimethyl-2-oxo-butoxy)-3-methyl-phenyl]-1'-ethyl-propyl}-3-methyl-thiophene-2-sulfonic acid amide

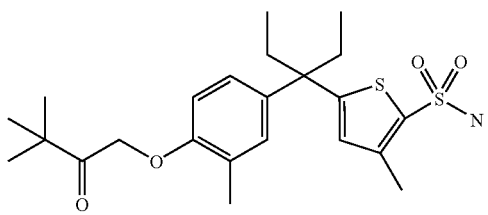

A solution of 5-{1-[4-(3,3-Dimethyl-2-oxo-butoxy)-3-methyl-phenyl]-1-ethyl-propyl}-3-methyl-thiophene-2-sulfonic acid dimethylaminemethyleneamide (6.11 g, 12.06 mmol) in 5N HCl/MeOH (180/200 ml) is refluxed overnight. The reaction mixture is concentrated and the residue redissolved in EtOAc (500 ml) and is washed with water (100 ml), brine (100 ml), dried (MgSO₄), concentrated and chromatographed (120 g SiO₂, 60% EtOAc/Hex) to yield the title compound (5.50 g, quant.).

¹NMR (400 MHz, CDCl₃) δ 7.01-6.95 (m, 2H), 6.57 (s, 1H), 6.51 (d, 1H, J=7.9 Hz), 4.92 (s, 2H), 4.85 (s, 2H), 2.41 (s, 3H), 2.26 (s, 3H), 2.09-2.03 (m, 4H), 1.25 (s, 9H), 0.69 (t, 6H, =7.3 Hz).

EI-MS: 507.3 (M+1)

Example 163

Preparation of 5-{1-[4-(3,3-dimethyl-2-oxo-butoxy)-3-methyl-phenyl]-1-ethyl-propyl}-3-methyl-thiophene-2-sulfonic acid propionyl-amide A mixture of 5-{1-[4-(3,3-dimethyl-2-oxo-butoxy)-3-methyl-phenyl]-1-ethyl-propyl}-3-methyl-thiophene-2-sulfonic acid amide (330 mg, 0.73 mmol), EDCI (210 mg, 1.1 mmol), propionic acid (82 µL, 1.1 mmol) and DMAP (50 mg) in dichloromethane (10 ml) is stirrred overnight. The reaction is diluted with dichloromethane and washed with 1N HCl. The organic phase is concentrated and chromatographed (Hex to 30% EtOAc/Hex) to give the title compound (92%).

¹H NMR (CDC₃) δ 8.10 (s, 1H), 6.98 (s, 1H), 6.97 (d, 1H, J=8.3 Hz), 6.56 (s, 1H), 6.51 (d, 1H, J=8.3 Hz), 4.86 (s, 2H), 2.48 (s, 3H), 2.34 (q, 2H), 2.26 (s, 3H), 2.06 (m, 4H), 1.26 (s, 9H), 1.10 (t, 3H), 0.69 (t, 6H);

HRMS: calcd. for C26H41N2O5S2 (M+18), 525.2457, found, 525.2433.

Example 164

Preparation of 5-{1-[4-(3,3-Dimethyl-2-oxo-butoxy)-3-methyl-phenyl]-1-ethyl-propyl}-3-methyl-thiophene-2-sulfonic acid isobutyryl-amide

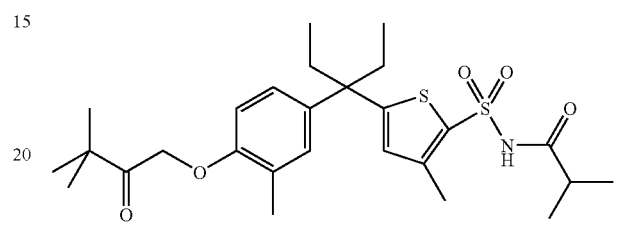

Using a procedure analogous to Example 163, 5-{1-[4-(3,3-dimethyl-2-oxo-butoxy)-3-methyl-phenyl]-1-ethyl-propyl}-3-methyl-thiophene-2-sulfonic acid amide and 2-methylpropionic acid give the title compound (56%).

¹NMR (400 MHz, CDCl₃) δ 8.00 (s, 1H), 6.99-6.94 (m, 2H), 6.55 (s, 1H), 6.50 (d, 1H, J=8.4 Hz), 4.85 (s, 2H), 2.49 (s, 3H), 2.44 (sept, 1H, J=7.0 Hz), 2.25 (s, 3H), 2.11-2.02 (m, 4H), 1.25 (s, 9H), 1.11 (d, 6H, J=7.0 Hz), 0.68 (t, 6H, J=7.3 Hz).

ES-MS: 522 (M+1)

Example 165

Preparation of 5-{1-[4-(3,3-Dimethyl-2-oxo-butoxy)-3-methyl-phenyl]-1-ethyl-propyl}-3-methyl-thiophene-2-sulfonic acid cyclopropanecarbonyl-amide

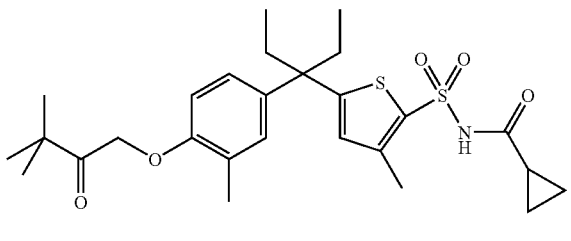

Using a procedure analogous to Example 163, 5-{1-[4-(3,3-dimethyl-2-oxo-butoxy)-3-methyl-phenyl]-1-ethyl-propyl}-3-methyl-thiophene-2-sulfonic acid amide and cyclopropanecarboxylic acid give the title compound (60%).

¹NMR (400 MHz, CDCl₃) δ 8.43 (s, 1H), 6.99-6.94 (m, 2H), 6.56 (s, 1H), 6.51 (d, 1H, J=8.4 Hz), 4.86 (s, 2H), 2.46 (s, 3H), 2.25 (s, 3H), 2.12-2.01 (m, 4H), 1.68-1.58 (m, 1H), 1.26 (s, 9H), 1.05-0.99 (m, 2H), 0.89-0.82 (m, 2H), 0.68 (t, 6H, J=7.3 Hz).

EI-MS: 520.2 (M+H), 518.4 (M−H)

Example 166

Preparation of 5-{1-[4-(3,3-Dimethyl-2-oxo-butoxy)-3-methyl-phenyl]-1-ethyl-propyl}-3-methyl-thiophene-2-sulfonic acid (2-methoxy-acetyl)-amide

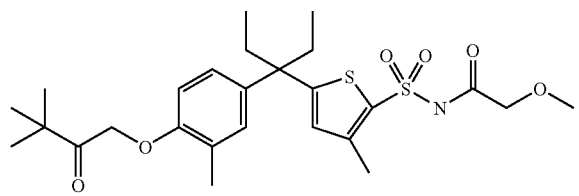

Using a procedure analogous to Example 163, 5-{1-[4-(3,3-dimethyl-2-oxo-butoxy)-3-methyl-phenyl]-1-ethyl-propyl}-3-methyl-thiophene-2-sulfonic acid amide and methoxy-acetic acid give the title compound (84%).

$^1$H NMR (CDC$_3$) δ 8.91 (s, 1H), 7.00 (s, 1H), 6.97 (dd, 1H, J=2.6, 8.3 Hz), 6.54 (s, 1H), 6.51 (d, 1H, J=8.3 Hz), 4.86 (s, 2H), 3.90 (s, 2H), 3.43 (s, 3H), 2.48 (s, 3H), 2.26 (s, 3H), 2.06 (m, 4H), 1.26 (s, 9H), 0.69 (t, 6H);

HRMS: calcd. for C26H41N2O6S2 (M+18), 541.2406, found, 541.2400.

Example 169

Preparation of 5-(5-{1-Ethyl-1-[4-(2-hydroxy-3,3-dimethyl-butoxy)-3-methyl-phenyl]-propyl}-3-methyl-thiophen-2-yl)-3H-[1,3,4]oxadiazol-2-one

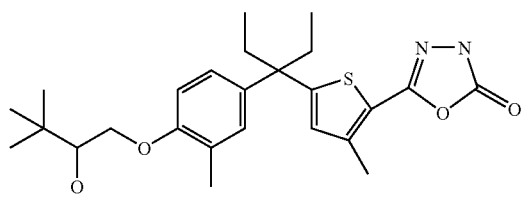

A mixture of 5-{1-ethyl-1-[4-(2-hydroxy-3,3-dimethyl-butoxy)-3-methyl-phenyl]-propyl}-3-methyl-thiophene-2-carboxylic acid hydrazide (432 mg, 1 mmol), 1,1'-carbonyldiimidazole (405 mg, 2.5 mmol) and triethylame (0.28 ml, 2 mmol) in THF (10 ml) is stirred at reflux overnight. It is diluted with EtOAc, washed with 1N HCl solution. The organic phase is concentrated and chromatographed (Hex to 20% EtOAc/Hex to give the title compound (290 mg, 63%).

$^1$HNMR (CDCl$_3$) δ 8.51 (s, 1H), 7.05 (dd, 1H, J=2.4, 8.8 Hz), 7.01 (s, 1H), 6.73 (d, 1H, J=8.8 Hz), 6.62 (s, 1H), 4.09 (dd, 1H, J=2.6, 9.2 Hz), 3.87 (dd, 1H, J=8.8, 9.2 Hz), 3.70 (dd, J=2.6, 8.8 Hz), 2.42 (s, 3H), 2.20 (s, 3H), 2.08 (m, 4H), 1.01 (s, 9H), 0.69 (t, 6H);

HRMS: calcd. for C25H35N2O4S (M+1), 459.2318, found, 459.2325.

Example 170

Preparation of enantiomer 1 of 5-(5-{1-ethyl-1-[4-(2-hydroxy-3,3-dimethyl-butoxy)-3-methyl-phenyl]-propyl}-3-methyl-thiophen-2-yl)-3H-[1,3,4]oxadiazol-2-one

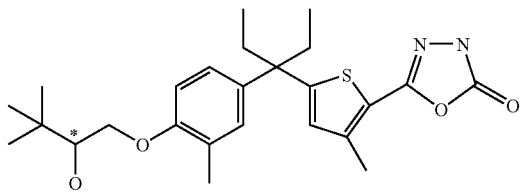

Using an analogous procedure as Example 169, enantiomer 1 of 5-{1-ethyl-1-[4-(2-hydroxy-3,3-dimethyl-butoxy)-3-m ethyl-ph enyl]-propyl}-3-methyl-thiophene-2-carboxylic acid hydrazide (Example 168) gives the title compound (65%). Enantiomer 1: $^1$H NMR (CDC$_3$) equivalent to Example 169;

HRMS: calcd. for C25H35N2O4S (M+1), 459.2318, found, 459.2321.

Example 171

Preparation of enantiomer 2 of 5-(5-{1-ethyl-1-[4-(2-hydroxy-3,3-dimethyl-butoxy)-3-methyl-phenyl]-propyl}-3-methyl-thiophen-2-yl)-3H-[1,3,4]oxadiazol-2-one

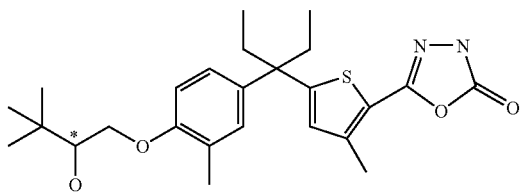

Using analogous procedures as in Example 168 and Example 169, enantiomer 2 of 1-{4-[1-ethyl-1-(5-methoxycarbonyl-4-methyl-thiophen-2-yl)-propyl]-2-methyl-phenoxy}-3,3-dimethyl-butan-2-ol (Example 6B) gives the title compound (83%). Enantiomer 2: $^1$H NMR (CDCl$_3$) equivalent to Example 169;

HRMS: calcd. for C25H35N2O4S (M+1), 459.2318, found, 459.2320.

Example 172

Preparation of 5-(5-{1-Ethyl-1-[4-(2-hydroxy-3,3-dimethyl-butoxy)-3-methyl-phenyl]-propyl}-3-methyl-thiophen-2-yl)-3H-[1,3,4]oxadiazole-2-thi one

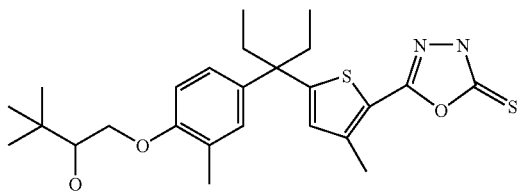

A mixture of 5-{1-ethyl-1-[4-(2-hydroxy-3,3-dimethyl-butoxy)-3-methyl-phenyl]-propyl}-3-methyl-thiophene-2-carboxylic acid hydrazide (432 mg, 1 mmol), carbon disulfide (0.15 ml, 2.5 mmol) and KOH (62 mg, 1.1 mmol) in methanol (15 ml) is refluxed overnight. The reaction is concentrated and partitioned between EtOAc and 1N HCl. The organic phase is concentrated and chromatographed to give the title compound (320 mg, 68%).

$^1$H NMR (CDC$_3$) δ 7.05 (d, 1H, J=8.3 Hz), 7.00 (s, 1H), 6.74 (d, 1H, J=8.3 Hz), 6.66 (s, 1H), 4.10 (dd, 1H, J=2.6, 9.2 Hz), 3.87 (dd, 1H, J=8.8, 9.2 Hz), 3.71 (dd, J=2.6, 8.8 Hz), 2.46 (s, 3H), 2.20 (s, 3H), 2.08 (m, 4H), 1.01 (s, 9H), 0.71 (t, 6H);

HRMS: calcd. for C25H35N2O3S2 (M+1), 475.2089, found, 475.2094.

Example 173

Preparation of enantiomer 1 of 5-(5-{1-ethyl-1-[4-(2-hydroxy-3,3-dimethyl-butoxy)-3-methyl-phenyl]-propyl}-3-methyl-thiophen-2-yl)-3H-[1,3,4]oxadiazole-2-thione

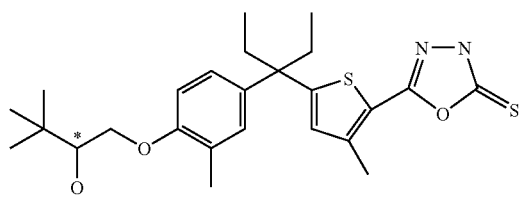

Using an analogous procedure as in Example 172, enantiomer 1 of 5-{1-ethyl-1-[4-(2-hydroxy-3,3-dimethyl-butoxy)-3-methyl-phenyl]-propyl}-3-methyl-thiophene-2-carboxylic acid hydrazide (Example 168) gives the title compound (72%).

$^1$H NMR (CDC$_3$): equivalent to Example 172;

HRMS: calcd. for C25H35N2O3S2 (M+1), 475.2089, found, 475.2084.

Example 174

Preparation of 5-{1-Ethyl-1-[4-(3-hydroxy-4,4-dimethyl-pentyl)-3-methyl-phenyl]-propyl}-3-methyl-thiophene-2-carboxylic acid methyl ester

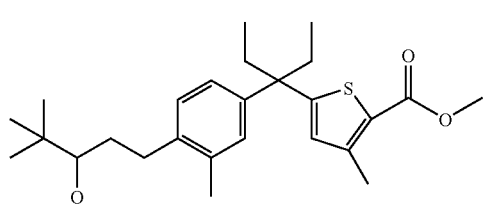

A. Trifluoromethanesulfonic acid 4-[1-ethyl-1-(4-methyl-thiophen-2-yl)propyl]-2-methyl-phenyl ester

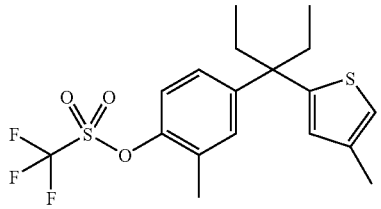

To a mixture of 3'-[4-(hydroxy)-3-methylphenyl]-3'-[4-methylthiophen-2-yl]pentane (8.8 g, 32.2 mmol) and triethylamine (6.8 ml, 48.3 mmol) in dichloromethane (200 ml) at −78° C. is added trifluoromethanesulfonic anhydride (6.5 ml, 38.6 mmol) dropwise and warmed to RT. The reaction is stirred for 1 h, diluted with dichloromethane and washed with 0.2 N HCl followed by brine. The organic layer is concentrated to give the title compound (12 g, 92%).

B. 4-[1-Ethyl-1-(4-methyl-thiophen-2-yl)-propyl]-2-methyl-benzoic acid methyl ester

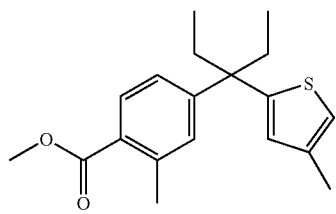

A mixture of trifluoromethanesulfonic acid 4-[1-ethyl-1-(4-methyl-thiophen-2-yl) propyl]-2-methyl-phenyl ester (12 g, 29.62 mmol), Pd(OAc)$_2$ (699 mg, 3 mmol), dppf (3.3 g, 6 mmol), triethylamine (12.5 ml, 90 mmol), methanol (12 ml, 300 mmol), and N,N-dimethylformamide (40 ml) is treated with carbon monoxide (1000 psi) at 110° C. in a Parr-reactor for 48 h. The reaction is concentrated, dissolved in is evaporated in EtOAc and filtered through a silica gel pad. The filtrate is concentrated and chromatographed (Hex to 10% EtOAc/Hex) to give the title compound (6.9 g, 73%).

$^1$H NMR (CDCl$_3$) δ 7.83 (d, 1H, J=8.8 Hz), 7.16 (m, 2H), 6.73 (s, 1H), 6.60 (s, 1H), 3.87 (s, 3H), 2.58 (s, 3H), 2.21 (s, 3H), 2.13 (m, 4H), 0.71 (t, 6H).

C. {4-[1-Ethyl-1-(4-methyl-thiophen-2-yl)-propyl]-2-methyl-phenyl}-methanol

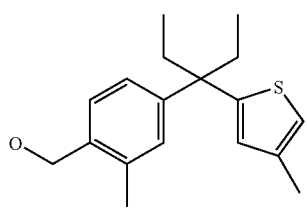

221

To a 0° C. solution of 4-[1-ethyl-1-(4-methyl-thiophen-2-yl)-propyl]-2-methyl-benzoic acid methyl ester (6.7 g, 21.2 mmol) in THF (100 ml) is added 1M LiAlH4/THF (32 ml, 32 mmol). After stirring at RT for 2 h, the reaction is quenched with water (1 ml) followed by 5N NaOH solution (1 ml) and water (3 ml). The mixture is filtered and the filtrate is concentrated to give the title compound as a clear oil (6 g, 98%).

D. 1-{4-[1-Ethyl-1-(4-methyl-thiopben-2-yl)-propyl]-2-methyl-phenyl}-4,4-dimethyl-pentan-3-one

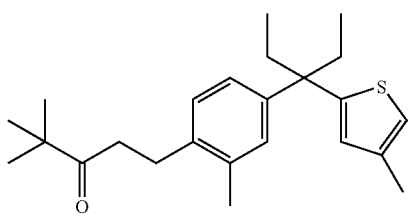

To a 0° C. solution of {4-[1-ethyl-1-(4-methyl-thiophen-2-yl)-propyl]-2-methyl-phenyl}-methanol (6 g,) in THF (50 ml) is treated with PBr₃ (2.2 ml, 23.3 mmol) and warmed to RT. After stirring for 2 h, the mixture is partitioned between EtOAc and brine. The organic layer is MgSO₄ dried, concentrated, and dissolved in anhydrous THF (30 ml) to give a solution of {4-[1-ethyl-1-(4-methyl-thiophen-2-yl)-propyl]-2-methyl-phenyl}-methane bromide. Separately, a solution of 3,3-dimethyl-butan-2-one (5.3 ml, 42.4 mmol) in THF (15 ml) is treated with LiHMDS (42.4 ml, 42.4 mmol, 1M in THF) at −70° C. for 1 h. This solution is transferred (via cannula) into a −70° C. solution of {4-[1-ethyl-1-(4-methyl-thiophen-2-yl)-propyl]-2-methyl-phenyl}-methanebromide/THF. The mixture is warmed to RT and stirred for 1 h. The reaction is diluted with EtOAc and washed with 0.2 N HCl until the aq layer is pH 2. The organic layer is concentrated to give the title compound (6.2 g, 79%).

E. 1-{4-[1-ethyl-1-(4-methyl-thiophen-2-yl)-propyl]-2-methyl-phenyl}-4,4-dimethyl-pentan-3-ol

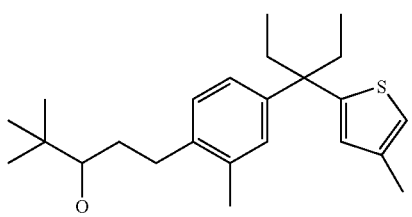

Using a procedure analogous to Example 134B, 1-{4-[1-ethyl-1-(4-methyl-thiophen-2-yl)-propyl]-2-methyl-phenyl}-4,4-dimethyl-pentan-3-one and NaBH₄ give the title compound (quant).

¹H NMR (CDC₃) δ 7.02, 7.07 (m, 3H), 6.71 (s, 1H), 6.61 (s, 1H), 3.26 (dd, 1H, J=2.0, 10.3 Hz), 2.88 (m, 1H), 2.56 (m, 1H), 2.28 (s, 3H), 2.20 (s, 3H), 2.08 (m, 4H), 1.78 (m, 1H), 1.58 (m, 1H), 0.90 (s, 9H), 0.70 (t, 6H).

222

F. tert-Butyl-[1-(2-{4-[1-ethyl-1-(4-methyl-thiophen-2-yl)-propyl]-2 methyl-phenyl}-ethyl)-2,2-dimethyl-propoxy]-dimethyl-silane

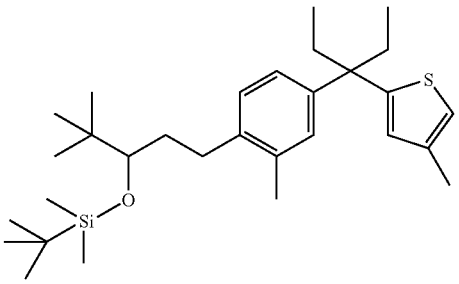

Using a procedure analogous to Example 134C, 1-{4-[1-ethyl-1-(4-methyl-thiophen-2-yl)-propyl]-2-methyl-phenyl}-4,4-dimethyl-pentan-3-ol gives the title compound (quant).

G. 5-(1-{4-[3-(tert-butyl-dimethyl-silanyloxy)-4,4-dimethyl-pentyl]-3-methyl-phenyl}-1-ethyl-propyl)-3-methyl-thiophene-2-carboxylic acid methyl ester

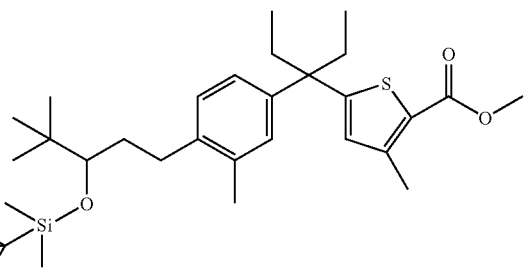

To a 0° C. solution of tert-butyl-[1-(2-{4-[1-ethyl-1-(4-methyl-thiophen-2-yl)-propyl]-2 methyl-phenyl}-ethyl)-2,2-dimethyl-propoxy]-dimethyl-silane (1.46 g, 3 mmol) in THF (15 ml) is added 1.6 M n-BuLi/Hex (2 ml, 3.3 mmol). After 45 m, the mixture is transferred (via cannula) into a −70° C. solution of methyl chloroformate (0.26 ml, 3.3 mmol) in pentane (10 ml). The mixture is warmed to RT and stirred for 3 h. The reaction is diluted with EtOAc, washed with 0.2 N HCl until the aq layer is pH 2, and followed by washing with satd sodium bicarbonate. The organic layer is concentrated and chromatographed (Hex to 5% EtOAc/Hex) to give the title compound (1.05 g, 64%). ¹H NMR (CDC₃) δ 6.99, 7.04 (m, 3H), 6.62 (s, 1H), 3.80 (s, 3H), 3.35 (dd, 1H, J=2.9, 7.3 Hz), 2.76 (m, 1H), 2.48 (s, 3H), 2.41 (m, 1H), 2.26 (s, 3H), 2.08 (m, 4H), 1.78 (m, 1H), 1.59 (m, 1H), 0.93 (s, 9H), 0.88 (s, 9H), 0.70 (t, 6H), 0.10 (s, 3H), 0.07 (s, 3H).

223

H. 5-{1-Ethyl-1-[4-(3-hydroxy-4,4-dimethyl-pentyl)-3-methyl-phenyl]-propyl}-3-methyl-thiophene-2-carboxylic acid methyl ester

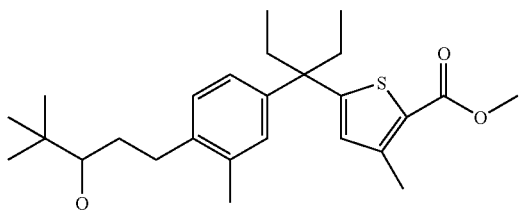

Using a procedure analogous to Example 134F, 5-(1-{4-[3-(tert-butyl-dimethyl-silanyloxy)-4,4-dimethyl-pentyl]-3-methyl-phenyl}-1-etllyl-propyl)-3-methyl-thiophene-2-carboxylic acid methyl ester gives the title compound (94%).

$^1$H NMR (CDCl$_3$) δ 7.00, 7.07 (m, 3H), 6.62 (s, 1H), 3.80 (s, 3H), 3.25 (dd, 1H, J=1.8, 10.5 Hz), 2.88 (m, 1H), 2.55 (m, 1H), 2.48 (s, 3H), 2.28 (s, 3H), 2.08 (m, 4H), 1.79 (m, 1H), 1.58 (m, 1H), 0.90 (s, 9H), 0.70 (t, 6H);

HRMS: calcd. for C26H38O3NaS (M+23), 453.2439, found 453.2465.

Example 175

Preparation of 5-{1-Ethyl-1-[4-(3-hydroxy-4,4-dimethyl-pentyl)-3-methyl-phenyl]-propyl}-3-methyl-thiophene-2-carboxylic acid

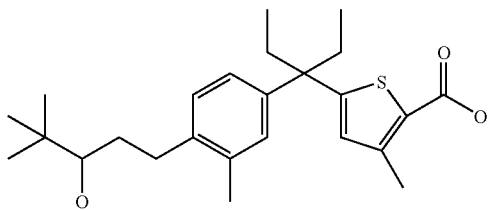

Using LiOH hydrolysis as described in Example 137, 5-{1-ethyl-1-[4-(3-hydroxy-4,4-dimethyl-pentyl)-3-methyl-phenyl]-propyl}-3-methyl-thiophene-2-carboxylic acid methyl ester gives the title compound (94%).

$^1$H NMR (CDCl$_3$) δ 7.00, 7.07 (m, 3H), 6.62 (s, 1H), 3.25 (dd, 1H, J=1.8, 10.5 Hz), 2.88 (m, 1H), 2.55 (m, 1H), 2.48 (s, 3H), 2.28 (s, 3H), 2.08 (m, 4H), 1.79 (m, 1H), 1.58 (m, 1H), 0.90 (s, 9H), 0.70 (t, 6H);

HRMS: calcd. for C25H36O3NaS (M+23), 439.2283, found 439.2283.

Example 176

Preparation of [(5-{1-Ethyl-1-[4-(3-hydroxy-4,4-dimethyl-pentyl)-3-methyl-phenyl]-propyl}-3-methyl-thiophene-2-carbonyl)-amine]-acetic acid methyl ester

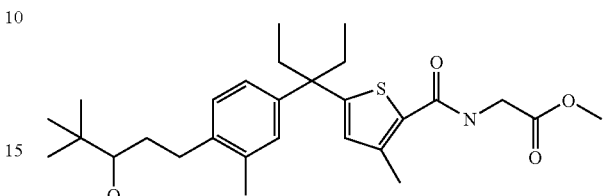

A mixture of 5-{1-ethyl-1-[4-(3-hydroxy-4,4-dimethyl-pentyl)-3-methyl-phenyl]-propyl}-3-methyl-thiophene-2-carboxylic acid (160 mg, 0.38 mmol), 2-amino-acetic acid methyl ester hydrochloride (53 mg, 0.42 mmol), EDCl (89 mg, 0.46 mmol) and triethylamine (0.134 ml, 0.96 mmol) in dichloromethane (5 ml) is stirred at RT overnight. The reaction is concentrated, partitioned between 1N HCl and EtOAc. The organic layer is concentrated and chromatographed (Hex to 30% EtOAc/Hex) to give the title compound (75 mg, 40%).

$^1$H NMR (CDCl$_3$) δ 7.07 (d, 1H, J=8.7 Hz), 7.00 (d, 1H, J=8.7 Hz), 6.99 (s, 1H), 6.63 (s, 1H), 6.20 (t, 1H), 4.16 (d, 2H, J=5.3 Hz), 3.78 (s, 3H), 3.26 (bd, 1H, J=9.3 Hz), 2.88 (m, 1H), 2.56 (m, 1H), 2.47 (s, 3H), 2.28 (s, 3H), 2.08 (m, 4H), 1.78 (m, 1H), 1.58 (m, 1H), 0.90 (s, 9H), 0.70 (t, 6H).

ES-MS: 488 (M+1).

Example 177

Preparation of [(5-{1-Ethyl-1-[4-(3-hydroxy-4,4-dimethyl-pentyl)-3-methyl-phenyl]-propyl}-3-methyl-thiophene-2-carbonyl)-amino]-acetic acid

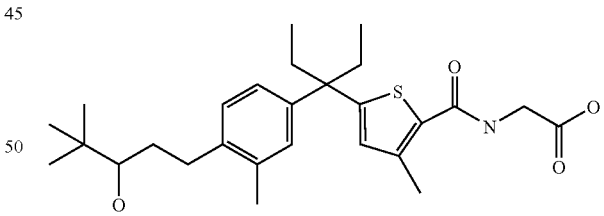

Using LiOH hydrolysis as described in Example 136, [(5-{1-ethyl-1-[4-(3-hydroxy-4,4-dimethyl-pentyl)-3-methyl-phenyl]-propyl}-3-methyl-thiophene-2-carbonyl)-amino]-acetic acid methyl ester gives the title compound (quant). $^1$H NMR (CDCl$_3$) δ 7.07 (d, 1H, J=8.7 Hz), 7.00 (d, 1H, J=8.7 Hz), 6.99 (s, 1H), 6.63 (s, 1H), 6.21 (t, 1H), 4.20 (d, 2H, J=5.3 Hz), 3.26 (bd, 1H, J=9.3 Hz), 2.88 (m, 1H), 2.56 (m, 1H), 2.47 (s, 3H), 2.28 (s, 3H), 2.08 (m, 4H), 1.78 (m, 1H), 1.58 (m, 1H), 0.90 (s, 9H), 0.70 (t, 6H);

HRMS: calcd. for C27H40NO4S (M+1), 474.2678, found 474.2687.

Example 178

Preparation of (5-{1-Ethyl-1-[4-(3-hydroxy-4,4-dimethyl-pentyl)-3-methyl-phenyl]-propyl}-3-methyl-thiophene-2-sulfonylamine)-acetic acid methyl ester

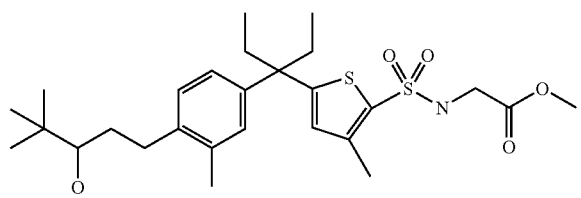

Using procedures analogous to Example 134D to Example 134F, from tert-butyl-[1-(2-{4-[1-ethyl-1-(4-methyl-thiophen-2-yl)-propyl]-2 methyl-phenyl}-ethyl)-2,2-dimethyl-propoxy]-dimethyl-silane and 2-amino-acetic acid methyl ester hydrochloride gives the title compound (24%).

$^1$H NMR (CDCl$_3$) δ 7.07 (d, 1H, J=7.9 Hz), 7.02 (s, 1H), 6.97 (d, 1H, J=7.9 Hz), 6.64 (s, 1H), 5.12 (t, 1H), 3.82 (d, 2H, J=5.3 Hz), 3.65 (s, 3H), 3.32 (d, 1H, J=9.3 Hz), 2.88 (m, 1H), 2.56 (m, 1H), 2.42 (s, 3H), 2.30 (s, 3H), 2.08 (m, 4H), 1.88 (m, 1H), 1.54 (m, 1H), 0.87 (s, 9H), 0.72 (t, 6H).

ES-MS: 524 (M+1).

Example 179

(5-{1-Ethyl-1-[4-(3-hydroxy-4,4-dimethyl-pentyl)-3-methyl-phenyl]-propyl}-3-methyl-thiophene-2-sulfonylamino)-acetic acid

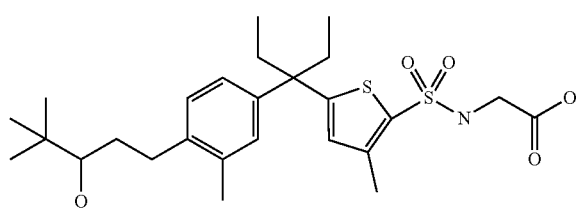

Using LiOH hydrolysis as described in Example 136, (5-{1-ethyl-1-[4-(3-hydroxy-4,4-dimethyl-pentyl)-3-methyl-phenyl]-propyl}-3-methyl-thiophene-2-sulfonylamine)-acetic acid methyl ester gives the title compound (quant).

$^1$H NMR (CDCl$_3$) δ7.08 (d, 1H, J=7.9 Hz), 7.03 (s, 1H), 6.98 (d, 1H, J=7.9 Hz), 6.65 (s, 1H), 5.12 (t, 1H), 3.82 (d, 2H, J=5.3 Hz), 3.32 (d, 1H, J=9.3 Hz), 2.88 (m, 1H), 2.56 (m, 1H), 2.42 (s, 3H), 2.30 (s, 3H), 2.08 (m, 4H), 1.88 (m, 1H), 1.54 (m, 1H), 0.87 (s, 9H), 0.72 (t, 6H).

HRMS: calcd. for C26H43N2O5S2 (M+18), 527.2613, found 527.2639.

Example 180 and Example 181

Preparation of enantiomers of (5-{1-ethyl-1-[4-(3-hydroxy-4,4-dimethyl-pentyl)-3-methyl-phenyl]-propyl}-3-methyl-thiophene-2-sulfonylaminoo)-acetic acid

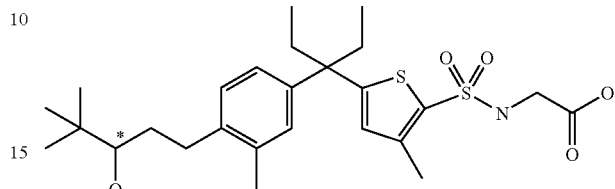

A racemic mixture of (5-{1-ethyl-1-[4-(3-hydroxy-4,4-dimethyl-pentyl)-3-methyl-phenyl]-propyl}-3-methyl-thiophene-2-sulfonylamine)-acetic acid (180 mg) is chromatographed on a Chiralpak AD column (0.46×25 cm) to give the title compounds.

HPLC condition: 0.1% trfluoroacetic acid in 30% isopropanol/hept; flow rate: 1.0 ml/m;

UV: 225 nm.

Enantiomer 1, Example 179: 70 mg (39%); rt: 6.63 m;

$^1$H NMR (CDCl$_3$) equivalent to Example 179

HRMS: calcd. for C26H40NO5S2 (M+1), 510.2348, found 510.2333.

Enantiomer 2, Example 180: 60 mg (33%); rt: 8.60 m.

$^1$H NMR (CDC$_3$) equivalent to Example 179;

HRMS: calcd. for C26H40NO5S2 (M+1), 510.2348, found 510.2359.

Example 182

Preparation of (5-{1-[4-(4,4-Dimethyl-3-oxo-pentyl)-3-methyl-phenyl]-1-ethyl-propyl}-3-methyl-thiophene-2-sulfonylamine)-acetic acid

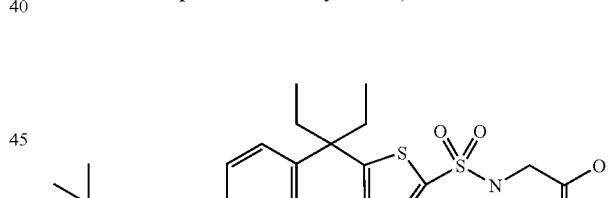

A. (5-{1-[4-(4,4-Dimethyl-3-oxo-pentyl)-3-methyl-phenyl]-1-ethyl-propyl}-3-methyl-thiophene-2-sulfonylamine)-acetic acid methyl ester

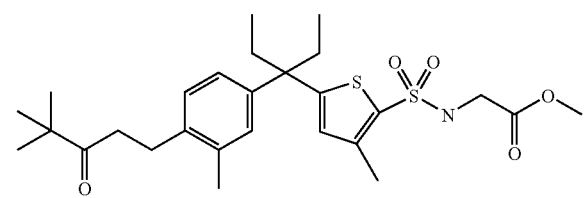

Using the pyridinium dichromate oxidation analogous to Example 139C, (5-{1-ethyl-1-[4-(3-hydroxy-4,4-dimethyl-pentyl)-3-methyl-phenyl]-propyl}-3-methyl-thiophene-2-sulfonylamine)-acetic acid methyl ester gives the title compound (96%). ¹H NMR (CDCl₃) δ 6.96, 7.02 (m, 3H), 6.59 (s, 1H), 5.22 (t, 1H), 3.83 (d, 1H, J=5.7 Hz), 3.65 (s, 3H), 2.82 (t, 2H), 2.72 (t, 2H), 2.40 (s, 3H), 2.27 (s, 3H), 2.07 (m, 4H), 1.10 (s, 9H), 0.68 (t, 6H);
ES-MS: 522 (M+1).

B. (5-{1-[4-(4,4-Dimethyl-3-oxo-pentyl)-3-methyl-phenyl]-1-ethyl-propyl}-3-methyl-thiophene-2-sulfonylamine)-acetic acid

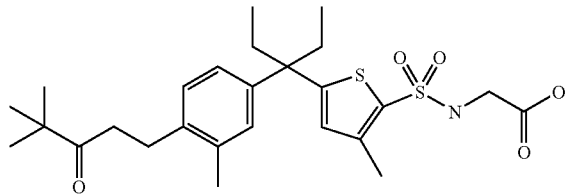

Using LiOH hydrolysis as described in Example 137, (5-{1-[4-(4,4-dimethyl-3-oxo-pentyl)-3-methyl-phenyl]-1-ethyl-propyl}-3-methyl-thiophene-2-sulfonylamine)-acetic acid methyl ester gives the title compound (quant).
¹H NMR (CDCl₃) δ 6.94, 7.01 (m, 3H), 6.60 (s, 1H), 5.30 (t, 1H), 3.86 (d, 1H, J=4.8 Hz), 2.82 (t, 2H), 2.74 (t, 2H), 2.39 (s, 3H), 2.27 (s, 3H), 2.07 (m, 4H), 1.10 (s, 9H), 0.68 (t, 6H);
ES-MS: 508 (M+1).

Example 183

Preparation of (5-{1-[4-(3,3-Dimethyl-2-oxo-butoxy)-3-methyl-phenyl]-1-ethyl-propyl}-3-methyl-thiophen-2-ylmethylsulfanyl)-acetic acid ethyl ester

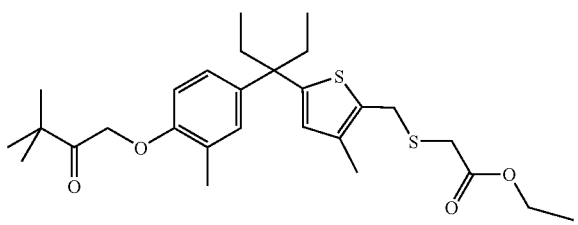

A. (5-{1-[4-(tert-Butyl-dimethyl-silanyloxy)-3-methyl-phenyl]-1-ethyl-propyl}-3-methyl-thiophen-2-yl)-methanol

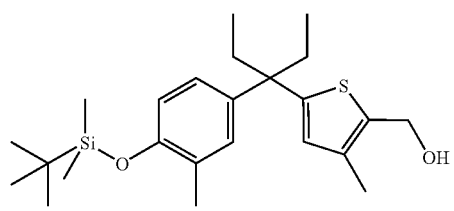

To a 0° C. solution of 5-{1-[4-(tert-butyl-dimethyl-silanyloxy)-3-methyl-phenyl]-1-ethyl-propyl}-3-methyl-thiophene-2-carboxylic acid methyl ester (10.0 g, 22.39 mmol) in THF (200 ml) is added portionwise lithium aluminum hydride (1.70 g, 44.78 mmol) and the reaction mixture is warmed to RT for 1 h. The reaction is quenched with water (1.7 ml), 5N NaOH (1.7 ml), and water (5.1 ml). The reaction mixture is filtered, concentrated and chromatographed (120 g SiO₂, 10% EtOAc/Hex) to yield the title compound (7.0 g, 75%).
¹NMR (400 MHz, CDCl₃) δ 7.01 (d, 1H, J=2.2 Hz), 6.94 (dd, 1H, J=8.4, 2.2 Hz), 6.65 (d, 1H, J=8.4 Hz), 6.52 (s, 1H), 4.65 (d, 2H, J=4.8 Hz), 2.17 (s, 6H), 2.09-1.99 (m, 4H), 1.54 (t, 1H, J=5.5 Hz), 1.00 (s, 9H), 0.69 (t, 6H, J=7.3 Hz), 0.20 (s, 6H).

B. Toluene-4-sulfonic acid 5-{1-[4-(tert-butyl-dimethyl-silanyloxy)-3-methyl-phenyl]-1-ethyl-propyl}-3-methyl-thiophen-2-ylmethyl ester

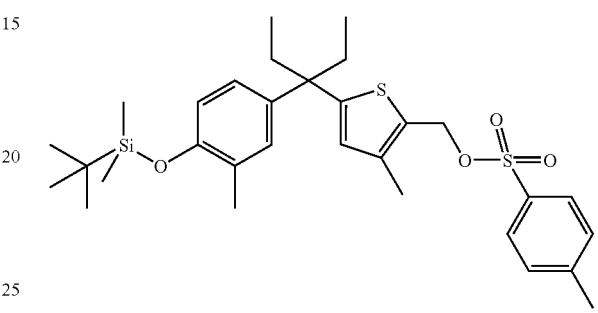

To a solution of (5-{1-[4-(tert-butyl-dimethyl-silanyloxy)-3-methyl-phenyl]-1-ethyl-propyl}-3-methyl-thiophen-2-yl)-methanol (1.0 g, 2.39 mmol) in Et₂O (5 ml) is added triethyl amine (666 µl, 4.78 mmol). The mixture is added to a solution of p-toluenesulfonyl chloride (501 mg, 2.62 mmol) in Et₂O (5 ml) and stirred overnight. The reaction is filtered, concentrated and chromatographed (12 g SiO₂, 5% EtOAc/Hex) to yield the title compound (740 mg, 55%).
¹NMR (400 MHz, CDCl₃) δ 7.93 (d, 2H, J=8.4 Hz), 7.41 (d, 2H, J=8.8 Hz), 7.00 (s, 1H), 6.93 (dd, 1H, J=8.4, 2.2 Hz), 6.63 (d, 1H, J=8.4 Hz), 6.48 (s, 1H), 4.49 (s, 2H), 2.49 (s, 3H), 2.15 (s, 3H), 2.09 (s, 3H), 2.05-2.00 (m, 4H), 0.99 (s, 9H), 0.67 (t, 6H, J=7.3 Hz), 0.19 (s, 6H).
EI-MS: 401.2

C. (5-{1-[4-(tert-Butyl-dimethyl-silanyloxy)-3-methyl-phenyl]-1-ethyl-propyl}-3-methyl-thiophen-2-ylmethylsulfanyl)-acetic acid ethyl ester

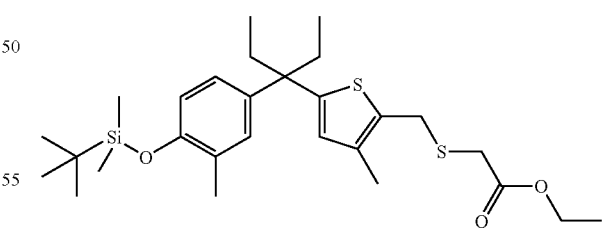

To a solution of 2.68 M sodium ethoxide (507 µl, 1.36 mmol) in EtOH (2 ml) is added ethyl 2-mercaptoacetate (149 µl, 1.36 mmol) and stirred at RT for 30 m. The mixture is added a solution of toluene-4-sulfonic acid 5-{1-[4-(tert-butyl-dimethyl-silanyloxy)-3-methyl-phenyl]-1-ethyl-propyl}-3-methyl-thiophen-2-ylmethyl ester (740 mg, 1.29 mmol) in EtOH (2 ml) is added and refluxed for 15 m. The reaction is concentrated and partitioned between EtOAc (100 ml) and 0.2N HCl (50 ml). The organic layer is washed with water (50 ml), dried (MgSO$_4$), concentrated, and chromatographed (12 g SiO$_2$, 5% EtOAc/Hex) to yield the title compound (180 mg, 27%). $^1$NMR (400 MHz, CDCl$_3$) δ 7.00 (d, 1H, J=2.2 Hz), 6.92 (dd, 1H, J=8.4, 2.2 Hz), 6.64 (d, 1H, J=8.4 Hz), 6.46 (s, 1H), 4.17 (q, 2H, J=7.2 Hz), 3.92 (s, 2H), 3.14 (s, 2H), 2.16 (s, 3H), 2.12 (s, 3H), 2.07-1.98 (m, 4H), 1.28 (t, 3H, J=7.0 Hz), 1.00 (s, 9H), 0.68 (t, 6H, J=7.3 Hz), 0.20 (s, 6H).

EI-MS: 538.2 (M+NH$_4$)

D. {5-[1-Ethyl-1-(4-hydroxy-3-methyl-phenyl)-propyl]-3-methyl-thiophen-2-ylmethylsulfanyl}-acetic acid ethyl ester

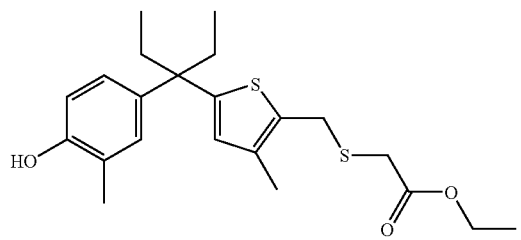

Using an analogous procedure to Example 12F, (5-{1-[4-(tert-Butyl-dimethyl-silanyloxy)-3-methyl-phenyl]-1-ethyl-propyl}-3-methyl-thiophen-2-ylmethylsulfanyl)-acetic acid ethyl ester (180 mg, 0.346 mmol) gives the title compound (147 mg, quant.). $^1$NMR (400 MHz, CDC$_3$) δ 7.00 (s, 1H), 6.97 (d, 1H, J=7.9 Hz), 6.67 (d, 1H, J=8.4 Hz), 6.47 (s, 1H), 4.58 (s, 1H), 4.17 (q, 2H, J=7.2 Hz), 3.92 (s, 2H), 3.14 (s, 2H), 2.21 (s, 3H), 2.12 (s, 3H), 2.06-1.99 (m, 4H), 1.28 (t, 3H, J=7.0 Hz), 0.68 (t, 6H, J=7.3 Hz).

E. (5-{1-[4-(3,3-Dimethyl-2-oxo-butoxy)-3-methyl-phenyl]-1-ethyl-propyl}-3-methyl-thiophen-2-ylmethylsulfanyl)-acetic acid ethyl ester

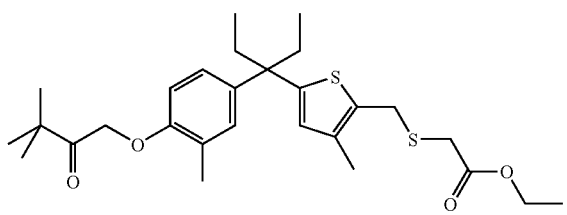

Using an analogous procedure to Example 134A, {5-[1-Ethyl-1-(4-hydroxy-3-methyl-phenyl)-propyl]-3-methyl-thiophen-2-ylmethylsulfanyl}-acetic acid ethyl ester (141 mg, 0.347 mmol) gives the title compound (145 mg, 83%). $^1$NMR (400 MHz, CDCl$_3$) δ 7.02 (s, 1H), 7.00 (d, 1H, J-8.4 Hz), 6.51 (d, 1H, J=8.4 Hz), 6.46 (s, 1H), 4.83 (s, 2H), 4.17 (q, 2H, J=7.2 Hz), 3.92 (s, 2H), 3.14 (s, 2H), 2.25 (s, 3H), 2.12 (s, 3H), 2.08-1.97 (m, 4H), 1.30-1.19 (m, 12H), 0.67 (t, 6H, J=7.3 Hz).

EI-MS: 522.2 (M+NH$_4$).

Example 184

Preparation of 3'-[4-(2-Oxo-3,3-dimethylbutoxy-3-methylphenyl)]-3'-[5-(methylmercaptylmethyl)thiophen-2-yl]pentane

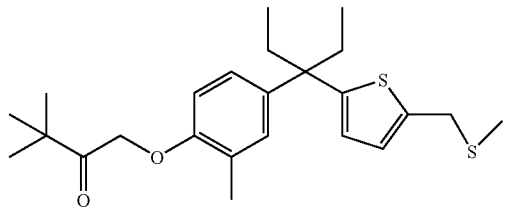

L. 2-(Methylmercaptylmethyl)-thiophene

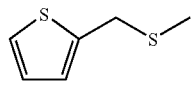

To a 25° C. solution of 2-hydroxymethyl thiophene (2.28 g, 20 mmol), and S-methyl-N,N'tetramethylisothiouronium iodide [(5.48 g, 20 mmol); [S. Fujisaki et al, Bull. Chem. Soc. Jpn., 58, 2429-30 (1985)] in anhydrous DMF (10 ml) under a N$_2$ atmosphere, is added NaH (1.44 g, 60 mmol, 2.40 g of 60% mineral oil dispersion) in small portions. After the resulting vigorous liberation of hydrogen ceases, hexane (10 ml) is added. After stirring for 1 h, the reaction is cooled to 0° C. and water (10 ml) is added dropwise. The mixture is extracted with hexane (3×50 ml). The combined extract is K$_2$CO$_3$, concentrated, and chromatographed with (Hex to 20% CHC$_3$/Hex) to give the title compound as a colorless liquid (2.4 g, 83%).

$^1$NMR (300 MHz, CDCl$_3$) δ ppm: 2.10 (s, 3H), 3.92 (s, 2H), 6.95 (m, 2H), 7.23 (1H).

M. 3'-[4-(Hydroxy)-3-methylphenyl]-3'-[5-(methylmercaptylmethyl)thiophen-2-yl]pentane

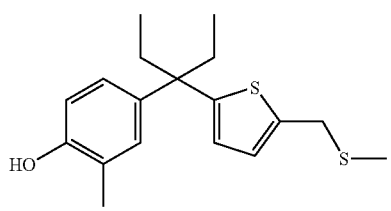

To a 0° C. mixture of 3'-[4-(hydroxy)-3-methylphenyl]pentan-3-ol (582 mg, 3.0 mmol) and 2-(methylmercaptylmethyl)-thiophene (2.16 g, 15.0 mmol) is added BF$_3$-Et$_2$O (171 mg, 0.15 ml, 1.20 mmol). After stirring for 30 m at 0 to 5° C., the reaction is quenched with satd aq NaHCO$_3$ and is extracted with EtOAc (2×). The combined extract is washed with brine, Na$_2$SO$_4$ dried, concentrated, and chromatographed by radial chromatography (4 mm plate, 25% to 80% CHCl3/Hex to give the title compound as a pale brown oil (695 mg, 72%).

¹NMR (300 MHz, CDCl₃) δ ppm: 0.0.71 (t, J=7.3 Hz, 6H), 2.06 (s, 3H), 2.07 (m, 4H), 2.23 (s, 3H), 3.82 (s, 3H), 4.52 (s, 1H), 6.60 to 6.75 (m, 3H), 6.96-7.05 (m, 2H).

TOF(+) MS m/z: 320.2; calc. for C₁₈H₂₄OS₂: 320.20.

ES (−) MS m/z 319.1, [M−H]; calc. for C₁₈H₂₃OS₂: 319.24.

C. 3'-[4-(2-Oxo-3,3-dimethylbutoxy-3-methylphenyl)]-3'-[5-(methylmercaptyl-methyl)-thiophen-2-yl] pentane

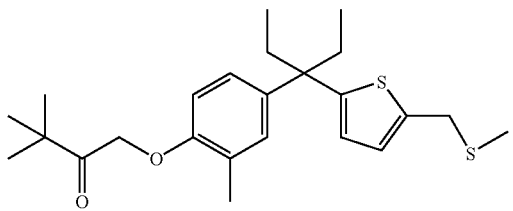

To a mixture of 3'-[4-(hydroxy)-3-methylphenyl]-3'-[5-(methylmercaptyl-methyl)-thiophen-2-yl]pentane (586 mg, 1.83 mmol), KI (122 mg, 0.73 mmol), 3,3-dimethyl-1-chloro-2-butanone (370 mg, 2.75 mmol) and DMF (10 ml) at 25° C. is added 60% NaH dispersion (92 mg, 2.29 mmol) in small portions. The reaction is stirred for 15 m and quenched with satd NaHCO₃ solution (50 ml). The mixture is extracted with EtOAc (2×50 ml) and the combined organic layer is washed with brine, Na2SO4 dried, and concentrated. The resulting oil is radial chromatographed (50% to 75% CHC13/Hex) to give the title product as a pale yellow oil (516 mg, 67%).

¹NMR (400 MHz, DMSO-d₆) δ ppm: 0.64 (t, J=7.3 Hz, 6H), 1.18 (s, 9H), 1.97 (s, 3H), 2.02 (m, 4H), 2.15 (s, 3H), 3.84 (s, 2H), 5.07 (s, 2H), 6.55 to 6.76 (m, 3H), 6.93 to 7.04 (m, 2H).

FAB(+) MS m/z [M−H]: 417.3; calc. for C₂₄H₃₄O₂S₂(—H): 417.20 IR (CHC₃): 1724.08 cm⁻¹.

Example 185

Preparation of 3'-[4-(2-hydroxy-3,3-dimethylbutoxy)-3-methylphenyl]-3'-[5-(methylmercaptylmethyl)-thiophen-2-yl]pentane

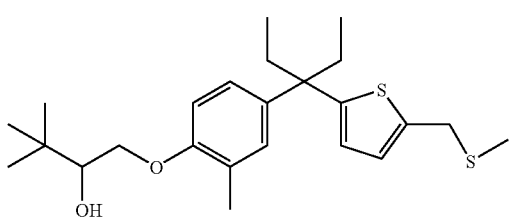

To a 25° C. solution of 3'-[4-(2-Oxo-3,3-dimethylbutoxy-3-methylphenyl)]-3'-[5-(methylmercaptylmethyl)thiophen-2-yl]pentane (90 mg, 0.22 mmol) in MeOH (10 ml) is added NaBH₄ (8.1 mg, 0.22 mmol). The reaction mixture is stirred overnight at ambient temperature. Then 1 ml of acetone is added, the reaction is concentrated and the residue is distributed between H₂O and CH₂Cl₂. The organic layer is washed with water, dried with anhydrous Na₂SO₄, and concentrated to give the title compound as a colorless oil (90 mg, quant).

¹NMR (300 MHz, CDCl₃) δ ppm: 0.63 (t, J=7.3 Hz, 6H), 0.94 (s, 9H), 1.95-2.08 (m, 4H), 1.97 (s, 3H), 2.12 (s, 3H), 3.63 (m, 1H), 3.73 (s, 2H), 3.79 (dd, J=7.3, 10.2 Hz, 1H), 4.02 (dd, J=3.4, 10.2 Hz, 1H), 6.54 (m, 1H), 6.64 (m, 2H), 6.97 (m, 2H).

FAB(+) MS m/z [M−H]: 419.3; calc. for C₂₄H₃₆O₂S₂ (—H): 419.22.

ES (+) MS m/z 438.2, [MNH₄+]; calc. for C₂₄H₄₀NO₂S₂: 438.24.

Example 186A and Example 186B

Preparation of enantiomers of 3'-[4-(2-hydroxy-3,3-dimethylbutoxy-3-methylphenyl)]-3'-[5-(methylmercaptylmethyl)-thiophen-2-yl]pentane

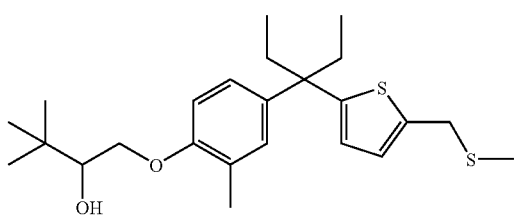

A racemic mixture of 3'-[4-(2-oxo-3,3-dimethylbutoxy-3-methylphenyl)]-3'-[5-(methylmercaptylmethyl)thiophen-2-yl]pentane (76 mg) is chromatographed with a Chiralcel AD column to give enantiomer 1, Example 186A (28 mg, 37%) and enantiomer 2, Example 186B (22 mg, 29%).

Enantiomer 1, Example 186A

HPLC: Chiralcel AD (4.6×250 mm); 40% IPA/60% heptane; 1 ml/m (flow rate); rt=4.21 m; 225 nm; ee 100% by HPLC.

FAB(+) MS m/z [M−H]: 419.3; calc. for C₂₄H₃₆O₂S₂ (—H): 419.22.

Enantiomer 2, Example 186B

HPLC: Chiralcel AD (4.6×250 mm); 40% IPA/60% heptane; 1 ml/m (flow rate); rt=5.67 m; 225 nm; ee 100% by HPLC.

FAB(+) MS m/z [M−H]: 419.3; calc. for C₂₄H₃₆O₂S₂ (—H): 419.22.

Example 187

Preparation of 3'-[4-(2-oxo-3,3-dimethylbutoxy-3-methylphenyl)]-3'-[5-(methylsulphonylmethyl)-thiophen-2-yl]pentane

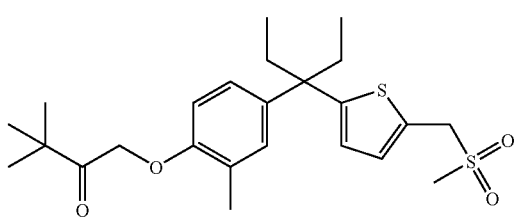

Using a procedure analogous to Example 9C, 3'-[4-(2-oxo-3,3-dimethylbutoxy-3-methylphenyl)]-3'-[5-(methylmercaptylmethyl)-thiophen-2-yl]pentane gives the title compound as a pale yellow oil (287 mg, 85%).

$^1$NMR (300 MHz, CDC$_3$) δ ppm: 0.71 (t, J=7.3 Hz, 6H), 1.28 (s, 9H), 2.04-2.25 (m, 4H), 2.27 (s, 3H), 2.79 (s, 3H), 4.37 (s, 2H), 4.86 (s, 2H), 6.53 (d, J=8.3 Hz, 1H), 6.76 (d, J=3.6 Hz, 1H), 6.99 to 7.02 (m, 3H).

FAB(+) MS m/z: 452.3; calc. for C$_{24}$H$_{34}$O$_4$S$_2$: 450.19.

ES (+) MS m/z 468.2, [MNH$_4$+]; calc. for C$_{24}$H$_{38}$NO$_4$S$_2$: 468.22.

IR (CHCl$_3$): 1725.04 cm$^{-1}$.

UV (EtOH): 227 nm (e=17500), 255 nm (shoulder, e=10,000).

Example 188

Preparation of 3'-[4-(2-hydroxy-3,3-dimethylbutoxy)-3-methylphenyl]-3'-[5-(methylsulfonylmethyl)-thiophen-2-yl]pentane

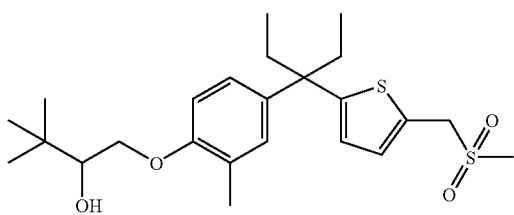

Using a procedure analogous to Example 2, 3'-[4-(2-oxo-3,3-dimethylbutoxy-3-methylphenyl)]-3'-[5-(methylsulfonylmethyl)-thiophen-2-yl]pentane gives the title compound as a colorless oil (188 mg, 94%).

$^1$NMR (400 MHz, CDCl$_3$) δ ppm: 0.67 (t, J=7.3 Hz, 6H), 1.04 (s, 9H), 2.12 (m, 4H), 2.22 (s, 3H), 2.14 (s, 3H), 2.80 (s, 3H), 3.72 (m, 1H), 3.99 (m, 1H), 4.12 (dd, J=2.9, 9.8 Hz, 1H), 4.36 (s, 2H), 6.74 (d, J=8.3 Hz, 1H), 6.78 (d, J=3.6 Hz, 1H), 6.96 to 7.08 (m, 3H).

FAB(+) MS m/z: 452.3; calc. for C$_{24}$H$_{36}$O$_4$S$_2$: 452.21.

Example 189A and Example 189B

Preparation of enantiomers of 3'-[4-(2-hydroxy-3,3-dimethylbutoxy)-3-methylphenyl]-3'-[5-(methylsulfonylmethyl)-thiophen-2-yl]pentane

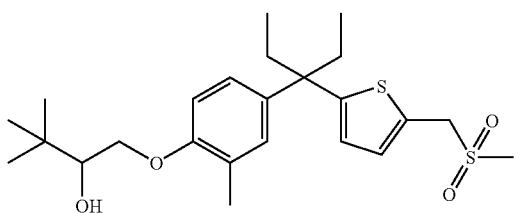

A racemic mixture of 3'-[4-(2-hydroxy-3,3-dimethylbutoxy)-3-methylphenyl]-3'-[5-(methylsulfonylmethyl)-thiophen-2-yl]pentane (174 mg) is chromatographed (Chiralcel AD column) to give enantiomer 1, Example 189A (78 mg, 43%) and enantiomer 2, Example 189B (86 mg, 49 g)

Enantiomer 1, Example 189A

HPLC: Chiralcel AD (4.6×250 mm); 40% IPA/60% heptane; 1 ml/m (flow rate); rt=5.75 m; 240 nm; ee=99.8%.

FAB(+) MS m/z: 452.3; calc. for C$_{24}$H$_{36}$O$_4$S$_2$: 452.21.

ES (+) MS m/z 470.1, [MNH4+]; calc. for C$_{24}$H$_{40}$NO$_4$S$_2$: 470.24.

Enantiomer 2, Example 189B

HPLC: Chiralcel AD (4.6×250 mm); 40% IPA/60% heptane; 1 ml/m (flow rate); rt=7.75 m; 260 nm; ee=99.6%.

FAB(+) MS m/z: 452.3; calc. for C$_{24}$H$_{36}$O$_4$S$_2$: 452.21.

ES (+) MS m/z 470.1, [MNH4+]; calc. for C$_{24}$H$_4$ONO$_4$S$_2$: 470.24.

Methods of Using the Compounds of the Invention:

When administration of the Active Ingredient is to be parenteral, such as intravenous on a daily basis, injectable pharmaceuticals may be prepared in conventional forms, either as liquid Solutions or suspensions; solid forms suitable for solution or suspension in liquid prior to injection; or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxiliary substances, such as wetting agents, pH buffering agents, and the like. If desired, absorption enhancing preparations (e.g. liposomes) may be utilized.

Method of Making the Compounds of the Invention

Scheme 1: synthesis of Phenyl-thiophene acids.

Bromophenol 1 is O-silylated with TBSCl and treated with Mg/THF at reflux to form the corresponding Grignard reagent. Condensation of the Grignard reagent with the 3-pentanone provides tertiary alcohol 2. Tertiary alcohol 2 is condensed with 3-methylthiophene and boron trifluoride etherate to yield scaffold 3. Scaffold 3 is O-benzylated with NaH/benzyl bromide to give benzyl ether 4. Benzyl ether 4 is reacted with nBuLi and chloromethyl formate to give methyl ester 5. Methyl ester 5 is debenzylated with palladium on carbon/hydrogen to yield phenol 6. Phenol 6 is alkylated with sodium hydride and bromopinacolone to give ketone 7. Ketone 7 is reduced with sodium borohydride/MeOH to yield alcohol 8. Alcohol 8 is treated with potassium hydroxide/EtOH at 70° C. to give acid 9. Acid 9 is resolved with a ChiralPak AD column to give enantiomer 1 (9A) and enantiomer 2 (9B). Alternatively, alcohol 8 is resolved with a ChiralPak AD column to give enantiomer 1 (8A) and enantiomer 2 (8B). Enantiomer 1 (8A) and enantiomer 2 (8B) are converted to enantiomer 1 (9A) and enantiomer 2 (9B) with KOH/EtOH, respectively.

Scheme 2: synthesis of phenyl-thiophene amides.

Acid 9 is converted to amide 10 by treatment with 1) diphenylphosphoryl azide/triethyl amine, DMAP and 2) appropriate amine HNR1R2.

Scheme 3: synthesis of phenyl-thiophene amide-acids.

Acid 9 is reacted with EDCI/(N-methylmorpholine or Et3N)/(HOBT or HOAT)/a substituted glycine ester to give amide-ester 11. Amide-ester 11 is hydrolyzed with LiOH/H20/THF to yield amide-acid 12.

Scheme 4: synthesis of phenyl-3-unsubstituted thiophene.

Ester 13 is reacted with EtMgBr/Et2O to give tertiary alcohol 14. Tertiary alcohol 14 is treated with nBuLi (2 eq) and CO2 (g) to yield acid 15. Acid 15 is dehydrated and esterified with MeOH/HCl (g) to give a mixture of olefinic ester 16. Olefinic ester 16 is reacted with o-cresol and BF3-Et2O to yield phenol 17. Phenol 17 is treated with NaH/DMF and 1-chloropinacolone/KI to give ketone 18. Ketone 18 is reacted with NaBH4/MeOH and KOH/EtOH to yield acid 19.

Alternatively, Phenol 17 (step 5i of scheme 4) is treated with $K_2CO_3$/ACN/KI catalyst to give ketone 18.

Scheme 5: synthesis of phenyl-thiophene sulfones.

Methyl ester 5 is reacted with LAH/THF/45° C. to give alcohol 20. Alcohol 20 is treated with PBr3 and then sodium alkyl thiolate to afford sulfide 21. Sulfide 21 is oxidized with mCBPA to yield sulfone 22. Sulfone 22 is hydrogenolyzed with Pd—C/H2 to give phenol 23. Phenol 23 is reacted with NaH/DMF and 1-bromopinacolone to afford ketone 24. Ketone 24 is reduced with NaBH4/MeOH to yield alcohol 25.

Scheme 6: synthesis of pentan-3-ol phenyl-thiophene amide-acids.

Phenol 3 is reacted with Tf2O and pyridine to give triflate 26. Triflate 26 is methoxy carbonylated with Pd(OAc)2/(DPPF or DPPB)/Et3N/(DMF or DMSO) at 80-100 C to yield ester 27. Ester 27 is treated with LAH/THF to afford alcohol 28. Alcohol 28 is reacted with PBr3 to give bromide 29. Bromide 29 is reacted with the lithium enolate of pinacolone to yield ketone 30. Ketone 30 is treated with NaBH4/MeOH and TBSOTf/2,6-methylpyridine to give silyl ether 31. Silyl ether 31 is reacted with nBuLi/THF and methyl chloroformate to afford ester 32. Ester 32 is desilylated with aq HF to yield alcohol 32A. Alcohol 32A is hydrolyzed with aq KOH/EtOH/70° C. to afford acid 32B. Acid 32B is coupled with EDCl/(N-methylmorpholine or Et3N)/(HOBT or HOAT)/a substituted glycine ester to give amide-ester 32C. Amide-ester 32C is hydrolyzed with LiOH/H20/THF to yield amide-acid 32D.

Scheme 7: synthesis of pentan-3-ol thiophene phenyl sulfonates.

Alcohol 20 is reacted with PBr3 to give bromide 33. Bromide 33 is reacted with the lithium enolate of pinacolone to afford ketone 34. Ketone 34 is hydrogenolyzed with Pd—C/H2 to yield phenol 35. Phenol 35 is sulfonated with a substituted alkyl sulfonyl chloride to give sulfonate 36. Sulfonate 36 is reduced with NaBH4/MeOH to yield alcohol 37. Alcohol 37 is treated with dilute aq LiOH/MeOH/dioxane to give sulfonate-acids 38.

Scheme 8: synthesis of pentan-3-ol thiophenyl phenyl sulfonamides.

Phenol 20 is treated with Tf2O/pyridine and Pd(OAc)2/(DPPF or DPPB)/CO (g)/MeOH/Et3N/(DMF or DMSO) at 80-100° C. to give ester 39. Ester 39 is reacted with NaBH4/MeOH and NaH/BnBr to afford benzyl ether 40. Benzyl ether 40 is hydrolyzed with KOH/EtOH/80° C. to yield acid 41. Acid 41 is reacted diphenyl phosphoryl azide/Et3N and tBuOH/90° C. to afford Boc-amine 42. Boc-amine 42 is treated with TFA/anisole to give aniline 43. Aniline 43 is subjected to R3SO$_2$Cl/pyridine and Pd—C/H2 to afford sulfonamide 44. Sulfonamide 44 is hydrolyzed with aq LiOH/MeOH to yield sulfonamide-acid 45.

Scheme 9: synthesis of α-methylated pinacolol phenyl-thiophene acids and amide acids.

Ester 7 is treated with LiHMDS; MeI and NaBH4/MeOH to give alcohol 46. Alcohol 46 is reacted with KOH/EtOH/heat to afford acid 47. Acid 47 is coupled with EDCl/(N-methylmorpholine or Et3N)/(HOBT or HOAT)/a substituted glycine ester to give amide-ester 48. Amide-ester 48 is hydrolyzed with LiOH/H20/THF to yield amide-acid 49.

Scheme 10: synthesis of tertiary alcohol phenyl-thiophene acids and amide-acids.

Phenol 3 is reacted with NaH/DMF and 1-bromopinacolone to give ketone 50. Ketone 50 is treated with MeMgBr/Et2O to afford tertiary alcohol 51. Tertiary alcohol 51 reacted with s-BuLi (2.5 eq) and CO2 (g) to give acid 52. Acid 52 is coupled with EDCl/(N-methylmorpholine or Et3N)/(HOBT or HOAT)/a substituted glycine ester to give amide-ester 53. Amide-ester 53 is hydrolyzed with LiOH/H2O/dioxane to yield amide-acid 54. Alternatively, Phenol 3 may be reacted with $K_2CO_3$ and KI catalyst in place of NaH/DMF to give ketone 50.

Scheme 11: synthesis of cis-pentynol phenyl-thiophene acids and amide-acids.

Phenol 3 is reacted with TBSCl/imidazole. To give silyl ether 55. Silyl ether 55 is treated with n-BuLi/THF and methyl chloroformate to afford ester 56. Ester 56 is reacted with TBAF/THF and Tf2O/pyridine to yield triflate 57. Triflate 57 is coupled with TMS-acetylene/Et3N/DMF/Pd(PPh3) 2C12 and desilylated with TBAF/THF to give acetylene 58. Acetylene 58 is treated with Zn(OTf)2Et$_3$N//t-butyl aldehyde/chiral auxiliary (with or without) to give alcohol 60. Alternatively, Acetylene 58 is reacted with LiHMDS/ketone 59 to give alcohol 60. Alcohol 60 is hydrolyzed with KOH/EtOH to afford acid 61.

Optionally, the acetylenic bond may be hydrogenated by conventional methods.

Scheme 12: synthesis of cis-pentenol phenyl-thiophene acids and amide-acids.

Alcohol 60 is treated with Lindlar's catalyst/H2 and KOH/EtOH to yield acid 62.

Scheme 13: synthesis of trans-pentenol phenyl-thiophene acids and amide-acids.

Phenol 3 is reacted with Tf2O/pyridine to give triflate 63. Triflate 63 is coupled with TMS-acetylene/Et3N/DMF/Pd (PPh3)2C12 and desilylated with TBAF/THF to give acetylene 64. Acetylene 64 is treated with Zn(OTf)2/t-butyl aldehyde/chiral auxiliary (with or without) to give alcohol 65. For tertiary alcohols, acetylene 64 is reacted with LiHMDS/ketone 59 to give alcohol 65. Alcohol 65 is reduce with LAH or DiBAH to afford trans-pentenol 66. Trans-pentenol 66 is treated with s-BuLi (2.5 eq) and C02 (g) to give acid 67.

Scheme 14: synthesis of pentynol thiophenyl-pheny acids.

Phenol 3 is reacted with DPTBSCl/imidazole. to give silyl ether 68. Silyl ether 68 is reacted with n-BuLi/THF and iodine to afford iodide 69. Iodide 69 is coupled with TMS-acetylene/Et3N/DMF/Pd(PPh3)2C12 and desilylated with TBAF/THF to give acetylene 70. Acetylene 70 is treated with Zn(OTf)2/t-butyl aldehyde/chiral auxiliary (with or without) to give alcohol 71. For tertiary alcohols, acetylene 70 is reacted with LiHMDS/ketone 59 to give alcohol 71. Alcohol 71 is subjected to TBAF/THF and Tf2O/pyridine to yield triflate 72. Triflate 72 is methoxycarbonylated with Pd(OAc)2/(DPPF or DPPB)/CO (g)/MeOH/Et3N/(DMF or DMSO) at 80-100° C. to give ester 73. Ester 73 is hydrolyzed with KOH/EtOH to afford acid 74.

Optionally, the acetylenic bond may be hydrogenated by conventional methods.

Scheme 15: synthesis of cis-pentenol thiophenyl-phenyl acids.

Acid 74 is reduced with Lindlar's catalyst/H2 to give acid 75.

Scheme 16: synthesis of trans-pentenol thiophenyl-phenyl acids.

Acetylene 71 is reduced with LAH or DiBAlH to give trans-pentenol 76. Trans-pentenol 76 is treated with TBAF/THF and Tf2O/pyridine to afford triflate 77. Triflate 77 is methoxycarbonylated with Pd(OAc)2/(DPPF or DPPB)/CO (g)/MeOH/Et3N/(DMF or DMSO) at 80-100° C. to give an ester which is hydrolyzed with KOH/EtOH to afford acid 78.

Scheme 17: synthesis of phenyl-thiophenyl acid mimics.

Acid 9 is coupled with EDCl/H2NSO2R3/DMAP to give acyl-sulfonamide 79. Acid 9 is coupled with EDCl/5-aminotetrazole/DMAP to give acyl-aminotetrazole 80. For tetrazole 83, acid 9 is reacted with formamide/NaOMe at 100° C. to afford amide 81. Amide 81 is treated with trifluoroacetic acid and methylene chloride followed by 2-chloro-1,3-dimethyl-2-imidazolinium hexafluorophosphate to give nitrile 82. Nitrile 82 is reacted with sodium azide and triethylammonium hydrochloride in N-methylpyrrolidin-2-one to afford tetrazole 83.

Scheme 18: synthesis of phenyl-thiophenyl acid analogs.

Alcohol 20 is reacted with Pd—C/H2 to give phenol 84. Phenol 84 is treated with NaH/DMF (1.0 eq) and 1-bromopinacolone to afford ketone 85. Ketone 85 is reacted with PBr3 to afford bromide 86. Bromide 86 is couple with KCN/DMF to give nitrile 87. Nitrile 87 is reduced with NaBH4/MeOH to yield alcohol 88. Alcohol 88 is reacted with KOH/H20/dioxane/heat to give acid 89. Acid 89 is coupled with EDCI/5-aminotetrazole/DMAP to give acyl-aminotetrazole 90.

Scheme 19: synthesis of additional phenyl-thiophene acid analogs.

Alcohol 88 is reacted with NaN3/Et3N-HCl/NMP at 150 C to afford tetrazole 91. Bromide 86 is treated with the sodium enolate of dimethyl malonate and KOH/EtOH/heat to give propionic acid 93. Acid 93 is reduced with NaBH4/MeOH to give 93A.

Scheme 20: synthesis of pentan-3-ol thiophenyl phenyl oxyacetic acid.

Phenol 35 is reacted with K2CO3/BrCH2CO2Me to give oxyacetate 94. Oxyacetate is hydrolyzed with aq LiOH/MeOH/dioxane to yield oxyacetic acid 95. Oxyacetic acid 95 is reduced with NaBH4/MeOH to afford alcohol-oxyacetic acid 96.

Scheme 21: synthesis of pentan-3-ol phenyl thiophene propionic acid.

Silyl ether 31 is reacted with n-BuLi/THF and bromine to give bromide 97. Bromide 97 is coupled with BrZnCH2CH2CO2Et/Pd(DPPF)C12/THF/heat to afford ester 98. Ester 98 is reacted with aq LiOH/MeOH and TBAF/THF to yield propionic acid 99.

Scheme 22: synthesis of pentan-3-ol thiophenyl phenyl propionic acid.

Phenol 35 is reacted with Tf2O/pyridine to give triflate 100. Triflate 100 is coupled with BrZnCH2CH2CO2Et/Pd(DPPF)C12/THF/heat to afford ester 101. Ester 101 is reacted with aq LiOH/MeOH/dioxane and NaBH4/MeOH to yield propionic acid 102.

Scheme 23: Improved synthesis of phenyl thiophene derivatives.

Acid 103 is esterified with MeOH/HCl (g) and reacted with EtMgBr (6 eq) to give alcohol 104. Alcohol 104 is coupled with 3-methylthiophene and BF3-OEt2 to afford phenol 3. Phenol 3 is treated with TBSCl/imidazole. to yield silyl ether 55. Silyl ether 55 is reacted with nBuLi and methyl chloroformate to give ester 56. Ester 56 is sequentially reacted with 6) TBAF; 7) 1-bromopinacolone/K2C03; 8) NaBH4; and 9) KOH to afford acid 9.

Scheme 24: Synthesis of phenyl-3-unsubstituted-thiophene sulfones and sulfides.

Commercially available 2-hydroxymethyl thiophene is reacted with NaH (3 eq) and S-methyl-N,N'-tetramethylisothiuronium iodide to give 2-(methylmercaptylmethyl)-thiophene (105). Compound (105) is coupled with alcohol (104) and BF3-OEt2 to afford phenol 106. Phenol 106 is reacted with NaH/DMF and 1-chloropinacolone/KI to provide ketone 107. The sulfide moiety of 107 is oxidized with mCPBA to yield sulfone 108. Compound 108 is reacted with NaBH4/MeOH to yield sulfone-alcohol 109. In addition, ketone 107 is reduced by NaBH4/MeOH to yield the sulfide-alcohol 110.

Scheme 25: Preparation of sulfonyl aminoalkylcarboxylic acids.

Silyl ether 55 is reacted with nBuLi/THF followed by sulfuryl chloride to give sulfonyl chloride 111. Sulfonyl chloride 111 is reacted with allyl amine to yield a sulfonamide 112. Sulfonamide 112 is alkylated with K2CO3/BrCH2CO2Me to afford ester 113. Ester 113 is reacted sequentially with 1) HF/H20/acetonitrile; 2) K2CO3/1-chloropinacolone to give ketone-ester 114. Ketone-ester 114 is treated with 1) Pd(PPh3)4/N,N-dimethyl barbituric acid; 2) NaBH4/MeOH; aq LiOH/dioxane to yield sulfonamide-acid 115.

Scheme 1: Synthesis of Phenyl-Thiophene Acids

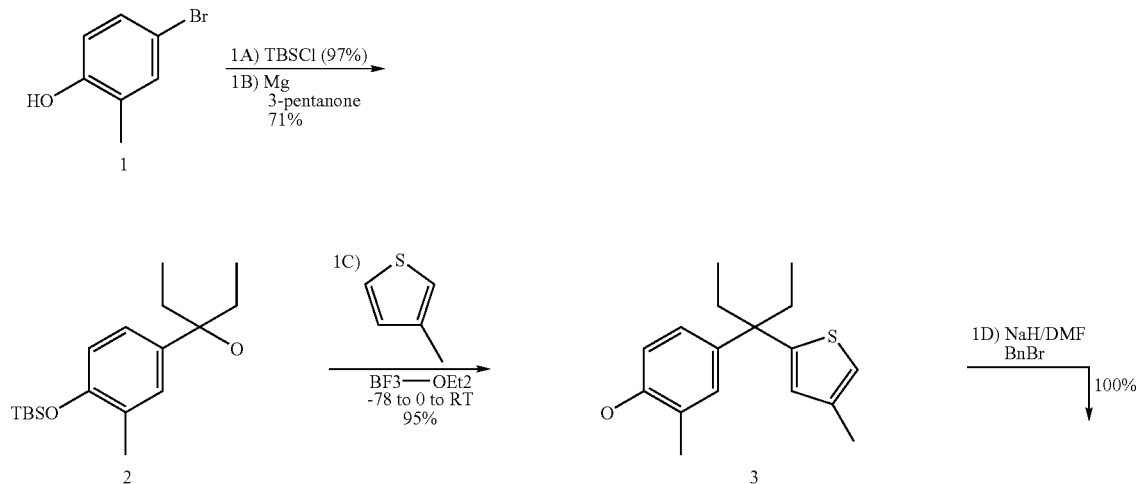

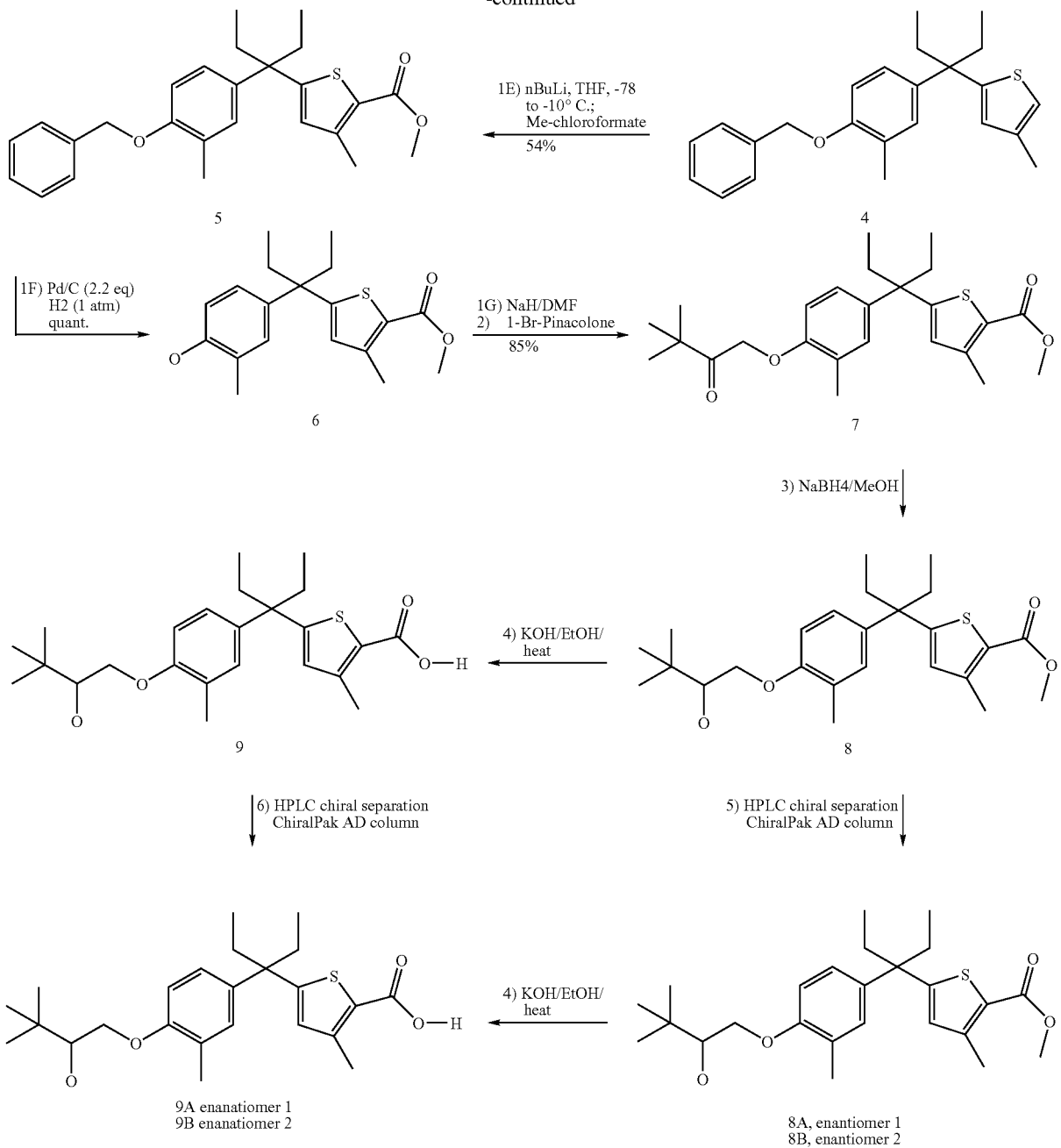
Scheme 3: Synthesis of Phenyl-Thiophene Amides Amide-Acids
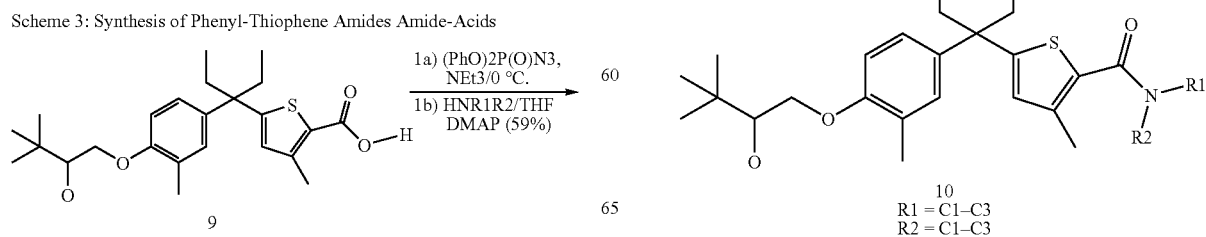

Scheme 3: Synthesis of Phenyl-Thiophene Amide-Acids
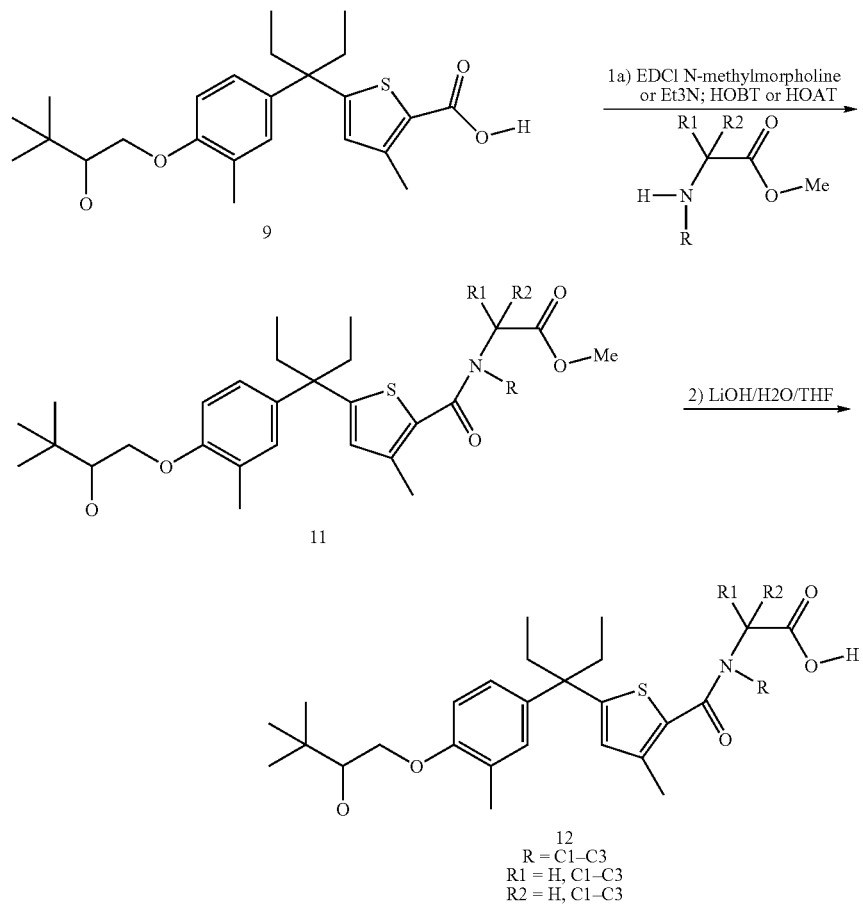
Scheme 4: Synthesis of Phenyl-3-Unsubstituted Thiophene
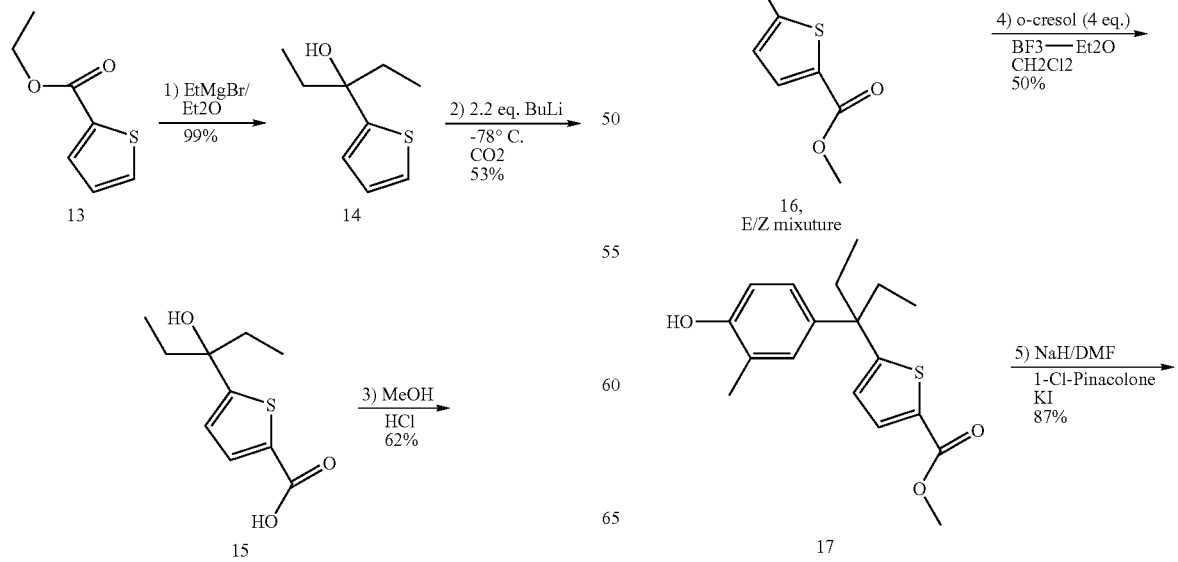

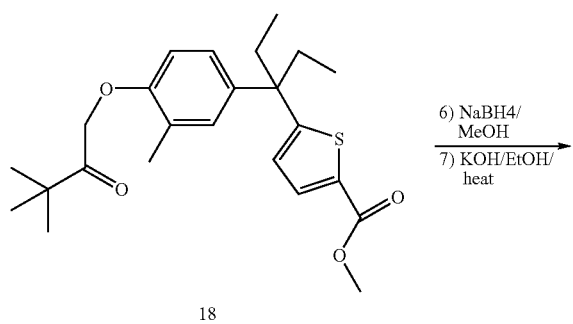
Scheme 5: Synthesis of Phenyl-Thiophene Sulfones
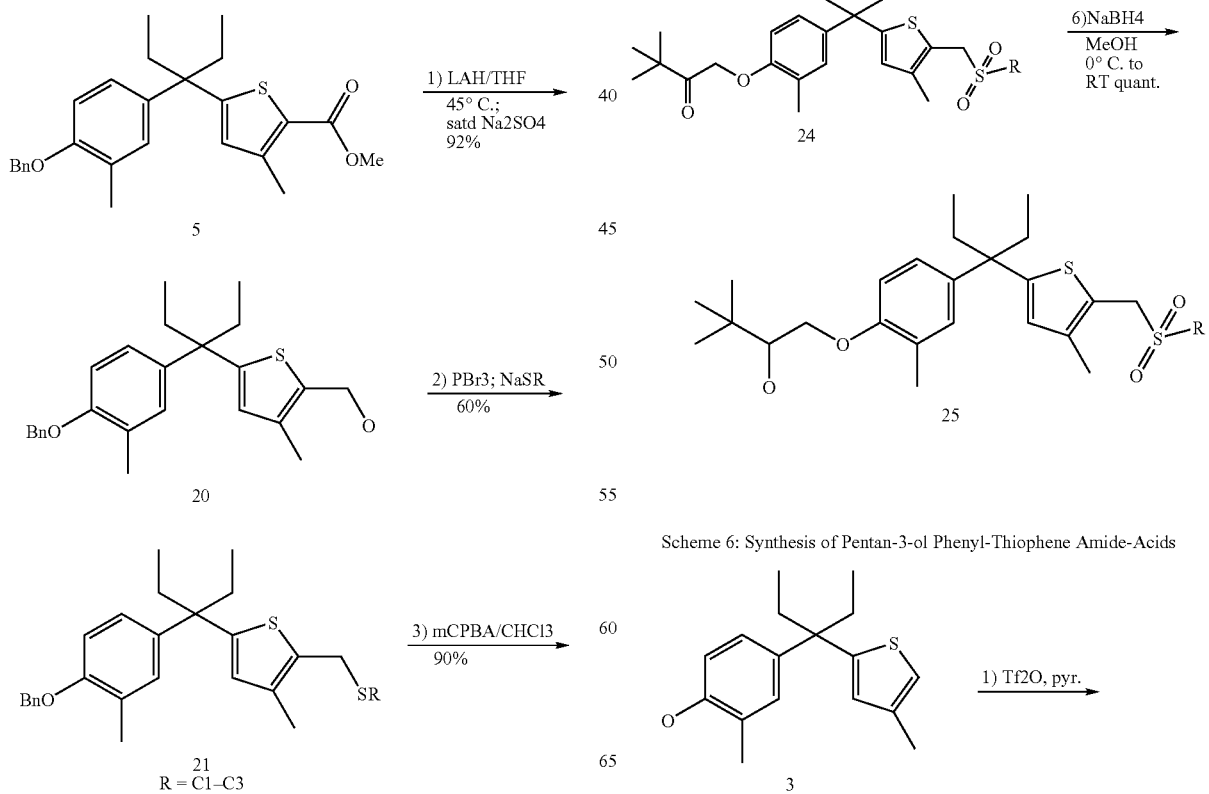
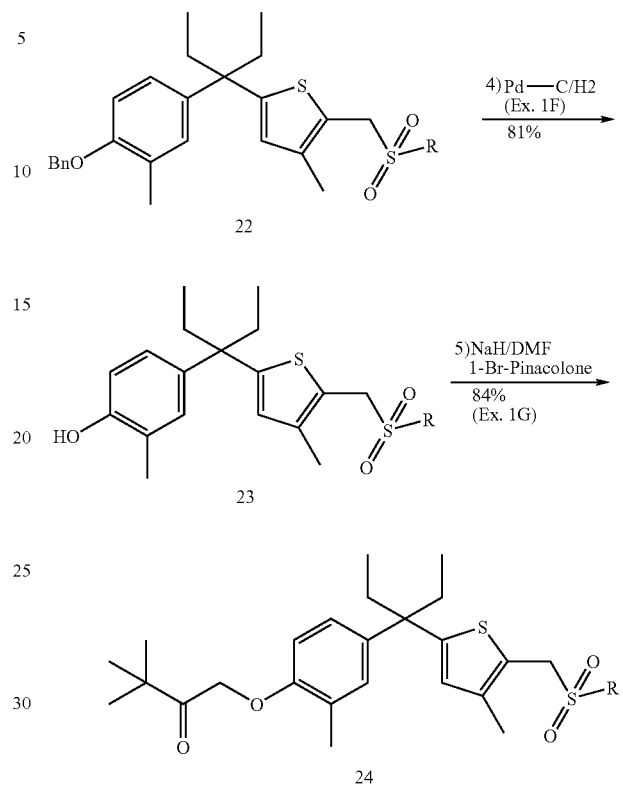
Scheme 6: Synthesis of Pentan-3-ol Phenyl-Thiophene Amide-Acids -continued

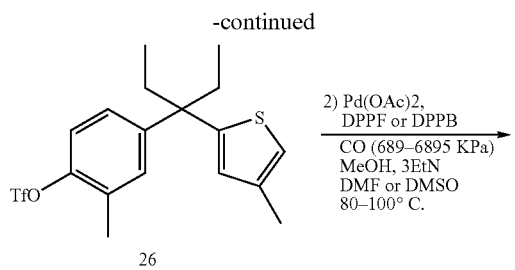
26

2) Pd(OAc)2,
DPPF or DPPB
―――――――――→
CO (689–6895 KPa)
MeOH, 3EtN
DMF or DMSO
80–100° C.

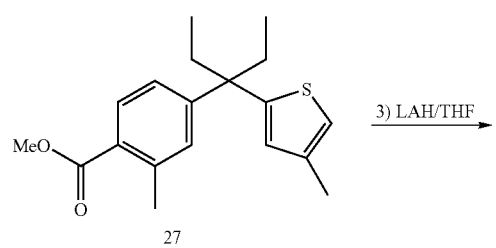
27

3) LAH/THF
―――――→

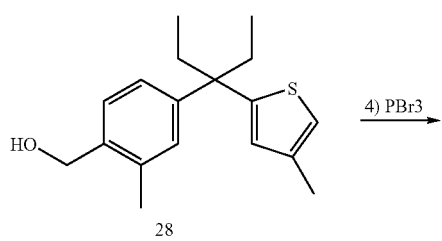
28

4) PBr3
――――→

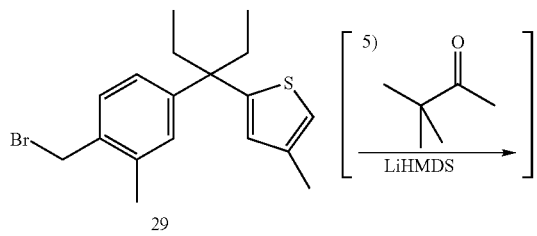
29

5) [ketone]
―――――→
LiHMDS

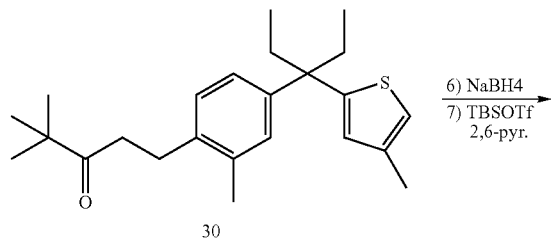
30

6) NaBH4
7) TBSOTf
2,6-pyr.
――――→

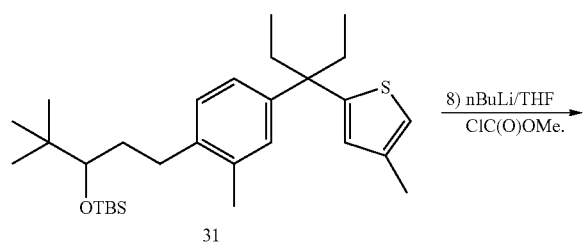
31

8) nBuLi/THF
―――――――→
ClC(O)OMe.

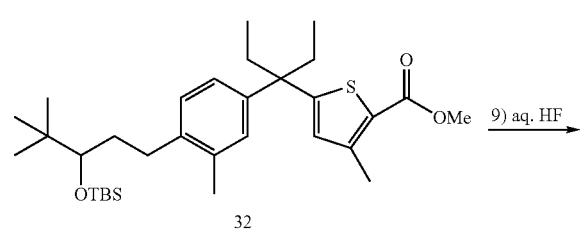
32

9) aq. HF
―――――→

-continued

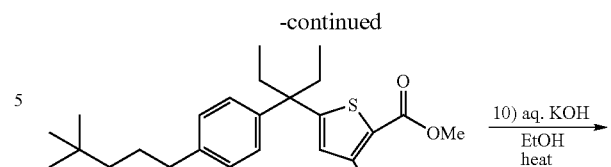
32A 10) aq. KOH
―――――――→
EtOH
heat

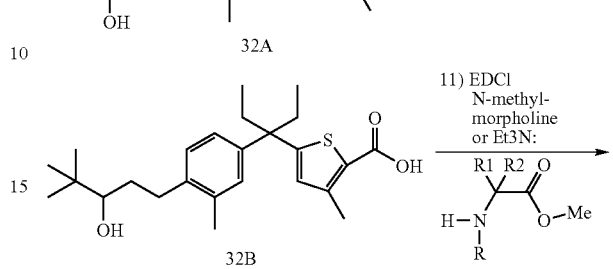
32B

11) EDCl
N-methyl-
morpholine
or Et3N:
―――――――→

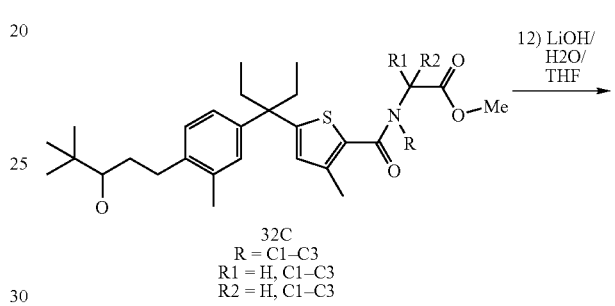
32C
R = C1–C3
R1 = H, C1–C3
R2 = H, C1–C3

12) LiOH/
H2O/
THF
―――――→

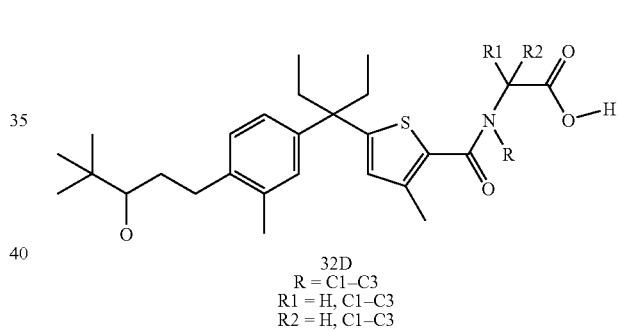
32D
R = C1–C3
R1 = H, C1–C3
R2 = H, C1–C3

Scheme 7: Synthesis of Petan-3-ol Thiophenyl Phenyl Sulfonates

[Structure 20]
1) PBr3
―――→

[Structure 33]
2) [ketone]
―――――→
LiHMDS

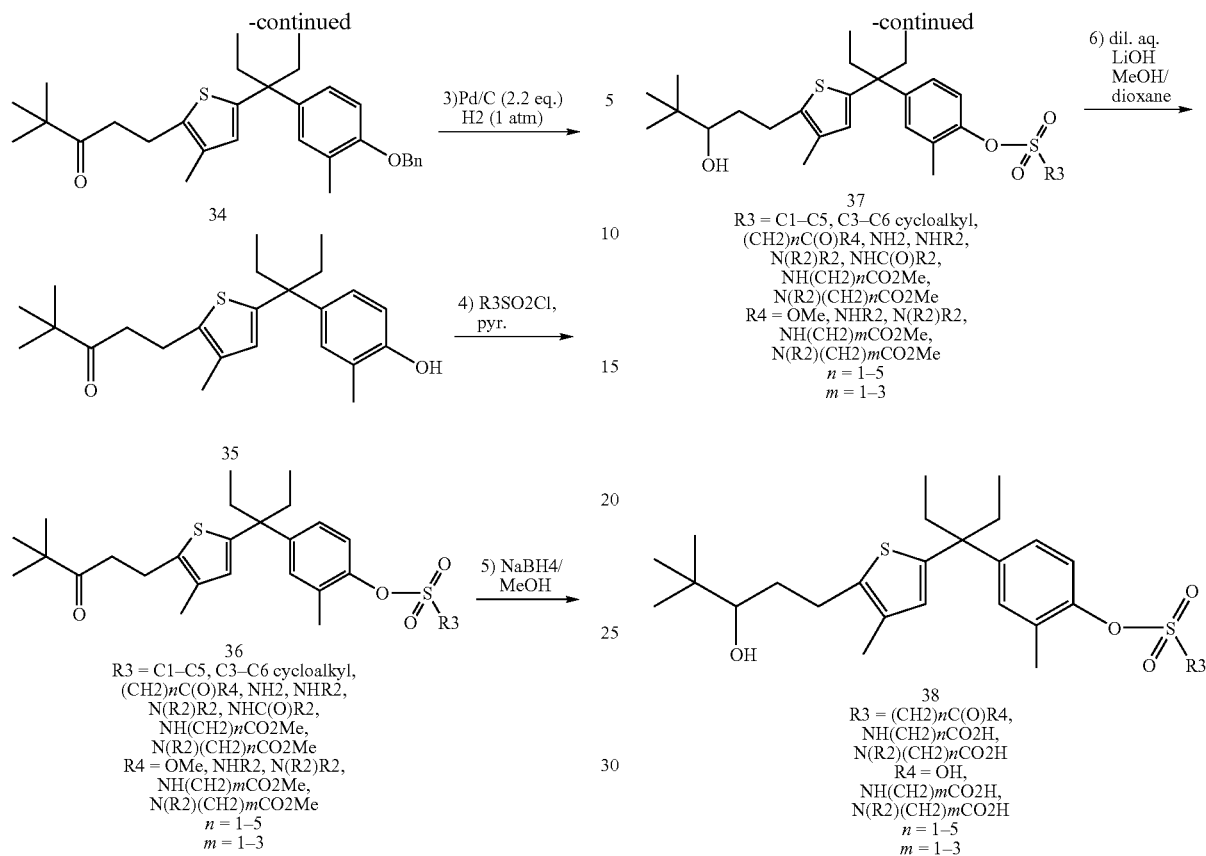
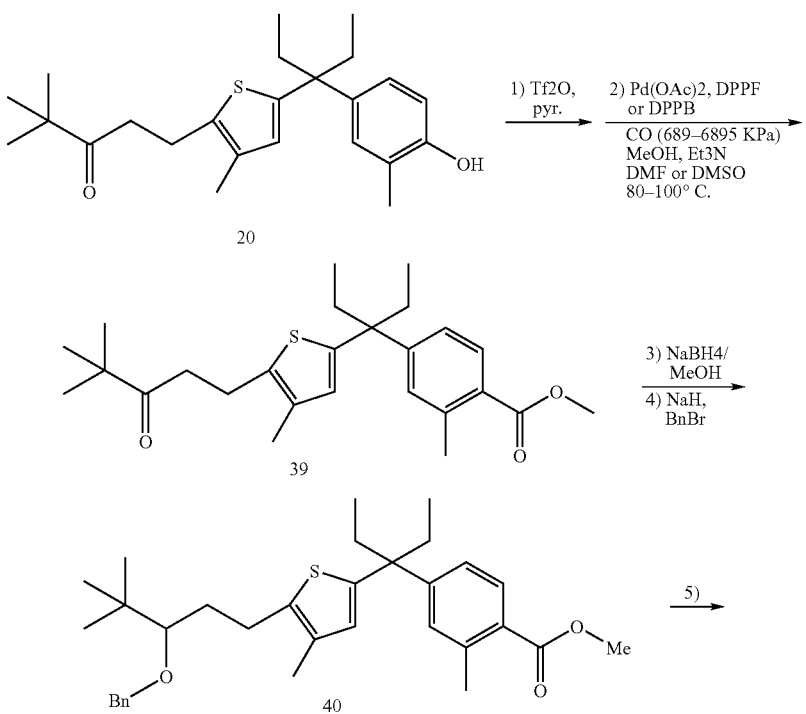
Scheme 8: Synthesis of Pentan-3-ol Thiophenyl Phenyl Sulfonamides -continued
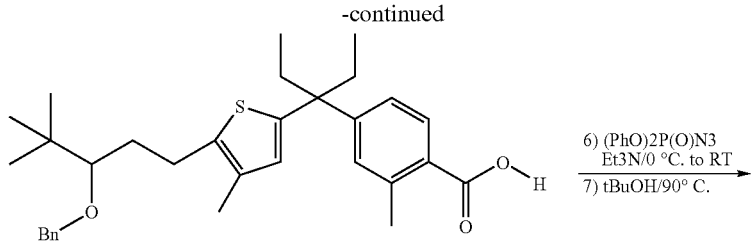
41
6) (PhO)2P(O)N3
Et3N/0 °C. to RT
7) tBuOH/90° C.
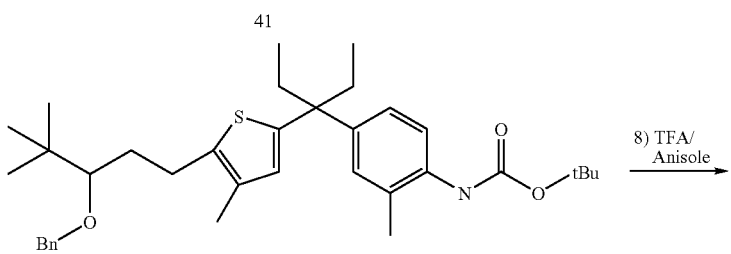
42
8) TFA/
Anisole
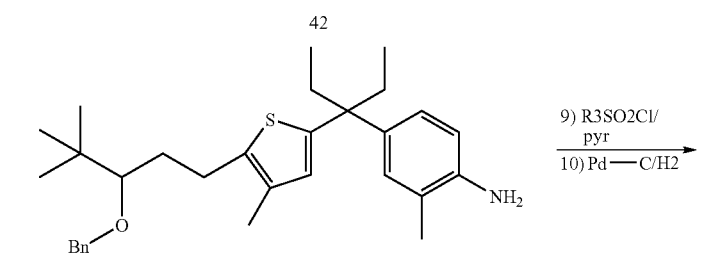
43
9) R3SO2Cl/
pyr
10) Pd—C/H2
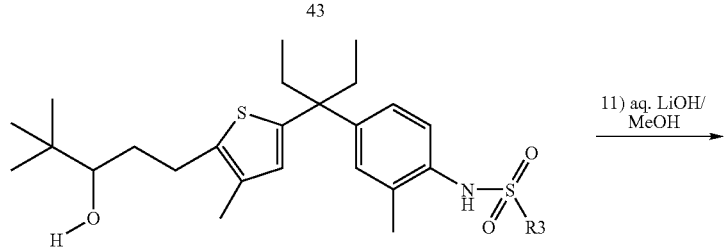
44
R3 = C1–C5, C3–C6 cycloalkyl,
(CH2)nC(O)R4, NH2, NHR2,
N(R2)R2, NHC(O)R2,
NH(CH2)nCO2Me,
N(R2)(CH2)nCO2Me
R4 = OMe, NHR2, N(R2)R2,
NH(CH2)mCO2Me,
N(R2)(CH2)mCO2Me
n = 1–5
m = 1–3
11) aq. LiOH/
MeOH
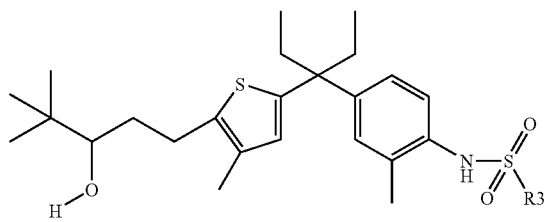
45
R3 = (CH2)nC(O)R4,
NH(CH2)nCO2H,
N(R2)(CH2)nCO2H
R4 = OH,
NH(CH2)mCO2H,
N(R2)(CH2)mCO2H
n = 1–5
m = 1–3

Scheme 9: Synthesis of α-Methylated Pinacolol Phenyl-Thiophene Acids & Amide-Acids
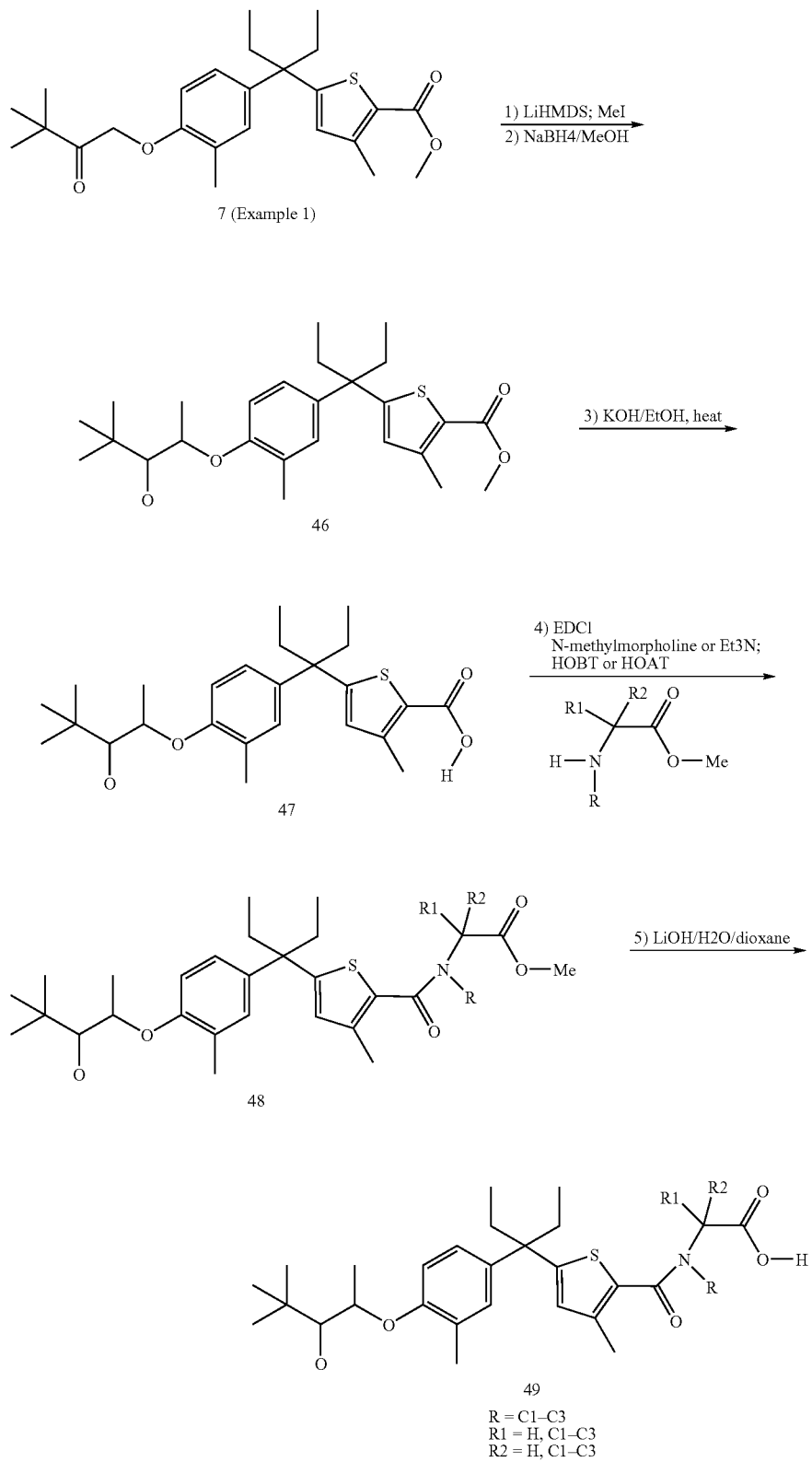
R = C1–C3
R1 = H, C1–C3
R2 = H, C1–C3

Scheme 10: Synthesis of Tertiary Alcohol Phenyl-Thiophene Acids & Amide-Acids
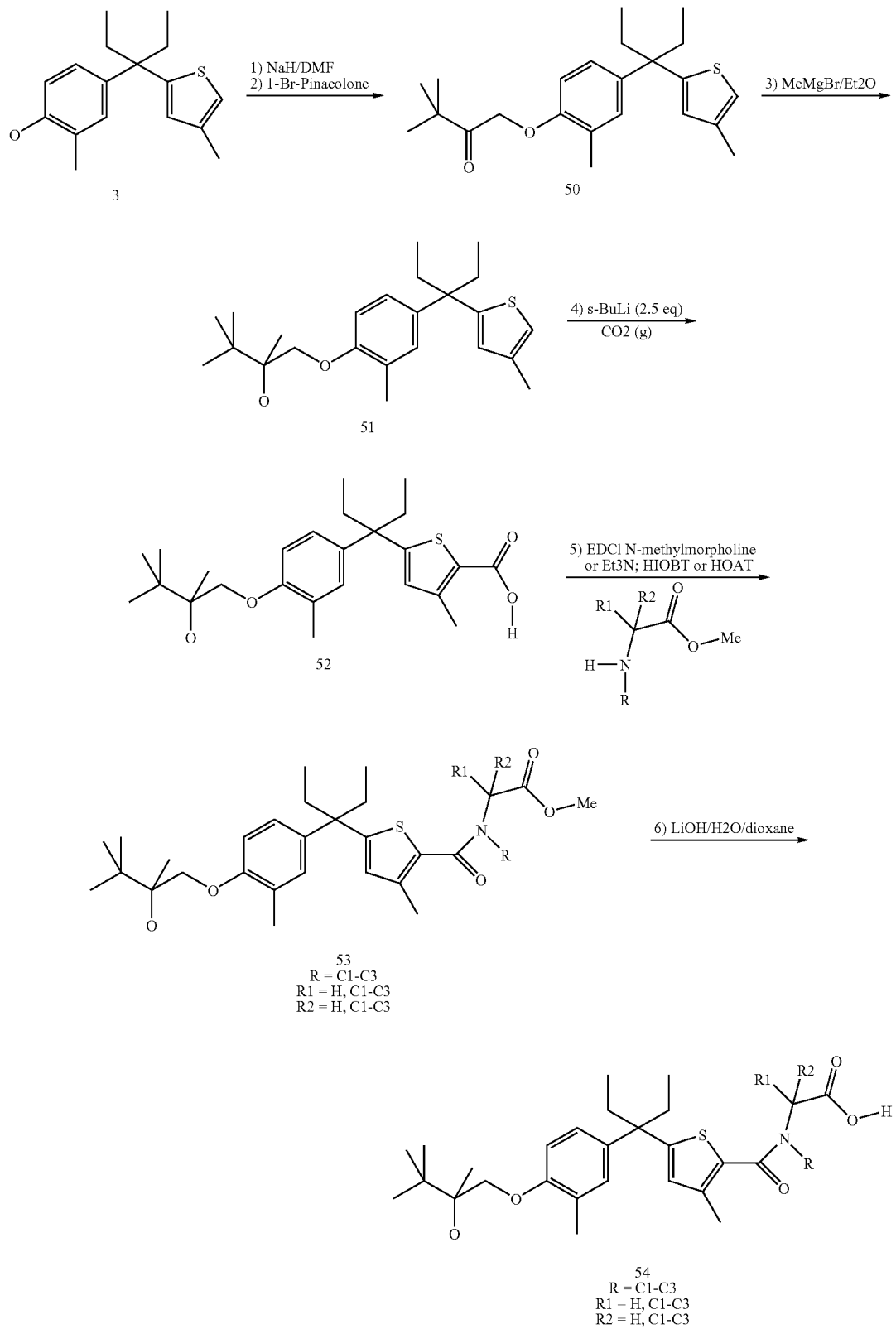

Scheme 11: Synthesis of Pentynol Phenyl-Thiophene Acids

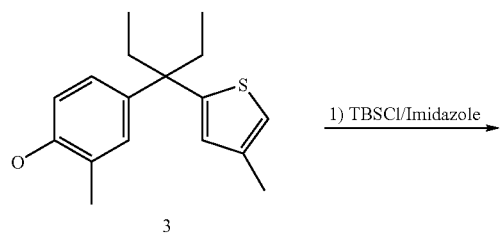
3

1) TBSCl/Imidazole →

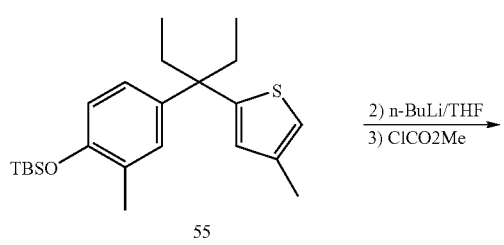
55

2) n-BuLi/THF
3) ClCO2Me →

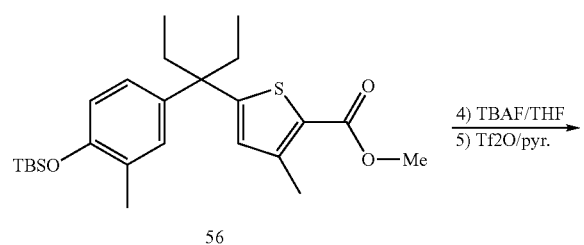
56

4) TBAF/THF
5) Tf2O/pyr. →

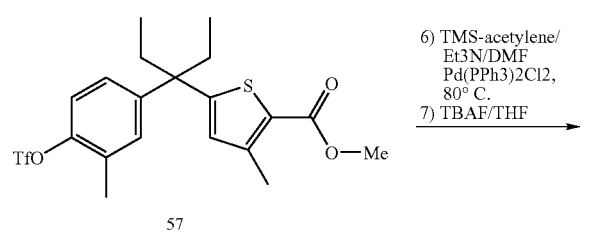
57

6) TMS-acetylene/
Et3N/DMF
Pd(PPh3)2Cl2,
80° C.
7) TBAF/THF →

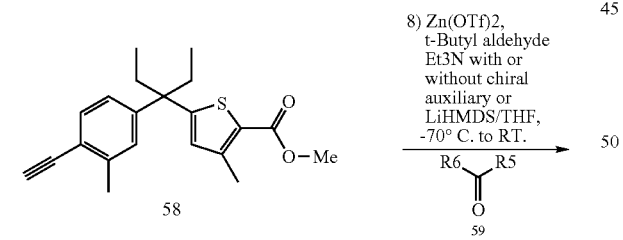
58

8) Zn(OTf)2,
t-Butyl aldehyde
Et3N with or
without chiral
auxiliary or
LiHMDS/THF,
−70° C. to RT.

R6 R5
 \\/
  C
  ‖
  O
59
→

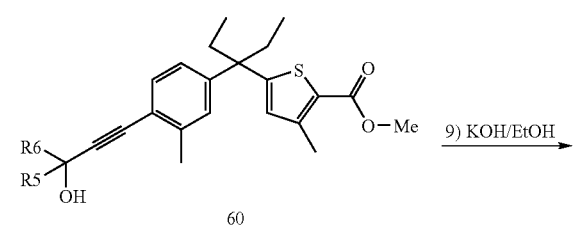
60

R5 = H, Me, Et, Pr
R6 = Et, Pr, tBu
R5 & R6 (to form ring) = (CH2)4, (CH2)5

9) KOH/EtOH →

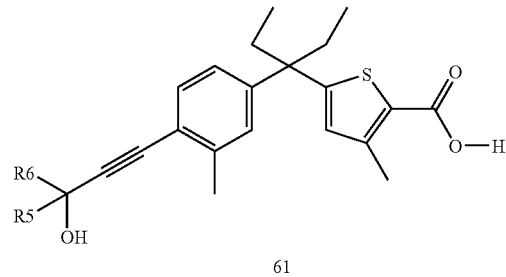
61

R5 = H, Me, Et, Pr
R6 = Et, Pr, tBu
R5 & R6 (to form ring) = (CH2)4, (CH2)5

Scheme 12: Synthesis of Cis-Pentenol Phenyl-Thiophene Acids

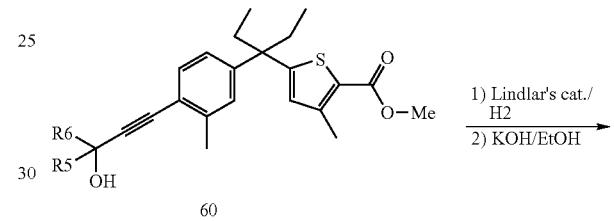
60

R5 = H, Me, Et
R6 = Et, Pr, tBu
R5 & R6 (to form ring) = (CH2)n
n = 4, 5

1) Lindlar's cat./H2
2) KOH/EtOH →

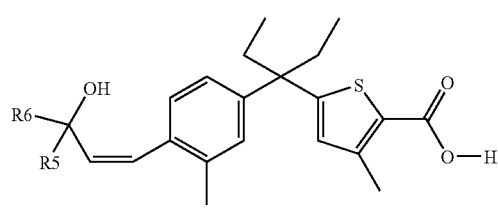
62

R5 = H, Me, Et,
R6 = Et, Pr, tBu
R5 & R6 (to form ring) = (CH2)n
n = 4, 5

Scheme 13: Synthesis of Trans-Pentenol Phenyl-Thiophene Acids

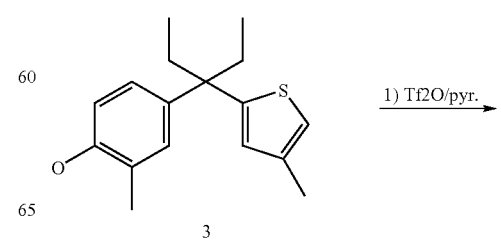
3

1) Tf2O/pyr. →

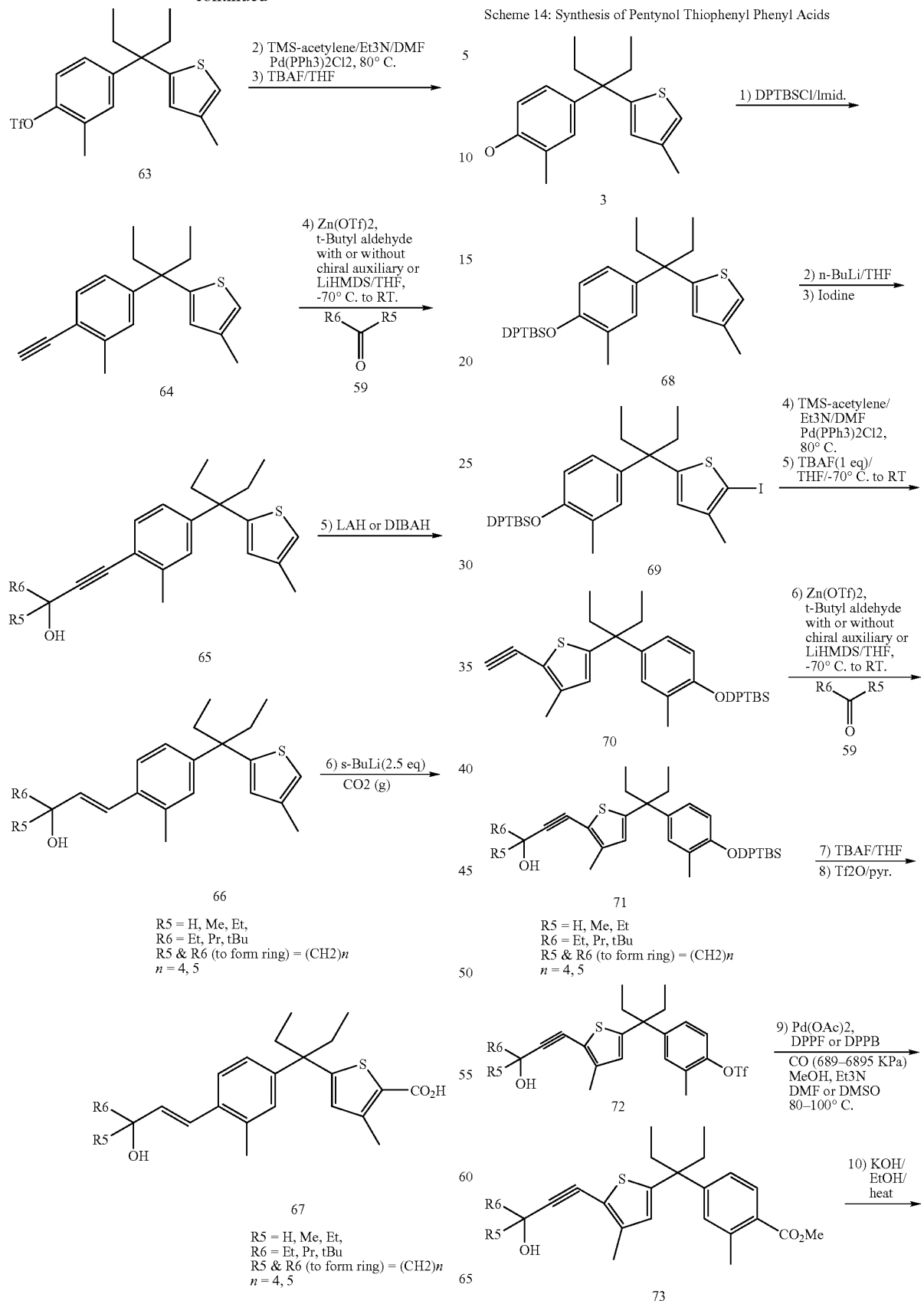
Scheme 14: Synthesis of Pentynol Thiophenyl Phenyl Acids

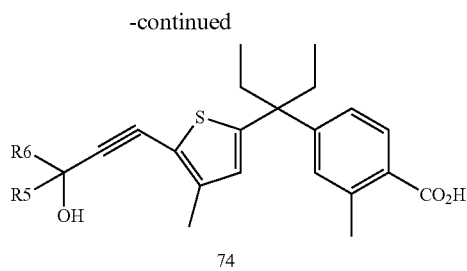

74

R5 = H, ME, Et
R6 = Et, Pr, tBu
R5 & R6 (to form ring) = (CH2)n
n = 4, 5

Scheme 15: Synthesis of Cis-Pentenol Thiophenyl Phenyl Acids

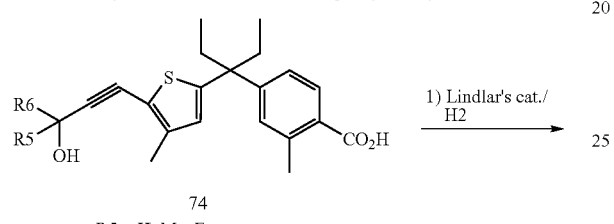

1) Lindlar's cat./ H2 →

74
R5 = H, Me, Et
R6 = Et, Pr, tBu
R5 & R6 (to form ring) = (CH2)n
n = 4, 5

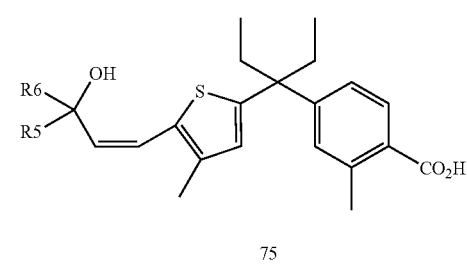

75

Scheme 16: Synthesis of Trans-Pentenol Thiophenyl Phenyl Acids

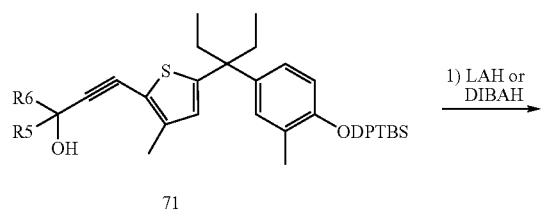

1) LAH or DIBAH →

71
R5 = H, Me, Et
R6 = Et, Pr, tBu
R5 & R6 (to form ring) = (CH2)n
n = 4, 5

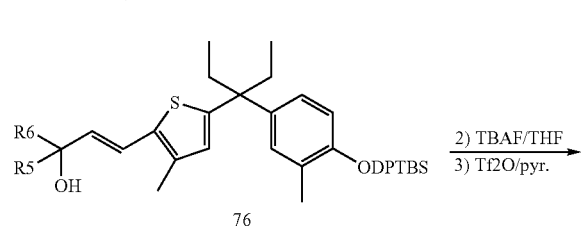

2) TBAF/THF
3) Tf2O/pyr.

76

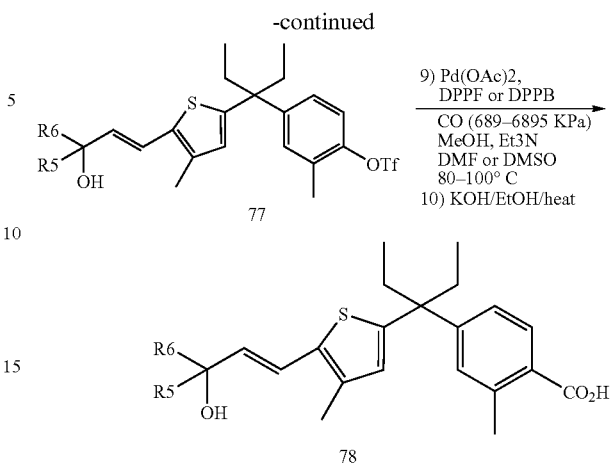

9) Pd(OAc)2, DPPF or DPPB
CO (689–6895 KPa)
MeOH, Et3N
DMF or DMSO
80–100° C
10) KOH/EtOH/heat

77

78

R5 = H, Me, Et
R6 = Et, Pr, tBu
R5 & R6 (to form ring) = (CH2)n
n = 4, 5

Scheme 17: Synthesis of Phenyl-Thiophene Acid Mimics

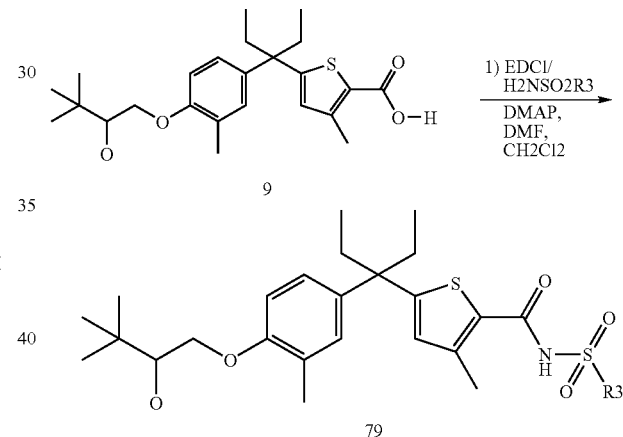

9

1) EDCl/ H2NSO2R3
DMAP, DMF, CH2Cl2 →

79

R3 = Me, Et, Pr,
NH(CH2)nCO2H,
N(R2)(CH2)nCO2H
R2 = H, Me
n = 1–5

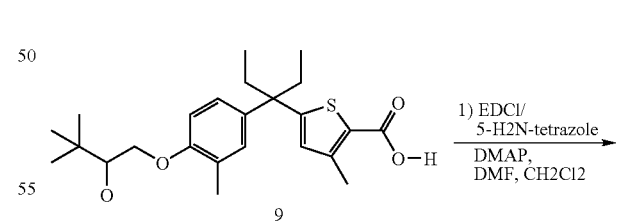

9

1) EDCl/ 5-H2N-tetrazole
DMAP, DMF, CH2Cl2 →

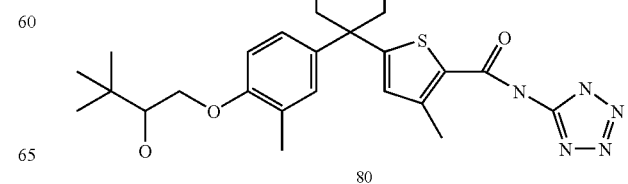

80

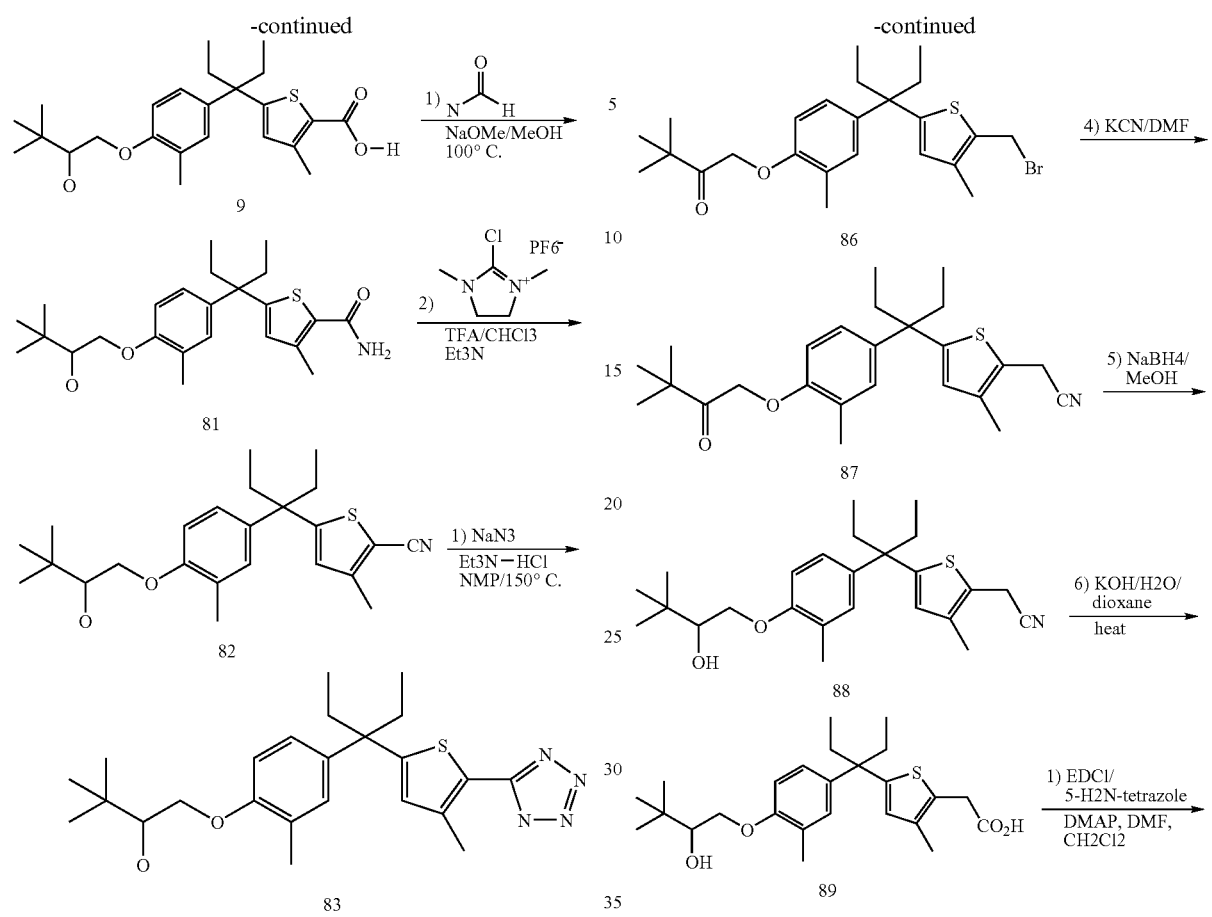
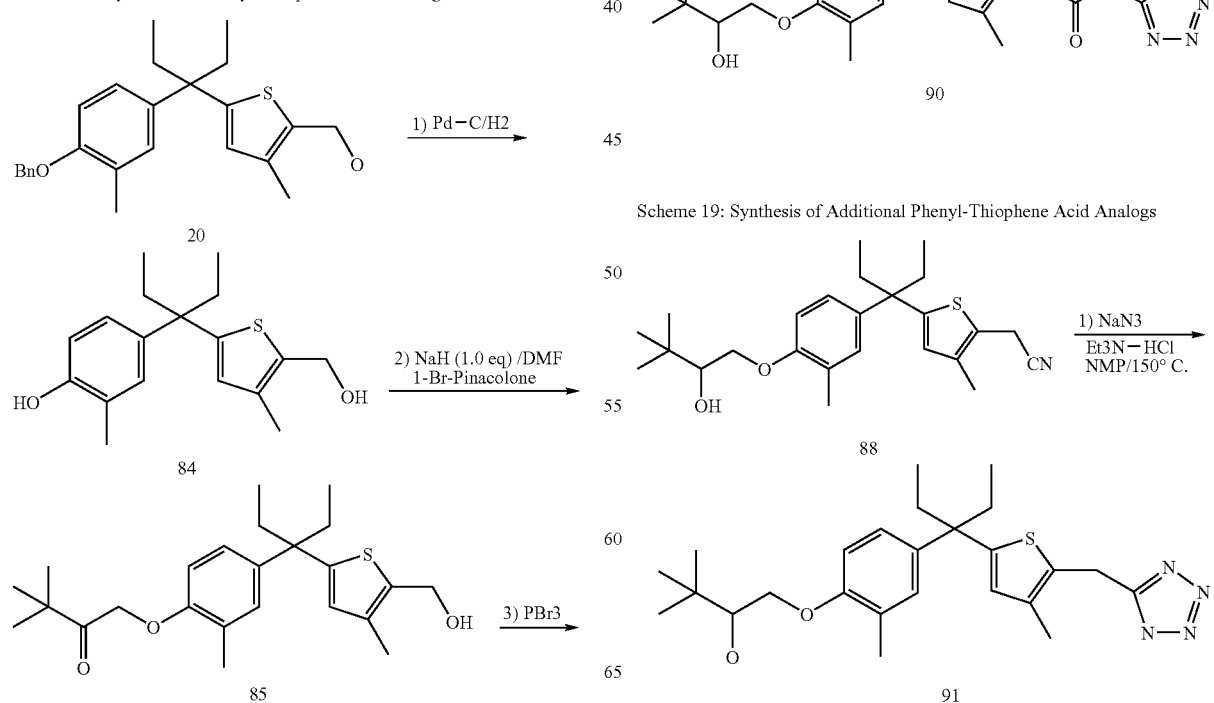
Scheme 18: Synthesis of Phenyl-Thiophene Acid Analogs
Scheme 19: Synthesis of Additional Phenyl-Thiophene Acid Analogs

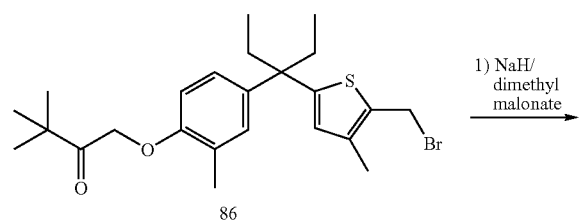
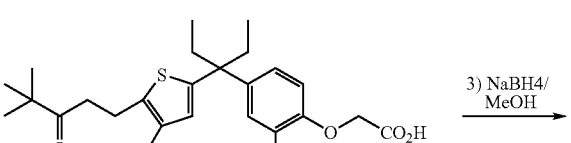
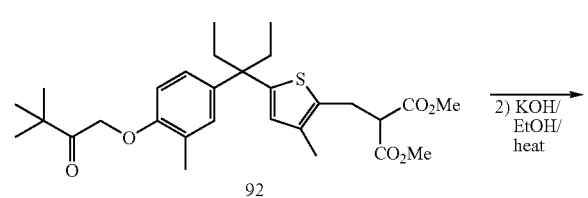
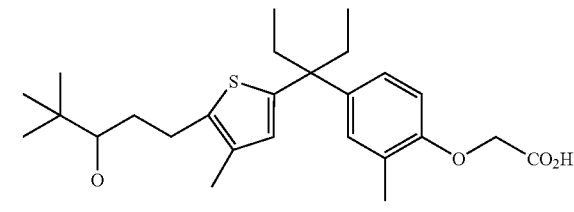
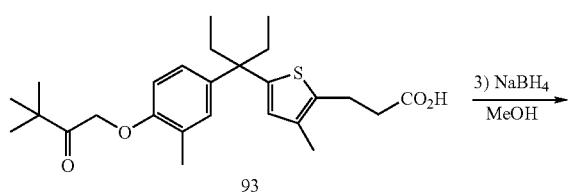
Scheme 21: Synthesis of Pentan-3-ol Phenyl Thiophene Propionic Acid
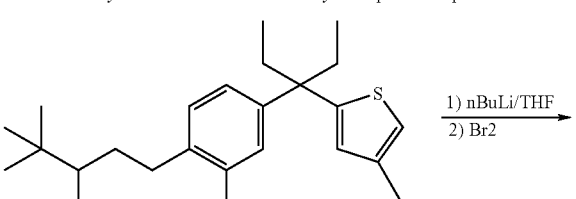
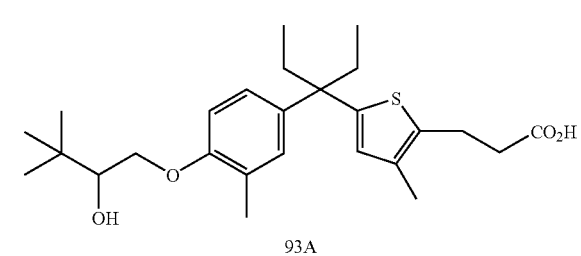
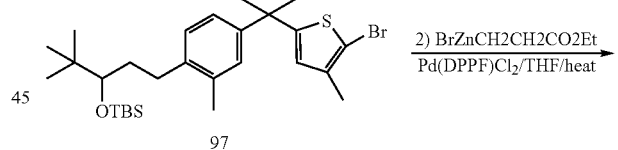
Scheme 20: Synthesis of Pentan-3-ol Thiophenyl Phenyl Oxyacetic Acid
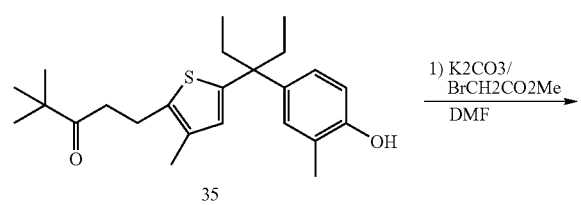
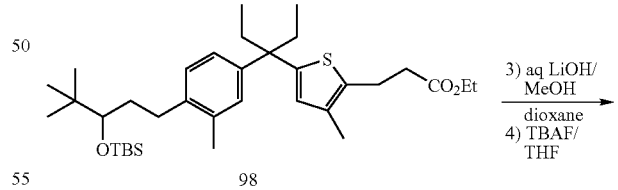
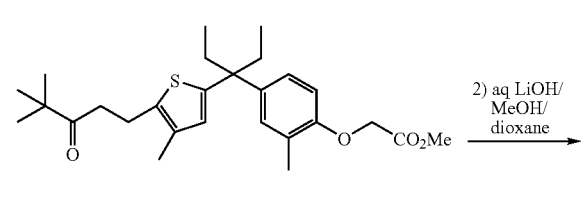
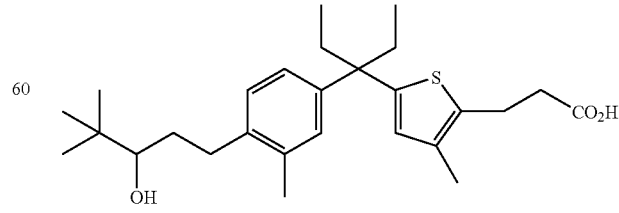

Scheme 22: Synthesis of Pentan-3-ol Thiophenyl Phenyl Propionic Acid
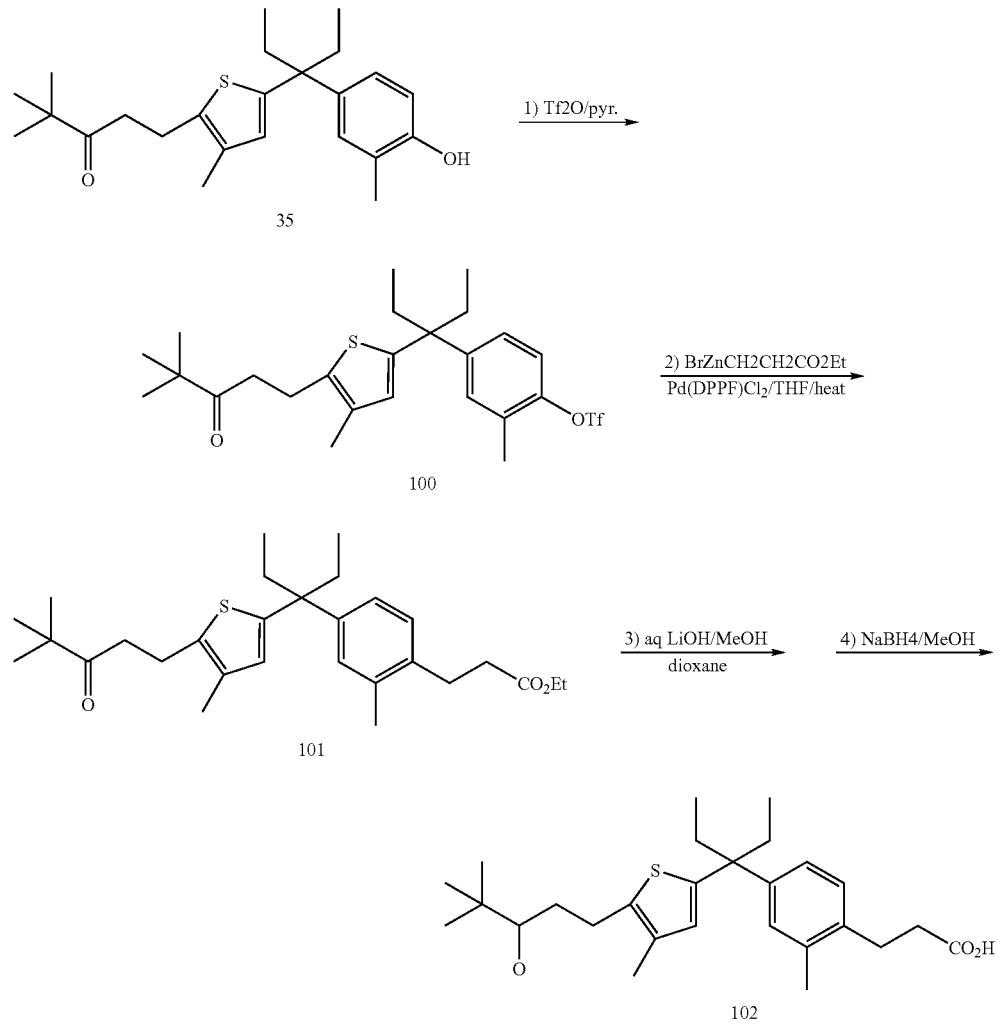
Scheme 23: Improved Synthesis of Phenyl Thiophene Derivatives
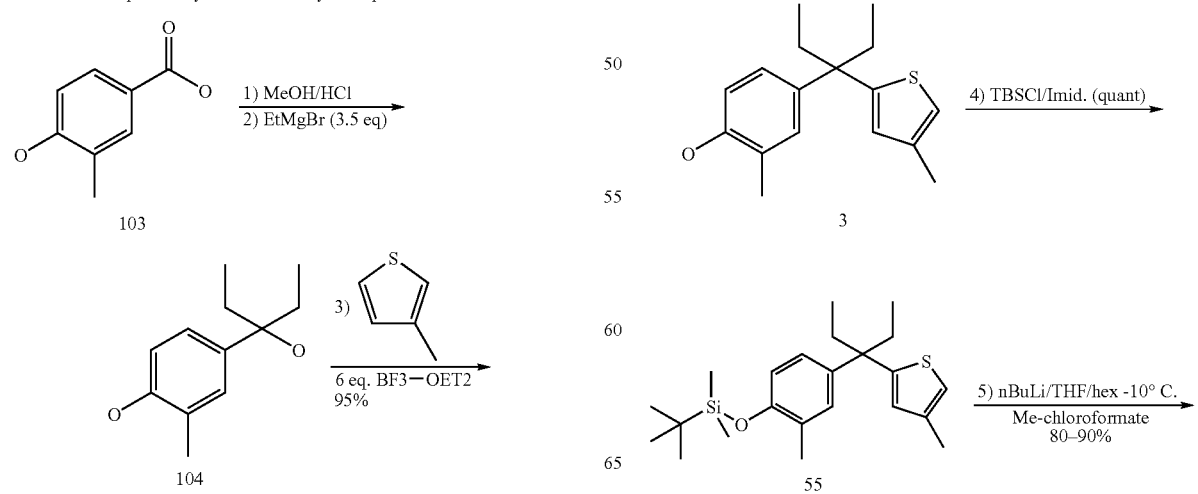

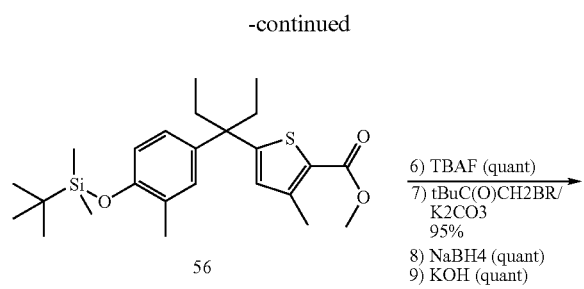
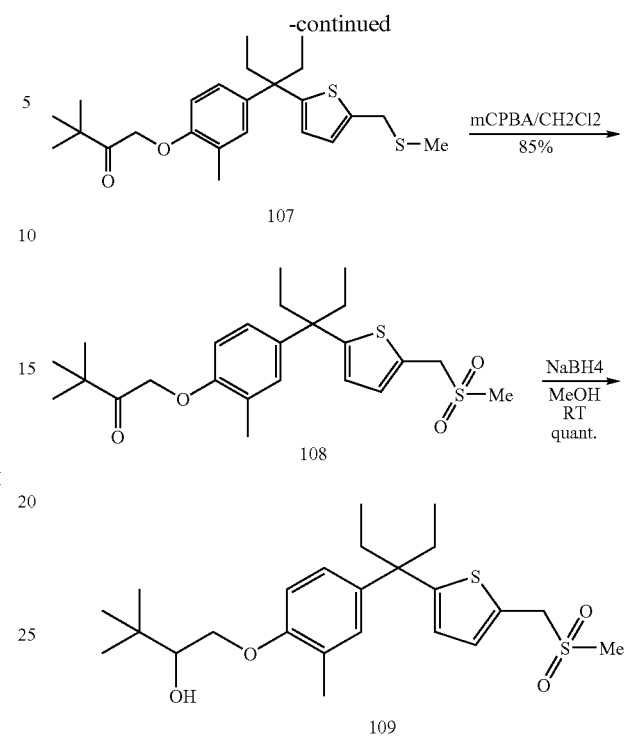
Scheme 24: Synthesis of Phenyl-3-Unsubstituted Thiophene Sulfones and Sulfides
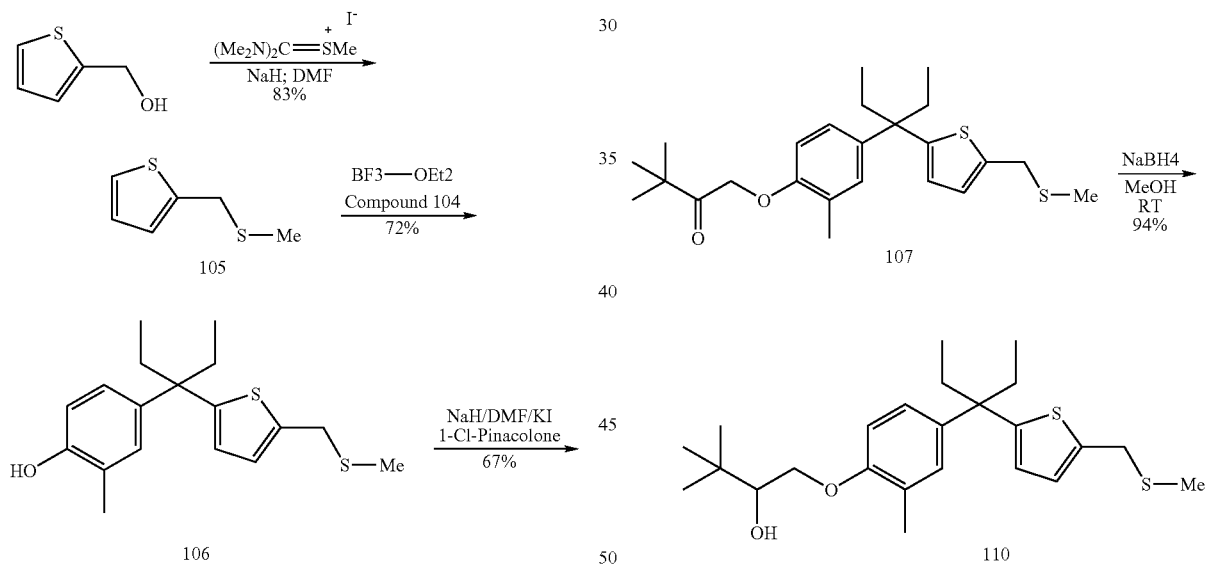
Scheme 25: Synthesis of Phenyl Thiophene Sulfonamide and Sulfonamide-Acids
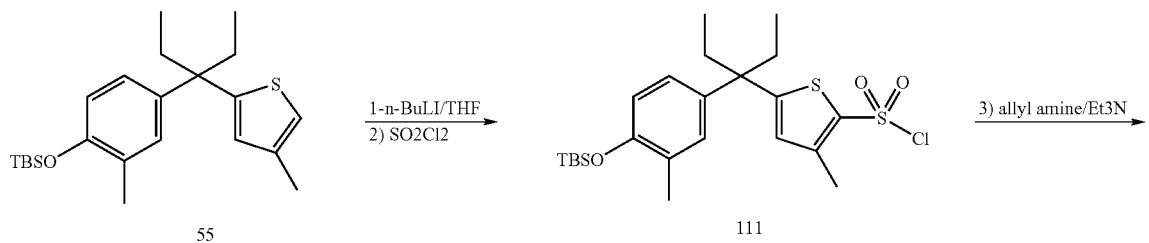

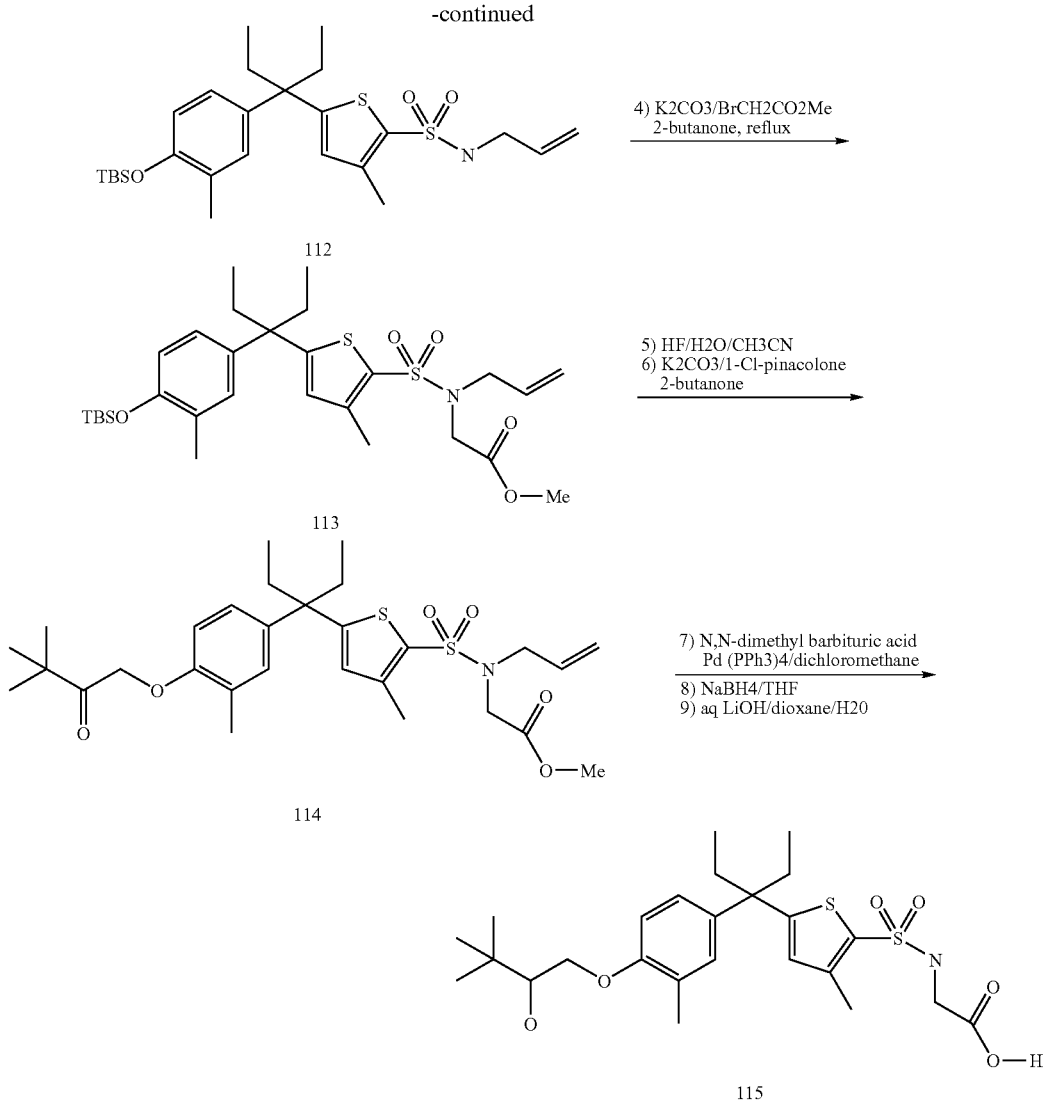
Experimental Results:
TABLE 5
Summary of Experimental Results
| Test Cmpd.[1] | RXR-VDR (SaOS-2 cells)[2] EC$_{50}$ (nM) | VDR CTF (Caco-2 cells)[3] EC$_{50}$ (nM) | OCN Promoter[4] EC$_{50}$ (nM) | Mouse Hypercal[5] μg/Kg/d |
|---|---|---|---|---|
| Ex. 1 | | 3696 | 140.5 | |
| Ex. 2 | | 1112 | 30.65 | >1000 |
| Ex. 3 | | | 72.675 | 3000 |
| Ex. 4 | | 374 | 147.2 | 1000 |
| Ex. 5 | | 1027 | 146.1 | >3000 |
| Ex. 6A | 81.54 | 599.84 | 63.8 | 1000 |
| Ex. 6B | 323.06 | 1056.5 | 325.57 | >6000 |
| Ex. 7 | 397.36 | 274.50 | 112.35 | 6000 |
| Ex. 8 | 956.98 | | 367.2 | >3000 |
| Ex. 9 | 295.3 | 1091.1 | 46.65 | 6000 |
| Ex. 10 | 58.89 | 80.71 | 51.31 | |
| Ex. 11A | 18.12 | 206.61 | 42.75 | 1500 |
| Ex. 11B | 96.14 | 365.96 | 150.15 | |
| Ex. 13 | — | — | 312.7 | — |
| Ex. 14 | 85.30 | 264.11 | 46.65 | |
| Ex. 15A | 40.57 | 361.28 | 46.82 | >1000 |
| Ex. 15B | 211.66 | 244.69 | 19.72 | 9000 |
| Ex. 16 | 96.84 | 866.39 | 31 | >3000 |
| Ex. 18 | 9.00 | 551.78 | 11.16 | |
| Ex. 19A | 14.24 | 310.59 | 26.2 | >3000 |
| Ex. 19B | 186.18 | 450.04 | 10.2 | >1000 |
| Ex. 20 | | | 862 | |
| Ex. 21 | | | 139.7 | |
| Ex. 24 | 560.73 | | 4.7 | |
| Ex. 25A | 96.27 | 699.28 | 9.9 | |
| Ex. 26 | 74.54 | 589.16 | 7.95 | 1000 |
| Ex. 27 | | | 49.1 | >3000 |
| Ex. 28 | | 535.75 | 0.76 | |
| Ex. 29 | 269.60 | 790.90 | 8.65 | |

TABLE 5-continued

Summary of Experimental Results

| Test Cmpd.[1] | RXR-VDR (SaOS-2 cells)[2] EC$_{50}$ (nM) | VDR CTF (Caco-2 cells)[3] EC$_{50}$ (nM) | OCN Promoter[4] EC$_{50}$ (nM) | Mouse Hypercal[5] μg/Kg/d |
|---|---|---|---|---|
| Ex. 30A | 24.88 | 573.73 | 11.22 | 1000 |
| Ex. 30B | 150.40 | 1046.08 | 14.1 | 2000 |
| Ex. 31 | 513.63 | 1919.23 | 7.8 | |
| Ex. 32 | 2025.58 | | 9.35 | |
| Ex. 33A | 136.16 | 1697.32 | 43.55 | >9000 |
| Ex. 33B | 94.61 | 778.39 | 7.55 | 1000 |
| Ex. 34 | 735.72 | 1228.95 | 96.8 | 3000 |
| Ex. 35 | 311.89 | 1166.83 | 21.13 | 3000 |
| Ex. 36 | 185.38 | 702.55 | 67.87 | 2000 |
| Ex. 37 | 441.60 | | 239.87 | |
| Ex. 38 | | | 379.5 | |
| Ex. 39 | 189.14 | | 299.66 | |
| Ex. 40 | 450.82 | | 612.8 | |
| Ex. 41 | | | 300.5 | |
| Ex. 42 | 10.74 | 1154.56 | 33.5 | |
| Ex. 43 | 80.55 | 598.43 | 19.7 | 1000 |
| Ex. 44 | 584.10 | 910.97 | 30.4 | 1000 |
| Ex. 45 | 23.76 | 1671.30 | 40.95 | >1500 |
| Ex. 46 | 2.495 | 855.72 | 43.6 | |
| Ex. 47 | 10.047 | | 27.7 | |
| Ex. 48 | 176.42 | 949.33 | 12.3 | 3000 |
| Ex. 49 | 526.80 | 798.80 | 62.34 | >3000 |
| Ex. 50 | 186.85 | 1480.00 | 21.63 | >3000 |
| Ex. 51 | | | 781 | |
| Ex. 53 | 821.55 | | 267.2 | |
| Ex. 54 | 465.43 | 1436.67 | 27.5 | |
| Ex. 55 | 170.75 | 779.46 | 29.63 | 1000 |
| Ex. 56 | | | 164.1 | |
| Ex. 57 | | | 114.95 | |
| Ex. 58 | | | 276.7 | |
| Ex. 59 | 503 | 888.71 | 319 | |
| Ex. 64 | 173.87 | 411.13 | 4.1 | |
| Ex. 65 | 23.39 | 497.97 | 3.4 | 300 |
| Ex. 66 | 313.33 | 1457.87 | 28.45 | |
| Ex. 67 | 202.57 | 796.53 | 19.45 | 3000 |
| Ex. 68 | 505 | | 56 | |
| Ex. 69 | 558.83 | | 487.1 | |
| Ex. 70 | 149.36 | 1377.99 | 25.8 | |
| Ex. 71 | 137.79 | 497.41 | 3.5 | <300 |
| Ex. 72 | 498.39 | 1026.70 | 218.55 | |
| Ex. 73 | 670.15 | | 265.8 | |
| Ex. 74 | 319.27 | | 478.6 | |
| Ex. 75 | 722.03 | | 423.17 | |
| Ex. 76 | 552.77 | | 57.8 | |
| Ex. 77 | 53.70 | 534.56 | 2 | 300 |
| Ex. 81 | 381.62 | | 200 | |
| Ex. 82 | 1284 | | | |
| Ex. 86 | 321.74 | | 204.6 | |
| Ex. 87 | 744 | | >1000 | |
| Ex. 88 | 469.50 | | 168.83 | |
| Ex. 89 | 286.16 | 360.27 | 313.67 | |
| Ex. 90 | 656 | 1312 | | |
| Ex. 91 | | | 212 | |
| Ex. 92 | | | 75.35 | 1000 |
| Ex. 93 | | 598.50 | 38.5 | 3000 |
| Ex. 94 | 51.08 | 599.40 | 4.05 | 1000 |
| Ex. 95 | 420.73 | 1176.73 | 21.45 | >6000 |
| Ex. 97 | 16.67 | 858.15 | 22.45 | 3000 |
| Ex. 98 | 65.30 | 1019.59 | 15.85 | 4000 |
| Ex. 99 | | | 38.1 | >1000 |
| Ex. 100 | 53.13 | 615.07 | 5.63 | 3000 |
| Ex. 101 | 379.25 | | 29.35 | 12000 |
| Ex. 103 | 548.21 | 1284.03 | 102.25 | 3000 |
| Ex. 104 | 286.18 | 801.07 | 90.93 | 1000 |
| Ex. 105 | 633.62 | | 735.55 | |
| Ex. 106 | 83.75 | 899.38 | 8.05 | >=1000 |
| Ex. 107 | 372.20 | 1031.12 | 42.3 | |
| Ex. 108 | 159.89 | 352.20 | 5.25 | 300 |
| Ex. 110 | 18.81 | 113.37 | 0.225 | <300 |
| Ex. 111 | 188.97 | 319.84 | 34.45 | |
| Ex. 112 | 485 | 658 | 5 | |
| Ex. 113 | 542 | | 118 | |
| Ex. 114 | 8.13 | 85.02 | 0.28 | <300 |
| Ex. 115 | 859.39 | 1109.87 | 19.95 | |
| Ex. 116 | 571.99 | 860.61 | 16.85 | >3000 |
| Ex. 117 | 2212.29 | | 101.3 | |
| Ex. 118 | 384.82 | | 32.25 | |
| Ex. 122 | 526.60 | | 67.45 | |
| Ex. 123 | 667.80 | | 474.65 | |
| Ex. 124 | 453.07 | | 101 | |
| Ex. 125 | | | 144.2 | |
| Ex. 126 | 2.754 | 358.01 | 111.4 | |
| Ex. 127 | 38.19 | 1503.75 | 956 | |
| Ex. 128 | 433.89 | 2522.75 | 12.6 | |
| Ex. 129 | 390.64 | | 68.4 | |
| Ex. 130 | 336.51 | 1105.33 | 49.7 | |
| Ex. 131 | 461.51 | 693.30 | 59.35 | 3000 |
| Ex. 132 | 355.90 | 969.29 | 51.25 | 1000 |
| Ex. 133 | 603.09 | 957.74 | 49.25 | >9000 |
| Ex. 134 | 4.05 | 1302.99 | 30.6 | |
| Ex. 135 | 318.10 | 620.06 | 29.9 | |
| Ex. 136 | 430.68 | 901.03 | 145.8 | |
| Ex. 137 | 409.00 | | 24.2 | >3000 |
| Ex. 138 | 476.09 | 1060.24 | 27.13 | 2000 |
| Ex. 139 | 479.30 | | 30.97 | >3000 |
| Ex. 140 | 436.81 | | 72.45 | |
| Ex. 141 | 196.86 | | 43.7 | |
| Ex. 142 | 604.77 | 783.08 | 113.7 | 3000 |
| Ex. 2123818 | | | | |
| Ex. 143 | 735.29 | | 687.93 | |
| Ex. 144 | 687.94 | 1513.74 | 29.2 | 3000 |
| Ex. 145 | 284.27 | | 221.8 | |
| Ex. 146 | 676.02 | | 27.7 | >3000 |
| Ex. 147 | 351.94 | | 128.27 | |
| Ex. 148 | 848.32 | 1146.189 | 236.2 | |
| Ex. 149 | 371.94 | 1206.25 | 98.35 | |
| Ex. 150 | 103.99 | 1128.4 | 55.2 | |
| Ex. 151 | 257.44 | 714.98 | 48.2 | >3000 |
| Ex. 152 | 473.97 | | 110 | |
| Ex. 153 | 376.02 | | 187 | |
| Ex. 154 | 171.33 | 470.46 | 20.5 | |
| Ex. 155 | 270.66 | 799.30 | 18.4 | 6000 |
| Ex. 157 | 235.83 | 484.31 | 7.65 | >1000 |
| Ex. 158 | 732.37 | 2414.37 | 84.97 | |
| Ex. 159 | 400.62 | 1336.75 | 89.67 | |
| Ex. 160 | 900.63 | | 40.3 | 3000 |
| Ex. 161 | | | 77 | |
| Ex. 162 | | | 131 | |
| Ex. 163 | 649.14 | | 105.9 | |
| Ex. 164 | 1054.86 | | 150.4 | |
| Ex. 165 | 1783.20 | | 137.7 | |
| Ex. 166 | 1072.82 | | 151 | |
| Ex. 169 | 80.70 | 370.91 | 17.65 | <1000 |
| Ex. 170 | 96.53 | 589.04 | 8.4 | 1000 |
| Ex. 171 | 229.78 | 930.62 | 92.6 | |
| Ex. 172 | 417.83 | 781.88 | 17.2 | |
| Ex. 173 | 80.93 | 645.18 | 25.4 | 3000 |
| Ex. 174 | 58.90 | 1100.63 | 172 | |
| Ex. 175 | 687.78 | | 126.9 | |
| Ex. 176 | 135.98 | 288.78 | 174.2 | |
| Ex. 177 | 362.21 | | 45.97 | |
| Ex. 178 | | | 25.5 | |
| Ex. 179 | 142.50 | 279.42 | 27.85 | |
| Ex. 180 | 394.35 | 603.53 | 40.52 | >3000 |
| Ex. 181 | 403.35 | 645.03 | 83.57 | >3000 |
| Ex. 182 | | | 231.3 | |
| Ex. 183 | 134.13 | 781.17 | 38.6 | |
| AA | 5.02 | 16 | 5 | 0.06 |
| BB | 10.32 | 169.81 | 8.24 | >=20 |
| CC | 2427.7 | | >1000 | |
| DD | 109.44 | | 31.1 | 1000 |
| EE | 429.99 | 891.16 | 34'1.25 | 1000 |
| FF | 3 | 57 | | |

TABLE 6

Summary of Experimental Results

| Test Cmpd.[1] | Kera. Prolif. IC$_{50}$ (nM) | IL-10 IC$_{50}$ (nM) |
|---|---|---|
| Ex. 1 | | |
| Ex. 2 | | |
| Ex. 3 | | |
| Ex. 4 | 122.5 | |
| Ex. 5 | | |
| Ex. 6A | 439.0 | |
| Ex. 9 | 129 | 98 |
| Ex. 10 | 25.0 | |
| Ex. 11A | | |
| Ex. 11B | 216.0 | |
| Ex. 15A | 76 | 26 |
| Ex. 15B | 84.0 | 66 |
| Ex. 16 | 257.0 | |
| Ex. 18 | 24.5 | |
| Ex. 19A | 18 | 60 |
| Ex. 19B | 20 | 48 |
| Ex. 29 | 4.6 | |
| Ex. 30A | 13.0 | |
| Ex. 30B | 40 | 120 |
| Ex. 33B | 22.5 | |
| Ex. 35 | 474.0 | |
| Ex. 39 | 367.0 | |
| Ex. 48 | 71.5 | |
| Ex. 49 | 430.0 | |
| Ex. 55 | 0.1 | |
| Ex. 65 | 56 | 41 |
| Ex. 66 | 277.0 | |
| Ex. 67 | 197.0 | |
| Ex. 71 | 29.0 | |
| Ex. 77 | 194.0 | |
| Ex. 89 | 105.0 | |
| Ex. 93 | 178.0 | |
| Ex. 100 | 215.0 | |
| Ex. 106 | 13.0 | |
| Ex. 108 | 66.0 | 597 |
| Ex. 110 | 9.5 | 288 |
| Ex. 124 | 216.3 | |
| Ex. 138 | 102.0 | 110 |
| Ex. 142 | 300.0 | |
| Ex. 145 | 702.0 | |
| Ex. 155 | 788.0 | |
| Ex. 158 | 500.0 | |
| Ex. 159 | 234.3 | |
| Ex. 160 | 1095.0 | |
| Ex. 169 | 522.0 | |
| Ex. 170 | 36 | 100 |
| Ex. 173 | 478.0 | |
| Ex. 176 | 114.0 | |
| Ex. 177 | 81.3 | |
| Ex. 179 | 221.0 | |
| AA | 120 | 1.2 |
| BB | 10 | 28 |
| CC | — | — |
| DD | 1060 | |
| EE | | |
| FF | 103 | 0.5 |

Explanation of Table 5 and 6 column numerical superscripts:

1. Test Compound numbers refer to the products of the corresponding Example Nos. that is, compounds within the scope of the invention. For example, the number "Ex. 2" refers to the compound, 3'-[4-(2-hydroxy-3,3-dimethylbutoxy)-3-methylphenyl]-3'-[5-methoxycarbonyl-4-methylthiophen-2-yl]pentane, prepared in Example 2. The control experiments are done with the double letter coded compounds identified as follows:

"AA"=1α,25-dihydroxyvitamin D$_3$

"BB"=3-(4-{1-Ethyl-1-[4-(2-hydroxy-3,3-dimethyl-butoxy)-3-methyl-phenyl]-10 propyl}-2-methyl-phenoxy)-propane-1,2-diol  "CC"=1-(4-{1-[4-(3,3-Dimethyl-2-oxo-butoxy)-3-methyl-phenyl]-cyclohexyl}-2-methyl-phenoxy)-3,3-dimethyl-butan-2-one "DD"=compound represented by the formula:

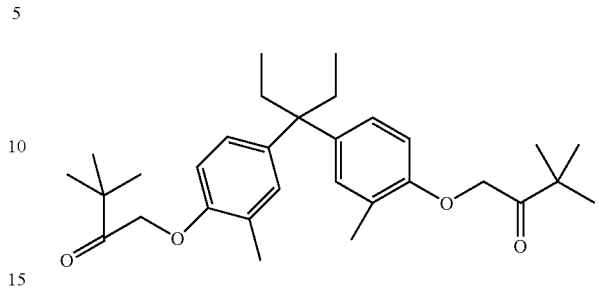

"EE"=compound represented by the formula:

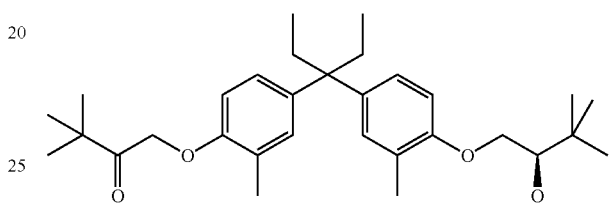

calcipotriol (structural formula below):

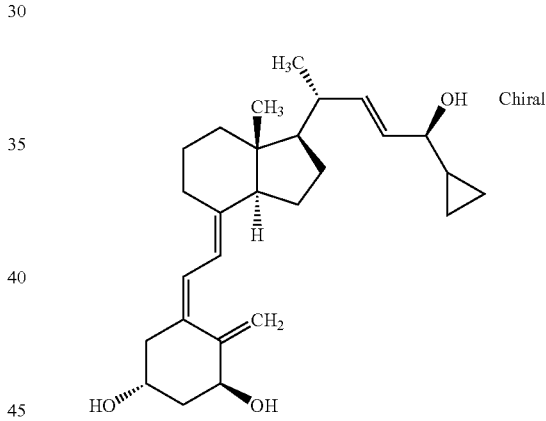

2. The RXR-VDR heterodimerization (SaOS-2 cells) test is described in the "Assay" section of the Description, infra.

3. The VDR CTF (Caco-2 cells) test is described in the "Assay" section of the Description, infra.

4. The OCN Promoter test is described in the "Assay" section of the Description, infra.

5. The Mouse Hypercalcemia test is described in the "Assay" section of the Description, infra.

6. The keratinocyte proliferation assay is described in the "Assay" section of the Description, infra.

7. The IL-10 induction assay is described in the "Assay" section of the Description, infra.

Assay Methods

Use of the Assay Methods:

The evaluation of the novel compounds of the invention for osteoporosis and other related diseases is done using a plurality of test results. The use of multiple assays is necessary since the combined properties of (i) high activity for the vitamin D receptor, and (ii) prevention of hypercalcemia must be achieved to have utility for the methods of treating diseases, which are also, aspects of this invention. Some of the tests described below are believed related to other tests and measure related properties of compounds. Consequently, a compound may be considered to have utility in the practice of the invention if is meets most, if not all, of the acceptance criteria for the above described tests.

The evaluation of the novel compounds of the invention for psoriasis is done using the Keratinocyte Proliferation Assay in combination with other assays that measure inhibition of IL-2 production and stimulation of IL-10 production in peripheral blood mononuclear cells (PBMCs).

Brief Description, Utility and Acceptance Criteria for the Assay Methods:

1. The RXR-VDR heterodimer Assay:

This assay provides the VDR activity of a test compound. It is desirable to have low EC50 values for a compound in this assay. The lower the EC50 value, the more active the compound will be as a VDR agonist. Desired assay results are EC50 values less than or equal to 600 nM. Preferred assay results are less than 250 nM, and most preferably less than 150 nM.

2. The Caco-2 Cell Co-Transfection Assay:

The Caco-2 cell assay is an indicator for the undesirable condition of hypercalcemia. This co-transfection assay is a surrogate assay for in vivo calcemic activity of VDR ligands. It is desirable to have high EC50 values for a test compound in this assay. The higher the EC50 values for a compound the less calcemic it will be in vivo. Desired assay results are EC50 greater than or equal to 300 nM. Preferred assay results are greater than 1000 nM.

3. The OCN (Osteocalcin) Promoter Assay

The OCN Promoter Assay is an indicator and marker for osteoporosis. Desired assay results are EC50 less than or equal to 325 nM. Preferred assay results are less than 50 nM.

4. The Mouse Hypercalcemia Assay

The Mouse Hypercalcemia Assay is a six day hypercalcemia test for toxicity and selectivity. Acceptable test results are levels greater than 300 µg/kg/day. Preferred assay results are levels greater than 1000 µg/kg/day.

5. The Keratinocyte Proliferation Assay

This Assay is indicative for the treatment of psoriasis. An acceptable test result is IC50 value of less than or equal to 300 nM. Preferred assay results are IC50 values of less than 100 nM.

6. The IL-1 Induction Assay

This is an in vitro efficacy assay for psoriasis, abscess and adhesion. Psoriasis involves both keratinocytes and immune cells. IL-10 is a unique cytokine because it is anti-inflammatory and immunosuppressive. This assay tells us whether a VDRM is able to function as an agonist in PBMCs (primary blood mononuclear cells) or not. A lower EC50 value is desirable in this assay since a compound with a lower EC50 value will be a better agonist in PBMCs. An acceptable test result is an EC50 value of less than 200 nM. Preferred assay results are EC50 values of less than 100 nM.

Details of the Assay Methods:

(1) Materials and Method for RXR-VDR Heterodimerization Assay:

Transfection Method:
FuGENE 6 Transfection Reagent (Roche Cat # 1 814 443)

Growth Media:
D-MEM High Glucose (Gibco BRL Cat # 11054-020), 10% FBS, 1% antibiotic-antimycotic (Ab-Am)

FBS heat inactivated (Gibco BRL Cat # 10092-147)

Ab-Am (Gibco BRL Cat # 15240-062)

Cells:
Grow SaOs-2 cells in T-152 $cm^2$ culture flasks in growth media.
Keep the density at 5-6×$10^5$ cells/ml
Passage cells 1:3 twice a week
Add Trypsin EDTA (Gibco BRL Cat # 25300-020) and incubate
Resuspend cells in plating media and transfer into growth media.

Wash Media:
HBSS Low Glucose Without Phenol Red (Gibco BRL Cat # 14175-095), 1% Ab-Am Plating Media:
D-MEM Low Glucose Without Phenol Red (Gibco BRL Cat # 11054-020), 1% Ab-Am D-MEM Stripped FBS (Hyclone Cat# SH30068.03 Lot # AHM9371)

Ab-Am

Transfection/Treatment Media:
D-MEM Low Glucose Without Phenol Red only

T-152 $cm^2$ culture flask:
Use Corning Coastar T-152 $cm^2$ culture flask (Cat # 430825) to grow the cells Flat well Plates:
Use well plate to plate cells
Use Deep well plate sterile to make up treatment media.

Luciferase Assay Reagent:
Use Steady-Glo Luciferase Reagent from Promega (Cat # E2550) Consists of:
a. E2533 Assay Substrate, lyopholized product and
b. E2543 Assay Buffer.
Thaw at room temperature
Store DAY 1: Cell Plating:
Cell Harvesting
Aspirate media from culture flask, rinse cells with HBSS and aspirate.
Add trypsin and incubate.
When cells appear detached, resuspend cells in growth media.
Transfer into a new flask with fresh growth media for passaging the cells.
Plate well plates and two extra plates
B. Cell Count
Mix the cell suspension using pipette
Use Hematocytometer to count the cells
Load cell suspension onto the hemocytometer chamber
Count cells.
Plate seeding:
Use plating media 10% Stripped FBS in D-MEM Low Glucose, Without Phenol Red, 1% Ab-Am
Plate 14 plates @ 165 µl/well.
In sterile flask add cell suspension
to plating media.
Mix.
Add cells/well.
Place the cells in the incubator.
Cells should be about 75% confluent prior to transfection.

DAY 2: Transfection

Step 1: DNA and Media
Add plain DMEM media to tubes for mixing the DNA
Add the Reporter gene pFR-LUC
Add the Gal-4-RXR-DEF and VP16-VDR-LBD Step 2: FuGENE and Media
Prepare plain DMEM media in a ubes for mixing FuGENE
Add FuGENE 6 Transfection Reagent
Incubate Step 3: FuGENE, DNA and Media Complex
Add FuGENE Media complex from step 2 to DNA Media complex from step 1
Incubate Step 4: FuGENE, DNA and Media Complex to-well plate
Add FuGENE-DNA-Media complex from step 3 to each plate
Incubate.

DAY 3: Dosing
Treatment preparation
Allow for transfection time
Make a stock solution of the compounds in DMSO
Vortex until all the compounds has been dissolved.
Further dilute in D-MEM (Low Glucose—With out Phenol Red)
Add compounds in quadruplicate to give final volume
Incubate.

Day 4: Luciferase Assay
Read the plates after drug treatment
Remove part of media from all the wells and leave remainder
Add Steady-Glo Luciferase Reagent mixture/wells
Incubate
Count each well using a Luminescence counter, Top Count NXT by Packard
Set a delay between plates to reduce the background.

(2) Materials and Method for The Caco-2 Cell Assay:

Caco-2 cells, grown in phenol red free, DMEM (Invitrogen, Carlsbad, Calif.) containing 10% charcoal-stripped FCS (Hyclone, Logan, Utah), were transfected with Fugene 6 reagent (Roche Diagnostics, Indianapolis, Ind.). Cells (5000/well) were plated 18 h before transfection in a 96 well plate. The Cells were transfected with Gal-4-responsive reporter pFRLuc (150 ng, Stratagene, La Jolla Calif.) and the receptor expression vector pGa14-VDR-LBD (10 ng), along with Fugene 6 reagent (0.2 □l/well). The DNA-Fugene complex was formed by incubating the mixture for 30 min at room temperature. The cells were transfected in triplicate for 5 h, and treated with various concentrations of VDR ligands (form 0.01 nM to 10,000 nM concentration range) 18 h post-transfection. The luciferase activity was quantified using Steady-Glo reagent kit (Promega, Madison, Wis.) as per manufacturer's specifications.

(3) Materials and Method for The OCN Promoter Assay:

The activation of osteocalcin by VDR ligands was evaluated in a rat osteoblast-like cell line RG-15 (ROS 17/2.8) stably expressing rat osteocalcin promoter fused with luciferase reporter gene. The stable cell lines were established as reported before (Activation of Osteocalcin Transcription involves interaction of protein kinase A- and Protein kinase C-dependent pathways. Boguslawski, G., Hale, L. V., Yu, X.-P., Miles, R. R., Onyia, J. E., Santerre R. F., Chandrasekhar, S. J Biol. Chem. 275, 999-1006, 2000). Confluent RG-15 cells maintained in DMEM/F-12 medium (3:1) containing 5% FBS, 300 □g/ml G418 and at 37° C. under 5% $CO_2$/95% air atmosphere were trypsinized (0.25% trypsin) and plated into white opaque 96-well cell culture plates (25000 cells/well). After 24 hr, cells (in DMEM/F-12 medium+2% FBS) were treated with various concentrations of compounds, dissolved in DMSO. The final DMSO concentration remained at 0.01% (v/v). After 48 hr treatment, the medium was removed, cells were lysed with 50 □l of lysis buffer (From Luciferase reporter assay system, Roche Diagnostics, Indianapolis, Ind.) and assayed for luciferase activity using the Luciferase Reporter Gene Assay kit from Boehringer Mannheim as per manufacturer's specifications.

(4) Materials and Method for The Mouse Hypercalcemia Assay:

Weanling, virus-antibody-free, five to six weeks old female DBF mice (Harlan, Indianapolis, Ind.) are used for all the studies. Animals are allowed to acclimate to local vivarium conditions for 2 days. Mice are maintained on a 12 hr light/dark cycle at 22° C. with ad lib access to food (TD 5001 with 1.2% Ca and 0.9% P, Teklad, Madison, Wis.) and water. The animals then are divided into groups with 4-5 mice per group. Different doses of test compounds prepared in 10% Ethanol and 90% sesame oil are administered to mice orally via gavage for 6 days. $1\alpha$-25(OH)$_2$D$_3$ 0.5 µg/kg/d was also given to one group of mice as the positive control. Serum ionized calcium is evaluated at 6 hours after the last dosing under isoflurane anesthesia by Ciba-Corning Ca++/PH Analyzer, (Model 634, Chiron Diagnostics Corp., East Walpole, Mass.). Raw data of group differences is assessed by analysis of variance (ANOVA) using Fisher's protected least significant difference (PLSD) where the significance level was $P<0.05$.

(5) The Keratinocyte Proliferation Assay:

KERtr cells (Human skin keratinocyte transformed with a retrovirus vector, obtained from ATCC) were plated in 96-well flat-bottomed plates (3000 cells/well) in 100 □l keratinocyte serum free medium supplemented with bovine pituitary extract in the absence of EGF (Life Technologies, Rockville, Md.) and incubated at 37° C. for two days. The cells were treated with various concentrations of VDR ligands (ten-fold serial dilution from 10,000 nM to 0.1 nM in triplicate), dissolved in 100 □l keratinocyte serum free medium supplemented with bovine pituitary extract in the absence of EGF and incubated at 37° C. for 72 hr. BrdU (5-bromo-2'-deoxyuridine) incorporation was analyzed as a measure of DNA replication (Cell proliferation ELISA kit, Roche Diagnostics, Indianapolis, Ind.) and absorbance was measured at 405 nm. Potency values ($IC_{50}$) values were determined as the concentration (nM) of compound that elicited a half-maximal response.

(6) Materials and Method for Human IL-10 Induction Assay:

Isolation of peripheral blood mononuclear cells (PBMCs):
  A. Collect 50 ml of human blood and dilute with media, RPMI-1640.
  B. Prepare sterile tubes with ficol.
  C. Add diluted blood to tubes.
  D. Centrifuge.
  E. Discard the top layer and collect the cells from middle layer.
  F. Divide all cells into four tubes and add media.
  G. Centrifuge.
  H. Aspirate off media and resuspend.
  I. Collect all cells
  J. Centrifuge. at 1200 rpm for 10 minutes.
  K. Resuspend in RPMI-1640 with 2% FBS and count cells Stimulation of PBMC:
L. Prepare TPA in DMSO.
M. Dissolve PHA in water.
N. Plate TPA/PHA treated PBMCs in well plates.
O. Incubate.
Treatment:
P. Prepare all compound dilutions in plain RPMI-1640 media.
Q. Add diluted compound.
R. Incubate.
Sample Collection and assay:
S. Remove all the cells by centrifugation and assay the supernatant for IL-10 by immunoassay.
1) T. Perform IL-10 assay using anti-human IL-10 antibody coated beads, as described by the manufacturer (Linco Research Inc., St. Charles, Mo.).

We claim:

1. A compound represented by formula I or a pharmaceutically acceptable salt thereof:

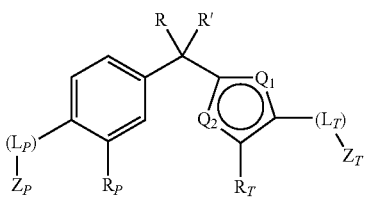

(I)

wherein;
R and R' are independently $C_1$-$C_5$ alkyl, $C_1$-$C_5$ fluoroalkyl, or together R and R' form a substituted or unsubstituted, saturated or unsaturated carbocyclic ring having from 3 to 8 carbon atoms;
Ring atoms $Q_1$ and $Q_2$ are independently selected from carbon or sulfur, with the proviso that one atom is sulfur and the other atom is carbon;
$R_P$ is $C_1$—$C_5$ alkyl;
$R_T$ is selected from hydrogen, $C_1$-$C_5$ alkyl, $C_1$-$C_5$ fluoroalkyl, —O—$C_1$-$C_5$ alkyl;
($L_P$) and ($L_T$) are divalent linking groups independently selected from the group consisting of

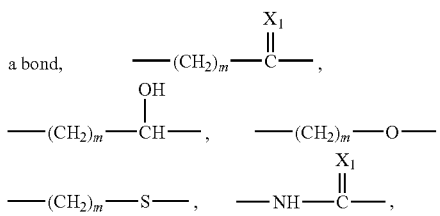

where m is 0, 1 or 2, $X_1$ is oxygen or sulfur;
$Z_P$ and $Z_T$ are independently selected from
—($C_1$-$C_5$ alkyl),
—($C_1$-$C_5$ alkyl)-C(O)—($C_1$-$C_5$ alkyl),
—($C_1$-$C_5$ alkyl)-C(O)—(O—$C_1$-$C_5$ alkyl),
—($C_1$-$C_5$ alkyl)-C(O)—OH,
—($C_1$-$C_5$ alkyl)-$SO_2$—($C_1$-$C_5$ alkyl),
—($C_1$-$C_5$ alkyl)-S(O)—($C_1$-$C_5$ alkyl),
—($C_1$-$C_5$ alkyl)-N(C(O)($C_1$-$C_5$ alkyl)$CH_2$C(O)OH,
—($C_1$-$C_5$ alkyl)-N(C(O)($C_1$-$C_5$ alkyl)$CH_2$C(O)—($C_1$-$C_5$ alkyl),
—CH(OH)—($C_1$-$C_5$ alkyl)
—C(O)—O—($C_1$-$C_5$ alkyl),
—C(O)—NH(OH),
—C(O)—N—($C_1$-$C_5$ alkyl)$_2$,
—C(O)—NH—($C_1$-$C_5$ alkyl)-$SO_2$—($C_1$-$C_5$ alkyl),
—C(O)—NH—($C_1$-$C_5$ alkyl)-S(O)—($C_1$-$C_5$ alkyl),
—C(O)—NH—$CH_2$—C(O)OH,
—C(O)—NH—$CH_2$—C(O)—(O—$C_1$-$C_5$ alkyl),
—C(O)—N—($C_1$-$C_5$ alkyl)(C(O)OH),
—C(O)—N—($C_1$-$C_5$ alkyl)(C(O)—(O—$C_1$-$C_5$ alkyl)),
—C(O)—NH—CH((CH2)($CO_2$H))($CO_2$H),
—C(O)—NH—CH((CH2)(C(O)—($C_1$-$C_5$ alkyl)))(C(O)—(O—$C_1C_5$ alkyl)),
—C(O)—NH—CH(($CH_2$)(C(O)—(—O—$C_1$-$C_5$ alkyl)))(C(O)—(O—$C_1C_5$ alkyl)),
—C(O)—NH—CH(($CH_2$OH)($CO_2$H)),
—C(O)—NH—CH(($CH_2$OH)(C(O)(O—$C_1$-$C_5$ alkyl)),
—C(O)—NH—C(($C_1$-$C_5$ alkyl)($C_1$-$C_5$ alkyl))($CO_2$H),
—C(O)—NH—C(($C_1$-$C_5$ alkyl)($C_1$-$C_5$ alkyl))(C(O)—(O—$C_1$-$C_5$ alkyl)),
—C(O)—NH—5-tetrazolyl,
—C(O)—N-pyrrolidin-2-($CO_2$H),
—C(O)—N-pyrrolidin-2-(C(O)—(O—$C_1$-$C_5$ alkyl)),
—C(O)—N—($C_1$-$C_5$ alkyl))$CH_2$($CO_2$H),
—O—($C_1$-$C_5$ alkyl)-C(O)—OH,
—O—($C_1$-$C_5$ alkyl)-C(O)—NH—5-tetrazolyl,
—O—($C_1$-$C_5$ alkyl)-C(O)—($C_1$-$C_5$ alkyl),
—O—($C_1$-$C_5$ alkyl)-C(O)—(O—$C_1$-$C_5$ alkyl),
—O—($C_1$-$C_5$ alkyl)-S(O)—($C_1$-$C_5$ alkyl),
—O—$SO_2$—($C_1$-$C_5$ alkyl),
—$SO_2$—($C_1$-$C_5$ alkyl),
—$SO_2$—$NH_2$,
—$SO_2$—NH—($C_1$-$C_5$ alkyl)-C(O)OH,
—$SO_2$—NH—($C_1$-$C_5$ alkyl)-C(O)(O—$C_1$-$C_5$ alkyl),
—$SO_2$—NHC(O)—($C_3$-$C_6$ cycloalkyl),
—$SO_2$—NH—C(O)—($C_1$-$C_5$ alkyl),
—$SO_2$—N—($C_1$-$C_5$ alkyl)$_2$,
—$SO_2$—N=CHN($C_1$-$C_5$ alkyl)$_2$,
—N(OH)($CH_3$),

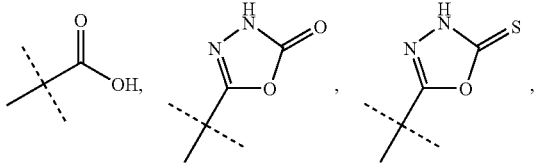

—I,
—Br
—Cl
—F, provided that the combined groups of formula I represented by

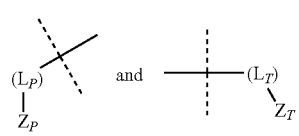

may both be lipophilic, or either one may be lipophilic and the other one polar; but both combined groups may not be polar.

2. A pharmaceutical formulation comprising a compound of claim 1, or a pharmaceutically acceptable salt thereof, together with a pharmaceutically acceptable carrier or diluent therefor.

3. A method of treating a mammal for osteoporosis, psoriasis, scleroderma, or seborrheic dermatitis; wherein the method comprises administering a pharmaceutically effective amount of at least one compound of claim 1, or a pharmaceutically acceptable salt thereof.

4. A compound represented by any one of formula (X1) through (X188), or a pharmaceutically acceptable salt thereof:

X1)
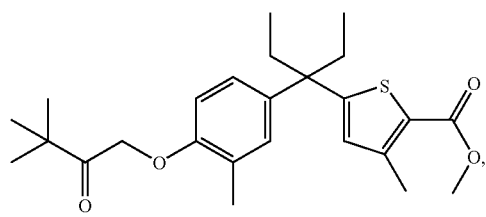

X2)
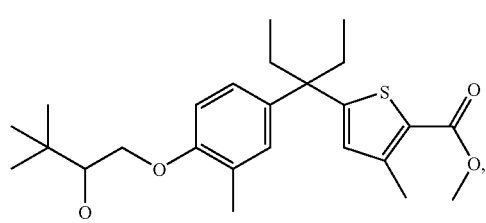

X3)
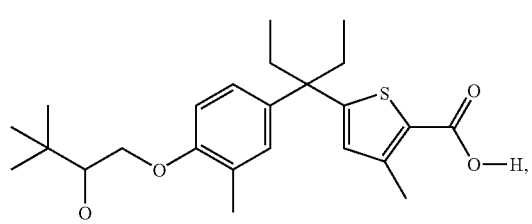

X4)
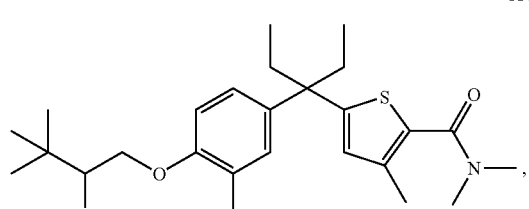

X5)
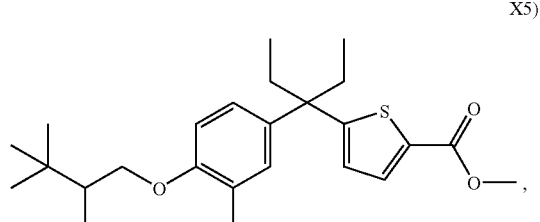

-continued

X9)
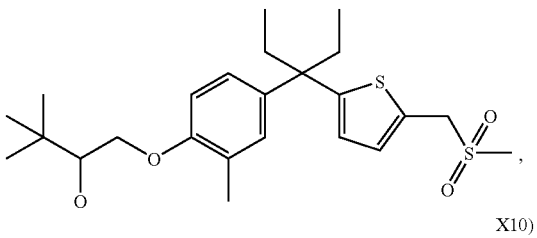

X10)
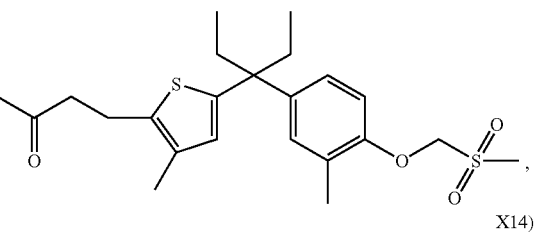

X13)
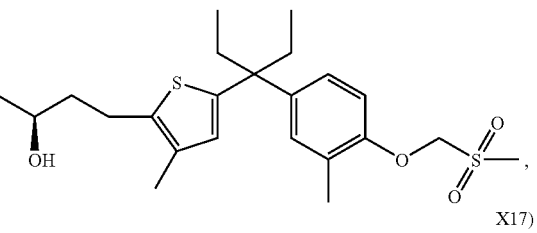

X14)
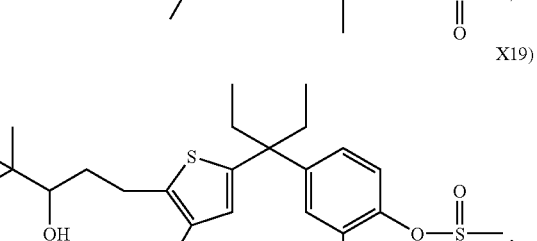

X17)

X19)

X20)
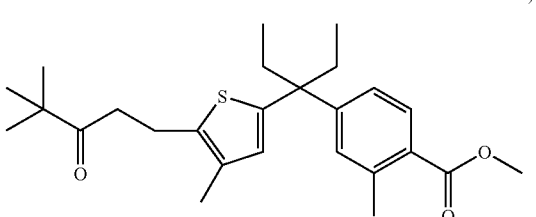

-continued
X21)
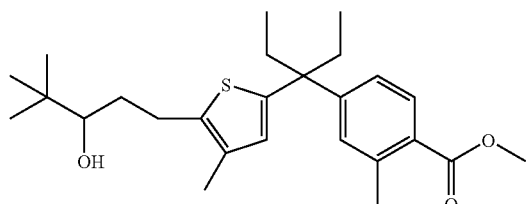
X22)
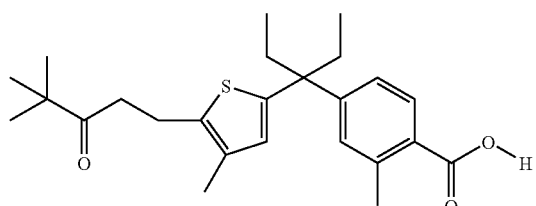
X24)
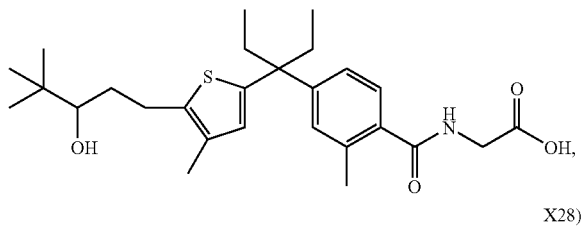
X28)
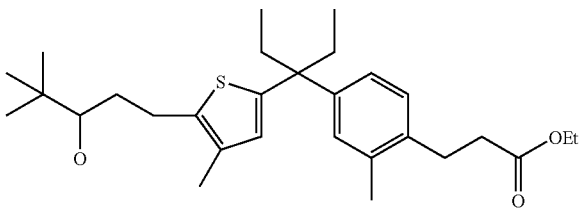
X29)
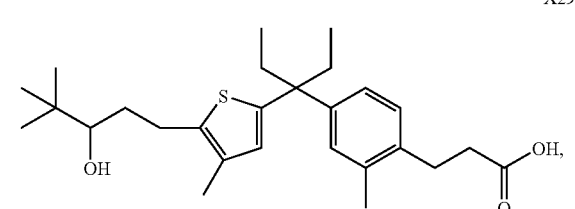
X31)
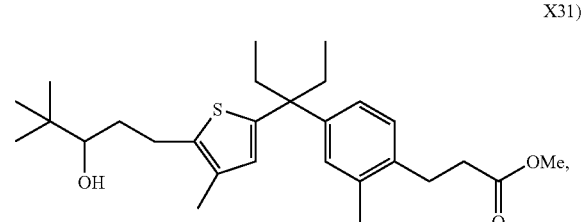
X32)
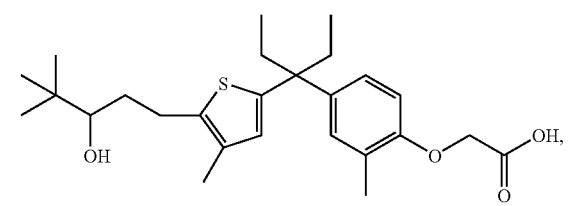
-continued
X34)
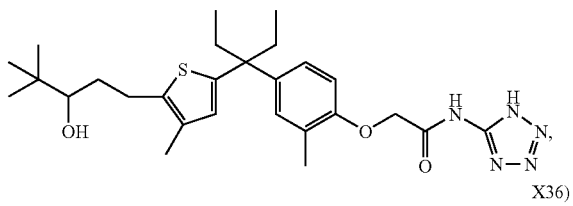
X36)
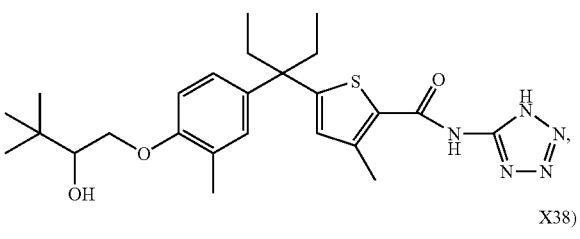
X38)
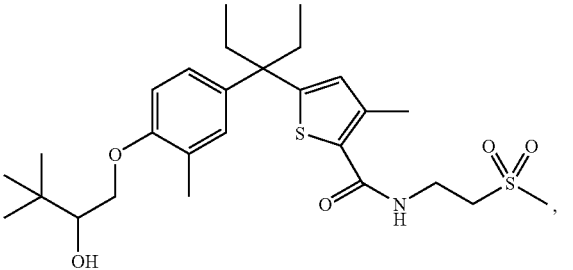
X41)
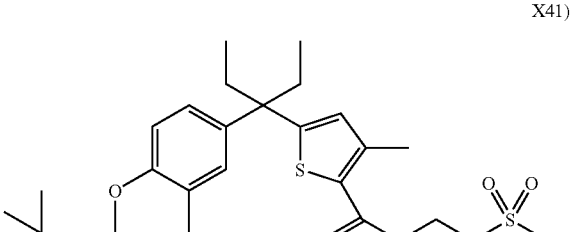
X42)
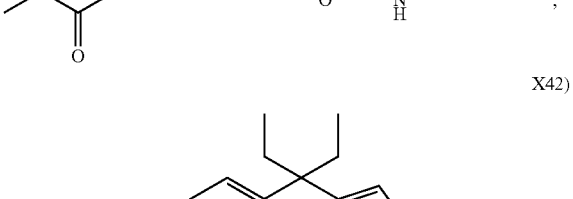
X45)
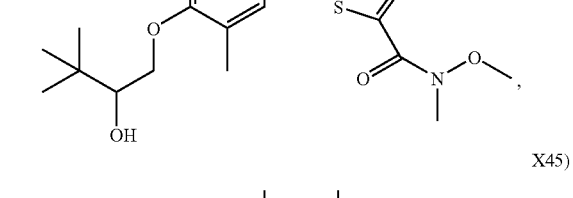
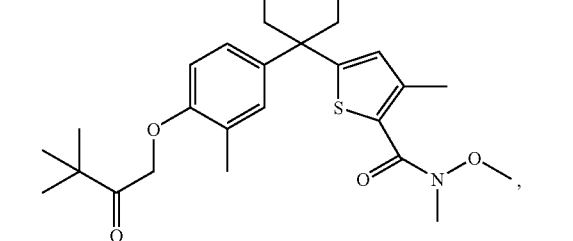

285
-continued
X46)
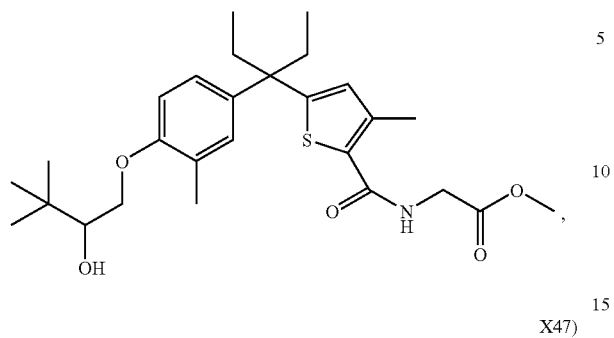
X47)
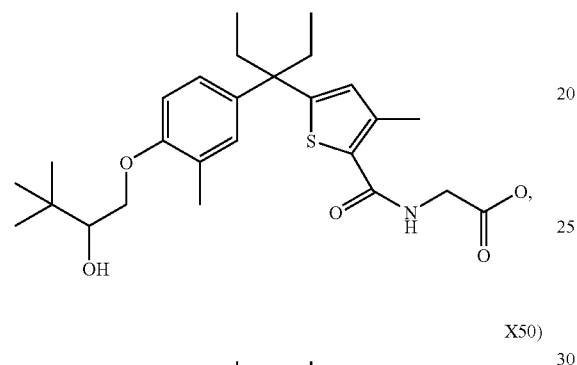
X50)
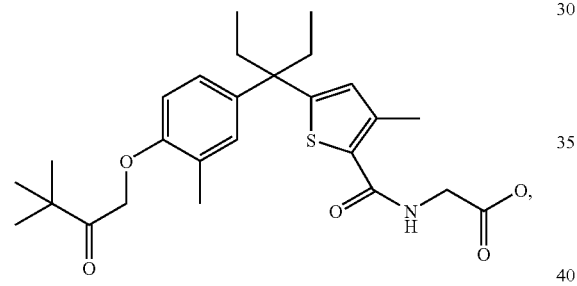
X51)
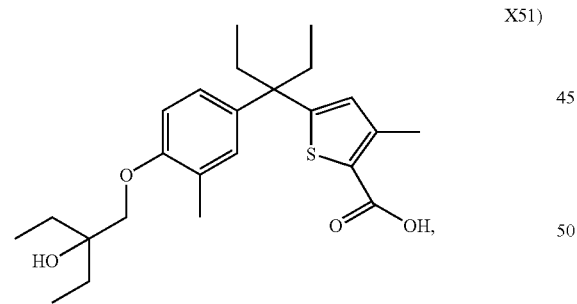
X52)
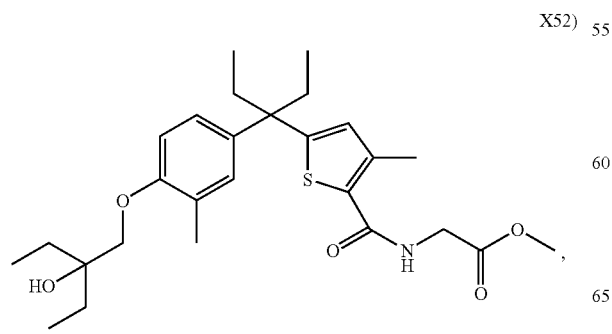
286
-continued
X53)
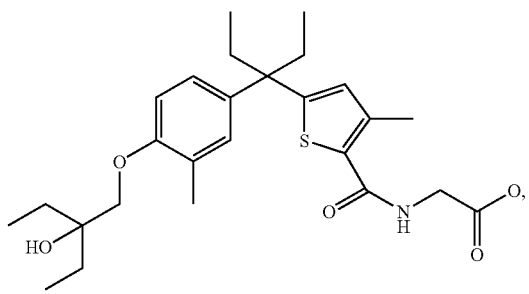
X54)
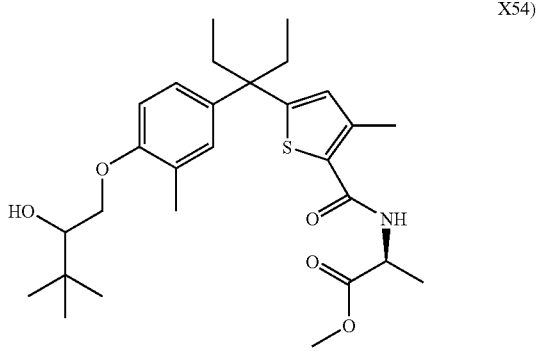
X56)
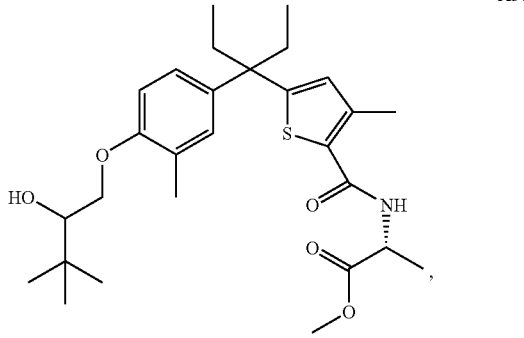
X58)
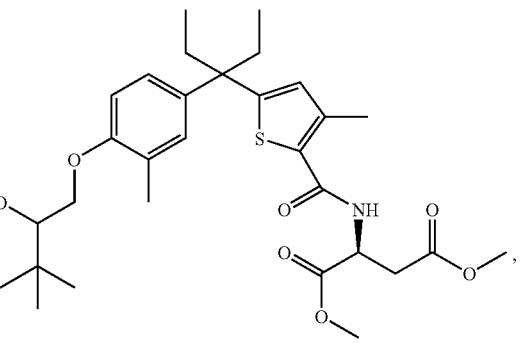

287 288
-continued -continued
X60)
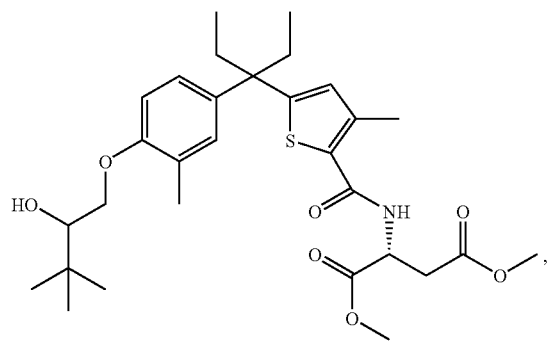
X62)
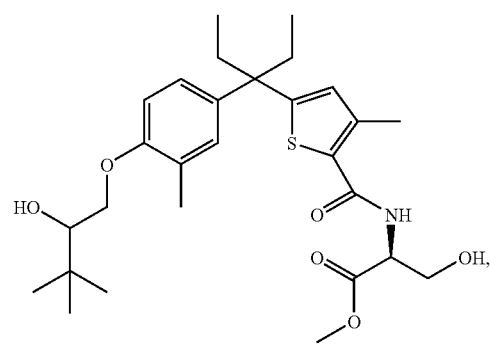
X64)
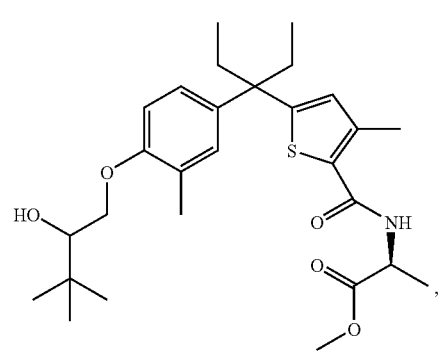
X65)
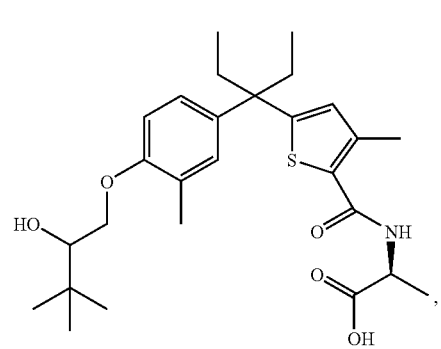
X66)
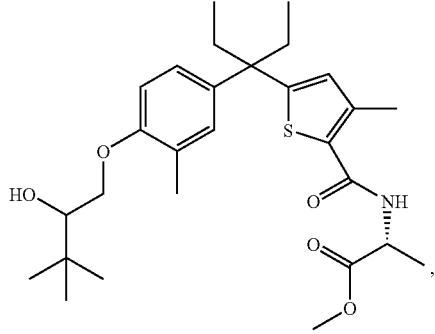
X69)
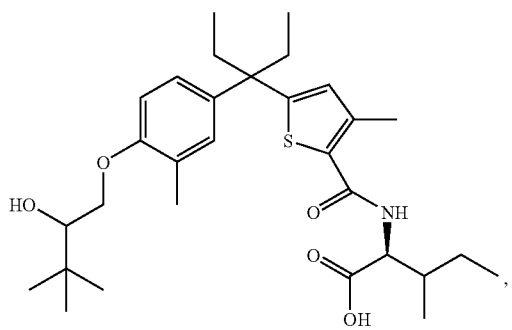
X70)
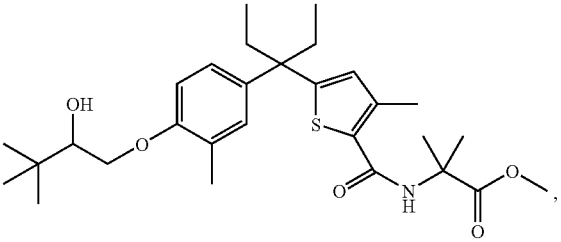
X71)
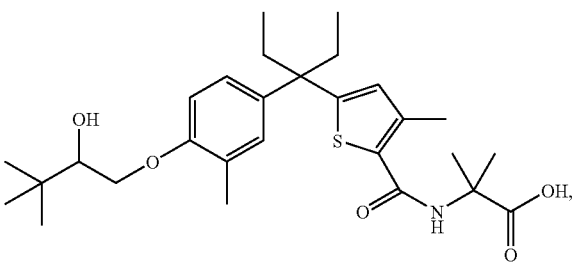
X72)
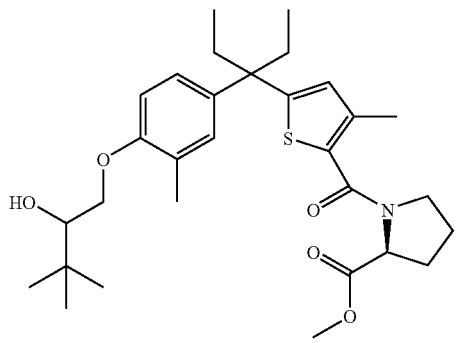

-continued
X75) 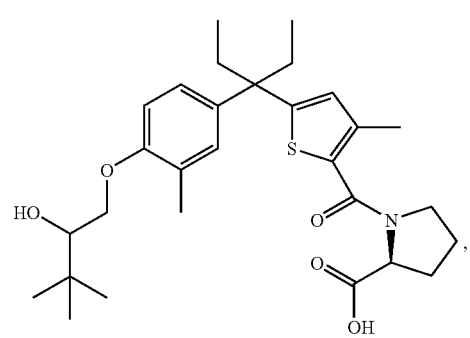
X78) 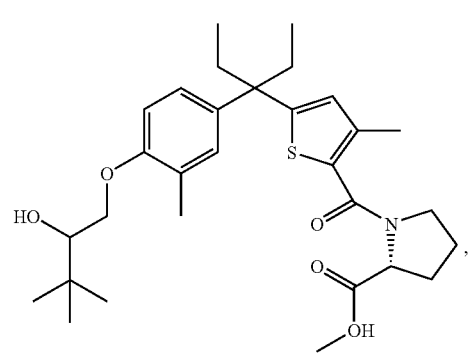
X81) 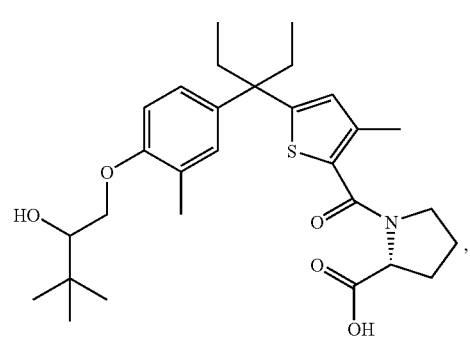
X83) 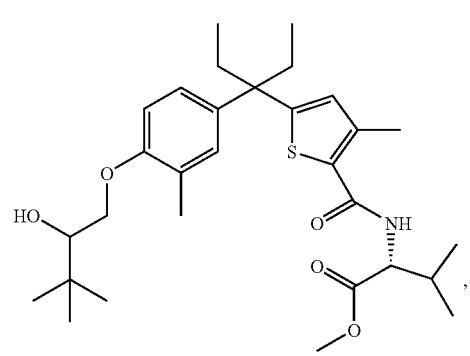
-continued
X86) 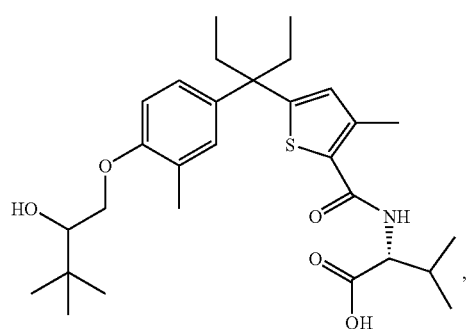
X88) 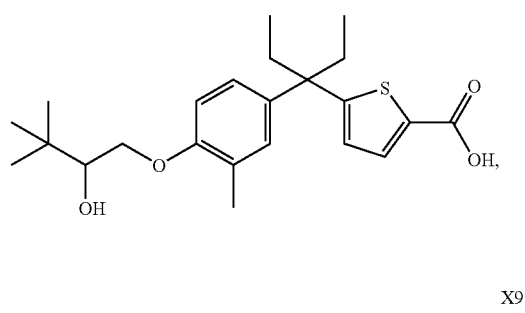
X91) 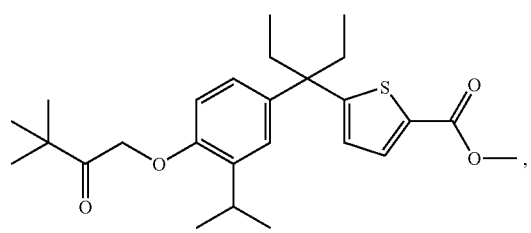
X92) 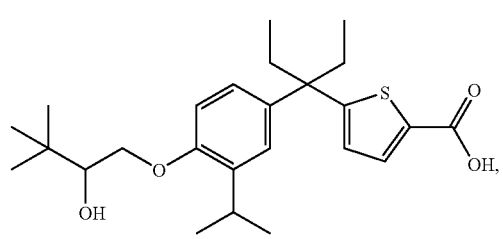
X93) 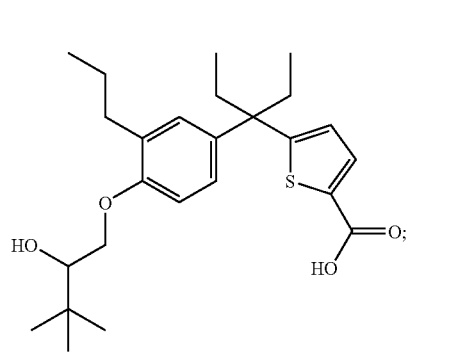

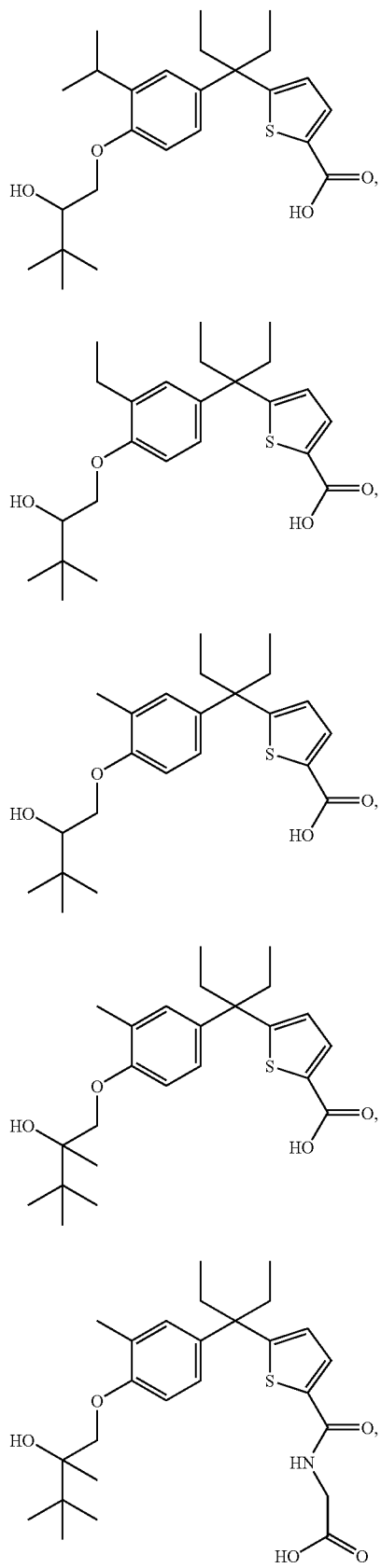
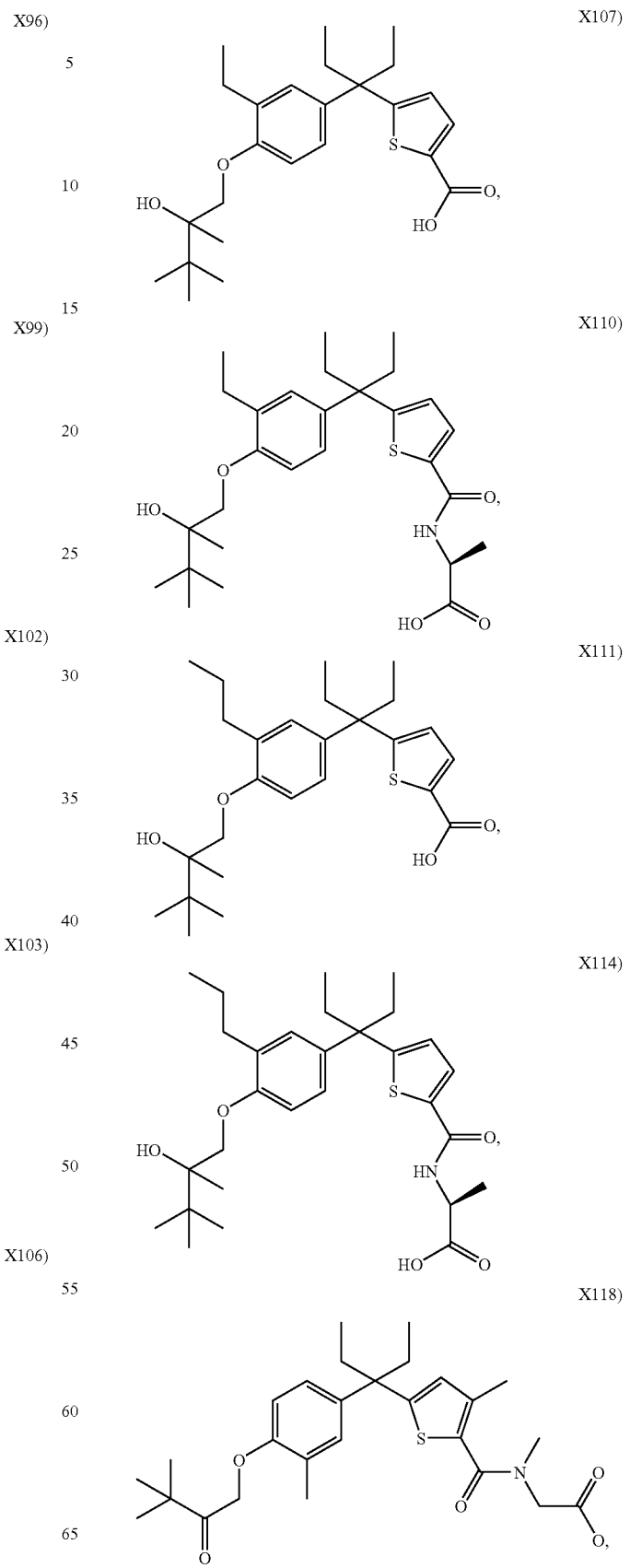

-continued
X119)
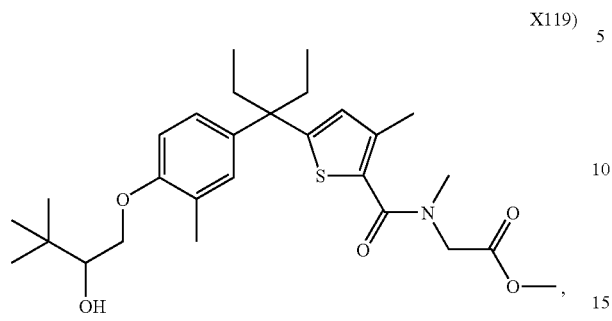
X122)
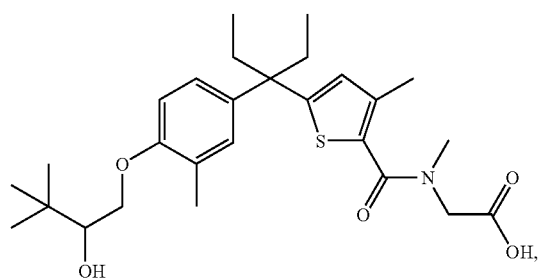
X124)
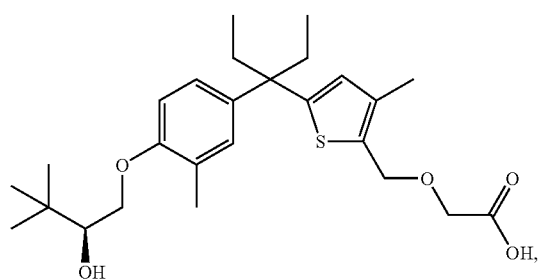
X125)
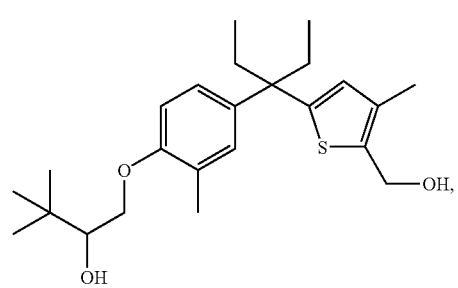
X128)
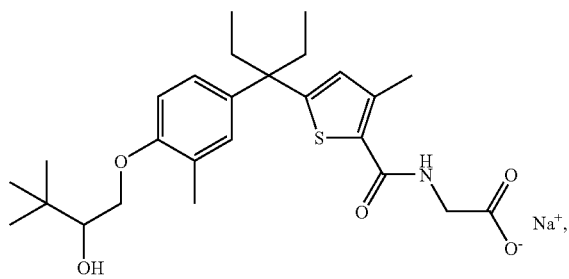
-continued
X130)
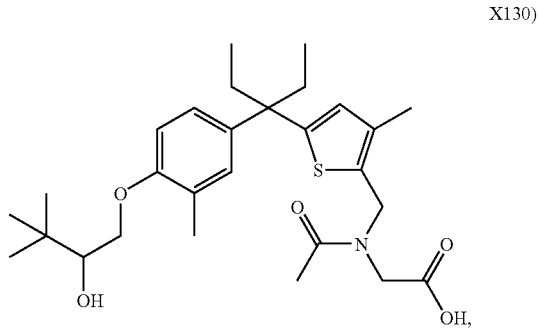
X131)
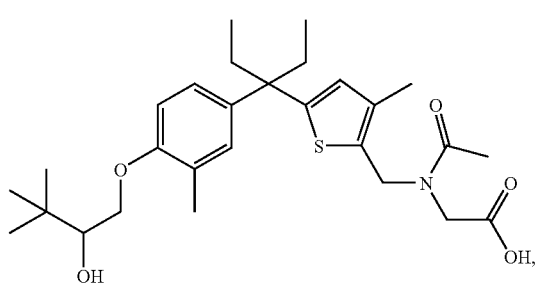
X134)
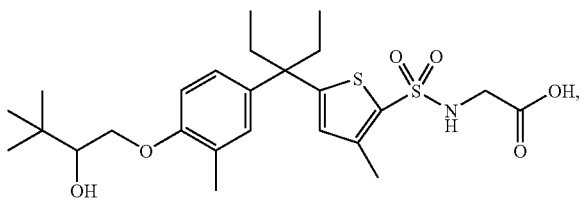
X137)
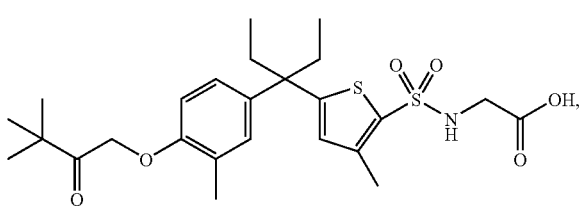
X139)
X140)
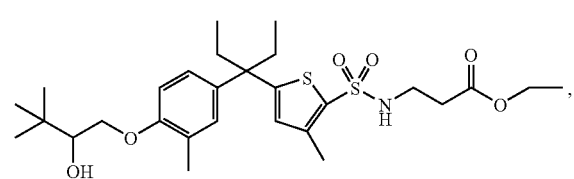

295
-continued
X141)
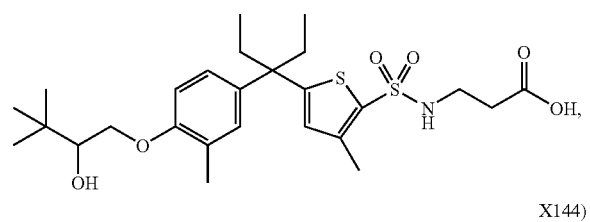
X144)
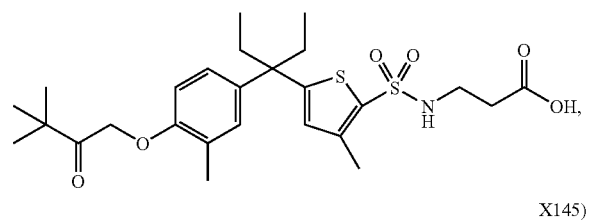
X145)
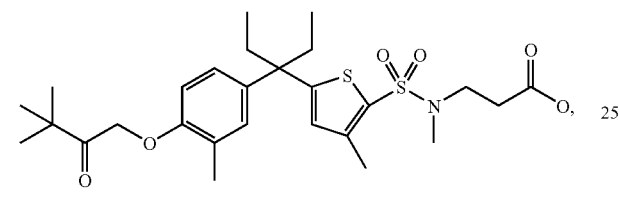
X146)
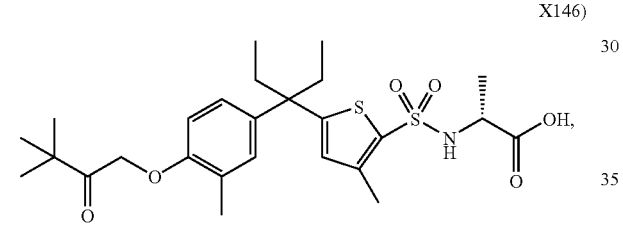
X147)
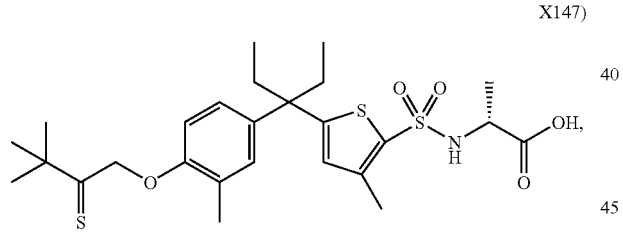
X148)
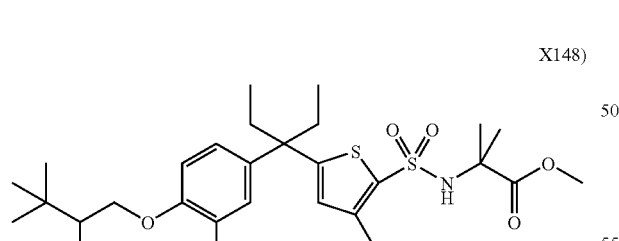
X149)
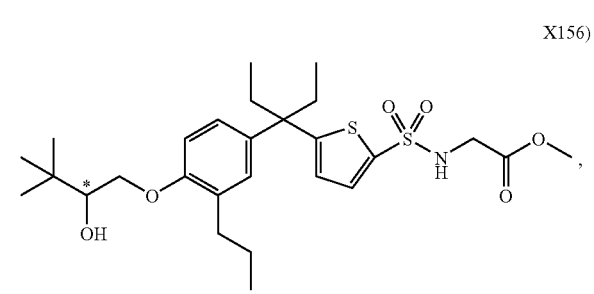
296
-continued
X150)
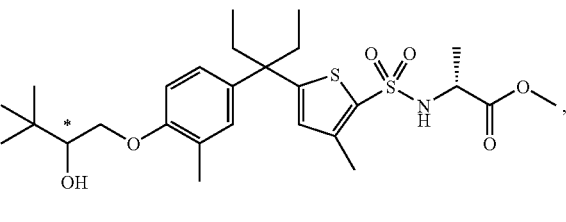
X152)
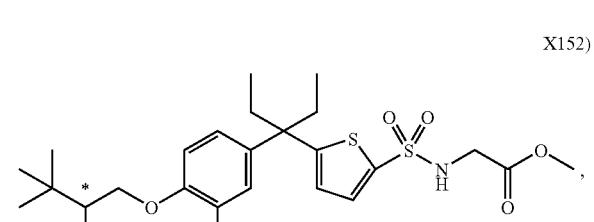
X153)
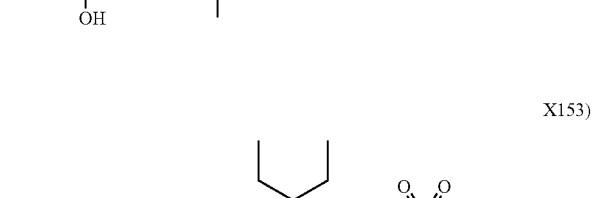
X154)
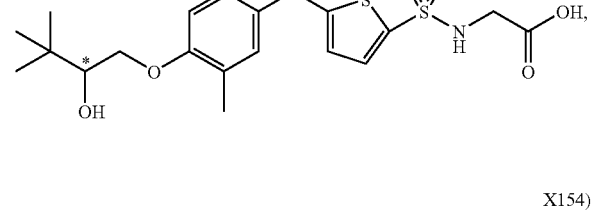
X155)
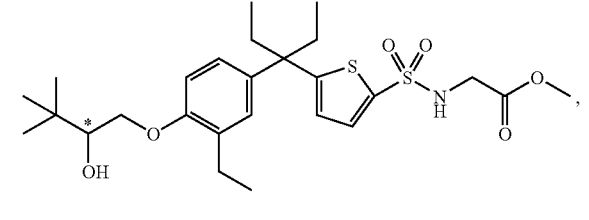
X156)
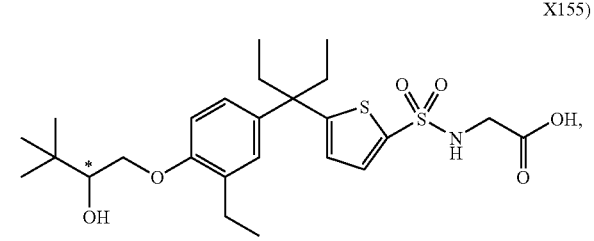

X157)
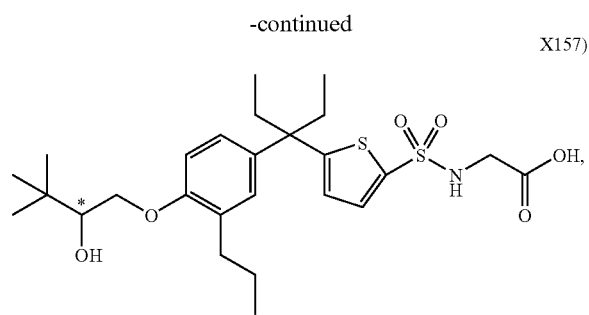
X158)
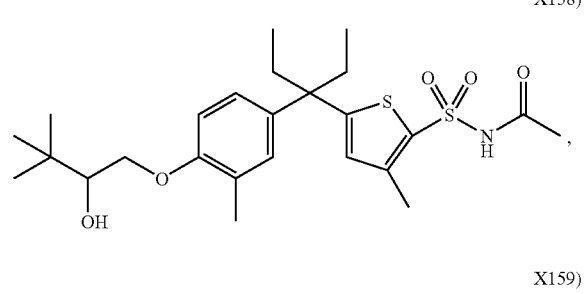
X159)
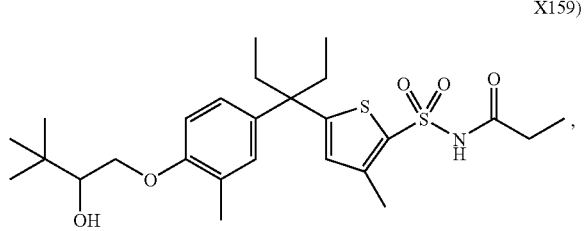
X160)
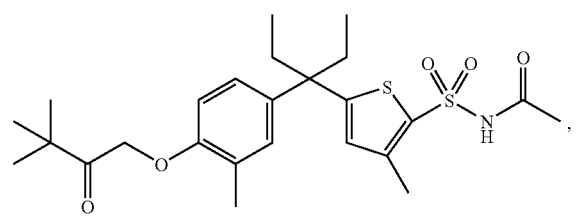
X161)
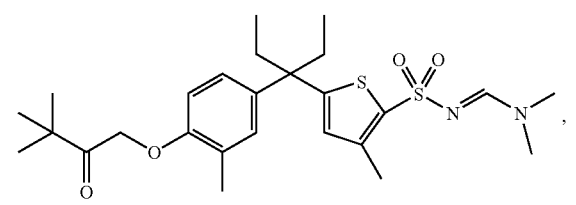
X162)
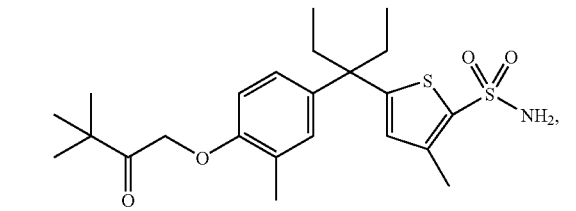
X163)
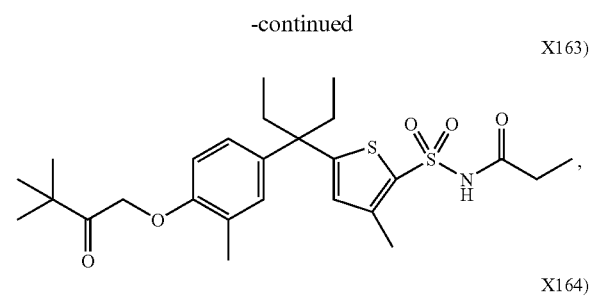
X164)
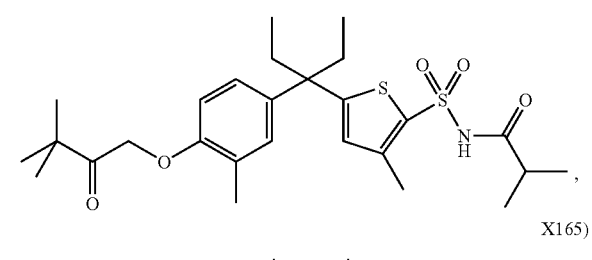
X165)
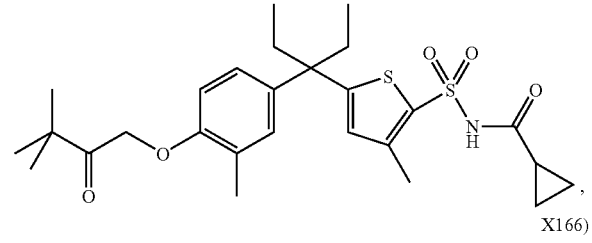
X166)
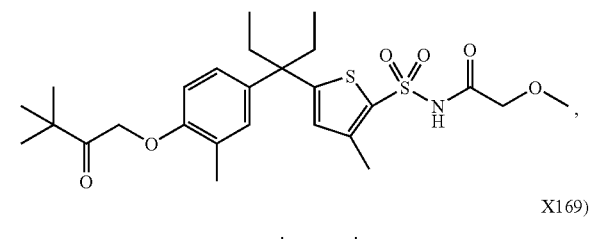
X169)
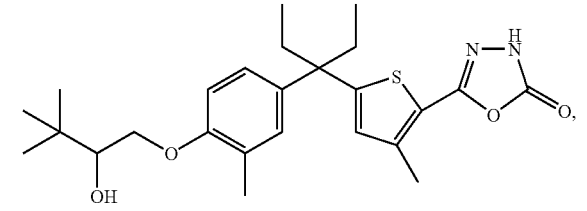
X171)
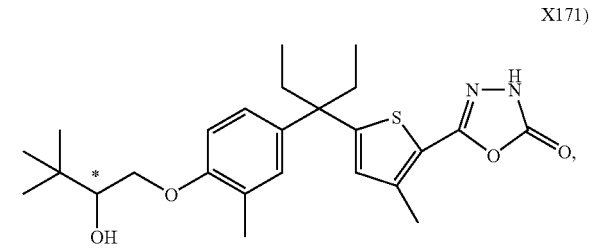
X172)
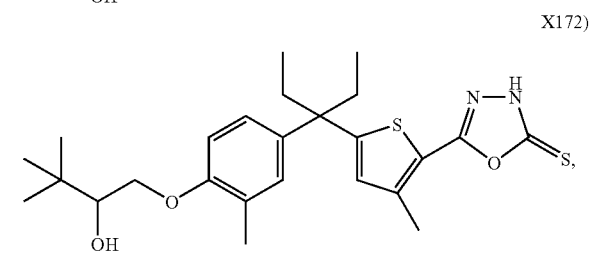

-continued
X174)
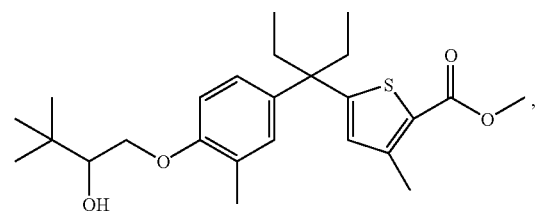
X175)
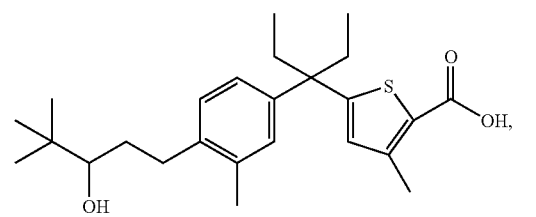
X176)
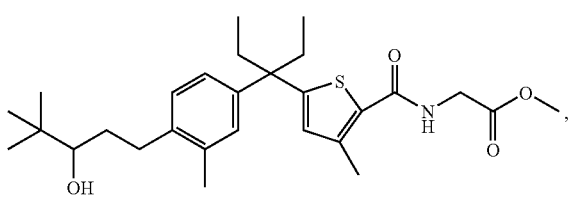
X177)
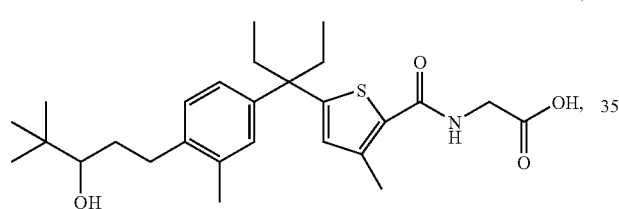
X178)
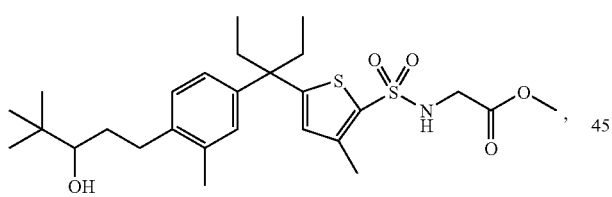
X179)
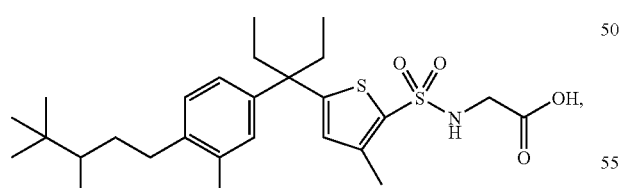
X183)
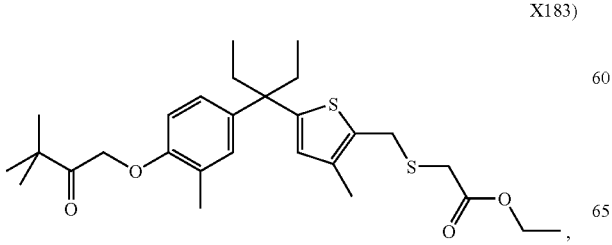
-continued
X184)
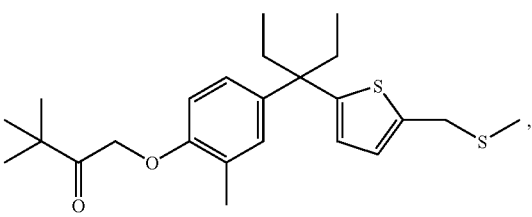
X185)
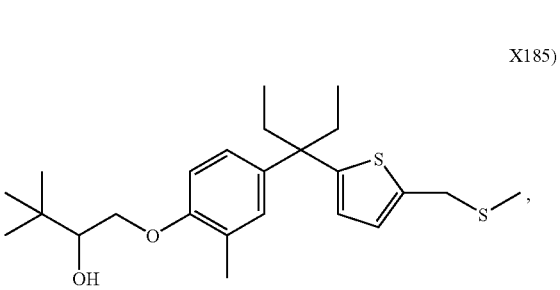
X187)
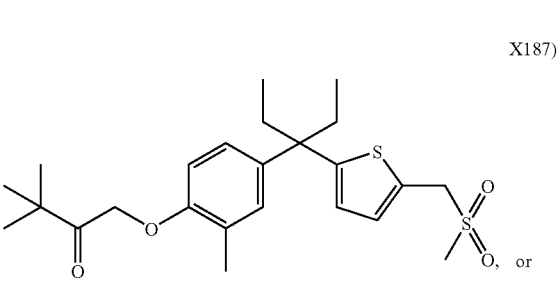
or
X188)
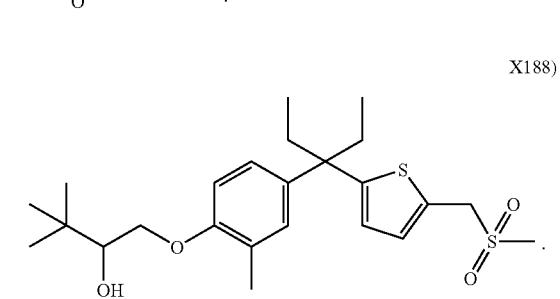
5. A compound selected from the group consisting of compounds represented by the formula:
P100
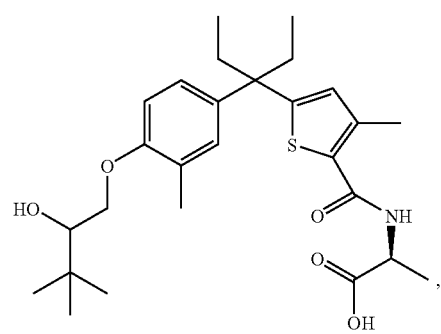

-continued
P101
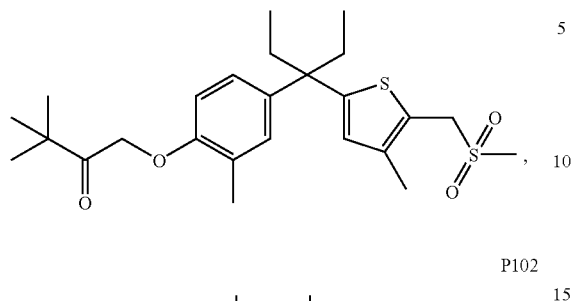
P102
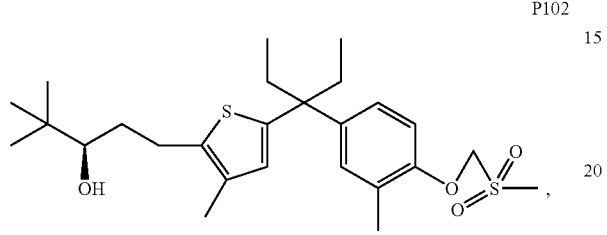
P103
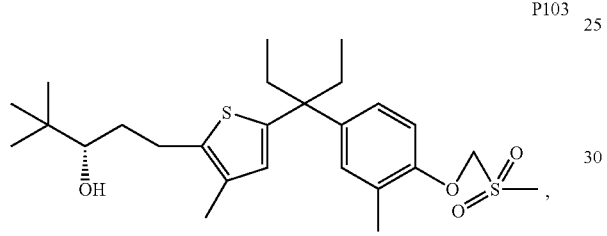
P104
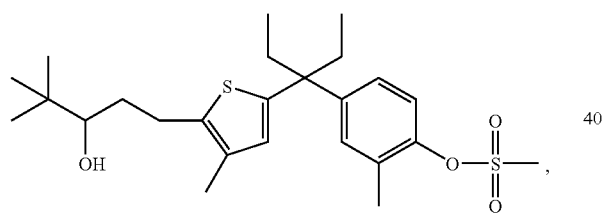
P105
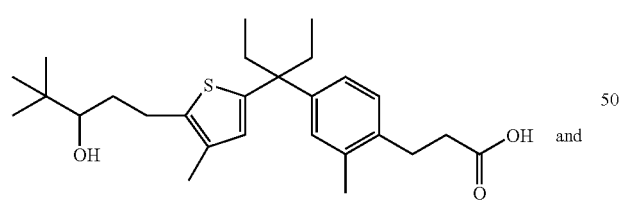
P106
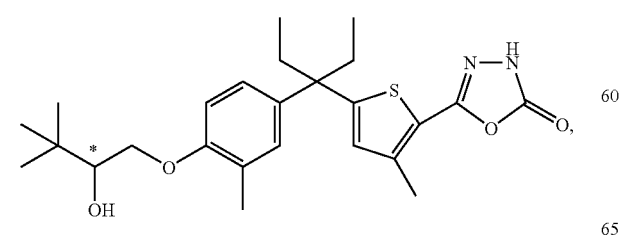
or a pharmaceutically suitable salt, thereof
6. A compound selected from the group consisting of compounds represented by the formula:
P101
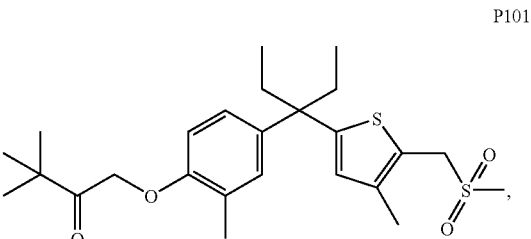
P200
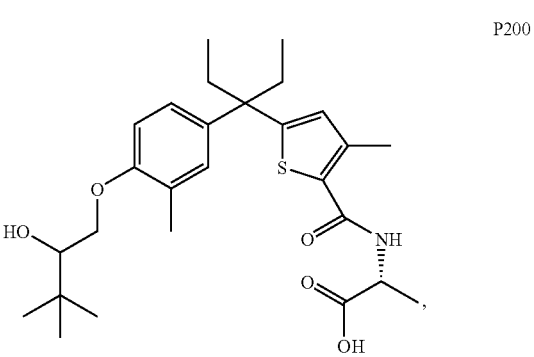
P201
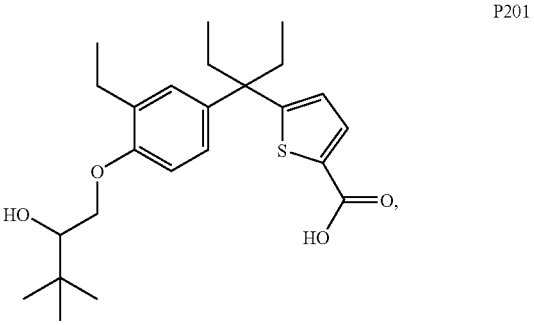
P202
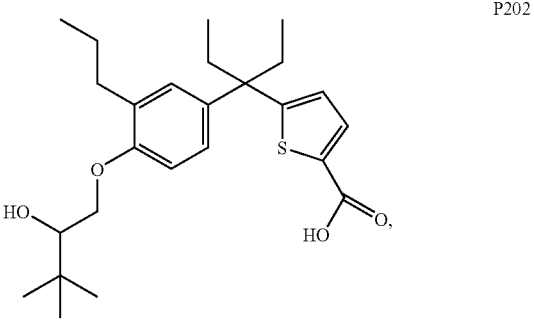
P203
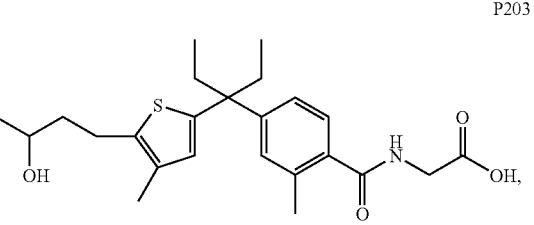

P204

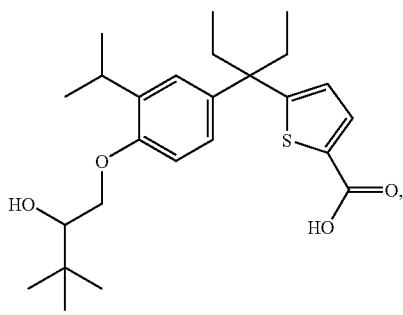

P205

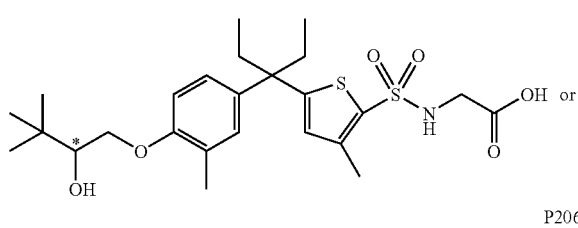

P206

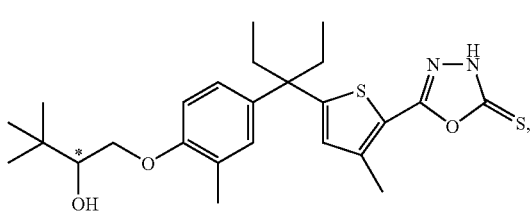

or a pharmaceutically suitable salt, thereof.

7. A method of treating osteoporosis, wherein a mammal in need thereof is administered a pharmaceutically effective amount of a compound of claim 6.

8. A method of treating psoriasis, wherein a mammal in need thereof is administered a pharmaceutically effective amount of a compound of claim 5.

9. A method of treating abscess or adhesion, within a mammal in need thereof is administered a pharmaceutically effective amount of a compound of claim 5.

10. A compound according to claim 4 represented by the formula:

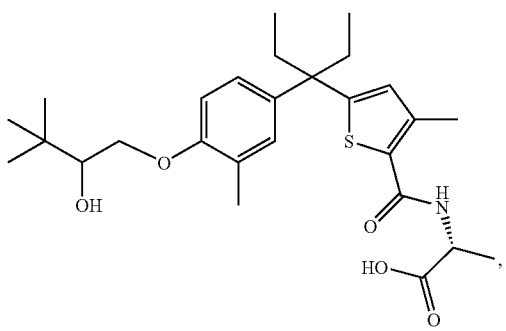

or a pharmaceutically suitable salt thereof.

11. A compound according to claim 4 represented by the formula:

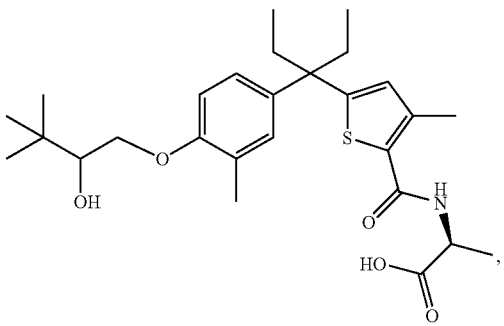

or a pharmaceutically suitable salt thereof.

12. A compound as claimed in any one of claims 4, 5, and 6 for use in treating a mammal for psoriasis, scleroderma, or seborrheic dermatitis.

13. A compound represented by the formula:

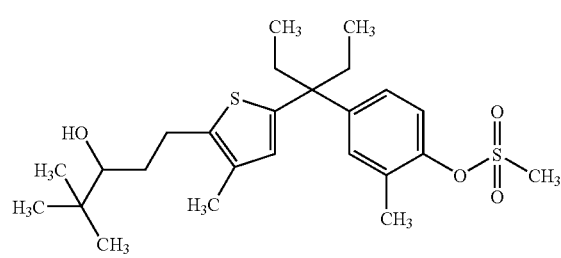

or a pharmaceutically acceptable salt thereof.

14. A compound represented by the formula:

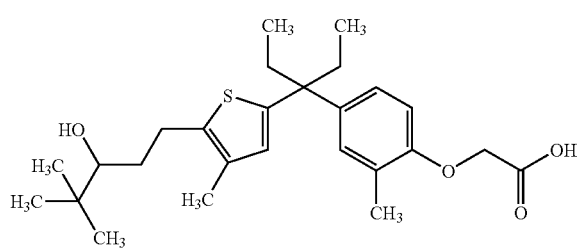

or a pharmaceutically acceptable salt thereof.

15. A compound represented by the formula:

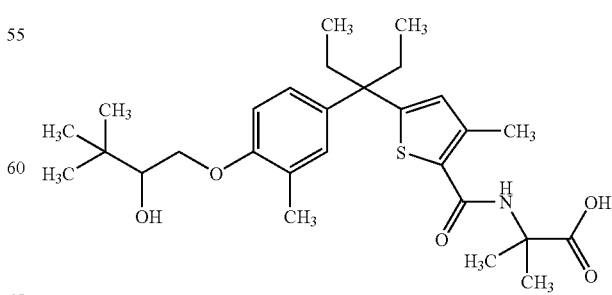

or a pharmaceutically acceptable salt thereof.

16. A method of treating a mammal for psoriasis, scleroderma, or seborrheic dermatitis comprising administered a pharmaceutically effective amount of a compound of claim 13, or a pharmaceutically acceptable salt thereof.

17. A method of treating a mammal for psoriasis, scleroderma, or seborrheic dermatitis comprising administered a pharmaceutically effective amount of a compound of claim 14, or a pharmaceutically acceptable salt thereof.

18. A method of treating a mammal for psoriasis, scleroderma, or seborrheic dermatitis comprising administered a pharmaceutically effective amount of a compound of claim 15, or a pharmaceutically acceptable salt thereof.

19. A pharmaceutical formulation comprising a compound as claimed in any one of claims 13, 14, and 15, or a pharmaceutically acceptable salt thereof, together with a pharmaceutically acceptable carrier or diluent therefor.

* * * * *

UNITED STATES PATENT AND TRADEMARK OFFICE
CERTIFICATE OF CORRECTION

PATENT NO. : 7,601,850 B2  Page 1 of 1
APPLICATION NO. : 10/515403
DATED : October 13, 2009
INVENTOR(S) : Dahnke et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 552 days.

Signed and Sealed this

Fifth Day of October, 2010

David J. Kappos
*Director of the United States Patent and Trademark Office*